(12) United States Patent
Tanaka

(10) Patent No.: US 7,951,433 B2
(45) Date of Patent: *May 31, 2011

(54) FIVE-RING LIQUID CRYSTAL COMPOUND HAVING $CF_2O$ BONDING GROUP, LIQUID CRYSTAL COMPOSITION, AND LIQUID CRYSTAL DISPLAY DEVICE

(75) Inventor: Hiroyuki Tanaka, Chiba (JP)

(73) Assignees: Chisso Corporation, Osaka (JP); Chisso Petrochemical Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 12/528,370

(22) PCT Filed: Feb. 20, 2008

(86) PCT No.: PCT/JP2008/052820
§ 371 (c)(1),
(2), (4) Date: Aug. 24, 2009

(87) PCT Pub. No.: WO2008/105286
PCT Pub. Date: Sep. 4, 2008

(65) Prior Publication Data
US 2010/0127211 A1    May 27, 2010

(30) Foreign Application Priority Data

Feb. 28, 2007 (JP) .................................. 2007-049732
Apr. 17, 2007 (JP) .................................. 2007-108285

(51) Int. Cl.
*C09K 19/34* (2006.01)
*C09K 19/30* (2006.01)
*C09K 19/12* (2006.01)
*C07C 25/13* (2006.01)
*C07C 19/08* (2006.01)
*C07C 43/225* (2006.01)
*C07D 319/06* (2006.01)

(52) U.S. Cl. ............... 428/1.1; 252/299.61; 252/299.63; 252/299.66; 570/126; 570/127; 570/128; 570/129; 549/369; 549/374; 568/656

(58) Field of Classification Search ................... 428/1.1; 252/299.61, 299.63, 299.66, 299.67; 570/126, 570/127, 128, 129; 549/369, 374; 568/656
See application file for complete search history.

(56) References Cited

U.S. PATENT DOCUMENTS

| | | | | |
|---|---|---|---|---|
| 5,728,319 A | * | 3/1998 | Matsui et al. | ............. 252/299.63 |
| 5,858,270 A | * | 1/1999 | Matsui et al. | ............. 252/299.01 |
| 7,419,706 B2 | * | 9/2008 | Heckmeier et al. | ............. 428/1.1 |
| 7,531,106 B2 | * | 5/2009 | Kirsch et al. | ............. 252/299.01 |
| 7,722,783 B2 | * | 5/2010 | Haseba et al. | ............ 252/299.01 |
| 2005/0017216 A1 | | 1/2005 | Poetsch et al. | |
| 2005/0279968 A1 | | 12/2005 | Manabe et al. | |
| 2006/0061699 A1 | | 3/2006 | Kirsch et al. | |
| 2006/0210724 A1 | | 9/2006 | Heckmeier et al. | |
| 2006/0286308 A1 | | 12/2006 | Kirsch et al. | |
| 2008/0193682 A1 | | 8/2008 | Lietzau et al. | |

FOREIGN PATENT DOCUMENTS

| | | | |
|---|---|---|---|
| EP | 0786445 | | 7/1997 |
| EP | 0844229 | | 5/1998 |
| GB | 2229438 | | 9/1990 |
| JP | 10-251186 | | 9/1998 |
| JP | 2006241040 A | * | 9/2006 |
| WO | 2005/019378 | | 3/2005 |
| WO | 2005/019381 | | 3/2005 |
| WO | 2006/061094 | | 6/2006 |
| WO | 2006/125530 | | 11/2006 |

* cited by examiner

*Primary Examiner* — Shean C Wu
(74) *Attorney, Agent, or Firm* — J.C. Patents

(57) ABSTRACT

The invention provides a five-ring liquid crystal compound having a $CF_2O$ bonding group as a new compound having a general physical properties necessary for compounds, stability to heat, light and so forth, a wide temperature range of liquid crystal phases, a high clearing point, a good compatibility with other compounds, a large dielectric anisotropy and refractive index anisotropy, and an especially high clearing point and an especially large refractive index anisotropy, and provides a liquid crystal composition and a liquid crystal display device.

16 Claims, No Drawings

US 7,951,433 B2

FIVE-RING LIQUID CRYSTAL COMPOUND HAVING CF$_2$O BONDING GROUP, LIQUID CRYSTAL COMPOSITION, AND LIQUID CRYSTAL DISPLAY DEVICE

BACKGROUND OF THE INVENTION

1. Field of the Invention

The invention relates to a new liquid crystal compound useful as a material for a display device, and a liquid crystal composition. The invention relates more specifically to a new liquid crystal compound having a wide temperature range of liquid crystal phases, a high clearing point, a large dielectric anisotropy, a large refractive index anisotropy, and a good compatibility with other liquid crystal compounds, and also being usable in a wide temperature range, drivable at a low voltage, and possible to exhibit a steep electrooptical characteristics when used for a liquid crystal display device, and to the liquid crystal display device comprising the composition.

2. Description of Related Art

Display devices using liquid crystal compounds (The term liquid crystal compound is used in this specification as a generic term for a compound having a liquid crystal phase and a compound having no liquid crystal phases but useful as a component of a liquid crystal composition.) have been widely applied to displays for timepieces, electronic calculators, word processors, and so forth. In these display devices, the refractive index anisotropy, the dielectric anisotropy, and so forth of the liquid crystal compounds have been utilized.

In the liquid crystal display devices, a classification based on the operation mode of liquid crystals includes phase change (PC), twisted nematic (TN), super twisted nematic (STN), bistable twisted nematic (BTN), electrically controlled birefringence (ECB), optically compensated bend (OCB), in-plane switching (IPS), vertical alignment (VA), and so forth. A classification based on the driving mode of devices includes a passive matrix (PM) and an active matrix (AM). The PM is further classified into static, multiplex and so forth, and the AM is classified into a thin film transistor (TFT), a metal insulator metal (MIM) and so forth.

These liquid crystal display devices comprise liquid crystal compositions having suitable physical properties. The liquid crystal compositions desirably have suitable physical properties for improving the characteristics of the devices. General physical properties necessary for liquid crystal compounds which are the components of the liquid crystal compositions are as follows:
(1) being chemically stable and physically stable,
(2) having a high clearing point (the phase transition temperature of a liquid crystal phase to an isotropic phase),
(3) being low in the minimum temperature of liquid crystal phases (a nematic phase, a smectic phase and so forth), especially of the nematic phase,
(4) having an excellent compatibility with other liquid crystal compounds,
(5) having an appropriate dielectric anisotropy, and
(6) having an appropriate optical anisotropy.

A voltage holding ratio can be increased by using a composition containing a chemically and physically stable liquid crystal compound as described in item (1).

The temperature range of a nematic phase can be widened in a composition containing a liquid crystal compound having a high clearing point or a low minimum temperature of liquid crystal phases as described in items (2) and (3), and thus a display device is usable in a wide temperature range.

The liquid crystal compound is generally used as a composition prepared by being mixed with many other liquid crystal compounds to exhibit characteristics which cannot be attained with a single compound. Thus, it is desirable that a liquid crystal compound used for a display device has a good compatibility with other liquid crystal compounds and so forth, as described in item (4).

Recently, a liquid crystal display device has been required to have higher quality especially in display performance such as contrast, display capacity, and response time. Further, a liquid crystal material to be used has been required to have a lower driving voltage, that is, a liquid crystal compound capable of decreasing threshold voltage and a liquid crystal composition with a lower driving voltage comprising this compound has been required.

The threshold voltage ($V_{th}$), as is well known, is represented by the following equation. Refer to H. J. Deuling, et al., Mol. Cryst. Liq. Cryst., 27 (1975) 81.

$$V_{th} = \pi (K/\epsilon_0 \Delta \epsilon)^{1/2}$$

In the equation above, K is an elastic constant and $\epsilon_0$ is a dielectric constant in a vacuum. As is shown by the equation, two methods are possible to decrease the $V_{th}$, either by increasing the value of $\Delta \epsilon$ (dielectric anisotropy) or by decreasing K. However, K is not easily controlled by the present technology, and the present demand has been commonly dealt with the use of a liquid crystal material having a large $\Delta \epsilon$. Under these circumstances, liquid crystal compounds having an appropriate dielectric anisotropy as described in item (5), and in particular, liquid crystal compounds having a large dielectric anisotropy have been developed actively.

It is desirable that the cell thickness of a liquid crystal display device and the value of refractive index anisotropy ($\Delta n$) of a liquid crystal material used are constant to attain a good liquid crystal display. Refer to E. Jakeman, et al., Phys. Lett., 39A. 69 (1972). The response speed of a liquid crystal display device is in inverse proportion to the square of the thickness of a cell used. Thus, a liquid crystal composition having a large refractive index anisotropy should be used to manufacture a liquid crystal display device capable of a high-speed response and applicable to the display of moving images and so forth. Accordingly, a liquid crystal compound having an appropriate refractive index anisotropy as described in item (6), and a liquid crystal compound having an especially large refractive index anisotropy have been demanded.

A variety of liquid crystal compounds having a large dielectric anisotropy and refractive index anisotropy have been synthesized until now, and some of them are used practically. For example, four-ring compounds having a CF$_2$O bonding group are disclosed in patent documents 1 to 6. However, these compounds do not have an sufficiently high clearing point, so that the usable temperature range of their compositions are not sufficiently wide for the use of display devices.

Further, five-ring compounds (compounds (S-1) to (S-3)) comprising a tetrahydropyran ring and having a CF$_2$O bonding group are disclosed in patent documents 7 to 12. None of these compounds also have a sufficiently high clearing point. Compounds (compounds (S-4) to (S-5)) comprising a tetrahydropyran ring and a dioxane ring are also disclosed in patent document 11. However, these compounds do not have a sufficiently large refractive index anisotropy.

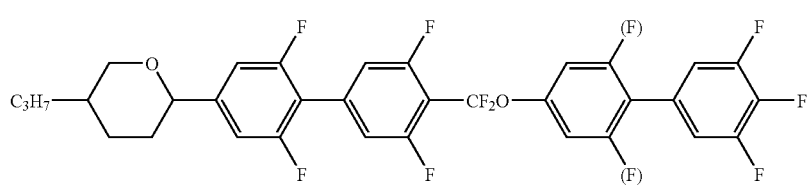
(S-1)

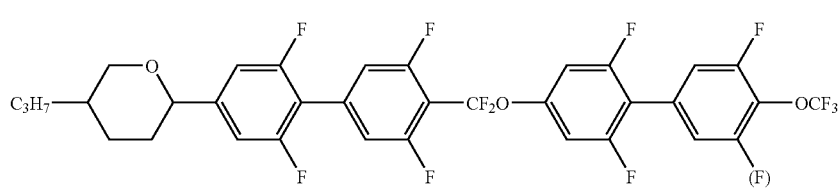
(S-2)

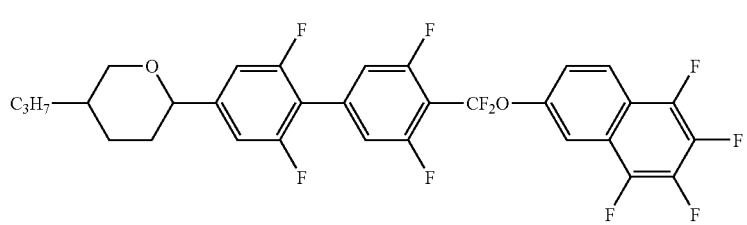
(S-3)

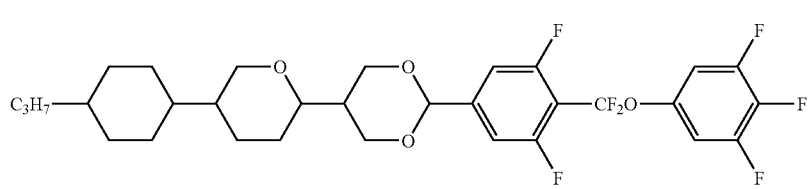
(S-4)

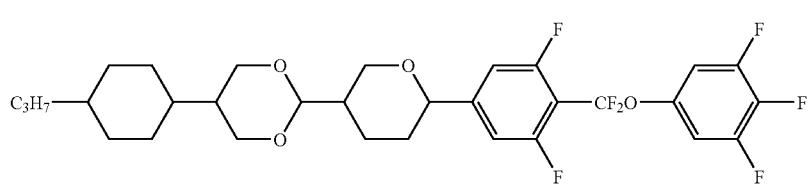
(S-5)

The patent documents cited are No. 1: WO 1996/11897 A;
No. 2: JP H10-204016 A (1998);
No. 3: GB 2229438 B;
No. 4; DE 4023106 A;
No. 5; JP H10-251186 A (1998);
No. 6; WO 2004/035710 A;
No. 7; WO 2004/048501 A;
No. 8; JP 2004-352721 A;
No. 9; WO 2005/019378 A;
No. 10; WO 2005/019381 A;
No. 11; WO 2006/125511 A; and
No. 12; WO 2006/125530 A.

DISCLOSURE OF THE INVENTION

Subjects to be Solved by the Invention

The first aim of the invention is a liquid crystal compound having general physical properties required for compounds, stability to heat, light and so forth, a wide temperature range of liquid crystal phases, a high clearing point, a good compatibility with other compounds, a large dielectric anisotropy and a large refractive index anisotropy, and to provide a liquid crystal compound having an especially high clearing point and a large refractive index anisotropy. The second aim is a liquid crystal composition comprising this compound and having a wide temperature range of liquid crystal phases, a small viscosity, a large refractive index anisotropy and a low threshold voltage, and to provide a liquid crystal composition having an especially wide temperature range of a nematic phase. The third aim is to provide a liquid crystal display device comprising this composition, and having a wide temperature range usable, a short response time, a small electric power consumption, a large contrast, and a low driving voltage.

Means to Solve the Subjects

The invention provides a liquid crystal compound, a liquid crystal composition, a liquid crystal display device comprising the liquid crystal composition, and so forth as described below. Desirable examples will also be described below with regard to terminal groups, rings, bonding groups and so forth in the compounds represented by formula (1).

[Item 1] A compound represented by formula (1):

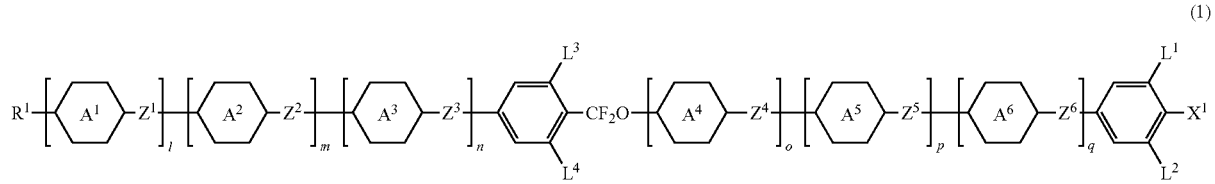

(1)

wherein $R^1$ is alkyl having 1 to 20 carbons, and in the alkyl, arbitrary —CH$_2$— may be replaced by —O—, —S—, or —CH=CH—; ring $A^1$, ring $A^2$, ring $A^3$, ring $A^4$, ring $A^5$, and ring $A^6$ are each independently 1,4-cyclohexylene, 1,3-dioxane-2,5-diyl, 1,4-phenylene, or 1,4-phenylene in which arbitrary hydrogen is replaced by halogen; $Z^1$, $Z^2$, $Z^3$, $Z^4$, $Z^5$, and $Z^6$ are each independently a single bond, —CH$_2$CH$_2$—, —CH=CH—, —C≡—, —COO—, —OCO—, —CF$_2$O—, —OCF$_2$—, —CH$_2$O—, —OCH$_2$—, —CF=CF—, —(CH$_2$)$_4$—, —(CH$_2$)$_2$CF$_2$O—, —(CH$_2$)$_2$OCF$_2$—, —CF$_2$O—(CH$_2$)$_2$—, —OCF$_2$(CH$_2$)$_2$—, —CH=CH—(CH$_2$)$_2$—, or —(CH$_2$)$_2$—CH=CH—; $L^1$, $L^2$, $L^3$, and $L^4$ are each independently hydrogen or halogen; $X^1$ is hydrogen, halogen, —C≡N, —N=C=S, —SF$_5$, or alkyl having 1 to 10 carbons, and in the alkyl, arbitrary —CH$_2$— may be replaced by —O—, —S—, or —CH=CH— and arbitrary hydrogen may be replaced by halogen; and l, m, n, o, p, and q are each independently 0 or 1, and l+m+n+o+p+q=3.

[Item 2] The compound according to item 1, wherein in formula (1) $R^1$ is alkyl having 1 to 20 carbons, alkenyl 2 to 21 carbons, alkoxy having 1 to 19 carbons, alkenyloxy having 2 to 20 carbons, or alkylthio having 1 to 19 carbons; $X^1$ is hydrogen, halogen, —C≡N, —N=C=S, —SF$_5$, alkyl having 1 to 10 carbons, alkenyl having 2 to 11 carbons, alkoxy having 1 to 9 carbons, alkenyloxy having 2 to 10 carbons, thioalkyl having 1 to 9 carbons, —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F, —(CF$_2$)$_5$—F, —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, —O—(CF$_2$)$_5$—F, —CH=CHF, —CH=CF$_2$, —CF=CHF, —CH=CHCH$_2$F, —CH=CHCF$_3$, —(CH$_2$)$_2$—CH=CF$_2$, —CH$_2$CH=CHCF$_3$, or —CH=CHCF$_2$CF$_3$.

[Item 3] The compound according to item 1 or 2, wherein in formula (1) $Z^1$, $Z^2$, $Z^3$, $Z^4$, $Z^5$, and $Z^6$ are each independently a single bond, —CH$_2$CH$_2$—, —CH=CH—, —C≡C—, —COO—, —CF$_2$O—, —CH$_2$O—, or —OCH$_2$—.

[Item 4] The compound according to item 1, which is represented by any one of formulas (1-1) to (1-4):

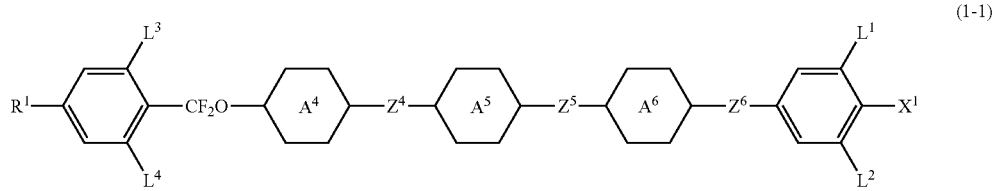

(1-1)

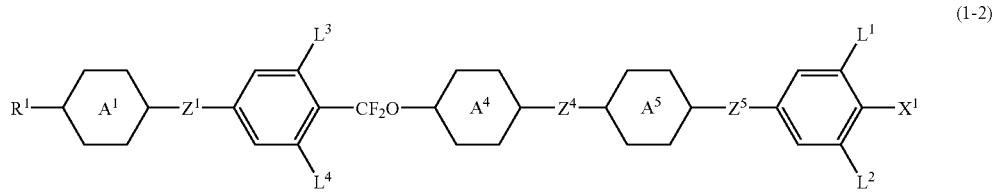

(1-2)

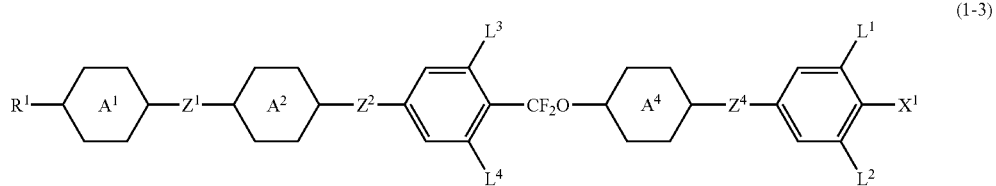

(1-3)

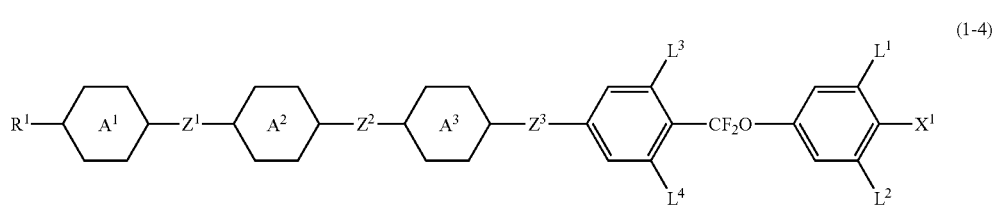

(1-4)

wherein R¹ is alkyl having 1 to 15 carbons, alkenyl having 2 to 15 carbons, alkoxy having 1 to 15 carbons, or alkenyloxy having 2 to 15 carbons; ring A¹, ring A², ring A³, ring A⁴, ring A⁵, and ring A⁶ are each independently 1,4-cyclohexylene, 1,3-dioxane-2,5-diyl, 1,4-phenylene, or 1,4-phenylene in which arbitrary hydrogen is replaced by fluorine, and in each formula, at least one of ring A¹, ring A², ring A³, ring A⁴, ring A⁵, and ring A⁶ is 1,4-cyclohexylene or 1,3-dioxane-2,5-diyl; $Z^1$, $Z^2$, $Z^3$, $Z^4$, $Z^5$, and $Z^6$ are each independently a single bond, —CH₂CH₂—, —CH=CH—, —C≡C—, —COO—, —CF₂O—, —CH₂O—, or —OCH₂—; L¹, L², L³, and L⁴ are each independently hydrogen or fluorine; and X¹ is fluorine, chlorine, —C≡N, —CF₃, —CHF₂, —CH₂F, —OCF₃, —OCHF₂, or —OCH₂F.

[Item 5] The compound according to item 1, which is represented by any one of formulas (1-5) to (1-8):

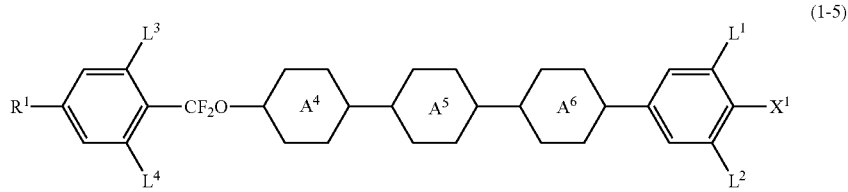

(1-5)

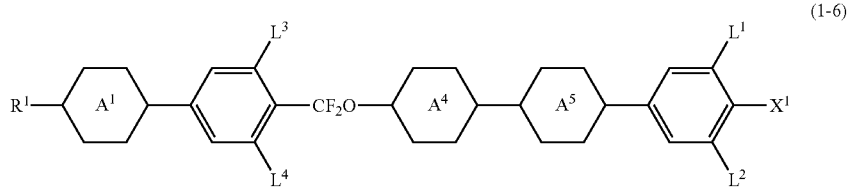

(1-6)

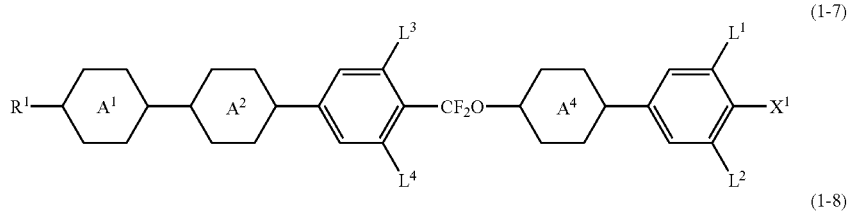

(1-7)

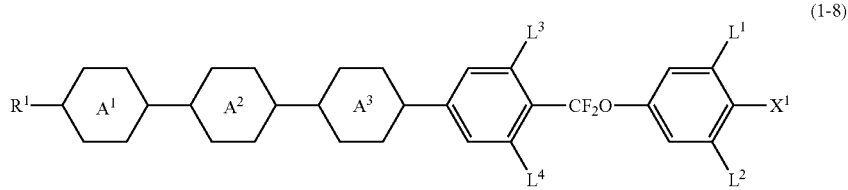

(1-8)

wherein R¹ is alkyl having 1 to 15 carbons or alkenyl having 2 to 15 carbons; ring A¹, ring A², ring A³, ring A⁴, ring A⁵, and ring A⁶ are each independently 1,4-cyclohexylene, 1,3-dioxane-2,5-diyl, 1,4-phenylene, or 1,4-phenylene in which arbitrary hydrogen is replaced by fluorine; L¹, L², L³, and L⁴ are each independently hydrogen or fluorine; and X¹ is fluorine, chlorine, —C≡N, —CF₃, —CHF₂, —CH₂F, —OCF₃, —OCHF₂, or —OCH₂F.

[Item 6] The compound according to item 1, which is represented by any one of formulas (1-9) to (1-19):

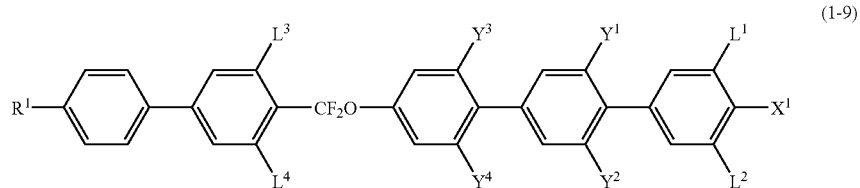

(1-9)

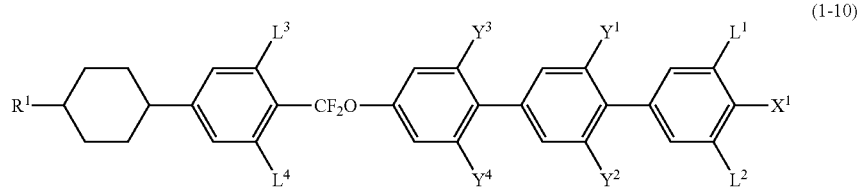

(1-10)

(1-11)
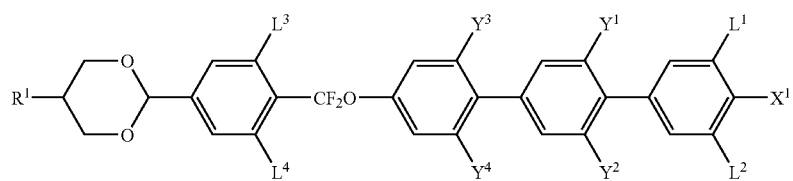
(1-12)
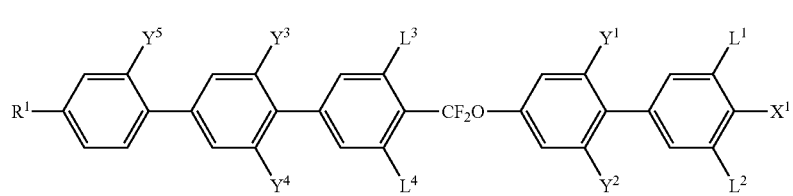
(1-13)
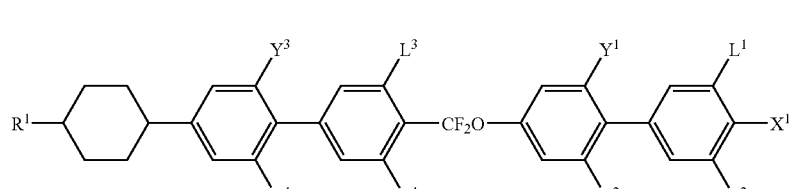
(1-14)
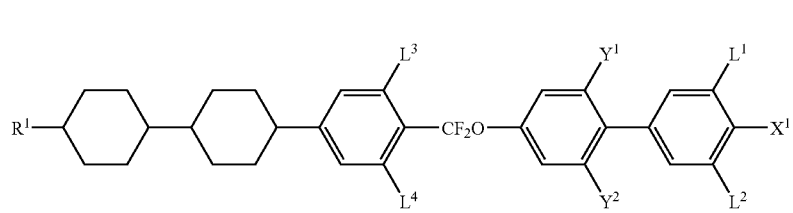
(1-15)
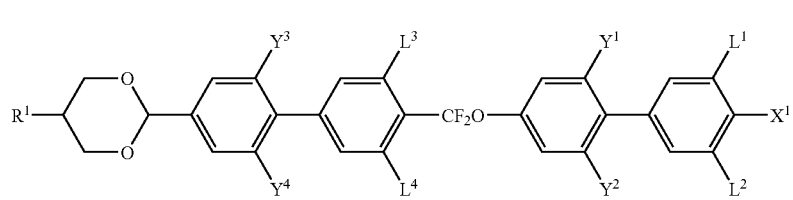
(1-16)
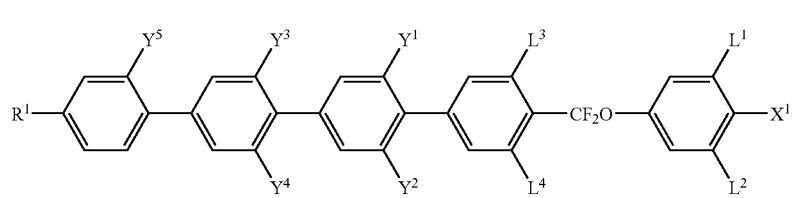
(1-17)
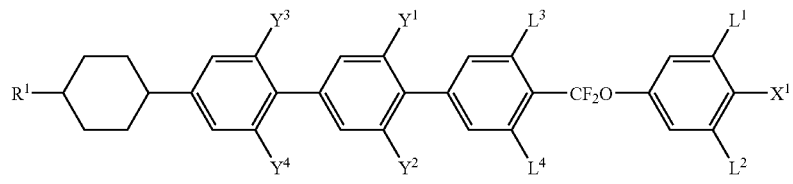
(1-18)
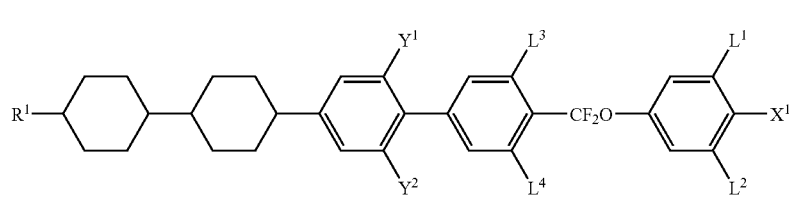

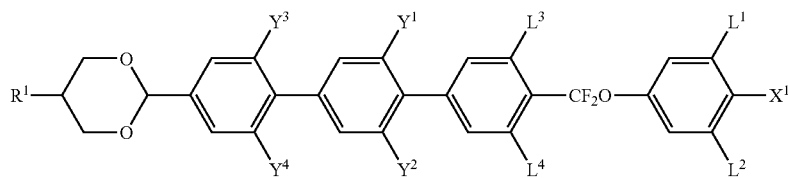
(1-19)
wherein $R^1$ is alkyl having 1 to 15 carbons; $L^1$, $L^2$, $L^3$, $L^4$, $Y^1$, $Y^2$, $Y^3$, $Y^4$, and $Y^5$ are each independently hydrogen or fluorine; and $X^1$ is fluorine or —$OCF_3$.
[Item 7] The compound according to item 1, which is represented by any one of formulas (1-20) to (1-41):
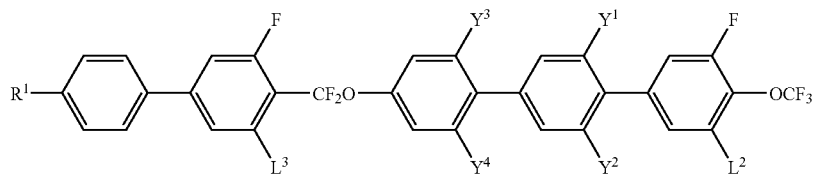
(1-20)
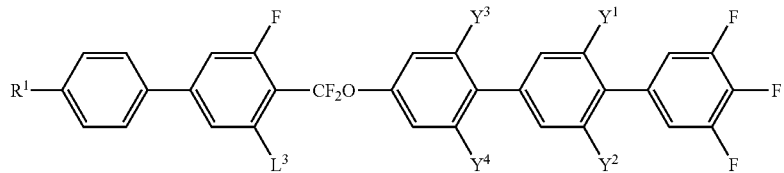
(1-21)
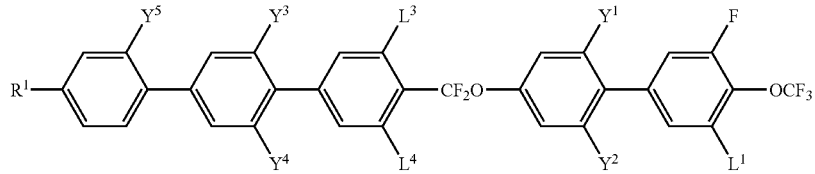
(1-22)
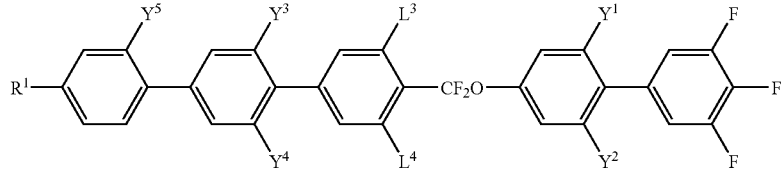
(1-23)
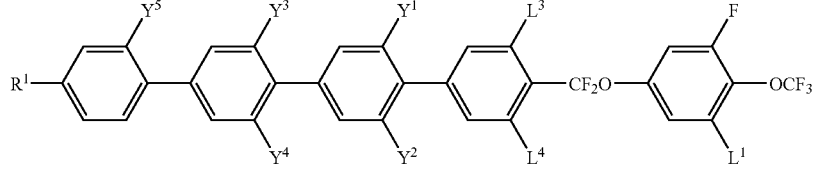
(1-24)
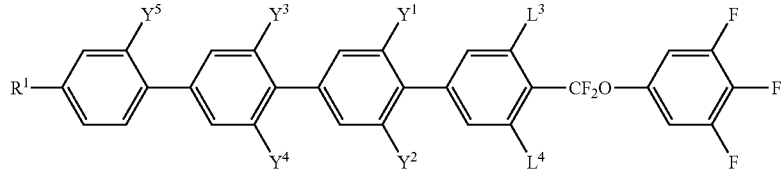
(1-25)

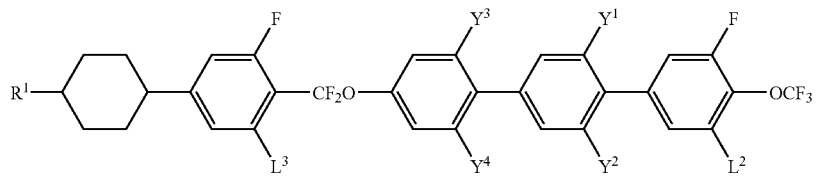
(1-26)
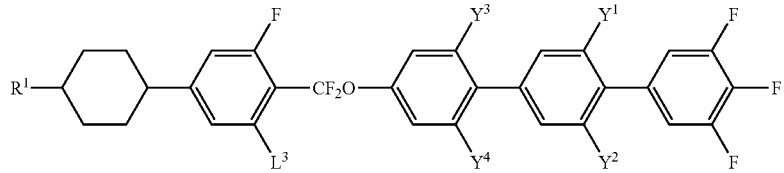
(1-27)
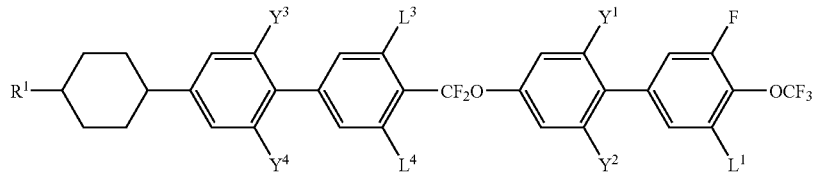
(1-28)
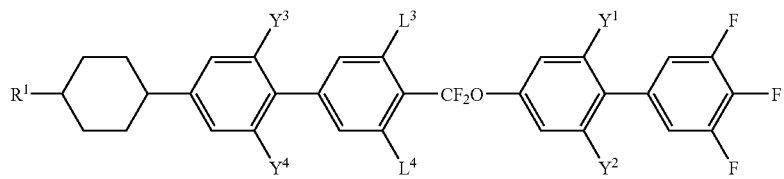
(1-29)
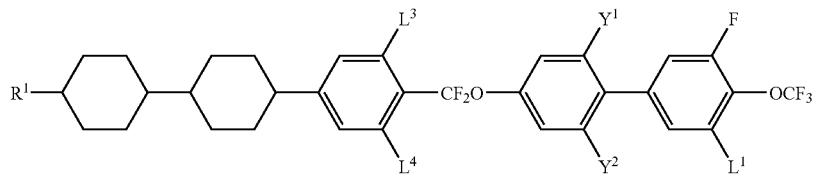
(1-30)
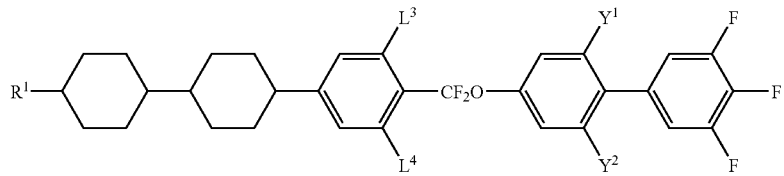
(1-31)
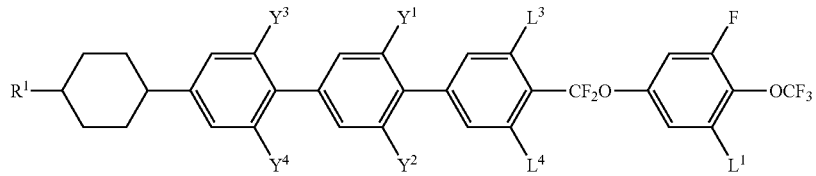
(1-32)
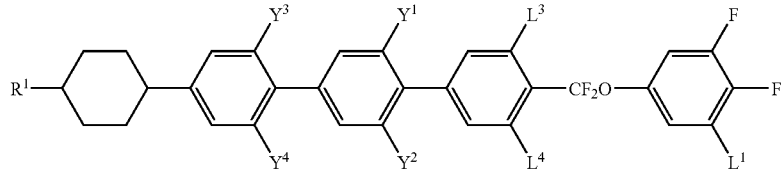
(1-33)
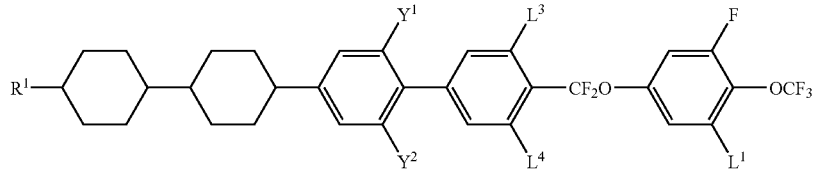
(1-34)

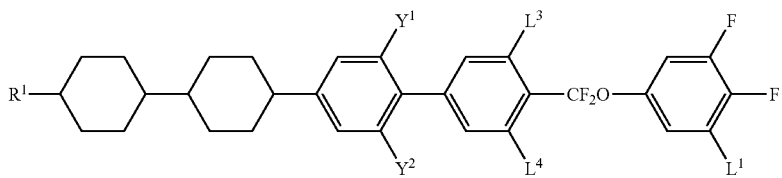 (1-35)

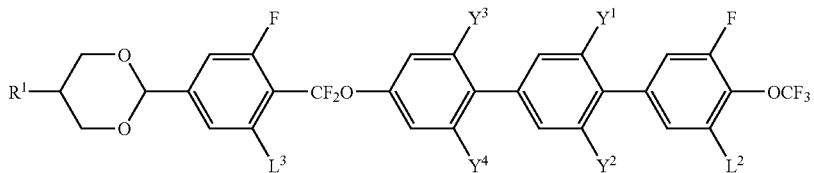 (1-36)

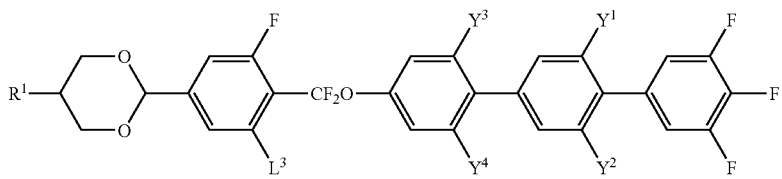 (1-37)

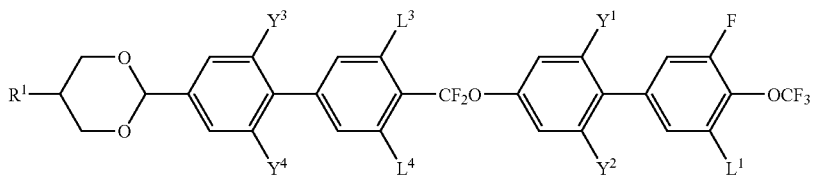 (1-38)

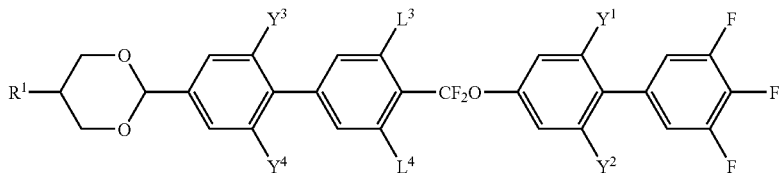 (1-39)

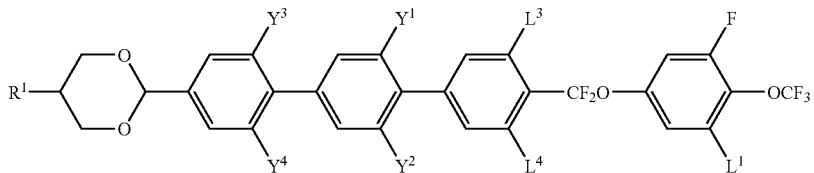 (1-40)

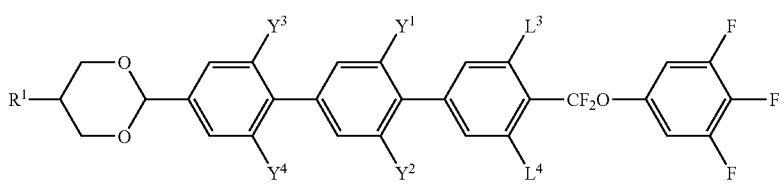 (1-41)

wherein $R^1$ is alkyl having 1 to 15 carbons; and $L^1, L^3, L^4, Y^1, Y^2, Y^3, Y^4$, and $Y^5$ are each independently hydrogen or fluorine.

[Item 8] A liquid crystal composition composed of two or more components comprising at least one compound according to any one of items 1 to 7.

[Item 9] The liquid crystal composition according to item 8, comprising at least one compound selected from the group of compounds represented by each of general formulas (2), (3), and (4) as a component:

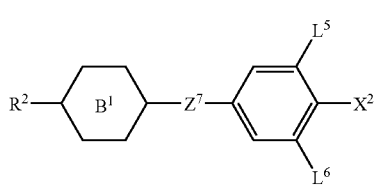 (2)

-continued

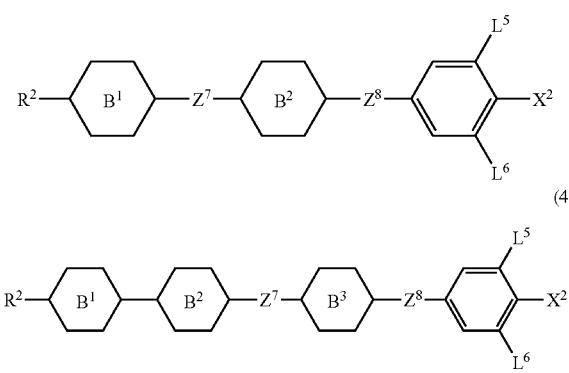
(3)

(4)

wherein $R^2$ is alkyl having 1 to 10 carbons, or alkenyl having 2 to 10 carbons, and in the alkyl and alkenyl, arbitrary hydrogen may be replaced by fluorine and arbitrary —$CH_2$— may be replaced by —O—; $X^2$ is fluorine, chlorine, —$OCF_3$, —$OCHF_2$, —$CF_3$, —$CHF_2$, —$CH_2F$, —$OCF_2CHF_2$, or —$OCF_2CHFCF_3$; ring $B^1$, ring $B^2$, and ring $B^3$ are each independently 1,4-cyclohexylene, 1,3-dioxane-2,5-diyl, pyrimidine-2,5-diyl, tetrahydropyran-2,5-diyl, 1,4-phenylene, or 1,4-phenylene in which arbitrary hydrogen is replaced by fluorine; $Z^7$ and $Z^8$ are each independently —($CH_2$)$_2$—, —($CH_2$)$_4$—, —COO—, —$CF_2O$—, —$OCF_2$—, —CH=CH—, —C≡C—, —$CH_2O$—, or a single bond; and $L^5$ and $L^6$ are each independently hydrogen or fluorine.

[Item 10] The liquid crystal composition according to item 8, comprising at least one compound selected from the group of compounds represented by general formula (5) as a component:

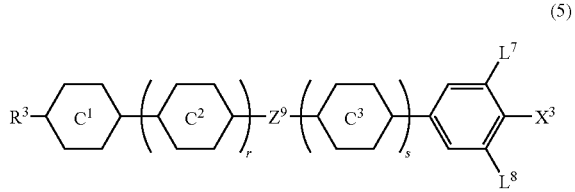
(5)

wherein $R^3$ is alkyl having 1 to 10 carbons or alkenyl having 2 to 10 carbons, and in the alkyl and alkenyl, arbitrary hydrogen may be replaced by fluorine and arbitrary —$CH_2$— may be replaced by —O—; $X^3$ is —C≡N or —C≡C—C≡N; ring $C^1$, ring $C^2$, and ring $C^3$ are each independently 1,4-cyclohexylene, 1,4-phenylene, 1,4-phenylene in which arbitrary hydrogen is replaced by fluorine, 1,3-dioxane-2,5-diyl, tetrahydropyran-2,5-diyl, or pyrimidine-2,5-diyl; $Z^9$ is —($CH_2$)$_2$—, —COO—, —$CF_2O$—, —$OCF_2$—, —C≡C—, —$CH_2O$—, or a single bond; $L^7$ and $L^8$ are each independently hydrogen or fluorine; and r is 0 or 1, s is 0 or 1, and r+s is 0, 1 or 2.

[Item 11] The liquid crystal composition according to item 8, comprising at least one compound selected from the group of compounds represented by each of general formulas (6), (7), (8), (9), and (10) as a component:

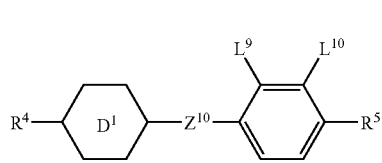
(6)

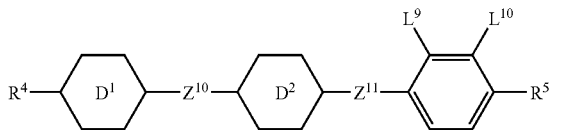
(7)

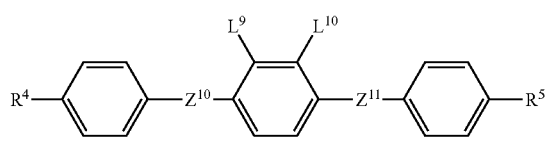
(8)

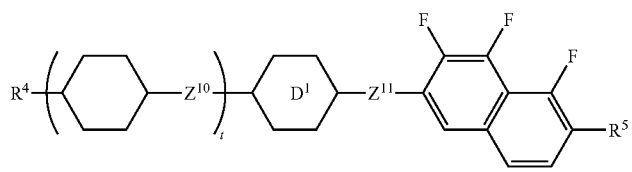
(9)

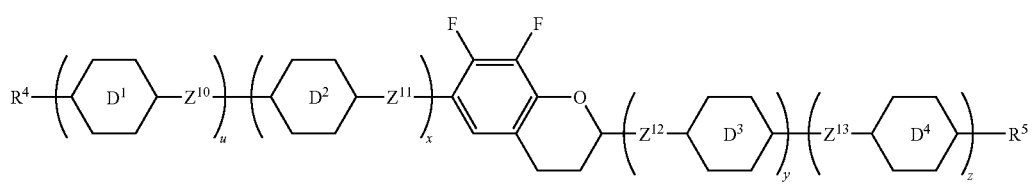
(10)

wherein $R^4$ and $R^5$ are each independently alkyl having 1 to 10 carbons or alkenyl having 2 to 10 carbons, and in the alkyl and alkenyl, arbitrary hydrogen may be replaced by fluorine and arbitrary —$CH_2$— may be replaced by —O—; ring $D^1$, ring $D^2$, ring $D^3$, and ring $D^4$ are each independently 1,4-cyclohexylene, 1,4-cyclohexenylene, 1,4-phenylene, 1,4-phenylene in which arbitrary hydrogen is replaced by fluorine, tetrahydropyran-2,5-diyl, or decahydronaphthalene-2,6-diyl; $Z^{10}$, $Z^{11}$, $Z^{12}$, and $Z^{13}$ are each independently —$(CH_2)_2$—, —COO—, —$CH_2O$—, —$OCF_2$—, —$OCF_2(CH_2)_2$—, or a single bond; $L^9$ and $L^{10}$ are each independently fluorine or chlorine; and t, u, x, y, and z are each independently 0 or 1, and u+x+y+z is 1 or 2.

[Item 12] The liquid crystal composition according to item 8, comprising at least one compound selected from the group of compounds represented by each of general formulas (11), (12), and (13) as a component:

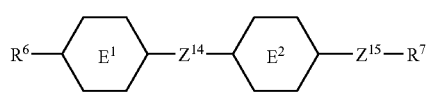
(11)

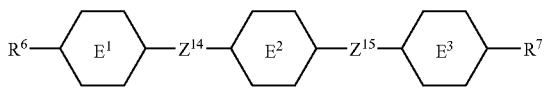
(12)

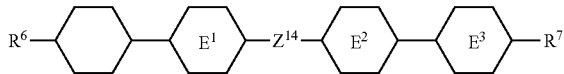
(13)

wherein $R^6$ and $R^7$ are each independently alkyl having 1 to 10 carbons or alkenyl having 2 to 10 carbons, and in the alkyl and alkenyl, arbitrary hydrogen may be replaced by fluorine and arbitrary —$CH_2$— may be replaced by —O—; ring $E^1$, ring $E^2$, and ring $E^3$ are each independently 1,4-cyclohexylene, pyrimidine-2,5-diyl, 1,4-phenylene, 2-fluoro-1,4-phenylene, 3-fluoro-1,4-phenylene, or 2,5-difluoro-1,4-phenylene; and $Z^{14}$ and $Z^{15}$ are each independently —C≡C—, —COO—, —$(CH_2)_2$—, —CH=CH—, or a single bond.

[Item 13] The liquid crystal composition according to item 9, further comprising at least one compound selected from the group of compounds represented by general formula (5) according to item 10.

[Item 14] The liquid crystal composition according to item 9, further comprising at least one compound selected from the group of compounds represented by each of general formulas (11), (12), and (13).

[Item 15] The liquid crystal composition according to item 10, further comprising at least one compound selected from the group of compounds represented by each of general formulas (11), (12), and (13).

[Item 16] The liquid crystal composition according to item 11, further comprising at least one compound selected from the group of compounds represented by each of general formulas (11), (12), and (13).

[Item 17] The liquid crystal composition according to any one of items 8 to 16, further comprising at least one optically active compound.

[Item 18] The liquid crystal composition according to any one of items 8 to 17, comprising at least one antioxidant and/or ultraviolet absorbing agent.

[Item 19] A liquid crystal display device comprising the liquid crystal composition according to any one of items 8 to 18.

Terms are used in this specification as follows. A liquid crystal compound is a generic term for a compound having liquid crystal phases such as a nematic phase and a smectic phase, and also for a compound having no liquid crystal phases but useful as a component for a liquid crystal composition. The terms of a liquid crystal compound, a liquid crystal composition, and a liquid crystal display device may be abbreviated to a compound, a composition, and a device, respectively. A liquid crystal display device is a generic term for a liquid crystal display panel and a liquid crystal display module. A maximum temperature of a nematic phase is the phase transition temperature of the nematic phase to an isotropic phase, and may simply be abbreviated to a clearing point or a maximum temperature. A minimum temperature of the nematic phase may simply be abbreviated to a minimum temperature. The compounds represented by formula (1) may be abbreviated to the compound (1). This abbreviation may also apply to the compounds represented by formula (2) and so forth. In formulas (1) to (13), the symbols B, D, E, and so forth surrounded by a hexagonal shape correspond to ring B, ring D, ring E, and so forth, respectively. The amount of a compound expressed as a percentage means a weight percentage (% by weight) based on the total weight of its composition. A plurality of the same symbols, such as rings $A^1$, $Y^1$ and B, were described in the same formulas or different formulas, and each of these may be identical or different.

The term "arbitrary" indicates that both the position and the number are arbitrary, excluding the case where the number is 0. The expression of "arbitrary A may be replaced by B, C, or D" includes a case in which arbitrary A is replaced by B, a case in which arbitrary A is replaced by C, and a case in which arbitrary A is replaced by D, and also a case in which a plurality of A are replaced by at least two of B to D. For example, alkyl in which arbitrary —$CH_2$— may be replaced by —O— or —CH=CH— includes alkyl, alkenyl, alkoxy, alkoxyalkyl, alkoxyalkenyl, alkenyloxyalkyl, and so forth. In the invention, it is undesirable that two successive —$CH_2$— are replaced by two —O— affording —O—O—. It is also undesirable that terminal —$CH_2$— in alkyl is replaced by —O—. The invention will be further explained below.

EFFECT OF THE INVENTION

The compounds of the invention have general physical properties required for compounds, stability to heat, light and so forth, a wide temperature range of liquid crystal phases, a good compatibility with other compounds, and a large dielectric anisotropy and refractive index anisotropy. The liquid crystal compositions of the invention comprise at least one of these compounds, and have a high maximum temperature of a nematic phase, a low minimum temperature of the nematic phase, a small viscosity, a large refractive index anisotropy, and a low threshold voltage. The liquid crystal display devices of the invention comprise these compositions, and have a wide temperature range usable, a short response time, a small electric power consumption, a large contrast ratio, and a low driving voltage.

DESCRIPTION OF THE EMBODIMENTS 1-1. Compounds of the Invention

The first aspect of the invention concerns the compounds represented by formula (1).

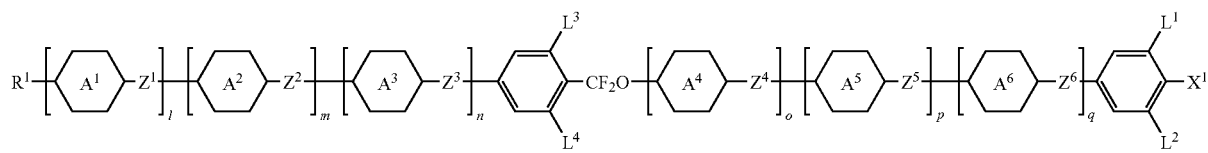

(1)

In formula (1), $R^1$ is alkyl having 1 to 20 carbons, and in the alkyl, arbitrary —$CH_2$— may be replaced by —O—, —S—, or —CH═CH—. Examples of a group in which arbitrary —$CH_2$— in $CH_3(CH_2)_3$— is replaced by —O—, —S—, or —CH═CH— are $CH_3(CH_2)_2O$—, $CH_3$—O—$(CH_2)_2$—, $CH_3$—O—$CH_2$—O—, $CH_3(CH_2)_2S$—, $CH_3$—S—$(CH_2)_2$—, $CH_3$—S—$CH_2$—S—, $CH_2$═CH—$(CH_2)_3$—, $CH_3$—CH═CH—$(CH_2)_2$—, $CH_3$—CH═CH—$CH_2O$—, and so forth.

Examples of such $R^1$ are alkyl, alkoxy, alkoxyalkyl, alkoxyalkoxy, thioalkyl, thioalkylalkoxy, alkenyl, alkenyloxy, alkenyloxyalkyl, alkoxyalkenyl, and so forth. In these groups, a straight chain is preferable to a branched chain. When $R^1$ is optically active, even the branched chain is desirable. A desirable configuration of —CH═CH— in the alkenyl depends on the position of a double bond. A trans configuration is desirable in the alkenyl having a double bond at an odd-numbered position, such as —CH═$CHCH_3$, —CH═$CHC_2H_5$, —CH═$CHC_3H_7$, —CH═$CHC_4H_9$, —$C_2H_4$CH═$CHCH_3$, and —$C_2H_4$CH═$CHC_2H_5$. A cis configuration is desirable in the alkenyl having a double bond at an even-numbered position, such as —$CH_2$CH═$CHCH_3$, —$CH_2$CH═$CHC_2H_5$, and —$CH_2$CH═$CHC_3H_7$. An alkenyl compound having a desirable configuration has a high maximum temperature or a wide temperature range of liquid crystal phases. Details are described in Mol. Cryst. Liq. Cryst., 1985, 131, 109 and Mol. Cryst. Liq. Cryst., 1985, 131, 327.

The alkyl may be a straight chain or a branched chain. Specific examples of the alkyl are —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, and —$C_{15}H_{31}$.

The alkoxy may be a straight chain or a branched chain. Specific examples of the alkoxy are —$OCH_3$, —$OC_2H_5$, —$OC_3H_7$, —$OC_4H_9$, —$OC_5H_{11}$, —$OC_6H_{13}$, and —$OC_7H_{15}$, —$OC_8H_{17}$, —$OC_9H_{19}$, —$OC_{10}H_{21}$, —$OC_{11}H_{23}$, —$OC_{12}H_{25}$, —$OC_{13}H_{27}$, and —$OC_{14}H_{29}$.

The alkoxyalkyl may be a straight chain or a branched chain. Specific examples of the alkoxyalkyl are —$CH_2OCH_3$, —$CH_2OC_2H_5$, —$CH_2OC_3H_7$, —$(CH_2)_2$—$OCH_3$, —$(CH_2)_2$—$OC_2H_5$, —$(CH_2)_2$—$OC_3H_7$, —$(CH_2)_3$—$OCH_3$, —$(CH_2)_4$—$OCH_3$, and —$(CH_2)_5$—$OCH_3$.

The alkenyl may be a straight chain or a branched chain. Specific examples of the alkenyl are —CH═$CH_2$, —CH═$CHCH_3$, —$CH_2$CH═$CH_2$, —CH═$CHC_2H_5$, —$CH_2$CH═$CHCH_3$, —$(CH_2)_2$—CH═$CH_2$, —CH═$CHC_3H_7$, —$CH_2$CH═$CHC_2H_5$, —$(CH_2)_2$—CH═$CHCH_3$, and —$(CH_2)_3$—CH═$CH_2$.

The alkenyloxy may be a straight chain or a branched chain. Specific examples of the alkenyloxy are —$OCH_2$CH═$CH_2$, —$OCH_2$CH═$CHCH_3$, and —$OCH_2$CH═$CHC_2H_5$.

Desirable $R^1$ is alkyl having 1 to 15 carbons or alkenyl having 2 to 15 carbons. Most desirable examples of $R^1$ are —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$—$C_{11}H_{23}$, —$C_{12}H_{25}$, —$C_{13}H_{27}$, —$C_{14}H_{29}$, —$C_{15}H_{31}$, —CH═$CH_2$, —CH═$CHCH_3$, —$CH_2$CH═$CH_2$, —CH═$CHC_2H_5$, —$CH_2$CH═$CHCH_3$, —$(CH_2)_2$—CH═$CH_2$, —CH═$CHC_3H_7$, —$CH_2$CH═$CHC_2H_5$, —$(CH_2)_2$—CH═$CHCH_3$, and —$(CH_2)_3$—CH═$CH_2$.

In formula (1), ring $A^1$, ring $A^2$, ring $A^3$, ring $A^4$, ring $A^5$, and ring $A^6$ are each independently 1,4-cyclohexylene (14-1), 1,3-dioxane-2,5-diyl (14-2), 1,4-phenylene (14-3), or 1,4-phenylene in which arbitrary hydrogen is replaced by halogen. Examples of 1,4-phenylene in which arbitrary hydrogen is replaced by halogen are represented by the following formulas (14-4) to (14-20). Desirable examples are groups represented by formulas (14-4) to (14-9).

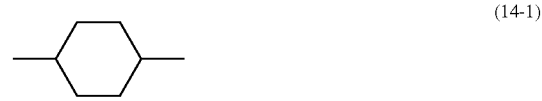

(14-1)

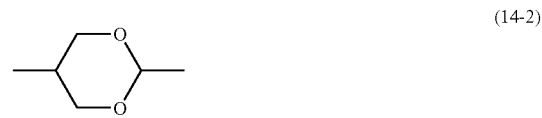

(14-2)

(14-3)

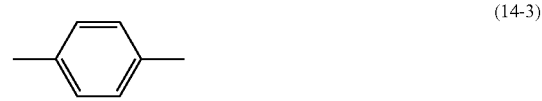

(14-4)

(14-5)

(14-6)

(14-7)

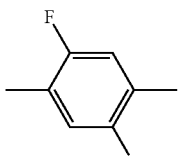 (14-8)

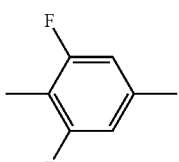 (14-9)

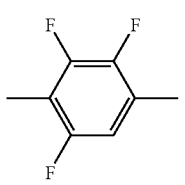 (14-10)

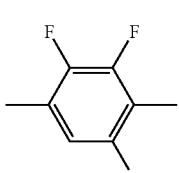 (14-11)

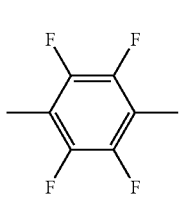 (14-12)

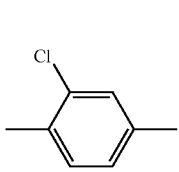 (14-13)

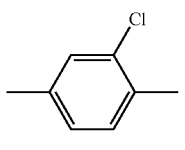 (14-14)

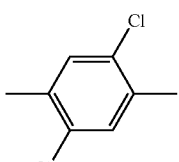 (14-15)

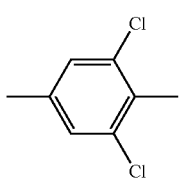 (14-16)

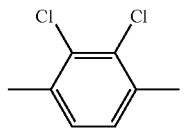 (14-17)

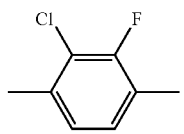 (14-18)

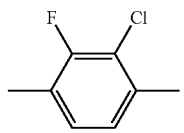 (14-19)

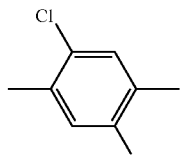 (14-20)

Desirable examples of ring $A^1$, ring $A^2$, ring $A^3$, ring $A^4$, ring $A^5$, and ring $A^6$ are 1,4-cyclohexylene (14-1), 1,3-dioxane-2,5-diyl (14-2), 1,4-phenylene (14-3), 2-fluoro-1,4-phenylene (14-4) and (14-5), 2,3-difluoro-1,4-phenylene (14-6), 2,5-difluoro-1,4-phenylene (14-8), and 2,6-difluoro-1,4-phenylene (14-7) and (14-9).

Most desirable examples of ring $A^1$, ring $A^2$, ring $A^3$, ring $A^4$, ring $A^5$, and ring $A^6$ are 1,4-cyclohexylene, 1,3-dioxane-2,5-diyl, 1,4-phenylene, 2-fluoro-1,4-phenylene, and 2,6-difluoro-1,4-phenylene.

In formula (1), $Z^1$, $Z^2$, $Z^3$, $Z^4$, $Z^5$, and $Z^6$ are each independently a single bond, —CH$_2$CH$_2$—, —CH=CH—, —C≡C—, —COO—, —OCO—, —CF$_2$O—, —OCF$_2$—, —CH$_2$O—, —OCH$_2$—, —CF=CF—, —(CH$_2$)$_4$—, —(CH$_2$)$_2$—CF$_2$O—, —(CH$_2$)$_2$—OCF$_2$—, —CF$_2$O—(CH$_2$)$_2$—, —OCF$_2$(CH$_2$)$_2$—, —CH=CH—(CH$_2$)$_2$—, or —(CH$_2$)$_2$—CH=CH—.

Desirable examples of $Z^1$, $Z^2$, $Z^3$, $Z^4$, $Z^5$, and $Z^6$ are a single bond, —CH$_2$CH$_2$—, —CH=CH—, —C≡C—, —COO—, —CF$_2$O—, —CH$_2$O—, or —OCH$_2$—. In these bonds, trans is preferable to cis in the configuration with regard to a double bond of bonding groups, such as —CH=CH—, —CF=CF—, —CH=CH—(CH$_2$)$_2$—, and —(CH$_2$)$_2$—CH=CH—. The most desirable $Z^1$, $Z^2$, $Z^3$, $Z^4$, $Z^5$, and $Z^6$ are a single bond.

In formula (1), $L^1$, $L^2$, $L^3$, and $L^4$ are each independently hydrogen or halogen. Desirable $L^1$, $L^2$, $L^3$, and $L^4$ are each independently hydrogen or fluorine.

In formula (1), $X^1$ is hydrogen, halogen, —C≡N, —N=C=S, —SF$_5$, or alkyl having 1 to 10 carbons, and in the alkyl, arbitrary —CH$_2$— may be replaced by —O—, —S—, or —CH=CH— and arbitrary hydrogen may be replaced by halogen.

Specific examples of alkyl in which arbitrary hydrogen is replaced by halogen are —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F, and —(CF$_2$)$_5$—F.

Specific examples of alkoxy in which arbitrary hydrogen is replaced by halogen are —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, and —O—(CF$_2$)$_5$—F.

Specific examples of alkenyl in which arbitrary hydrogen is replaced by halogen are —CH=CHF, —CH=CF$_2$, —CF=CHF, —CH=CHCH$_2$F, —CH=CHCF$_3$, —(CH$_2$)$_2$—CH=CF$_2$, —CH$_2$CH=CHCF$_3$, and —CH=CHCF$_2$CF$_3$.

Specific examples of X$^1$ are hydrogen, fluorine, chlorine, —C≡N, —N=C=S, —SF$_5$, —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F, —(CF$_2$)$_5$—F, —OCH$_3$, —OC$_2$H$_5$, —OC$_3$H$_7$, —OC$_4$H$_9$, —OC$_5$H$_{11}$, —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, —O—(CF$_2$)$_5$—F, —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$, —(CH$_2$)$_3$—CH=CH$_2$, —CH=CHF, —CH=CF$_2$, —CF=CHF, —CH=CHCH$_2$F, —CH=CHCF$_3$, —(CH$_2$)$_2$—CH=CF$_2$, —CH$_2$CH=CHCF$_3$, and —CH=CHCF$_2$CF$_3$.

Desirable examples of X$^1$ are fluorine, chlorine, —C≡N, —CF$_3$, —CHF$_2$, —CH$_2$F, —OCF$_3$, —OCHF$_2$, and —OCH$_2$F. The most desirable examples of X$^1$ are fluorine and —OCF$_3$.

In formula (1), l, m, n, o, p, and q are each independently 0 or 1, and l+m+n+o+p+q=3. Desirable combinations of l, m, n, o, p, and q are (l=o=p=1 and m=n=q=0), (l=m=o=1 and n=p=q=0), and (l=m=n=1 and o=p=q=0).

1-2. Properties of the Compounds of the Invention and Controlling Method Thereof The compound (1) of the invention will be further explained in detail. The compound (1) is a five-ring liquid crystal compound having a CF$_2$O bonding group. The compound is highly stable physically and chemically under the condition that a device is usually used, and has a good compatibility with other liquid crystal compounds. A composition comprising the compound is stable under the condition that a device is usually used. The compound does not deposit as crystals (or a smectic phase) even when the composition is stored at low temperature. The compound is the five-ring compound and has a wide temperature range of liquid crystal phases and a high clearing point. Consequently, the compound can widen a temperature range of a nematic phase in its composition, and can be used as a display device in a wide temperature range. Further, the compound has a large refractive index anisotropy. Therefore, it is suitable for preparing a liquid crystal display device which can respond at high speed. Further, the compound is useful as a component for reducing the threshold voltage of the composition because of a large dielectric anisotropy.

Physical properties, such as a clearing point, refractive index anisotropy, and dielectric anisotropy, can arbitrarily be adjusted by appropriately selecting the combination of l, m, n, o, p, and q, kind of rings A$^1$ to A$^6$, the left-terminal group R$^1$, groups on the rightmost benzene ring and their substituted positions (L$^1$, L$^2$, and X$^1$), or bonding groups Z$^1$ to Z$^6$ in the compound (1). Effects of the combination of l, m, n, o, p, and q, and the kind of rings A$^1$ to A$^6$, left-terminal group R$^1$, right-terminal group X$^1$, bonding groups Z$^1$ to Z$^6$, and L$^1$ and L$^2$ on the physical properties of the compound (1) will be explained below.

When the combination of l, m, n, o, p, and q is (l=m=n=1 and o=p=q=0), the temperature range of liquid crystal phases is wide and the clearing point is high. When the combination is (l=m=o=1 and n=p=q=0), the compatibility with other compounds is high and the dielectric anisotropy is large. When the combination is (l=o=p=1 and m=n=q=0), the dielectric anisotropy is large.

When all of rings A$^1$ to A$^6$ are 1,4-phenylene and the combination is (l=m=n=1 and o=p=q=0), chemical stability is excellent and the refractive index anisotropy is especially large. When all of rings A$^1$ to A$^6$ are 1,4-phenylene and the combination is (l=m=o=1 and n=p=q=0), the compatibility with other compounds is high and the dielectric anisotropy is especially large. When ring A$^1$ is 1,4-cyclohexylene and rings A$^2$ and A$^3$ are 1,4-phenylene or 1,4-phenylene in which arbitrary hydrogen is replaced by halogen, and the combination is (l=m=n=1 and o=p=q=0), the clearing point is high, the refractive index anisotropy is large, and the compatibility with other compounds is high. When ring A$^1$ is 1,3-dioxane-2,5-diyl and rings A$^2$ and A$^3$ are 1,4-phenylene or 1,4-phenylene in which arbitrary hydrogen is replaced by halogen, and the combination is (l=m=n=1 and o=p=q=0), the clearing point is high and the dielectric anisotropy is large. When ring A$^1$ is 1,3-dioxane-2,5-diyl and rings A$^2$ and A$^4$ are 1,4-phenylene or 1,4-phenylene in which arbitrary hydrogen is replaced by halogen, and the combination is (l=m=o=1 and n=p=q=0), the dielectric anisotropy is especially large and the compatibility with other compounds is high.

When R$^1$ is a straight chain, the temperature range of liquid crystal phases is wide and the viscosity is small. When R$^1$ is a branched chain, the compatibility with other liquid crystal compounds is good. A compound in which R$^1$ is an optically active group is useful as a chiral doping agent. A reverse twisted domain which may occur in a device can be prevented by adding the compound to the composition. A compound in which R$^1$ is not an optically active group is useful as a component of the composition. When R$^1$ is alkenyl, a desirable configuration depends on the position of the double bond. An alkenyl compound having a desirable configuration has a high maximum temperature or a wide temperature range of liquid crystal phases.

When bonding groups Z$^1$, Z$^2$, Z$^3$, Z$^4$, Z$^5$, and Z$^6$ are a single bond, —CH$_2$CH$_2$—, —CH=CH—, —CF$_2$O—, —OCF$_2$—, —CH$_2$O—, —OCH$_2$—, —CF=CF—, —(CH$_2$)$_3$—O—, —O—(CH$_2$)$_3$—, —(CH$_2$)$_2$—CF$_2$O—, —OCF$_2$—(CH$_2$)$_2$—, or —(CH$_2$)$_4$—, the viscosity is small. When the bonding groups are a single bond, —(CH$_2$)$_2$—, —CF$_2$O—, —OCF$_2$—, or —CH=CH—, the viscosity is smaller. When the bonding groups are —CH=CH—, the temperature range of liquid crystal phases is wide, and an elastic constant ratio K$_{33}$/K$_{11}$ is large, wherein K$_{33}$ stands for a bend elastic constant and K$_{11}$ stands for a splay elastic constant. When the bonding groups are the optical anisotropy is large. When Z$^1$, Z$^2$, Z$^3$, Z$^4$, Z$^5$, and Z$^6$ are a single bond, —(CH$_2$)$_2$—, —CH$_2$O—, —CF$_2$O—, —OCF$_2$—, or —(CH$_2$)$_4$—, the chemical stability is comparatively secured, and deterioration is comparatively hard to occur.

When the right-terminal group X$^1$ is fluorine, chlorine, —C≡N, —N=C=S, —SF$_5$, —CF$_3$, —CHF$_2$, —CH$_2$F, —OCF$_3$, —OCHF$_2$, or —OCH$_2$F, the dielectric anisotropy is large. When X$^1$ is —N=C=S, or alkenyl, the optical anisotropy is large. When X$^1$ is fluorine, —OCF$_3$, or alkyl, the chemical stability is secured.

When both of $L^1$ and $L^2$ are fluorine and $X^1$ is fluorine, chlorine, —C≡N, —N=C=S, —SF$_5$, —CF$_3$, —CHF$_2$, —CH$_2$F, —OCF$_3$, —OCHF$_2$, or —OCH$_2$F, the dielectric anisotropy is large. When $L^1$ is fluorine and $X^1$ is —OCF$_3$, or when both of $L^1$ and $L^2$ are fluorine and $X^1$ is —OCF$_3$, or when all of $L^1$, $L^2$, and $X^1$ are fluorine, the dielectric anisotropy value is large and the temperature range of liquid crystal phases is wide, and further, the chemical stability is secured and the deterioration is hard to occur.

As described above, a compound having intended physical properties can be obtained by suitably selecting the kinds of ring structures, terminal groups, bonding groups, and so forth. Accordingly, the compound (1) are useful as components of compositions used for devices, such as PC, TN, STN, ECB, OCB, IPS, and VA.

1-3. Specific Examples of the Compound (1)

Desirable examples of the compound (1) are represented by formulas (1-5) to (1-8) described in Item 5. More desirable examples are represented by formulas (1-9) to (1-19) described in Item 6. Still more desirable examples are represented by formulas (1-20) to (1-41) described in Item 7.

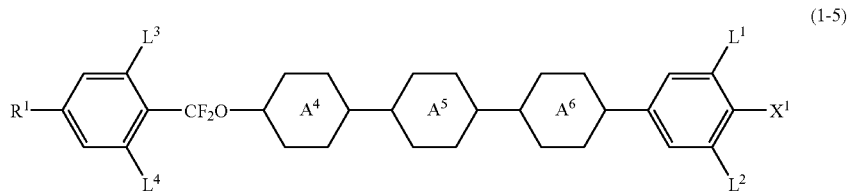

(1-5)

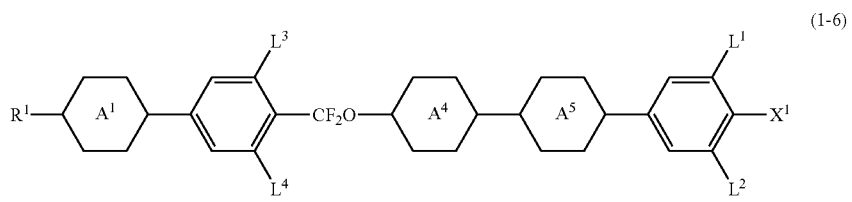

(1-6)

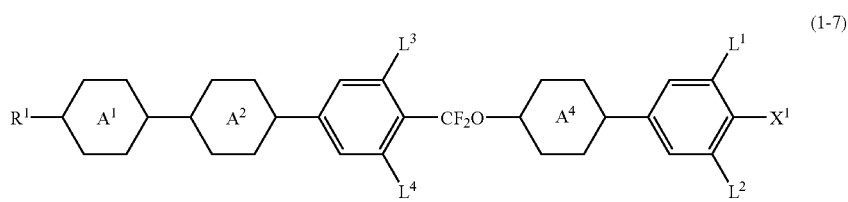

(1-7)

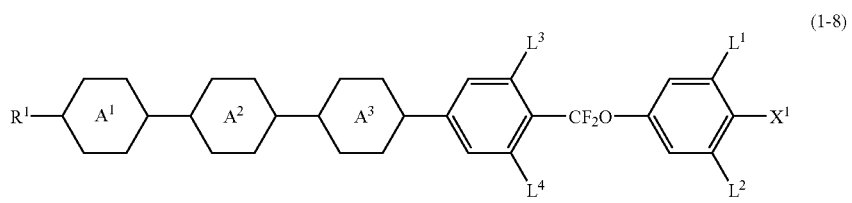

(1-8)

In these formulas, $R^1$ is alkyl having 1 to 15 carbons or alkenyl having 2 to 15 carbons; ring $A^1$, ring $A^2$, ring $A^3$, ring $A^4$, ring $A^5$, and ring $A^6$ are each independently 1,4-cyclohexylene, 1,3-dioxane-2,5-diyl, 1,4-phenylene, or 1,4-phenylene in which arbitrary hydrogen is replaced by fluorine; $L^1$, $L^2$, $L^3$, and $L^4$ are each independently hydrogen or fluorine; and $X^1$ is fluorine, chlorine, —C≡N, —CF$_3$, —CHF$_2$, —CH$_2$F, —OCF$_3$, —OCHF$_2$, or —OCH$_2$F.

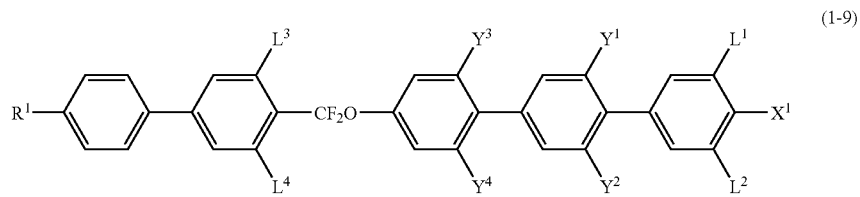

(1-9)

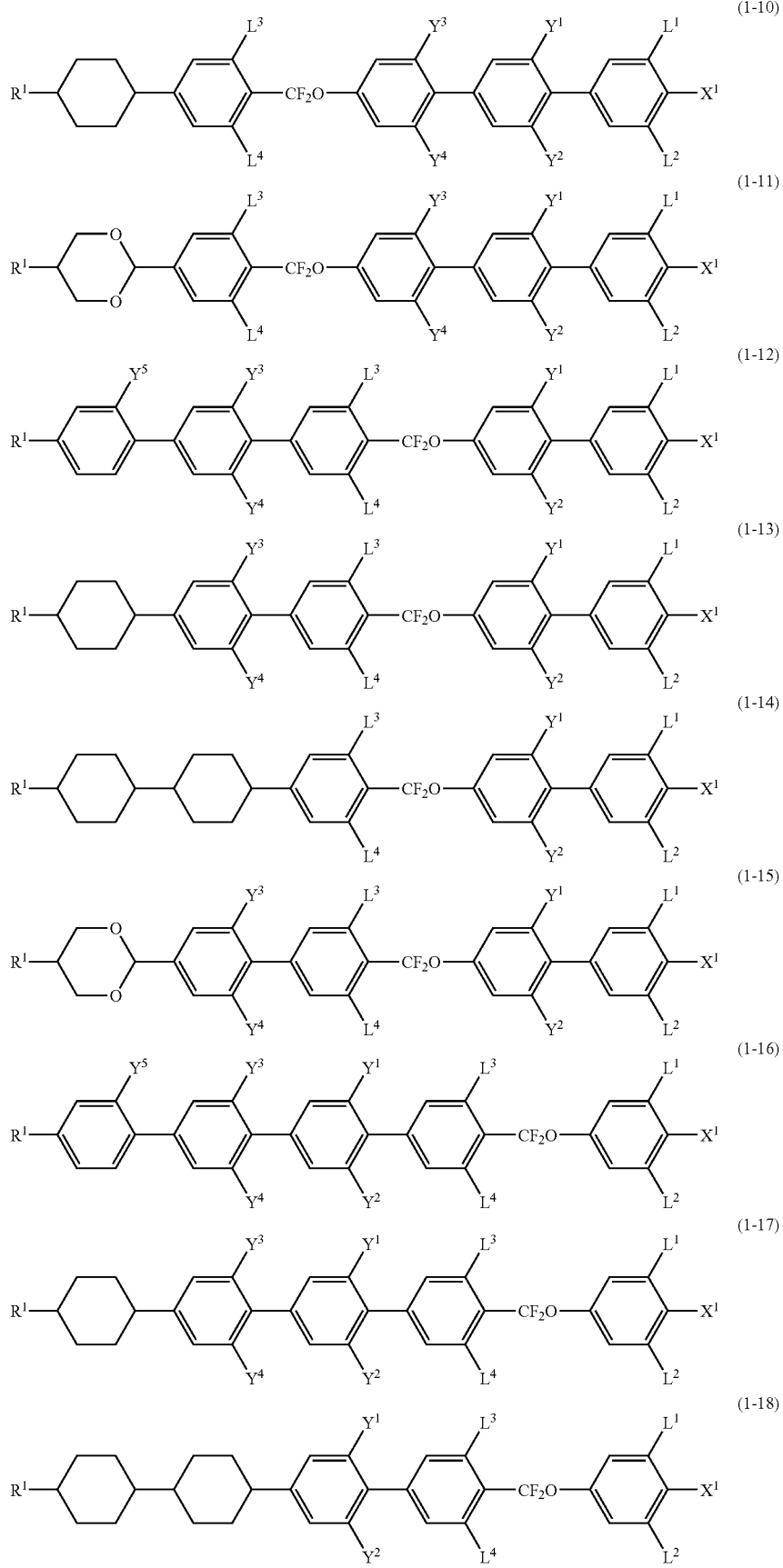

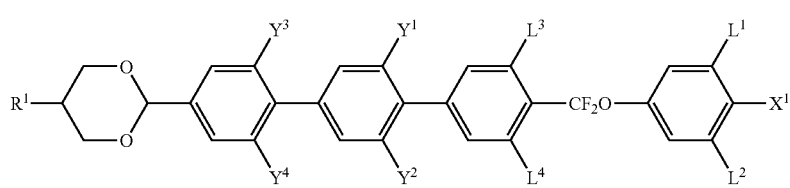
(1-19)
(In these formulas, $R^1$ is alkyl having 1 to 15 carbons; $L^1$, $L^2$, $L^3$, $L^4$, $Y^1$, $Y^2$, $Y^3$, $Y^4$, and $Y^5$ are each independently hydrogen or fluorine; and $X^1$ is fluorine or —$OCF_3$.)
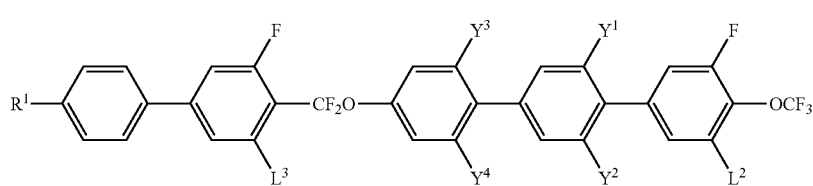
(1-20)
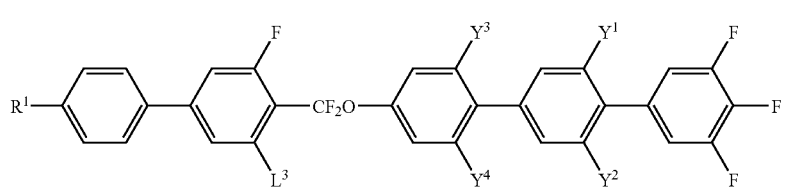
(1-21)
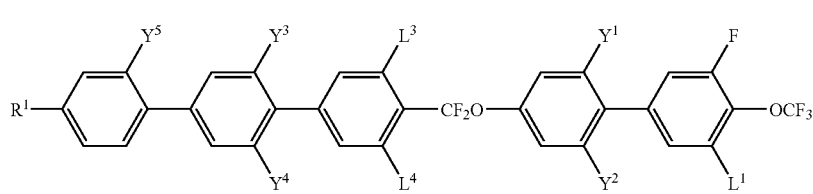
(1-22)
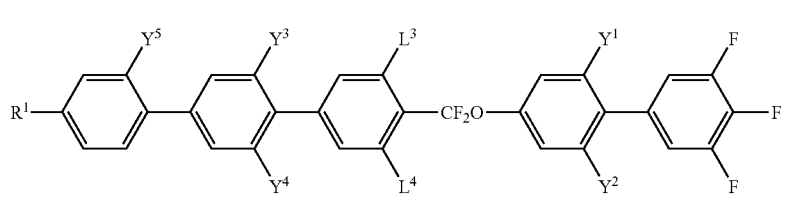
(1-23)
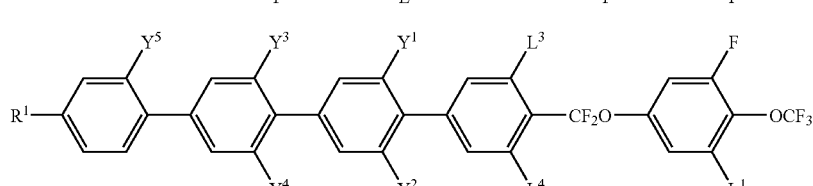
(1-24)
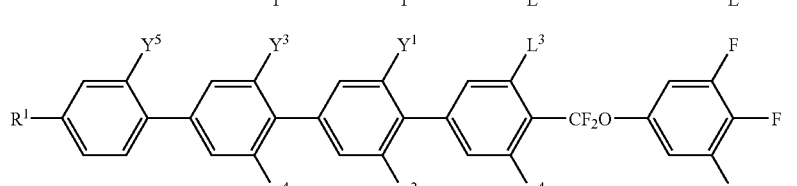
(1-25)
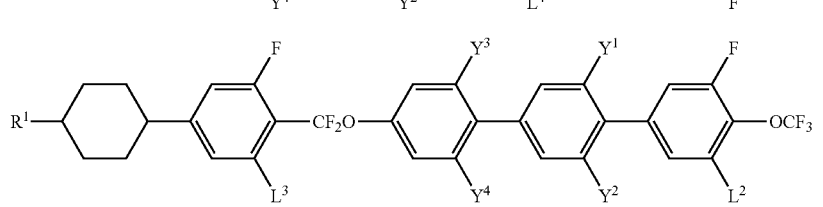
(1-26)

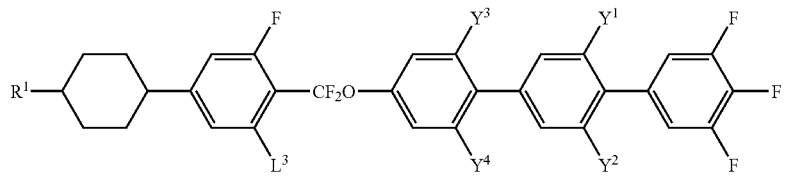 (1-27)
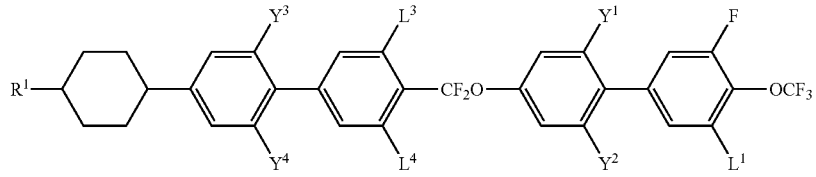 (1-28)
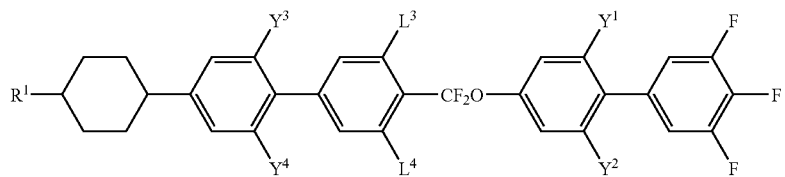 (1-29)
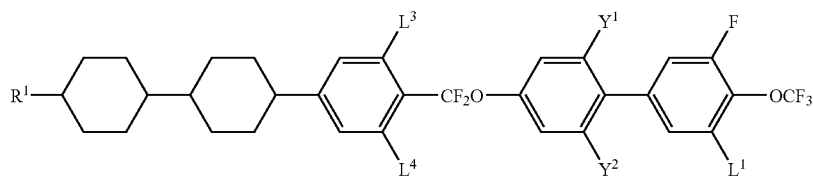 (1-30)
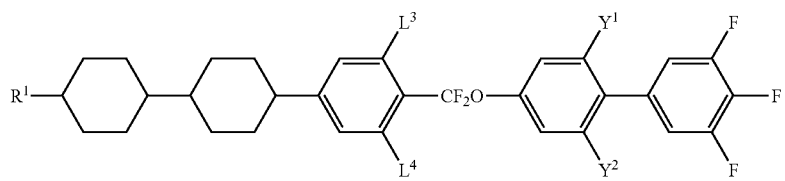 (1-31)
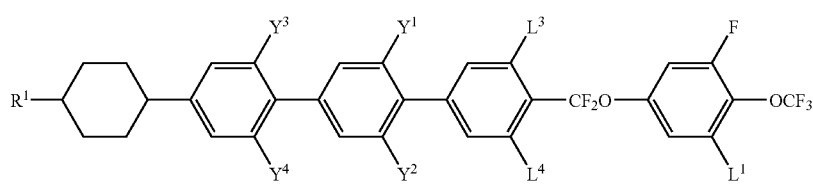 (1-32)
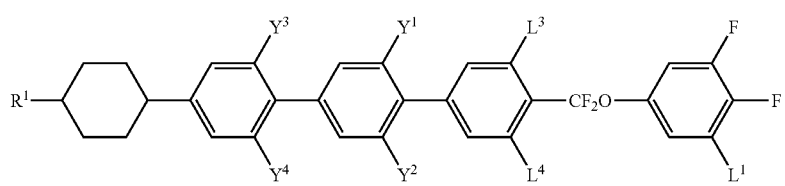 (1-33)
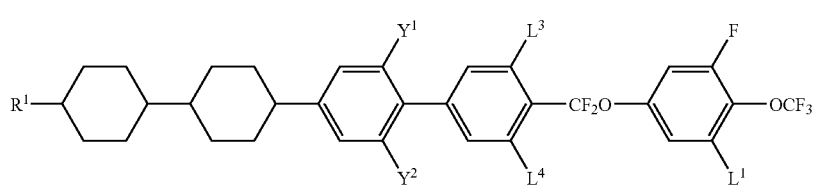 (1-34)
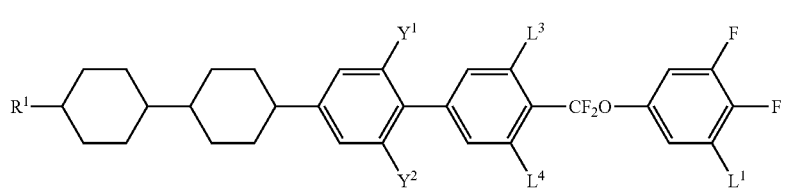 (1-35)

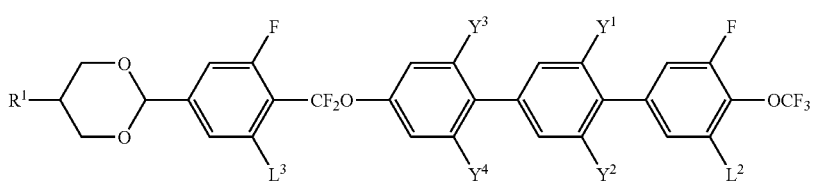
(1-36)

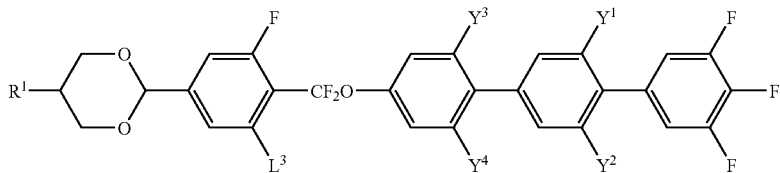
(1-37)

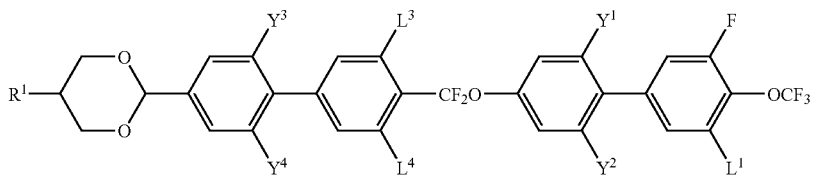
(1-38)

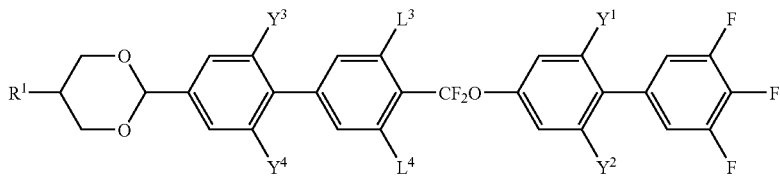
(1-39)

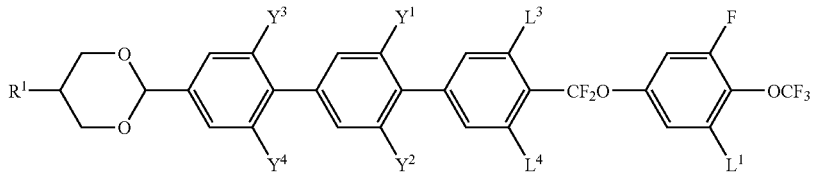
(1-40)

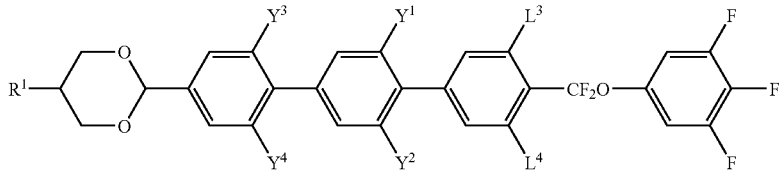
(1-41)

(In these formulas, $R^1$ is alkyl having 1 to 15 carbons; and $L^1$, $L^2$, $L^3$, $L^4$, $Y^1$, $Y^2$, $Y^3$, $Y^4$, and $Y^5$ are each independently hydrogen or fluorine.)

1-4. Synthesis of the Compound (1)

Next, the synthesis of the compound (1) will be explained. The compound (1) can be synthesized by suitably combining techniques in synthetic organic chemistry. Methods for introducing objective terminal groups, rings, and bonding groups into starting materials are described in ORGANIC SYNTHESES (John Wiley & Sons, Inc), ORGANIC REACTIONS (John Wiley & Sons, Inc), COMPREHENSIVE ORGANIC SYNTHESIS (Pergamon Press), NEW EXPERIMENTAL CHEMISTRY COURSE (Shin Jikken Kagaku Kouza, in Japanese title) (Maruzen), and so forth.

1-4-1. Methods for Forming Bonding Groups $Z^1$ to $Z^6$

One example of methods for forming bonding groups $Z^1$ to $Z^6$ in the compound (1) is as shown in the following scheme. In the scheme, $MSG^1$ or $MSG^2$ is a monovalent organic group having at least one ring. A plurality of $MSG^1$ (or $MSG^2$) used in the scheme may be the same or different. The compounds (1A) to (1J) correspond to the compound (1).

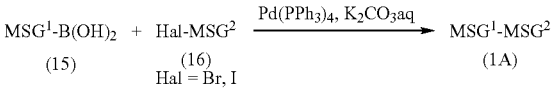

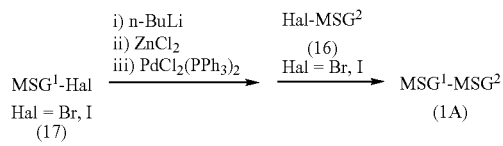

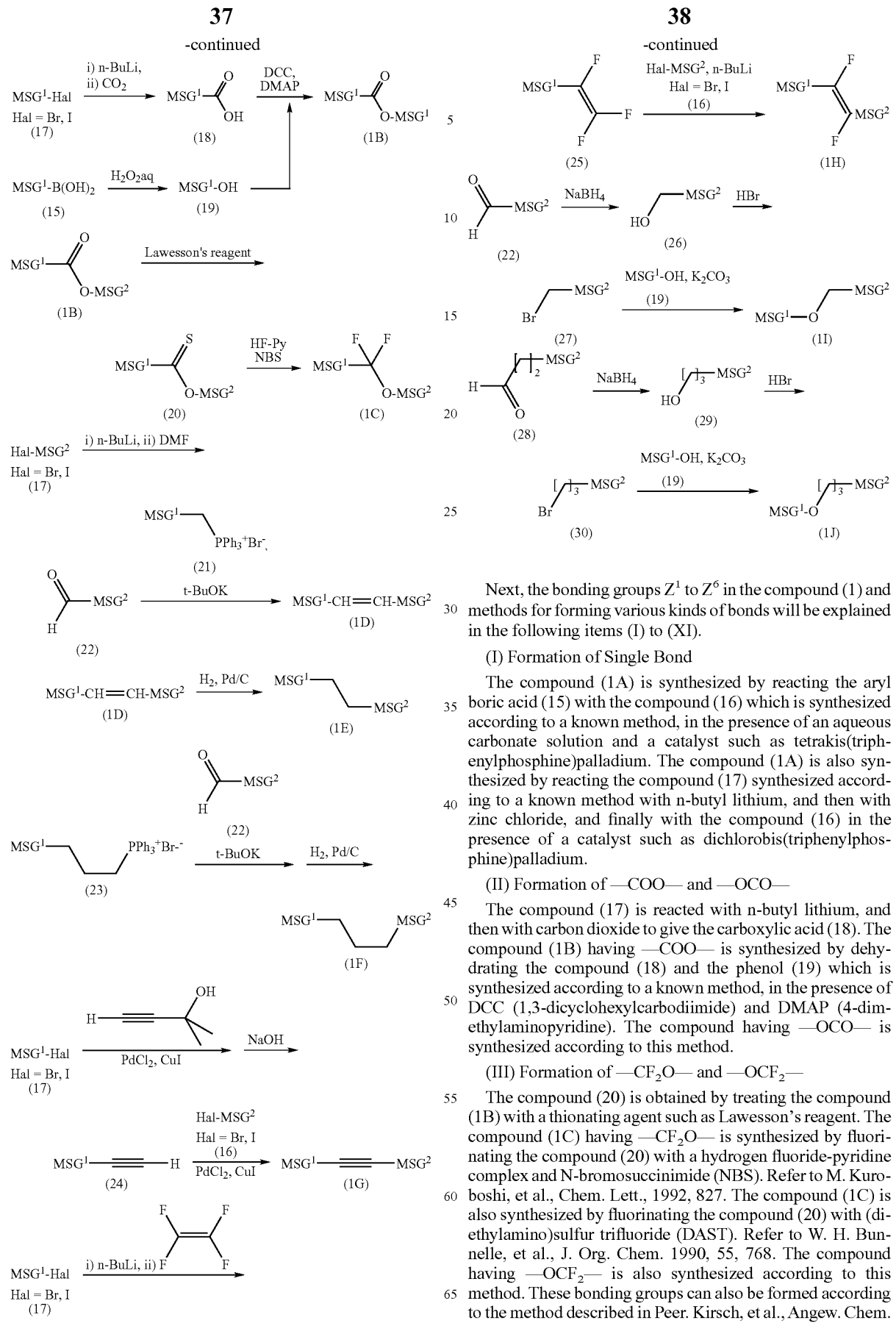

Next, the bonding groups $Z^1$ to $Z^6$ in the compound (1) and methods for forming various kinds of bonds will be explained in the following items (I) to (XI).

(I) Formation of Single Bond

The compound (1A) is synthesized by reacting the aryl boric acid (15) with the compound (16) which is synthesized according to a known method, in the presence of an aqueous carbonate solution and a catalyst such as tetrakis(triphenylphosphine)palladium. The compound (1A) is also synthesized by reacting the compound (17) synthesized according to a known method with n-butyl lithium, and then with zinc chloride, and finally with the compound (16) in the presence of a catalyst such as dichlorobis(triphenylphosphine)palladium.

(II) Formation of —COO— and —OCO—

The compound (17) is reacted with n-butyl lithium, and then with carbon dioxide to give the carboxylic acid (18). The compound (1B) having —COO— is synthesized by dehydrating the compound (18) and the phenol (19) which is synthesized according to a known method, in the presence of DCC (1,3-dicyclohexylcarbodiimide) and DMAP (4-dimethylaminopyridine). The compound having —OCO— is synthesized according to this method.

(III) Formation of —CF$_2$O— and —OCF$_2$—

The compound (20) is obtained by treating the compound (1B) with a thionating agent such as Lawesson's reagent. The compound (1C) having —CF$_2$O— is synthesized by fluorinating the compound (20) with a hydrogen fluoride-pyridine complex and N-bromosuccinimide (NBS). Refer to M. Kuroboshi, et al., Chem. Lett., 1992, 827. The compound (1C) is also synthesized by fluorinating the compound (20) with (diethylamino)sulfur trifluoride (DAST). Refer to W. H. Bunnelle, et al., J. Org. Chem. 1990, 55, 768. The compound having —OCF$_2$— is also synthesized according to this method. These bonding groups can also be formed according to the method described in Peer. Kirsch, et al., Angew. Chem. Int. Ed. 2001, 40, 1480.

(IV) Formation of —CH=CH—

The compound (17) is treated with n-butyl lithium and then reacted with a formamide such as N,N-dimethylformamide (DMF) to give the aldehyde (22). The compound (1D) is synthesized by reacting the aldehyde (22) with phosphorus ylide generated by treating the phosphonium salt (21) which is synthesized according to a known method, with a base such as potassium tert-butoxide. Since a cis isomer may be formed depending on reaction conditions, the cis isomer is isomerized to a trans isomer according to a known method as required.

(V) Formation of —(CH$_2$)$_2$—

The compound (1E) is synthesized by hydrogenating the compound (1D) in the presence of a catalyst such as palladium on carbon.

(VI) Formation of —(CH$_2$)$_4$—

The compound having —(CH$_2$)$_2$—CH=CH— is obtained according to the method described in item (IV) using the phosphonium salt (23) instead of the phosphonium salt (21). The compound (1F) is synthesized by catalytic hydrogenation of the compound obtained.

(VII) Formation of —C≡C—

The compound (24) is obtained by reacting the compound (17) with 2-methyl-3-butyne-2-ol in the presence of a catalyst of dithloropalladium and copper halide, and then deprotecting the resulting product under a basic condition. The compound (1G) is synthesized by reacting the compound (24) with the compound (16) in the presence of a catalyst of dichlorobis(triphenylphosphine)palladium and copper halide.

(VIII) Formation of —CF=CF—

The compound (17) is treated with n-butyl lithium, and then reacted with tetrafluoroethylene to give the compound (25). The compound (1H) is synthesized by treating the compound (16) with n-butyl lithium, and then reacting the resulting product with the compound (25).

(IX) Formation of —CH$_2$O— or —OCH$_2$—

The compound (26) is obtained by reducing the compound (22) with a reducing agent such as sodium borohydride. The product is halogenated with hydrobromic acid or the like to give the compound (27). The compound (1I) is synthesized by reacting the compound (27) with the compound (19) in the presence of potassium carbonate or the like.

(X) Formation of —(CH$_2$)$_3$O— or —O(CH$_2$)$_3$—

The compound (1J) is synthesized according to a method similar to that described in the preceding item (IX), using the compound (28) instead of the compound (22).

1-4-2. Methods for Synthesizing Rings A$^1$ to A$^6$

Starting materials are commercially available or synthetic methods thereof are well known with regard to rings, such as 1,4-cyclohexylene, 1,3-dioxane-2,5-diyl, 1,4-phenylene, 2-fluoro-1,4-phenylene, 2,3-difluoro-1,4-phenylene, 2,5-difluoro-1,4-phenylene, 2,6-difluoro-1,4-phenylene, and 2,3,5,6-tetrafluoro-1,4-phenylene.

1-4-3-1. Methods for Synthesizing the Compound (1)

There are a plurality of methods for synthesizing compounds represented by formula (1) and examples thereof are shown here. The ester derivative (33) can be derived by the dehydration condensation of the carboxylic acid derivative (31) and the alcohol derivative (32) in the presence of DCC, DMAP or the like, and then the ester derivative (33) is converted into the thion-O-ester derivative (34) by treatment with a thionating agent such as Lawesson's reagent. The compound (I) can be derived by fluorinating the derivative (34) with a hydrogen fluoride-pyridine complex and NBS.

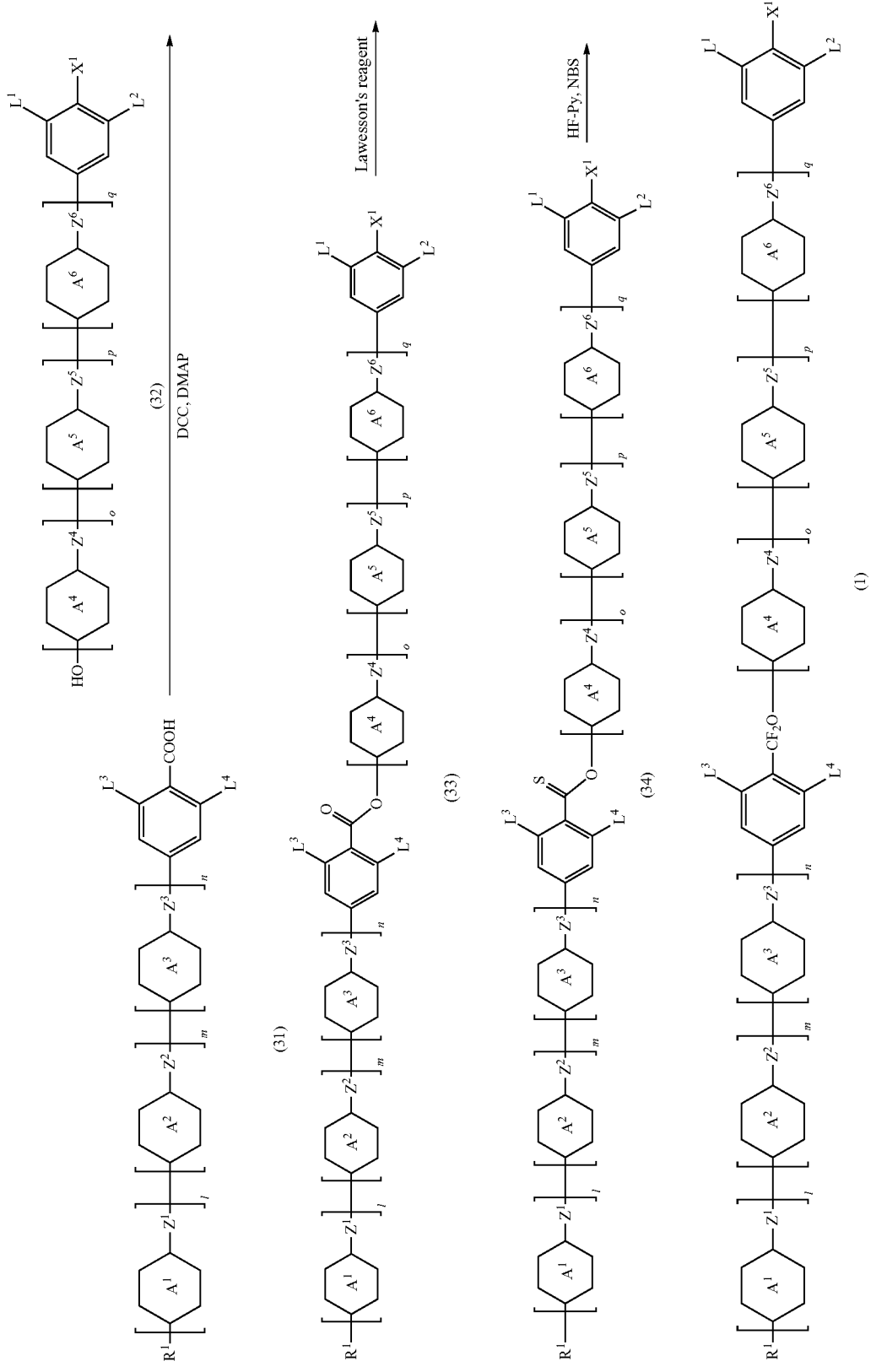

(In these formulas, rings $A^1$ to $A^6$, $Z^1$ to $Z^6$, $L^1$ to $L^4$, $R^1$, $X^1$, l, m, n, o, p, and q have the meanings identical to those described in Item 1.)

In the compounds represented by formula (1), when the subscripts are the combination (l=m=n=1 and o=p=q=0), or when o=1 and ring $A^4$ is 1,4-phenylene or 1,4-phenylene in which arbitrary hydrogen is replaced by fluorine, such compounds can also be synthesized according to the following two methods.

The bromodifluoromethane derivative (36) is obtained by reacting the compound (35) with n-butyl lithium and then with dibromodifluoromethane according to the method described in U.S. Pat. No. 6,231,785 B1. The compound (1) can be synthesized by reacting the bromodifluoromethane derivative (36) with the phenol derivative (37) in the presence of a base such as potassium carbonate.

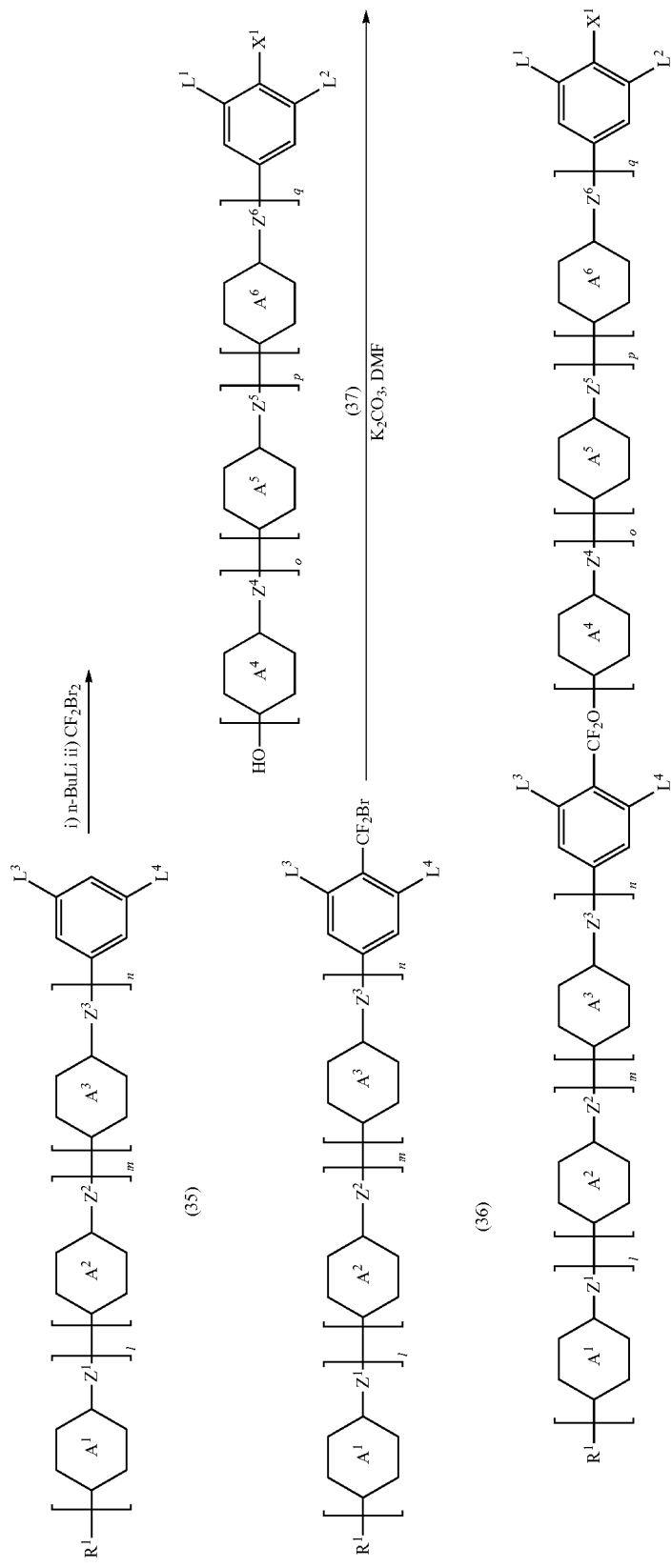

(In these formulas, ring $A^4$ is 1,4-phenylene or 1,4-phenylene in which arbitrary hydrogen is replaced by fluorine, and ring $A^1$, ring $A^2$, ring $A^3$, ring $A^5$, ring $A^6$, $Z^1$ to $Z^6$, $L^1$ to $L^4$, $R^1$, $X^1$, l, m, n, o, p, and q have the meanings identical to those described in Item 1.)

The dithianilium salt (38) is obtained by reacting the carboxylic acid derivative (31) with alkanedithiol and trifluoromethanesulfonic acid according to the method described in P. Kirsch, et al., Angew. Chem. Int. Ed., 2001, 40, 1480. The compound (1) can be obtained by reacting the phenol derivative (37) with the dithianilium salt (38), and then reacting with $Et_3N.3HF$, and with bromine.

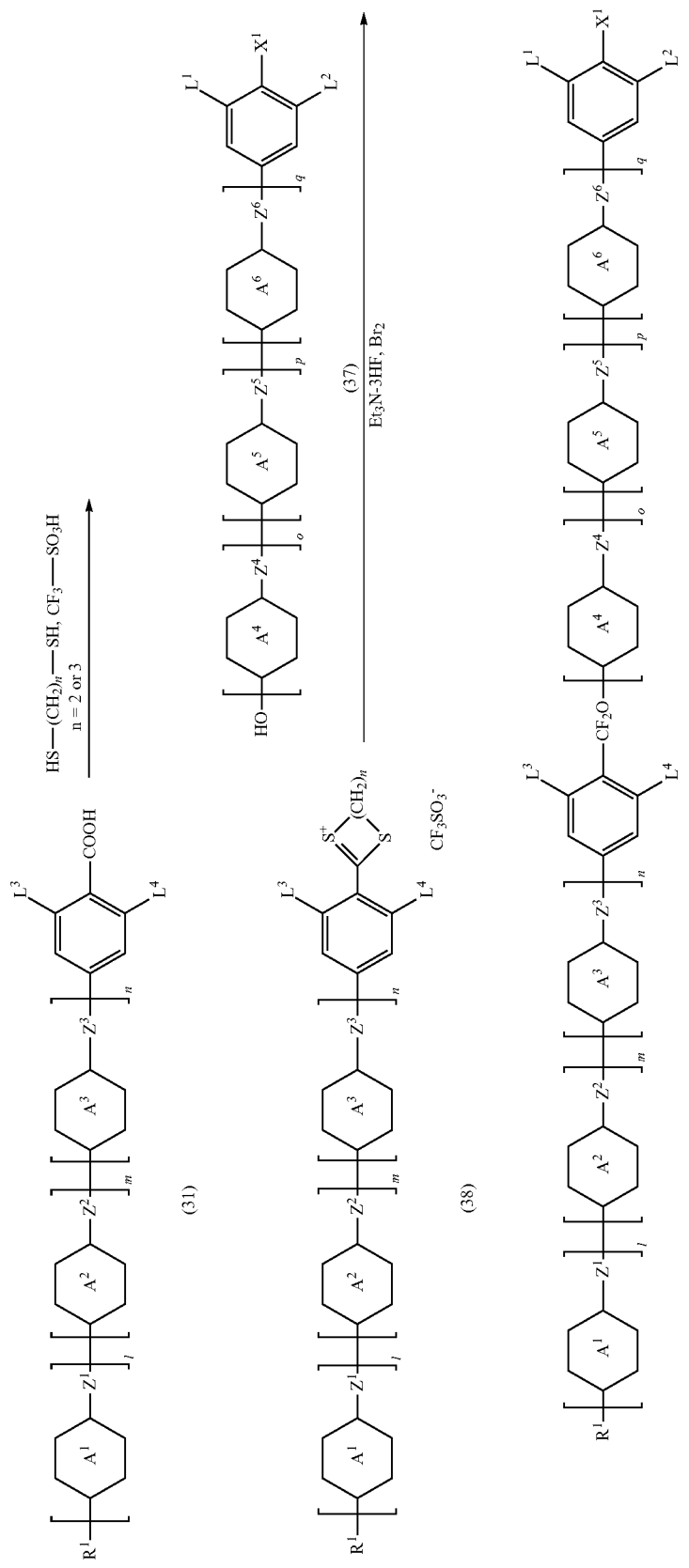

In these formulas, ring $A^4$ is 1,4-phenylene or 1,4-phenylene in which arbitrary hydrogen is replaced by fluorine, and ring $A^1$, ring $A^2$, ring $A^3$, ring $A^5$, ring $A^6$, $Z^1$ to $Z^6$, $L^1$ to $L^4$, $R^1$, $X^1$, l, m, n, o, p, and q have the meanings identical to those described in Item 1.

1-4-3-2. Method for Synthesizing the Compound (1) Having 1,3-dioxane-2,5-diyl as Ring Structure The compound (1) having 1,3-dioxane-2,5-diyl as a ring structure can be synthesized, for example, according to the following method. The intermediate (41) having a dioxane ring is synthesized by the action of an aldehyde derivative (40) on a propanediol derivative (39) in the presence of an acid catalyst such as p-toluenesulfonic acid. The object can be derived by using the intermediate (41) instead of the compound (35) according to the method for synthesizing the compound (1) described above.

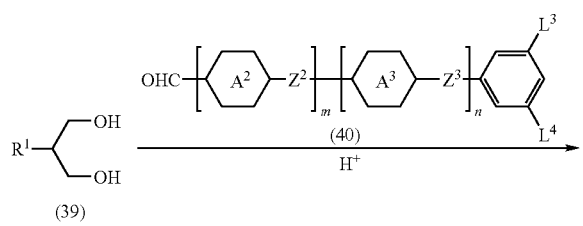

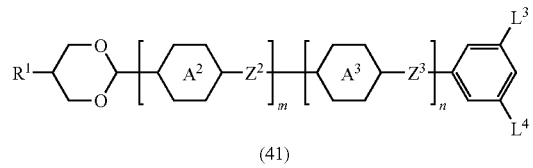

(In these formulas, ring $A^2$, ring $A^3$, $Z^2$, $Z^3$, $L^3$, $L^4$, $R^1$, m, and n have the meanings identical to those described in Item 1.)

In the compound (1), when ring $A^2$ or ring $A^3$ is 1,3-dioxane-2,5-diyl, such a compound is synthesized according to the following method. The diethyl malonate derivative (43) is synthesized by the action of the bromide (42) on diethyl malonate in the presence of sodium ethoxide, and then converted into the propanediol derivative (44) by reduction. The object is derived by constructing a dioxane ring by a method similar to that described above.

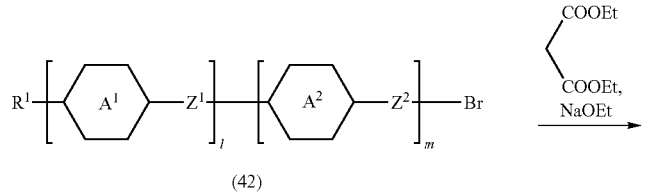

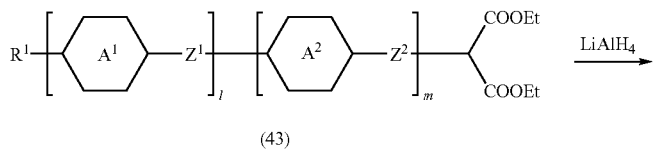

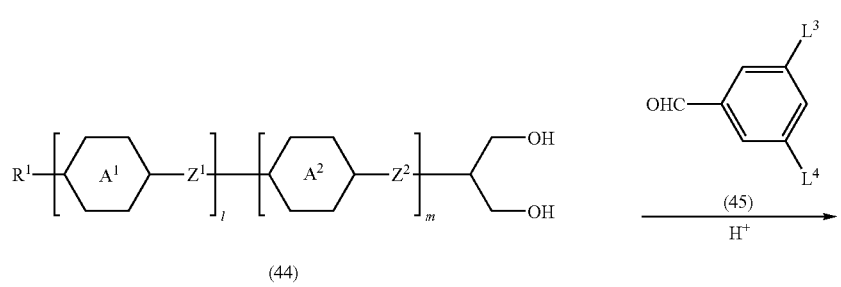

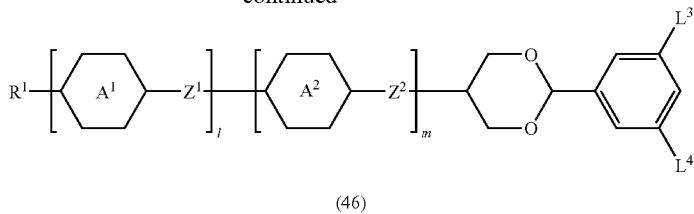

(46)

In these formulas, ring $A^1$, ring $A^2$, $Z^1$, $Z^2$, $L^3$, $L^4$, $R^1$, l, and m have the meanings identical to those described in Item 1.

1-4-3-3. Method for Synthesizing Phenol Derivative (37) as Synthetic Raw Material The phenol derivative (37) which is a synthetic raw material of the compound (1) is synthesized, for example, according to the following method. In the case of o=p=q=0 in formula (37), the objective phenol derivative (37-1) can easily be produced by the peracetic acid-oxidation of a boronic ester derivative obtained by the action of trialkylborate on a Grignard reagent prepared from the bromobenzene derivative (47) (refer to R. L. Kidwell, et al., ORGANIC SYNTHESES, Vol. 5, p. 918 (1973)), or by oxidizing, with peracetic acid, the boronic acid derivative (48) obtained easily by the acid hydrolysis of a boronic acid ester.

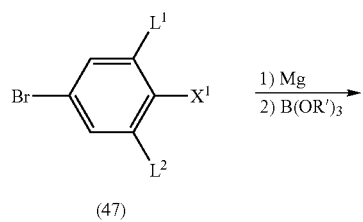

(47)

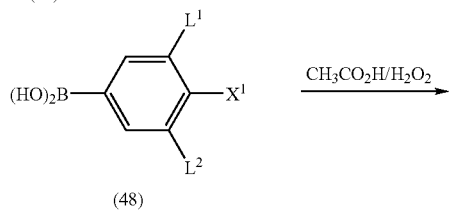

(48)

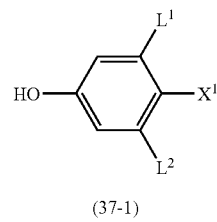

(37-1)

(In these Formulas, $L^1$, $L^2$, and $X^1$ have the Meanings Identical to Those Described in Item 1.)

In formula (37), when all of $Z^4$, $Z^5$, and $Z^6$ are a single bond, and o=p=0 and q=1, or when o=0 and p=q=1, or when o=p=q=1, the compound (50) is obtained, for example, by the coupling reaction of the anisole derivative (49) with the boronic acid derivative (48) in the presence of a base and tetrakis(triphenylphosphine)palladium (0) as a catalyst (refer to Akira Suzuki, et al., Journal of Synthetic Organic Chemistry, Japan, Vol. 46, No. 9, 848 (1988)). Next, the objective phenol derivative (37-2) can be synthesized by demethylating the compound (50) with the action of boron tribromide thereon.

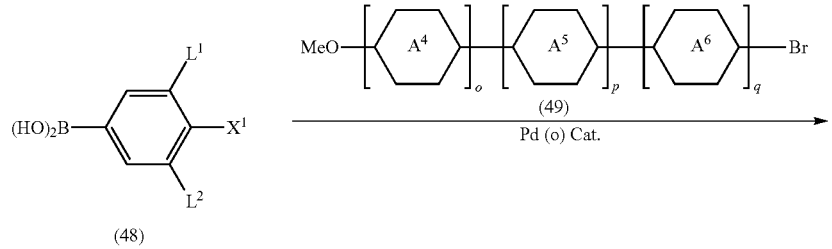

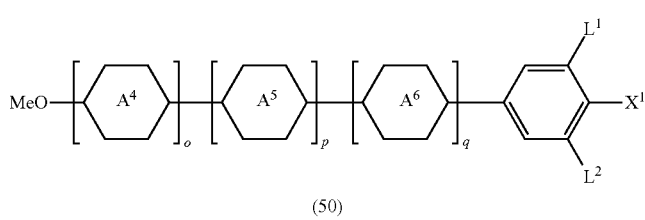

(50)

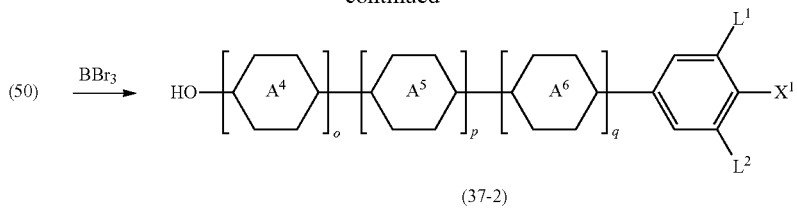

(37-2)

(In these formulas, rings $A^4$ to $A^6$, $L^1$, $L^2$, o, p, q, and $X^1$ have the meanings identical to those described above.)

In formula (37), when all of $Z^4$, $Z^5$, and $Z^6$ are a single bond and o=p=q=0, such a compound can also be synthesized according to the following method. The benzyl ether derivative (51) is treated with n- or sec-butyl lithium at −70° C. or lower in THF, and then reacted with trialkylborate to obtain a boric acid ester derivative. The obtained boric acid derivative or a boronic acid derivative obtained by acidic hydrolysis of the boric acid ester derivative was oxidized with peracetic acid, whereby the phenol derivative (52) is obtained. After the derivative (52) has been converted into its phenolate with sodium hydride, the phenolate is etherified by the action of fluoroalkyl bromide and then deprotected by catalytic dehydrogenation, whereby an objective phenol derivative (37-3) can be synthesized.

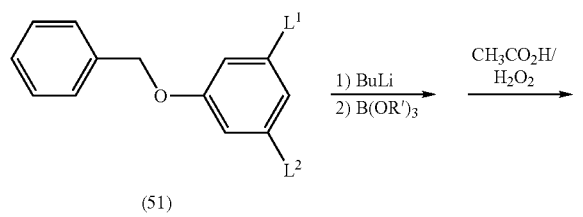

(51)

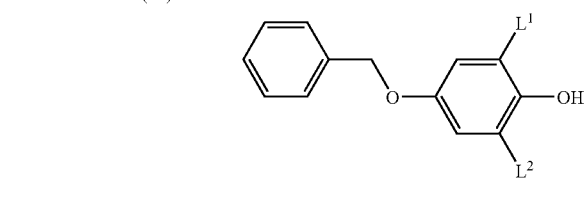

(52)

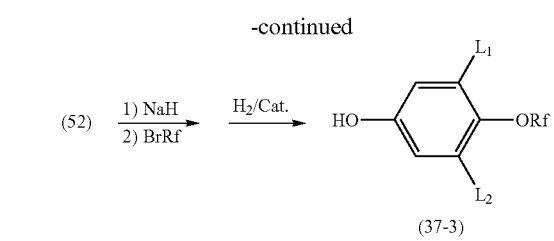

(37-3)

(In these formulas, $L^1$ and $L^2$ have the meanings identical to those described in Item 1, and Rf indicates a fluoroalkyl group excluding a trifluoromethyl group.)

In the compound (1), a derivative having a biphenyl structure on the right side of a $CF_2O$ bonding group, for example, a derivative in which l=m=q=1, n=o=p=0, and $Z^6$ is a single bond, a derivative having a terphenyl structure, for example, a derivative in which l=p=q=1 and both of $Z^5$ and $Z^6$ are a single bond, and a derivative having a quarterphenyl structure, for example, the derivative (1-33) in which o=p=q=1 and all of $Z^4$, $Z^5$, and $Z^6$ are a single bond, can be synthesized according to the method especially shown below. That is, the compound (53) is obtained from the compound (35) described above and the phenol derivative (37-1) or (37-2) according to a method similar to that for the synthesis of the compound represented by the general formula (1). After the compound (53) has been lithiated by the action of n- or sec-butyl lithium and then converted into an organometallic compound by the addition of zinc chloride, the objective derivative can be synthesized by reacting the obtained organometallic compound with the bromobenzene derivative (47) described above or the bromobenzene derivative (55) in the presence of a catalyst such as tetrakis(triphenylphosphine) palladium (0). The derivative (55) is obtained by the etherification of the compound (54) with fluoroalkyl bromide.

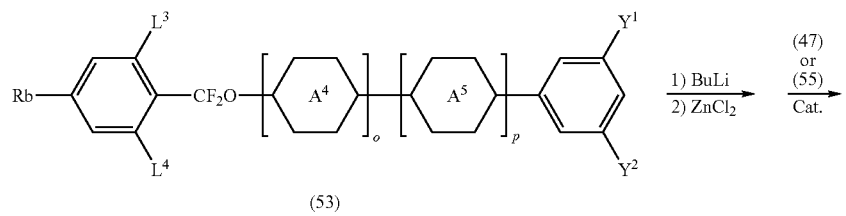

(53)

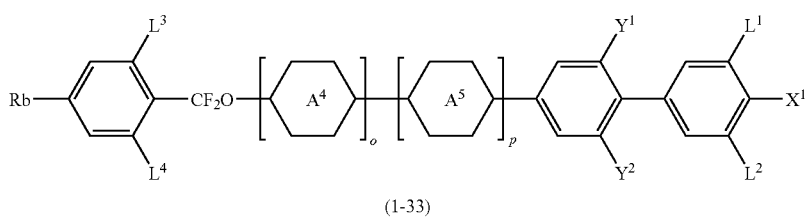

(1-33)

-continued

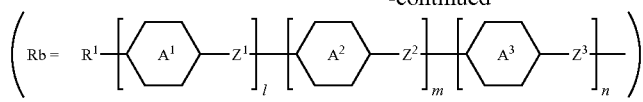

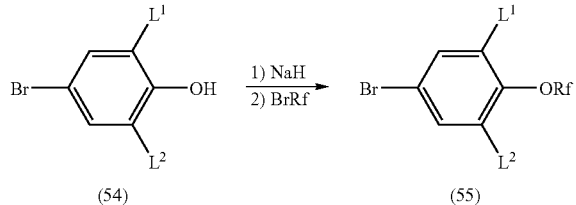

(In these formulas, rings $A^1$ to $A^5$, $Z^1$ to $Z^3$, $L^1$ to $L^4$, $R^1$, and $X^1$ have the meanings identical to those described in Item 1, and $Y^1$ and $Y^2$ are hydrogen or fluorine, and Rf is fluoroalkyl excluding trifluoromethyl.)

2. Composition of the Invention

The second aspect of the invention concerns a composition containing the compound represented by formula (1), preferably a liquid crystal composition which can be used for a liquid crystal material. The liquid crystal composition of the invention is required to contain the compound represented by formula (1) of the invention as a component A. The composition may contain the component A only, or the component A and other components whose names are not particularly indicated in this specification. The liquid crystal compositions (a), (b), (c), (d), (e), and so forth of the invention having various characteristics can be provided by adding components selected from components B, C, D, and E shown below to the component A.

A component to be added to the component A is preferably the component B consisting of at least one kind of compounds selected from the group represented by the formulas (2), (3) and (4) described above, or the component C consisting of at least one kind of compounds selected from the group represented by the formula (5) described above, or a component mixed with the component D consisting of at least one kind of compounds selected from the group represented by the formulas (6), (7), (8), (9), and (10) described above [the above-described liquid crystal compositions (b), (c), and (d)].

Further, the threshold voltage, the temperature range of liquid crystal phases, the refractive index anisotropy value, the dielectric anisotropy value, the viscosity, and so forth can be adjusted by mixing a component E consisting of at least one kind of compounds selected from the group represented by the formulas (11), (12), and (13) [the above-described liquid crystal composition (e)].

Each component of liquid crystal compositions used in the invention does not have a significant difference in physical properties even in the case of an analogue composed of the isotopic element of each element.

In the component B, suitable examples of compounds represented by formula (2) include formulas (2-1) to (2-16), suitable examples of compounds represented by formula (3) are compounds represented by formulas (3-1) to (3-112), and suitable examples of compounds represented by formula (4) are represented by formulas (4-1) to (4-52), respectively.

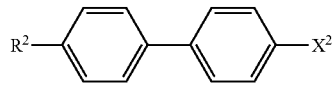
(2-1)

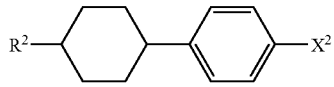
(2-2)

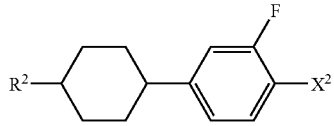
(2-3)

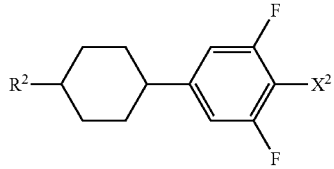
(2-4)

(2-5)

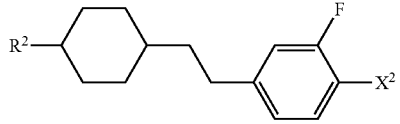
(2-6)

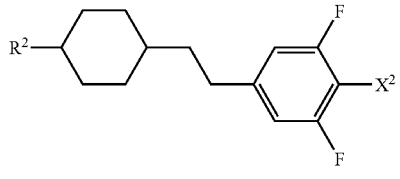
(2-7)

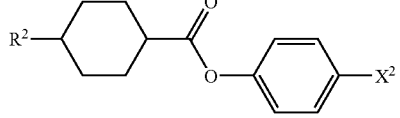
(2-8)

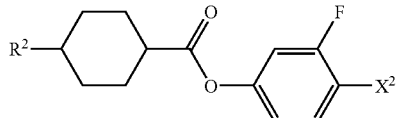
(2-9)

(2-10) 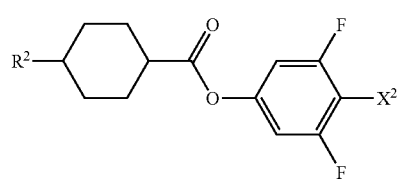
(2-11) 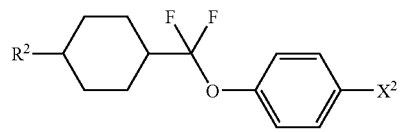
(2-12) 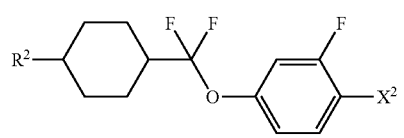
(2-13) 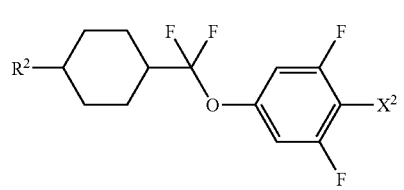
(2-14) 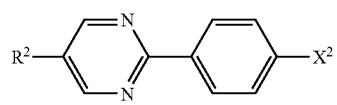
(2-15) 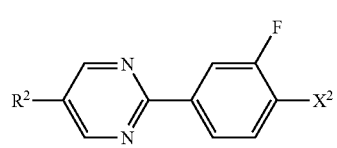
(2-16) 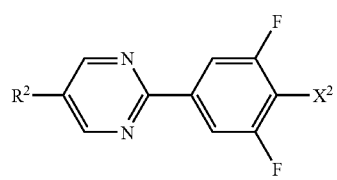
(3-1) 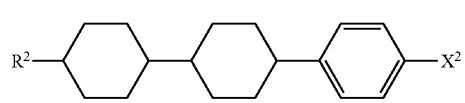
(3-2) 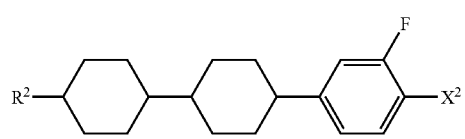
(3-3) 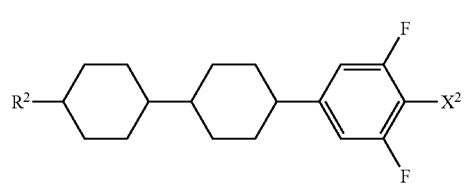
(3-4) 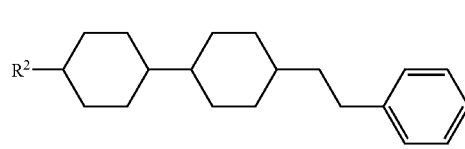
(3-5) 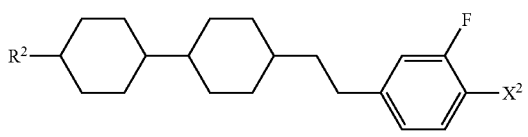
(3-6) 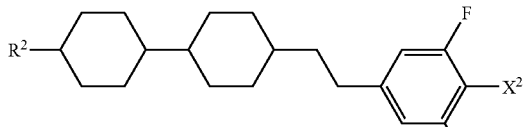
(3-7) 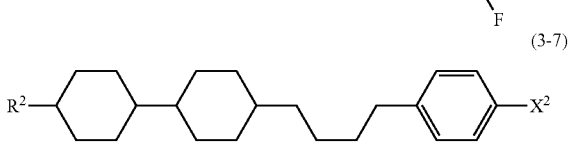
(3-8) 
(3-9) 
(3-10) 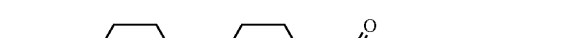
(3-11) 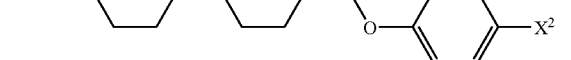
(3-12) 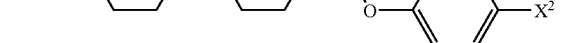
(3-13) 
(3-14) 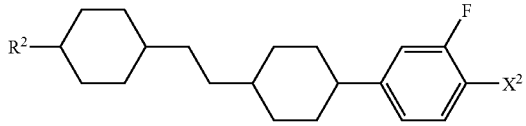

(3-15)
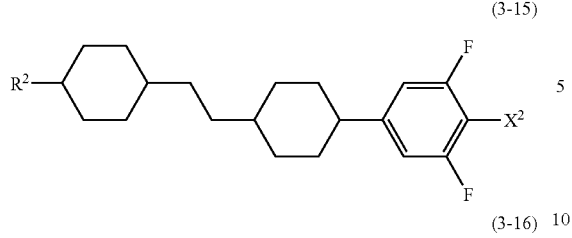
(3-16)
(3-17)
(3-18)
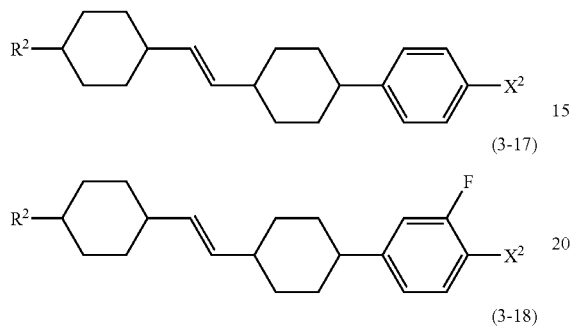
(3-19)
(3-20)
(3-21)

(3-22)
(3-23)
(3-24)
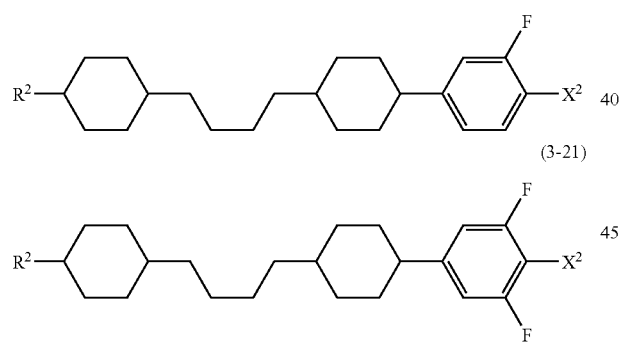
(3-25)
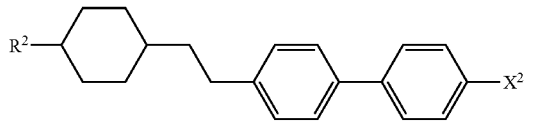
(3-26)
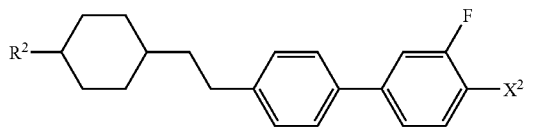
(3-27)

(3-28)
(3-29)
(3-30)
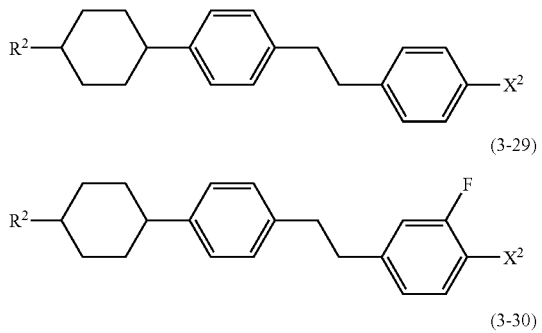
(3-31)
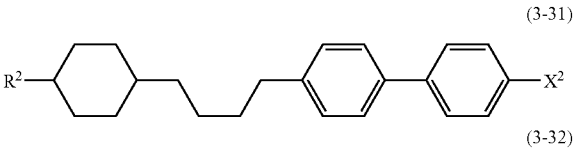
(3-32)
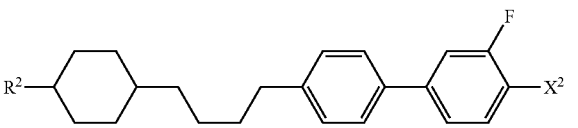
(3-33)
(3-34)
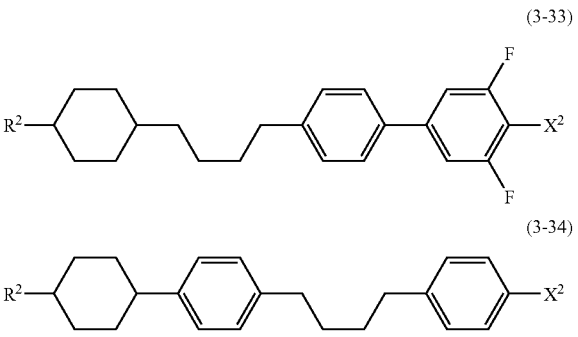

(3-35) 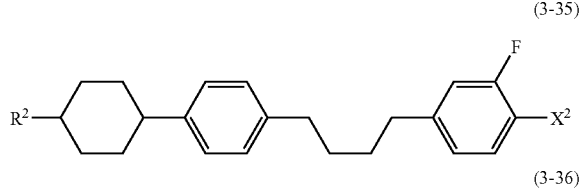
(3-36) 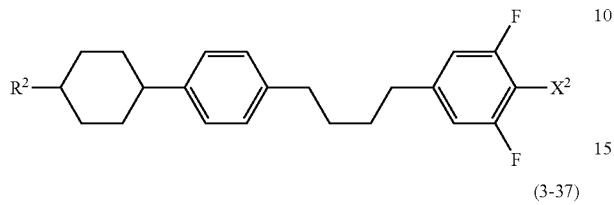
(3-37) 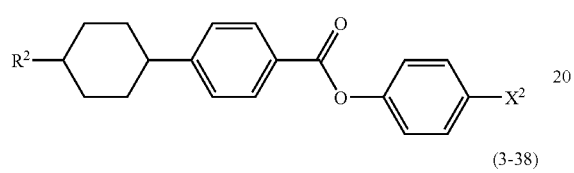
(3-38) 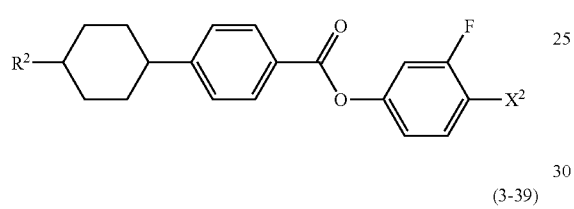
(3-39) 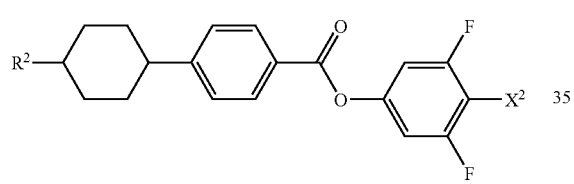
(3-40) 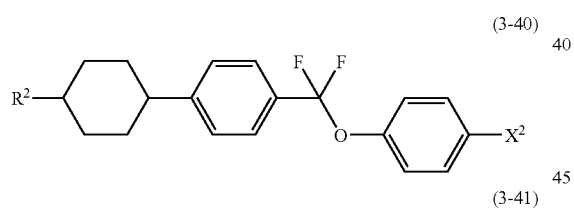
(3-41) 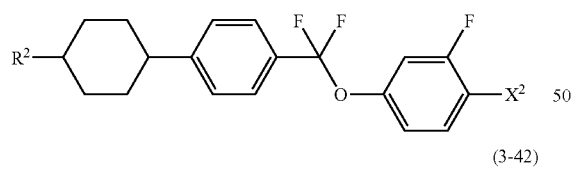
(3-42) 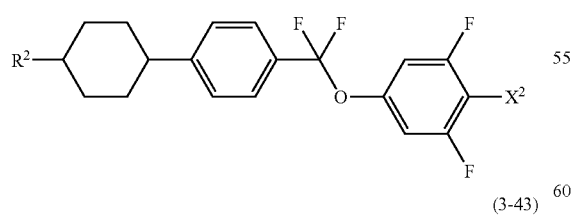
(3-43) 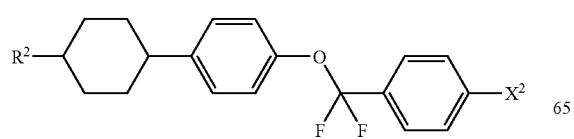
(3-44) 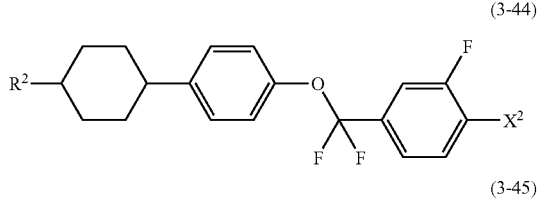
(3-45) 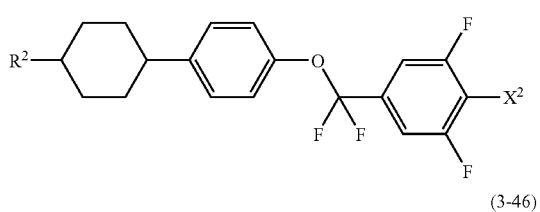
(3-46) 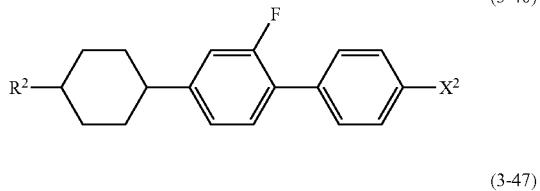
(3-47) 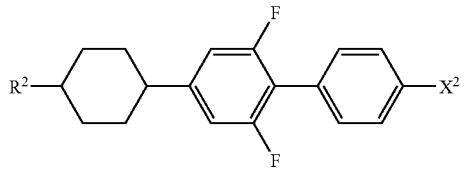
(3-48) 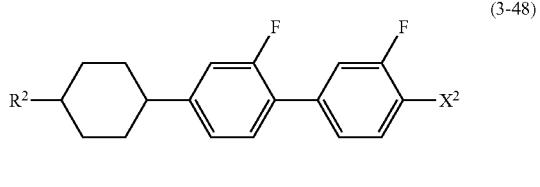
(3-49) 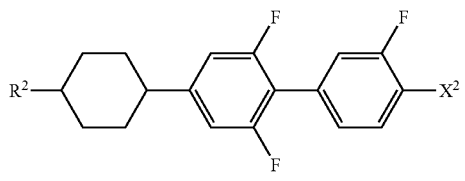
(3-50) 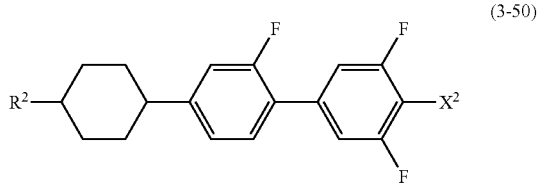
(3-51) 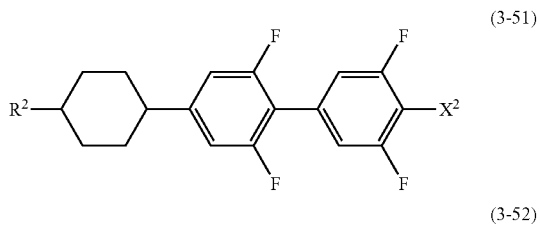
(3-52) 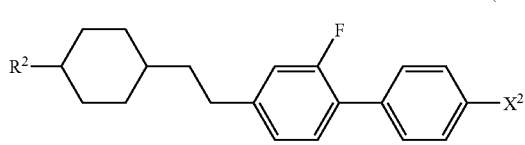

(3-53)
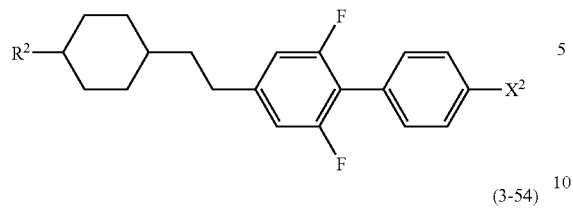
(3-54)
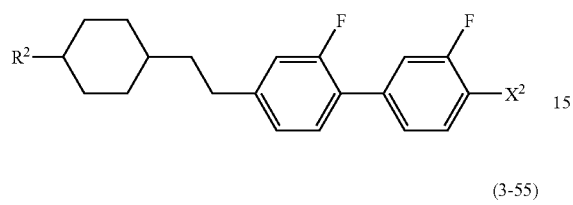
(3-55)

(3-56)
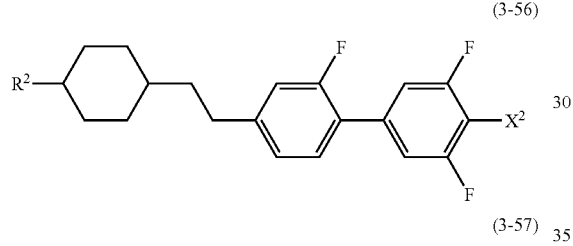
(3-57)

(3-58)

(3-59)

(3-60)
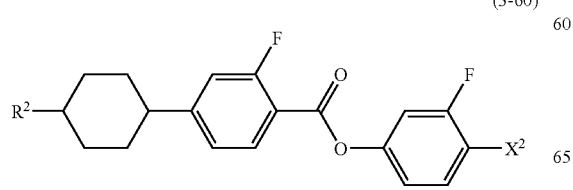
(3-61)
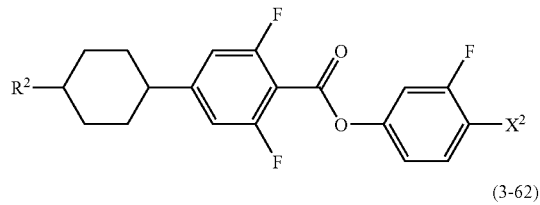
(3-62)
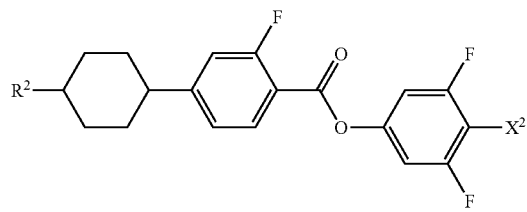
(3-63)
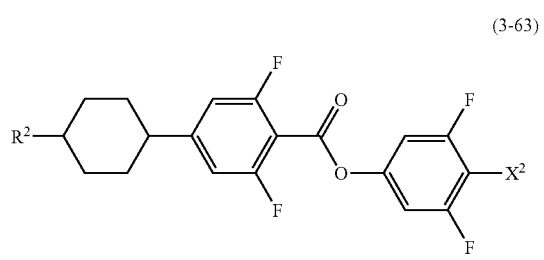
(3-64)
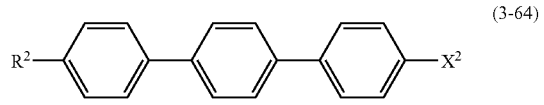
(3-65)

(3-66)

(3-67)

(3-68)
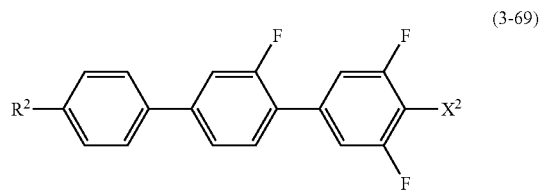
(3-69)

(3-70) 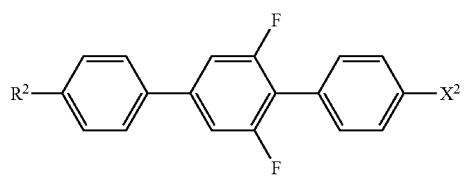
(3-71) 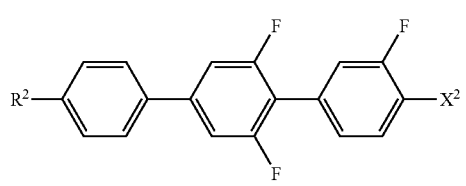
(3-72) 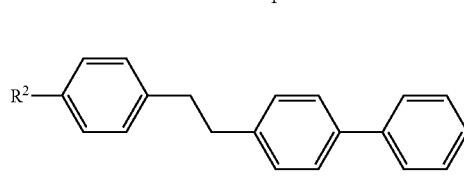
(3-73) 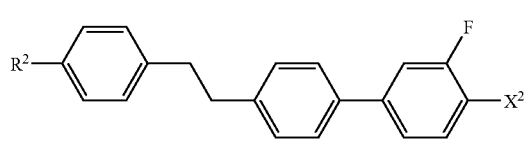
(3-74) 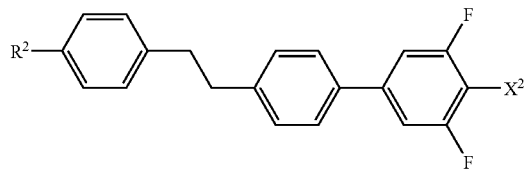
(3-75) 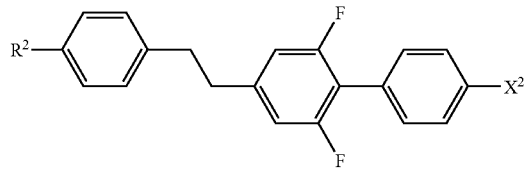
(3-76) 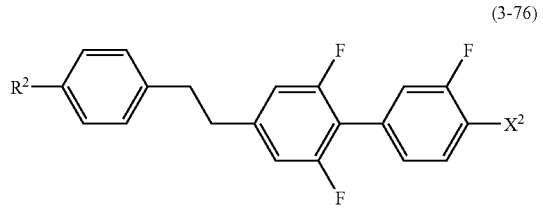
(3-77) 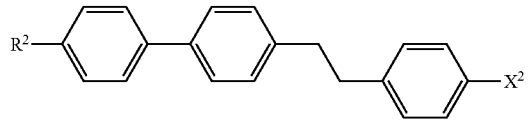
(3-78) 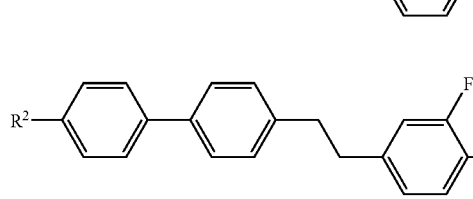
(3-79) 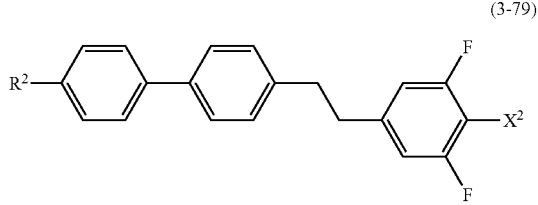
(3-80) 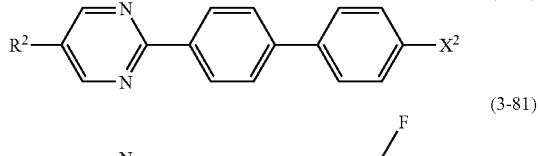
(3-81) 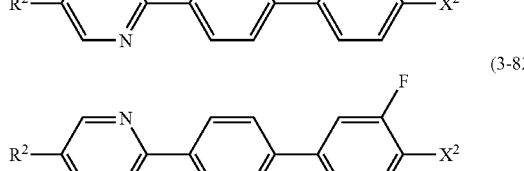
(3-82) 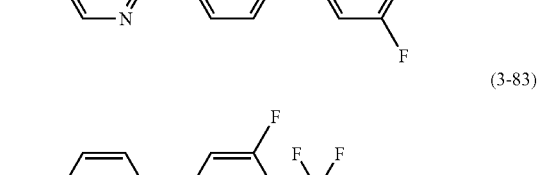
(3-83) 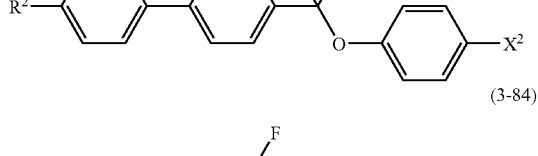
(3-84) 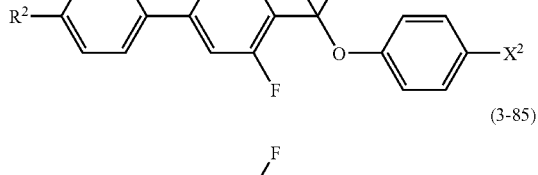
(3-85) 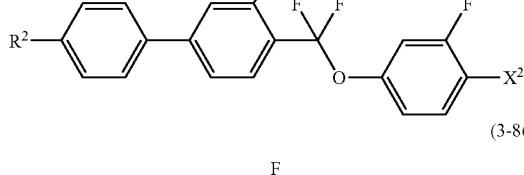
(3-86) 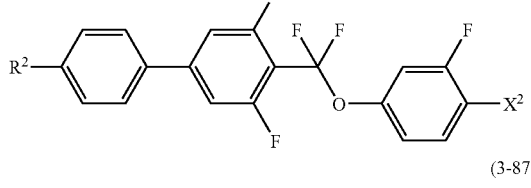
(3-87) 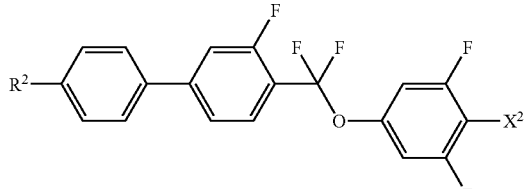

-continued (3-88)
(3-89)
(3-90)
(3-91)
(3-92)
(3-93)
(3-94)
(3-95)
(3-96)
(3-97)
(3-98)
(3-99)
(3-100)
(3-101)
(3-102)
(3-103)
(3-104)

-continued
(3-105)
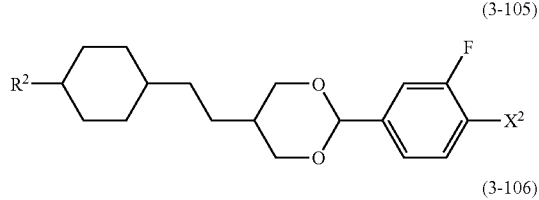
(3-106)
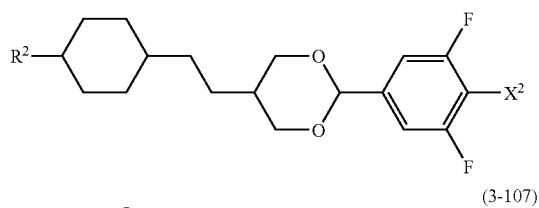
(3-107)

(3-108)
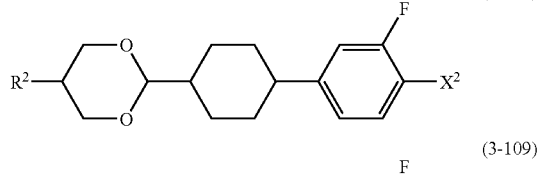
(3-109)
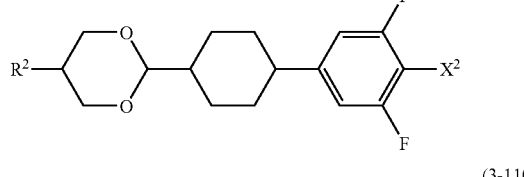
(3-110)
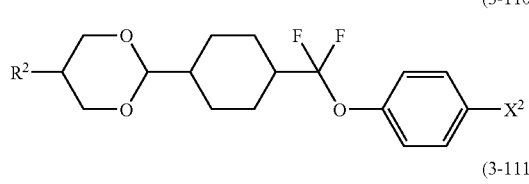
(3-111)
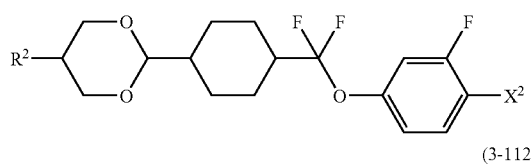
(3-112)
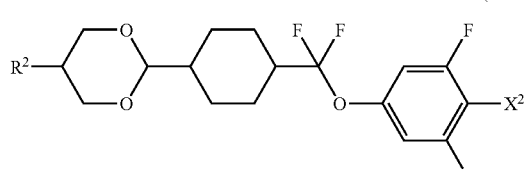
(4-1)
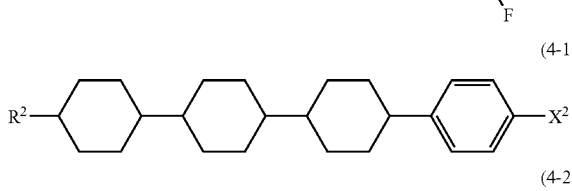
(4-2)
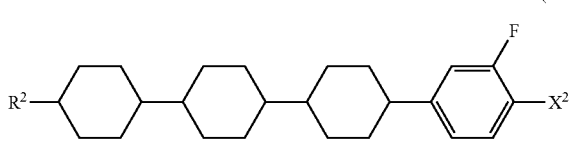
-continued
(4-3)
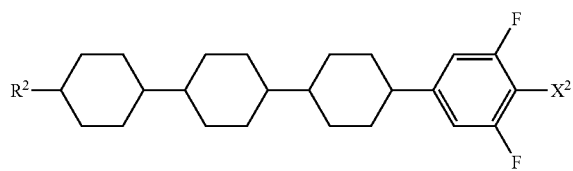
(4-4)
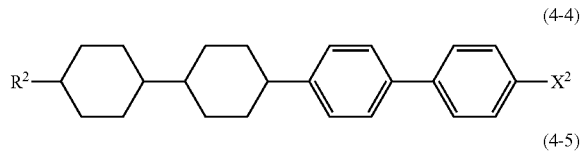
(4-5)
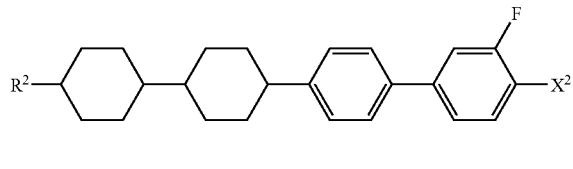
(4-6)
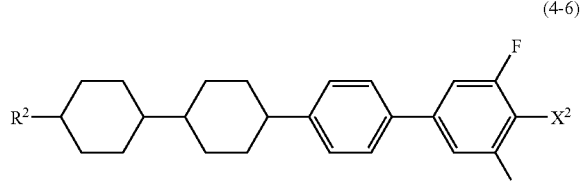
(4-7)
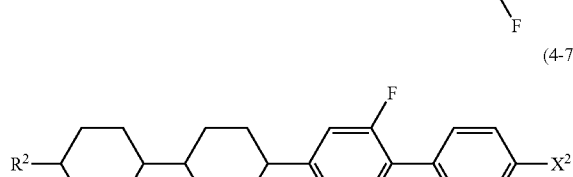
(4-8)
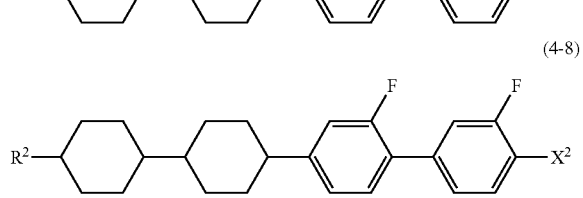
(4-9)
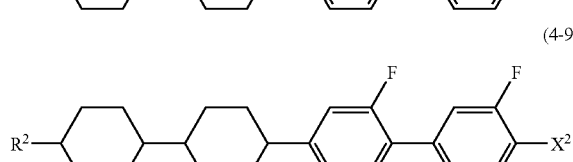
(4-10)
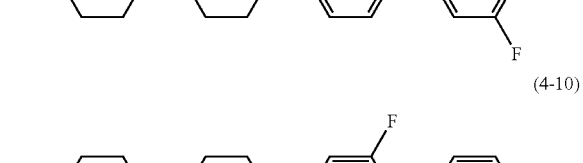
(4-11)
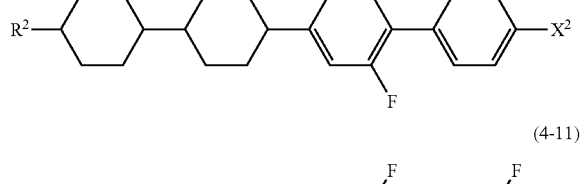
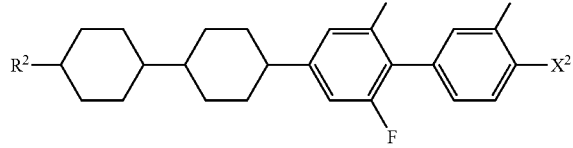

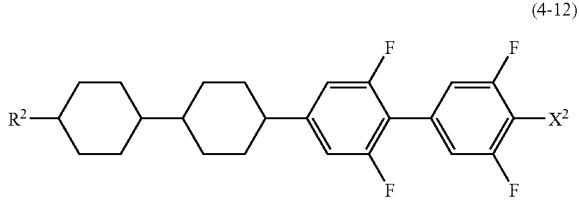
(4-12)
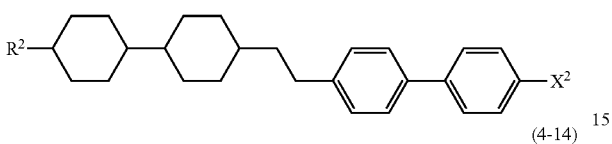
(4-13)

(4-14)
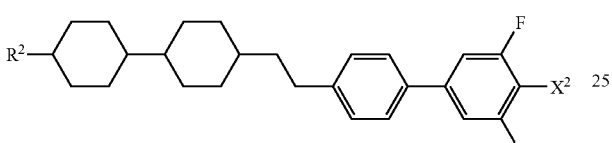
(4-15)

(4-16)
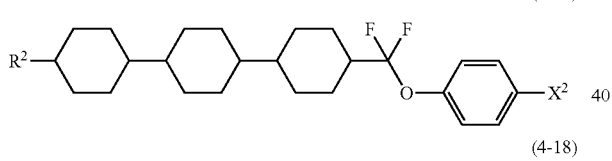
(4-17)

(4-18)
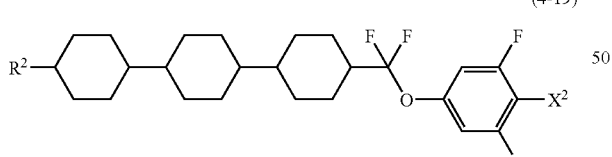
(4-19)

(4-20)
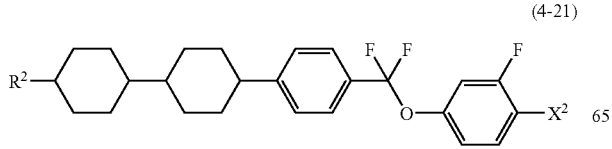
(4-21)
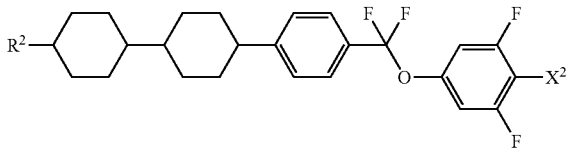
(4-22)
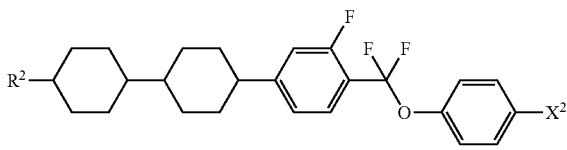
(4-23)

(4-24)
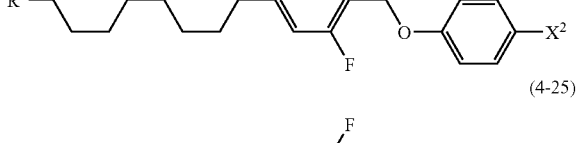
(4-25)
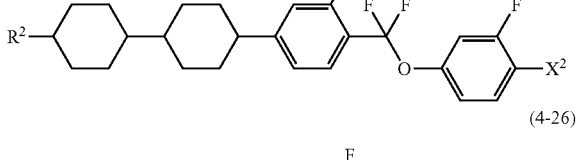
(4-26)
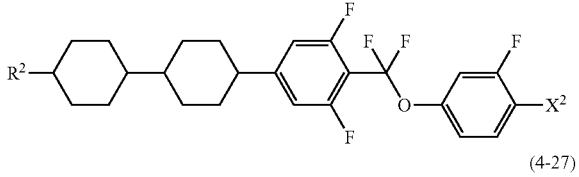
(4-27)

(4-28)
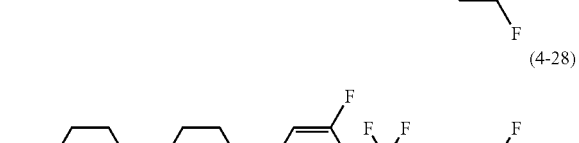
(4-29)
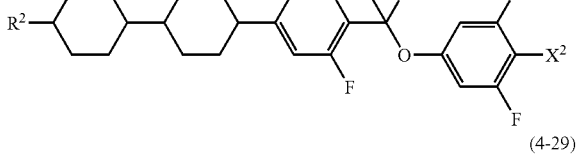
(4-30)
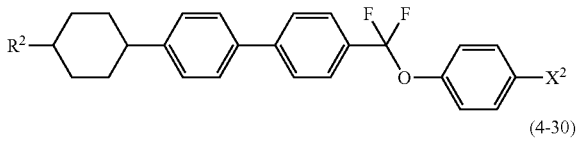
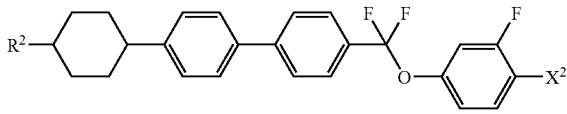

(4-31) 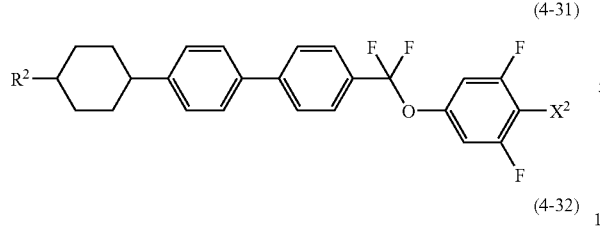
(4-32) 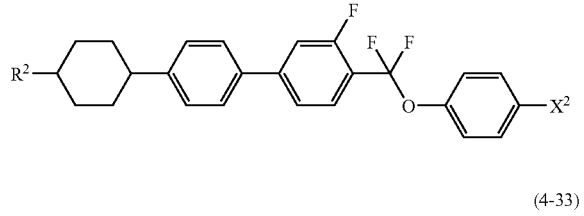
(4-33) 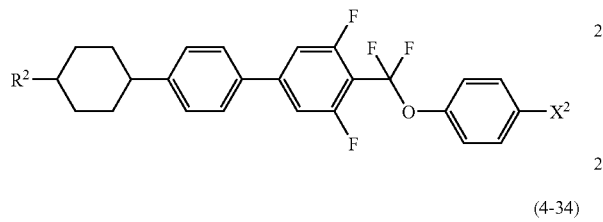
(4-34) 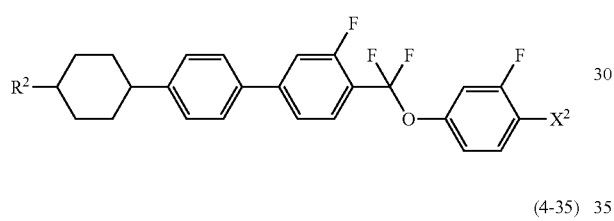
(4-35) 
(4-36) 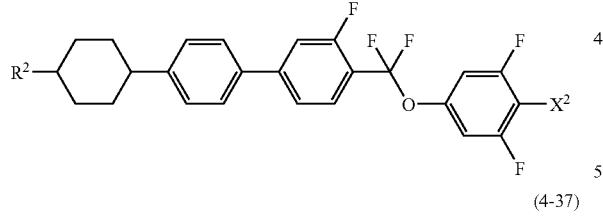
(4-37) 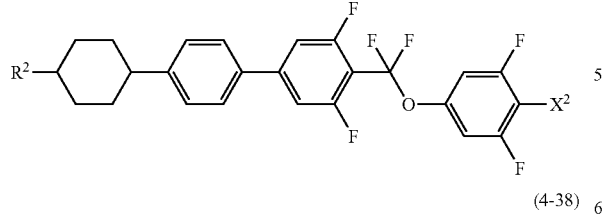
(4-39) 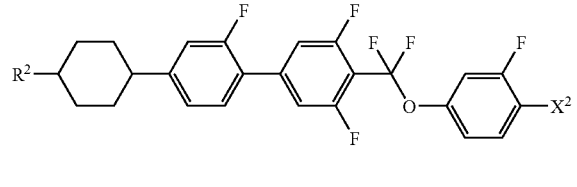
(4-40) 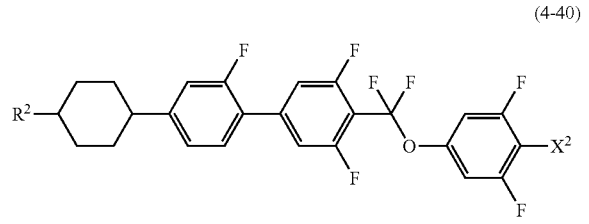
(4-41) 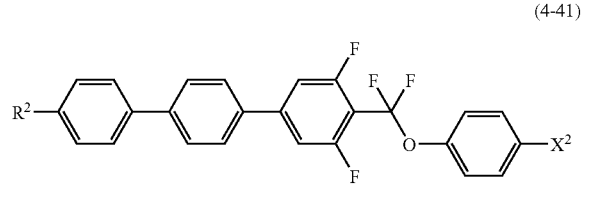
(4-42) 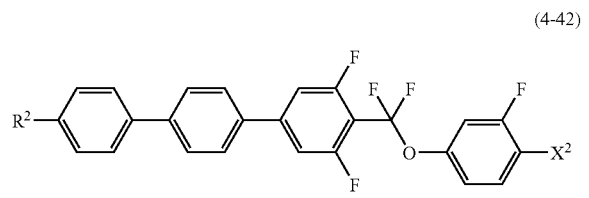
(4-43) 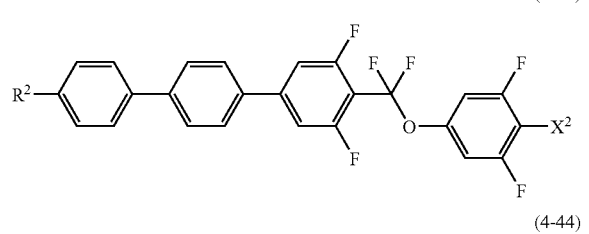
(4-44) 
(4-45) 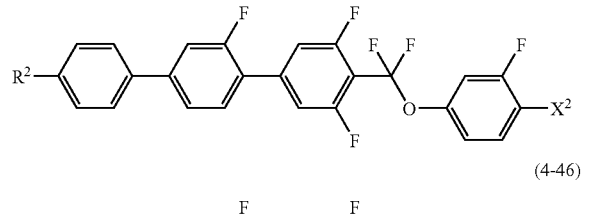
(4-38)
(4-46)
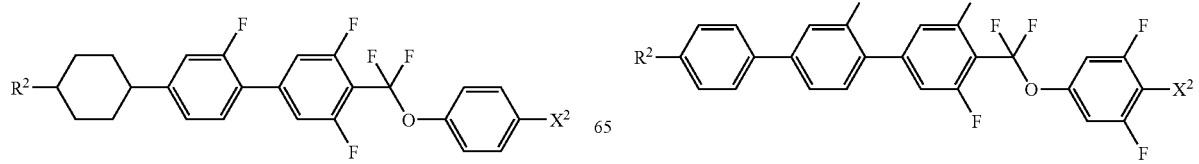

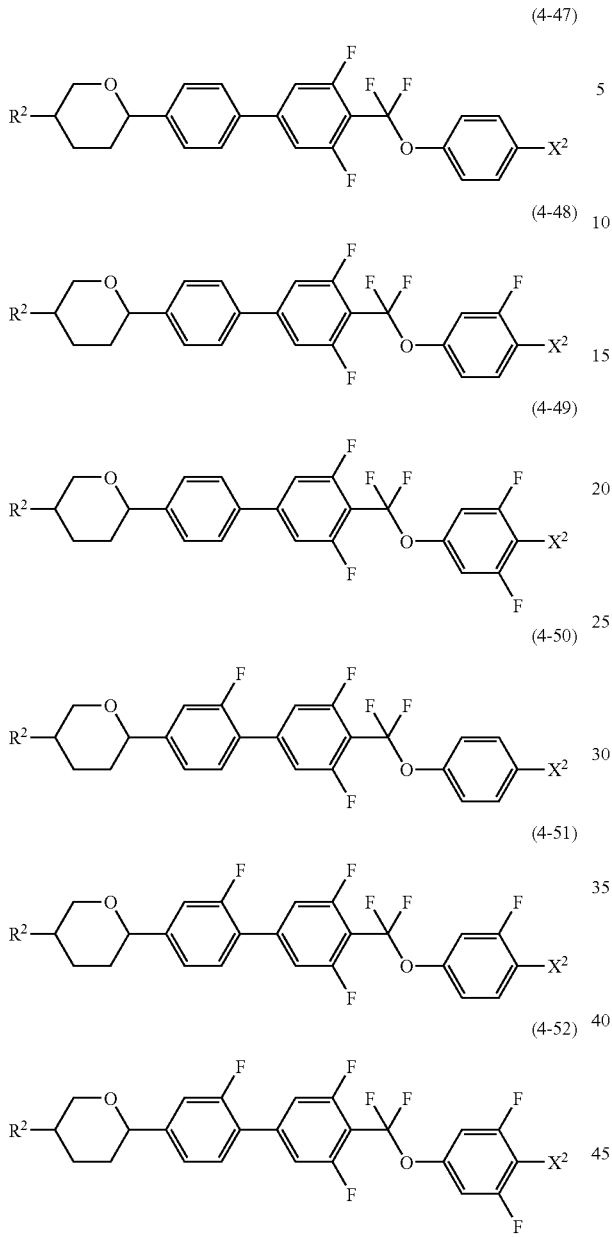

(In these formulas, $R^2$ and $X^2$ have the same meanings as described above.)

Since the compounds represented by these formulas (2) to (4), i.e. the component B, have a positive dielectric anisotropy value and an excellent thermal stability or chemical stability, they are used in preparing a liquid crystal composition for TFT. The content of component B in the liquid crystal composition of the invention is suitably in the range of 1% to 99% by weight, preferably 10% to 97% by weight, and more preferably 40% to 95% by weight based on the total weight of the liquid crystal composition. The viscosity can be adjusted by further adding the compound represented by formulas (11) to (13) (component E).

Suitable examples of compounds represented by formula (5) described above, i.e. the component C, include formulas (5-1) to (5-62).

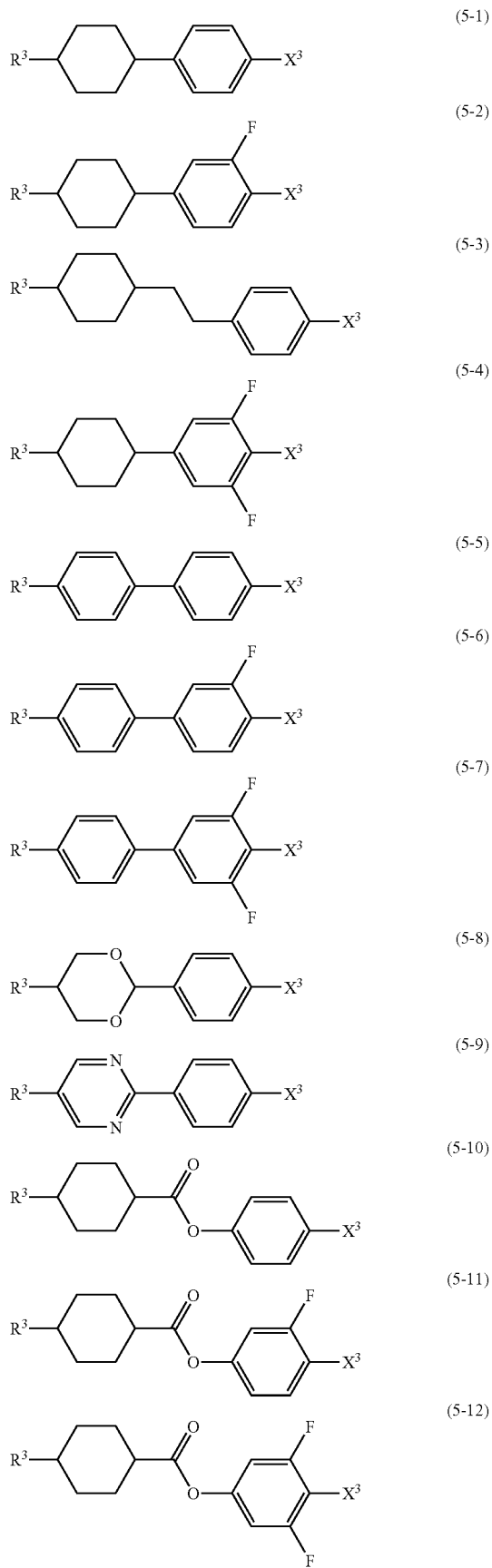

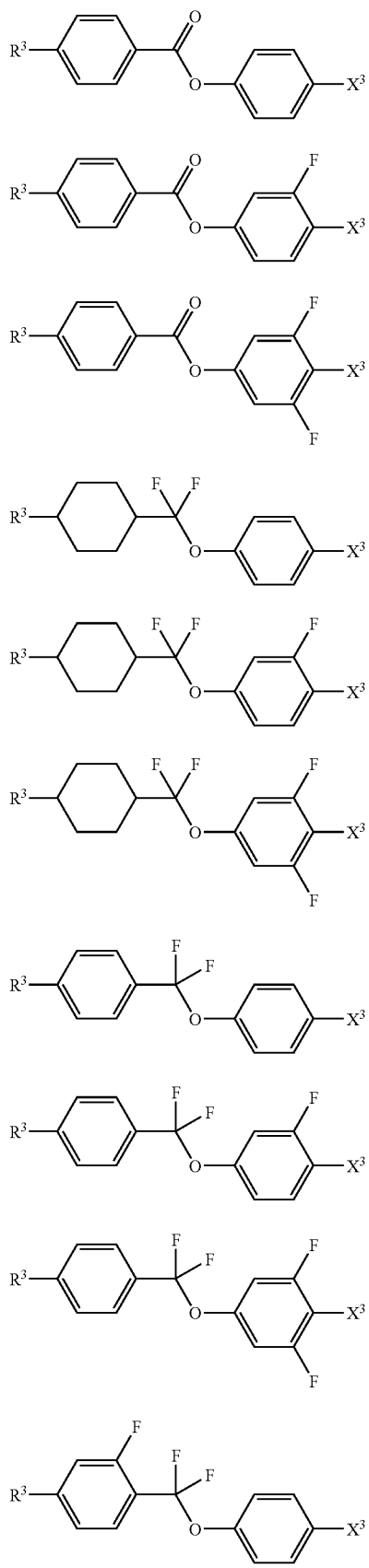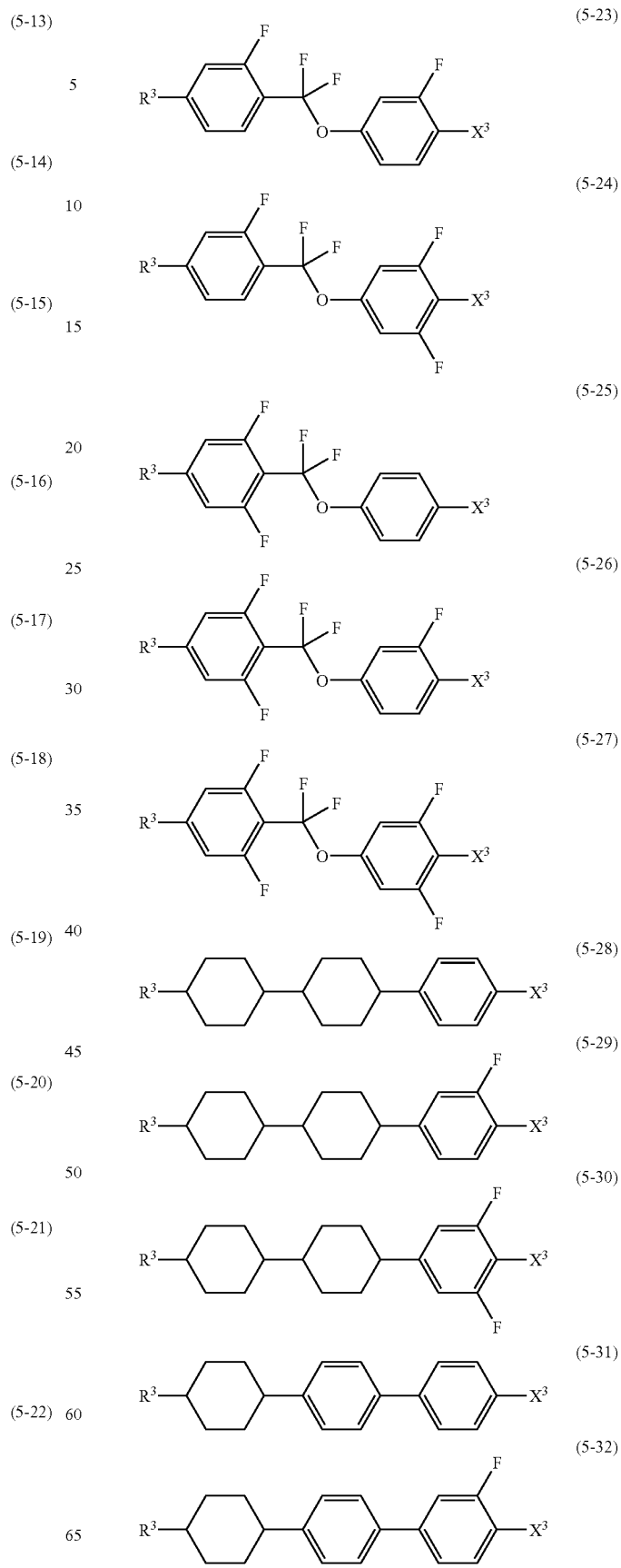

(5-33) 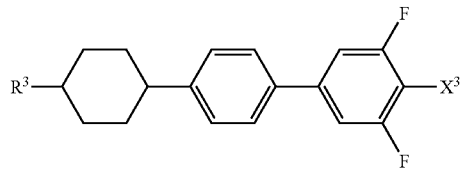
(5-34) 
(5-35) 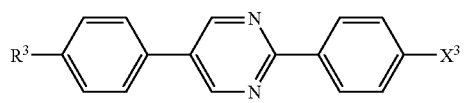
(5-36) 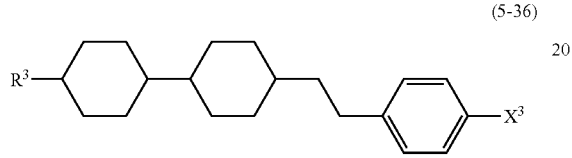
(5-37) 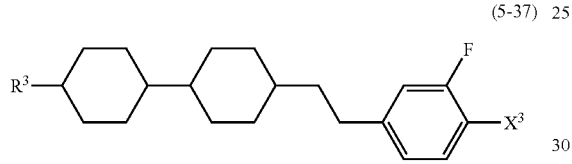
(5-38) 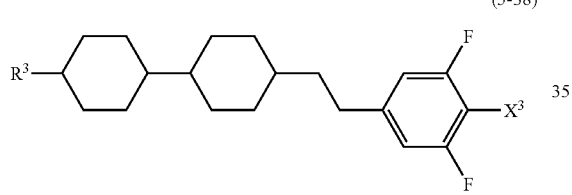
(5-39) 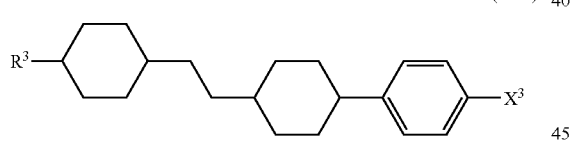
(5-40) 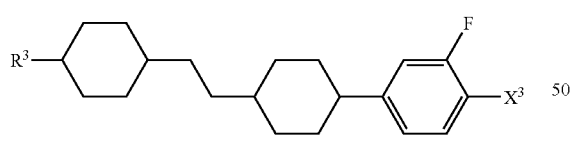
(5-41) 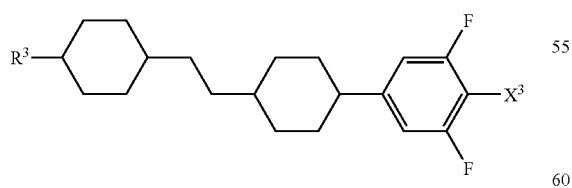
(5-42) 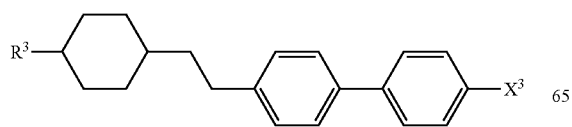
(5-43) 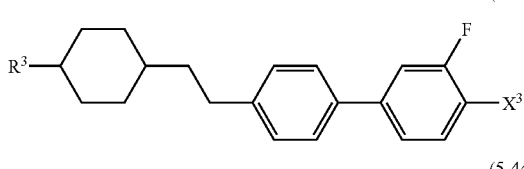
(5-44) 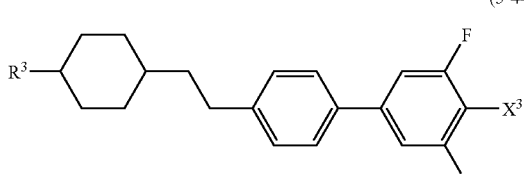
(5-45) 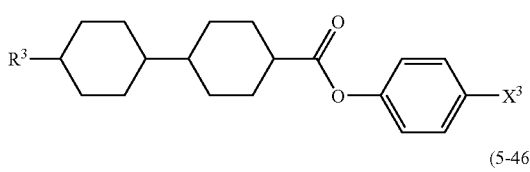
(5-46) 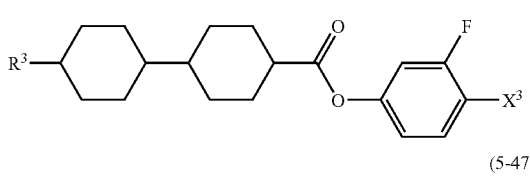
(5-47) 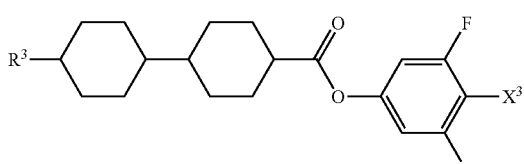
(5-48) 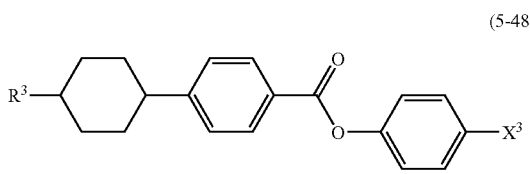
(5-49) 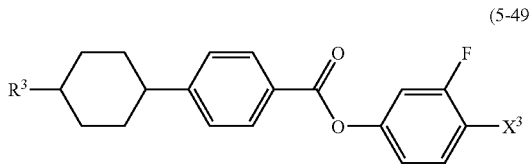
(5-50) 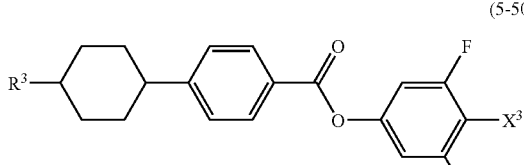
(5-51) 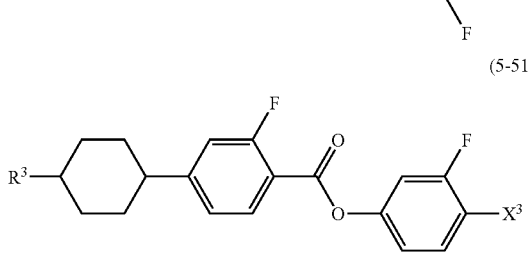

(5-52)
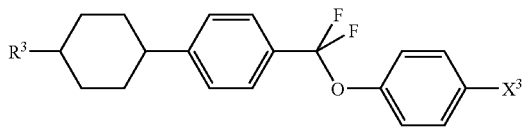

(5-53)
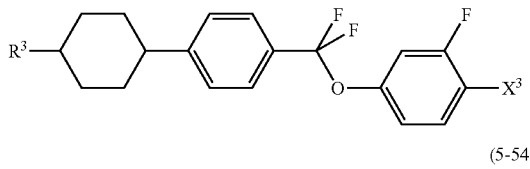

(5-54)

(5-55)
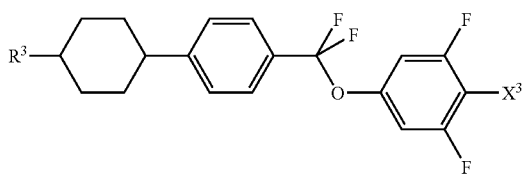

(5-56)
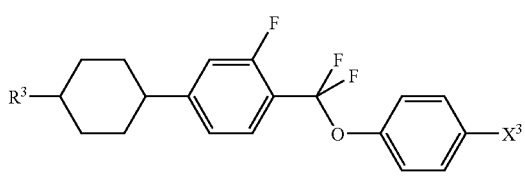

(5-57)

(5-58)
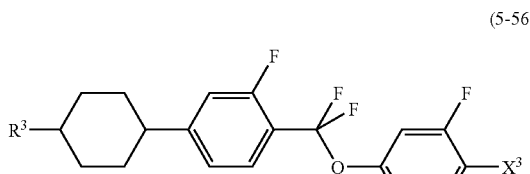

(5-59)

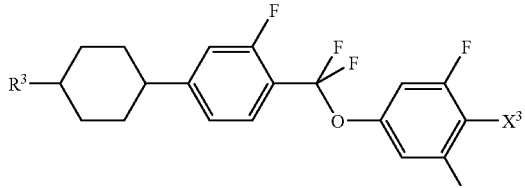

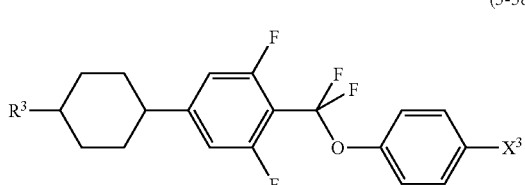

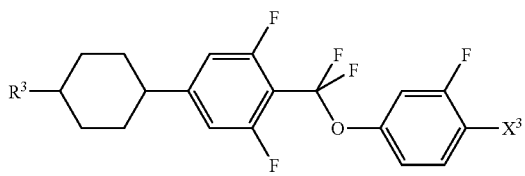

(5-60)
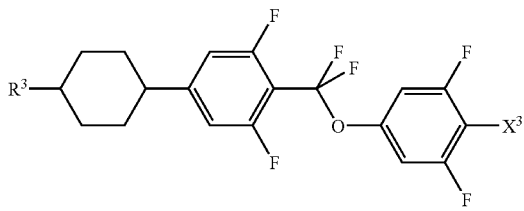

(5-61)
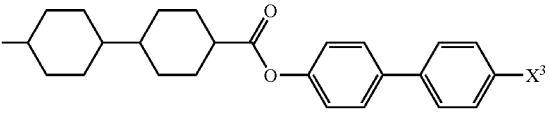

(5-62)
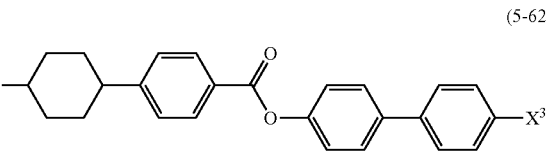

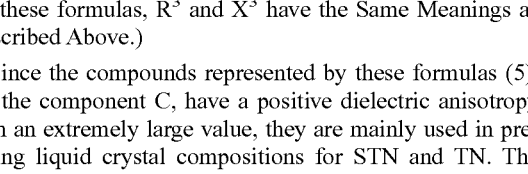

(In these formulas, $R^3$ and $X^3$ have the Same Meanings as Described Above.)

Since the compounds represented by these formulas (5), i.e. the component C, have a positive dielectric anisotropy with an extremely large value, they are mainly used in preparing liquid crystal compositions for STN and TN. The threshold voltage of the compositions can be reduced by adding the component C. The component C can adjust the viscosity and the refractive index anisotropy value, and can widen the temperature range of liquid crystal phases. Further, it can also be used for improving steepness.

When preparing a liquid crystal composition for STN or TN, the content of the component C is preferably in the range of 0.1% to 99.9% by weight, more preferably in the range of 10% to 97% by weight, and still more preferably in the range of 40% to 95% by weight based on the total amount of the composition. The threshold voltage, the temperature range of liquid crystal phases, the refractive index anisotropy value, the dielectric anisotropy value, the viscosity, and so forth can be adjusted by mixing components to be described below.

The component D consisting of at least one kind of compound selected from the group represented by formulas (6) to (8) and (10) is a suitable component in preparing the liquid crystal composition of the invention having a negative dielectric anisotropy used for a vertical alignment mode (VA mode) and so forth.

Suitable examples of the compounds represented by formulas (6) to (8) and (10) (component D) include formulas (6-1) to (6-5), (7-1) to (7-11), (8-1), and (10-1) to (10-11), respectively.

(6-1)
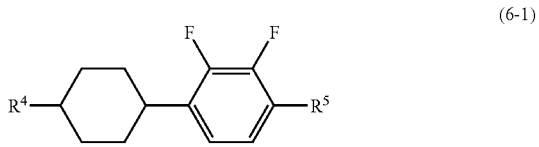

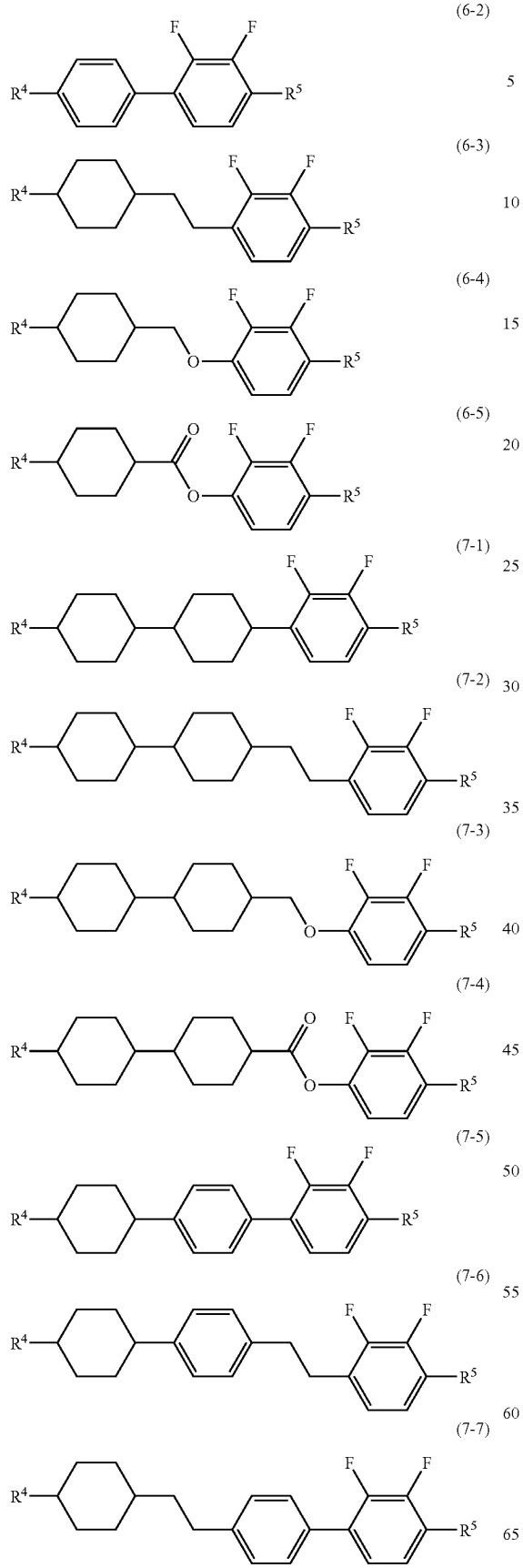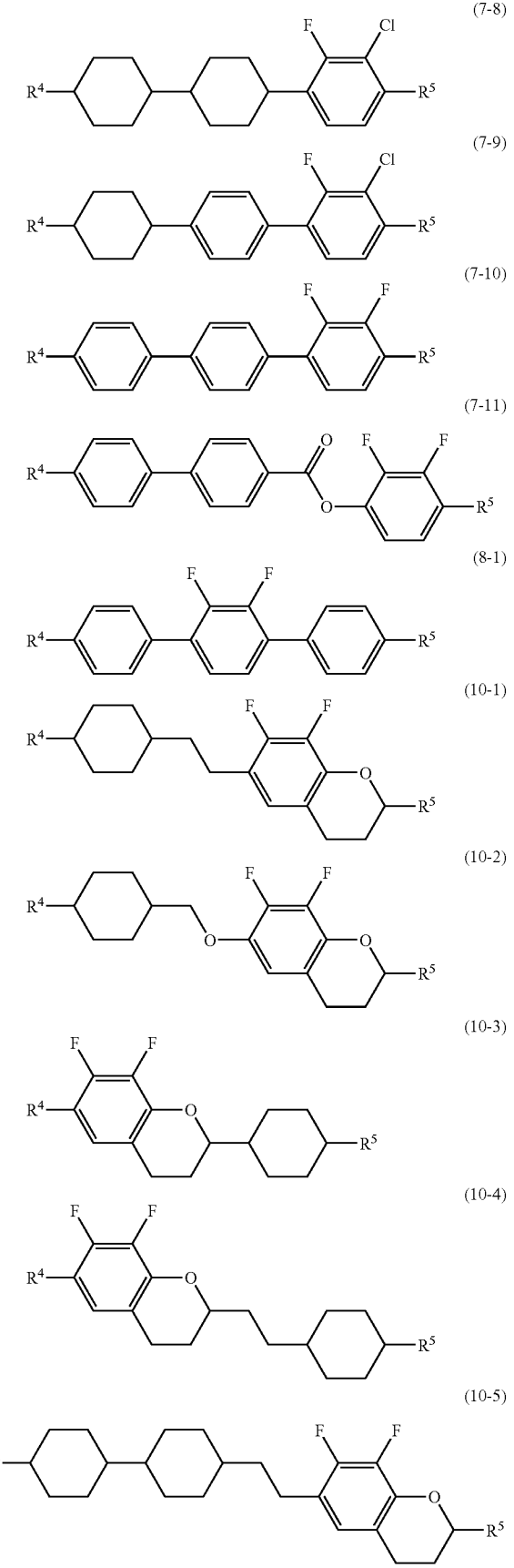

-continued

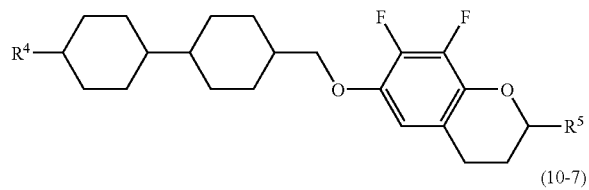
(10-6)

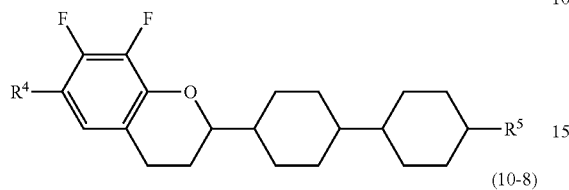
(10-7)

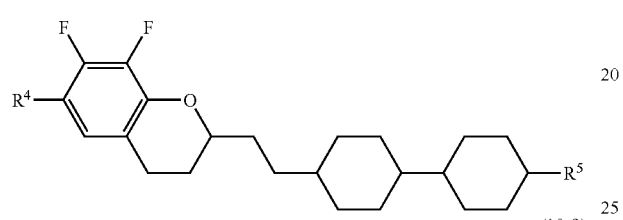
(10-8)

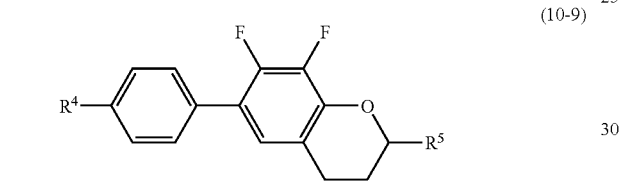
(10-9)

(10-10)

(10-11)

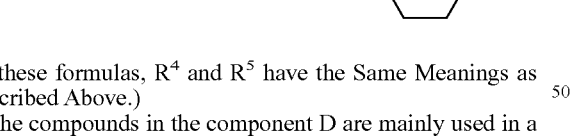

(In these formulas, $R^4$ and $R^5$ have the Same Meanings as Described Above.)

The compounds in the component D are mainly used in a liquid crystal composition for a VA mode having a negative dielectric anisotropy. When the content is increased, the threshold voltage of the composition is decreased, but the viscosity is increased, and thus the content is preferably reduced as long as a desired value of threshold voltage is satisfied. However, since the absolute value of the dielectric anisotropy is around 5, voltage-driving may not occasionally be driven when the content becomes 40% by weight or less.

Since the compounds represented by formula (6) among the component D are two-ring compounds, they are effective mainly in adjusting the threshold voltage, the viscosity, or the refractive index anisotropy value. Since the compounds represented by formulas (7) and (8) are three-ring compounds, they are effective in increasing the clearing point, widening the nematic range, lowering the threshold voltage, increasing the refractive index anisotropy value, and so forth.

When preparing a composition for a VA mode, the content of component D is disirably 40% by weight or more, more preferably in the range of 50% to 95% by weight based on the total amount of the composition. The elastic constant and the voltage transmittance curve of the composition can be controlled by mixing the component D. When the component D is mixed in a composition having a positive dielectric anisotropy value, its content is preferably 30% by weight or less based on the total amount of the composition.

Suitable examples of compounds represented by formulas (11), (12), and (13) (component E) include formulas (11-1) to (11-11), (12-1) to (12-18) and (13-1) to (13-6), respectively.

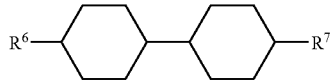
(11-1)

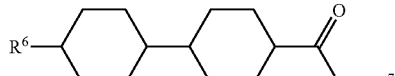
(11-2)

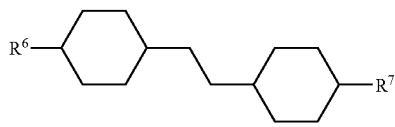
(11-3)

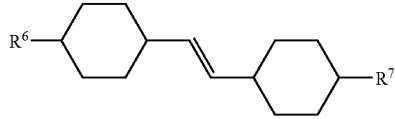
(11-4)

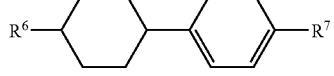
(11-5)

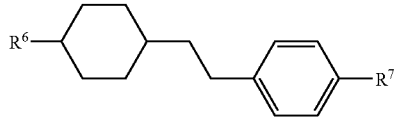
(11-6)

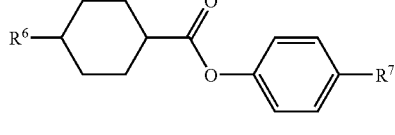
(11-7)

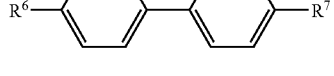
(11-8)

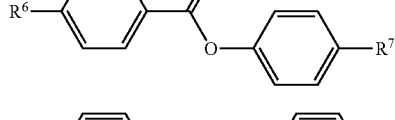
(11-9)

(11-10)

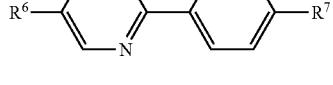
(11-11)

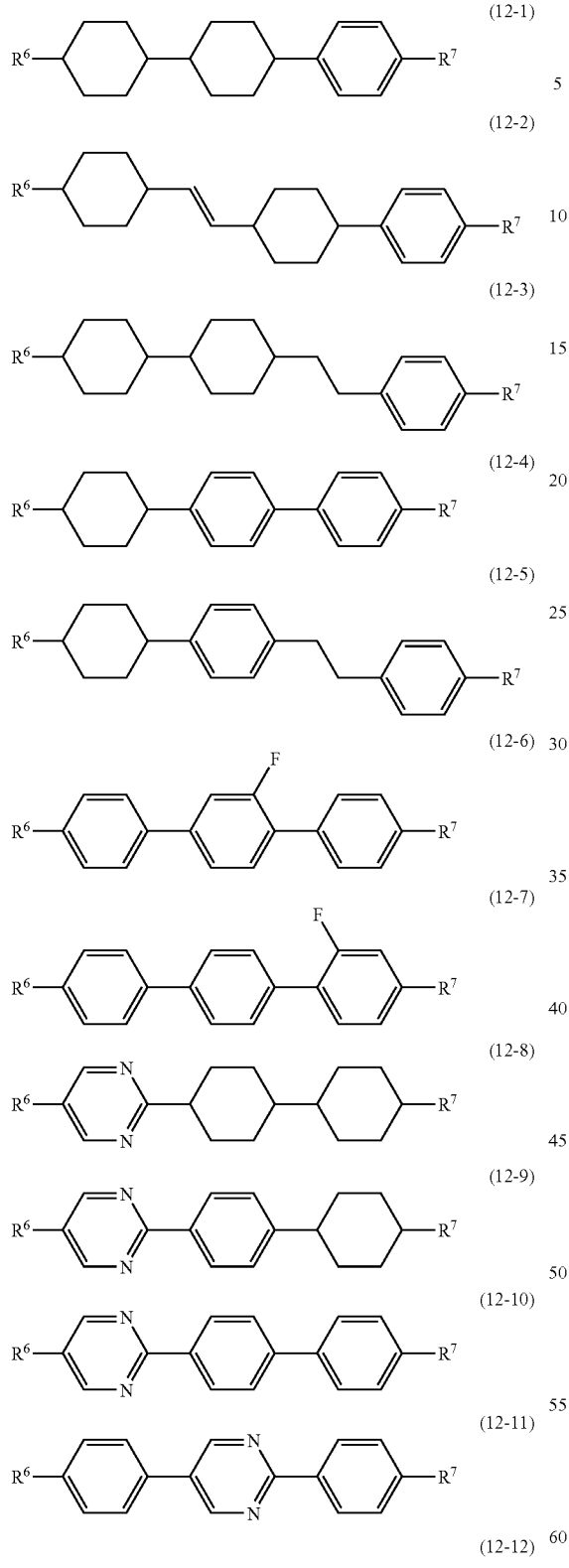
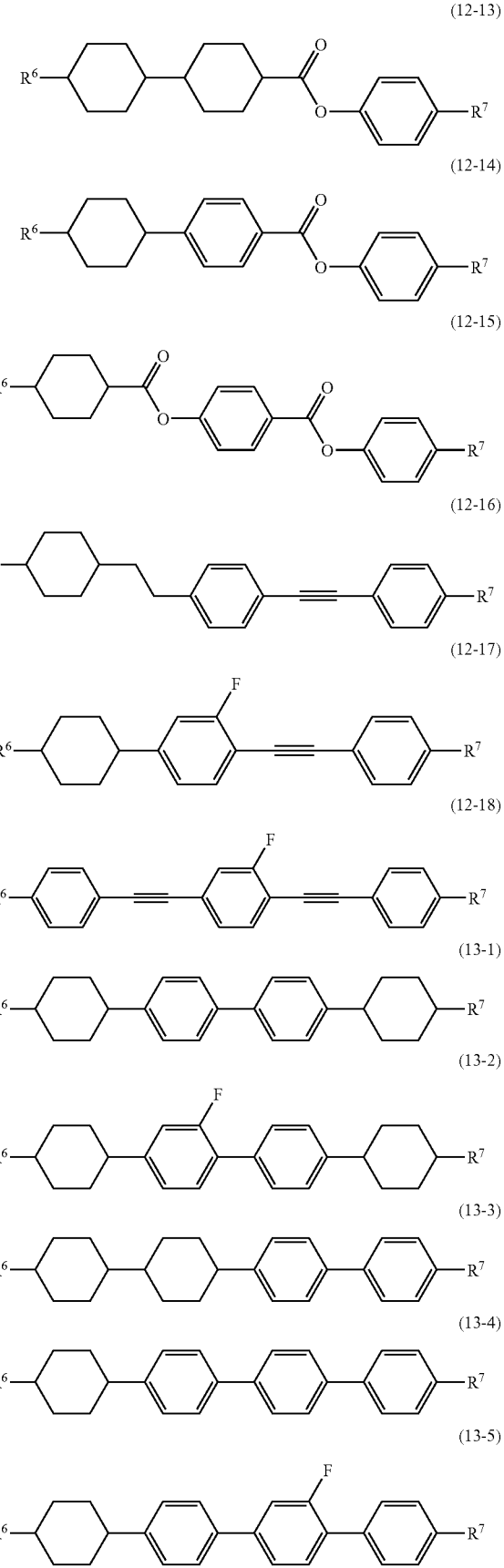

-continued

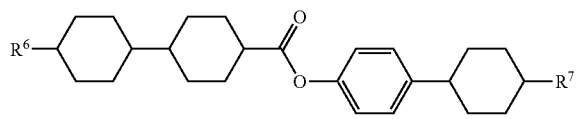
(13-6)

(In these formulas, $R^6$ and $R^7$ have the same meanings as described above.)

The compounds represented by formulas (11) to (13) (component E) are close to neutral because the absolute value of dielectric anisotropy value is small. The compounds represented by formula (11) are effective mainly in adjusting the viscosity or the refractive index anisotropy value, and the compounds represented by formulas (12) and (13) are effective in widening the nematic range, such as increasing the clearing point, or effective in adjusting the refractive index anisotropy value.

When the content of compound represented by the component E is increased, the threshold voltage of a liquid crystal composition is increased and the viscosity is decreased, and thus a larger content is desirable as long as a desired value of threshold voltage of the liquid crystal composition is satisfied. When preparing a liquid crystal composition for TFT, the content of component E is preferably 30% by weight or more, more preferably 50% by weight or more based on the total amount of the composition. When preparing a liquid crystal composition for STN or TN, the content of component E is preferably 30% by weight or more, more preferably 40% by weight or more based on the total amount of the composition.

The liquid crystal composition of the invention desirably comprise at least one kind of compounds represented by formula (1) of the invention in the range of 0.1% to 99% by weight for exhibiting excellent characteristics.

The liquid crystal composition of the invention is generally prepared according to known methods, such as a method for dissolving required components at a high temperature. Further, the liquid crystal composition (e) of the invention containing an optically active compound, for example, to be described below and a liquid crystal composition for a GH mode to which a dye is added can be prepared by adding additives well known to a person skilled in the art according to intended use. In general, the additives are well known to those in the art and are described in the literature and so forth in detail.

The liquid crystal composition (e) of the invention comprises the above liquid crystal composition of the invention and further comprises one or more kinds of optically active compounds.

A known chiral doping agent is added as an optically active compound. The chiral doping agent is effective in inducing a helical structure of liquid crystals, adjusting a twist angle required and then preventing a reverse twist. Examples of the chiral doping agents include the following optically active compounds (Op-1) to (Op-13).

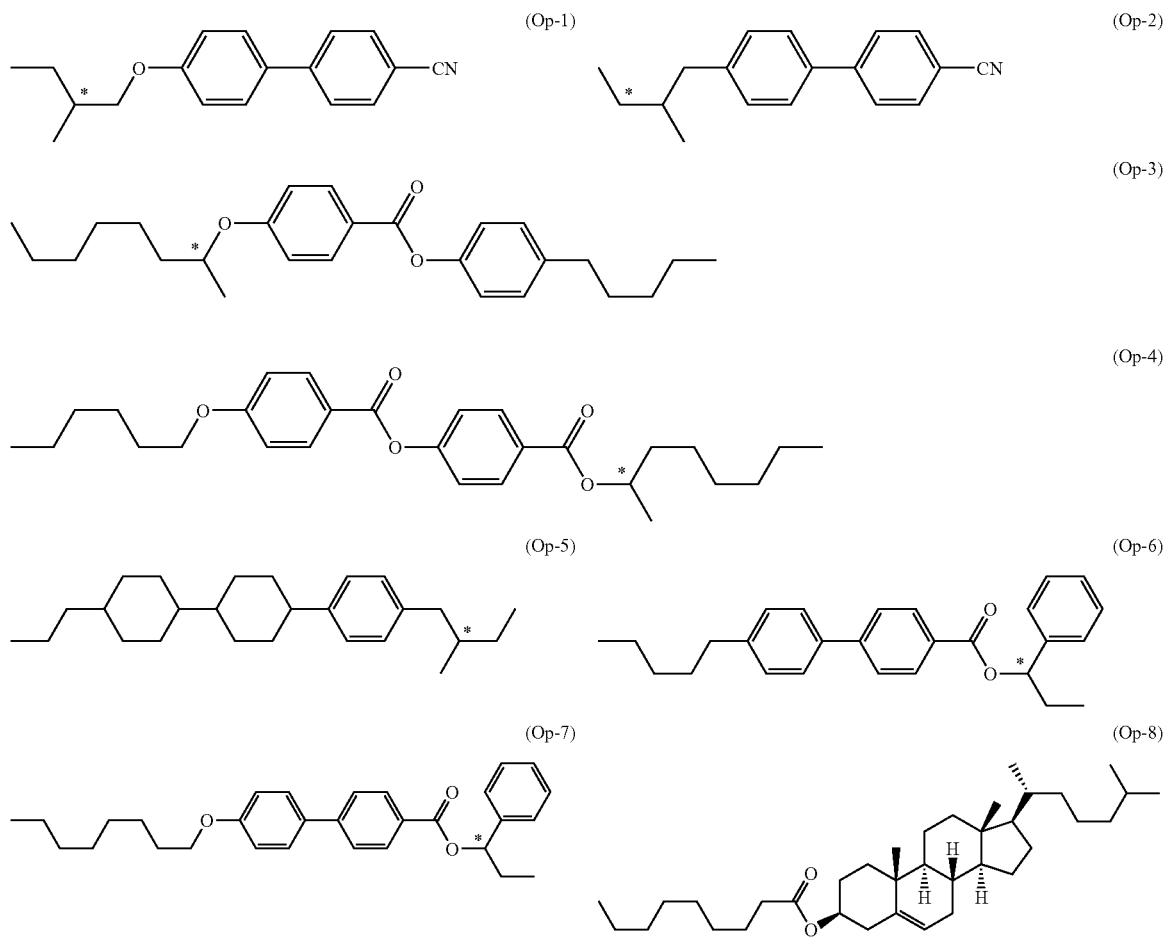

-continued

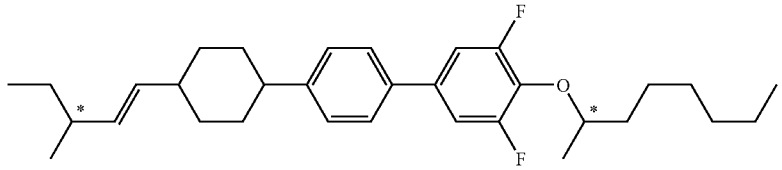
(Op-9)

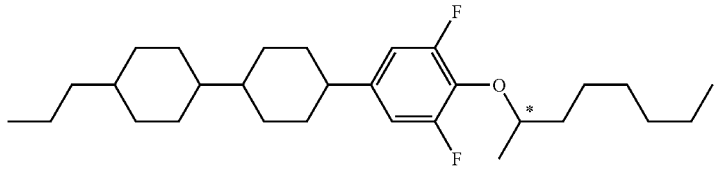
(Op-10)

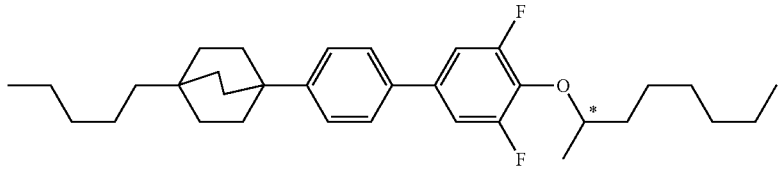
(Op-11)

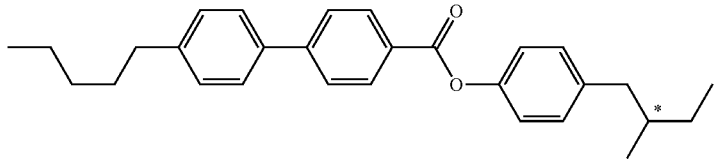
(Op-12)

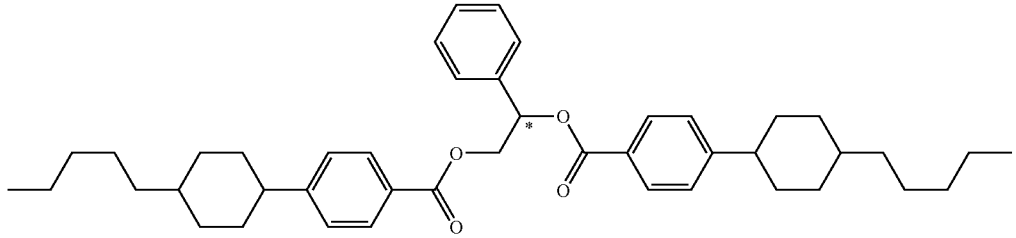
(Op-13)

These optically active compounds are generally added to the liquid crystal composition (e) of the invention to adjust a pitch of twisting. The pitch of twisting is desirably adjusted in the range of 40 micrometers to 200 micrometers in liquid crystal compositions for TFT and TN. In the case of a liquid crystal composition for STN, the pitch of twisting is desirably adjusted in the range of 6 micrometers to 20 micrometers. In the case of a bistable TN mode, the pitch of twisting is desirably adjusted in the range of 1.5 micrometers to 4 micrometers. Further, two or more kinds of optically active compounds may be added for the purpose of adjusting the temperature dependence of the pitch.

The liquid crystal composition of the invention can also be used as a liquid crystal composition for a GH mode by adding a dichroic dye, such as a merocyanine compound, a styryl compound, an azo compound, an azomethine compound, an azoxy compound, a quinophthalone compound, an anthraquinone compound, or a tetrazine compound.

Further, the liquid crystal composition of the invention can be used as liquid crystal compositions for NCAP prepared by micro-encapsulating nematic liquid crystals, and a polymer distributed liquid crystal display device (PDLCD) prepared by forming a three-dimensional network polymer in liquid crystals such as a polymer network liquid crystal display device (PNLCD), and also for a double refraction control (ECB) mode or a DS mode.

EXAMPLES

The invention will be explained below in more detail based on examples, but the invention is not limited to the examples. Unless otherwise specified, the term "%" means "% by weight".

Obtained compounds were identified by means of nuclear magnetic resonance spectra obtained by using $^1$H-NMR analyses, gas chromatograms obtained by using gas chromatography (GC) analyses and so forth, and methods for analyses will be explained.

$^1$H-NMR Analysis: A model DRX-500 apparatus (made by Bruker BioSpin Corporation) was used for measurement. Samples prepared in examples and so forth were dissolved in deuterated solvents such as $CDCl_3$ in which the samples were soluble, and measurement was carried out under the conditions of room temperature, twenty four times of accumulation and 500 MHz. In the explanation of obtained nuclear magnetic resonance spectra, s, t, d, t, q, and m stand for singlet, doublet, triplet, quartet, and multiplet, respectively. Tetramethylsilane (TMS) was used as a zero-point reference material for a chemical shift δ value.

GC Analysis: A Gas Chromatograph Model GC-14B made by Shimadzu Corporation was used for measurement. A capillary column CBP1-M25-025 (length 25 m, bore 0.22 mm, film thickness 0.25 μm; dimethylpolysiloxane as a stationary phase; non-polar) made by Shimadzu Corporation was used. Helium was used as a carrier gas, and the flow rate was adjusted to 1 ml per minute. The temperature of the sample injector was set at 300° C. and the temperature of the detector (FID) part at 300° C.

A sample was dissolved in toluene and prepared to be a solution of 1% by weight, and then 1 microliter of the obtained solution was injected into the sample injector.

Chromatopac Model C-R6A made by Shimadzu Corporation or its equivalent was used as a recorder. The resulting gas chromatogram indicated retention times of peaks and values of peak areas corresponding to component compounds.

Chloroform or hexane, for example, may be used as a solvent for diluting the sample. The following capillary columns may also be used: DB-1 (length 30 m, bore 0.32 mm, film thickness 0.25 μm) made by Agilent Technologies Inc., HP-1 (length 30 m, bore 0.32 mm, film thickness 0.25 μm) made by Agilent Technologies Inc., Rtx-1 (length 30 m, bore 0.32 mm, film thickness 0.25 μm) made by Restek Corporation, BP-1 (length 30 m, bore 0.32 mm, film thickness 0.25 μm) made by SGE International Pty. Ltd, and so forth.

An area ratio of peaks in the gas chromatogram corresponds to the ratio of component compounds. In general, the weight % of a component compound as an analytical sample is not completely the same with the area ratio of each peak of the analytical sample. In the invention, however, the weight % of the component compound in the analytical sample substantially corresponds to the area % of each peak in the analytical sample, when the columns described above are used, because the correction coefficient is essentially 1. This is because there is no significant difference in the correction coefficient of liquid crystal compounds as components. In the use of the gas chromatogram, an internal standard method based on the gas chromatogram is used in order to determine more accurately the composition ratio of the liquid crystal compounds in the liquid crystal composition. The components of each liquid crystal compound (test-component) weighed accurately in a fixed amount and a liquid crystal compound (standard reference) serving as a standard are mixed and measured by means of the gas chromatography. First, the relative intensity between the obtained area ratio of the peak of the test-component and the peak of the standard reference is calculated in advance. Next, the composition ratio of the liquid crystal compounds in the liquid crystal composition can be determined more accurately from the gas-chromatographic analysis by correcting with the relative intensity of the peak area of each component to the standard reference.

[Samples for Measuring Physical Property Values of Liquid Crystal Compounds and So Forth]

Two kinds of samples were used for measuring the physical property values of liquid crystal compounds: one was a compound itself, and the other was a mixture of a compound and mother liquid crystals.

In the latter case using a sample in which a compound is mixed with mother liquid crystals, measurement was carried out according to the following method. First, the sample was prepared by mixing 15% by weight of an obtained liquid crystal compound and 85% by weight of the mother liquid crystals. Then, extrapolated values were calculated from the measured values of the obtained sample according to an extrapolation method based on the following formula. The extrapolated values were regarded as the physical property values of the compound.

<Extrapolated value>=(100×<Measured value of sample>−<% by weight of mother liquid crystals>×<Measured value of mother liquid crystals>)/<% by weight of liquid crystal compound>

When a smectic phase or crystals separated out at even at this ratio of the liquid crystal compound to the mother liquid crystals 25° C., the ratio of the liquid crystal compound to the mother liquid crystals is changed in the order of 10% by weight:90% by weight, 5% by weight:95% by weight, and 1% by weight:99% by weight. The physical property values of a sample were measured using a composition ratio in which the smectic phase or the crystals are not deposited at 25° C. Extrapolated values are determined according to the above equation, and regarded as the physical property values of the liquid crystal compound.

There are a variety of kinds as mother liquid crystals used for measurement, and for example, the composition ratio (% by weight) of the mother liquid crystals A is as shown below.

Mother Liquid Crystals A:

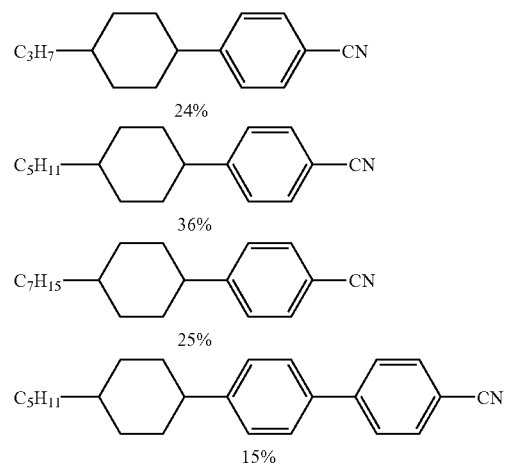

[Method for Measuring Physical Property Values of Liquid Crystal Compounds and So Forth]

Physical property values were measured according to methods to be described later. Most of the measurement methods are described in the Standard of Electronic Industries Association of Japan, EIAJ.ED-2521A, or those with some modifications. No TFT was attached to a TN device used for measurement.

As for measured values, obtained values were described as experimental data when a sample was a liquid crystal compound itself. When a sample was a mixture of a liquid crystal compound and mother liquid crystals, values obtained by means of the extrapolation method were described as experimental data.

Phase Structure and Phase Transition Temperature (° C.): Measurement was carried out according to the following methods (1) and (2).

(1) A compound was placed on a hot plate in a melting point apparatus equipped with a polarizing microscope (Hot Stage Model FP-52 made by Mettler Toledo International Inc.), and phase conditions and their changes were observed with the polarizing microscope while heating at the rate of 3° C. per minute to specify the kind of liquid crystal phase.

(2) A sample was heated and then cooled at the rate of 3° C. per minute using a Perkin-Elmer differential scanning calorimeter, a DSC-7 System or a Diamond DSC System. A starting point of an endothermic peak or an exothermic peak caused by a phase change of the sample was obtained by using the extrapolation and the phase transition temperature was determined.

In the following, the symbol C stands for crystals, which were expressed by $C_1$ or $C_2$ when kinds of crystals were distinguishable. The symbols S and N stand for a smectic phase and a nematic phase, respectively. The symbol I stands for a liquid (isotropic). When a smectic A phase, a smectic B phase, a smectic C phase, or a smectic F phase is distinguishable in the smectic phase, they were expressed as $S_A$, $S_B$, $S_C$, or $S_F$, respectively. Phase transition temperatures were expressed as, for example, "C 50.0 N 100.0 I", which means that a phase transition temperature from crystals to a nematic phase (CN) is 50.0° C., and a phase transition temperature from the nematic phase to a liquid (NI) is 100.0° C. The same applies to other phase transition temperatures.

Maximum Temperature of Nematic Phase ($T_{NI}$; ° C.): A sample (a mixture of a liquid crystal compound and mother liquid crystals) was placed on a hot plate in a melting point apparatus (Hot Stage Model FP-52 made by Mettler Toledo International Inc.) equipped with a polarizing microscope, and was observed with the polarizing microscope while heating at the rate of 1° C. per minute. The maximum temperature of a nematic phase was a temperature at which part of the sample began to change from a nematic phase to an isotropic liquid. In the following, the maximum temperature of the nematic phase may simply be abbreviated to "a maximum temperature".

Compatibility at low temperature: Samples were prepared by mixing a compound with mother liquid crystals so that the amount of the liquid crystal compound became 20% by weight, 15% by weight, 10% by weight, 5% by weight, 3% by weight, and 1% by weight, and placed in glass vials. After these glass vials had been kept in a freezer at −10° C. or −20° C. for a certain period, they were observed whether or not crystals or a smectic phase had been deposited.

Viscosity ($\eta$; measured at 20° C.; mPa·s): A mixture of a liquid crystal compound and mother liquid crystals was measured using an E-type viscometer.

Refractive Index Anisotropy ($\Delta n$): Measurement was carried out at 25° C. with an Abbe refractometer equipped with a polarizing plate on an ocular, using light at a wavelength of 589 nm. The surface of a main prism was rubbed in one direction, and then a sample (a mixture of a liquid crystal compound and mother liquid crystals) was dropped on the main prism. A refractive index (n∥) was measured when a direction of polarized light was parallel to the direction of the rubbing. A refractive index (n⊥) was measured when a direction of polarized light was perpendicular to the direction of the rubbing. The value of the refractive index anisotropy ($\Delta n$) was calculated from the equation: $\Delta n = n\| - n\bot$.

Dielectric Anisotropy ($\Delta \in$; measured at 25° C.): A sample (a mixture of a liquid crystal compound and mother liquid crystals) was put in a liquid crystal cell having a distance (a gap) between two glass plates of about 9 micrometers and a twist angle of 80 degrees. A voltage of 20 V was applied to the cell, and a dielectric constant ($\in\|$) in a major axis direction of liquid crystal molecules was measured. A voltage of 0.5 V was applied, and a dielectric constant ($\in\bot$) in a minor axis direction of liquid crystal molecules was measured. The value of the dielectric anisotropy was calculated from the equation: $\Delta\in = \in\| - \in\bot$.

Example 1

Synthesis of 4-[difluoro(3,4,5-trifluorophenoxy)methyl]-4''-pentyl-2',2'',3,5-tetrafluoro-1,1',4',1'',4'',1'''-quarterphenyl (No. 1-4-5)

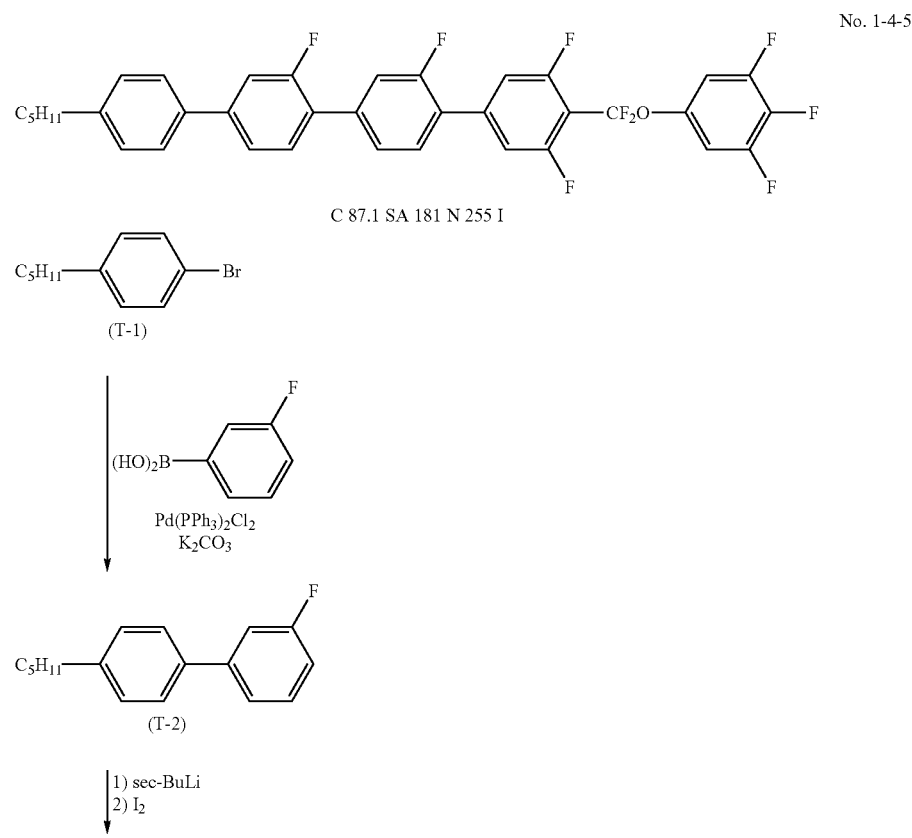

-continued
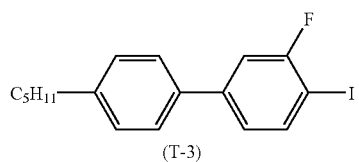
(T-3)
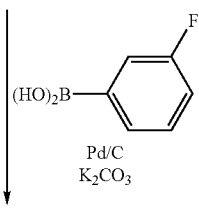
Pd/C
K₂CO₃
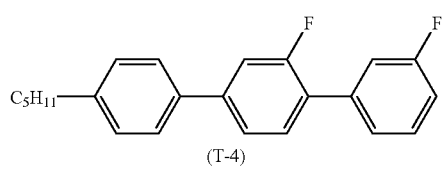
(T-4)
1) sec-BuLi
2) I₂
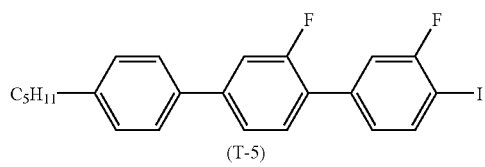
(T-5)
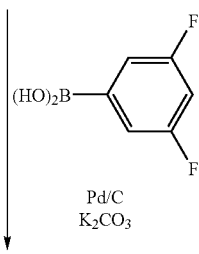
Pd/C
K₂CO₃
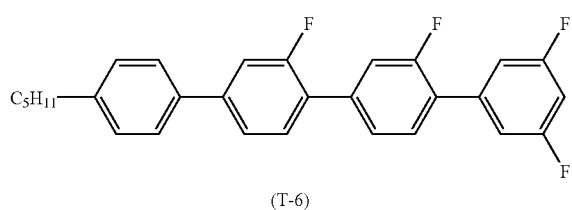
(T-6)
1) n-BuLi
2) CF₂Br₂

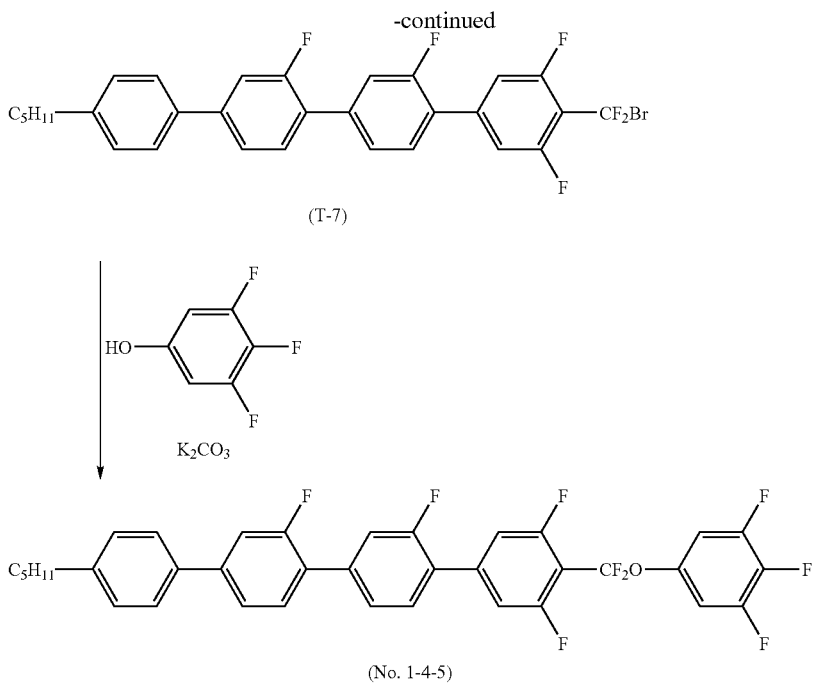

[Synthesis of the Compound (T-2)]

1-Bromo-4-pentylbenzene (T-1; 50.0 g), 3-fluorophenylboronic acid (31.4 g), potassium carbonate (91.2 g), Pd(Ph$_3$P)$_2$Cl$_2$ (4.63 g), toluene (150 ml), Solmix A-11 (150 ml), and water (150 ml) were added to a reaction vessel under a nitrogen atmosphere, and heated under reflux for 3 hours. The reaction mixture was cooled to 25° C., and then poured into water (500 ml) and toluene (500 ml) and mixed. Then, the mixture was allowed to stand to be separated into two layers of organic and aqueous layers, and the extraction to an organic layer was carried out. The obtained organic layer was fractionated, washed with water, and then dried over anhydrous magnesium sulfate. The obtained solution was concentrated under reduced pressure, and the residue was purified with a fractional operation by means of column chromatography using heptane as the eluent and silica gel as the stationary phase powder. The product was further purified by recrystallization from Solmix A-11 and dried, whereby 45.2 g of 3-fluoro-4'-pentylbiphenyl (T-2) was obtained. The yield based on the compound (T-1) was 85%.

[Synthesis of the Compound (T-3)]

The compound (T-2; 45.2 g) and THF (300 ml) were added to a reaction vessel under a nitrogen atmosphere, and cooled to −74° C., and sec-Butyl lithium (1.0 M, in cyclohexane and n-hexane solution; 222 ml) was added dropwise thereto in the temperature range of −74° C. to −68° C., and stirred for additional 120 minutes. Subsequently, iodine (61.7 g) in a THF (350 ml) solution was added dropwise in the temperature range of −75° C. to −68° C., and stirred for additional 60 minutes. The obtained reaction mixture was allowed to come to 25° C., and then poured into ice-water (650 ml) and mixed. Toluene (500 ml) was added and the extraction including separation into organic and aqueous layers was carried out. The obtained organic layer was fractionated, washed sequentially with an aqueous solution of sodium thio sulfate and brine, and then dried over anhydrous magnesium sulfate. The obtained solution was concentrated under reduced pressure, and the residue was purified with a fractional operation by means of column chromatography using heptane as the eluent and silica gel as the stationary phase powder. The solvent was distilled off and the product was dried, whereby 58.7 g of 3-fluoro-4-iodo-4'-pentylbiphenyl (T-3) was obtained. The yield based on the compound (T-2) was 85%.

[Synthesis of the Compound (T-4)]

3-Fluoro-4-iodo-4'-pentylbiphenyl (T-3; 30.0 g), 3-fluorophenylboronic acid (12.5 g), potassium carbonate (33.8 g), Pd/C (NX type; 0.175 g), toluene (100 ml), Solmix A-11 (100 ml), and water (100 ml) were added to a reaction vessel under a nitrogen atmosphere, and heated under reflux for 2 hours. The reaction mixture was cooled to 25° C., and then poured into water (300 ml) and toluene (200 ml) and mixed. Then, the mixture was allowed to stand to be separated into two layers of organic and aqueous layers, and the extraction to an organic layer was carried out. The obtained organic layer was fractionated, washed with water, and then dried over anhydrous magnesium sulfate. The obtained solution was concentrated under reduced pressure, and the residue was purified with a fractional operation by means of column chromatography using heptane as the eluent and silica gel as the stationary phase powder. The product was further purified by recrystallization from a mixed solvent of heptane and Solmix A-11 and dried, whereby 16.1 g of 2',3-difluoro-4"-pentyl-1,1',4,1"-terphenyl (T-4) was obtained. The yield based on the compound (T-3) was 59%.

[Synthesis of the Compound (T-5)]

The compound (T-4; 16.1 g) and THF (200 ml) were added to a reaction vessel under a nitrogen atmosphere, and cooled to −74° C. Then, sec-butyl lithium (1.0 M, in cyclohexane and n-hexane solution; 57.5 ml) was added dropwise thereto in the temperature range of −74° C. to −68° C., and stirred for additional 120 minutes. Subsequently, iodine (15.8 g) in a THF (100 ml) solution was added dropwise in the temperature range of −75° C. to −68° C., and stirred for additional 60 minutes. The obtained reaction mixture was allowed to come to 25° C., and then poured into ice-water (300 ml) and mixed. Toluene (200 ml) was added and extraction including separation into organic and aqueous layers was carried out. The obtained organic layer was fractionated, washed sequentially with an aqueous solution of sodium thiosulfate and brine, and then dried over anhydrous magnesium sulfate. The obtained solution was concentrated under reduced pressure, and the residue was purified with a fractional operation by means of column chromatography using heptane as the eluent and silica gel as the stationary phase powder. The solvent was distilled off and the product was dried, whereby 21.9 g of 2',3-difluoro-4-iodo-4'''-pentyl-1,1',4',1''-terphenyl (T-5) was obtained. The yield based on the compound (T-4) was 99%.

[Synthesis of the Compound (T-6)]

2',3-Difluoro-4-iodo-4''-pentyl-1,1',4',1''-terphenyl (T-5; 10.0 g), 3,5-difluorophenylboronic acid (3.76 g), potassium carbonate (8.96 g), Pd/C (NX type; 0.0460 g), toluene (70.0 ml), Solmix A-11 (70.0 ml), and water (70.0 ml) were put in a reaction vessel under a nitrogen atmosphere, and heated under reflux for 2 hours. The reaction mixture was cooled to 25° C., and then poured into water (200 ml) and toluene (200 ml) and mixed. Then, the mixture was allowed to stand to be separated into two layers of organic and aqueous layers, and the extraction to an organic layer was carried out. The obtained organic layer was fractionated, washed with water, and then dried over anhydrous magnesium sulfate. The obtained solution was concentrated under reduced pressure, and the residue was purified with a fractional operation by means of column chromatography using heptane as the eluent and silica gel as the stationary phase powder. The product was further purified by recrystallization from a mixed solvent of heptane/Solmix A-11 and dried, whereby 6.89 g of 4'''-pentyl-2',2'',3,5-tetrafluoro-1,1',4',1'',4'',1'''-quarterphenyl (T-6) was obtained. The yield based on the compound (T-5) was 71%.

[Synthesis of the Compound (T-7)]

The compound (T-6; 5.00 g) and THF (130 ml) were put in a reaction vessel under a nitrogen atmosphere, and cooled to −74° C. Then, n-butyl lithium (1.60 M, in n-hexane solution; 9.10 ml) was added dropwise thereto in the temperature range of −74° C. to −70° C., and stirred for additional 60 minutes. Subsequently, dibromodifluoromethane (3.50 g) in a THF (20.0 ml) solution was added dropwise in the temperature range of −75° C. to −70° C., and stirred for additional 60 minutes while allowing temperature to come to 25° C. The obtained reaction mixture was poured into ice-water (150 ml) and mixed. Then, toluene (150 ml) was added thereto and the extraction including separation into organic and aqueous layers was carried out. The obtained organic layer was fractionated, washed with brine, and then dried over anhydrous magnesium sulfate. The obtained solution was concentrated under reduced pressure, and the residue was purified with a fractional operation by means of column chromatography using heptane as the eluent and silica gel as the stationary phase powder. The solvent was distilled off and the product was dried, whereby 5.44 g of 4-bromodifluoromethyl-4'''-pentyl-2',2'',3,5-tetrafluoro-1,1',4',1'',4'',1'''-quarterphenyl (T-7) was obtained. The yield based on the compound (T-6) was 85%.

[Synthesis of the Compound (No. 1-4-5)]

3,4,5-Trifluorophenol (1.23 g), potassium carbonate (2.87 g), and N,N-dimethylformamide (DMF; 25.0 ml) were put in a reaction vessel under a nitrogen atmosphere, and stirred at 115° C. for 30 minutes. Subsequently, the compound (T-7; 4.00 g) in a DMF (75.0 ml) solution was added dropwise, and stirred at 115° C. for additional 1 hour. The reaction mixture was allowed to come to 25° C., and then poured into ice-water (100 ml) and mixed. Then, toluene (150 ml) was added thereto and the extraction including separation into organic and aqueous layers was carried out. The obtained organic layer was fractionated, washed sequentially with a saturated aqueous solution of sodium bicarbonate, an aqueous solution of 0.5N-sodium hydroxide and brine, and then dried over anhydrous magnesium sulfate. The obtained solution was concentrated under reduced pressure, and the residue was purified with a fractional operation by means of column chromatography using heptane as the eluent and silica gel as the stationary phase powder. The product was further purified by recrystallization from a mixed solvent of heptane/Solmix A-11 and dried, whereby 2.06 g of 4-[difluoro(3,4,5-trifluorophenoxy)methyl]-4''-pentyl-2',2'',3,5-tetrafluoro-1,1',4',1'',4'',1'''-quarterphenyl (No. 1-4-5) was obtained. The yield based on the compound (T-7) was 46%.

The phase transition temperature of the obtained compound (No. 1-4-5) was as follows.

Phase transition temperature: C 87.1 $S_A$ 181 N 255 I.

The chemical shift δ (ppm) of $^1$H-NMR analysis was as indicated below, and the obtained compound was identified as 4-[difluoro(3,4,5-trifluorophenoxy)methyl]-4'''-pentyl-2',2'',3,5-tetrafluoro-1,1',4',1'',4'',1'''-quarterphenyl. The measurement solvent was $CDCl_3$.

Chemical shift δ (ppm); 7.58-7.39 (m, 8H), 7.34-7.25 (m, 4H), 7.07-6.95 (m, 2H), 2.67 (t, J=8.00 Hz, 2H), 1.74-1.60 (m, 2H), 1.44-1.31 (m, 4H), 0.91 (t, J=6.65 Hz, 3H).

Example 2

Physical Properties of Liquid Crystal Compound (No. 1-4-5)

The above four compounds described as the mother liquid crystals A were mixed to prepare mother liquid crystals A having a nematic phase. The physical properties of the mother liquid crystals A were as follows.

Maximum temperature $(T_{NI})$=71.7° C.; refractive index anisotropy (Δn)=0.137; dielectric anisotropy (Δ∈)=11.0.

The liquid crystal composition B consisting of the mother liquid crystals A (85% by weight) and 4-[difluoro(3,4,5-trifluorophenoxy)methyl]-4'''-pentyl-2',2'',3,5-tetrafluoro-1,1',4',1'',4'',1'''-quarterphenyl (No. 1-4-5; 15% by weight) obtained in Example 1 was prepared. The physical property values of the obtained liquid crystal composition B were measured, and the extrapolated values of the physical properties of the liquid crystal compound (No. 1-4-5) were calculated by extrapolating the measured values. The values were as follows.

Maximum temperature $(T_{NI})$=169° C.; refractive index anisotropy (Δn)=0.257; dielectric anisotropy (Δ∈)=36.7.

From these results, it was found that the liquid crystal compound (No. 1-4-5) was a compound having a high maximum temperature $(T_{NI})$, a large refractive index anisotropy (Δn), and a large dielectric anisotropy (Δ∈).

Example 3
Synthesis of 4-[difluoro-[(2,3',4',5'-tetrafluoro[1,1'-biphenyl]-4-yl)-oxy]methyl]-4''-pentyl-2',3,5-trifluoro-1,1'4'1''-terphenyl (No. 1-3-5)
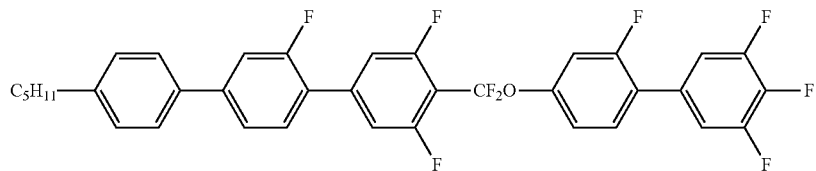
C 79.4 SA 138 N 223 I
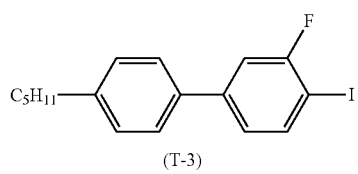
(T-3)
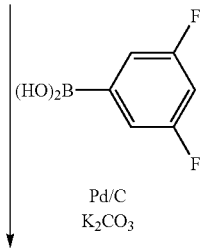
Pd/C
K$_2$CO$_3$
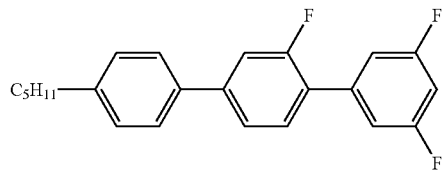
(T-8)
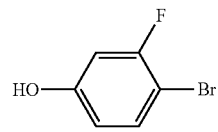
(T-10)
1) n-BuLi
2) CF$_2$Br$_2$
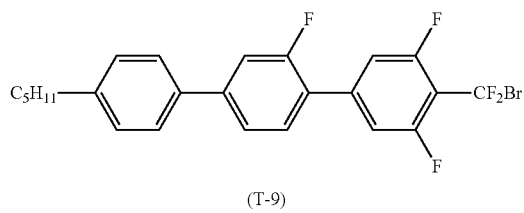
(T-9)
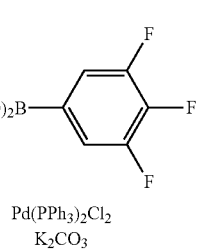
Pd(PPh$_3$)$_2$Cl$_2$
K$_2$CO$_3$
K$_2$CO$_3$
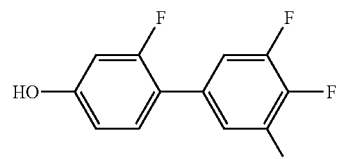
(T-11)

-continued

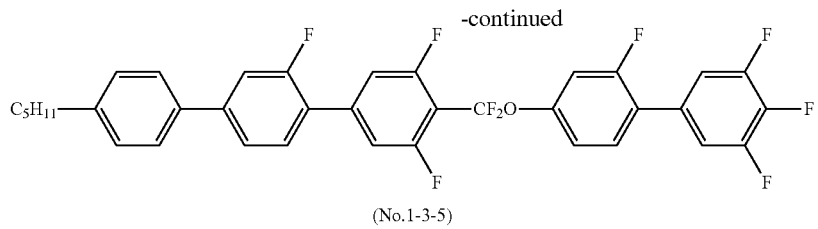

(No.1-3-5)

[Synthesis of the Compound (T-8)]

3-Fluoro-4-iodo-4'-pentylbiphenyl (T-3; 64.0 g), 3,5-difluorophenylboronic acid (30.3 g), potassium carbonate (73.0 g), Pd/C (NX type; 0.372 g), toluene (200 ml), Solmix A-11 (200 ml), and water (200 ml) were put in a reaction vessel under a nitrogen atmosphere, and heated under reflux for 2 hours. The reaction mixture was cooled to 25° C., and then poured into water (600 ml) and toluene (400 ml) and mixed. Then, the mixture was allowed to stand to be separated into two layers of organic and aqueous layers, and the extraction to an organic layer was carried out. The obtained organic layer was fractionated, washed with water, and then dried over anhydrous magnesium sulfate. The obtained solution was concentrated under reduced pressure, and the residue was purified with a fractional operation by means of column chromatography using heptane as the eluent and silica gel as the stationary phase powder. The product was further purified by recrystallization from a mixed solvent of heptane/Solmix A-11 and dried, whereby 40.2 g of 2',3,5-trifluoro-4"-pentyl-1,1',4'1"-terphenyl (T-8) was obtained. The yield based on the compound (T-3) was 65%.

[Synthesis of the Compound (T-9)]

The compound (T-8; 5.00 g) and THF (65 ml) were put in a reaction vessel under a nitrogen atmosphere, and cooled to −74° C. Then, n-butyl lithium (1.60 M, in n-hexane solution; 11.5 ml) was added dropwise thereto in the temperature range of −74° C. to −70° C., and stirred for additional 60 minutes. Subsequently, dibromodifluoromethane (4.45 g) in a THF (25.0 ml) solution was added dropwise in the temperature range of −75° C. to −70° C., and stirred for additional 60 minutes while temperature was allowed to come to 25° C. The obtained reaction mixture was poured into ice-water (90.0 ml) and mixed. Toluene (70 ml) was added thereto and the extraction including separation into organic and aqueous layers was carried out. The obtained organic layer was fractionated, washed brine, and then dried over anhydrous magnesium sulfate. The obtained solution was concentrated under reduced pressure, and the residue was purified with a fractional operation by means of column chromatography using heptane as the eluent and silica gel as the stationary phase powder. The solvent was distilled off and the product was dried, whereby 5.49 g of 4-bromodifluoromethyl-4"-pentyl-2',3,5-trifluoro-1,1',4',1"-terphenyl (T-9) was obtained. The yield based on the compound (T-8) was 81%.

[Synthesis of the Compound (T-11)]

4-Bromo-3-fluorophenol (T-10; 5.00 g), 3,4,5-trifluorophenylboronic acid (5.07 g), potassium carbonate (10.9 g), Pd(Ph$_3$P)$_2$Cl$_2$ (0.552 g), and 2-propanol were put in a reaction vessel under a nitrogen atmosphere, and heated under reflux for 5 hours. The reaction mixture was cooled to 25° C., and then poured into water (100 ml) and toluene (100 ml) and mixed. Then, the mixture was allowed to stand to be separated into two layers of organic and aqueous layers, and the extraction to an organic layer was carried out. The obtained organic layer was fractionated, washed with water, and then dried over anhydrous magnesium sulfate. The obtained solution was concentrated under reduced pressure, and the residue was purified with a fractional operation by means of column chromatography using toluene as the eluent and silica gel as the stationary phase powder. The product was further purified by recrystallization from a mixed solvent of heptane/Solmix A-11 and dried, whereby 4.79 g of 4-hydroxy-2,3',4',5'-tetrafluoro-1,1'-biphenyl (T-11) was obtained. The yield based on the compound (T-1) was 74%.

[Synthesis of the Compound (No. 1-3-5)]

The compound (T-11; 2.10 g) obtained as described above, potassium carbonate (3.00 g), and N,N-dimethylformamide (DMF; 30.0 ml) were put in a reaction vessel under a nitrogen atmosphere, and stirred at 115° C. for 30 minutes. Subsequently, the compound (T-9; 3.50 g) in a DMF (55.0 ml) solution was added dropwise, and stirred at 115° C. for additional 1 hour. The reaction mixture was allowed to come to 25° C., and then poured into ice-water (85.0 ml) and mixed. Toluene (100 ml) was added thereto and the extraction including separation into organic and aqueous layers was carried out. The obtained organic layer was fractionated, washed sequentially with a saturated aqueous solution of sodium bicarbonate, an aqueous solution of 0.5N-sodium hydroxide and brine, and then dried over anhydrous magnesium sulfate. The obtained solution was concentrated under reduced pressure, and the residue was purified with a fractional operation by means of column chromatography using heptane as the eluent and silica gel as the stationary phase powder. The product was further purified by recrystallization from a mixed solvent of heptane/Solmix A-11 and dried, whereby 2.30 g of 4-[difluoro[(2,3',4',5'-tetrafluoro[1,1'-biphenyl]-4-yl)oxy]methyl]-4"-pentyl-2',3,5-trifluoro-1,1',4',1"-terphenyl (No. 1-3-5) was obtained. The yield based on the compound (T-9) was 49%.

The phase transition temperature of the obtained compound (No. 1-3-5) was as follows.

Phase transition temperature: C 79.4 S$_A$ 138 N 223 I.

The chemical shift δ (ppm) of $^1$H-NMR analysis was as indicated below, and the obtained compound was identified as 4-[difluoro-[(2,3',4',5'-tetrafluoro[1,1'-biphenyl]-4-yl)oxy]methyl]-4"-pentyl-2',3,5-trifluoro-1,1',4',1"-terphenyl. The measurement solvent was CDCl$_3$.

Chemical shift δ (ppm); 7.58-7.46 (m, 4H), 7.46-7.35 (m, 2H), 7.32-7.24 (m, 4H), 7.24-7.13 (m, 4H), 2.67 (t, J=7.85 Hz, 2H), 1.74-1.60 (m, 2H), 1.44-1.31 (m, 4H), 0.91 (t, J=6.95 Hz, 3H).

Example 4

Physical Properties of Liquid Crystal Compound (No. 1-3-5)

The liquid crystal composition C consisting of the mother liquid crystals A (85% by weight) and 4-[difluoro[(2,3',4',5'-tetrafluoro[1,1'-biphenyl]-4-yl)oxy]methyl]-4"-pentyl-2',3,5-trifluoro-1,1',4'1"-terphenyl (No. 1-3-5; 15% by weight)

obtained in Example 3 was prepared. The physical property values of the obtained liquid crystal composition C were measured, and the extrapolated values of the physical properties of the liquid crystal compound (No. 1-3-5) were calculated by extrapolating the measured values. The values were as follows.

Maximum temperature $(T_{NI})$=146° C.; refractive index anisotropy $(\Delta n)$=0.237; dielectric anisotropy $(\Delta \in)$=39.0.

From these results, it was found that the liquid crystal compound (No. 1-3-5) was a compound having a high maximum temperature $(T_{NI})$, a large dielectric anisotropy $(\Delta \in)$, and a large refractive index anisotropy $(\Delta n)$.

Example 5

Synthesis of 4-[difluoro[(2,3',4',5'-tetrafluoro[1,1'-biphenyl]-4-yl)oxy]methyl]-4"-propyl-2',3,5-trifluoro-1,1',4',1"-terphenyl (No. 1-3-3)

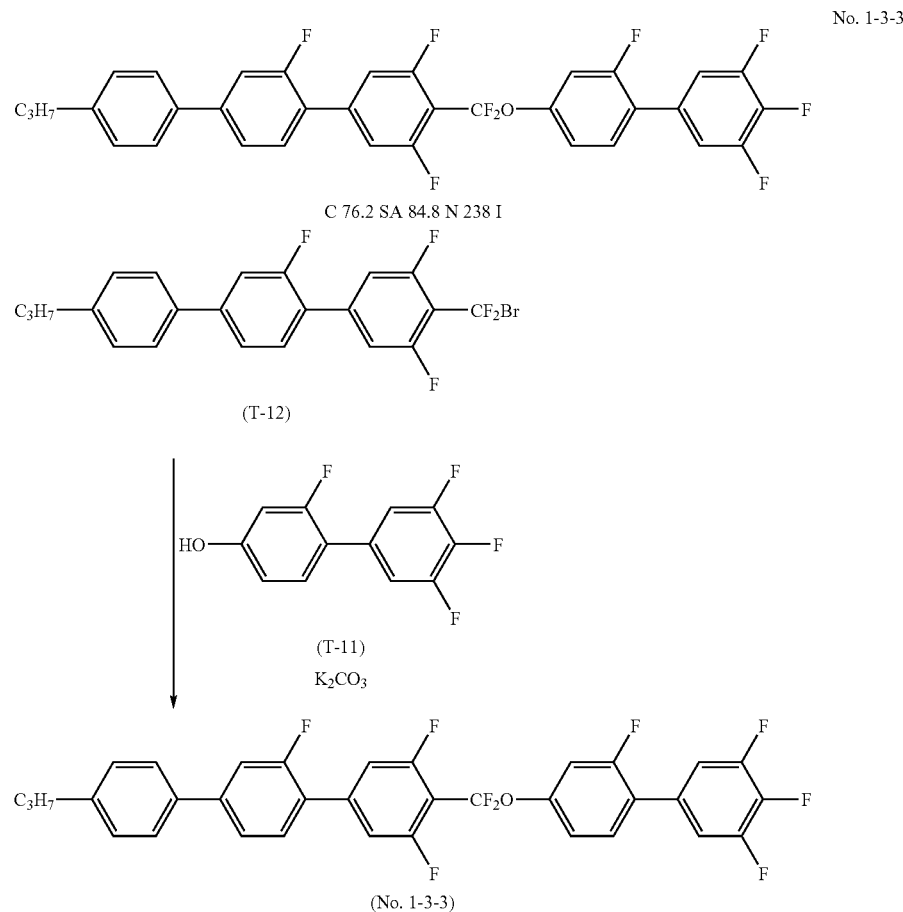

[Synthesis of the Compound (1-3-3)]

Using 4-bromodifluoromethyl-4"-propyl-2',3,5-trifluoro-1,1',4',1"-terphenyl (T-12; 5.00 g) as a raw material, 3.26 g of 4-[difluoro[(2,3',4',5'-tetrafluoro[1,1'-biphenyl]-4-yl)oxy]methyl]-4"-propyl-2',3,5-trifluoro-1,1',4',1"-terphenyl (1-3-3) was obtained according to a method similar to that for the synthesis of the compound (1-3-5) in Example 3. The yield based on the compound (T-12) was 48%.

The phase transition temperature of the obtained compound (No. 1-3-3) was as follows.

Phase transition temperature: C 76.2 $S_A$ 84.8 N 238 I.

The chemical shift δ (ppm) of $^1$H-NMR analysis is as indicated below, and the obtained compound was identified as 4-[difluoro[(2,3',4',5'-tetrafluoro[1,1'-biphenyl]-4-yl)oxy]methyl]-4"-propyl-2',3,5-trifluoro-1,1',4'1"-terphenyl. The measurement solvent was $CDCl_3$.

Chemical shift δ (ppm); 7.58-7.46 (m, 4H), 7.45-7.35 (m, 2H), 7.32-7.24 (m, 4H), 7.23-7.13 (m, 4H), 2.65 (t, J=7.80 Hz, 2H), 1.74-1.65 (m, 2H), 0.98 (t, J=7.45 Hz, 3H).

Example 6

Physical Properties of Liquid Crystal Compound (No. 1-3-3)

The liquid crystal composition D consisting of the mother liquid crystals A (85% by weight) and 4-[difluoro[(2,3',4',5'-tetrafluoro[1,1'-biphenyl]-4-yl)oxy]methyl]-4"-propyl-2',3,5-trifluoro-1,1',4',1"-terphenyl (No. 1-3-3; 15% by weight) obtained in Example 5 was prepared. The physical property values of the obtained liquid crystal composition D were measured, and the extrapolated values of the physical properties of the liquid crystal compound (No. 1-3-3) were calculated by extrapolating the measured values. The values were as follows.

Maximum temperature $(T_{NI})$=148° C.; refractive index anisotropy $(\Delta n)$=0.244; dielectric anisotropy $(\Delta \in)$=45.2.

From these results, it was found that the liquid crystal compound (No. 1-3-3) was a compound having a high maximum temperature $(T_{NI})$, a large refractive index anisotropy $(\Delta n)$, and an especially large dielectric anisotropy $(\Delta \in)$.

Example 7

Synthesis of 4-[difluoro[(2,3'-difluoro-4'-trifluoromethoxy[1,1'-biphenyl]-4-yl)oxy]methyl]-4"-pentyl-2',3,5-trifluoro-1,1',4',1"-terphenyl (No. 1-3-70)

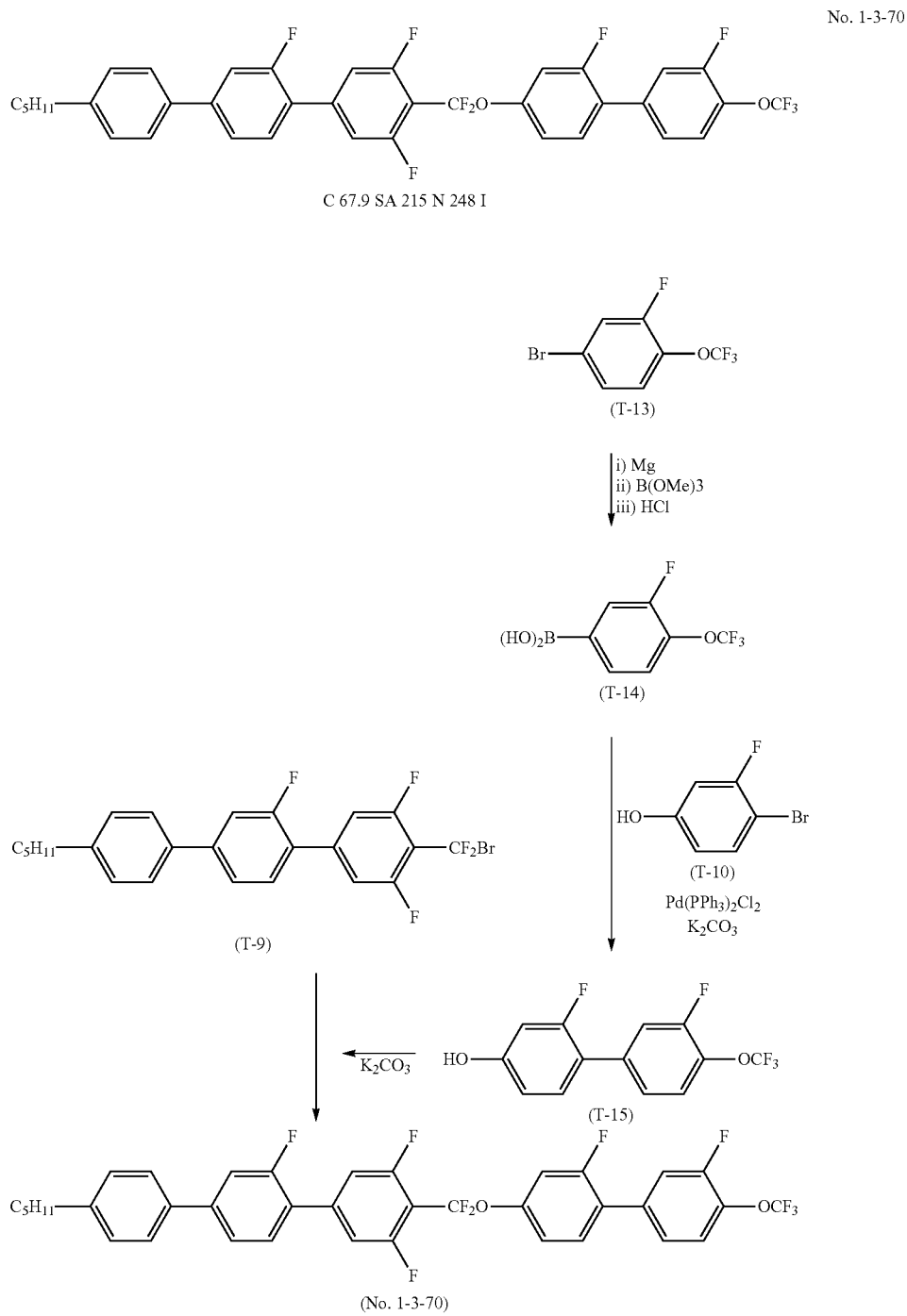

[Synthesis of the Compound (T-14)]

Well-dried magnesium (3.05 g) and THF (20.0 ml) were put in a reaction vessel under a nitrogen atmosphere, and heated to 55° C. Then, 1-bromo-3-fluoro-4-trifluoromethoxybenzene (T-13; 25.0 g) dissolved in THF (100 ml) was slowly added dropwise thereto in the temperature range of 47° C. to 60° C., and stirred for additional 60 minutes. The obtained Grignard reagent was added dropwise to trimethyl borate (14.0 g) in a THF (100 ml) solution in the temperature range of −74° C. to −65° C., and stirred for additional 180 minutes while allowing temperature to come to 25° C. After the reaction mixture had been cooled to −30° C., 6N-hydrochloric acid (90 ml) was slowly added dropwise and stirred for additional 180 minutes while temperature was allowed to come to 25° C. Then, the reaction mixture was poured into a vessel containing ice-water (250 ml) and 3,000 ml, and mixed. Ethyl acetate (300 ml) was added to separate the mixture into organic and aqueous layers, and an extraction operation was carried out. The obtained organic layer was fractionated, washed sequentially with water, a saturated aqueous solution of sodium bicarbonate and brine, and then dried over anhydrous magnesium sulfate. Then, the solvent was distilled off under reduced pressure, whereby 11.7 g of 3-fluoro-4-trifluoromethoxy phenylboronic acid (T-14) was obtained. The yield based on the compound (T-13) was 54%.

[Synthesis of the Compound (T-15)]

Using the compound (T-14) obtained as described above, 9.26 g of 2,3'-difluoro-4-hydroxy-4'-trifluoromethoxy-1,1'-biphenyl (T-15) was synthesized according to a method similar to that for the synthesis of the compound (T-11) described in Example 3. The yield based on the compound (T-10) was 79%.

[Synthesis of the Compound (No. 1-3-70)]

Using the compound (T-15) obtained as described above, 2.86 g of 4-[difluoro[(2,3'-difluoro-4'-trifluoromethoxy[1,1'-biphenyl]-4-yl)oxy]methyl]-4"-pentyl-2',3,5-trifluoro-1,1', 4',1"-terphenyl (No. 1-3-70) was obtained according to a method similar to that for the synthesis of the compound (No. 1-3-5) in Example 3. The yield based on the compound (T-9) was 48%.

The phase transition temperature of the obtained compound (No. 1-3-70) was as follows.

Phase transition temperature: C 67.9 $S_A$ 215 N 248 I.

The chemical shift δ (ppm) of $^1$H-NMR analysis was as indicated below, and the obtained compound was identified as 4-[difluoro[(2,3'-difluoro-4'-trifluoromethoxy[1,1'-biphenyl]-4-yl)oxy]methyl]-4"-pentyl-2',3,5-trifluoro-1,1',4',1"-terphenyl. The measurement solvent was $CDCl_3$.

Chemical shift δ (ppm); 7.57-7.46 (m, 4H), 7.46-7.35 (m, 4H), 7.35-7.25 (m, 5H), 7.24-7.16 (m, 2H), 2.67 (t, J=7.70 Hz, 2H), 1.74-1.60 (m, 2H), 1.45-1.31 (m, 4H), 0.91 (t, J=7.00 Hz, 3H).

Example 8

Physical Properties of Liquid Crystal Compound (No. 1-3-70)

The liquid crystal composition E consisting of the mother liquid crystals A (85% by weight) and 4-[difluoro[(2,3'-difluoro-4'-trifluoromethoxy[1,1'-biphenyl]-4-yl)oxy]methyl]-4"-pentyl-2',3,5-trifluoro-1,1',4',1"-terphenyl (No. 1-3-70; 15% by weight) obtained in Example 7 was prepared. The physical property values of the obtained liquid crystal composition E were measured, and the extrapolated values of the physical properties of the liquid crystal compound (No. 1-3-70) were calculated by extrapolating the measured values. The values were as follows.

Maximum temperature $(T_{NI})$=155° C.; refractive index anisotropy (Δn)=0.230; dielectric anisotropy (Δ∈)=30.9.

From these results, it was found that the liquid crystal compound (No. 1-3-70) was a compound having a high maximum temperature $(T_{NI})$ and a large refractive index anisotropy (Δn).

Example 9

Synthesis of 4-[difluoro(3,4,5-trifluorophenoxy)methyl]-2',2",3,5,6'-pentafluoro-4'''-pentyl-1,1',4',1",4", 1'''-quarterphenyl (compound No. 1-4-13)

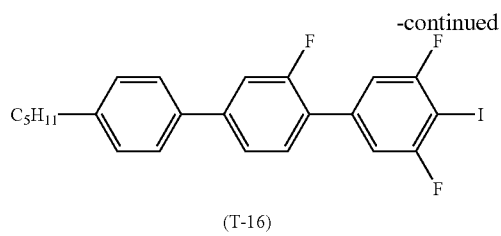

(T-16)

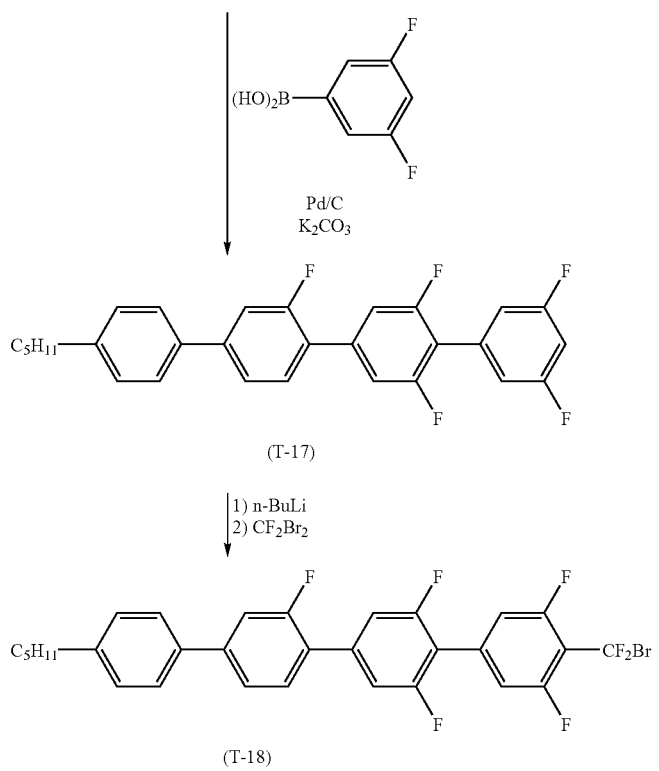

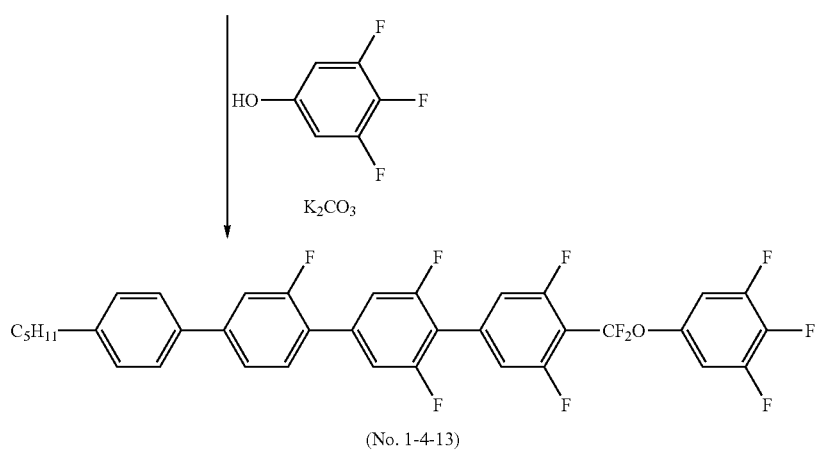

[Synthesis of the Compound (T-16)]

The compound (T-8; 7.00 g) and THF (85.0 ml) were put in a reaction vessel under a nitrogen atmosphere, and cooled to −74° C. Then, n-butyl lithium (1.60 M, in n-hexane solution; 45.0 ml) was added dropwise thereto in the temperature range of −74° C. to −70° C., and stirred for additional 60 minutes. Subsequently, iodine (6.52 g) in a THF (45.0 ml) solution was added dropwise in the temperature range of −75° C. to −70° C., and stirred for additional 60 minutes. The obtained reaction mixture was allowed to come to 25° C., and then poured into ice-water (130 ml) and mixed. Toluene (150 ml) was added thereto and the extraction including separation into organic and aqueous layers was carried out. The obtained organic layer was fractionated, washed sequentially with an aqueous solution of sodium thiosulfate and brine, and then dried over anhydrous magnesium sulfate. The obtained solution was concentrated under reduced pressure, and the residue was purified with a fractional operation by means of column chromatography using heptane as the eluent and silica gel as the stationary phase powder. The solvent was distilled off and the product was dried, whereby 9.38 g of 4-iodo-2',3,5-trifluoro-4"-pentyl-1,1',4',1"-terphenyl (T-16) was obtained. The yield based on the compound (T-8) was 99%.

[Synthesis of the Compound (T-17)]

Using the compound (T-16; 9.38 g) as a raw material, 7.77 g of 2',2",3,5,6'-pentafluoro-4"'-pentyl-1,1',4',1",4',1"'-quarterphenyl (T-17) was obtained according to a method similar to that for the synthesis of the compound (T-6) in Example 1. The yield based on the compound (T-16) was 85%.

[Synthesis of the Compound (T-18)]

Using the compound (T-17; 5.00 g) as a raw material, 4.56 g of 4-bromodifluoromethyl-2',2",3,5,6'-pentafluoro-4"'-pentyl-1,1',4',1",4",1"'-quarterphenyl (T-18) was obtained according to a method similar to that for the synthesis of the compound (T-7) in Example 1. The yield based on the compound (T-17) was 72%.

[Synthesis of the Compound (No. 1-4-13)]

Using the compound (T-18; 4.00 g) as a raw material, 1.81 g of 4-[difluoro(3,4,5-trifluorophenoxy)methyl]-2',2",3,5,6'-pentafluoro-4"-pentyl-1,1',4',1",4",1"'-quarterphenyl (No. 1-4-13) was obtained according to a method similar to that for the synthesis of the compound (No. 1-4-5) in Example 1. The yield base on the compound (T-18) was 41%.

The phase transition temperature of the obtained compound (No. 1-4-13) was as follows.
Phase transition temperature: C 125 $S_A$ 167 N 240 I.

The chemical shift δ (ppm) of $^1$H-NMR analysis was as indicated below, and the obtained compound was identified as 4-[difluoro(3,4,5-trifluorophenoxy)methyl]-2',2", 3,5,6'-pentafluoro-4"'-pentyl-1,1',4',1",4",1"'-quarterphenyl. The measurement solvent was CDCl$_3$.

Chemical shift δ (ppm); 7.58-7.41 (m, 5H), 7.36-7.26 (m, 4H), 7.26-7.19 (d, J=10.3 Hz, 2H), 7.06-6.98 (m, 2H), 2.67 (t, J=8.00 Hz, 2H), 1.74-1.60 (m, 2H), 1.45-1.31 (m, 4H), 0.92 (t, J=6.80 Hz, 3H).

Example 10

Physical Properties of Liquid crystal Compound (No. 1-4-13)

The liquid crystal composition F consisting of the mother liquid crystals A (95% by weight) and 4-[difluoro(3,4,5-trifluorophenoxy)methyl]-2',2",3,5,6'-pentafluoro-4"'-pentyl-1,1',4',1",4",1"'-quarterphenyl (No. 1-4-13; 5% by weight) obtained in Example 9 was prepared. The physical property values of the obtained liquid crystal composition F were measured, and the extrapolated values of the physical properties of the liquid crystal compound (No. 1-4-13) were calculated by extrapolating the measured values. The values were as follows.

Maximum temperature ($T_{NI}$)=156° C.; refractive index anisotropy (Δn)=0.257; dielectric anisotropy (Δ∈)=43.6. From these results, it was found that the liquid crystal compound (No. 1-4-13) was a compound having a high maximum temperature ($T_{NI}$), a large refractive index anisotropy (Δn), and an especially large dielectric anisotropy (Δ∈).

Example 11

Synthesis of 4-[difluoro[(2,3',3", 4",5"-pentafluoro[1,1',4',1"-terphenyl]-4-yl)oxy]methyl]-4'-pentyl-3,5-difluoro-1,1'-biphenyl (No. 1-5)

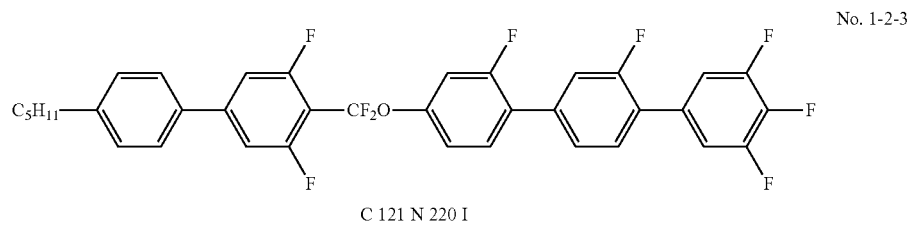

No. 1-2-3

C 121 N 220 I

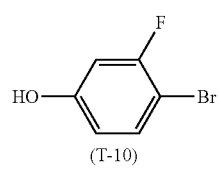

(T-10)

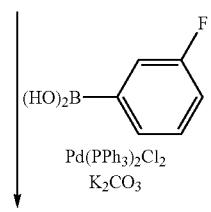

Pd(PPh$_3$)$_2$Cl$_2$
K$_2$CO$_3$

-continued
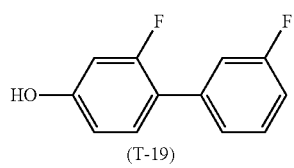
(T-19)
↓ MeI
  K₂CO₃

(T-20)
↓ 1) n-BuLi
  2) TMSCl
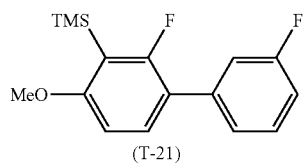
(T-21)
↓ 1) sec-BuLi
  2) I₂
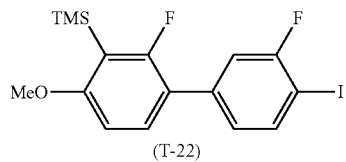
(T-22)
↓ (HO)₂B-(3,4,5-trifluorophenyl)
  Pd/C
  K₂CO₃
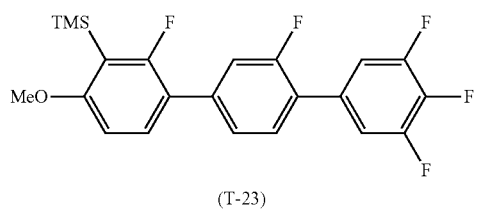
(T-23)
↓ TBAF -continued

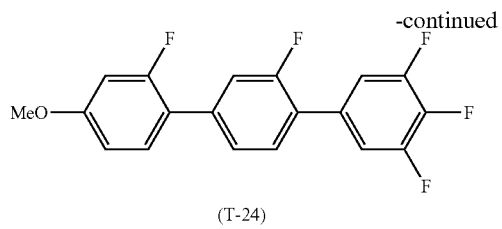
(T-24)

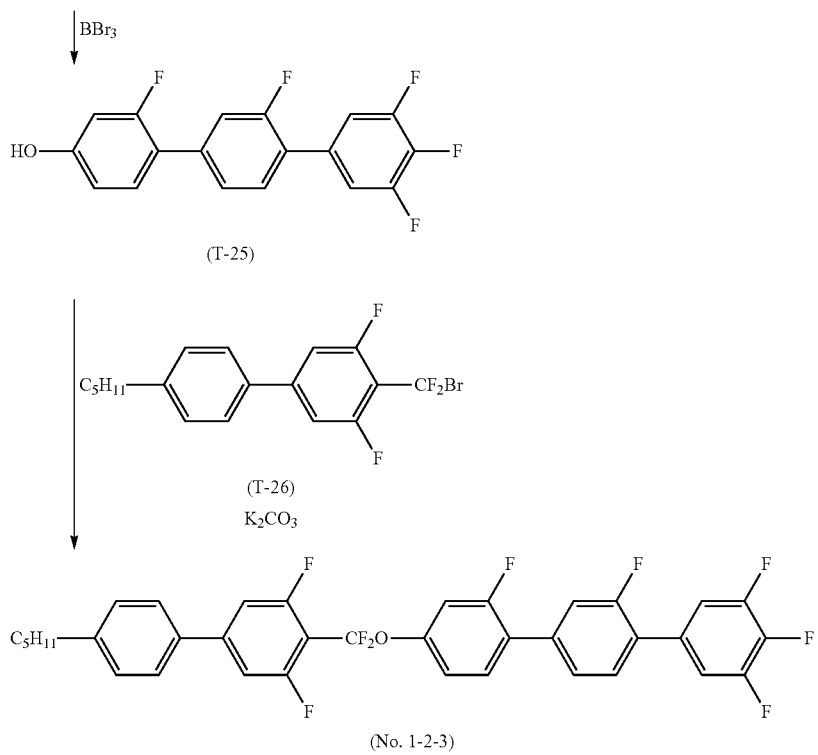

[Synthesis of the Compound (T-19)]

Using the compound (T-10) as a raw material and 4-fluorophenyl boronic acid, 11.6 g of 2,3'-difluoro-4-hydroxy-1,1'-biphenyl (T-19) was synthesized according to a method similar to that for the synthesis of the compound (T-11) described in Example 3. The yield based on the compound (T-10) was 72%.

[Synthesis of the Compound (T-20)]

The compound (T-19; 11.6 g), potassium carbonate (23.4 g), and DMF (100 ml) were put in a reaction vessel under a nitrogen atmosphere, and stirred at 80° C. for 30 minutes. Subsequently, methyl iodide (12.0 g) in a DMF (20.0 ml) solution was added dropwise, and stirred at 80° C. for additional 1 hour. The reaction mixture was allowed to come to 25° C., and then poured into ice-water (100 ml) and mixed. Subsequently, toluene (150 ml) was added thereto and the extraction including separation into organic and aqueous layers was carried out. The obtained organic layer was fractionated, washed with water, and then dried over anhydrous magnesium sulfate. The obtained solution was concentrated under reduced pressure, and the residue was purified with a fractional operation by means of column chromatography using toluene as the eluent and silica gel as the stationary phase powder, whereby 12.3 g of 2,3'-difluoro-4-methoxy-1,1'-biphenyl (T-20) was obtained. The yield based on the compound (T-19) was 99%.

[Synthesis of the Compound (T-21)]

The compound (T-20; 11.3 g) and THF (200 ml) were put in a reaction vessel under a nitrogen atmosphere, and cooled to −74° C. Then, n-butyl lithium (1.58 M, in n-hexane solution; 39.0 ml) was added dropwise thereto in the temperature range of −74° C. to −68° C., and stirred for additional 60 minutes. Subsequently, trimethylchlorosilane (TMSCl; 8.42 ml) was added dropwise in the temperature range of −75° C. to −73° C., and further stirred overnight. The obtained reaction mixture was allowed to come to 25° C., and then poured into ice-water (200 ml) and mixed. Toluene (200 ml) was added thereto and the extraction including separation into organic and aqueous layers was carried out. The obtained organic layer was fractionated, washed with water, and then dried over anhydrous magnesium sulfate. The obtained solution was concentrated under reduced pressure, and the residue was purified with a fractional operation by means of column chromatography using toluene as the eluent and silica gel as the stationary phase powder. The solvent was distilled off and the product was dried, whereby 14.1 g of 2,3'-difluoro-4-methoxy-3-trimethylsilyl-1,1'-biphenyl (T-21) was obtained. The yield based on the compound (T-20) was 94%.

[Synthesis of the Compound (T-22)]

Using the compound (T-21; 10.0 g) as a raw material, 13.7 g of 2,3'-difluoro-4'-iodo-4-methoxy-3-trimethylsilyl-1,1'-biphenyl (T-22) was obtained according to a method similar to that for the synthesis of the compound (T-3) in Example 1. The yield based on the compound (T-21) was 96%.

[Synthesis of the Compound (T-23)]

Using the compound (T-22; 13.7 g) as a raw material and 3,4,5-trifluorophenylboronic acid, 11.2 g of 4-methoxy-2-3', 3",4",5"-pentafluoro-3-trimethylsilyl-1,1',4',1"-terphenyl (T-23) was obtained according to a method similar to that for the synthesis of the compound (T-4) in Example 1. The yield based on the compound (T-22) was 81%.

[Synthesis of the Compound (T-24)]

The compound (1-23; 10.0 g) and THF (130 ml) were put in a reaction vessel under a nitrogen atmosphere, and cooled to 0° C. Then, tetrabutylammonium fluoride (TBAF, 1.00 M, THF solution; 26.0 ml) was added dropwise thereto and stirred for additional 60 minutes while allowing the solution to come to room temperature. The obtained reaction mixture was poured into ice-water (130 ml) and mixed. Toluene (130 ml) was added thereto and the extraction including separation into organic and aqueous layers was carried out. The obtained organic layer was fractionated, washed with water, and then dried over anhydrous magnesium sulfate. The obtained solution was concentrated under reduced pressure, and the residue was purified with a fractional operation by means of column chromatography using toluene as the eluent and silica gel as the stationary phase powder. The product was further purified by recrystallization from a mixed solvent of ethyl acetate/Solmix A-11 and dried, whereby 8.18 g of 4-methoxy-2,3', 3",4",5"-pentafluoro-1,1',4',1"-terphenyl (T-24) was obtained. The yield based on the compound (T-23) was 99%.

[Synthesis of the Compound (T-25)]

The compound (T-24; 6.20 g) and dichloromethane (6,000 ml) were put in a reaction vessel under a nitrogen atmosphere, and cooled to 10° C. Then, boron tribromide (1.00 M, dichloromethane solution; 35.4 ml) was added dropwise thereto, and further stirred overnight while allowing the solution to come to room temperature. The obtained reaction mixture was poured into ice-water (200 ml) and mixed. The mixture was separated into organic and aqueous layers and an extraction operation was carried out. The obtained organic layer was fractionated, washed with water, and then dried over anhydrous magnesium sulfate. The obtained solution was concentrated under reduced pressure, and the residue was purified with a fractional operation by means of column chromatography using toluene as the eluent and silica gel as the stationary phase powder. The product was further purified by recrystallization from a mixed solvent of ethyl acetate/heptane and dried, whereby 5.00 g of 4-hydroxy-2,3',3",4",5"-pentafluoro-1,1',4',1'"-terphenyl (T-25) was obtained. The yield based on the compound (T-24) was 84%.

[Synthesis of the Compound (No. 1-2-3)]

Using 4-bromodifluoromethyl-3,5-difluoro-4'-pentyl-1, 1'-biphenyl (T-26; 4.24 g) prepared separately as a raw material and the compound (T-25; 3.30 g), 4.60 g of 4-[difluoro[(2,3',3",4",5"-pentafluoro[1,1',4',1"-terphenyl]-4-yl)oxy]methyl]-4'-pentyl-3,5-difluoro-1,1'-biphenyl (No. 1-2-3) was obtained according to a method similar to that for the synthesis of the compound (No. 1-4-5) in Example 1. The yield based on the compound (T-26) was 65%.

The phase transition temperature of the obtained compound (No. 1-2-3) was as follows.
Phase transition temperature: C 121 N 220 I.

The chemical shift δ (ppm) of $^1$H-NMR analysis was as indicated below, and the obtained compound was identified as 4-[difluoro[(2,3',3",4",5"-pentafluoro[1,1',4',1"-terphenyl]-4-yl)oxy]methyl]-4'-pentyl-3,5-difluoro-1,1'-biphenyl. The measurement solvent was CDCl$_3$.

Chemical shift δ (ppm); 7.53-7.43 (m, 4H), 7.43-7.35 (m, 2H), 7.32-7.28 (d, J=8.10 Hz, 2H), 7.27-7.16 (m, 6H), 2.67 (t, J=8.00 Hz, 2H), 1.74-1.60 (m, 2H), 1.43-1.29 (m, 4H), 0.91 (t, J=6.80 Hz, 3H).

Example 12

Physical Properties of Liquid Crystal Compound (No. 1-2-3)

The liquid crystal composition G consisting of the mother liquid crystals A (90% by weight) and 4-[difluoro[(2,3',3",4", 5"-pentafluoro[1,1',4',1"-terphenyl]-4-yl)oxy]methyl]-4'-pentyl-3,5-difluoro-1,1'-biphenyl (No. 1-2-3; 10% by weight) obtained in Example 11 was prepared. The physical property values of the obtained liquid crystal composition G were measured, and the extrapolated values of the physical properties of the liquid crystal compound (No. 1-2-3) were calculated by extrapolating the measured value. The values were as follows.

Maximum temperature $(T_{NI})$=139° C.; refractive index anisotropy (Δn)=0.227; dielectric anisotropy (Δ∈)=39.7.

From these results, it was found that the liquid crystal compound (No. 1-2-3) was a compound having a large refractive index anisotropy (Δn) and a large dielectric anisotropy (Δ∈).

Example 13

Synthesis of 4-[difluoro(3,4-difluorophenoxy)methyl]-2',2",3,5-tetrafluoro-4'"-pentyl-1,1',4',1",4",1'"-quarterphenyl (compound No. 1-4-53)

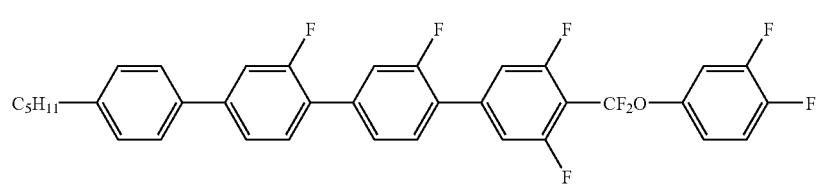

No. 1-4-53

-continued

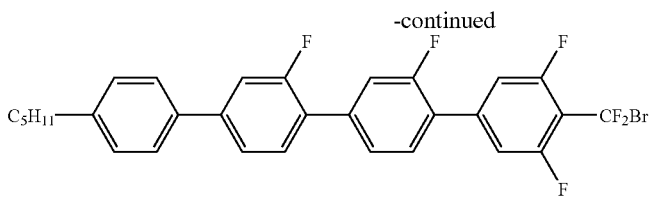

(T-7)

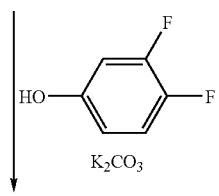

K₂CO₃

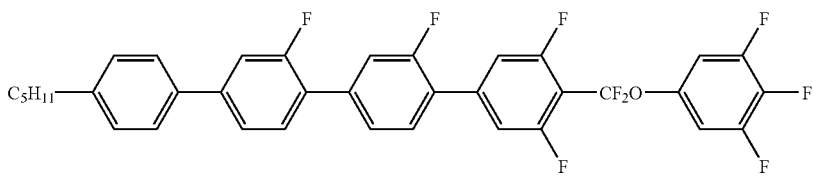

(No. 1-4-53)

[Synthesis of the Compound No. 1-4-53]

Using the compound (T-7; 2.37 g) as a raw material, 0.798 g of 4-[difluoro(3,4-difluorophenoxy)methyl]-2',2'',3,5-tetrafluoro-4'''-pentyl-1,1',4',1'',4'',1'''-quarterphenyl (No. 1-4-53) was obtained according to a method similar to that for the synthesis of the compound (No. 1-4-5) in Example 1. The yield based on the compound (T-7) was 31%.

The phase transition temperature of the obtained compound (No. 1-4-53) was as follows.
Phase transition temperature: C 79.3 $S_A$ 206 N 269 I.

The chemical shift δ (ppm) of ¹H-NMR analysis was indicated below, and the obtained compound was identified as 4-[difluoro(3,4-difluorophenoxy)methyl]-2',2'',3,5-tetrafluoro-4'''-pentyl-1,1',4',1'',4'',1'''-quarterphenyl. The measurement solvent was CDCl₃.

Chemical shift δ (ppm): 7.57-7.40 (m, 8H), 7.32-7.26 (m, 4H), 7.22-7.15 (m, 2H), 7.10-7.04 (m, 1H), 2.67 (t, J=7.85 Hz, 2H), 1.73-1.61 (m, 2H), 1.44-1.32 (m, 4H), 0.92 (t, J=6.85 Hz, 3H).

Example 14

Physical Properties of Liquid Crystal Compound (No. 1-4-53)

The liquid crystal composition H consisting of the mother liquid crystals A (85% by weight) and 4-[difluoro(3,4-difluorophenoxy)methyl]-2',2'', 3,5-tetrafluoro-4'''-pentyl-1,1',4', 1'',4'',1'''-quarterphenyl (No. 1-4-53; 15% by weight) obtained in Example 13 was prepared. The physical property values of the obtained liquid crystal composition H were measured, and the extrapolated values of the physical properties of the liquid crystal compound (No. 1-4-53) were calculated by extrapolating the measured values. The values were as follows.

Maximum temperature ($T_{NI}$)=175° C.; refractive index anisotropy (Δn)=0.270; dielectric anisotropy (Δ∈)=26.5.

From these results, it was found that the liquid crystal compound (No. 1-4-53) was a compound having a high maximum temperature ($T_{NI}$), a large dielectric anisotropy (Δ∈), and an especially large refractive index anisotropy (Δn).

Example 15

Synthesis of 4-[difluoro(3,4,5-trifluorophenoxy)methyl]-4''-(4-pentylcyclohexyl)-2',2'',3,5-tetrafluoro-1, 1',4',1''-terphenyl (No. 1-4-305)

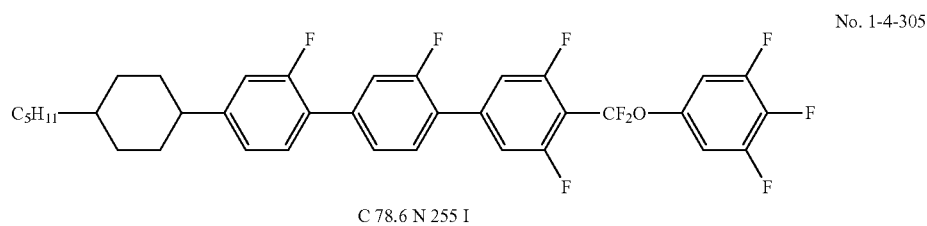

No. 1-4-305

C 78.6 N 255 I

-continued
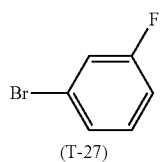
(T-27)
1) Mg
2) C$_5$H$_{11}$— 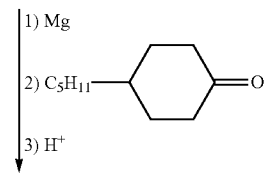
3) H$^+$
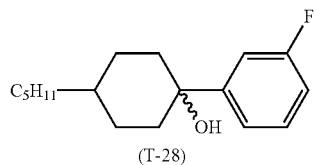
(T-28)
p-TsOH
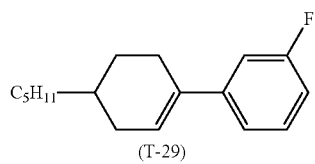
(T-29)
H$_2$, Pd/C
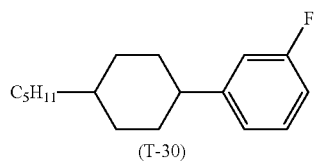
(T-30)
1) sec-BuLi
2) I$_2$
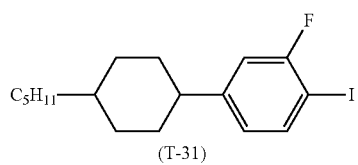
(T-31)
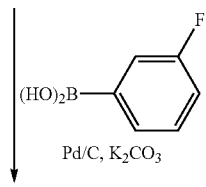
Pd/C, K$_2$CO$_3$ -continued
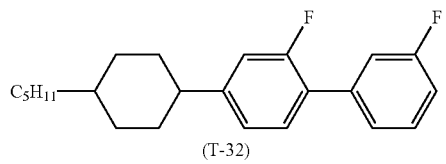
(T-32)
1) sec-BuLi
2) I₂
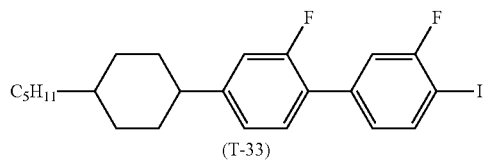
(T-33)
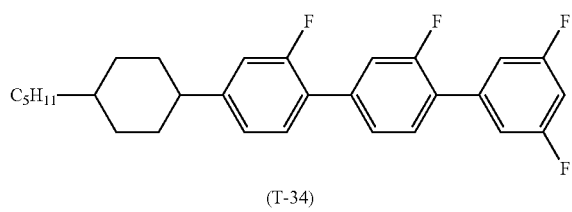
(T-34)
1) n-BuLi
2) CF₂Br₂
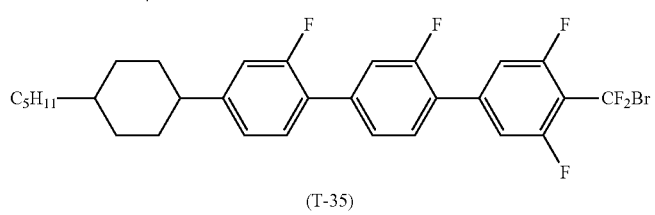
(T-35)
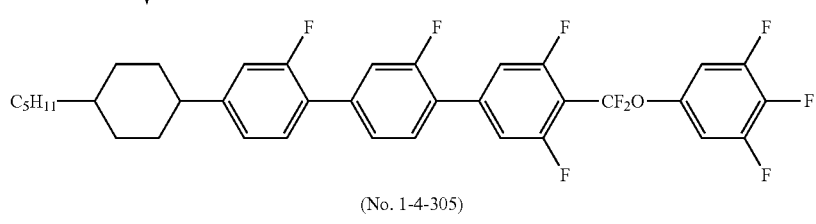
(No. 1-4-305)

[Synthesis of the Compound (T-28)]

Well-dried magnesium (16.7 g) and THF (20.0 ml) were put in a reaction vessel under a nitrogen atmosphere, and heated to 50° C. Then, 3-bromofluorobenzene (T-27; 100 g) dissolved in THF (100 ml) was slowly added dropwise thereto in the temperature range of 40° C. to 60° C., and stirred for additional 60 minutes. To the Grignard reagent obtained, 4-pentylcyclohexanone (115 g) in a THF (230 ml) solution was added dropwise in the temperature range of 20° C. to 30° C., and stirred for additional 180 minutes. The reaction mixture was poured into 1N-hydrochloric acid on an ice bath and mixed, and then toluene (800 ml) was added to separate the mixture into organic and aqueous layers, and an extraction operation was carried out. The obtained organic layer was washed with water, and then dried over anhydrous magnesium sulfate. Then, the solvent was distilled off under reduced pressure, whereby 168 g of 1-(3-fluorophenyl)-4-pentylcyclohexanol (T-28) was obtained.

[Synthesis of the Compound (T-29)]

The compound (T-28; 168 g), p-toluenesulfonic acid monohydrate (5.04 g), and toluene (500 ml) were put in a reaction vessel under a nitrogen atmosphere, and reacted for 120 minutes while heating under reflux and removing water being distilled. After the reaction mixture had been cooled to room temperature, toluene (200 ml) was added to the mixture, washed sequentially with water, a saturated aqueous solution of sodium bicarbonate and water, and then dried over anhydrous magnesium sulfate. The obtained solution was concentrated under reduced pressure, and the residue was purified with a fractional operation by means of column chromatography using heptane as the eluent and silica gel as the stationary phase powder. The solvent was distilled off and the product was dried, whereby 117 g of 1-fluoro-3-(4-pentylcyclohexene-1-yl)benzene (T-29) was obtained. The yield based on the compound (T-27) was 84%.

[Synthesis of the Compound (T-30)]

The compound (T-29; 117 g), Pd/C (NX type; 5.85 g), toluene (200 ml), and Solmix A-11 (400 ml) were put in a reaction vessel under a hydrogen atmosphere, and stirred at room temperature for 8 hours. After the catalyst had been removed by filtration, the reaction mixture was concentrated under reduced pressure. the residue was purified with a fractional operation by means of column chromatography using heptane as the eluent and silica gel as the stationary phase powder. The residue was purified with a fractional operation by means of column chromatography using heptane as the eluent and silica gel as the stationary phase powder. The product was further purified by recrystallization from a mixed solvent of heptane/Solmix A-11 and dried, whereby 80.3 g of 1-fluoro-3-(4-pentylcyclohexyl)benzene (T-30) was obtained. The yield based on the compound (T-29) was 68%.

[Synthesis of the compound (T-31)]

The compound (T-30; 50.0 g) and THF (300 ml) were put in a reaction vessel under a nitrogen atmosphere, and cooled to −74° C. Then, sec-butyl lithium (1.0 M, in cyclohexane and n-hexane solution; 237 ml) were added dropwise thereto in the temperature range of −74° C. to −68° C., and stirred for additional 120 minutes. Subsequently, iodine (66.3 g) in a THF (350 ml) solution was added dropwise in the temperature range of −75° C. to −68° C., and stirred for additional 60 minutes. The obtained reaction mixture was allowed to come to 25° C., and then poured into ice-water (650 ml) and mixed. Toluene (500 ml) was added thereto and the extraction including separation into organic and aqueous layers was carried out. The obtained organic layer was fractionated, washed sequentially with an aqueous solution of sodium thiosulfate and brine, and then dried over anhydrous magnesium sulfate. The obtained solution was concentrated under reduced pressure, and the residue was purified with a fractional operation by means of column chromatography using heptane as the eluent and silica gel as the stationary phase powder. The product was further purified by recrystallization from a mixed solvent of heptane/Solmix A-11 and dried, whereby 69.3 g of 2-fluoro-1-iodo-4-(4-pentylcyclohexyl)benzene (T-31) was obtained. The yield based on the compound (T-30) was 92%.

[Synthesis of the Compound (T-32)]

The compound (T-31; 20.0 g), 3-fluorophenyl boronic acid (8.20 g), potassium carbonate (22.1 g), Pd/C (NX type; 0.114 g), toluene (100 ml), Solmix A-11 (100 ml), and water (100 ml) were put in a reaction vessel under a nitrogen atmosphere, and heated under reflux for 5 hours. The reaction mixture was cooled to 25° C., and then poured into water (300 ml) and toluene (300 ml) and mixed. Then, the mixture was allowed to stand to be separated into two layers of organic and aqueous layers, and the extraction to an organic layer was carried out. The obtained organic layer was fractionated, washed with water, and then dried over anhydrous magnesium sulfate. The obtained solution was concentrated under reduced pressure, and the residue was purified with a fractional operation by means of column chromatography using heptane as the eluent and silica gel as the stationary phase powder. The product was further purified by recrystallization from a mixed solvent of heptane/Solmix A-11 and dried, whereby 14.2 g of 2,3'-difluoro-4-(4-pentylcyclohexyl)-1,1'-biphenyl (T-32) was obtained. The yield based on the compound (T-31) was 78%.

[Synthesis of the Compound (T-33)]

The compound (T-32; 10.0 g) and THF (140 ml) were put in a reaction vessel under a nitrogen atmosphere, and cooled to −74° C. Then, sec-butyl lithium (1.0 M, in cyclohexane and n-hexane solution; 34.4 ml) were added dropwise thereto in the temperature range of −74° C. to −68° C., and stirred for additional 120 minutes. Subsequently, iodine (9.63 g) in a THF (60.0 ml) solution was added dropwise in the temperature range of −75° C. to −68° C., and stirred for additional 60 minutes. The obtained reaction mixture was allowed to come to 25° C., and then poured into ice-water (200 ml) and mixed. Toluene (100 ml) was added thereto and the extraction including separation into organic and aqueous layers was carried out. The obtained organic layer was fractionated, washed sequentially with an aqueous solution of sodium thiosulfate and brine, and then dried over anhydrous magnesium sulfate. The obtained solution was concentrated under reduced pressure, and the residue was purified with a fractional operation by means of column chromatography using heptane as the eluent and silica gel as the stationary phase powder. The product was further purified by recrystallization from a mixed solvent of heptane/Solmix A-11 and dried, whereby 10.2 g of 2,3'-difluoro-4'-iodo-4-(4-pentylcyclohexyl)-1,1'-biphenyl (T-33) was obtained. The yield based on the compound (T-32) was 75%.

[Synthesis of the Compound (T-34)]

The compound (T-33; 10.0 g), 3,5-difluorophenyl boronic acid (3.71 g), potassium carbonate (8.87 g), Pd/C (NX type; 0.0455 g), toluene (100 ml), Solmix A-11 (100 ml), and water (100 ml) were put in a reaction vessel under a nitrogen atmosphere, and heated under reflux for 5 hours. The reaction mixture was cooled to 25° C., and then poured into water (300 ml) and toluene (300 ml) and mixed. Then, the solution was allowed to stand to be separated into two layers of organic and aqueous layers, and the extraction to an organic layer was carried out. The obtained organic layer was fractionated, washed with water, and then dried over anhydrous magnesium sulfate. The obtained solution was concentrated under reduced pressure, and the residue was purified with a fractional operation by means of column chromatography using heptane as the eluent and silica gel as the stationary phase powder. The product was further purified by recrystallization from a mixed solvent of heptane/Solmix A-11 and dried, whereby 8.20 g of 4-(4-pentylcyclohexyl)-2,3',3",5"-tetrafluoro-1,1',4',1"'-terphenyl (T-34) was obtained. The yield based on the compound (T-33) was 84%.

[Synthesis of the Compound (T-35)]

The compound (T-34; 5.00 g) and THF (130 ml) were put in a reaction vessel under a nitrogen atmosphere, and cooled to −74° C. Then, n-butyl lithium (1.60 M, in n-hexane solution; 7.00 ml) was added dropwise thereto in the temperature range of −74° C. to −70° C., and stirred for additional 60 minutes. Subsequently, dibromodifluoromethane (2.77 g) in a THF (20.0 ml) solution was added dropwise in the temperature range of −75° C. to −70° C., and stirred for additional 60 minutes while allowing the reaction mixture to come to 25° C. The obtained reaction mixture was poured into ice-water (150 ml) and mixed. Toluene (100 ml) was added thereto and the extraction including separation into organic and aqueous layers was carried out. The obtained organic layer was fractionated, washed with brine, and dried over anhydrous magnesium sulfate. The obtained solution was concentrated under reduced pressure, and the residue was purified with a fractional operation by means of column chromatography using heptane as the eluent and silica gel as the stationary phase powder. The solvent was distilled off and the product was dried, whereby 6.22 g of 4-bromodifluoromethyl-4"-(4-pentylcyclohexyl)-2',2",3,5-tetrafluoro-1,1',4',1"-terphenyl (T-35) was obtained. The yield based on the compound (T-34) was 97%.

[Synthesis of the Compound (No. 1-4-305)]

The compound (T-35; 6.22 g), 3,4,5-trifluorophenol (1.43 g), potassium carbonate (4.44 g), and N,N-dimethylformamide (DMF; 95.0 ml) were put in a reaction vessel under a nitrogen atmosphere, and stirred at 90° C. for 120 minutes. The reaction mixture was allowed to come to 25° C., and then poured into ice-water (100 ml) and mixed. Toluene (100 ml) was added to separate the mixture into organic and aqueous layers, and an extraction operation was carried out. The obtained organic layer was fractionated, washed sequentially with a saturated solution of sodium bicarbonate, 0.5N-aqueous sodium hydroxide solution and brine, and then dried over anhydrous magnesium sulfate. The obtained solution was concentrated under reduced pressure, and the residue was purified with a fractional operation by means of column chromatography using a mixed solvent of heptane/ethyl acetate the eluent and silica gel as the stationary phase powder. The product was further purified by recrystallization from a mixed solvent of heptane/Solmix A-11 and dried, whereby 3.94 g of 4-[difluoro(3,4,5-trifluorophenoxy)methyl]-4"-(4-pentylcyclohexyl)-2',2",3,5-tetrafluoro-1,1',4',1"-terphenyl (No. 1-4-305) was obtained. The yield based on the compound (T-35) was 57%.

The phase transition temperature of the obtained compound (No. 1-4-305) was as follows.

Phase transition temperature: C 78.6 N 255 I.

The chemical shift δ (ppm) of $^1$H-NMR analysis was as indicated below, and the obtained compound was identified as 4-[difluoro(3,4,5-trifluorophenoxy)methyl]-4"-(4-pentylcyclohexyl)-2',2",3,5-tetrafluoro-1,1',4',1"-terphenyl. The measurement solvent was $CDCl_3$.

Chemical shift δ (ppm); 7.52-7.34 (m, 4H), 7.26 (d, J=8.80 Hz, 2H), 7.09 (dd, J=8.05 Hz, J=1.45 Hz, 1H), 7.07-6.95 (m, 3H), 2.52 (tt, J=12.1 Hz, J=3.15 Hz, 1H), 1.98-1.86 (m, 4H), 1.53-1.41 (m, 2H), 1.39-1.19 (m, 9H), 1.14-1.02 (m, 2H), 0.90 (t, J=7.20 Hz, 3H).

Example 16

Physical Properties of Liquid Crystal Compound (No. 1-4-305)

The above four compounds described as the mother liquid crystals A were mixed to prepare mother liquid crystals A having a nematic phase. The physical properties of the mother liquid crystals A were as follows.

Maximum temperature $(T_{NI})$=71.7° C.; dielectric anisotropy $(\Delta\epsilon)$=11.0; refractive index anisotropy $(\Delta n)$=0.137.

The liquid crystal composition I consisting of the mother liquid crystals A (85% by weight) and 4-[difluoro(3,4,5-trifluorophenoxy)methyl]-4"-(4-pentyleyclohexyl)-2',2",3,5-tetrafluoro-1,1',4',1"-terphenyl (No. 1-4-5; 15% by weight) obtained in Example 15 was prepared. The physical property values of the obtained liquid crystal composition I were measured, and the extrapolated values of the physical properties of the liquid crystal compound (No. 1-4-305) were calculated by extrapolating the measured values. The values were as follows.

Maximum temperature $(T_{NI})$=166° C.; dielectric anisotropy $(\Delta\epsilon)$=30.3; refractive index anisotropy $(\Delta n)$=0.204.

From these results, it was found that the liquid crystal compound (No. 1-4-305) was a compound having an excellent compatibility with other liquid crystal compounds, a wide temperature range of the nematic phase, a high maximum temperature $(T_{NI})$, and also a large dielectric anisotropy $(\Delta\epsilon)$.

Example 17

Synthesis of 4-[difluoro(3,4,5-trifluorophenoxy)methyl]-4"-(4-pentylcyclohexyl)-2',3,5-trifluoro-1,1',4',1"-terphenyl (No. 1-4-319)

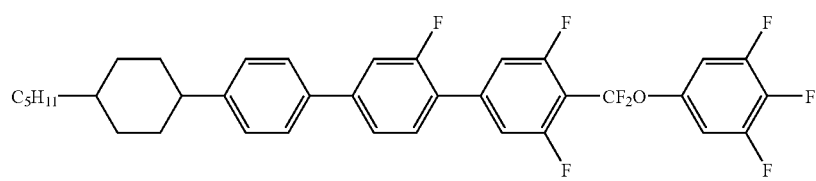

No. 1-4-319

C 87.5 N 271 I

-continued
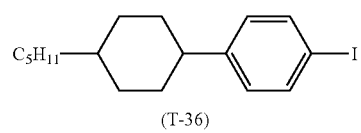
(T-36)
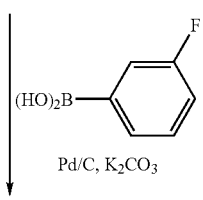
Pd/C, K₂CO₃
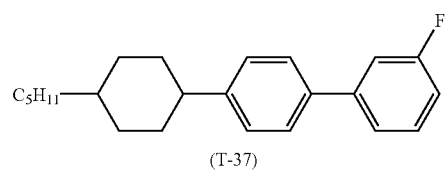
(T-37)
1) sec-BuLi
2) I₂
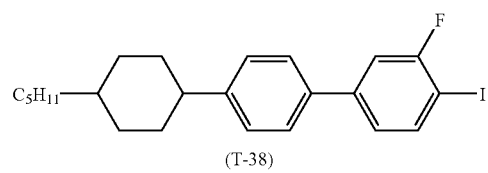
(T-38)
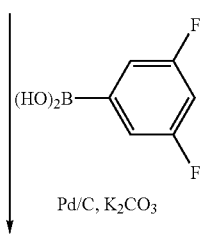
Pd/C, K₂CO₃
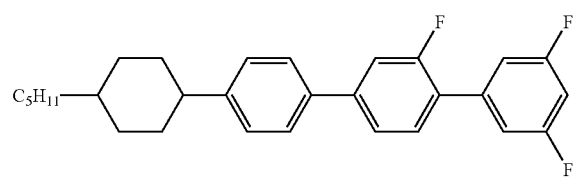
(T-39)
1) n-BuLi
2) CF₂Br₂

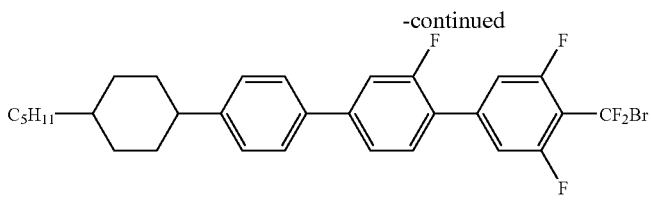

(T-40)

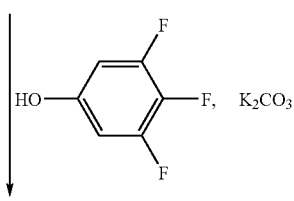

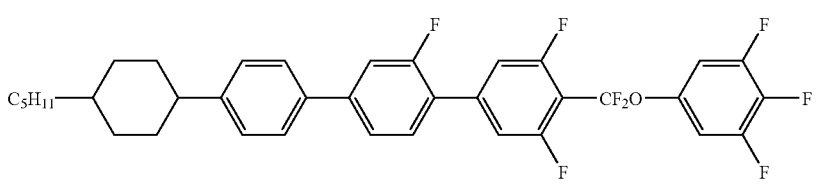

(No.1-4-319)

[Synthesis of the Compound (T-37)]

Using 1-iodo-4-(4-pentylcyclohexyl)benzene (T-36; 30.0 g) as a raw material, 22.6 g of 3-fluoro-4'-(4-pentylcyclohexyl)-1,1'-biphenyl (T-37) was obtained according to a method similar to that for the synthesis of (T-4) in Example 1. The yield based on the compound (T-36) was 83%.

[Synthesis of the Compound (T-38)]

Using the compound (T-37; 15.0 g) as a raw material, 20.1 g of 3-fluoro-4-iodo-4'-(4-pentylcyclohexyl)-1,1'-biphenyl (T-38) was obtained according to a method similar to that for the synthesis of (T-5) in Example 1. The yield based on the compound (1-37) was 97%.

[Synthesis of the Compound (T-39)]

Using the compound (T-38; 10.0 g) as a raw material, 7.47 g of 4"-(4-pentylcyclohexyl)-2',3,5-trifluoro-1,1',4',1"-terphenyl (T-39) was obtained according to a method similar to that for the synthesis of (T-6) in Example 1. The yield based on the compound (T-38) was 77%.

[Synthesis of the Compound (T-40)]

Using the compound (T-39; 5.00 g) as a raw material, 5.30 g of 4-bromodifluoromethyl-4"-(4-pentylcyclohexyl)-2',3,5-trifluoro-1,1',4',1"'-terphenyl (T-40) was obtained according to a method similar to that for the synthesis of (T-7) in Example 1. The yield based on the compound (T-39) was 84%.

[Synthesis of the Compound (No. 1-4-319)]

Using the compound (T-40; 5.30 g) as a raw material, 2.65 g of 4-[difluoro(3,4,5-trifluorophenoxy)methyl]-4"-(4-pentylcyclohexyl)-2',3,5-trifluoro-1,1',4',1"-terphenyl (No. 1-4-319) was obtained according to a method similar to that for the synthesis of (1-4-5) in Example 1. The yield based on the compound (T-40) was 45%.

The phase transition temperature of the obtained compound (No. 1-4-319) was as follows.

Phase transition temperature: C 87.5 N 271 I.

The chemical shift δ (ppm) of $^1$H-NMR analysis was as indicated below, and the obtained compound was identified as 4-[difluoro(3,4,5-trifluorophenoxy)methyl]-4"-(4-pentylcyclohexyl)-2',3,5-trifluoro-1,1',4',1"-terphenyl. The measurement solvent was $CDCl_3$.

Chemical shift δ (ppm); 7.54 (d, J=8.30 Hz, 2H), 7.51-7.45 (m, 2H), 7.41 (d, J=12.2 Hz, 1H), 7.32 (d, J=8.20 Hz, 2H), 7.26 (d, J=8.10 Hz, 2H), 7.03-6.95 (m, 2H), 2.53 (tt, J=12.1 Hz, J=3.00 Hz, 1H), 2.00-1.86 (m, 4H), 1.55-1.44 (m, 2H), 1.40-1.21 (m, 9H), 1.14-1.02 (m, 2H), 0.91 (t, J=7.10 Hz, 3H).

Example 18

Physical Properties of Liquid Crystal Compound (No. 1-4-319)

The liquid crystal composition J consisting of the mother liquid crystals A (85% by weight) and 4-[difluoro(3,4,5-trifluorophenoxy)methyl]-4"-(4-pentylcyclohexyl)-2',3,5-trifluoro-1,1',4',1"-terphenyl (No. 1-4-319; 15% by weight) obtained in Example 17 was prepared. The physical property values of the obtained liquid crystal composition J were measured, and the extrapolated values of the physical properties of the liquid crystal compound (No. 1-4-319) were calculated by extrapolating the measured values. The values were as follows.

Maximum temperature ($T_{NI}$)=189° C.; dielectric anisotropy (Δ∈)=22.9; refractive index anisotropy (Δn)=0.210.

From these results, it was found that the liquid crystal compound (No. 1-4-319) was a compound having an excellent compatibility with other liquid crystal compounds, a wide temperature range of a nematic phase, and a high maximum temperature ($T_{NI}$).

Example 19
Synthesis of 4-[difluoro(3,4,5-trifluorophenoxy)methyl]-4''-(4-pentylcyclohexyl)-2',2'',3,5,6'-pentafluoro-1,1',4',1''-terphenyl (No. 1-4-333)
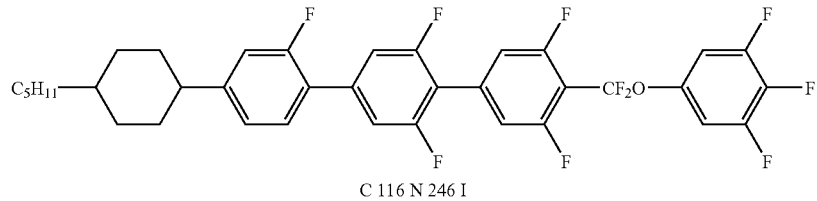
No. 1-4-333
C 116 N 246 I
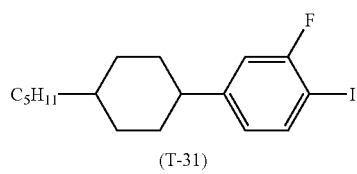
(T-31)
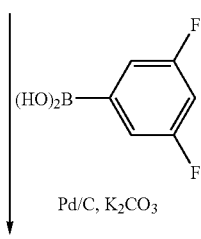
Pd/C, K$_2$CO$_3$
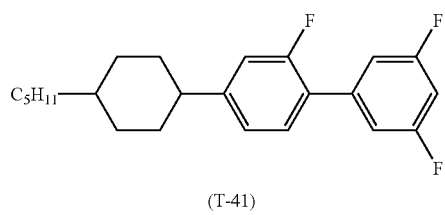
(T-41)
1) n-BuLi
2) I$_2$
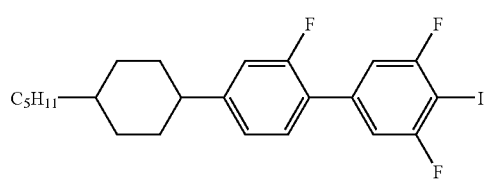
(T-42)
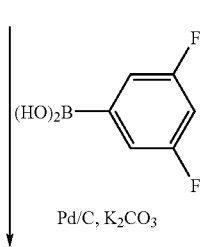
Pd/C, K$_2$CO$_3$ -continued

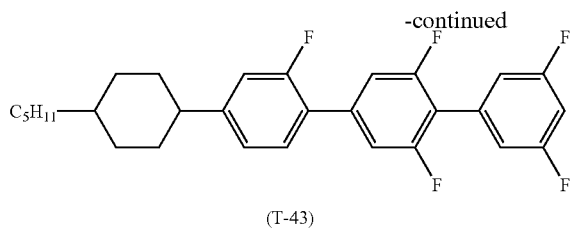
(T-43)

| 1) n-BuLi
| 2) CF₂Br₂

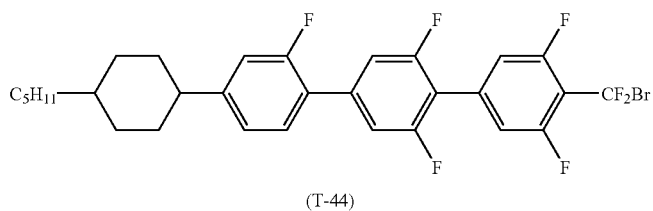
(T-44)

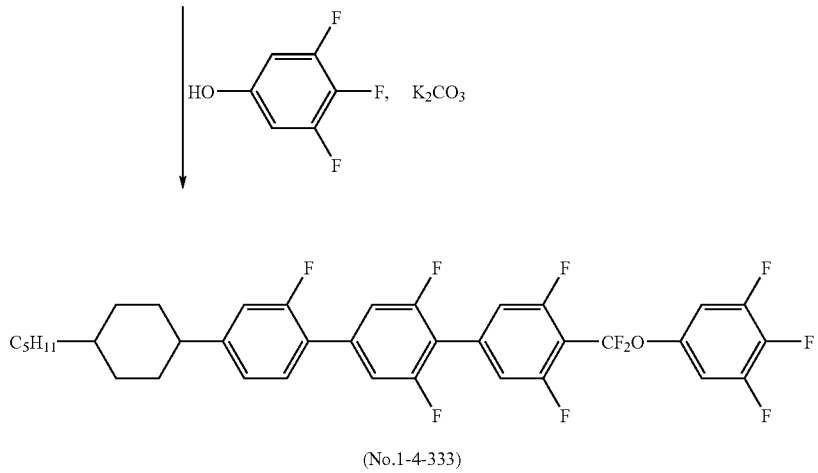
(No.1-4-333)

[Synthesis of the Compound (T-41)]

The compound (T-31; 30.0 g) and 3,5-difluorophenylboronic acid (13.9 g), potassium carbonate (33.3 g), Pd/C (NX type; 0.171 g), toluene (150 ml), Solmix A-11 (150 ml), and water (150 ml) were put in a reaction vessel under a nitrogen atmosphere, and heated under reflux for 5 hours. The reaction mixture was cooled to 25° C., and then poured into water (500 ml) and toluene (300 ml) and mixed. Then, the mixture was allowed to stand to be separated into two layers of organic and aqueous layers, and the extraction to an organic layer was carried out. The obtained organic layer was fractionated, washed with water, and then dried over anhydrous magnesium sulfate. The obtained solution was concentrated under reduced pressure, and the residue was purified with a fractional operation by means of column chromatography using heptane as the eluent and silica gel as the stationary phase powder. The product was further purified by recrystallization from Solmix A-11 and dried, whereby 25.0 g of 4'-(4-pentylcyclohexyl)-2',3,5-trifluoro-1,1'-biphenyl (T-41) was obtained. The yield based on the compound (T-31) was 87%.

[Synthesis of the Compound (T-42)]

The compound (T-41; 7.00 g) and THF (85.0 ml) were put in a reaction vessel under a nitrogen atmosphere, and cooled to −74° C. Then, n-butyl lithium (1.58 M, in n-hexane solution; 14.7 ml) was added dropwise thereto in the temperature range of −74° C. to −68° C., and stirred for additional 60 minutes. Subsequently, iodine (6.40 g) in a THF (45.0 ml) solution was added dropwise in the temperature range of −75° C. to −68° C., and stirred for additional 60 minutes. The obtained reaction mixture was allowed to come to 25° C., and then poured into ice-water (150 ml) and mixed. Toluene was added thereto and the extraction including separation into organic and aqueous layers was carried out. The obtained organic layer was fractionated, washed sequentially with an aqueous solution of sodium thiosulfate and brine, and then dried over anhydrous magnesium sulfate. The obtained solution was concentrated under reduced pressure, and the residue was purified with a fractional operation by means of column chromatography using heptane as the eluent and silica gel as the stationary phase powder and dried, whereby 9.36 g of 4-iodo-4'-(4-pentylcyclohexyl)-2',3,5-trifluoro-1,1'-biphenyl (T-16) was obtained. The yield based on the compound (T-41) was 99%.

[Synthesis of the Compound (T-43)]

Using the compound (T-42; 9.36 g) as a raw material, 6.54 g of 4"-(4-pentylcyclohexyl)-2',2",3,5,6'-pentafluoro-1,1',4', 1"-terphenyl (T-43) was obtained according to a method similar to that for the synthesis of (T-6) in Example 1. The yield based on the compound (T-42) was 72%.

[Synthesis of the Compound (T-44)]

Using the compound (T-43; 5.00 g) as a raw material, 6.12 g of 4-bromodifluoromethyl-4"-(4-pentylcyclohexyl)-2',2", 3,5,6'-pentafluoro-1,1',4',1"-terphenyl (T-44) was obtained according to a method similar to that for the synthesis of (T-7) in Example 1. The yield based on the compound (T-43) was 96%.

[Synthesis of the Compound (No. 1-4-333)]

Using the compound (T-44; 6.12 g) as a raw material, 3.89 g of 4-[difluoro(3,4,5-trifluorophenoxy)methyl]-4"-(4-pentylcyclohexyl)-2',2",3,5,6'-pentafluoro-1,1',4', 1"-terphenyl (No. 1-4-333) was obtained according to a method similar to that for the synthesis of (1-4-5) in Example 1. The yield based on the compound (T-44) was 57%.

The phase transition temperature of the obtained compound (No. 1-4-333) was as follows.

Phase transition temperature: C 116 N 246 I.

The chemical shift δ (ppm) of $^1$H-NMR analysis was as indicated below, and the obtained compound was identified as 4-[difluoro(3,4,5-trifluorophenoxy)methyl]-4"-(4-pentylcyclohexyl)-2',2",3,5,6'-pentafluoro-1,1',4',1"-terphenyl. The measurement solvent was CDCl$_3$.

Chemical shift δ (ppm); 7.37 (dd, J=8.15 Hz, J=8.15 Hz, 1H), 7.27-7.17 (m, 4H), 7.11 (dd, J=8.05 Hz, J=1.60 Hz, 1H), 7.08-6.97 (m, 3H), 2.53 (tt, J=12.1 Hz, J=3.15 Hz, 1H), 1.98-1.86 (m, 4H), 1.53-1.41 (m, 2H), 1.39-1.20 (m, 9H), 1.14-1.02 (m, 2H), 0.90 (t, J=7.35 Hz, 3H).

Example 20

Physical Properties of Liquid Crystal Compound (No. 1-4-333)

The liquid crystal composition K consisting of the mother liquid crystals A (95% by weight) and 4-[difluoro(3,4,5-trifluorophenoxy)methyl]-4"-(4-pentylcyclohexyl)-2',2",3,5,6'-pentafluoro-1,1',4',1"-terphenyl (No. 1-4-333; 5% by weight) obtained in Example 19 was prepared. The physical property values of the obtained liquid crystal composition K were measured, and the extrapolated values of the physical properties of the liquid crystal compound (No. 1-4-333) were calculated by extrapolating the measured values. The values were as follows.

Maximum temperature (T$_{NI}$)=146° C.; dielectric anisotropy (Δ∈)=39.6; refractive index anisotropy (Δn)=0.197.

From these results, it was found that the liquid crystal compound (No. 1-4-333) was a compound having a wide temperature range of a nematic phase, a high maximum temperature (T$_{NI}$), and also a large dielectric anisotropy (Δ∈).

Example 21

Synthesis of 4-[difluoro[(2,3',4',5'-tetrafluoro[1,1'-biphenyl]-4-yl)oxy]methyl]-4'-(4-pentylcyclohexyl)-2',3,5-trifluoro-1,1'-biphenyl (compound No. 1-3-255)

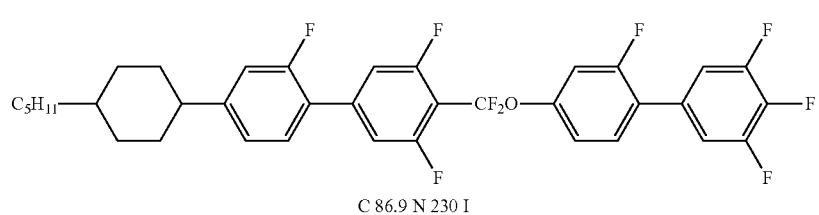

No. 1-3-255

C 86.9 N 230 I

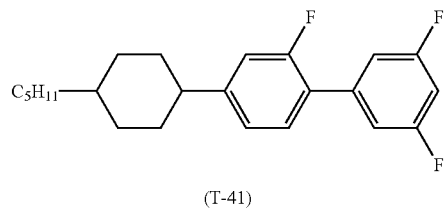

(T-41)

1) n-BuLi
2) CF$_2$Br$_2$

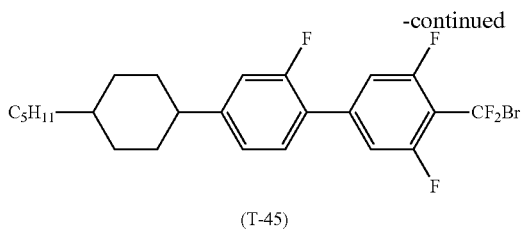

(T-45)

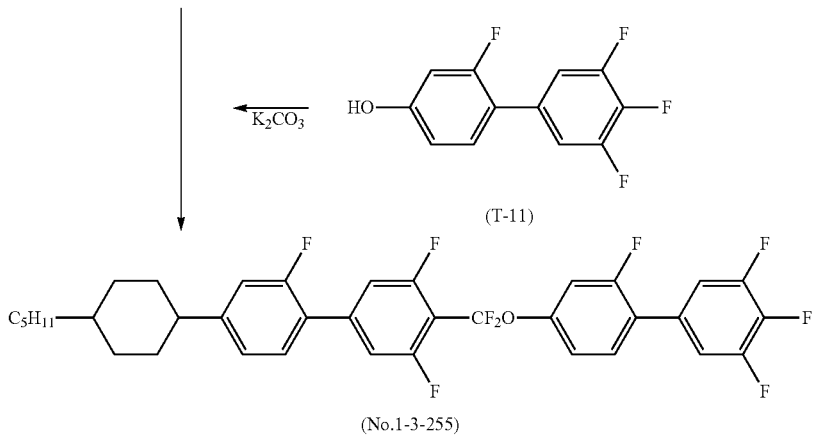

(No.1-3-255)

[Synthesis of the Compound (T-45)]

The compound (T-41; 8.00 g) and THF (140 ml) were put in a reaction vessel under a nitrogen atmosphere, and cooled to −74° C. Then, n-butyl lithium (1.58 M, in n-hexane solution; 14.9 ml) was added dropwise thereto in the temperature range of −74° C. to −70° C., and stirred for additional 60 minutes. Subsequently, dibromodifluoromethane (5.89 g) in a THF (20.0 ml) solution was added dropwise in the temperature range of −75° C. to −70° C., and stirred for additional 60 minutes while allowing the mixture to come to 25° C. The obtained reaction mixture was poured into ice-water (160 ml) and mixed. Toluene (120 ml) was added thereto and the extraction including separation into organic and aqueous layers was carried out. The obtained organic layer was fractionated, washed with brine, and then dried over anhydrous magnesium sulfate. The obtained solution was concentrated under reduced pressure, and the residue was purified with a fractional operation by means of column chromatography using heptane as the eluent and silica gel as the stationary phase powder. The solvent was distilled off and the product was dried, whereby 10.0 g of 4-bromodifluoromethyl-4'-(4-pentylcyclohexyl)-2',3,5-trifluoro-1,1'-biphenyl (T-45) was obtained. The yield based on the compound (T-41) was 87%.

[Synthesis of the Compound (No. 1-3-255)]

The compound (T-45; 5.00 g), the compound (T-11; 2.23 g), potassium carbonate (4.23 g), and DMF (75.0 ml) were put in a reaction vessel under a nitrogen atmosphere, and stirred at 90° C. for 120 minutes. The reaction mixture was cooled to 25° C., and then poured into ice-water (75.0 ml) and mixed. Toluene (75.0 ml) was added thereto and the extraction including separation into organic and aqueous layers was carried out. The obtained organic layer was fractionated, washed sequentially with a saturated solution of sodium bicarbonate, 0.5N-aqueous sodium hydroxide solution and brine, and then dried over anhydrous magnesium sulfate. The obtained solution was concentrated under reduced pressure, and the residue was purified with a fractional operation by means of column chromatography using a mixture of heptane/ethyl acetate as the eluent and silica gel as the stationary phase powder. The product was further purified by recrystallization from a mixed solvent of heptane/Solmix A-11 and dried, whereby 3.90 g of 4-[difluoro[(2,3',4',5'-tetrafluoro[1,1'-biphenyl]-4-yl)oxy]methyl]-4'-(4-pentylcyclohexyl)-2',3,5-trifluoro-1,1'-biphenyl (No. 1-3-255) was obtained. The yield based on the compound (T-45) was 59%.

The phase transition temperature of the obtained compound (No. 1-3-255) was as follows.

Phase transition temperature: C 86.9 N 230 I.

The chemical shift δ (ppm) of $^1$H-NMR analysis was as indicated below, and the obtained compound was identified as 4-[difluoro[(2,3',4',5'-tetrafluoro[1,1'-biphenyl]-4-yl)oxy]methyl]-4'-(4-pentylcyclohexyl)-2',3,5-trifluoro-1,1'-biphenyl. The measurement solvent was $CDCl_3$.

Chemical shift δ (ppm); 7.41-7.31 (m, 2H), 7.25-7.13 (m, 6H), 7.10 (dd, J=8.05 Hz, J=1.55 Hz, 1H), 7.04 (dd, J=12.2 Hz, J=1.20 Hz, 1H), 2.52 (tt, J=12.1 Hz, J=3.00 Hz, 1H), 1.97-1.86 (m, 4H), 1.51-1.40 (m, 2H), 1.38-1.20 (m, 9H), 1.13-1.01 (m, 2H), 0.90 (t, J=7.10 Hz, 3H).

Example 22

Physical Properties of Liquid Crystal Compound (No. 1-3-255)

The liquid crystal composition L consisting of the mother liquid crystals A (85% by weight) and 4-[difluoro[(2,3',4',5'-tetrafluoro[1,1'-biphenyl]-4-yl)oxy]methyl]-4'-(4-pentylcyclohexyl)-2',3,5-trifluoro-1,1'-biphenyl (No. 1-3-255; 15% by weight) obtained in Example 21 was prepared. The physical property values of the obtained liquid crystal composition L were measured, and the extrapolated values of the physical properties of the liquid crystal compound (No. 1-3-5) were calculated by extrapolating the measured values. The values were as follows.

Maximum temperature ($T_{NI}$)=146° C.; dielectric anisotropy ($\Delta\in$)=34.3; refractive index anisotropy ($\Delta$n)=0.184.

From these results, it was fount that the liquid crystal compound (No. 1-3-255) was a compound having an excellent compatibility with other liquid crystal compounds, a wide temperature range of a nematic phase, a high maximum temperature ($T_{NI}$), and also a large dielectric anisotropy ($\Delta\in$).

Example 23

Synthesis of 4-[difluoro[(2,3',4',5'-tetrafluoro[1,1'-biphenyl]-4-yl)oxy]methyl]-4'-(5-pentyl-1,3-dioxane-2-yl)-2',3,5-trifluoro-1,1'-biphenyl (compound No. 1-3-449)

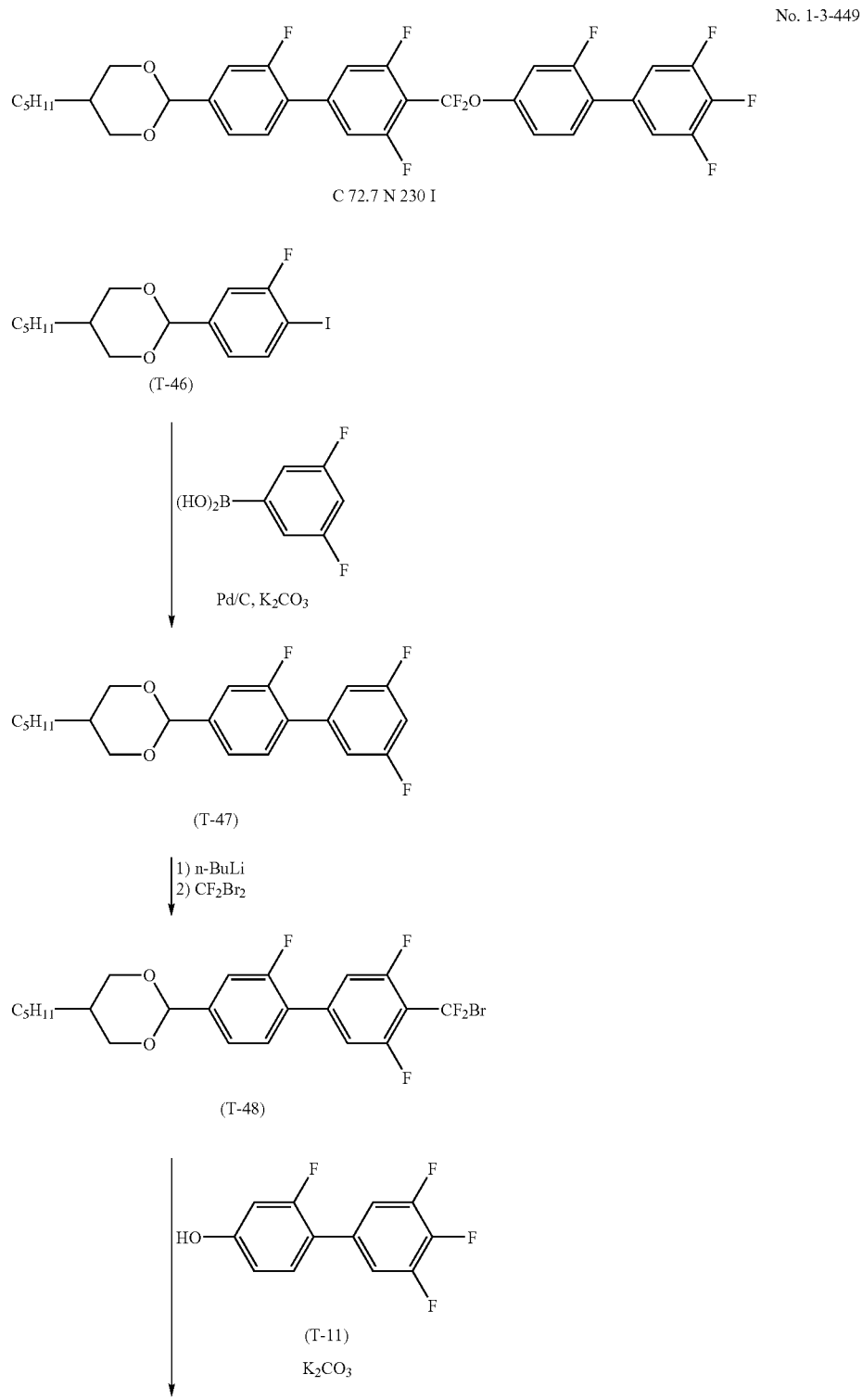

-continued

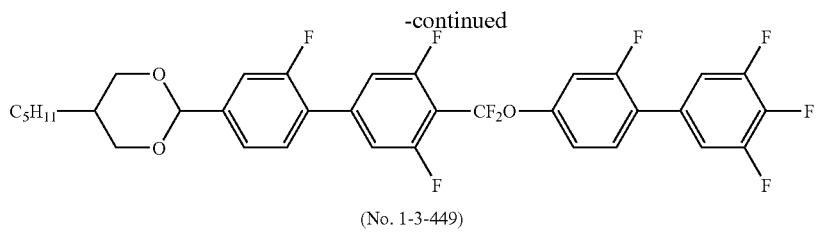

(No. 1-3-449)

[Synthesis of the Compound (T-47)]

Using 2-(3-fluoro-4-iodophenyl)-5-pentyl-1,3-dioxane (T-46; 6.00 g) as a raw material, 4.60 g of 4'-(5-pentyl-1,3-dioxane-2-yl)-2',3,5-trifluoro-1,1'-biphenyl (T-47) was obtained according to a method similar to that for the synthesis of the compound (T-15) in Example 5. The yield based on the compound (T-46) was 79%.

[Synthesis of the Compound (T-48)]

Using the compound (T-47; 4.60 g) as a raw material, 6.10 g of 4-bromodifluoromethyl-4'-(5-pentyl-1,3-dioxane-2-yl)-2',3,5-trifluoro-1,1'-biphenyl (T-48) was obtained according to a method similar to that for the synthesis of the compound (T-45) in Example 21. The yield based on the compound (T-47) was 98%.

[Synthesis of the Compound (No. 1-3-449)]

Using the compound (T-48; 6.10 g) as a raw material, 4.10 g of 4-[difluoro[(2,3',4',5'-tetrafluoro[1,1'-biphenyl]-4-yl)oxy]methyl]-4'-(5-pentyl-1,3-dioxane-2-yl)-2', 3,5-trifluoro-1,1'-biphenyl (No. 1-3-449) was obtained according to a method similar to that for the synthesis of the compound (No. 1-3-255) in Example 21. The yield based on the compound (T-48) was 48%.

The phase transition temperature of the obtained compound (No. 1-3-449) was as follows.
Phase transition temperature: C 72.7 N 203 I.

The chemical shift δ (ppm) of $^1$H-NMR analysis was as indicated below, and the obtained compound was identified as 4-[difluoro[(2,3',4',5'-tetrafluoro[1,1'-biphenyl]-4-yl)oxy]methyl]-4'-(5-pentyl-1,3-dioxane-2-yl)-2',3,5-trifluoro-1,1'-biphenyl. The measurement solvent was CDCl$_3$.

Chemical shift δ (ppm); 7.48-7.33 (m, 4H), 7.25-7.13 (m, 6H), 5.44 (s, 1H), 4.26 (dd, J=11.4 Hz, J=4.70 Hz, 2H), 3.55 (dd, J=11.4 Hz, 11.4 Hz, 2H), 2.22-2.09 (m, 1H), 1.40-1.27 (m, 6H), 1.20-1.08 (m, 2H), 0.90 (t, J=6.90 Hz, 3H).

Example 24

Physical Properties of Liquid Crystal Compound (No. 1-3-449)

The liquid crystal composition M consisting of the mother liquid crystals A (85% by weight) and 4-[difluoro[(2,3',4',5'-tetrafluoro[1,1'-biphenyl]-4-yl)oxy]methyl]-4'-(5-pentyl-1, 3-dioxane-2-yl)-2',3,5-trifluoro-1,1'-biphenyl (No. 1-3-449; 15% by weight) obtained in Example 23 was prepared. The physical property values of the obtained liquid crystal composition M were measured, and the extrapolated values of the physical properties of the liquid crystal compound (No. 1-3-449) were calculated by extrapolating the measured values. The values were as follows.

Maximum temperature ($T_{NI}$)=141° C.; dielectric anisotropy (Δ∈)=44.1; refractive index anisotropy (Δn)=0.184.

From these results, it was found that the liquid crystal compound (No. 1-3-449) was a compound having an excellent compatibility with other liquid crystal compounds, a wide temperature range of a nematic phase, a high maximum temperature (TNI), and also a large dielectric anisotropy (Δ∈).

Example 25

Synthesis of 4-[difluoro(3,4,5-trifluorophenoxy)methyl]-4''-(4-pentylcyclohexyl)-2',3-difluoro-1,1',4',1''-terphenyl (No. 1-4-343)

No. 1-4-343

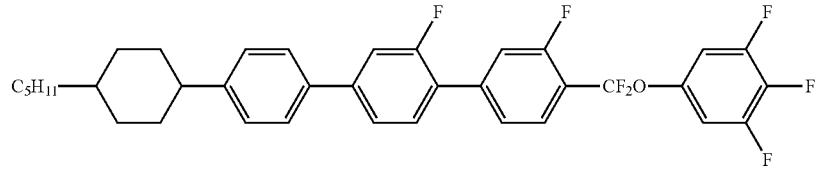

C 62.0 SC 110 SA 170 N 297 I

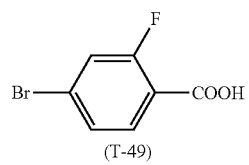

(T-49)

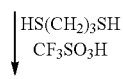

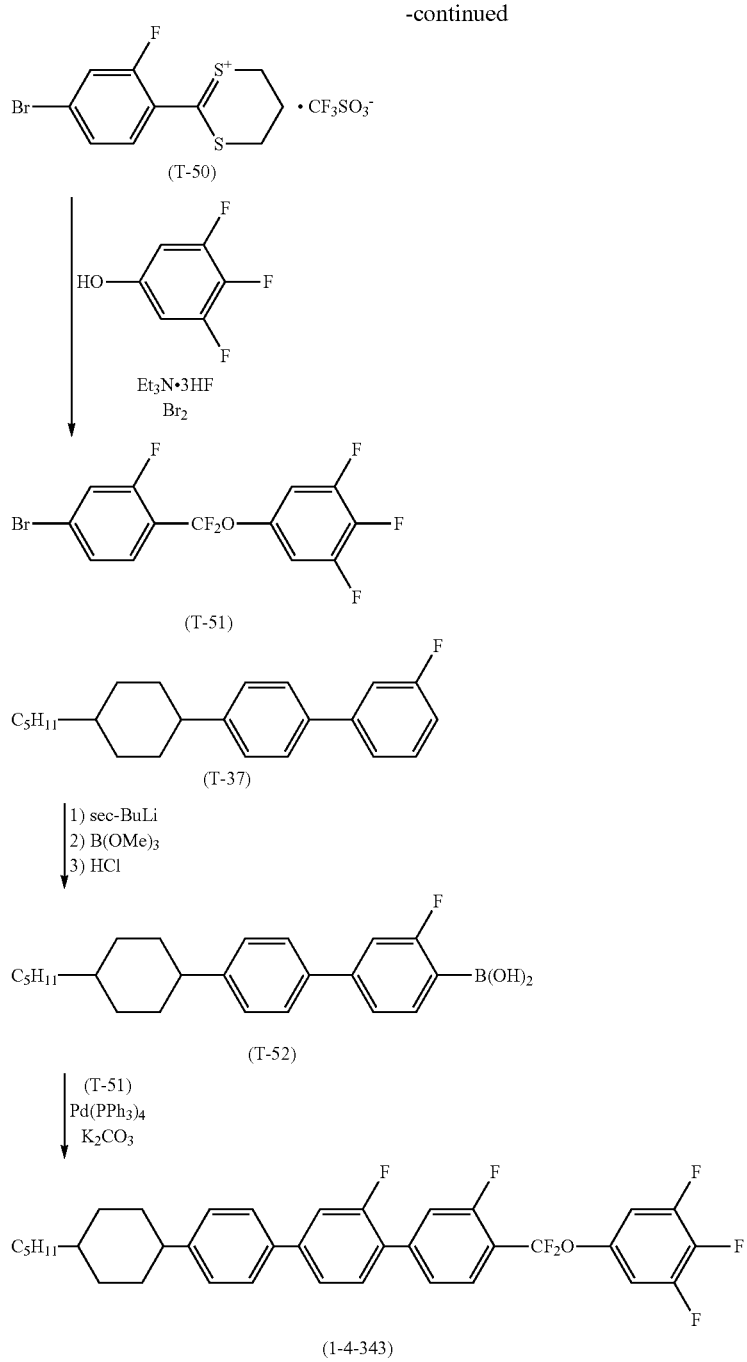

[Synthesis of the Compound (T-50)]

4-Bromo-2-fluorobenzoic acid (T-49; 25.0 g), isooctane (30.0 ml), and toluene (15.0 ml) were put in a reaction vessel under a nitrogen atmosphere, and heated to 60° C. Propanedithiol (12.6 ml) was added dropwise and stirred for additional 90 minutes, and then trifluoromethanesulfonic acid was slowly added dropwise and stirred at 60° C. for additional 60 minutes, and further stirred at 110° C. for 120 minutes for the complete reaction. The reaction mixture was cooled to 25° C. and concentrated under reduced pressure. The residue was purified by recrystallization from t-butylm ethyl ether and dried, whereby 32.4 g of dithianilium salt (T-50) was obtained. The yield based on the compound (T-49) was 64%.

[Synthesis of the Compound (T-51)]

3,4,5-Trifluorophenol (13.0 g), triethylamine (13.3 ml), and dichloromethane (140 ml) were put in a reaction vessel under a nitrogen atmosphere, and cooled to −70° C., and then the dithianilium salt (T-50) in a dichloromethane solution (280 ml) was slowly added dropwise. After stirring for 60 minutes, a hydrogen fluoride triethylamine complex (36.0 ml) was added dropwise, and stirred for additional 30 minutes. Subsequently, bromine (20.0 ml) was added slowly and stirred for additional 60 minutes. After the reaction mixture had been allowed to come to 25° C., the solution was poured into ice-water, and sodium hydrogen carbonate was added slowly to neutralize the reaction mixture. The mixture was washed sequentially with water, a saturated solution of sodium bicarbonate and water, and then concentrated under reduced pressure. The residue was purified with a fractional operation by means of column chromatography using heptane as the eluent and silica gel as the stationary phase powder and dried, whereby 18.5 g of 4-[difluoro(3,4,5-trifluorophenoxy)methyl]-3-fluorobromobenzene (T-51) was obtained. The yield based on the compound (T-50) was 68%.

[Synthesis of the Compound (T-52)]

The compound (T-37; 6.00 g) and THF (100 ml) were put in a reaction vessel under a nitrogen atmosphere, and cooled to −74° C. Then, sec-butyl lithium (1.0 M, in cyclohexane and n-hexane solution; 22.2 ml) were added dropwise thereto in the temperature range of −74° C. to −68° C., and stirred for additional 120 minutes. Subsequently, trimethyl borate (2.81 g) in a THF (25.0 ml) solution was added dropwise in the temperature range of −75° C. to −68° C., and further stirred overnight while allowing the reaction mixture to come to 25° C. Subsequently, the reaction mixture was cooled to −30° C., and 6N-hydrochloric acid (20 ml) was slowly added dropwise, and stirred for additional 180 minutes while allowing the reaction mixture to come to 25° C. Then, the reaction mixture was poured into ice-water (200 ml) and mixed. Ethyl acetate (200 ml) was added to separate the mixture into organic and aqueous layers, and an extraction operation was carried out. The obtained organic layer was fractionated, washed sequentially with water, a saturated solution of sodium bicarbonate and brine, and then dried over anhydrous magnesium sulfate. Then, the solvent is distilled off under reduced pressure, whereby 5.41 g of 4-(4-pentylcyclohexyl)-phenyl-2-fluorophenylboronic acid (T-52) was obtained. The yield based on the compound (T-37) was 79%.

[Synthesis of the Compound (No. 1-4-343)]

4-[Difluoro(3,4,5-trifluorophenoxy)methyl]-3-fluorobromobenzene (T-51; 1.97 g), 4-(4-pentylcyclohexyl)-phenyl-2-fluorophenylboronic acid (T-52; 2.00 g), tetrakis(triphenylphosphine)palladium (0.0627 g), potassium carbonate (2.21 g), toluene (40.0 ml), Solmix A-11 (40.0 ml), and water (40.0 ml) were put in a reaction vessel under a nitrogen atmosphere, and heated under reflux for 2 hours. The reaction mixture was cooled to 25° C., and then poured into water (80.0 ml) and toluene (80.0 ml) and mixed. Then, the mixture was allowed to stand to be separated into two layers of organic and aqueous layers, and the extraction to an organic layer was carried out. The obtained organic layer was fractionated, washed with water, and then dried over anhydrous magnesium sulfate. The obtained solution was concentrated under reduced pressure, and the residue was purified with a fractional operation by means of column chromatography using heptane as the eluent and silica gel as the stationary phase powder. The product was further purified by recrystallization from a mixed solvent of heptane/Solmix A-11 and dried, whereby 2.27 g of 4-[difluoro(3,4,5-trifluorophenoxy)methyl]-4"-(4-pentylcyclohexyl)-2',3-difluoro-1,1',4',1"-terphenyl (1-4-343) was obtained. The yield based on the compound (T-51) was 69%.

The phase transition temperature of the obtained compound (No. 1-4-343) was as follows.

Phase transition temperature: C 62.0 $S_C$ 110 $S_A$ 170 N 297 I.

The chemical shift δ (ppm) of $^1$H-NMR analysis was as indicated below, and the obtained compound was identified as 4-[difluoro(3,4,5-trifluorophenoxy)methyl]-4"-(4-pentylcyclohexyl)-2',3-difluoro-1,1',4',1"-terphenyl. The measurement solvent was $CDCl_3$.

Chemical shift δ (ppm); 7.73 (t, J=8.00 Hz, 1H), 7.55 (d, J=8.15 Hz, 2H), 7.51-7.38 (m, 5H), 7.32 (d, J=8.20 Hz, 2H), 7.04-6.95 (m, 2H), 2.53 (tt, J=12.1 Hz, J=3.00 Hz, 1H), 2.00-1.86 (m, 4H), 1.55-1.44 (m, 2H), 1.40-1.21 (m. 9H), 1.14-1.02 (m, 2H), 0.91 (t, J=7.10 Hz, 3H).

Example 26

Physical Properties of Liquid Crystal Compound (No. 1-4-343)

The liquid crystal composition N consisting of the mother liquid crystals A (85% by weight) and 4-[difluoro(3,4,5-trifluorophenoxy)methyl]-4"-(4-pentylcyclohexyl)-2',3-difluoro-1,1',4',1"-terphenyl (No. 1-4-343; 15% by weight) obtained in Example 25 was prepared. The physical property values of the obtained liquid crystal composition N were measured, and the extrapolated values of the physical properties of the liquid crystal compound (No. 1-4-343) were calculated by extrapolating the measured values. The values were as follows.

Maximum temperature ($T_{NI}$) 210° C.; dielectric anisotropy (Δ∈)=16.4; refractive index anisotropy (Δn)=0.217.

From these results, it was found that the liquid crystal compound (No. 1-4-343) was a compound having a wide temperature range of a nematic phase, an excellent compatibility with other liquid crystal compounds, and an especially high maximum temperature ($T_{NI}$).

Example 27

Synthesis of 4-[difluoro(3,4,5-trifluorophenoxy)methyl]-4"-(4-pentylcyclohexyl)-2'-fluoro-1,1',4',1"-terphenyl (No. 1-4-348)

No. 1-4-348

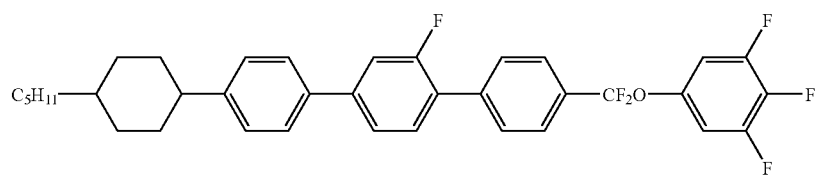

C 81.0 SF 118 SC 143
SA 220 N 305 I

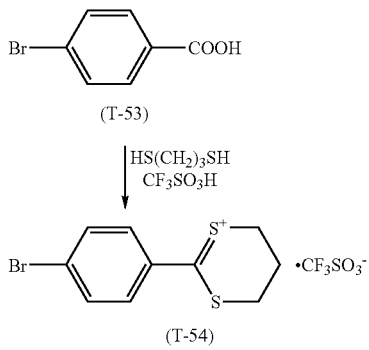
(T-53)

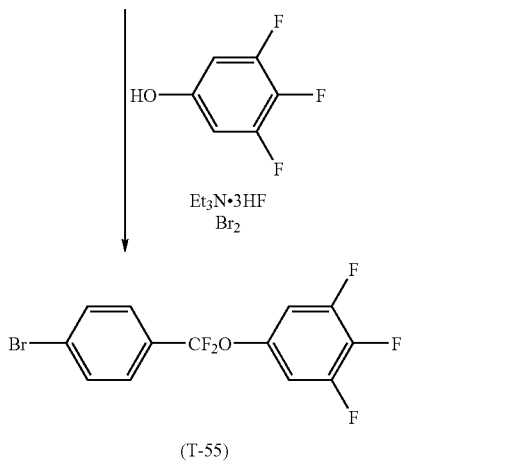
(T-54)

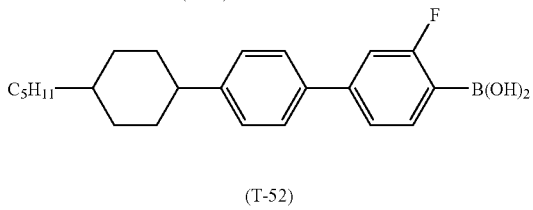
(T-55)

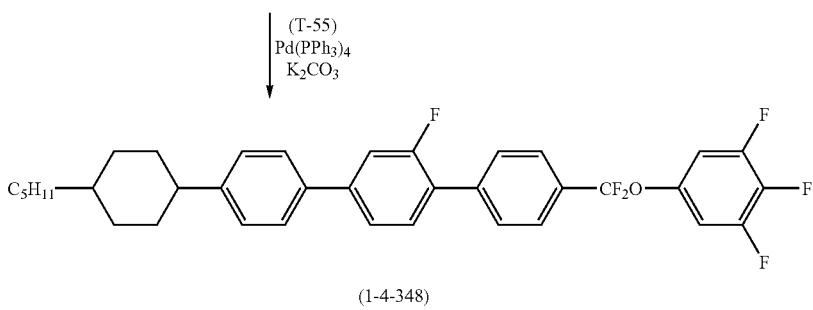
(T-52)

(1-4-348)

[Synthesis of the Compound (T-54)]

Using 4-bromobenzoic acid (T-53; 25.0 g) as a raw material, 34.5 g of the dithianilium salt (T-54) was obtained according to a method similar to that for the synthesis of the compound (T-50) in Example 25. The yield based on the compound (T-53) was 66%.

[Synthesis of the Compound (T-55)]

Using the dithianilium salt (T-54; 34.5 g) as a raw material, 20.9 g of 4-[difluoro(3,4,5-trifluorophenoxy)methyl]bromobenzene (T-55) was obtained according to a method similar to that for the synthesis of the compound (T-51) in Example 25. The yield based on the compound (T-54) was 73%.

[Synthesis of the Compound (No. 1-4-348)]

Using 4-[difluoro(3,4,5-trifluorophenoxy)methyl]bromobenzene (T-55; 3.00 g) and 4-(4-pentylcyclohexyl)-phenyl-2-fluorophenylboronic acid (T-52; 3.19 g) as raw materials, 4.45 g of 4-[difluoro(3,4,5-trifluorophenoxy)methyl]-4"-(4-pentylcyclohexyl)-2'-fluoro-1,1',4',1"-terphenyl (1-4-348) was obtained according to a method similar to that for the synthesis of the compound (No. 1-4-343) in Example 25. The yield based on the compound (T-55) was 86%.

The phase transition temperature of the obtained compound (No. 1-4-348) was as follows.

Phase transition temperature: C 81.0 $S_F$ 118 $S_C$ 143 $S_A$ 220 N 305 I.

The chemical shift δ (ppm) of $^1$H-NMR analysis was as indicated below, and the obtained compound was identified as 4-[difluoro(3,4,5-trifluorophenoxy)methyl]-4"-(4-pentylcyclohexyl)-2'-fluoro-1,1',4',1"-terphenyl. The measurement solvent was CDCl$_3$.

Chemical shift δ (ppm); 7.77 (d, J=8.50 Hz, 2H), 7.71 (d, J=7.85 Hz, 2H), 7.55 (d, J=8.20 Hz, 2H), 7.53-7.44 (m, 2H), 7.40 (dd, J=12.1 Hz, J=1.35 Hz, 1H), 7.02-6.94 (m, 2H), 2.53 (tt, J=9.10 Hz, J=3.25 Hz, 1H), 2.00-1.86 (m, 4H), 1.55-1.44 (m, 2H), 1.40-1.20 (m, 9H), 1.14-1.02 (m, 2H), 0.91 (t, J=7.05 Hz, 3H).

Example 28

Physical Properties of Liquid Crystal Compound (No. 1-4-348)

The liquid crystal composition O consisting of the mother liquid crystals A (85% by weight) and 4-[difluoro(3,4,5-trifluorophenoxy)methyl]-4"-(4-pentylcyclohexyl)-2'-fluoro-1,1',4',1"-terphenyl (No. 1-4-348; 15% by weight) obtained in Example 27 was prepared. The physical property values of the obtained liquid crystal composition O were measured, and the extrapolated values of the physical properties of the liquid crystal compound (No. 1-4-348) were calculated by extrapolating the measured values. The values were as follows.

Maximum temperature ($T_{NI}$)=218° C.; dielectric anisotropy (Δ∈)=11.7; refractive index anisotropy (Δn)=0.224.

From these results, it was found that the liquid crystal compound (No. 1-4-348) was a compound having a wide temperature range of a nematic phase, an excellent compatibility with other liquid crystal compounds, and an especially high maximum temperature ($T_{NI}$).

Example 29

Synthesis of 4-[difluoro(3,4,5-trifluorophenoxy)methyl]-4"-(5-pentyl-1,3-dioxane-2-yl)-2',3,5-trifluoro-1,1',4',1"-terphenyl (compound No. 1-4-667)

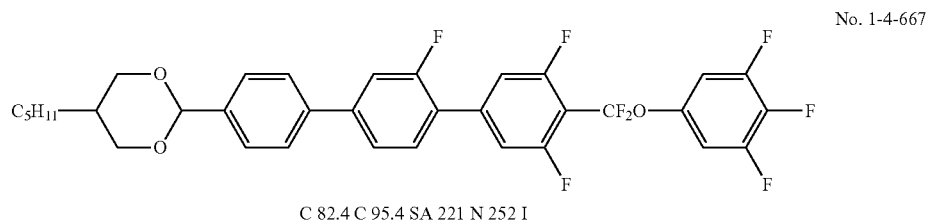

No. 1-4-667

C 82.4 C 95.4 SA 221 N 252 I

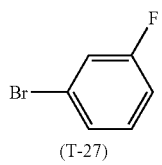

(T-27)

Pd(PPh$_3$)$_2$Cl$_2$
PPh$_3$, K$_2$CO$_3$

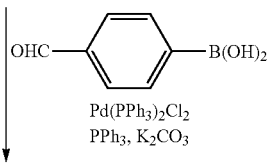

(T-56)

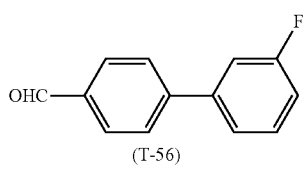

p-TsOH

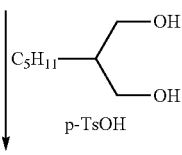

-continued
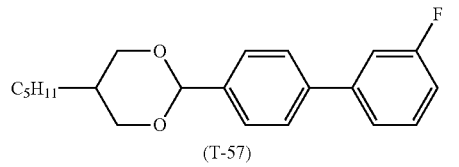
(T-57)
1) sec-BuLi
2) I₂
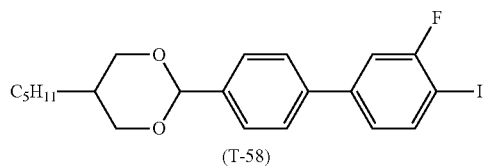
(T-58)
(HO)₂B—⟨3,5-diF-phenyl⟩
Pd/C, K₂CO₃
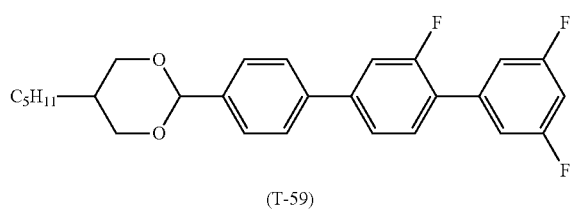
(T-59)
1) n-BuLi
2) CF₂Br₂
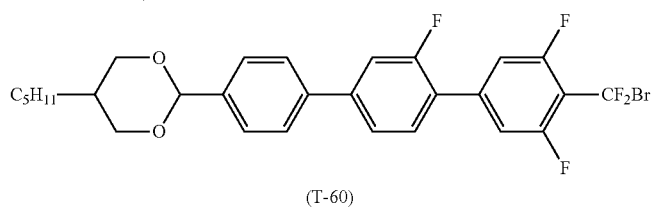
(T-60)
HO—⟨3,4,5-triF-phenyl⟩,
K₂CO₃
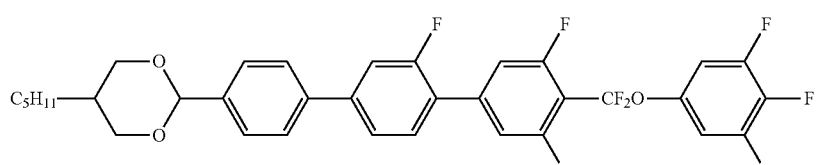
(No. 1-4-667)

[Synthesis of the Compound (T-56)]

Using the compound (T-27; 21.8 g) and 4-formylphenylboronic acid (25.0 g), 24.1 g of 3-fluoro-4'-formyl-1,1'-biphenyl (T-56) was obtained according to a method similar to that for the synthesis of the compound (T-2) in Example 1. The yield based on the compound (T-27) was 84%.

[Synthesis of the Compound (T-57)]

The compound (T-56; 24.1 g), 2-pentylpropanediol (36.2 g), p-toluenesulfonic acid monohydrate (3.14 g), and toluene (120 ml) were put in a reaction vessel under a nitrogen atmosphere, and reacted under heating reflux for 120 minutes while removing water being distilled. The obtained reaction mixture was washed sequentially with water, a saturated solution of sodium bicarbonate and water, and then dried over anhydrous magnesium sulfate. Then, the solvent was distilled off under reduced pressure, and the residue was purified with a fractional operation by means of column chromatography using toluene as the eluent and silica gel as the stationary phase powder. The product was further purified by recrystallization from a mixed solvent of ethyl acetate and Solmix A-11 and dried, whereby 26.0 g of 3-fluoro-4'-(5-pentyl-1,3-dioxane-2-yl)-1,1'-biphenyl (T-57) was obtained. The yield based on the compound (T-56) was 48%.

[Synthesis of the Compound (T-58)]

Using the compound (T-57; 10.0 g) as a raw material, 10.3 g of 3-fluoro-4-iodo-4'-(5-pentyl-1,3-dioxane-2-yl)-1,1'-biphenyl (T-58) was obtained according to a method similar to that for the synthesis of the compound (T-3) in Example 1. The yield based on the compound (T-57) was 75%.

[Synthesis of the Compound (T-59)]

Using the compound (T-58; 10.3 g) as a raw material, 8.92 g of 4"-(5-pentyl-1,3-dioxane-2-yl)-2',3,5-trifluoro-1,1',4',1"-terphenyl (T-59) was obtained according to a method similar to that for the synthesis of (T-6) in Example 1. The yield based on the compound (T-58) was 89%.

[Synthesis of the Compound (T-60)]

Using the compound (T-59; 4.00 g) as a raw material, 4.82 g of 4-bromodifluoromethyl-4"-(5-pentyl-1,3-dioxane-2-yl)-2',3,5-trifluoro-1,1',4',1"-terphenyl (T-60) was obtained according to a method similar to that for the synthesis of (T-7) in Example 1. The yield based on the compound (T-59) was 93%.

[Synthesis of the Compound (No. 1-4-667)]

Using the compound (T-60; 4.82 g) as a raw material, 3.07 g of 4-[difluoro(3,4,5-trifluorophenoxy)methyl]-4"-(5-pentyl-1,3-dioxane-2-yl)-2',3,5-trifluoro-1,1',4',1"-terphenyl (No. 1-4-667) was obtained according to a method similar to that for the synthesis of (1-4-5) in Example 1. The yield based on the compound (T-60) was 57%.

The phase transition temperature of the obtained compound (No. 1-4-667) was as follows.

Phase transition temperature: $C_1$ 82.4 $C_2$ 95.4 $S_A$ 221 N 252 I.

The chemical shift δ (ppm) of $^1$H-NMR analysis was as indicated below, and the obtained compound was identified as 4-[difluoro(3,4,5-trifluorophenoxy)methyl]-4"-(5-pentyl-1,3-dioxane-2-yl)-2',3,5-trifluoro-1,1',4',1"-terphenyl. The measurement solvent was $CDCl_3$.

Chemical shift δ (ppm); 7.65-7.57 (m, 4H), 7.54-7.46 (m, 2H), 7.43 (d, J=12.6 Hz, 1H), 7.26 (d, J=9.20 Hz, 2H), 7.00 (m, 2H), 5.48 (s, 1H), 4.27 (dd, J=11.6 Hz, J=4.70 Hz, 2H), 3.57 (dd, J=11.4 Hz, 11.4 Hz, 2H), 2.22-2.10 (m, 1H), 1.38-1.23 (m, 6H), 1.18-1.08 (m, 2H), 0.90 (t, J=7.10 Hz, 3H).

Example 30

Physical Properties of Liquid Crystal Compound (No. 1-4-667)

The liquid crystal composition P consisting of the mother liquid crystals A (85% by weight) and 4-[difluoro(3,4,5-trifluorophenoxy)methyl]-4"-(5-pentyl-1,3-dioxane-2-yl)-2',3,5-trifluoro-1,1',4',1"-terphenyl (No. 1-4-667; 15% by weight) obtained in Example 29 was prepared. The physical property values of the obtained liquid crystal composition P were measured, and the extrapolated values of the physical properties of the liquid crystal compound (No. 1-4-667) were calculated by extrapolating the measured values. The values were as follows.

Maximum temperature $(T_{NI})$=190° C.; dielectric anisotropy (Δ∈)=27.0; refractive index anisotropy (Δn)=0.210.

From these results, it was found that the liquid crystal compound (No. 1-4-667) was a compound having a wide temperature range of a nematic phase, an excellent compatibility with other liquid crystal compounds, a high maximum temperature $(T_{NI})$, and also a large dielectric anisotropy (Δ∈).

Example 31

The following compounds (No. 1-1-1) to (No. 1-1-368), (No. 1-2-1) to (No. 1-2-562), (No. 1-3-1) to (No. 1-3-616), and (No. 1-4-1) to (No. 1-4-838) can be synthesized based on Examples 1, 3, 5, 7, 9, 11, 13, 15, 17, 19, 21, 23, 25, 27, and 29, and also on the synthetic methods described above. Data noted are values determined according to the above-described methods. Phase transition temperatures are the measured values of the compounds themselves. Maximum temperature $(T_{NI})$, dielectric anisotropy (Δ∈), and optical anisotropy (Δn) are extrapolated values obtained by converting the measured values of samples having the compounds mixed in the mother liquid crystals (A) according to the extrapolation method as described in Examples 2, 4, 6, 8, 10, 12, 14, 16, 18, 20, 22, 24, 26, 28, and, 30.

No. 1-1-1

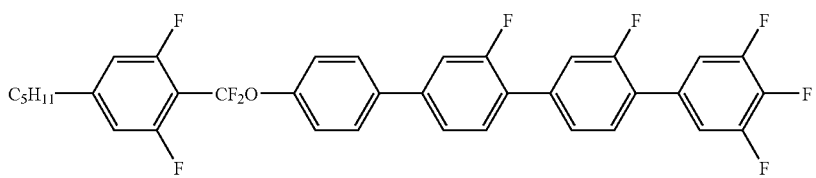

1-1-2

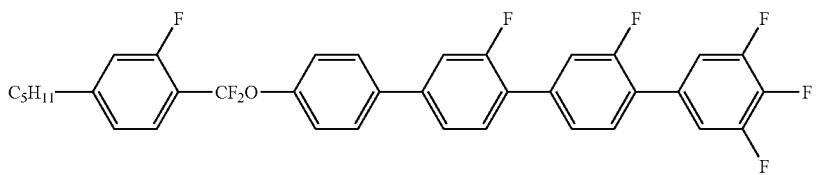

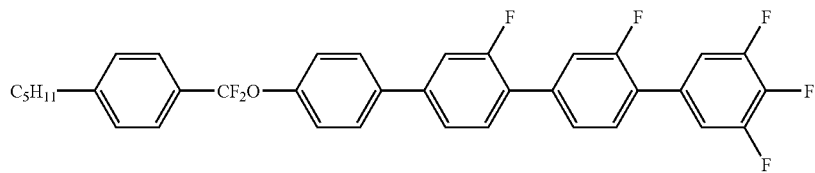
1-1-3
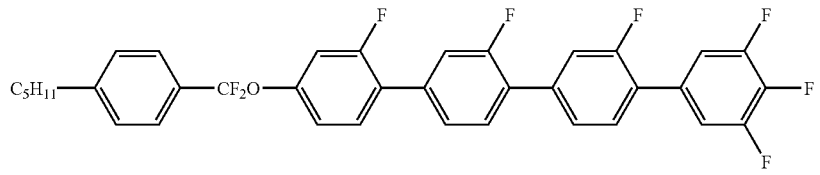
1-1-4
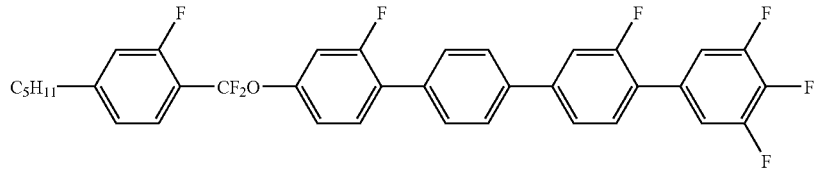
1-1-5
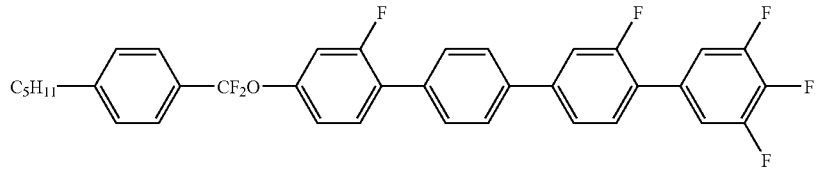
1-1-6
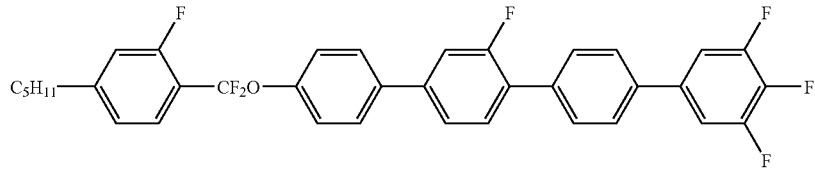
1-1-7
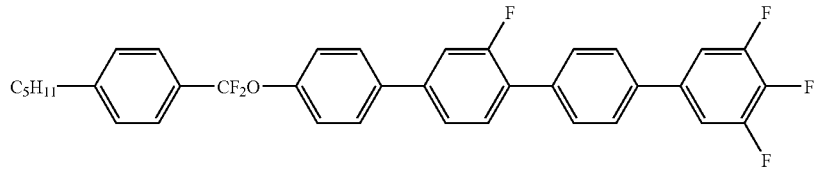
1-1-8
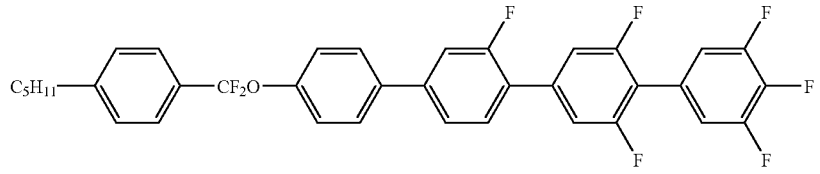
1-1-9
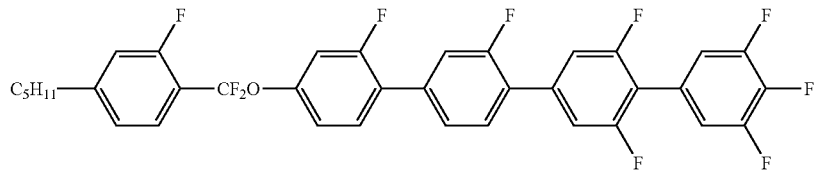
1-1-10
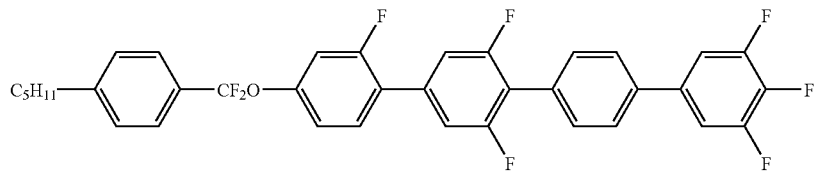
1-1-11

-continued
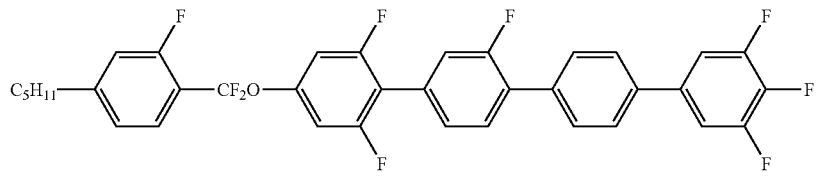
1-1-12
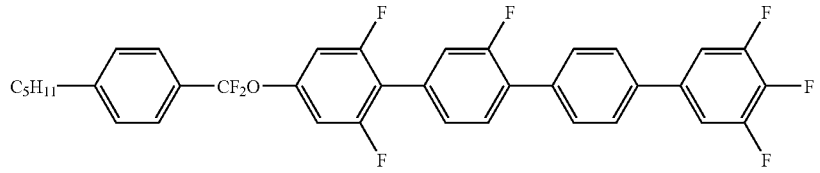
1-1-13
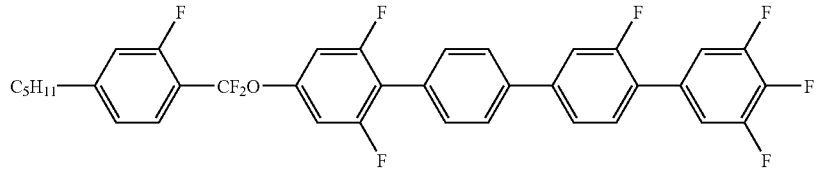
1-1-14
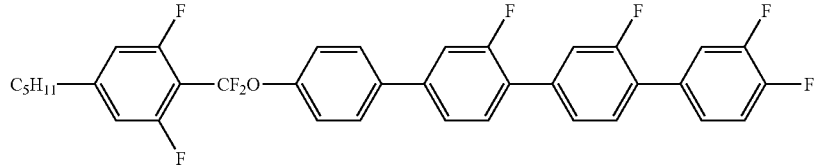
1-1-15
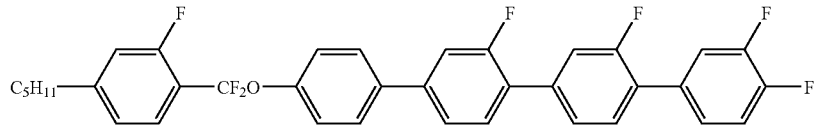
1-1-16
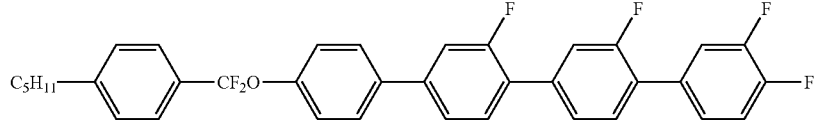
1-1-17
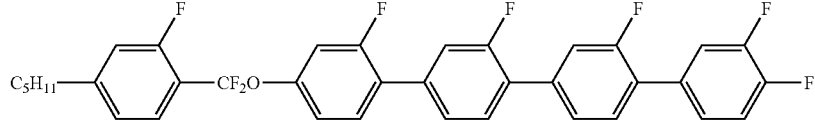
1-1-18
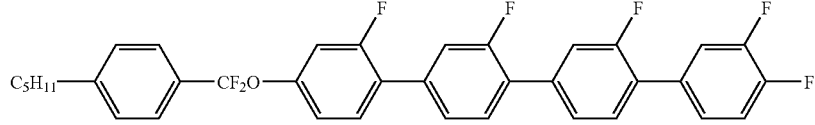
1-1-19
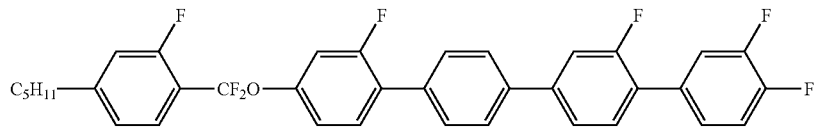
1-1-20
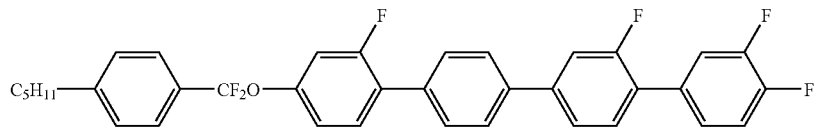
1-1-21

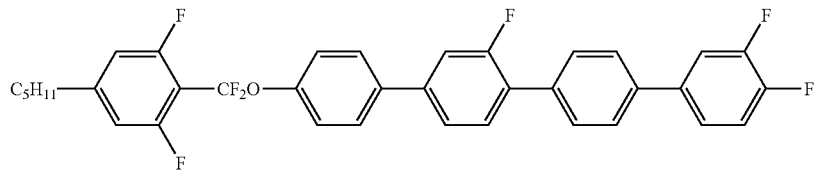
1-1-22
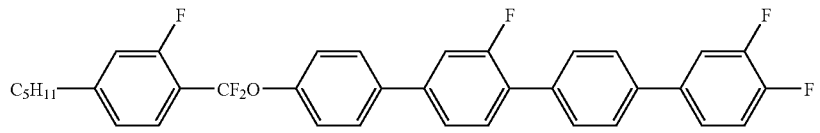
1-1-23
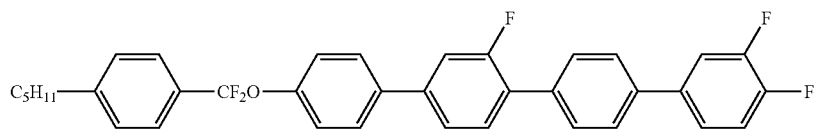
1-1-24
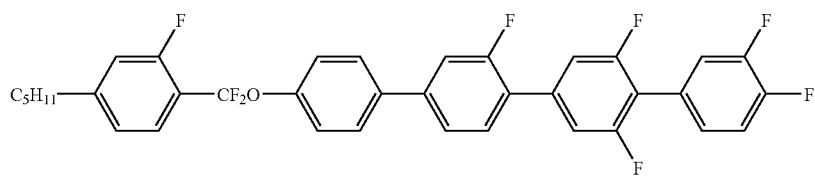
1-1-25
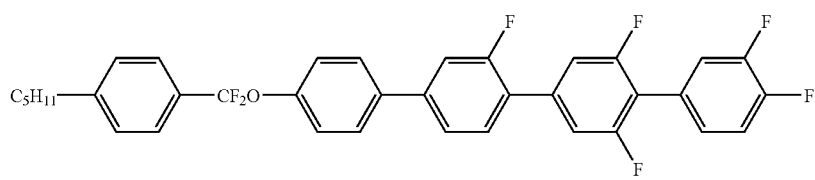
1-1-26
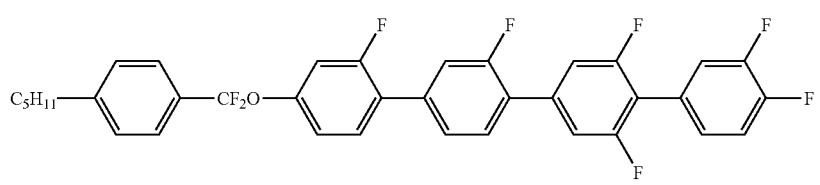
1-1-27
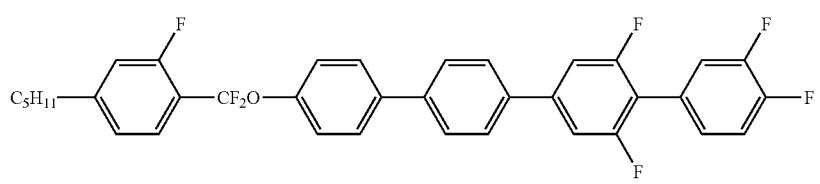
1-1-28
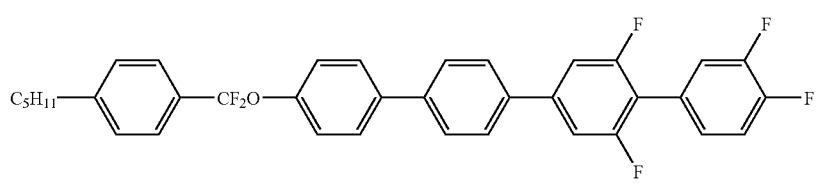
1-1-29
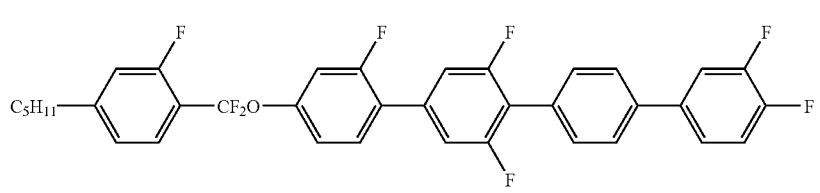
1-1-30

-continued
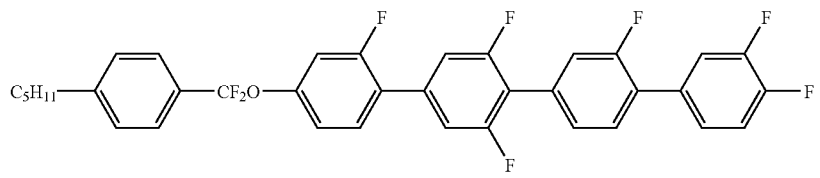
1-1-31
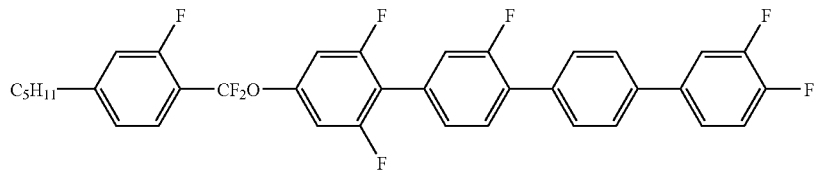
1-1-32
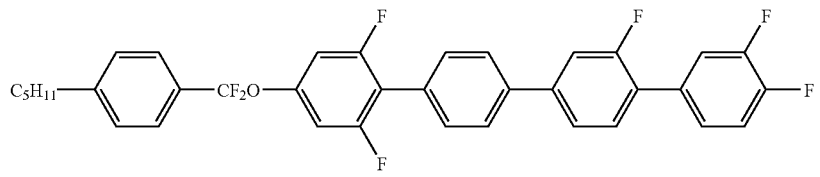
1-1-33
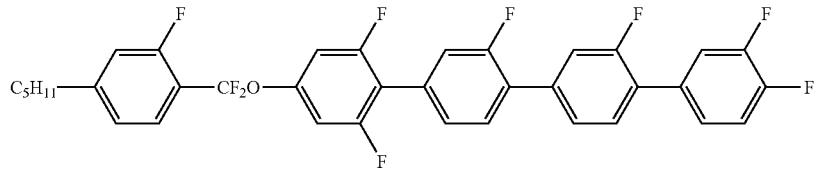
1-1-34
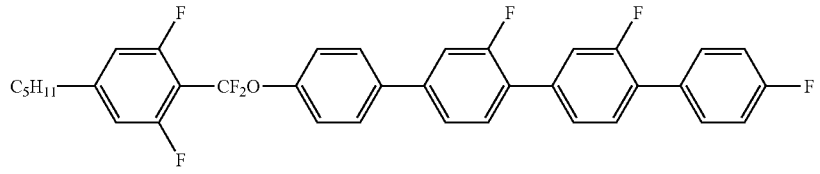
1-1-35
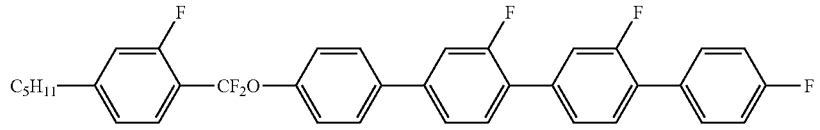
1-1-36
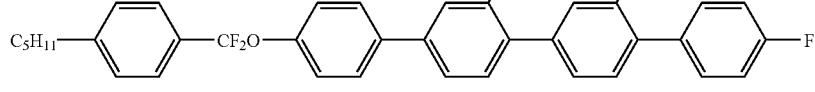
1-1-37
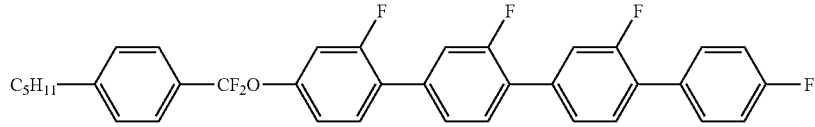
1-1-38
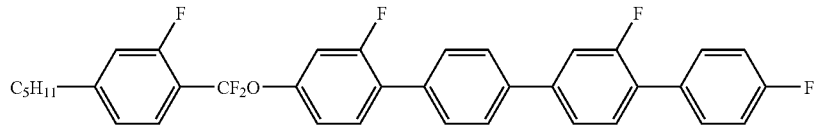
1-1-39
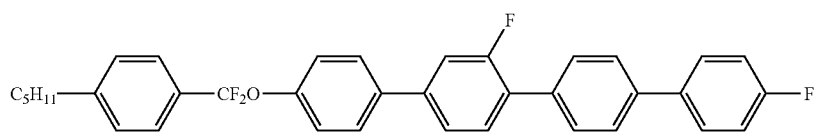
1-1-40

-continued
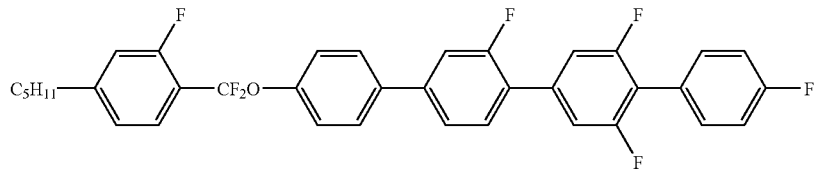
1-1-41
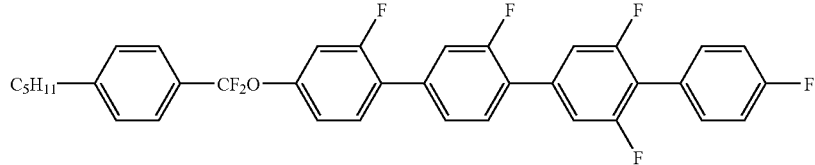
1-1-42
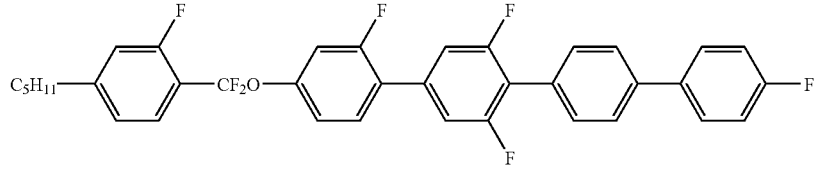
1-1-43
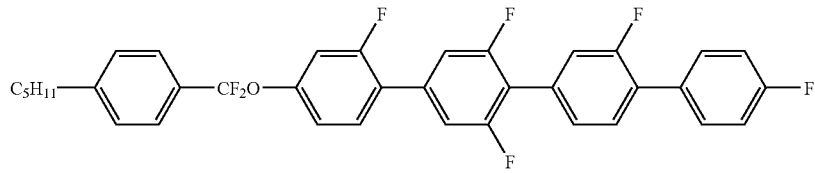
1-1-44
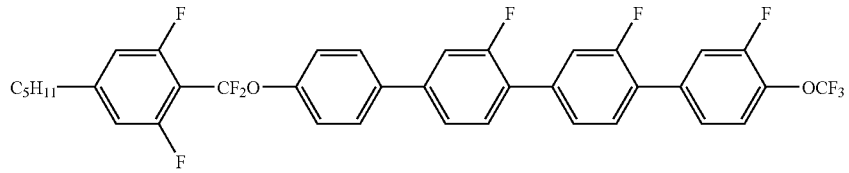
1-1-45
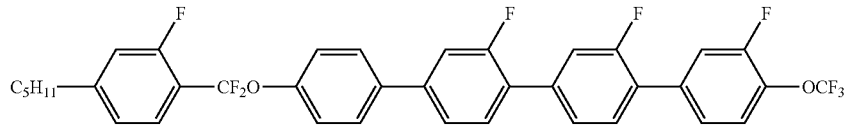
1-1-46
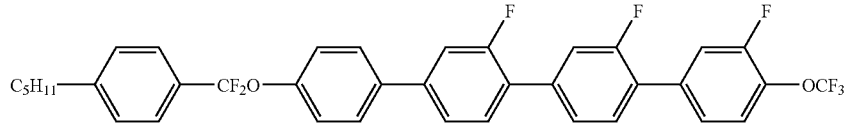
1-1-47
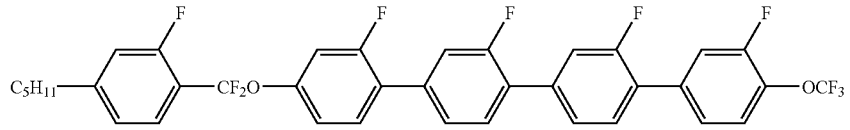
1-1-48
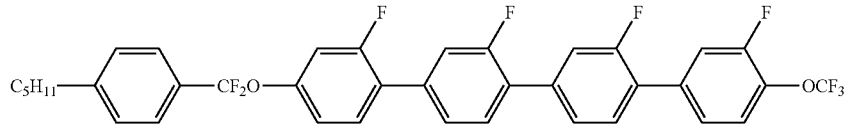
1-1-49
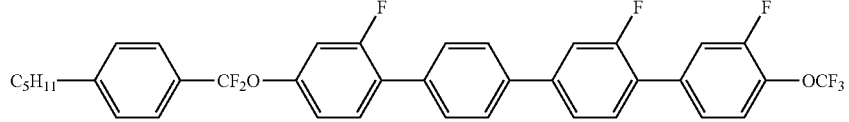
1-1-50

-continued
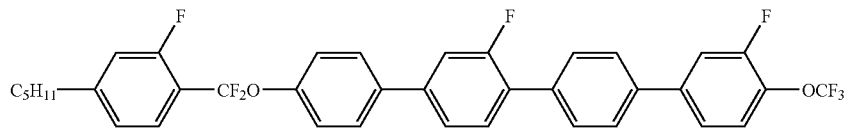
1-1-51
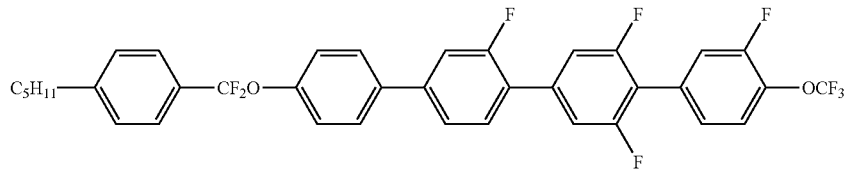
1-1-52
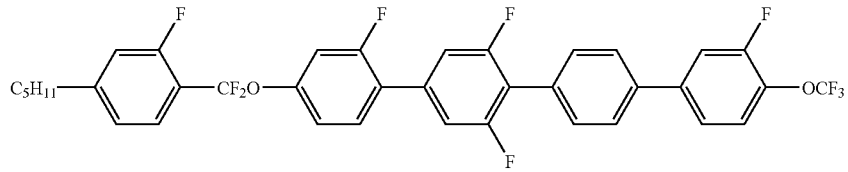
1-1-53
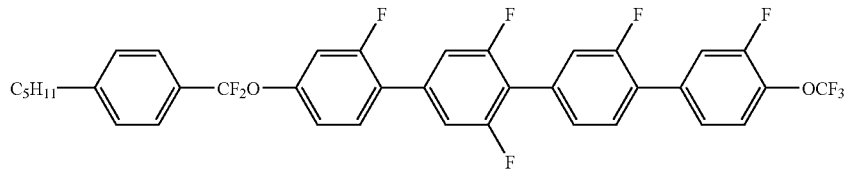
1-1-54
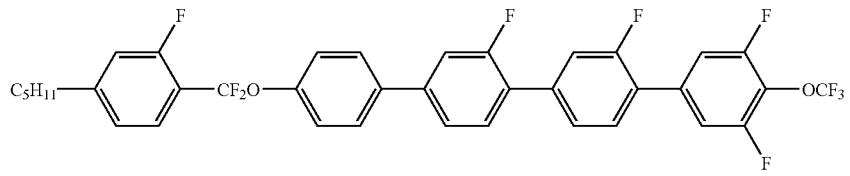
1-1-55
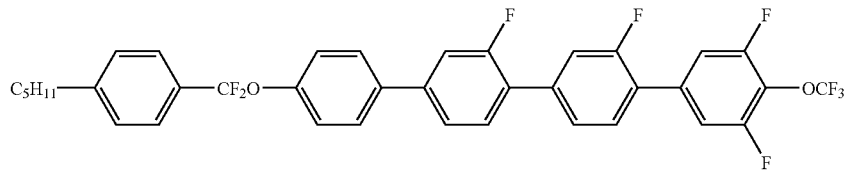
1-1-56
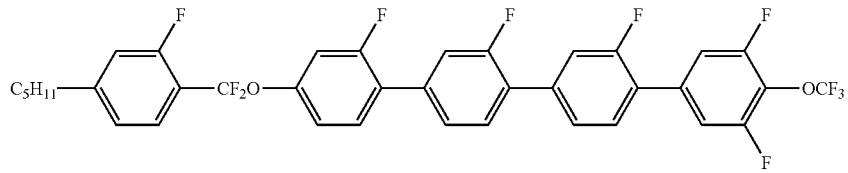
1-1-57
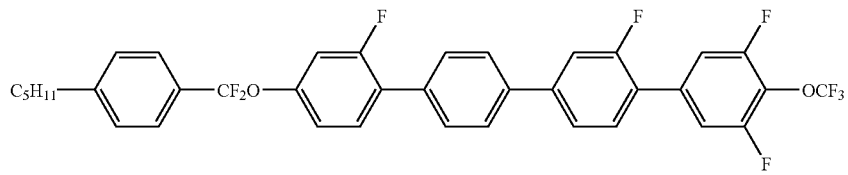
1-1-58
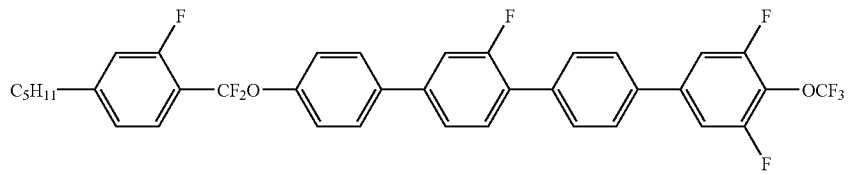
1-1-59

-continued
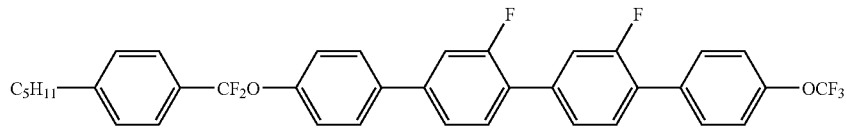
1-1-60
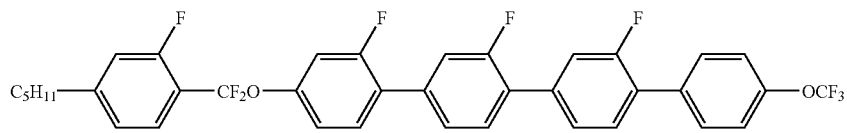
1-1-61
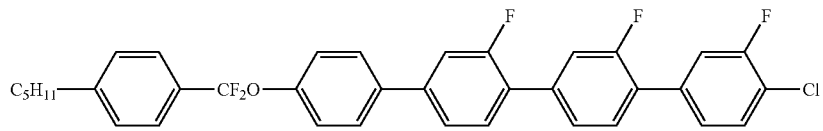
1-1-62
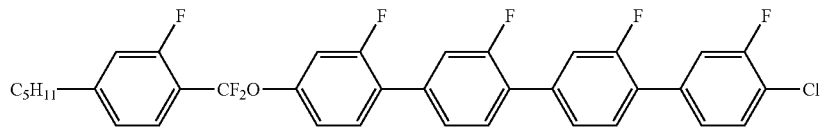
1-1-63
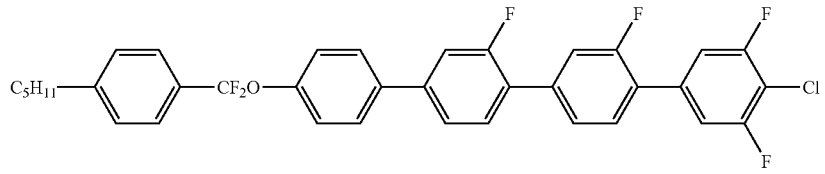
1-1-64
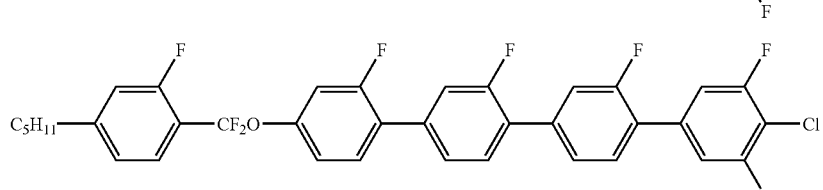
1-1-65
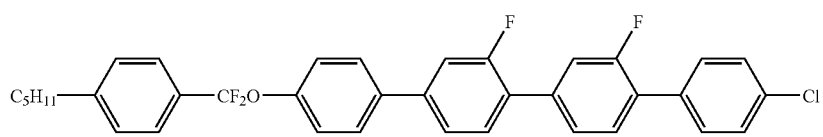
1-1-66
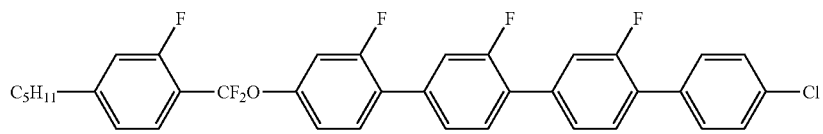
1-1-67
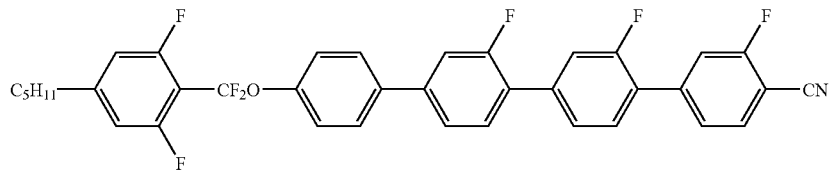
1-1-68
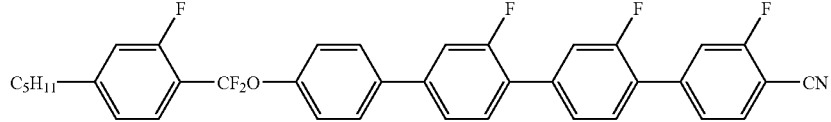
1-1-69
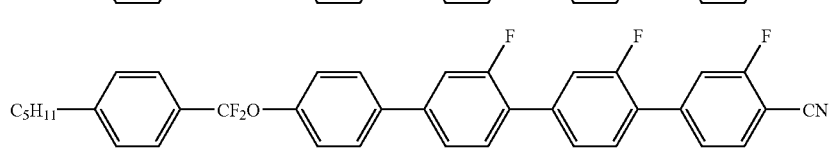
1-1-70

-continued
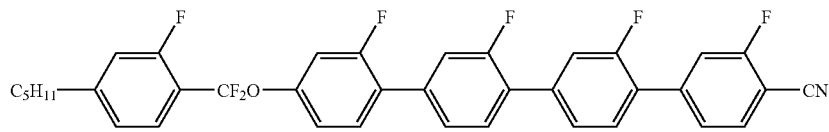
1-1-71
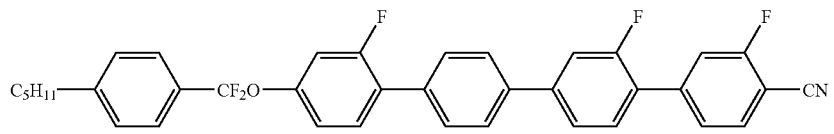
1-1-72
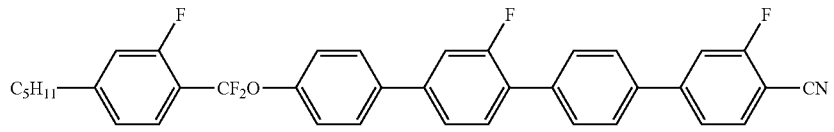
1-1-73
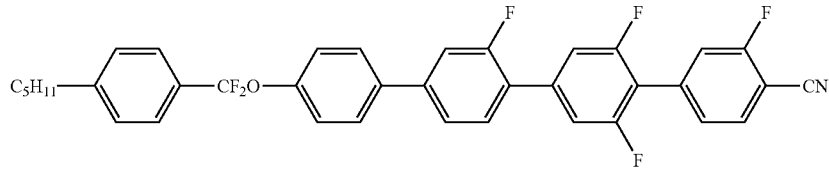
1-1-74
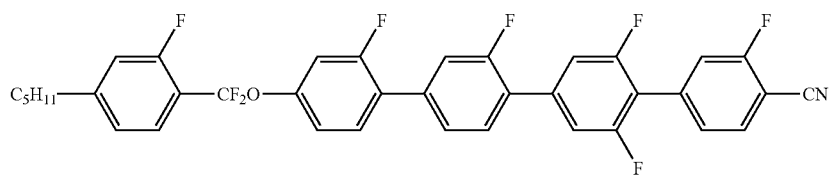
1-1-75
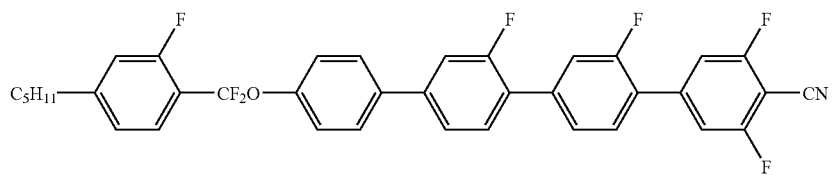
1-1-76
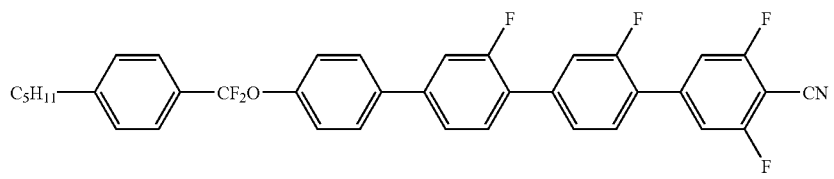
1-1-77
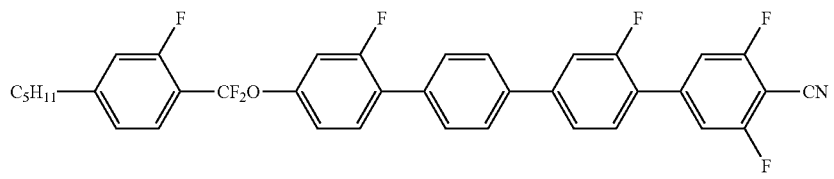
1-1-78
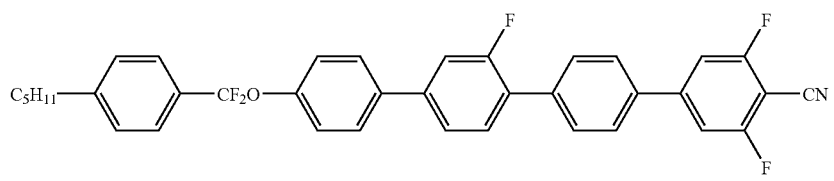
1-1-79
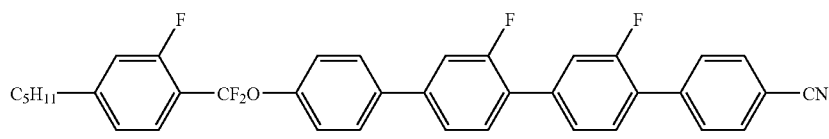
1-1-80

-continued
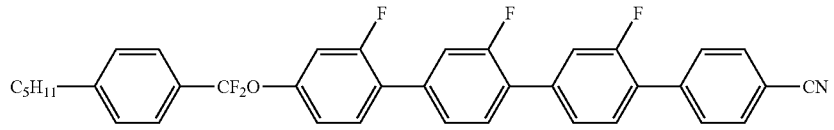
1-1-81
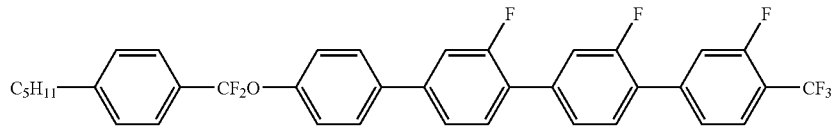
1-1-82
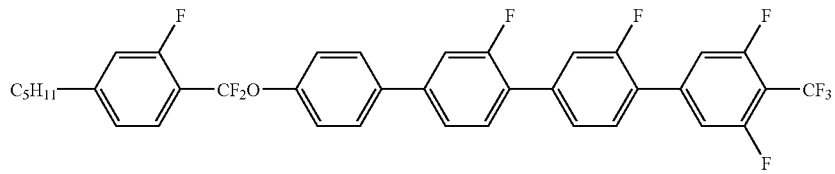
1-1-83
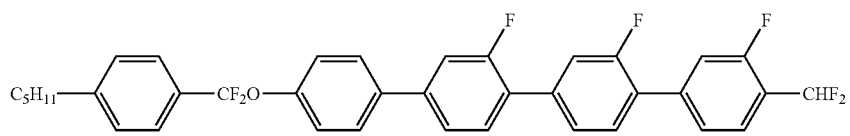
1-1-84
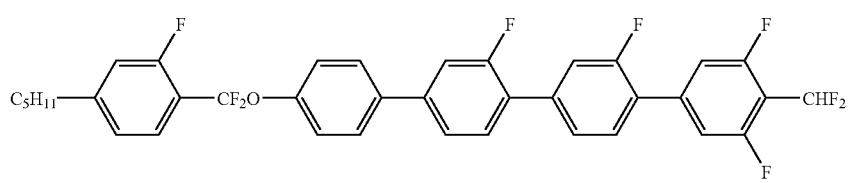
1-1-85
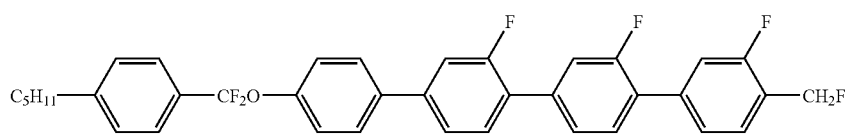
1-1-86
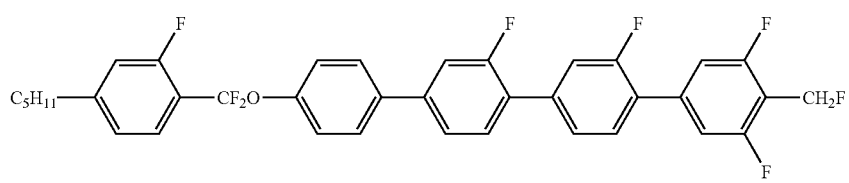
1-1-87
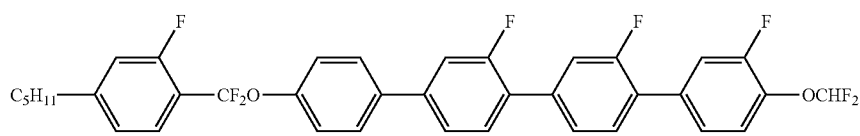
1-1-88
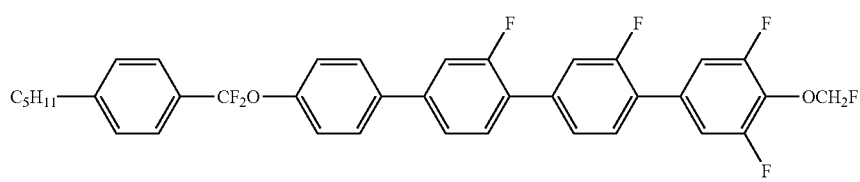
1-1-89
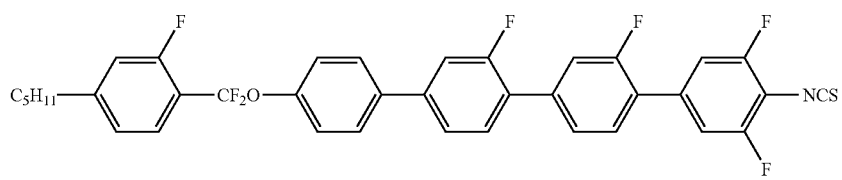
1-1-90

-continued
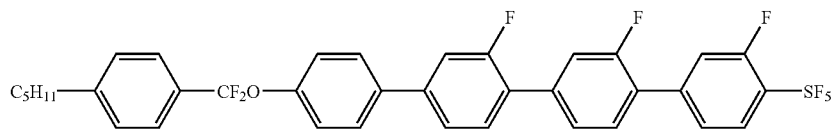
1-1-91
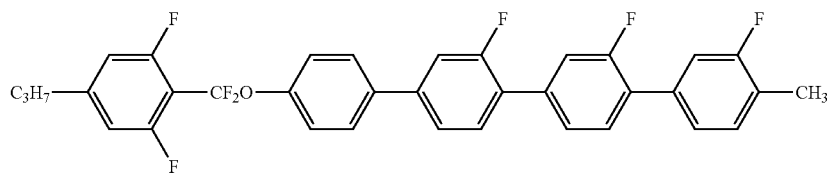
1-1-92
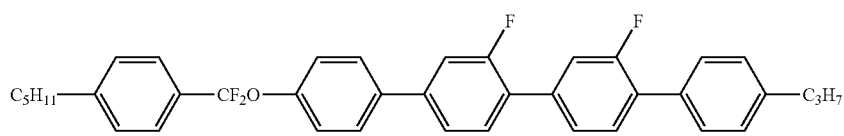
1-1-93
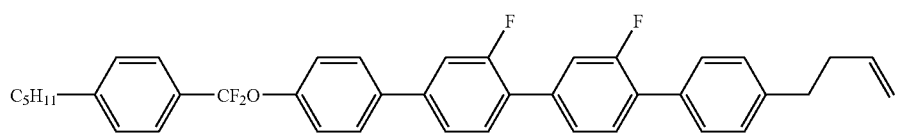
1-1-94
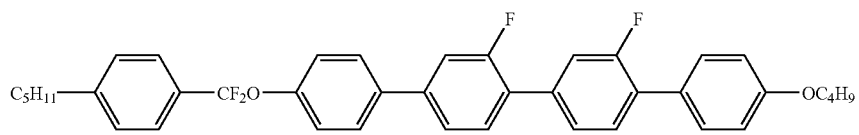
1-1-95
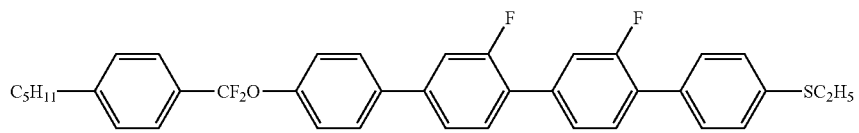
1-1-96
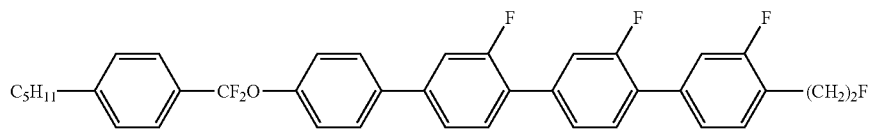
1-1-97
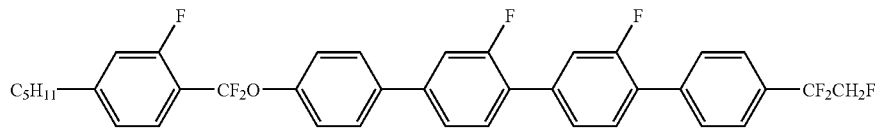
1-1-98
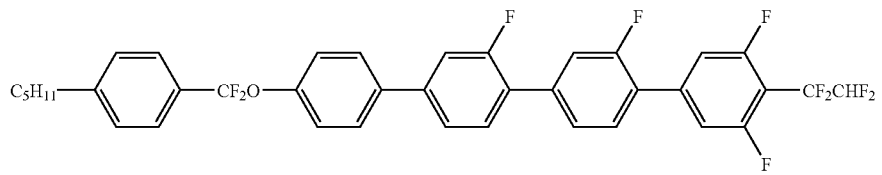
1-1-99
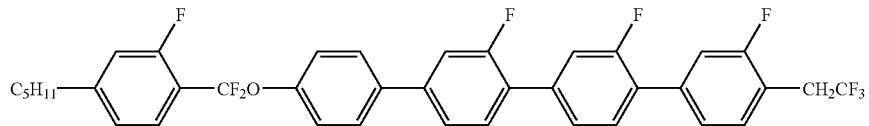
1-1-100

-continued
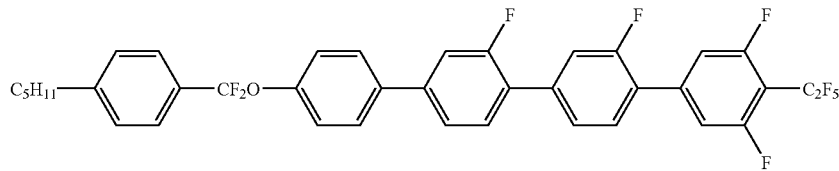
1-1-101
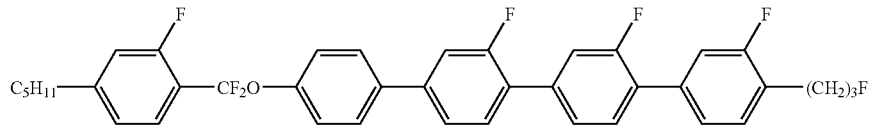
1-1-102
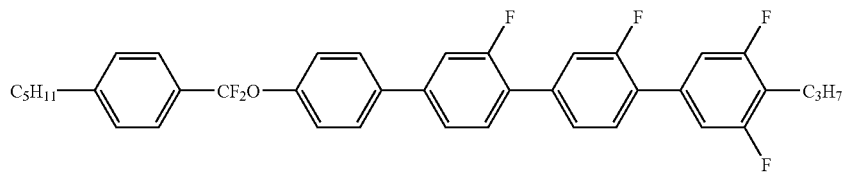
1-1-103
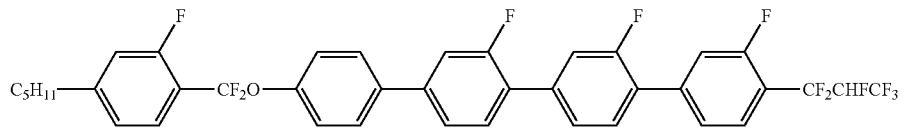
1-1-104
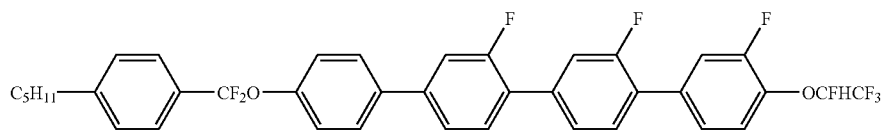
1-1-105
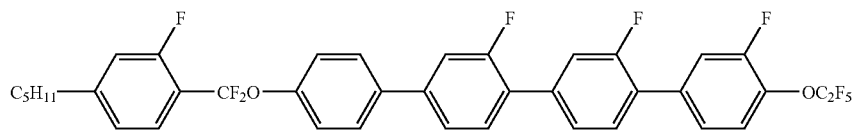
1-1-106
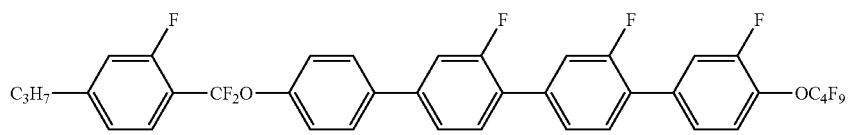
1-1-107
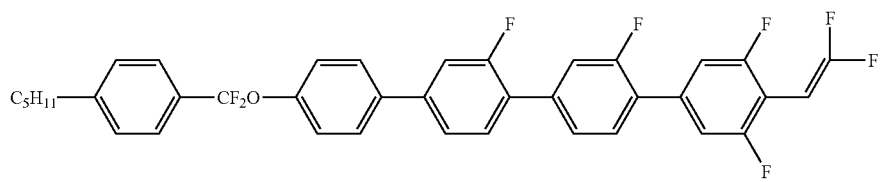
1-1-108
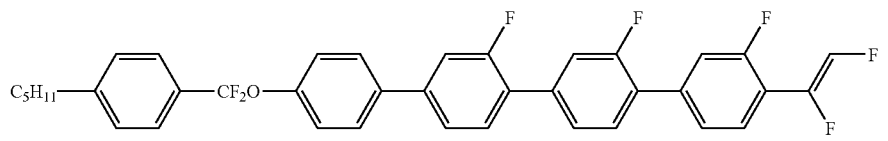
1-1-109
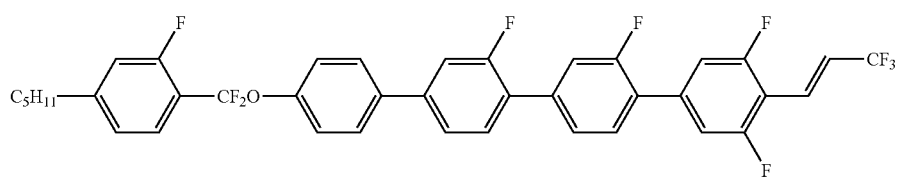
1-1-110

-continued
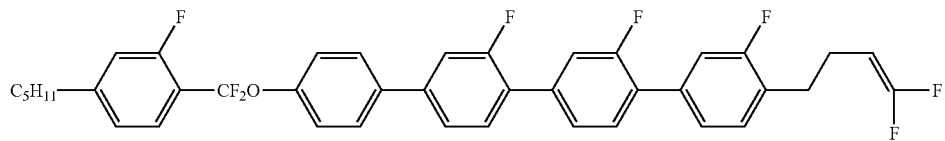
1-1-111
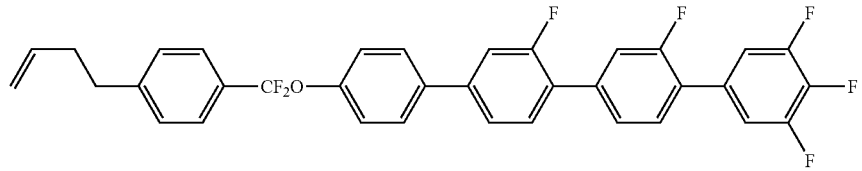
1-1-112
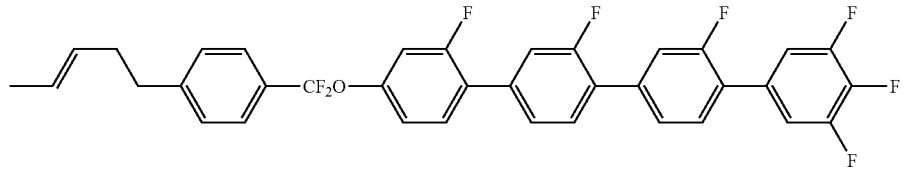
1-1-113
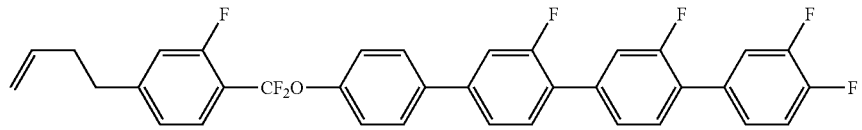
1-1-114
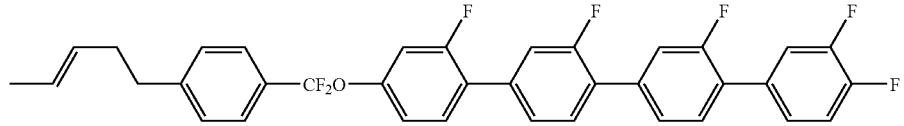
1-1-115
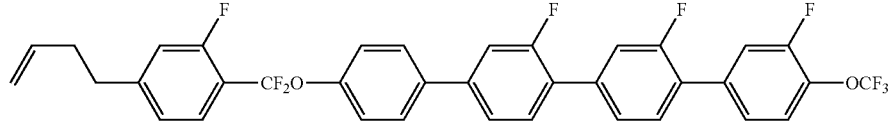
1-1-116
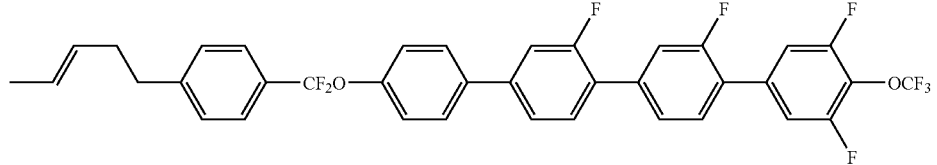
1-1-117
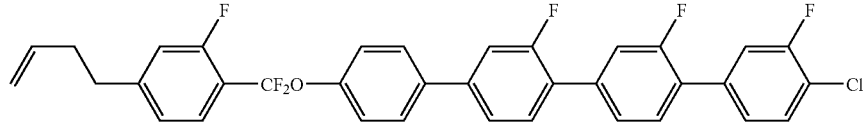
1-1-118
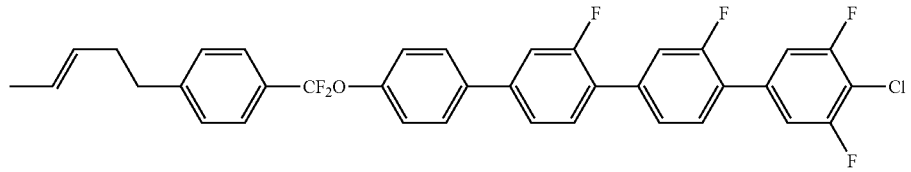
1-1-119
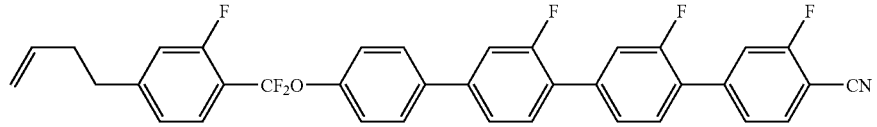
1-1-120

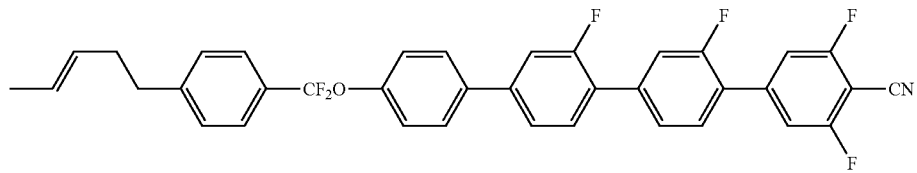
1-1-121
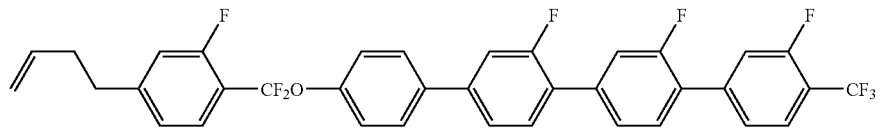
1-1-122
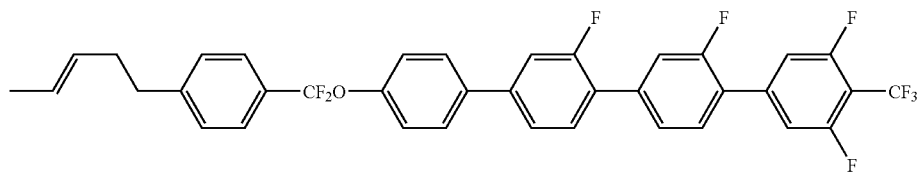
1-1-123
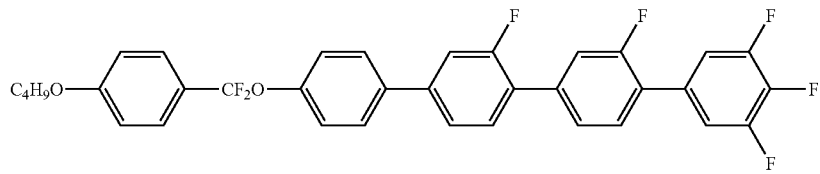
1-1-124
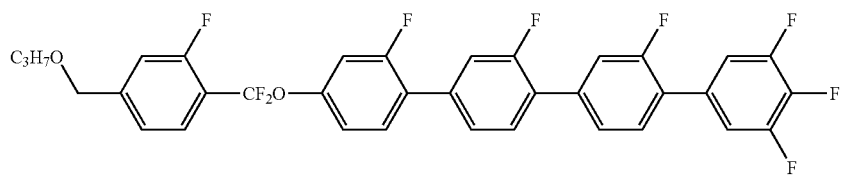
1-1-125
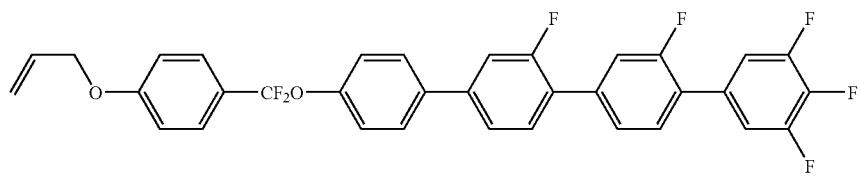
1-1-126
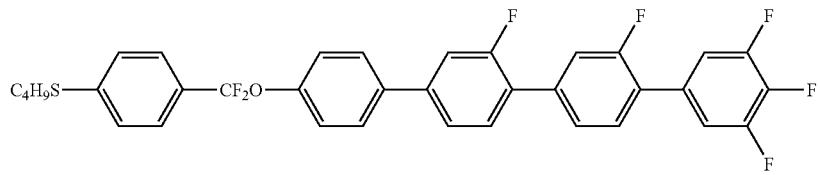
1-1-127
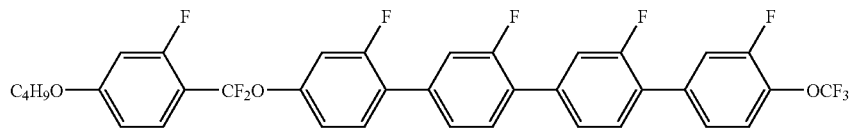
1-1-128
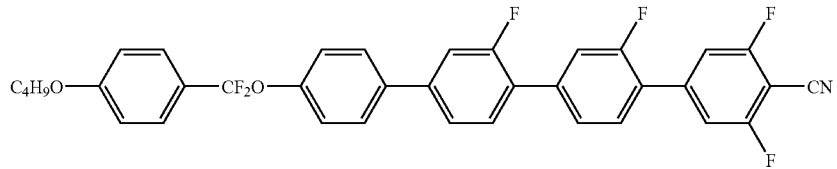
1-1-129

-continued
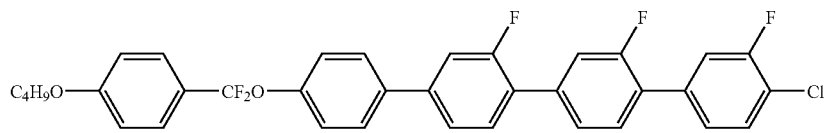
1-1-130
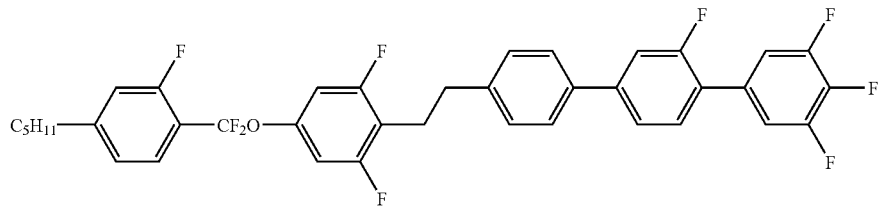
1-1-131
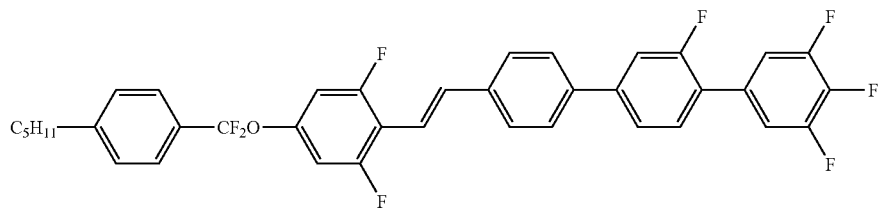
1-1-132
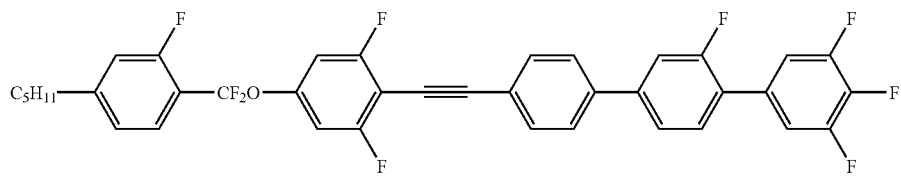
1-1-133
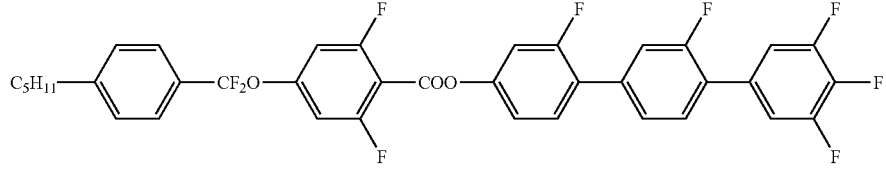
1-1-134
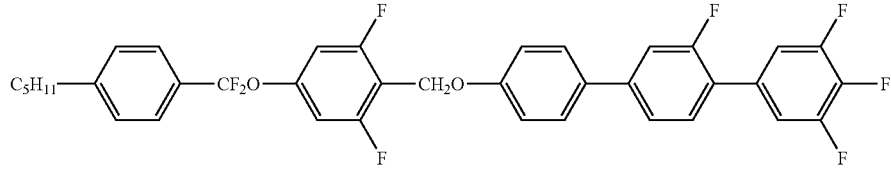
1-1-135
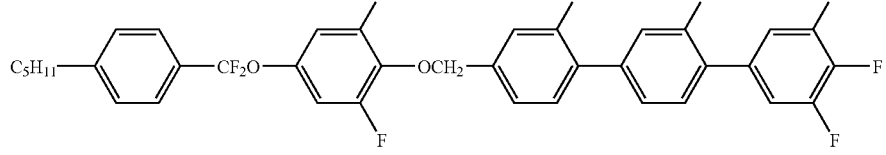
1-1-136
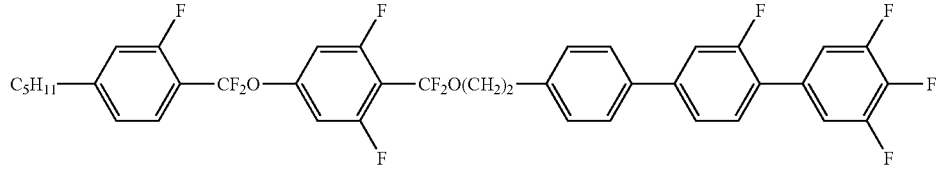
1-1-137
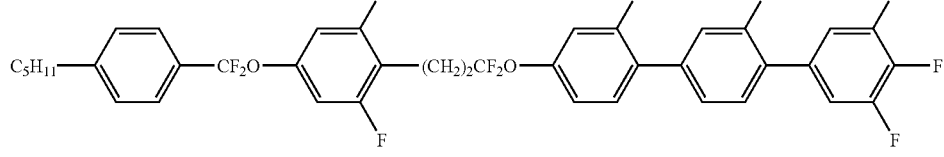
1-1-138

-continued
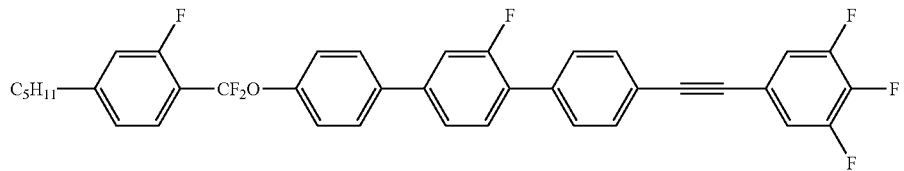
1-1-139
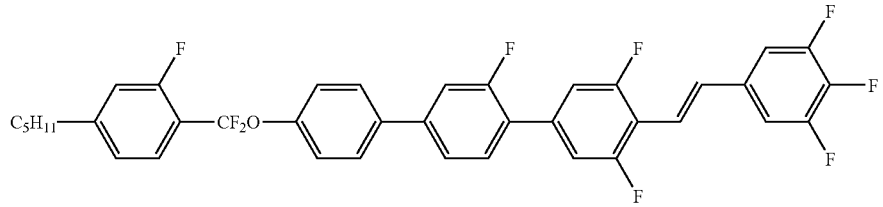
1-1-140
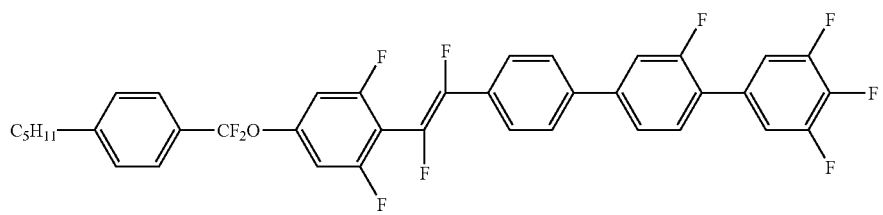
1-1-141
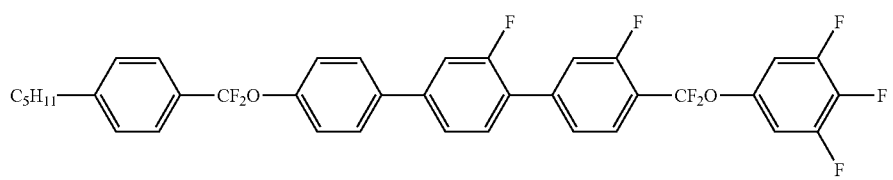
1-1-142
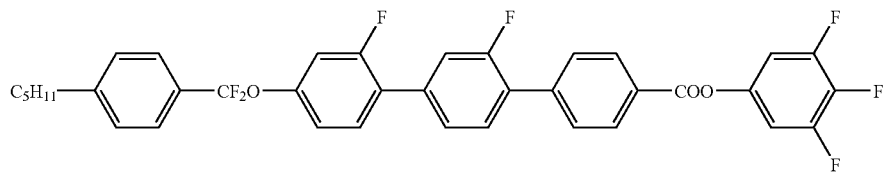
1-1-143
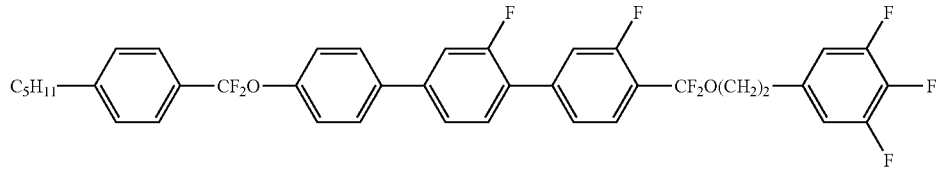
1-1-144
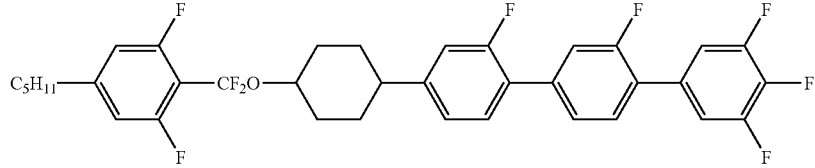
1-1-145
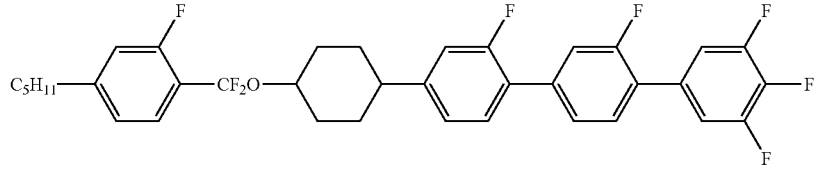
1-1-146

-continued
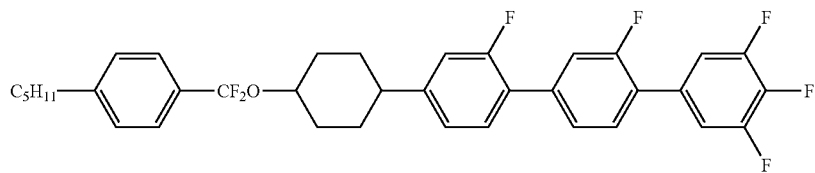
1-1-147
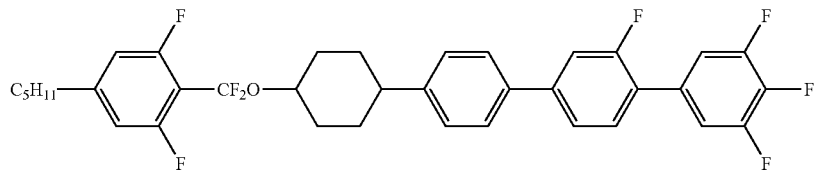
1-1-148
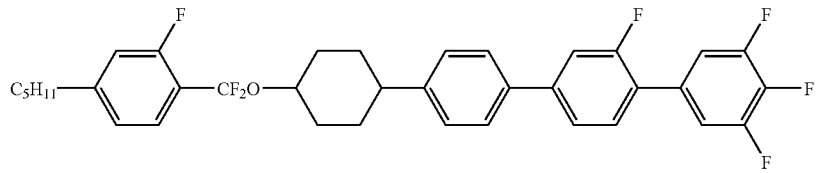
1-1-149
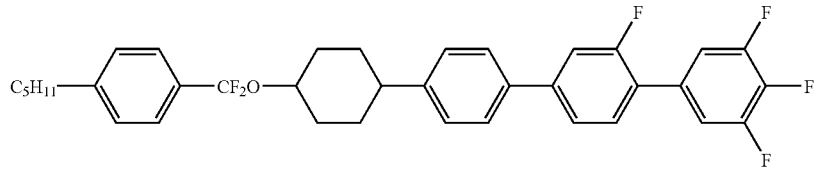
1-1-150
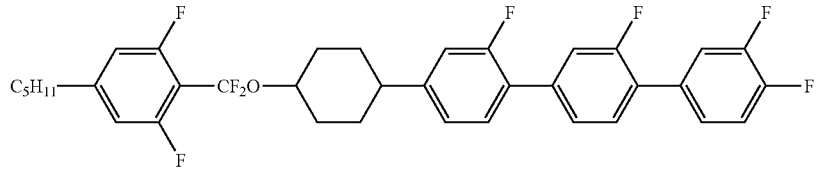
1-1-151
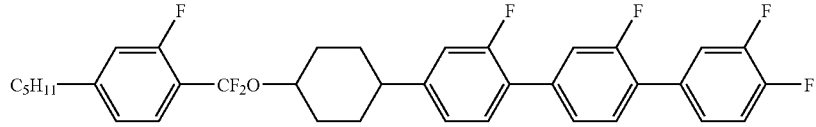
1-1-152
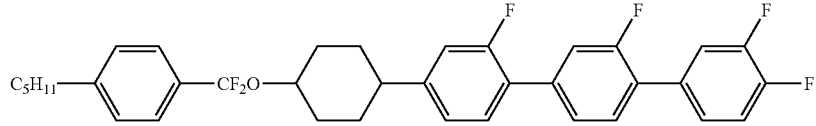
1-1-153
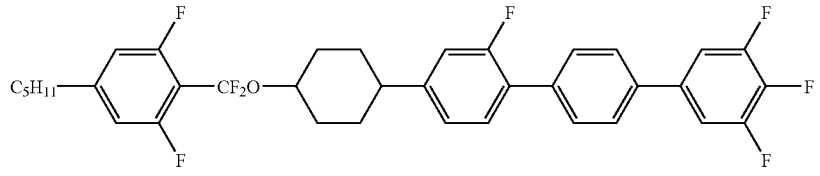
1-1-154
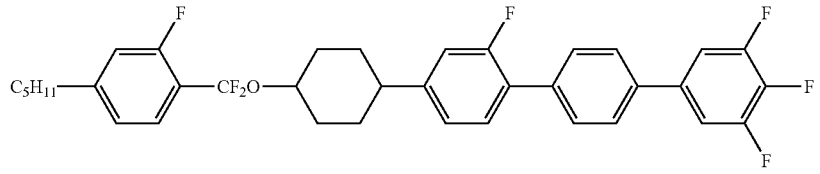
1-1-155

-continued
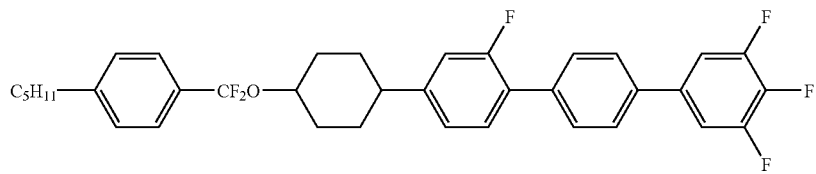
1-1-156
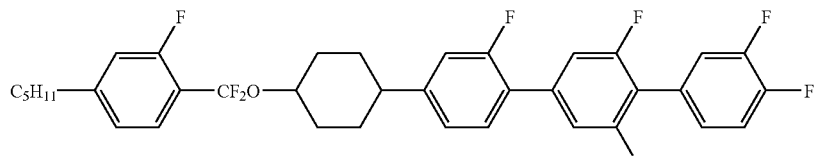
1-1-157
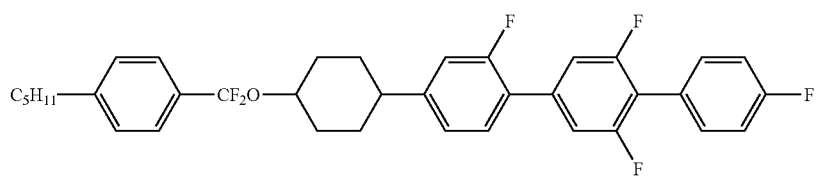
1-1-158
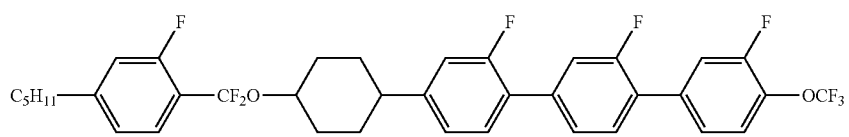
1-1-159
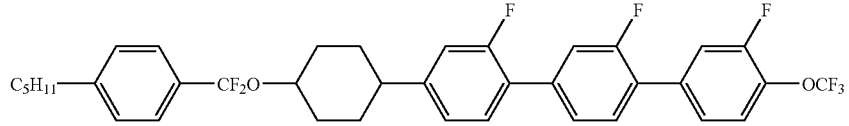
1-1-160
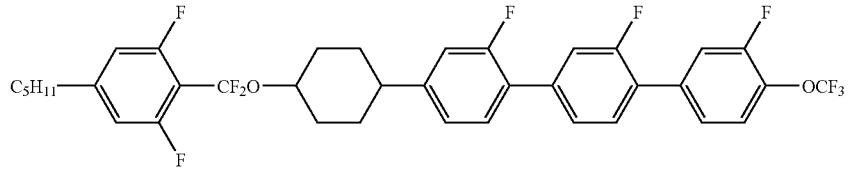
1-1-161
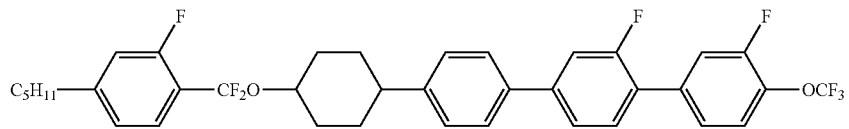
1-1-162
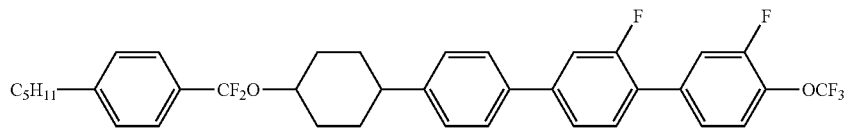
1-1-163
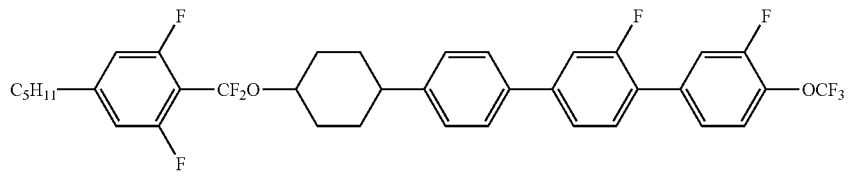
1-1-164
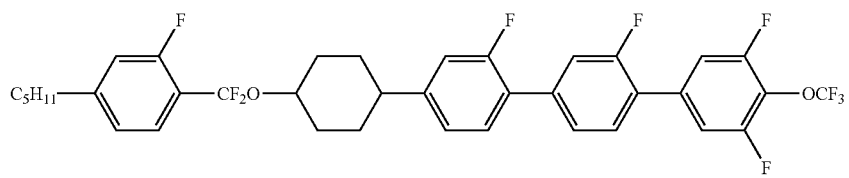
1-1-165

-continued
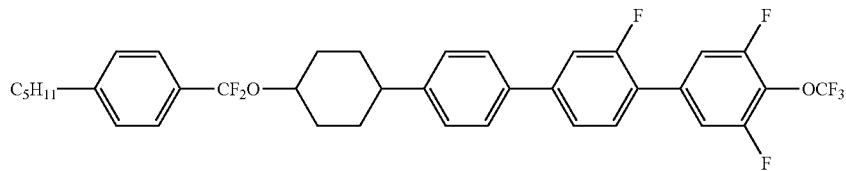
1-1-166
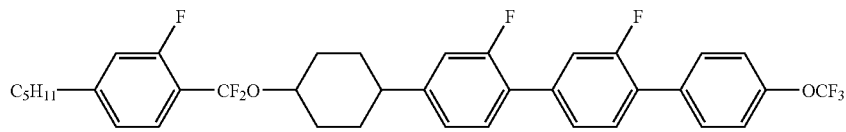
1-1-167
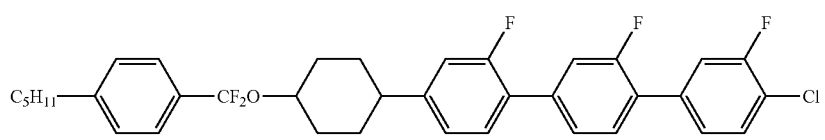
1-1-168
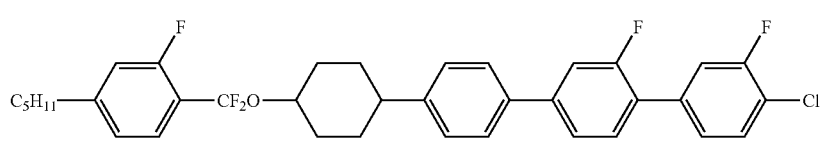
1-1-169
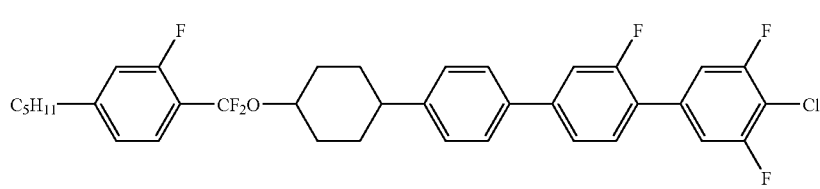
1-1-170
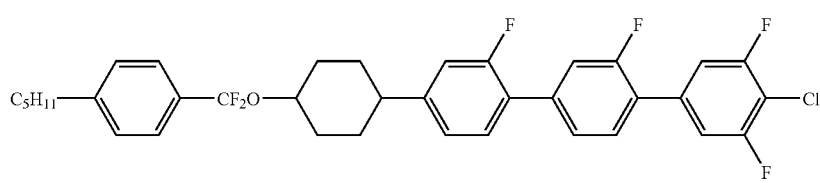
1-1-171
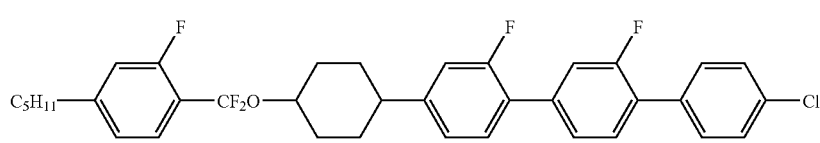
1-1-172
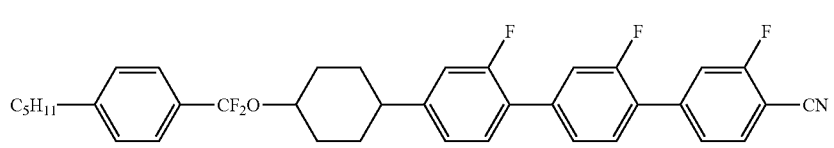
1-1-173
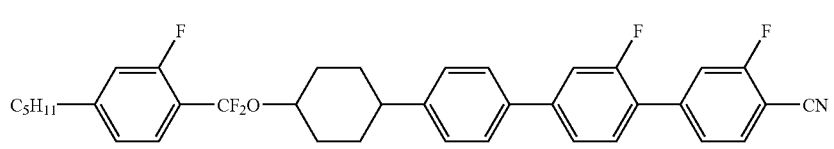
1-1-174
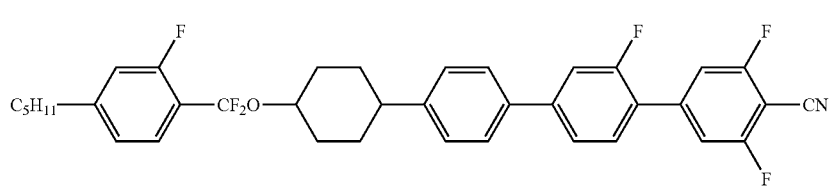
1-1-175

-continued
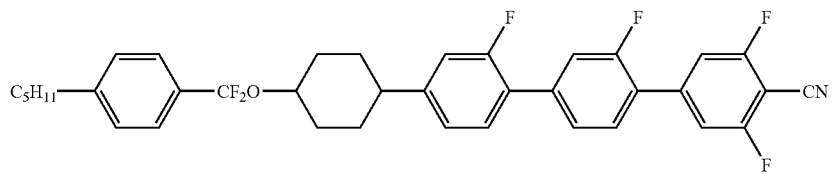
1-1-176
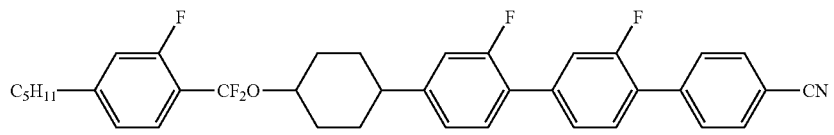
1-1-177
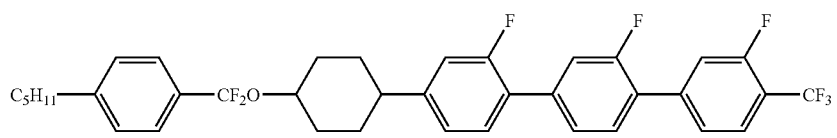
1-1-178
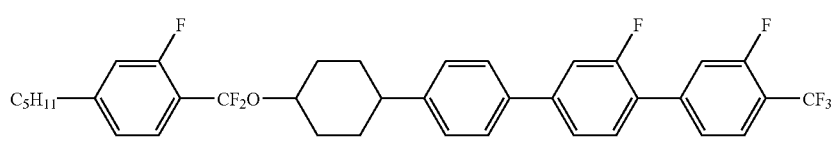
1-1-179
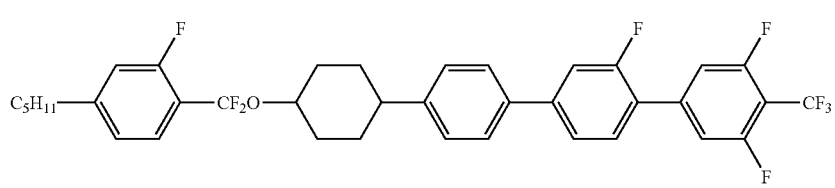
1-1-180
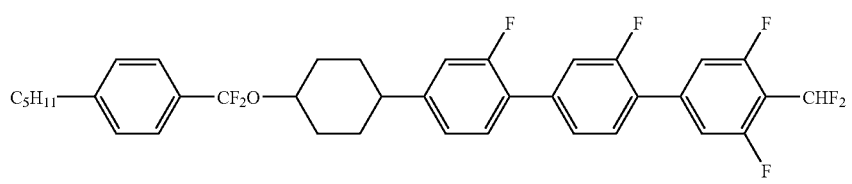
1-1-181
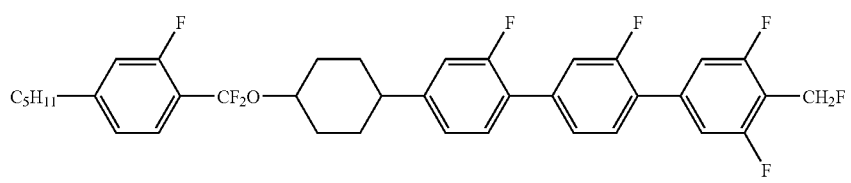
1-1-182
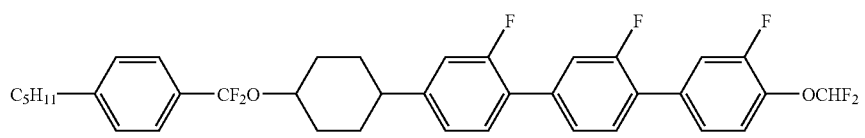
1-1-183
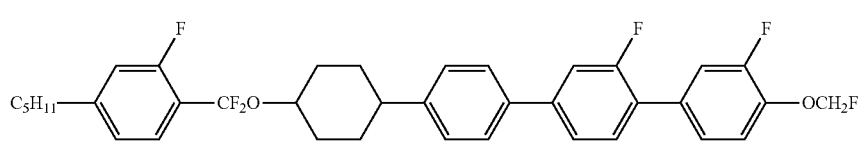
1-1-184
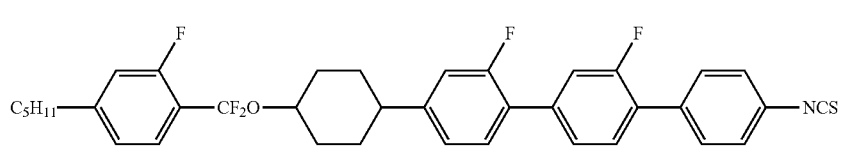
1-1-185

-continued
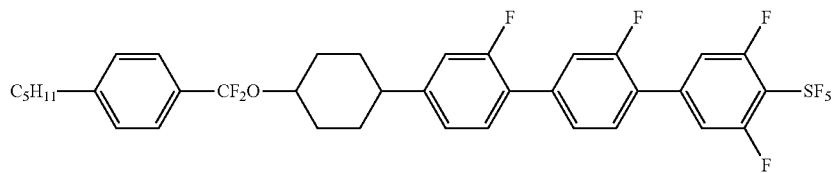
1-1-186
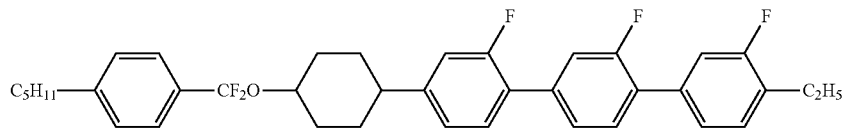
1-1-187
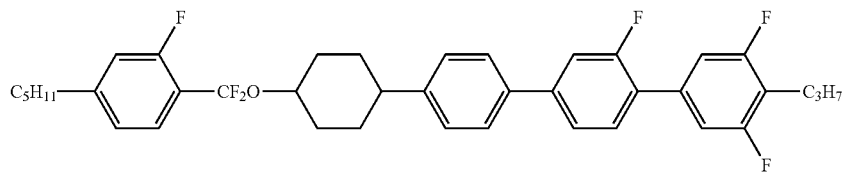
1-1-188
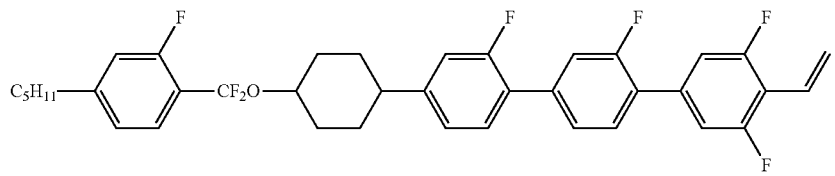
1-1-189
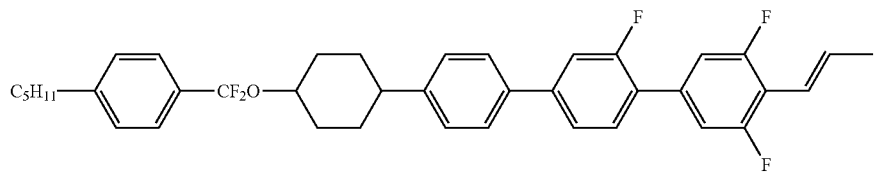
1-1-190
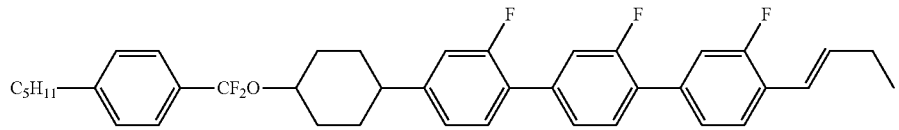
1-1-191
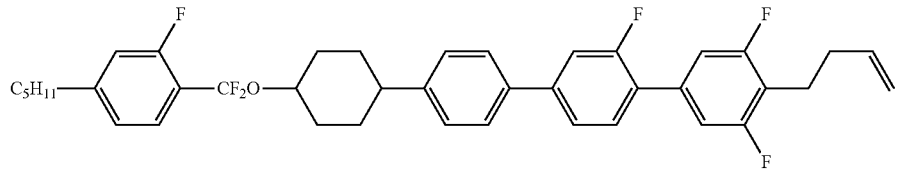
1-1-192
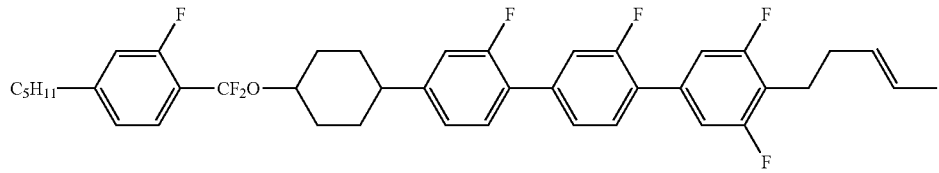
1-1-193
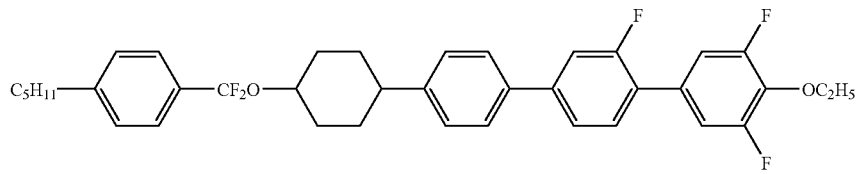
1-1-194

-continued
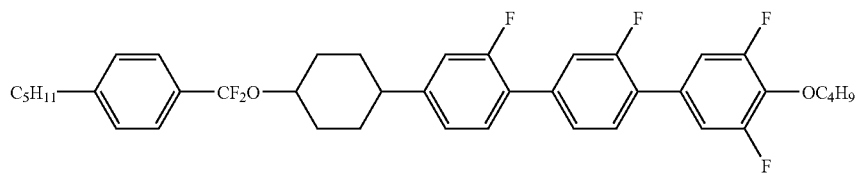
1-1-195
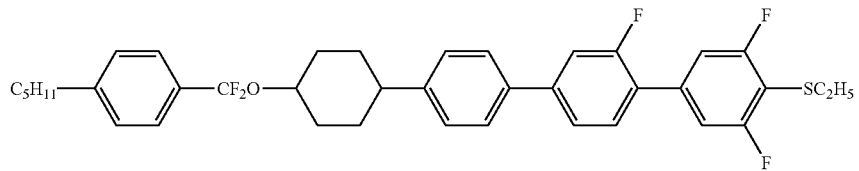
1-1-196
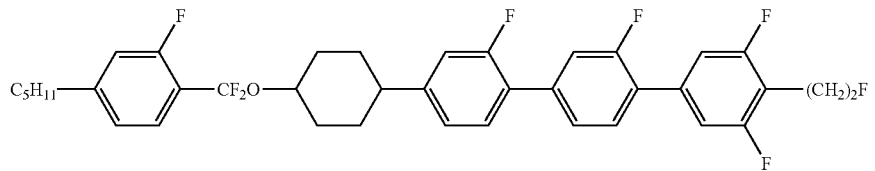
1-1-197
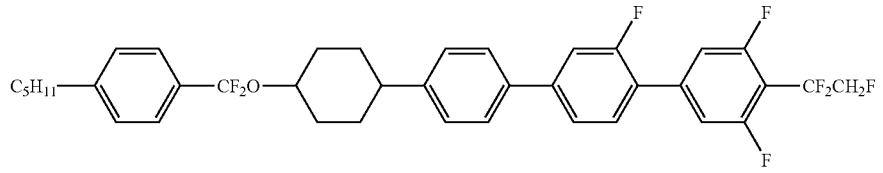
1-1-198
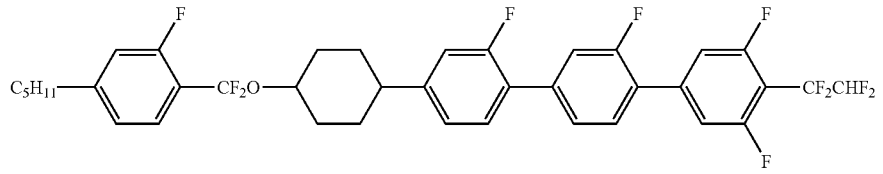
1-1-199
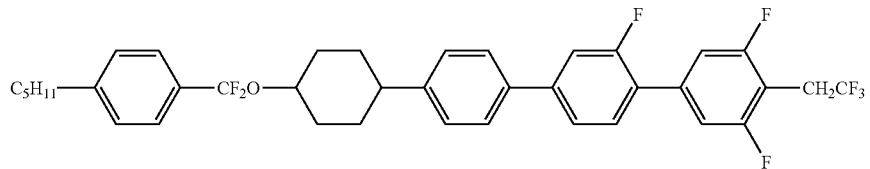
1-1-200
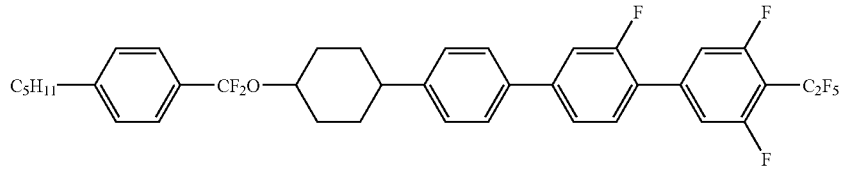
1-1-201
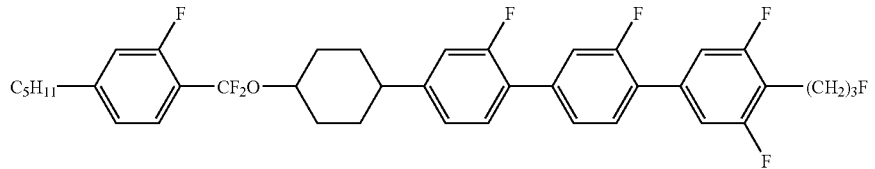
1-1-202
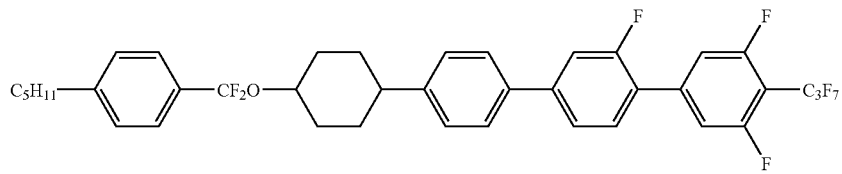
1-1-203

-continued
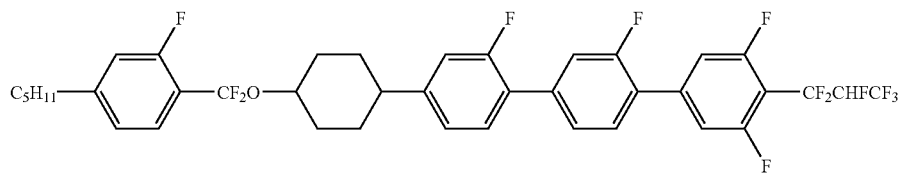
1-1-204
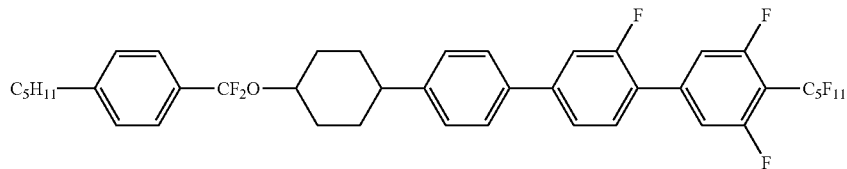
1-1-205
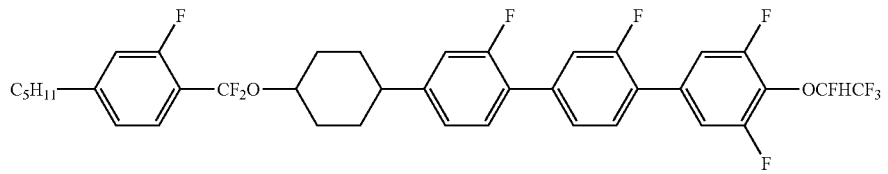
1-1-206
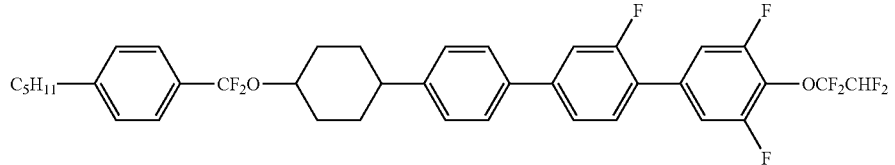
1-1-207
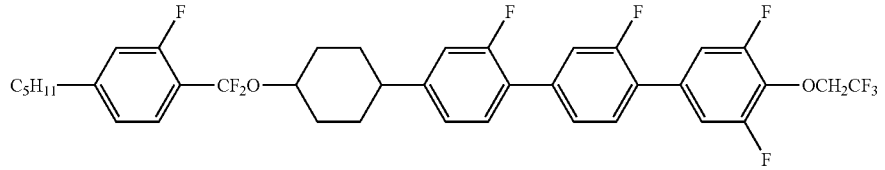
1-1-208
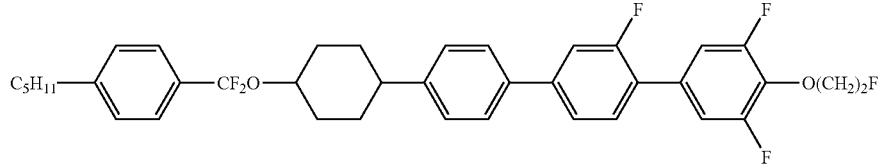
1-1-209
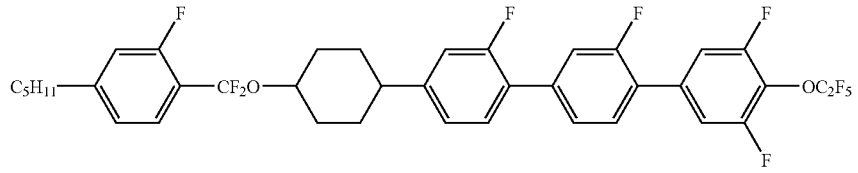
1-1-210
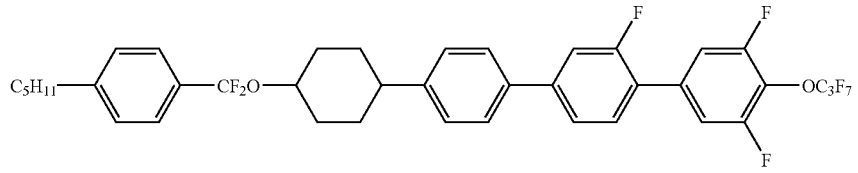
1-1-211
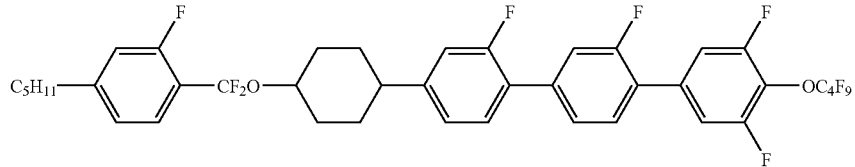
1-1-212

-continued
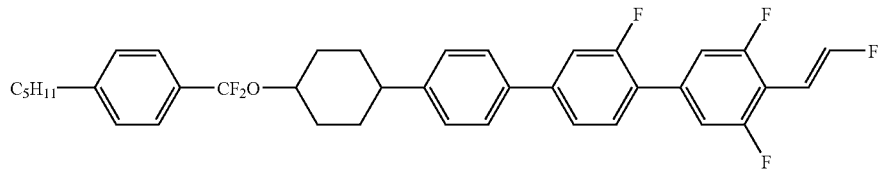
1-1-213
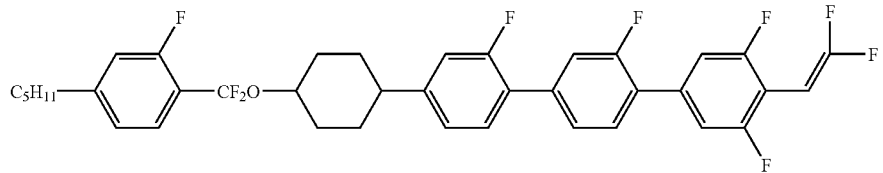
1-1-214
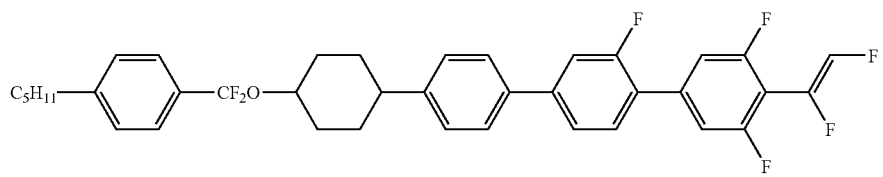
1-1-215
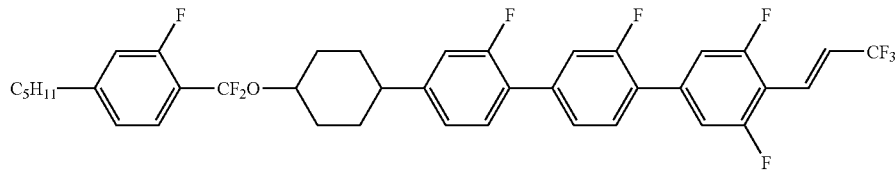
1-1-216
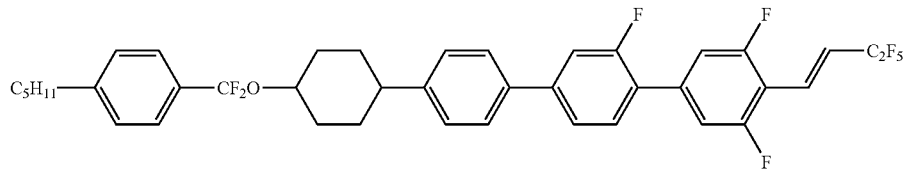
1-1-217
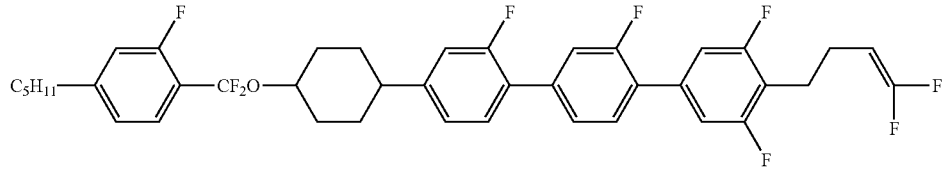
1-1-218
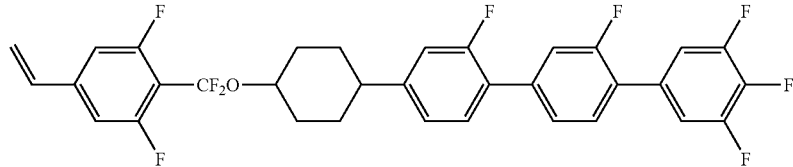
1-1-219
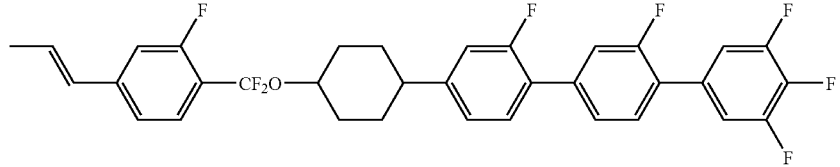
1-1-220
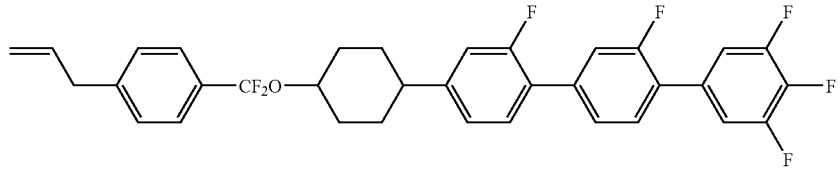
1-1-221

-continued
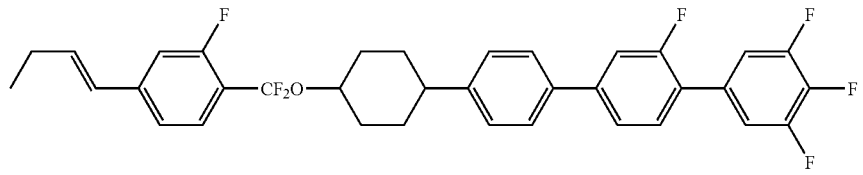
1-1-222
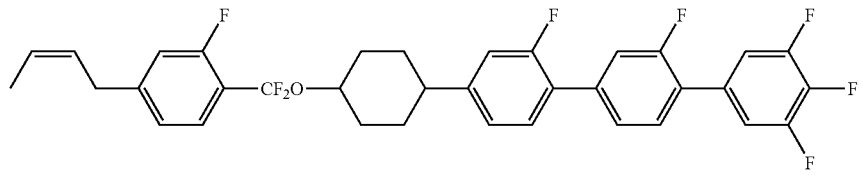
1-1-223
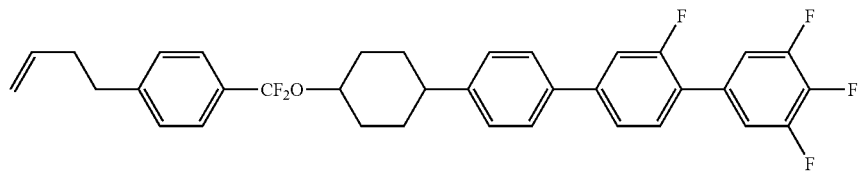
1-1-224
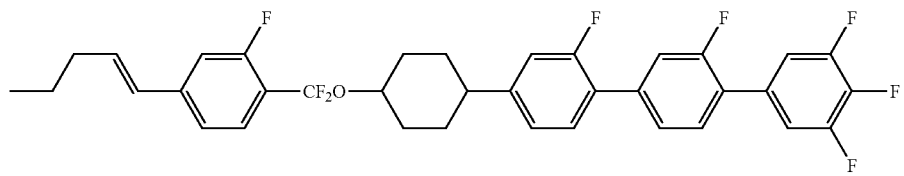
1-1-225
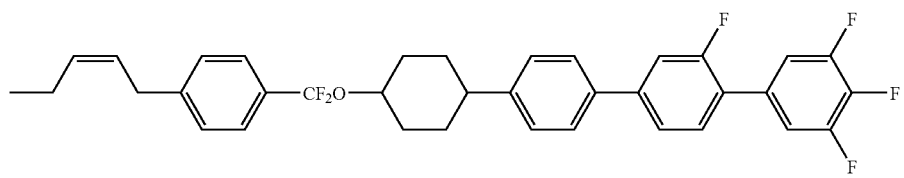
1-1-226
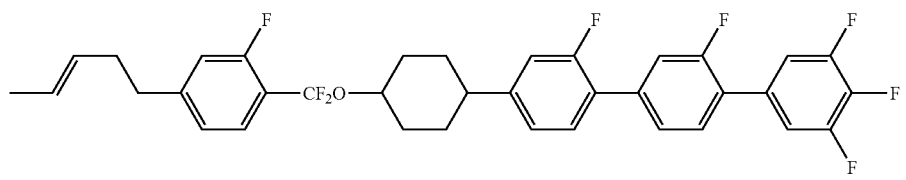
1-1-227
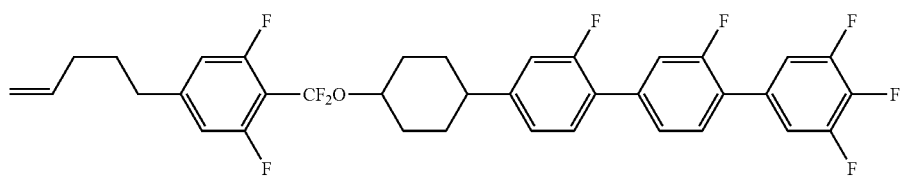
1-1-228
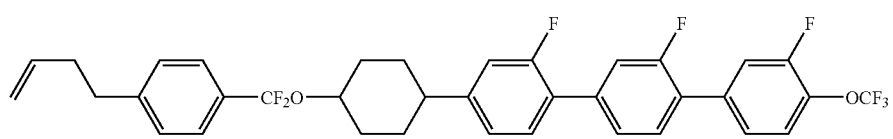
1-1-229
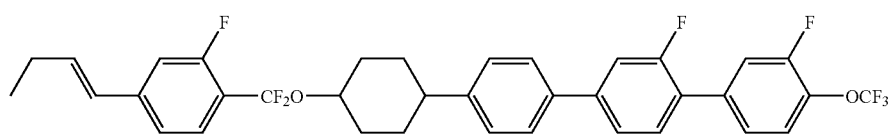
1-1-230

-continued
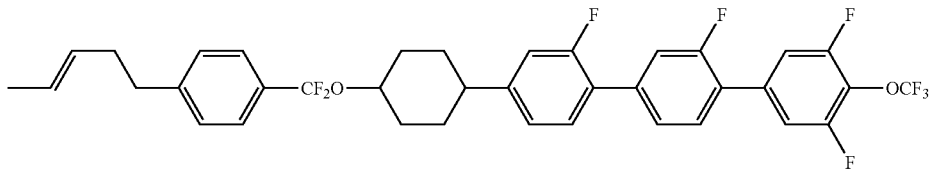
1-1-231
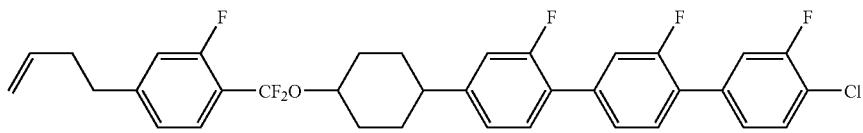
1-1-232
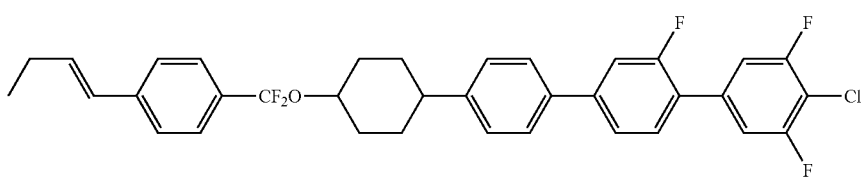
1-1-233
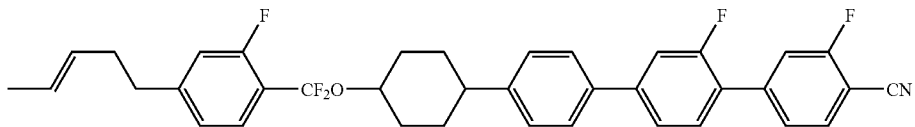
1-1-234
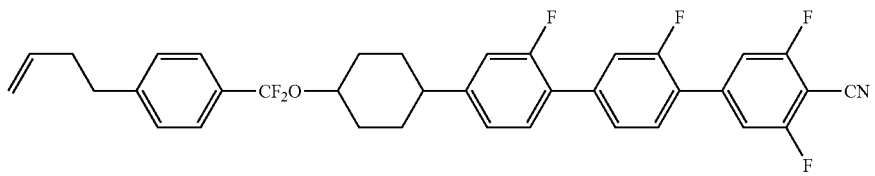
1-1-235
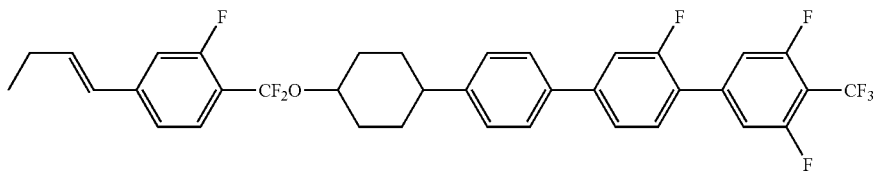
1-1-236
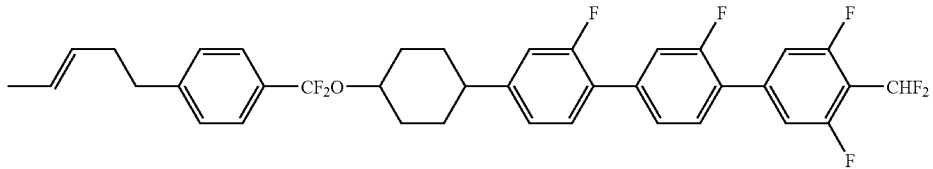
1-1-237
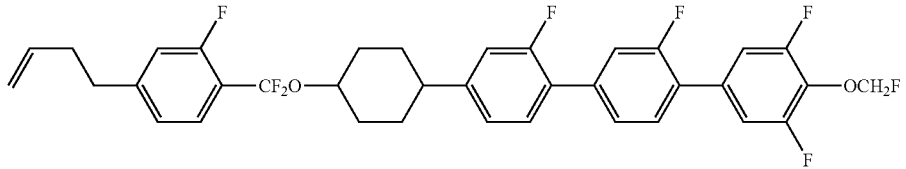
1-1-238
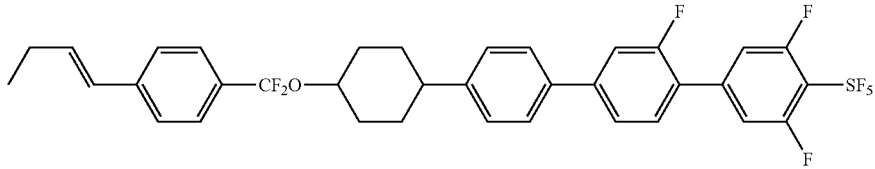
1-1-239

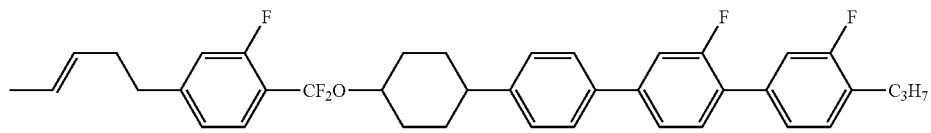
1-1-240
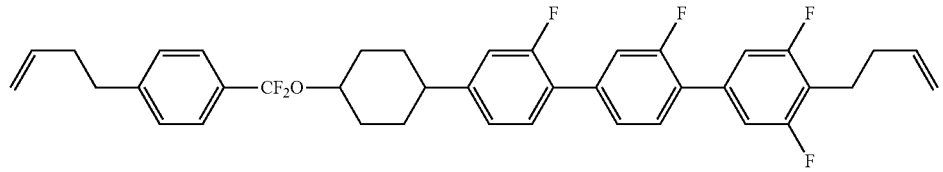
1-1-241
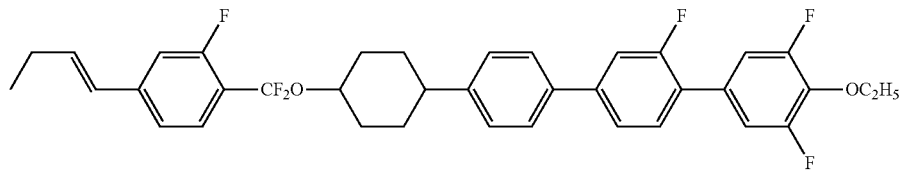
1-1-242
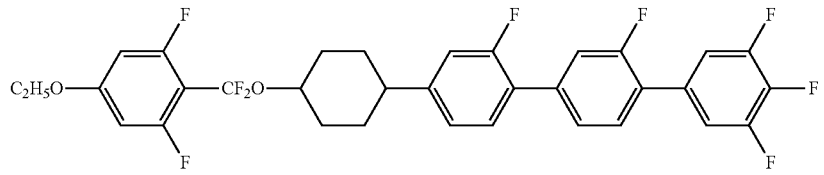
1-1-243
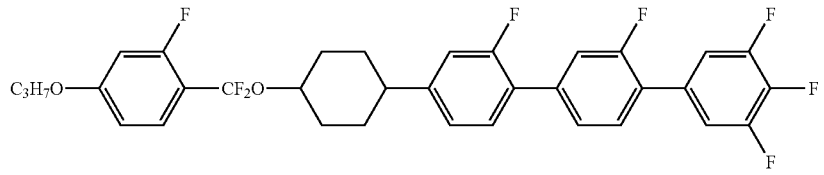
1-1-244
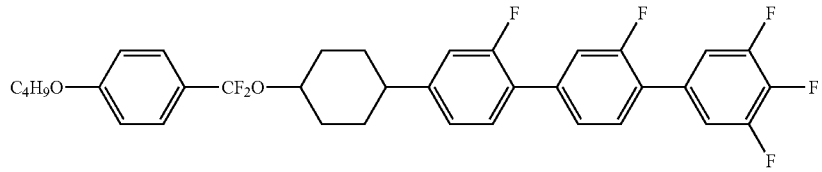
1-1-245
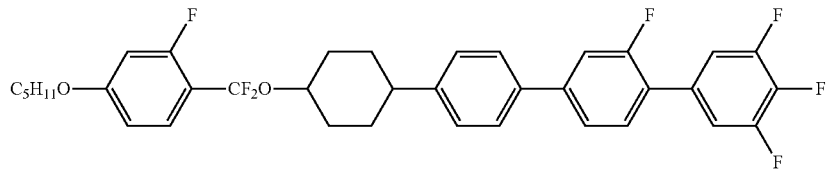
1-1-246
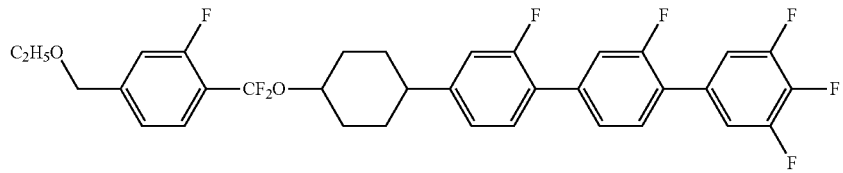
1-1-247
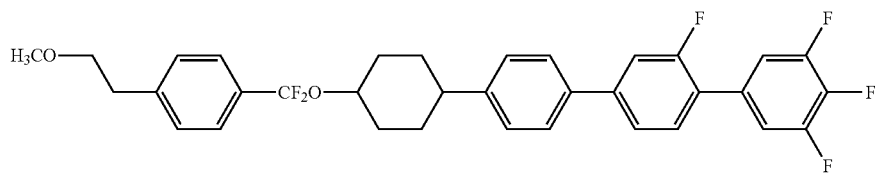
1-1-248

-continued
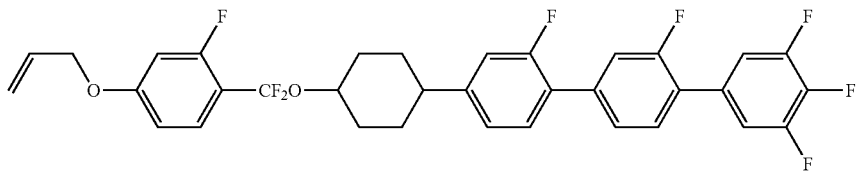
1-1-249
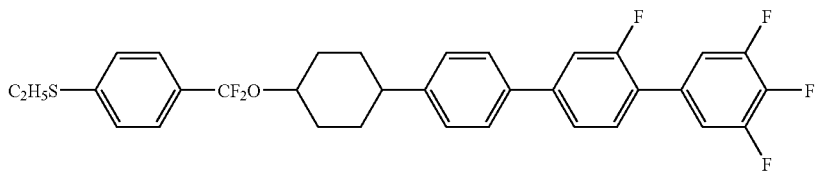
1-1-250
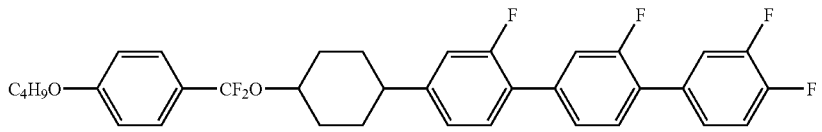
1-1-251

1-1-252
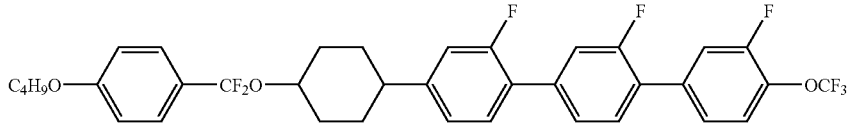
1-1-253
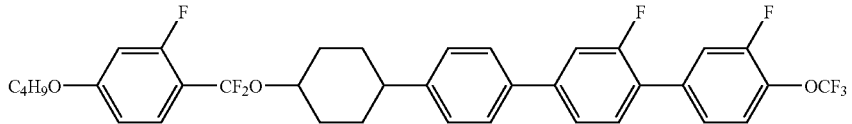
1-1-254
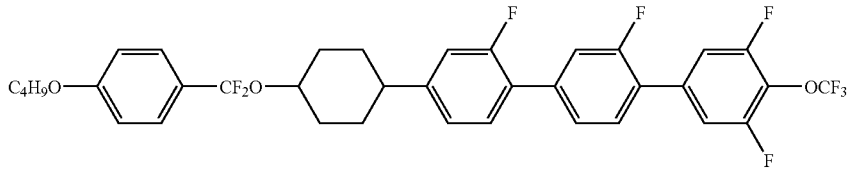
1-1-255
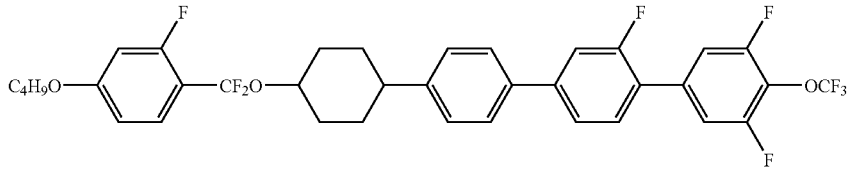
1-1-256
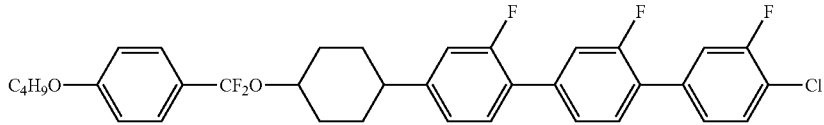
1-1-257
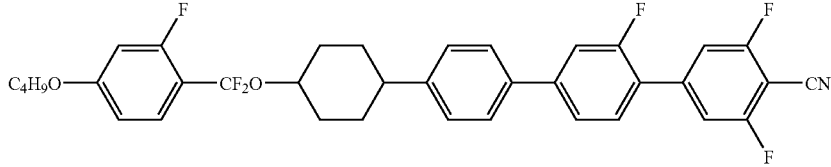
1-1-258

-continued
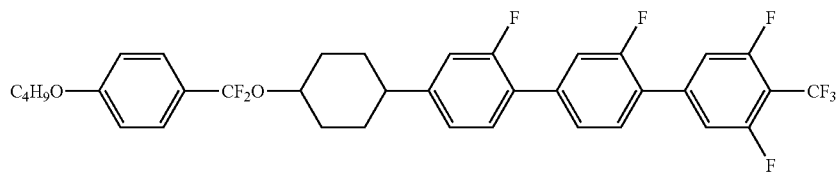
1-1-259
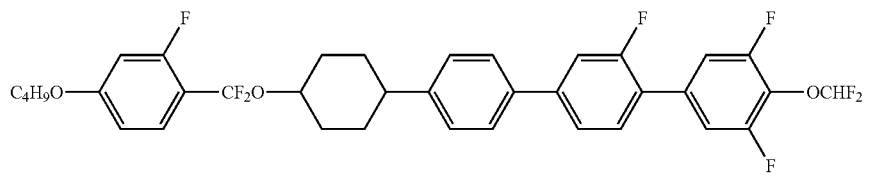
1-1-260
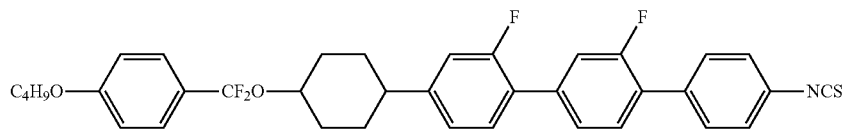
1-1-261
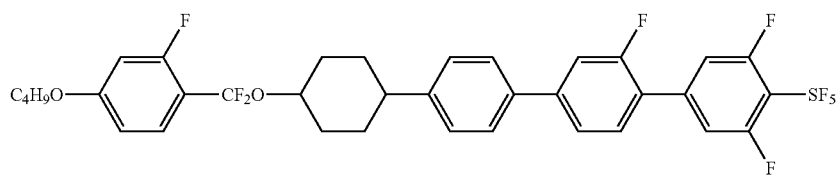
1-1-262
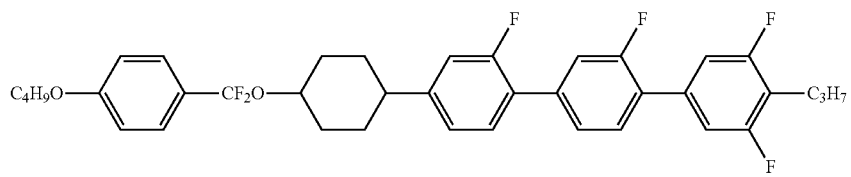
1-1-263
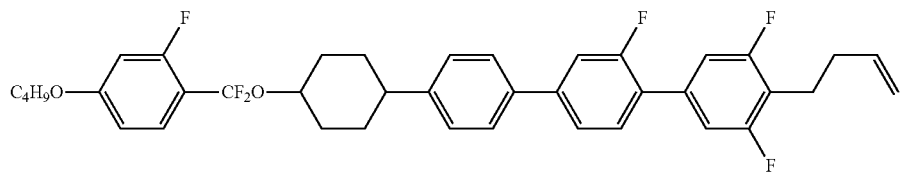
1-1-264
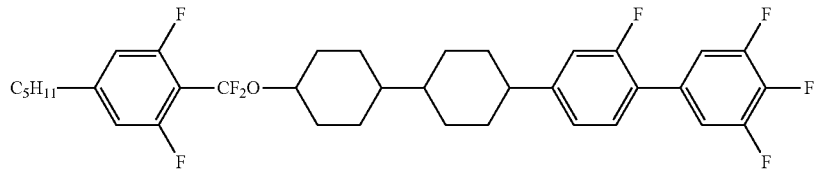
1-1-265
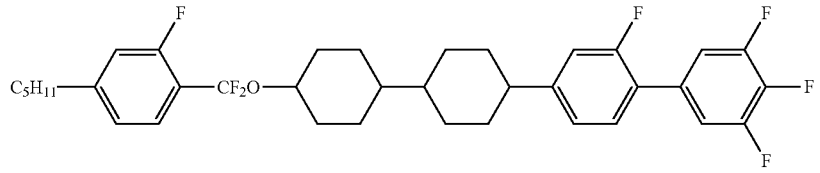
1-1-266
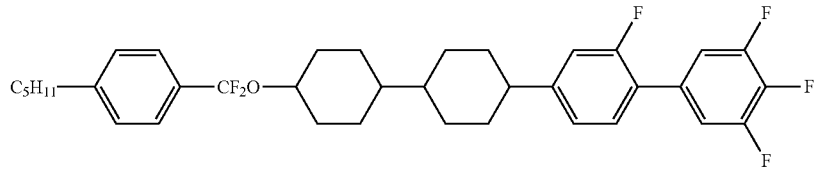
1-1-267

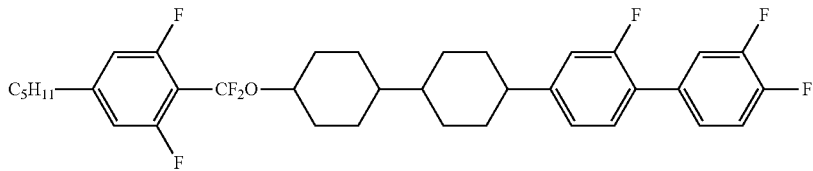
1-1-268
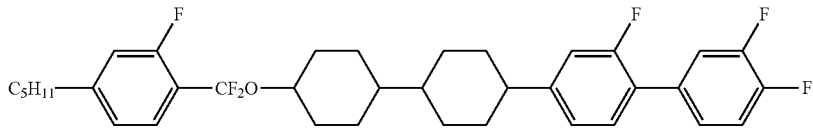
1-1-269
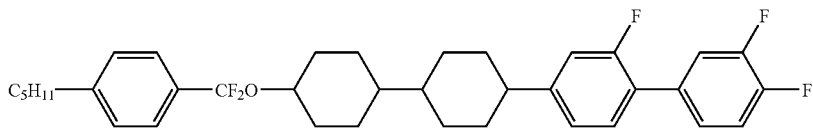
1-1-270
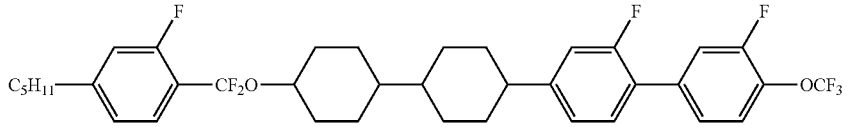
1-1-271
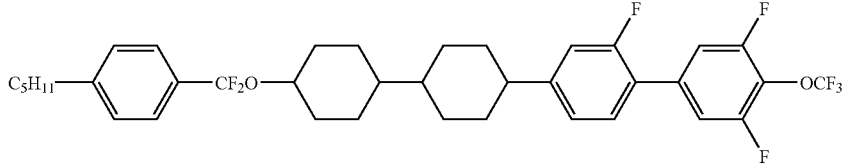
1-1-272
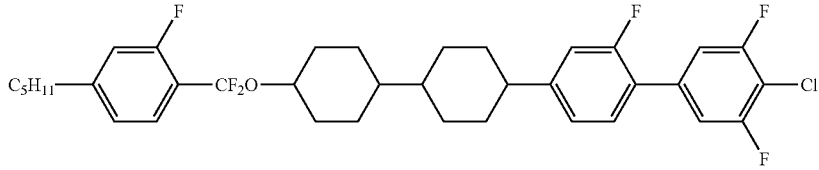
1-1-273
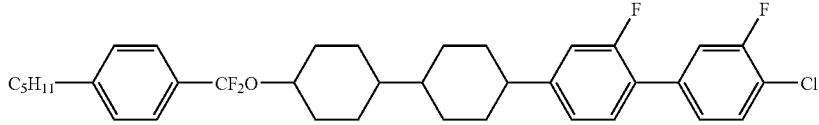
1-1-274
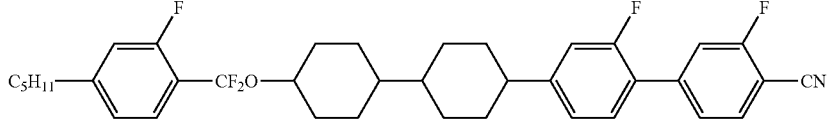
1-1-275
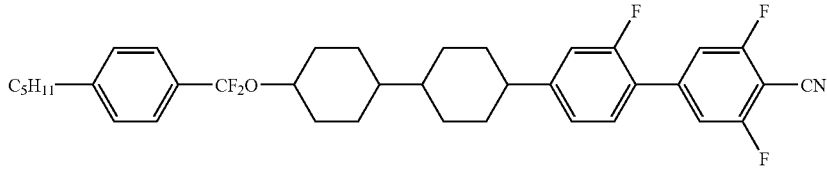
1-1-276
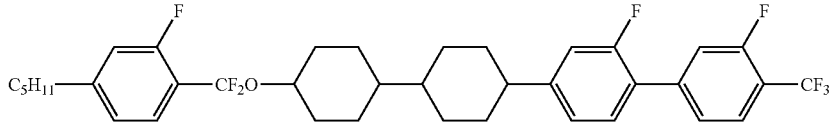
1-1-277

-continued
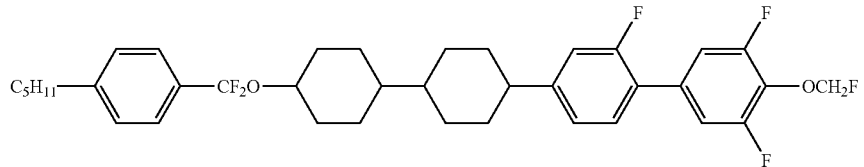
1-1-278
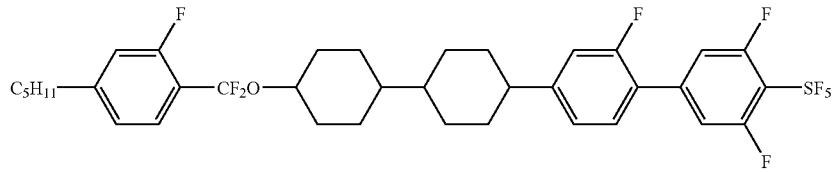
1-1-279
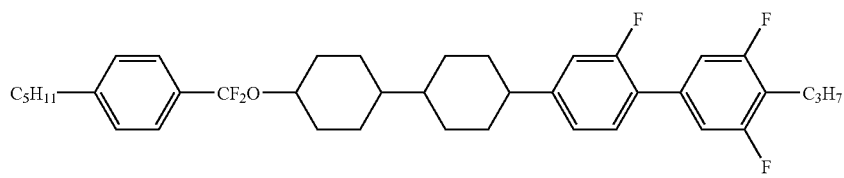
1-1-280
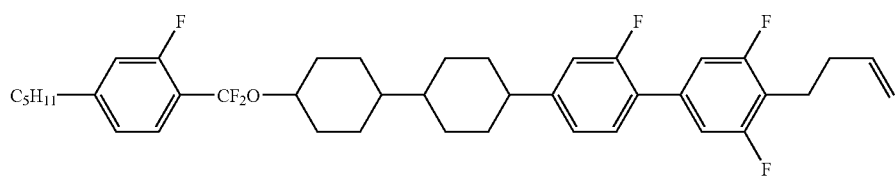
1-1-281
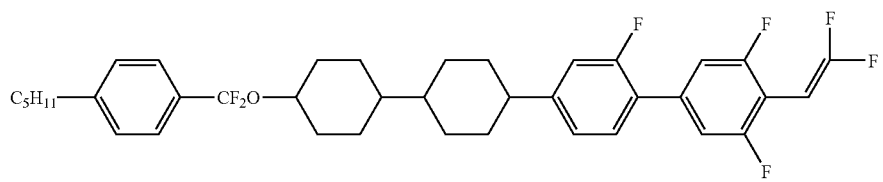
1-1-282
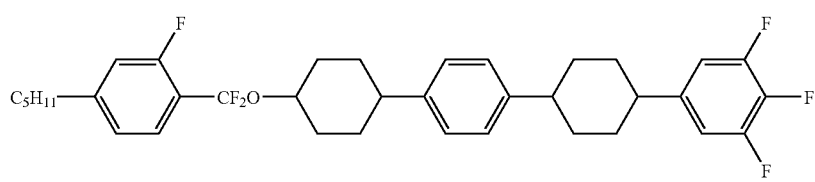
1-1-283
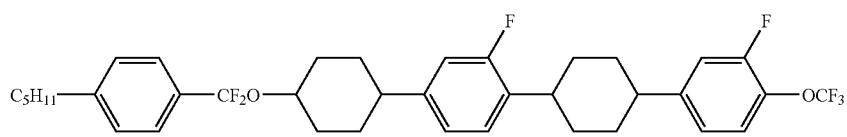
1-1-284
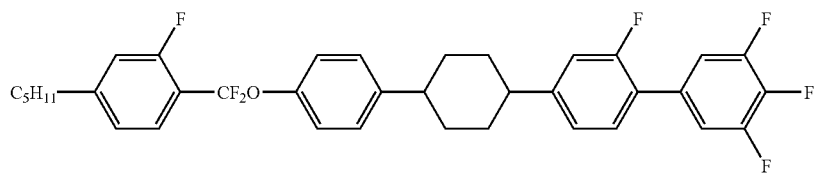
1-1-285
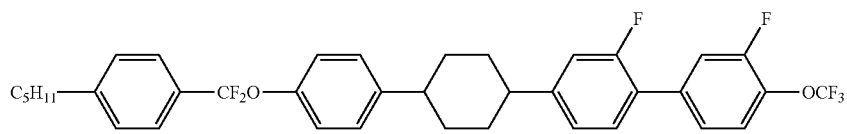
1-1-286

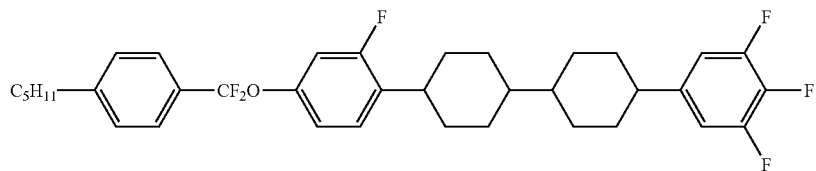
1-1-287
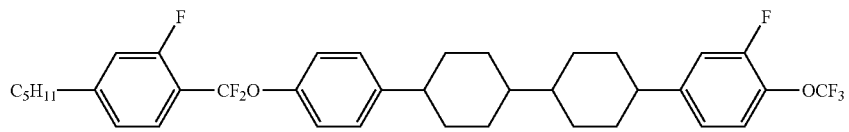
1-1-288
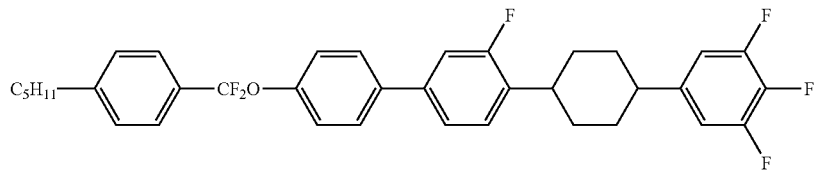
1-1-289
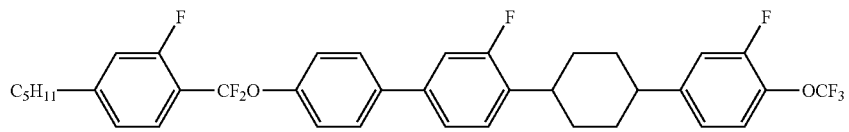
1-1-290
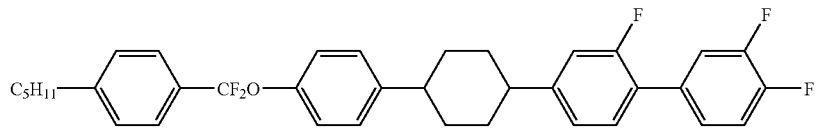
1-1-291
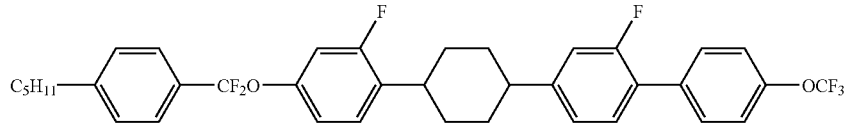
1-1-292
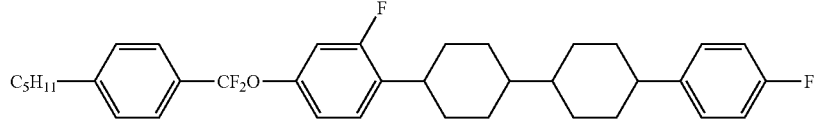
1-1-293
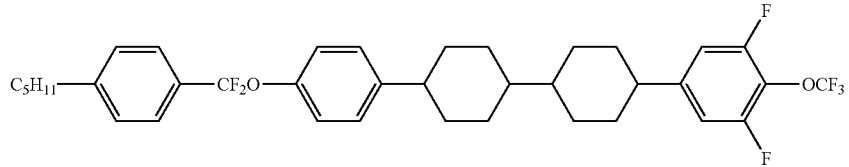
1-1-294
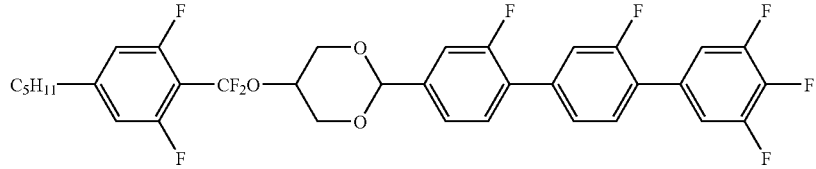
1-1-295
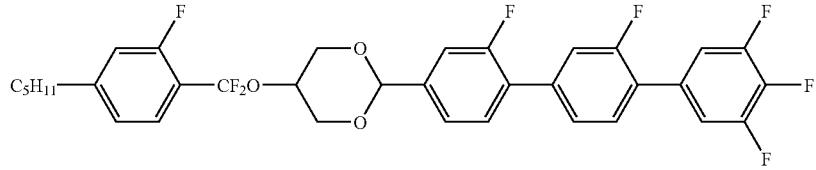
1-1-296

-continued
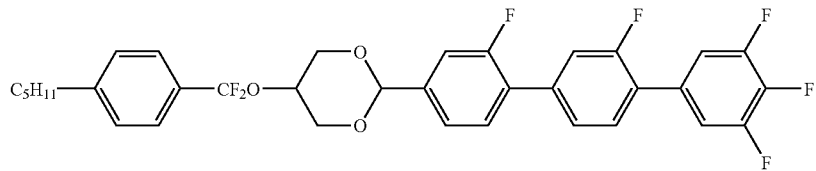 1-1-297
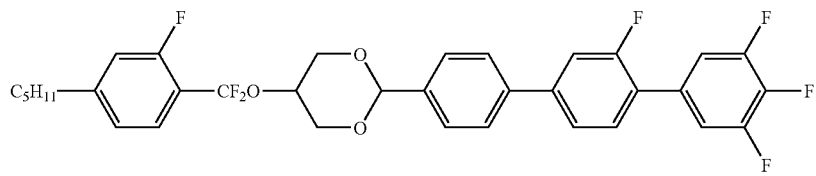 1-1-298
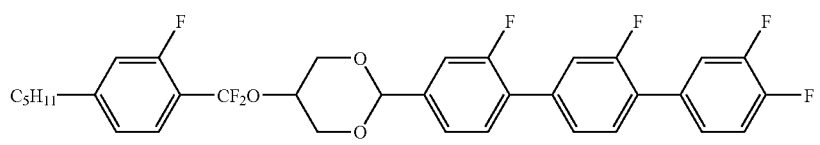 1-1-299
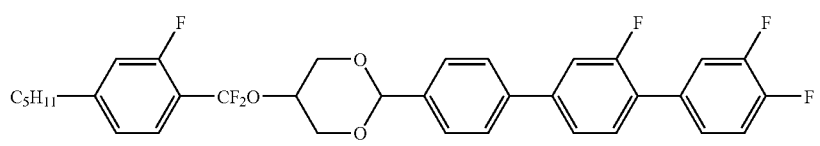 1-1-300
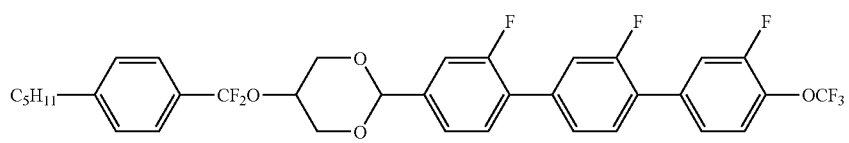 1-1-301
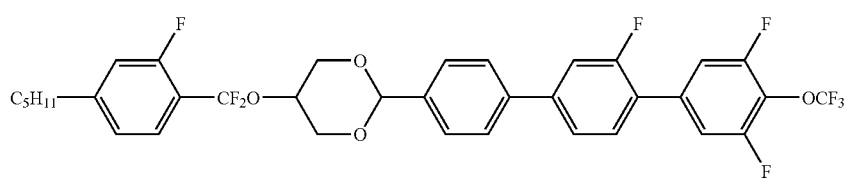 1-1-302
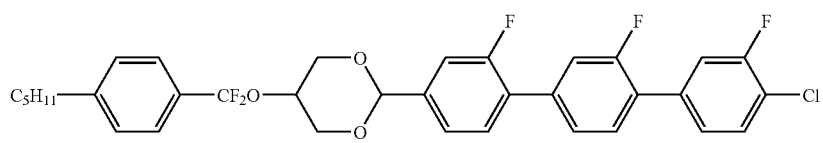 1-1-303
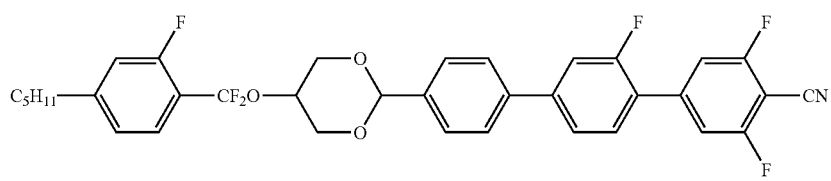 1-1-304
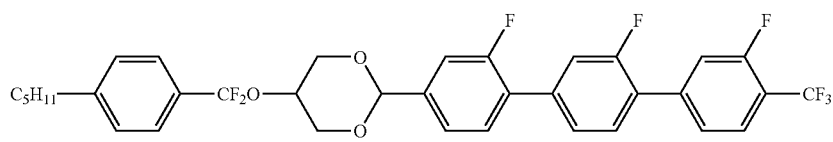 1-1-305
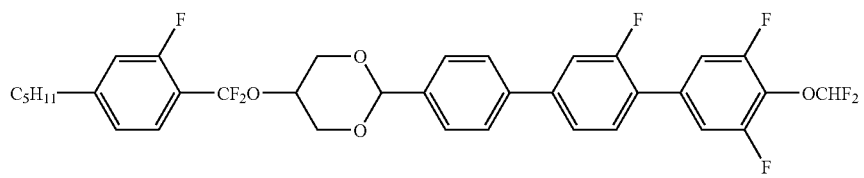 1-1-306

-continued
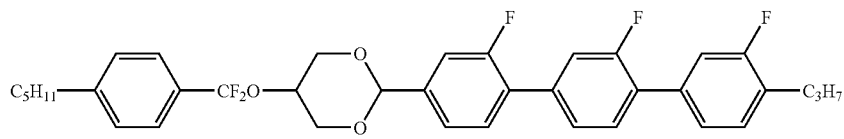
1-1-307
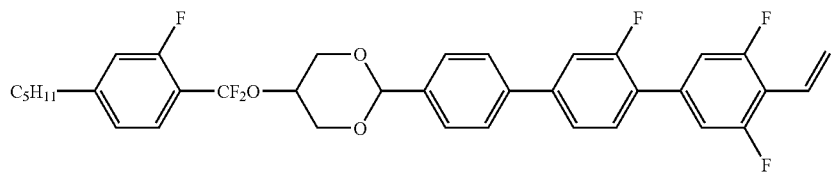
1-1-308
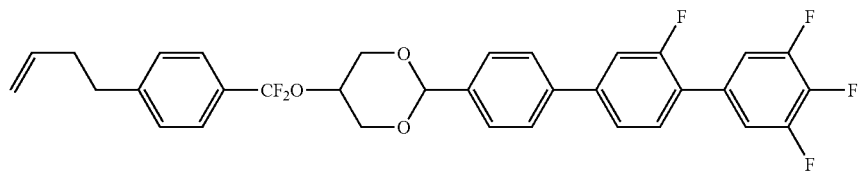
1-1-309
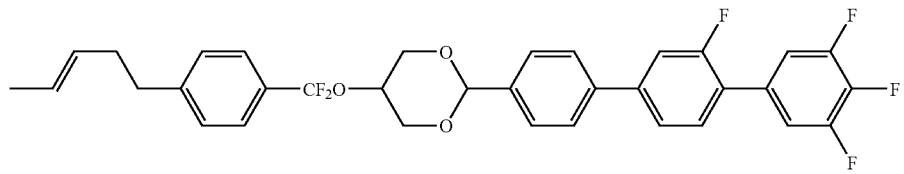
1-1-310
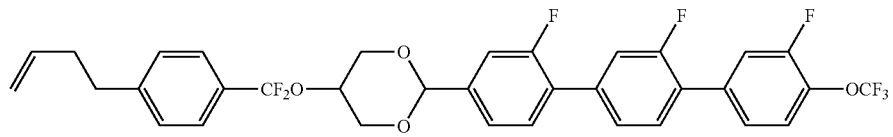
1-1-311
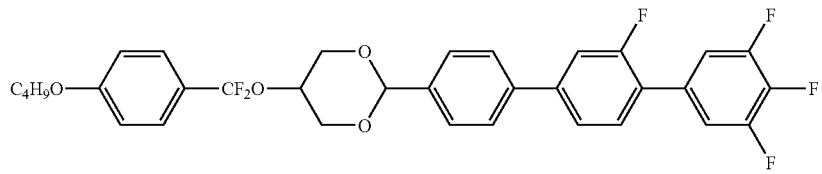
1-1-312
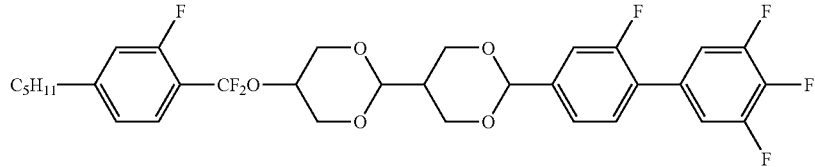
1-1-313
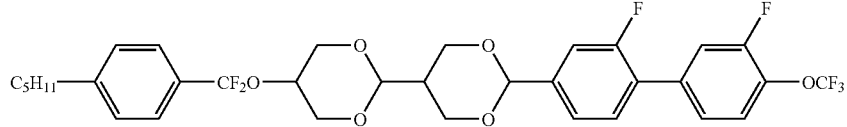
1-1-314
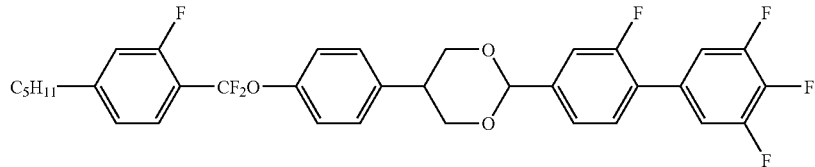
1-1-315

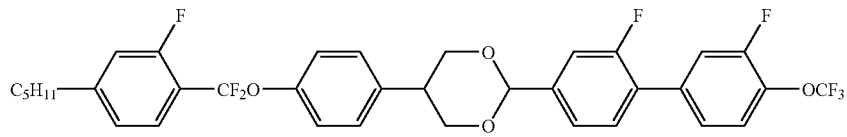
1-1-316
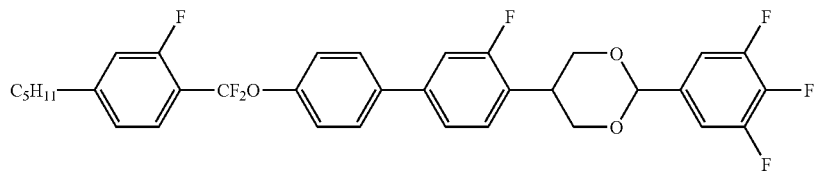
1-1-317
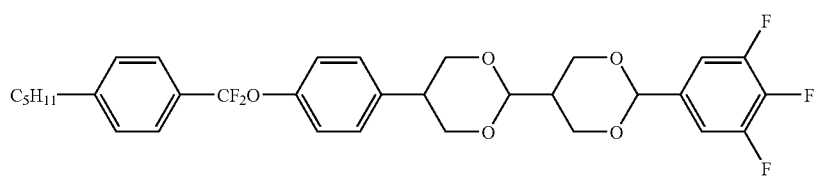
1-1-318
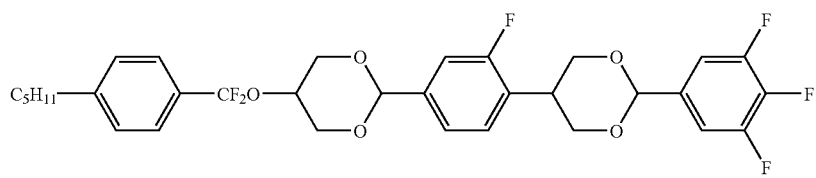
1-1-319
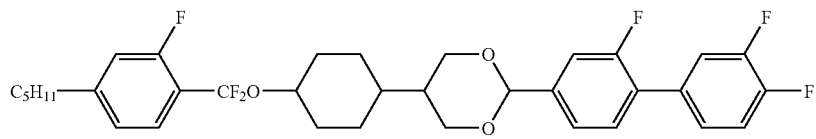
1-1-320
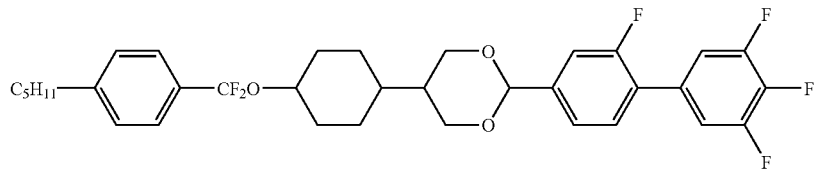
1-1-321
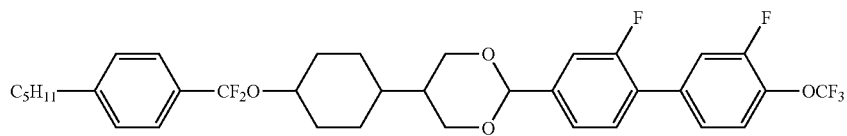
1-1-322
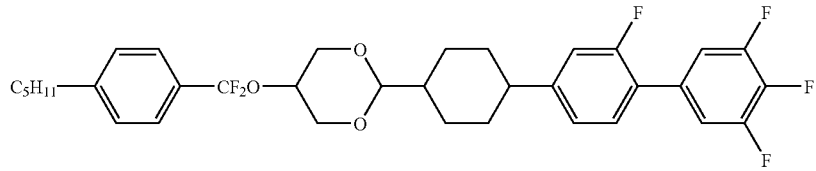
1-1-323
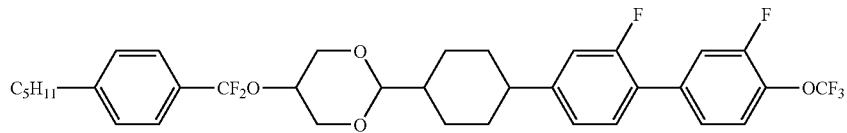
1-1-324

-continued
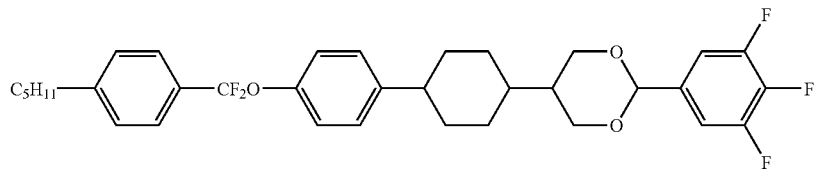
1-1-325
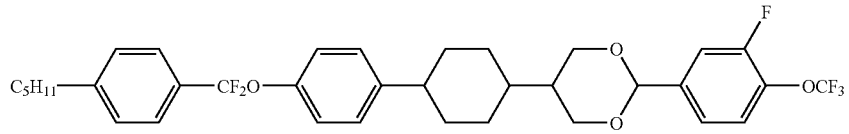
1-1-326
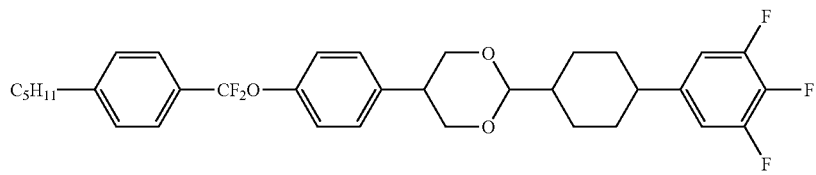
1-1-327
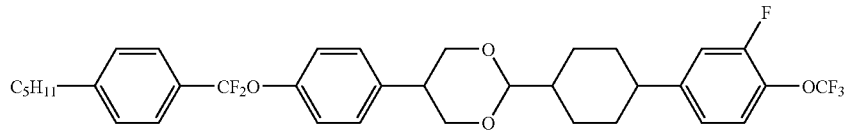
1-1-328
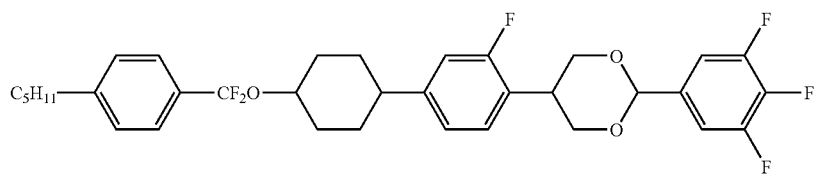
1-1-329
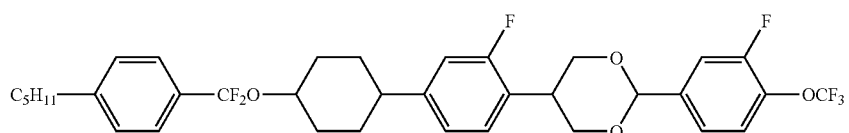
1-1-330
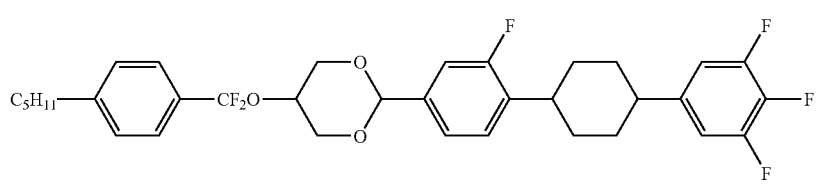
1-1-331
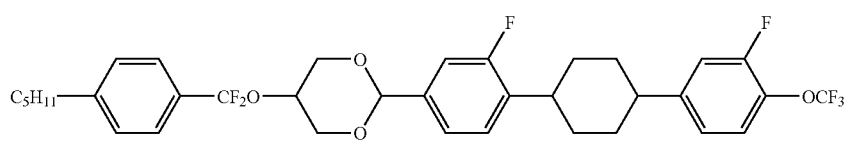
1-1-332
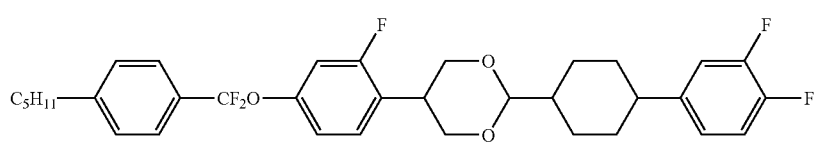
1-1-333
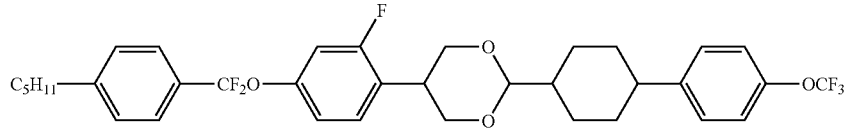
1-1-334

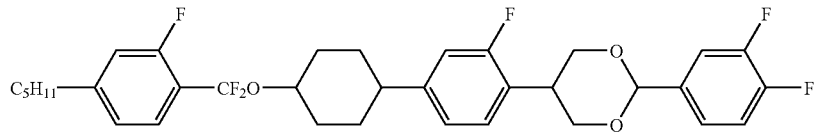
1-1-335
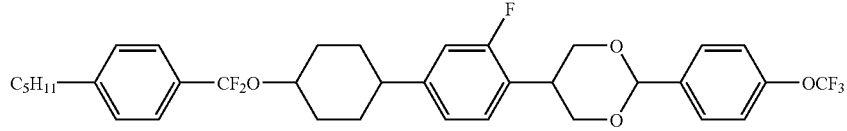
1-1-336
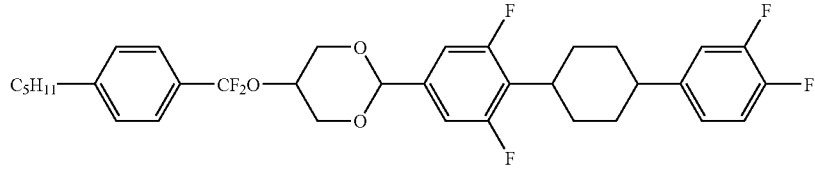
1-1-337
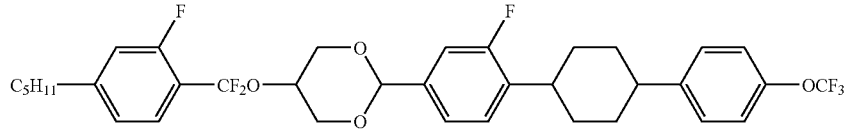
1-1-338
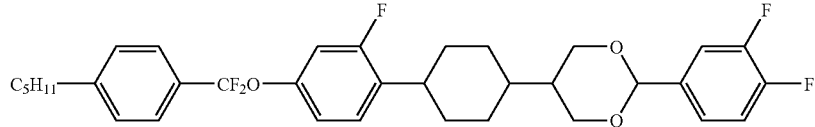
1-1-339
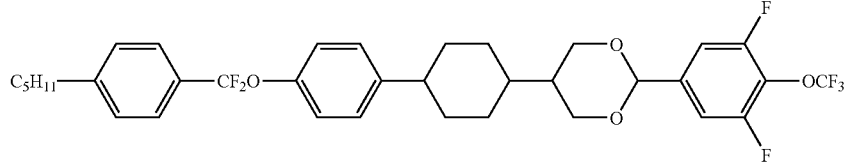
1-1-340
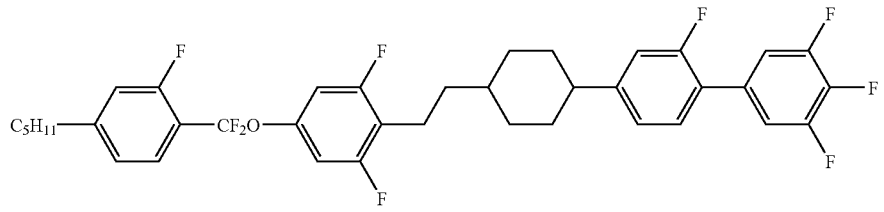
1-1-341
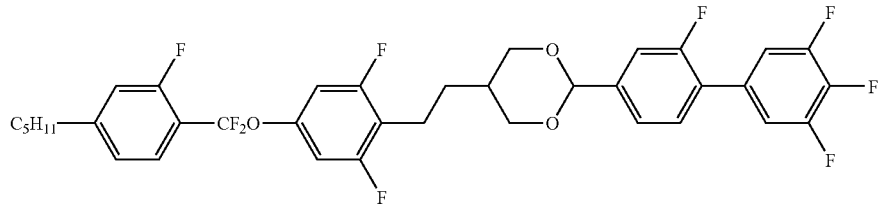
1-1-342
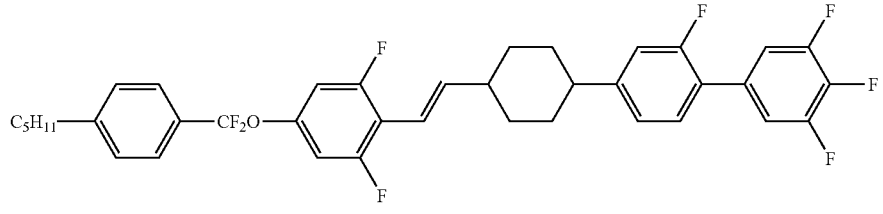
1-1-343

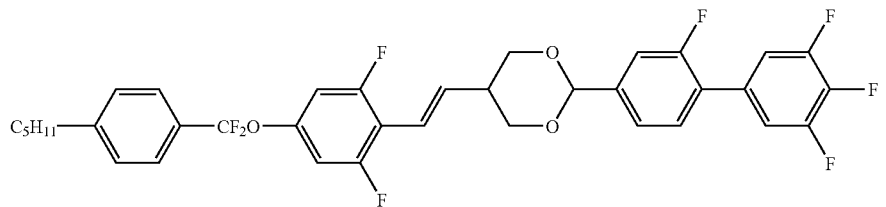
1-1-344
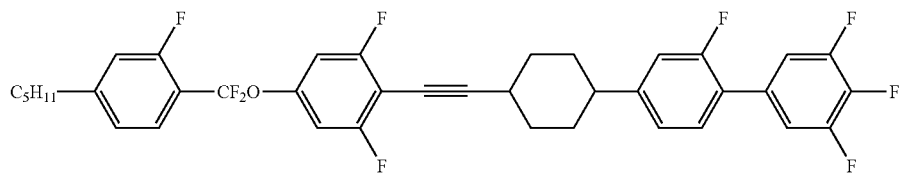
1-1-345
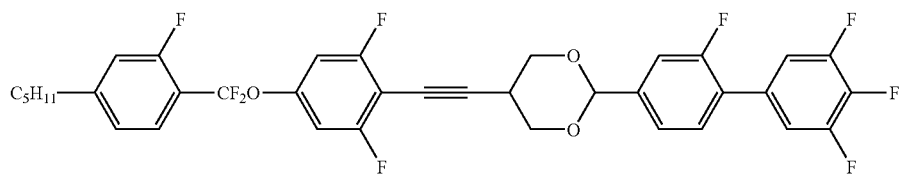
1-1-346
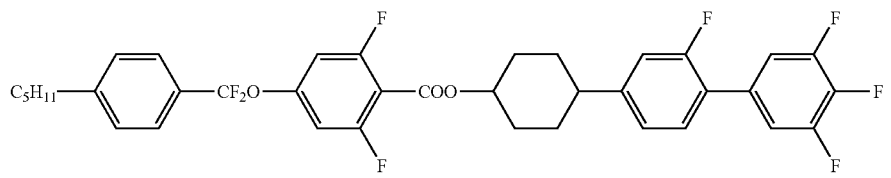
1-1-347
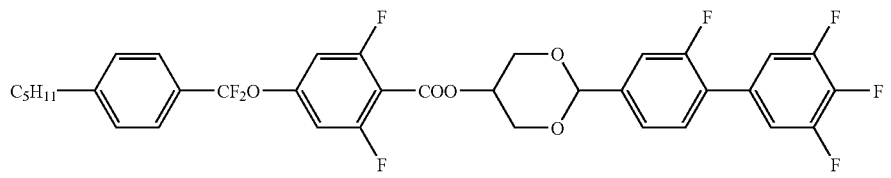
1-1-348
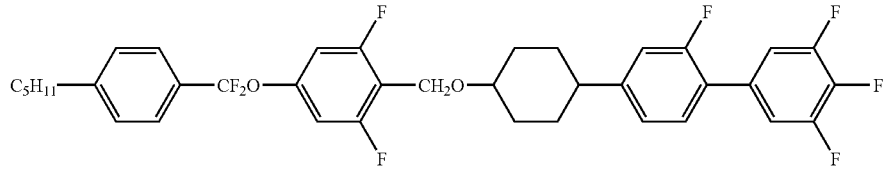
1-1-349
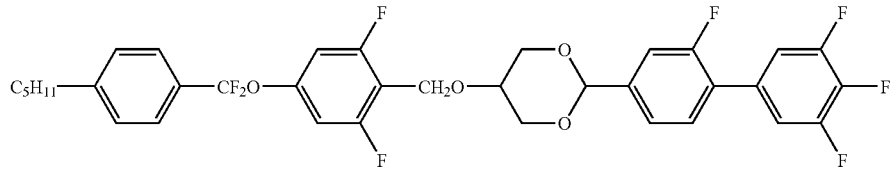
1-1-350
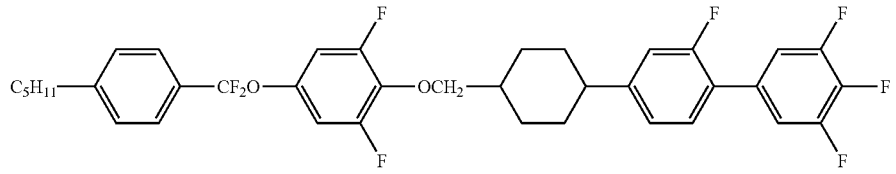
1-1-351

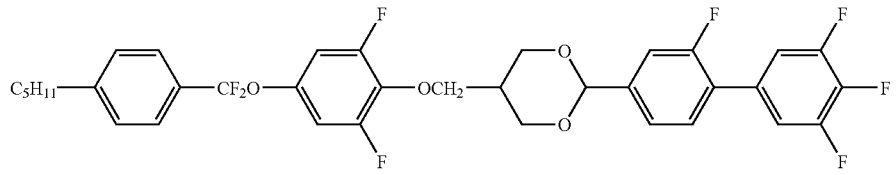
1-1-352
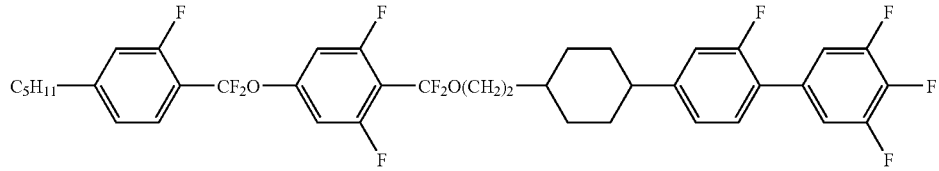
1-1-353
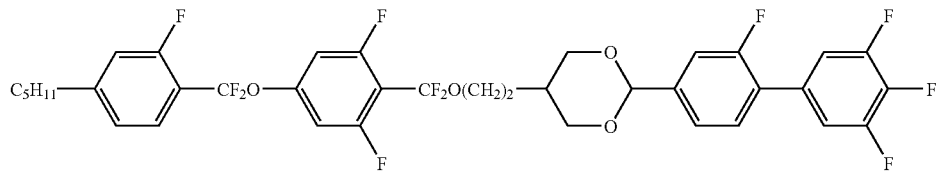
1-1-354
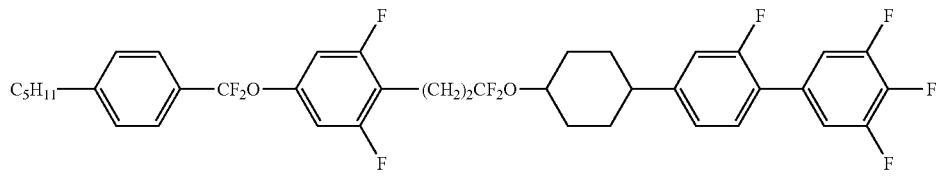
1-1-355
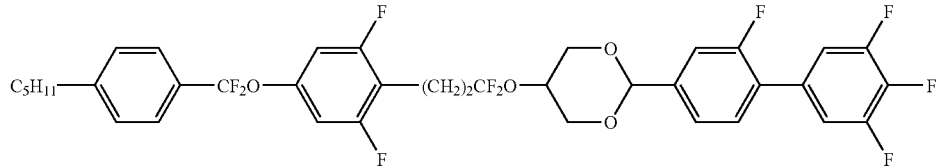
1-1-356
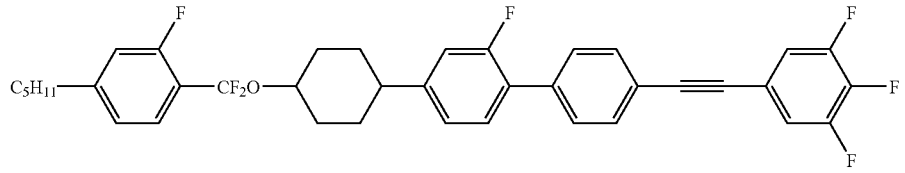
1-1-357
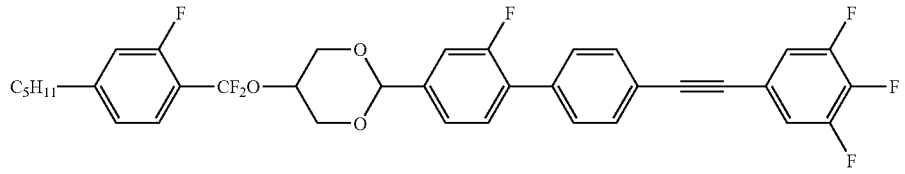
1-1-358
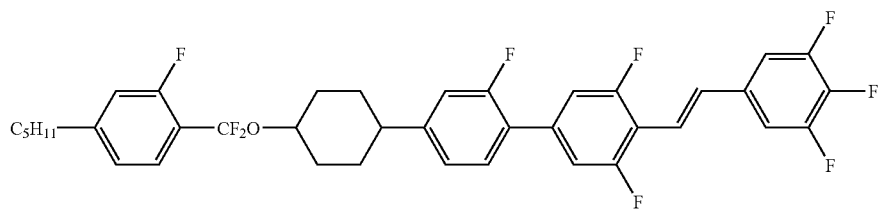
1-1-359

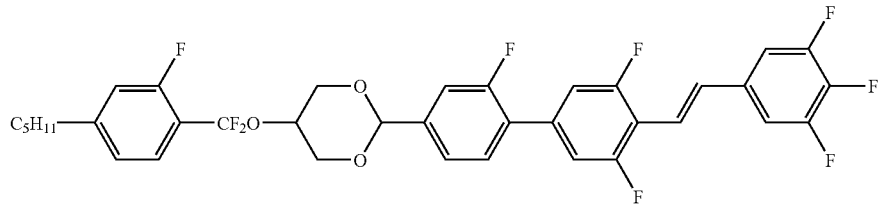
1-1-360
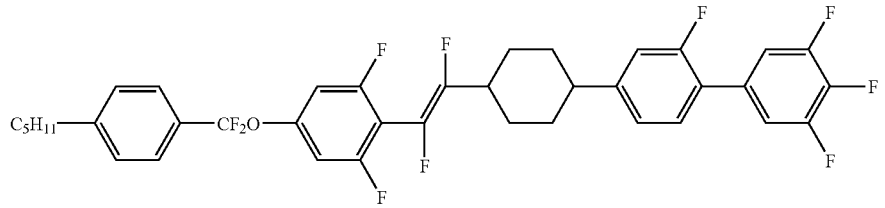
1-1-361
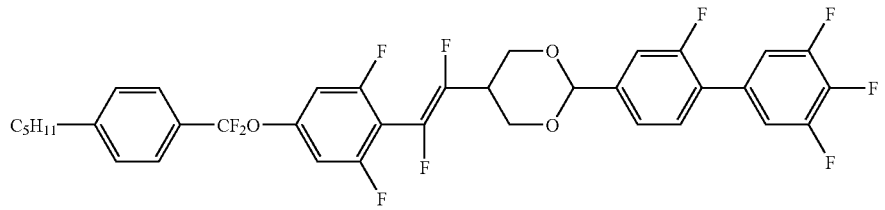
1-1-362
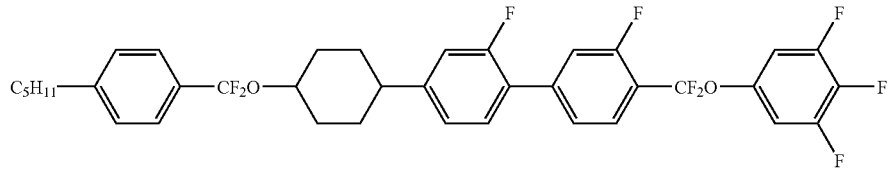
1-1-363
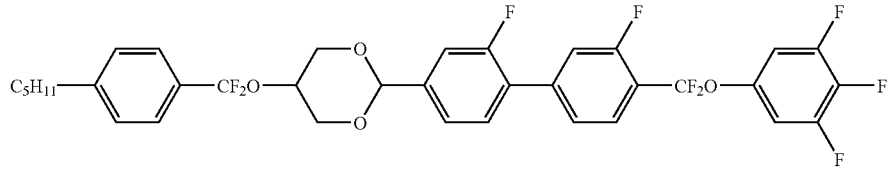
1-1-364
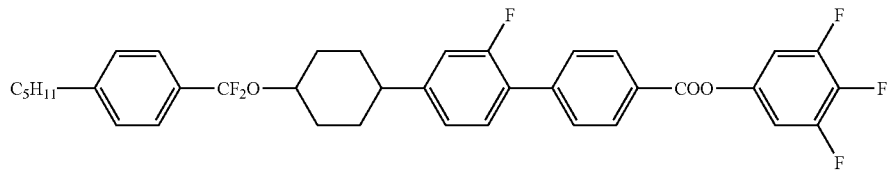
1-1-365
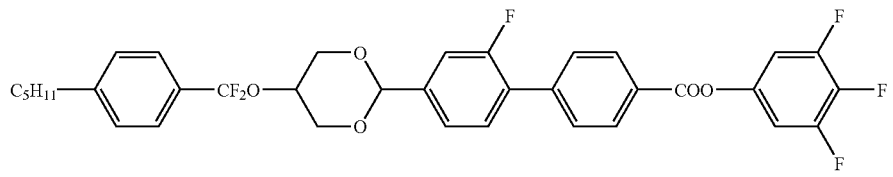
1-1-366
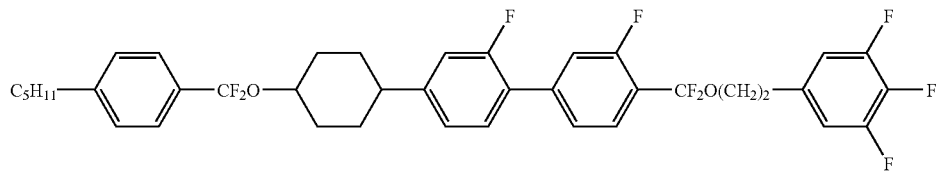
1-1-367

-continued
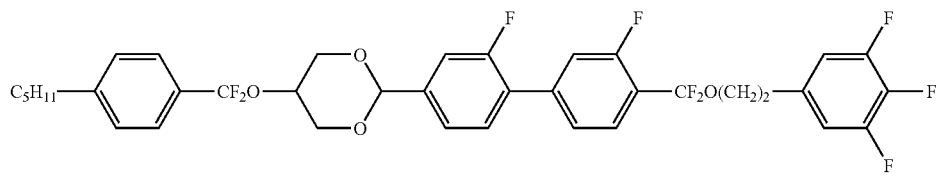
1-1-368
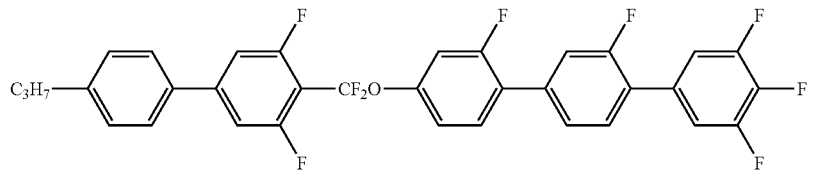
1-2-1
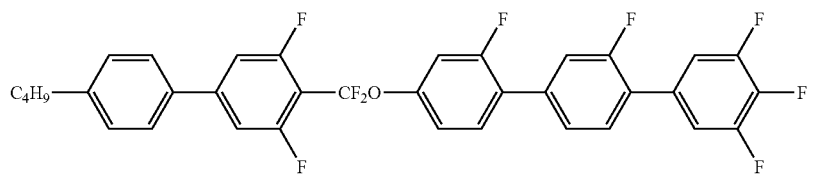
1-2-2
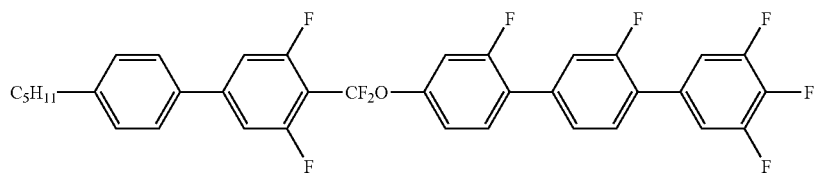
1-2-3
$T_{NI} = 139°$ C., $\Delta n = 0.227$, $\Delta \varepsilon = 39.7$
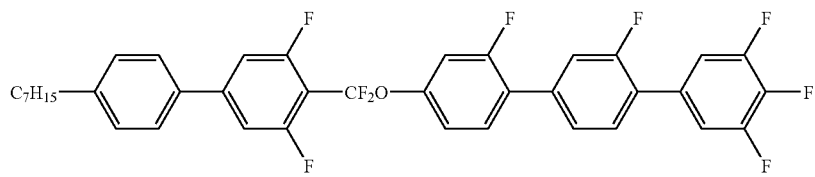
1-2-4
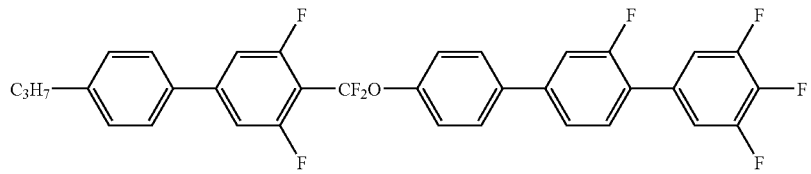
1-2-5
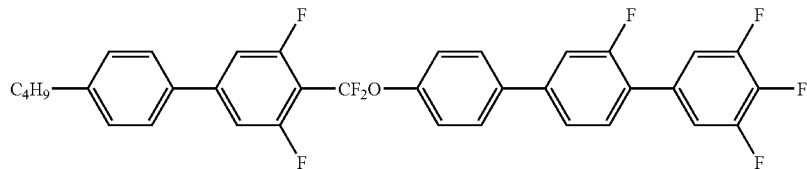
1-2-6
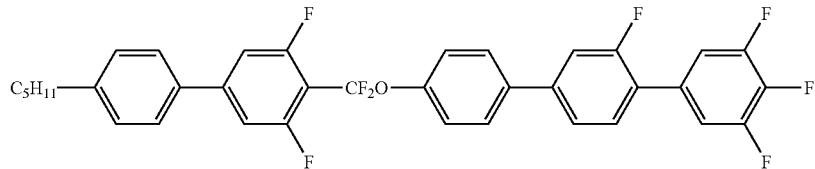
1-2-7

-continued
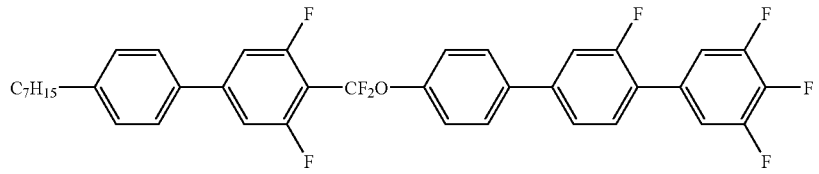
1-2-8
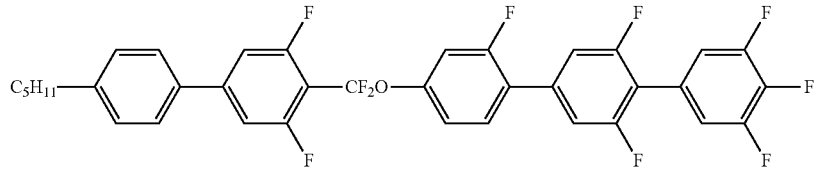
1-2-9
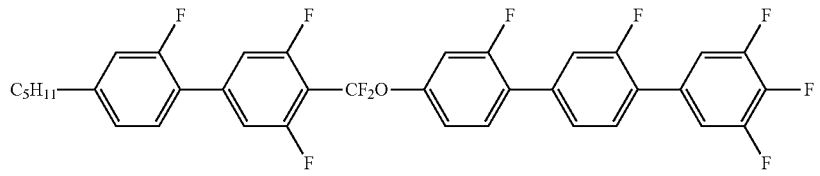
1-2-10
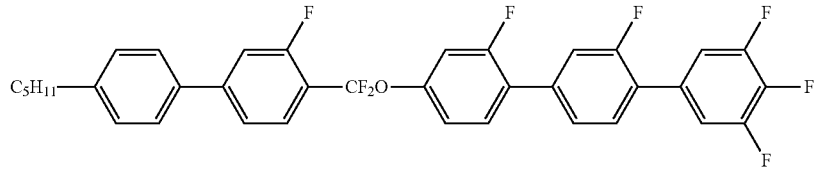
1-2-11
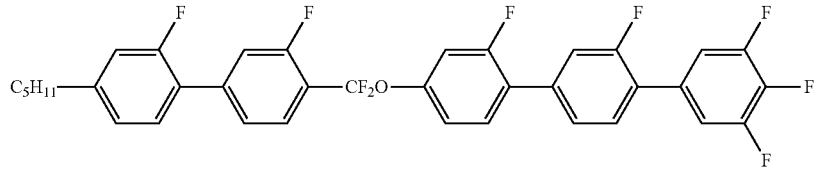
1-2-12
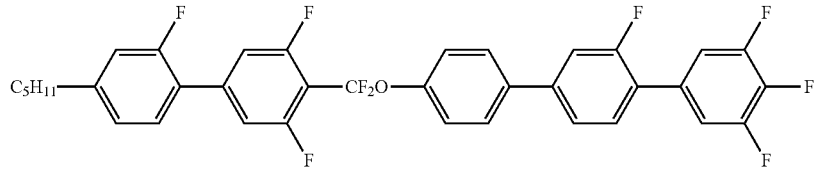
1-2-13
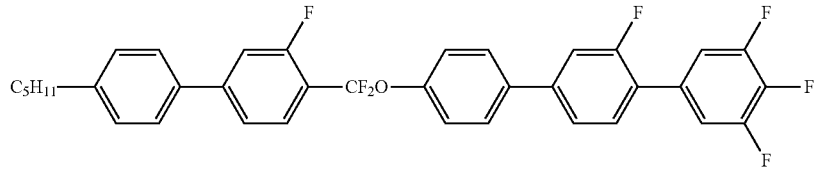
1-2-14
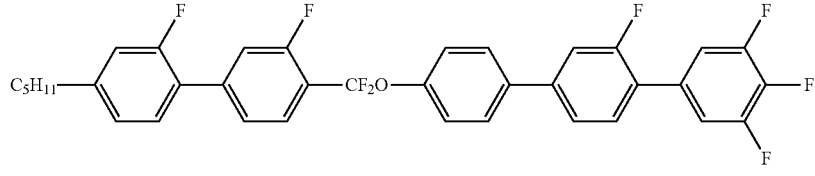
1-2-15
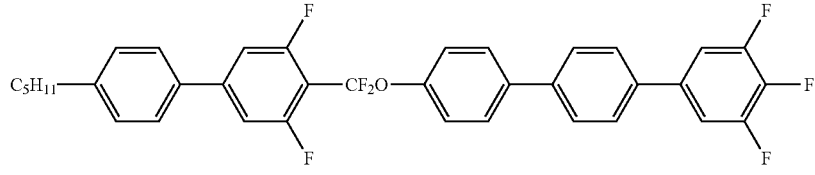
1-2-16

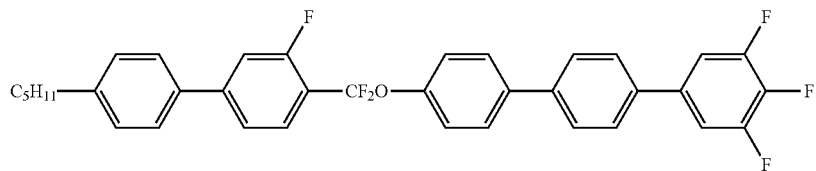
1-2-17
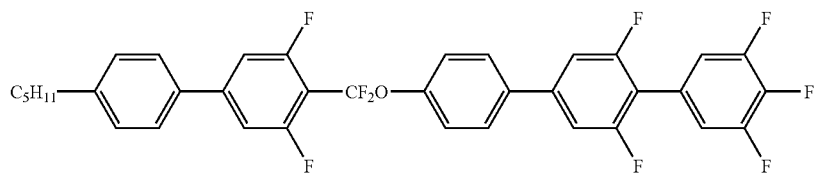
1-2-18
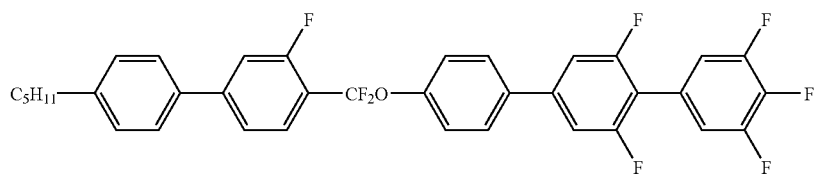
1-2-19
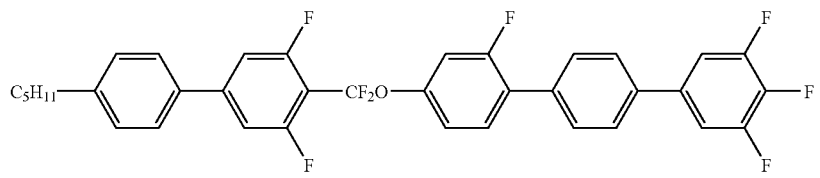
1-2-20
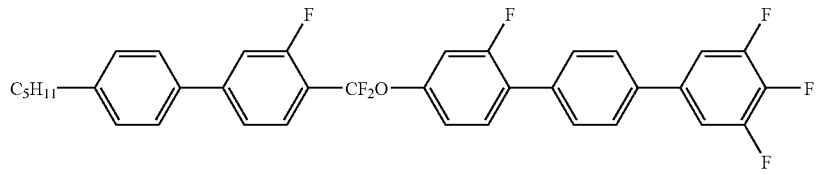
1-2-21
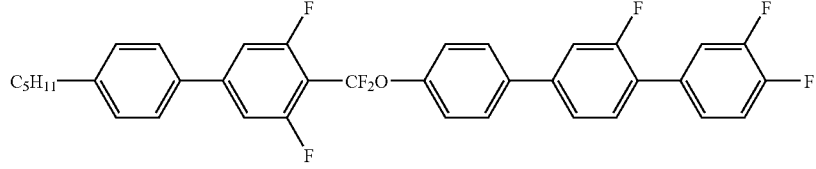
1-2-22
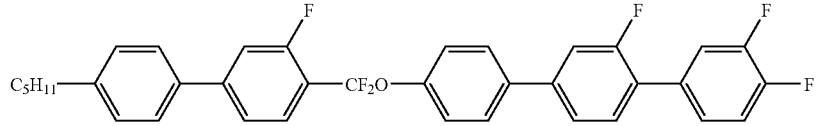
1-2-23
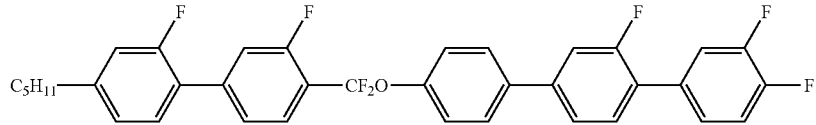
1-2-24
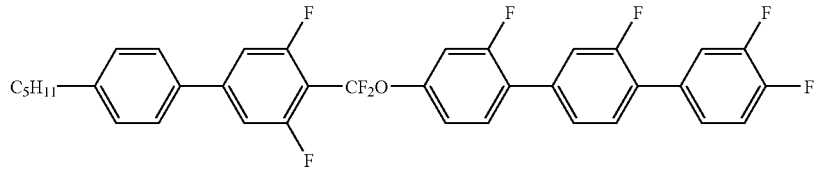
1-2-25

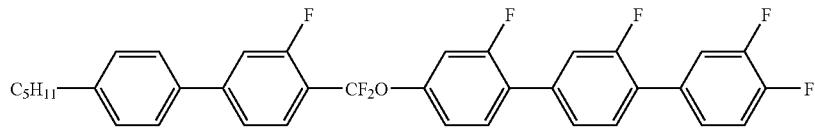
1-2-26
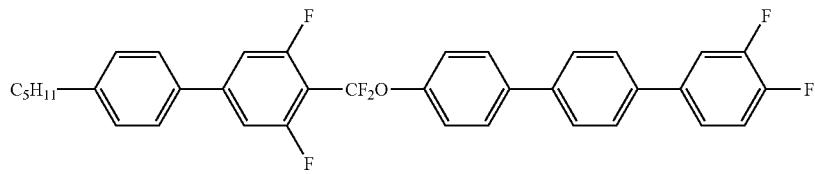
1-2-27
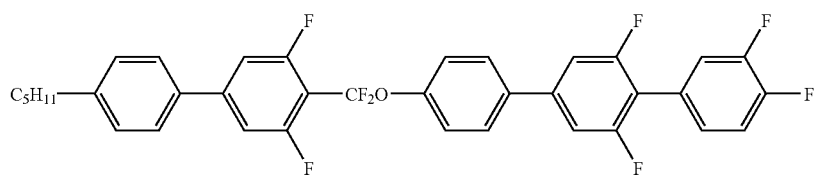
1-2-28
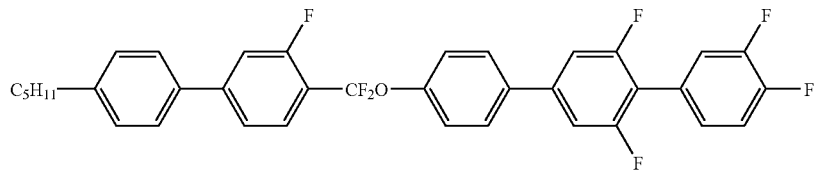
1-2-29
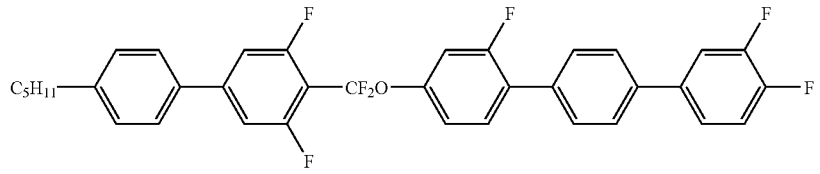
1-2-30
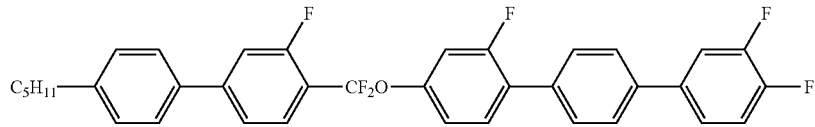
1-2-31
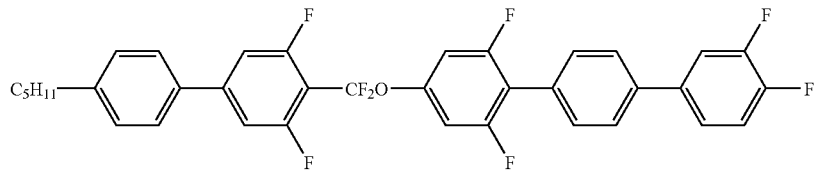
1-2-32
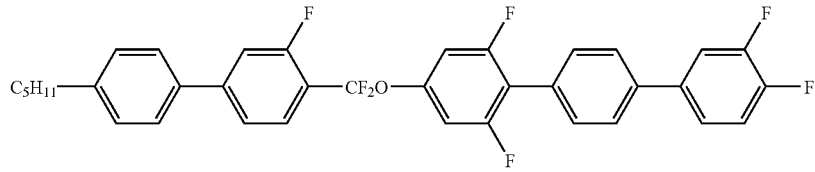
1-2-33
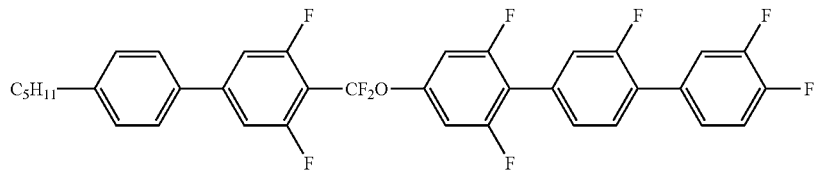
1-2-34

-continued
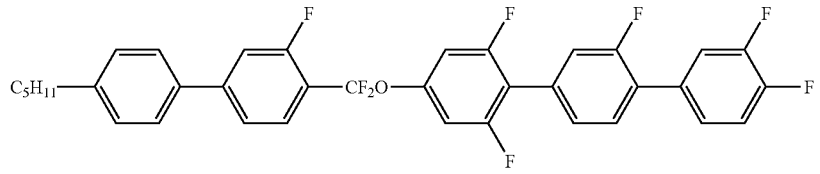
1-2-35
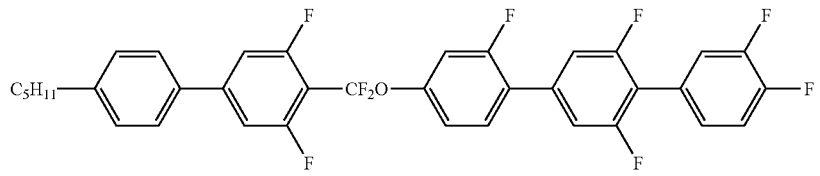
1-2-36
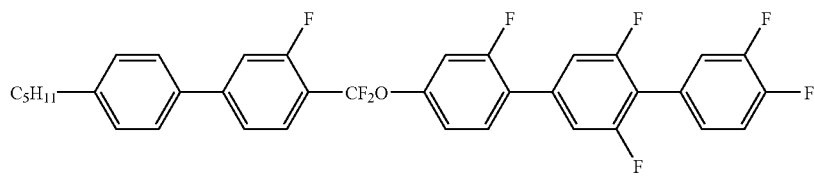
1-2-37
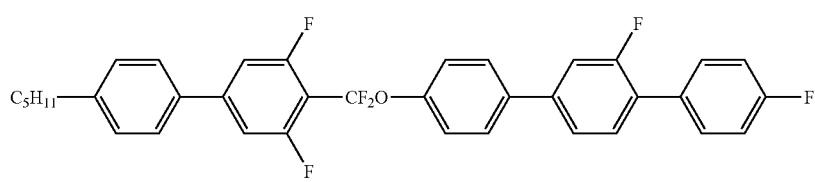
1-2-38
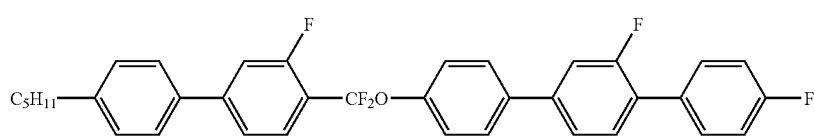
1-2-39
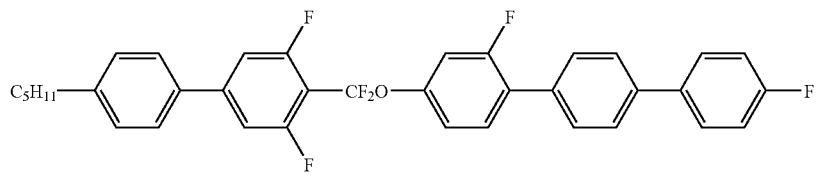
1-2-40
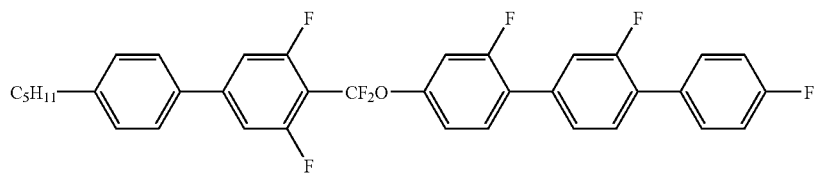
1-2-41
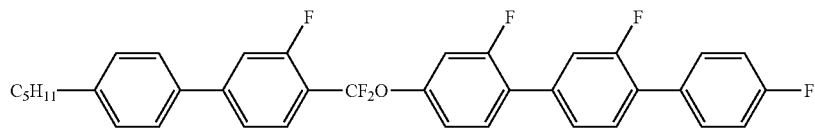
1-2-42
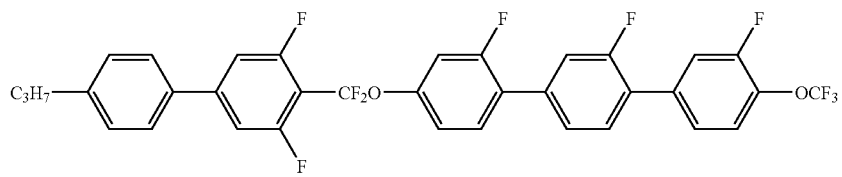
1-2-43

-continued
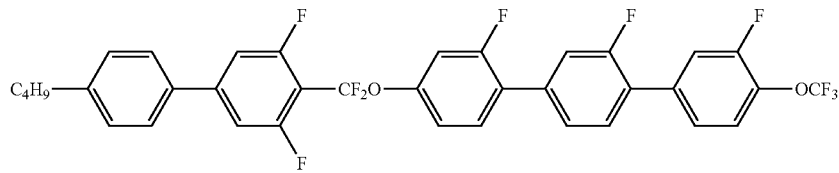
1-2-44
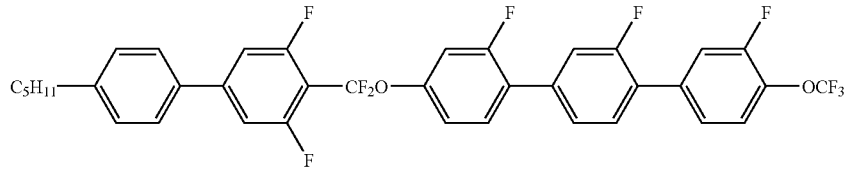
1-2-45
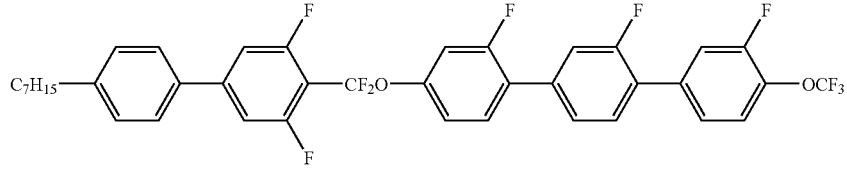
1-2-46
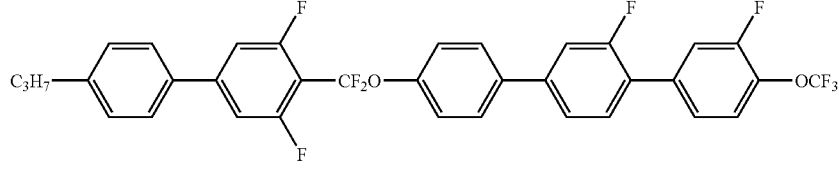
1-2-47
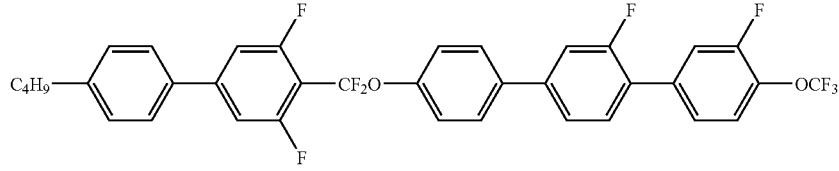
1-2-48
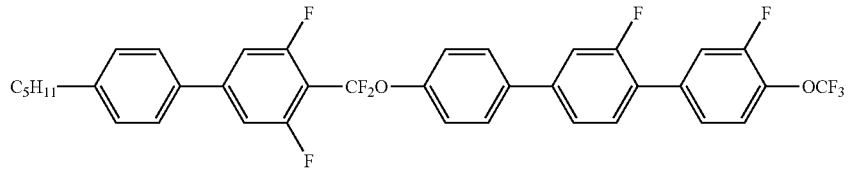
1-2-49
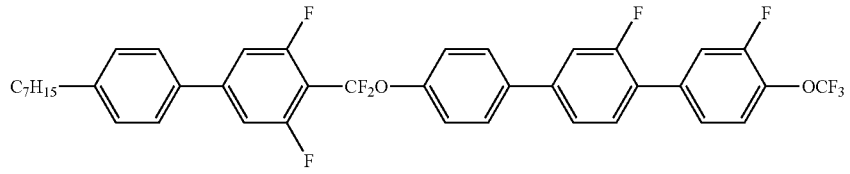
1-2-50
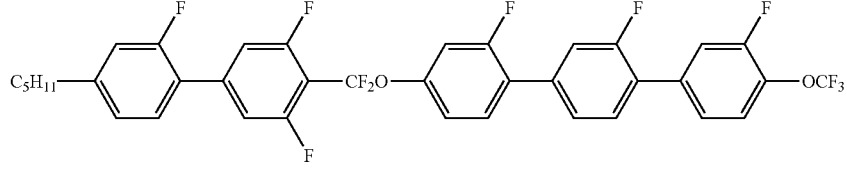
1-2-51
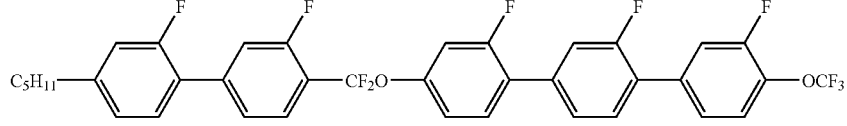
1-2-52

-continued
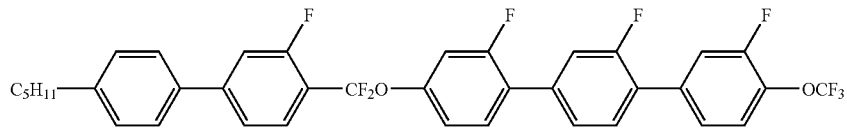
1-2-53
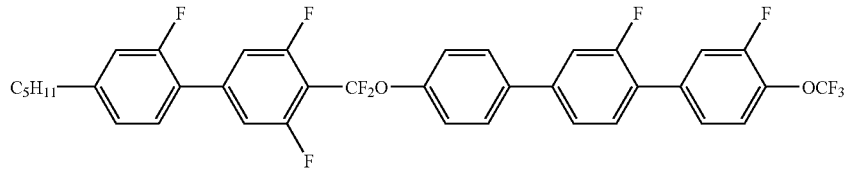
1-2-54
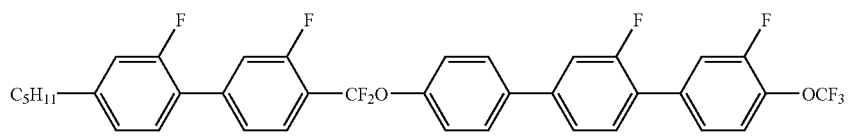
1-2-55
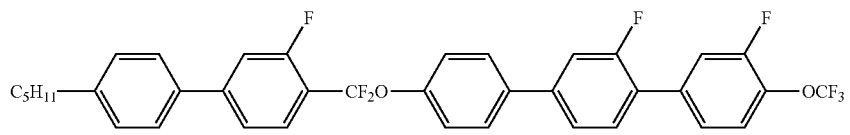
1-2-56
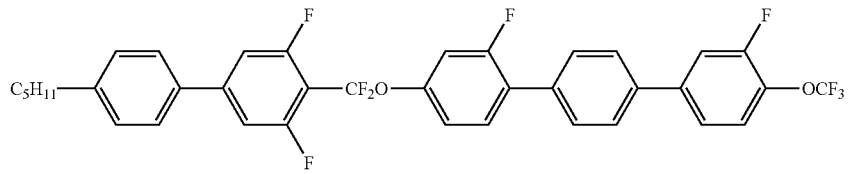
1-2-57
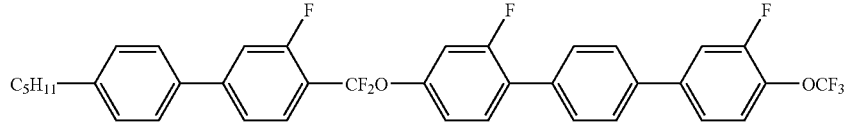
1-2-58
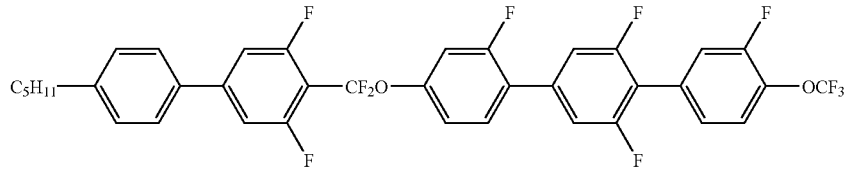
1-2-59
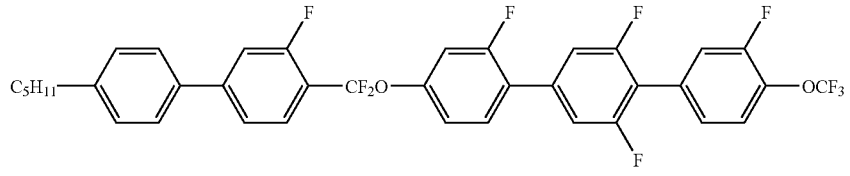
1-2-60
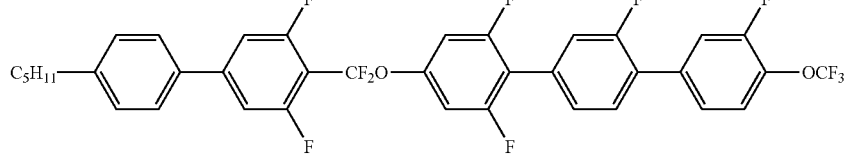
1-2-61
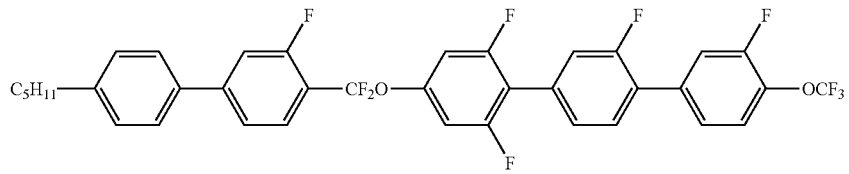
1-2-62

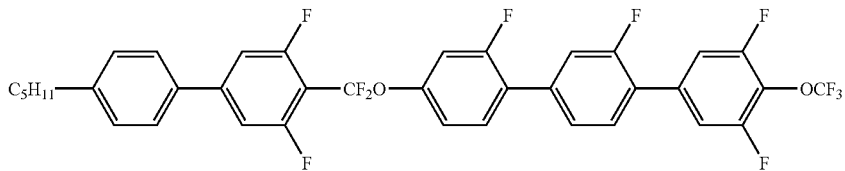
1-2-63
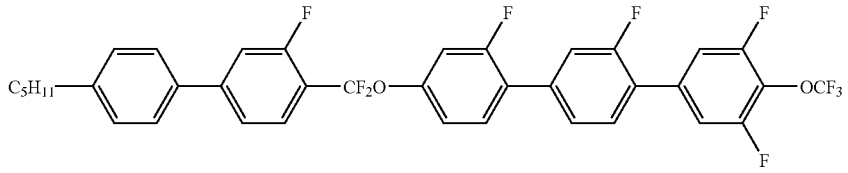
1-2-64
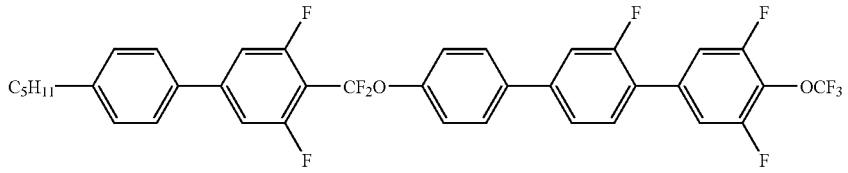
1-2-65
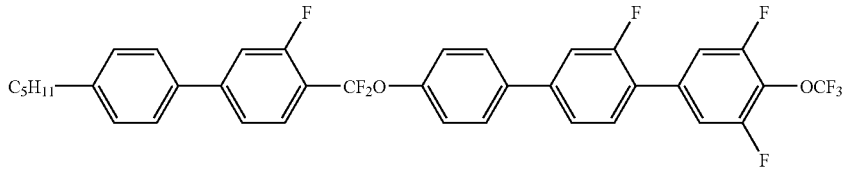
1-2-66
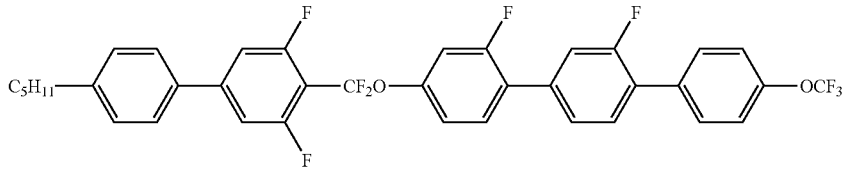
1-2-67
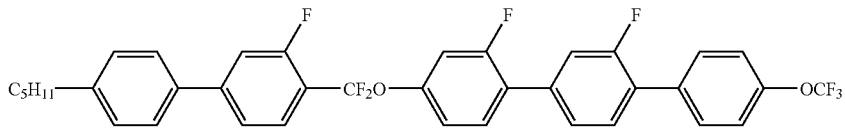
1-2-68
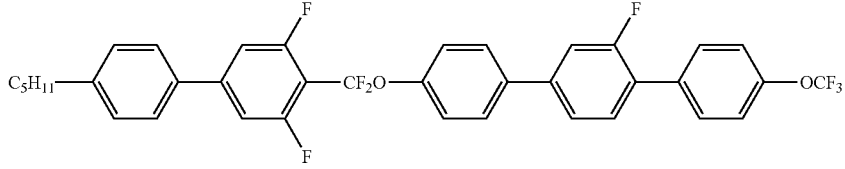
1-2-69
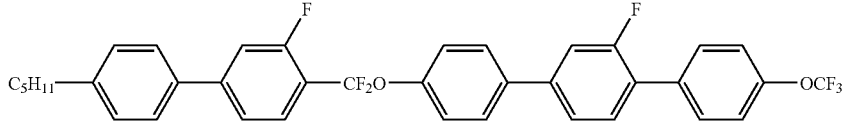
1-2-70
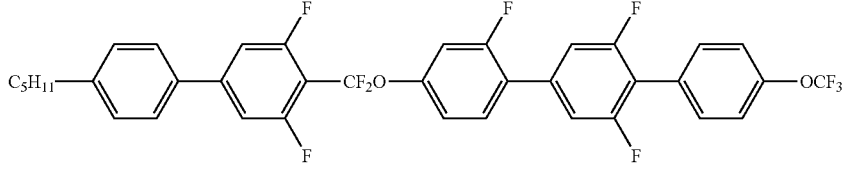
1-2-71

-continued
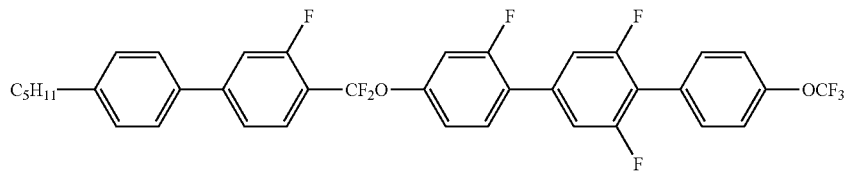
1-2-72
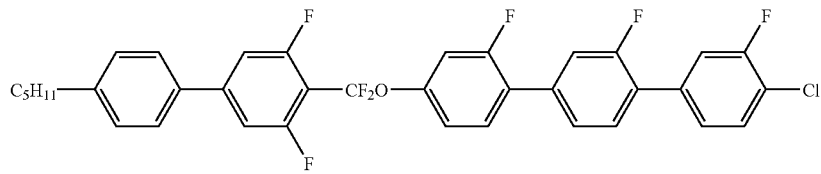
1-2-73
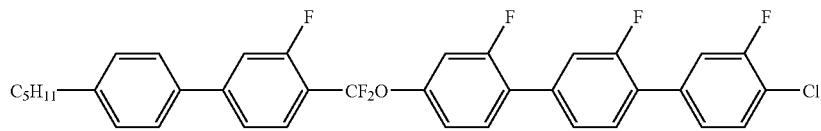
1-2-74
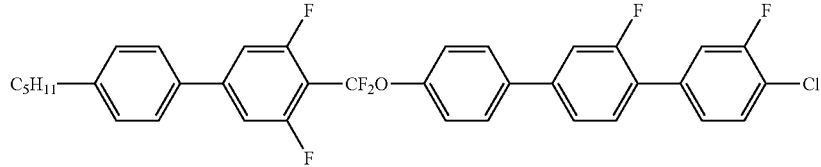
1-2-75
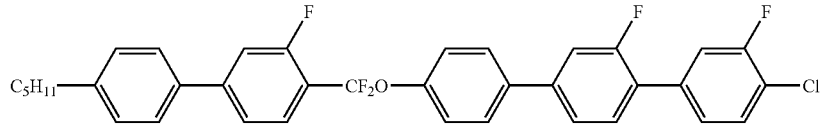
1-2-76
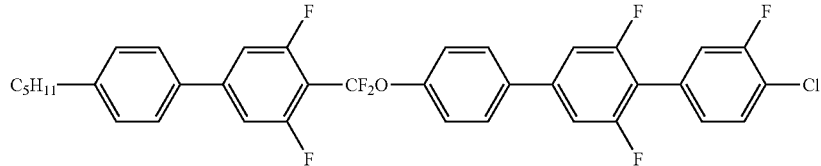
1-2-77
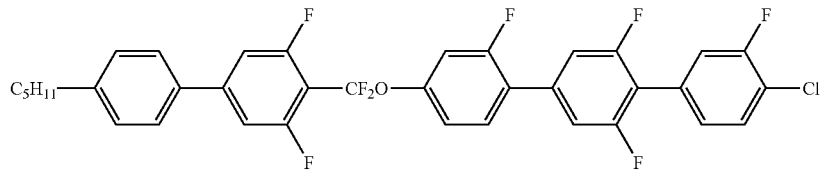
1-2-78
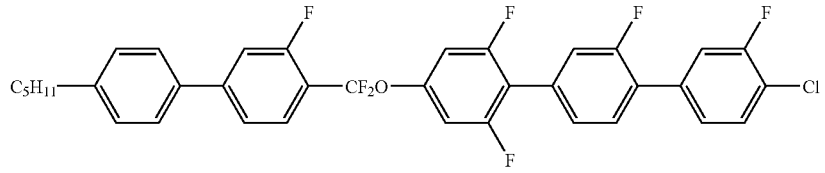
1-2-79
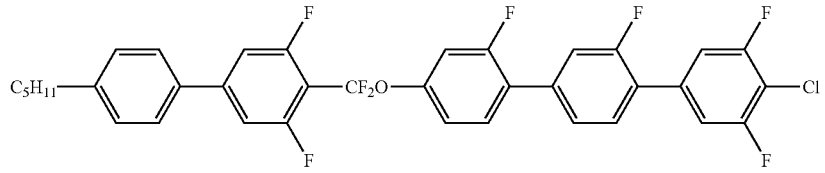
1-2-80

-continued
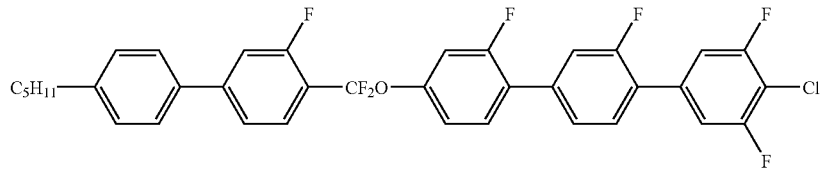
1-2-81
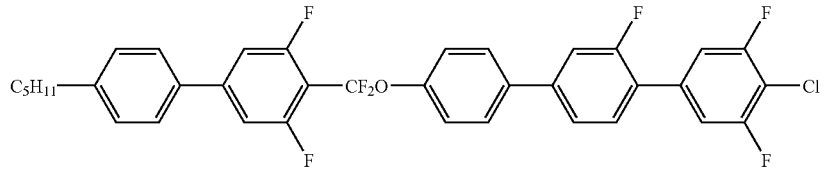
1-2-82
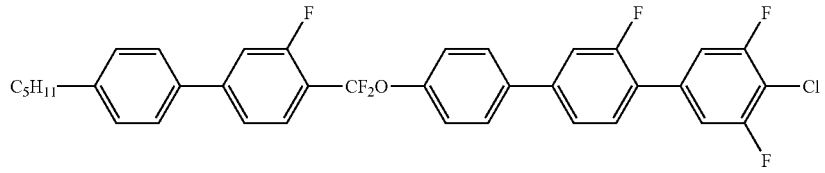
1-2-83
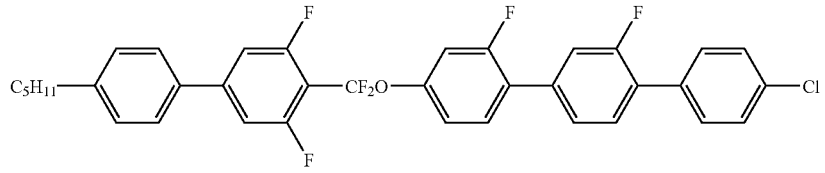
1-2-84
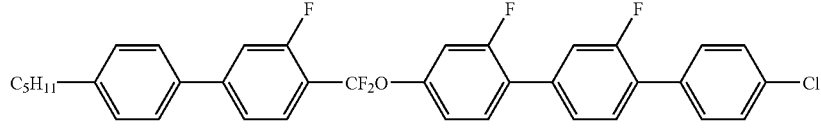
1-2-85

1-2-86
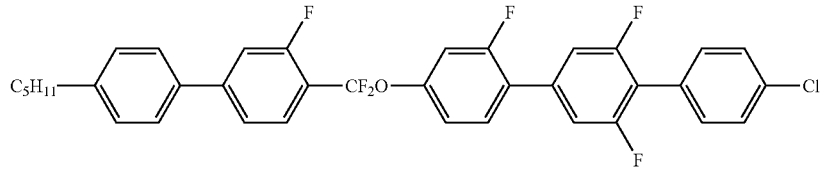
1-2-87
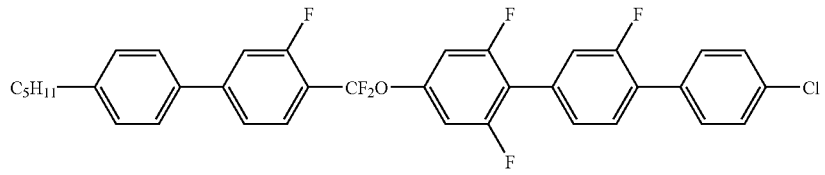
1-2-88
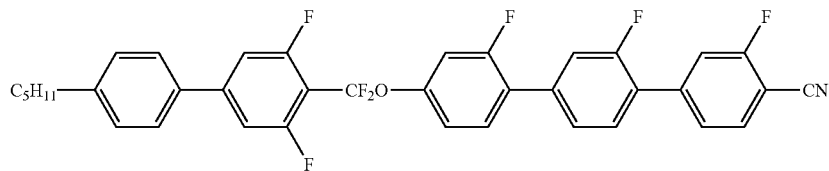
1-2-89

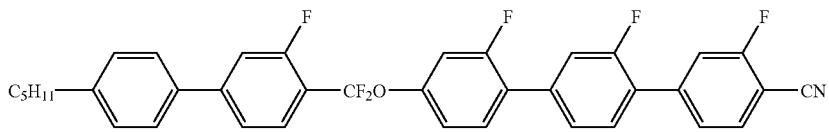 1-2-90
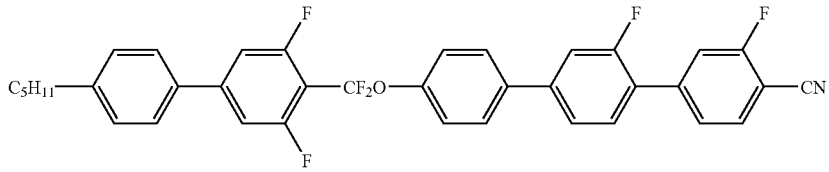 1-2-91
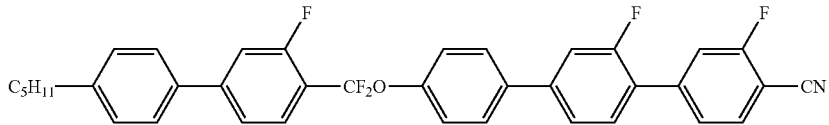 1-2-92
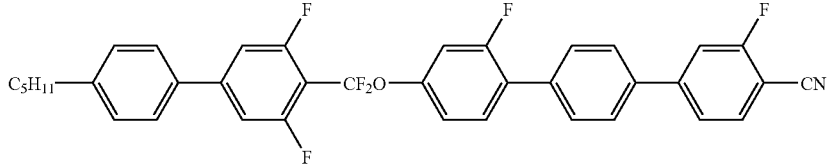 1-2-93
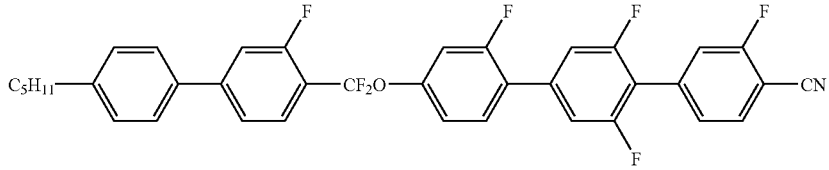 1-2-94
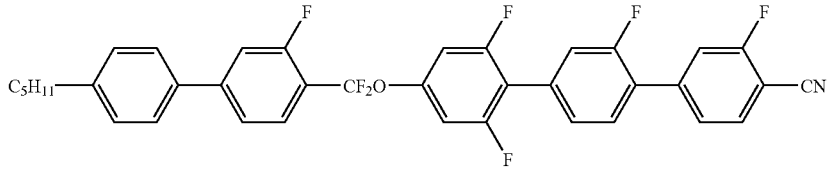 1-2-95
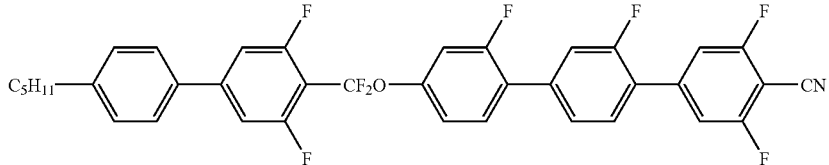 1-2-96
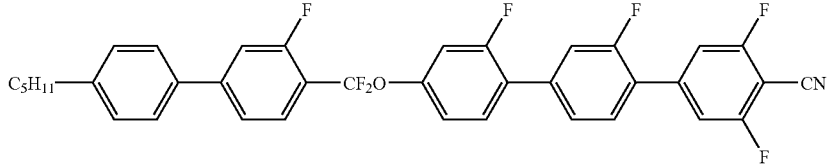 1-2-97
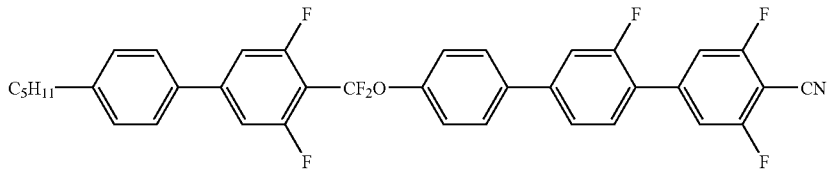 1-2-98

-continued
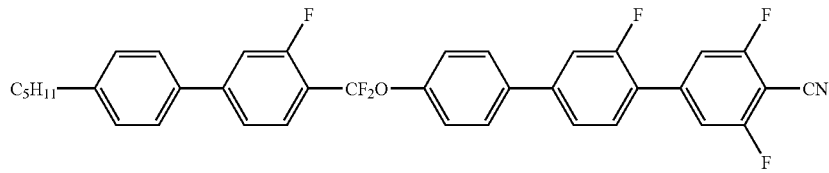
1-2-99
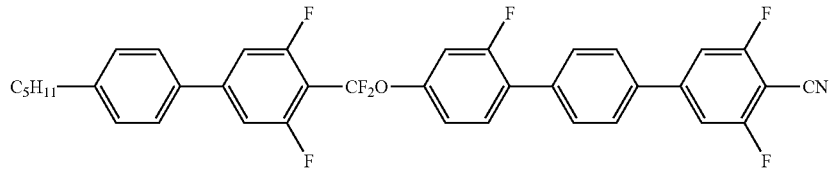
1-2-100
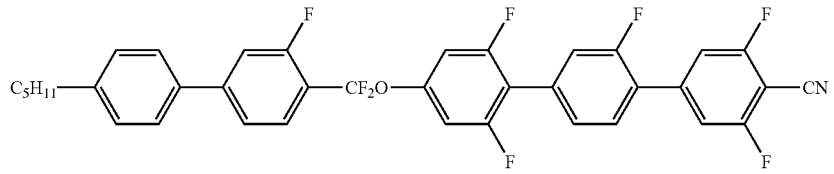
1-2-101
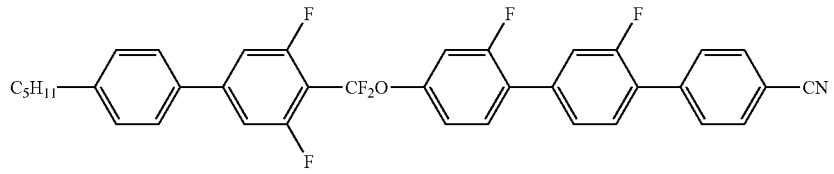
1-2-102
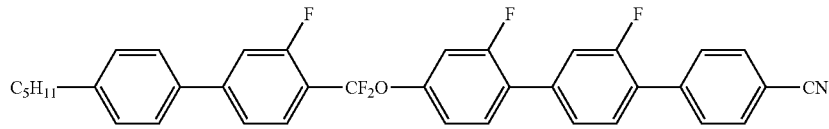
1-2-103
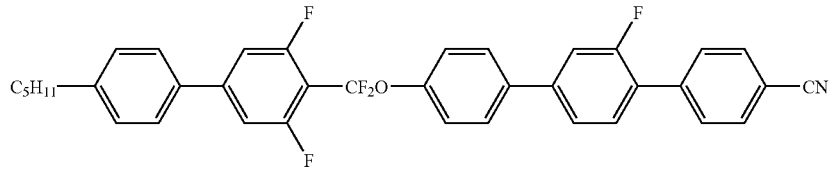
1-2-104
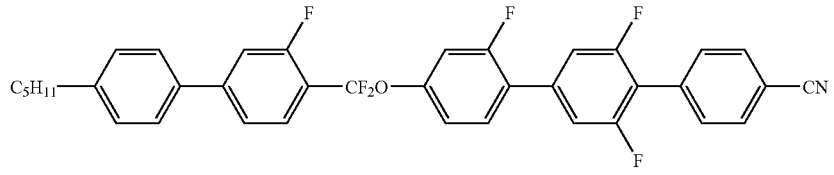
1-2-105
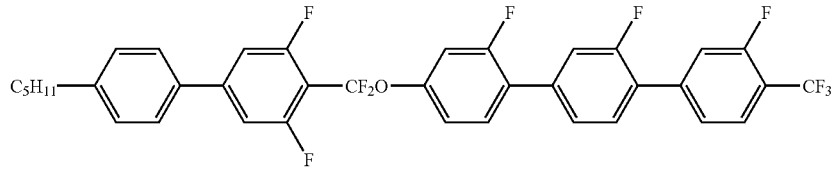
1-2-106
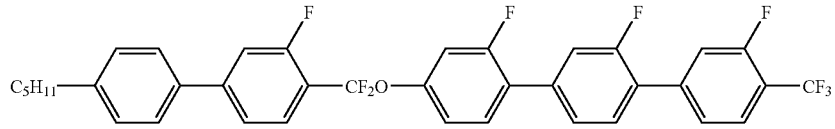
1-2-107

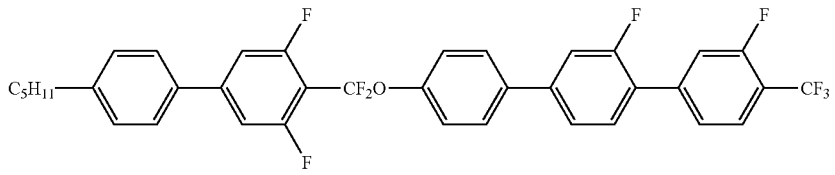
1-2-108
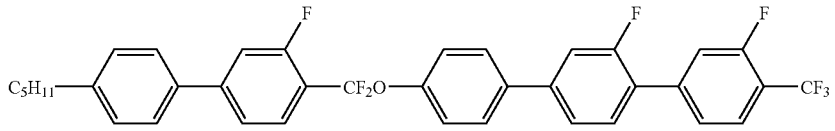
1-2-109
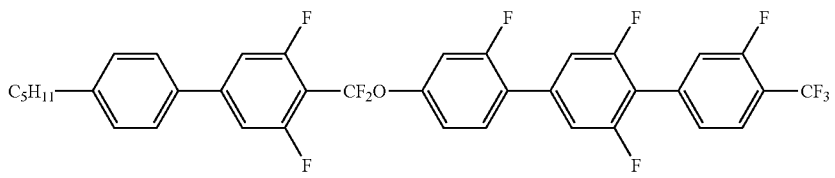
1-2-110
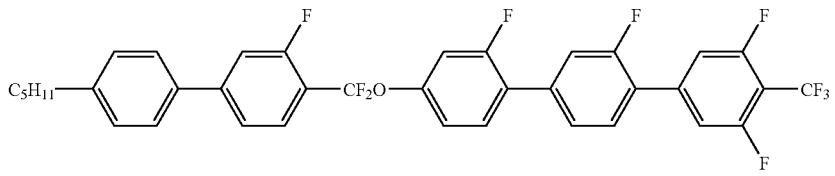
1-2-111
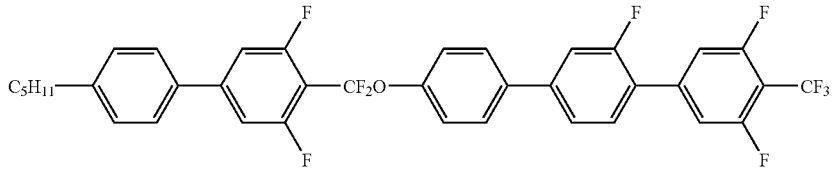
1-2-112
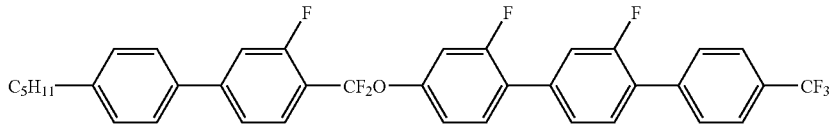
1-2-113
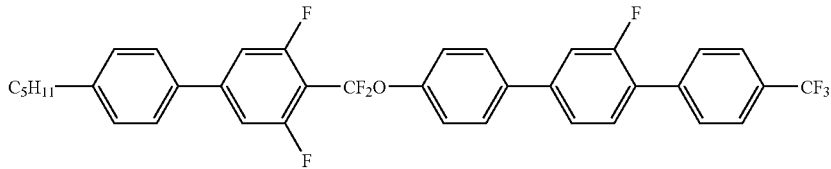
1-2-114
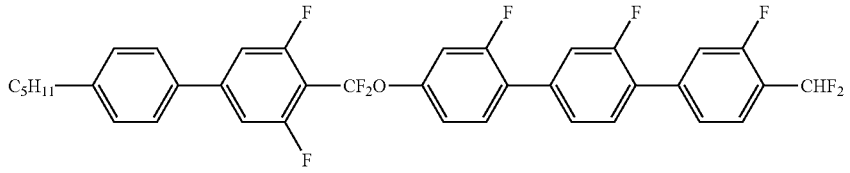
1-2-115
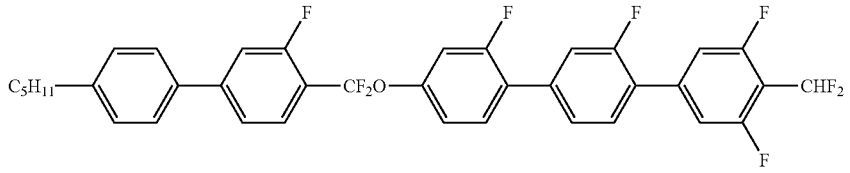
1-2-116

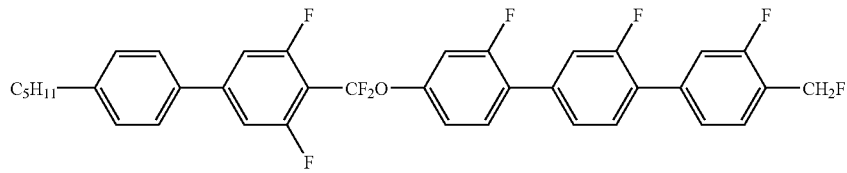 1-2-117
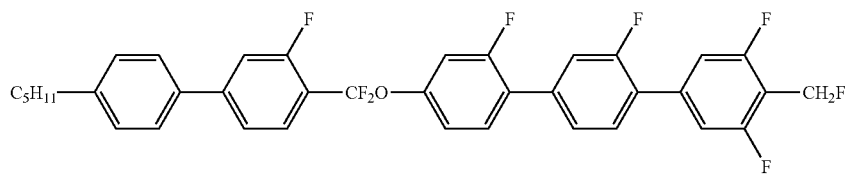 1-2-118
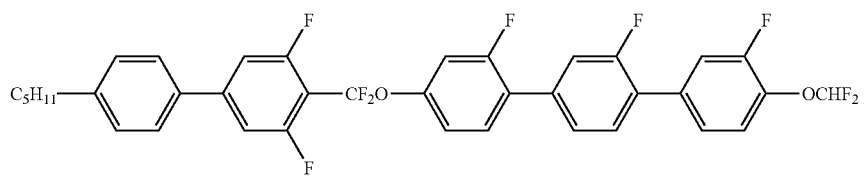 1-2-119
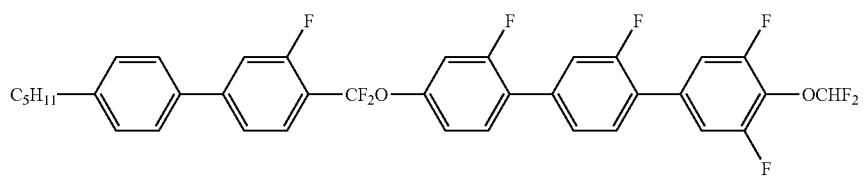 1-2-120
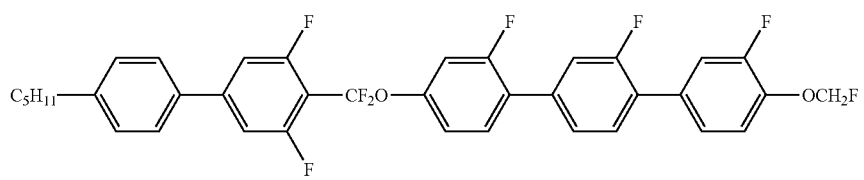 1-2-121
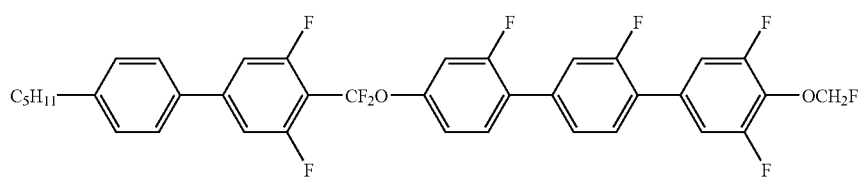 1-2-122
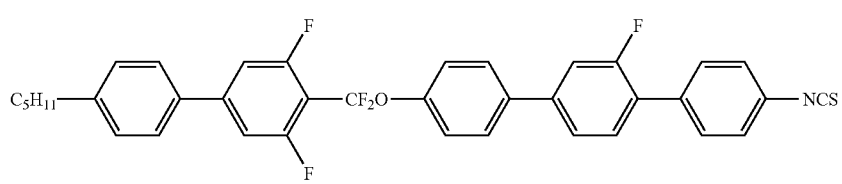 1-2-123
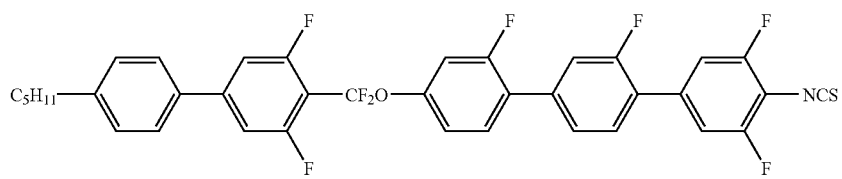 1-2-124
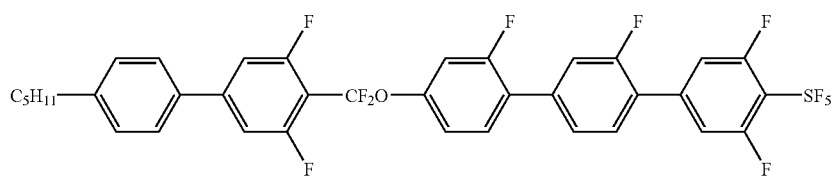 1-2-125

-continued
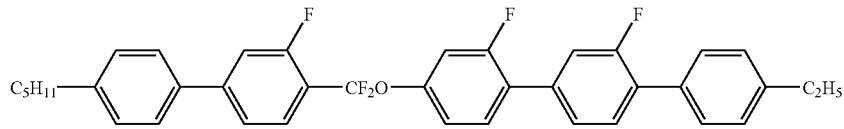
1-2-126
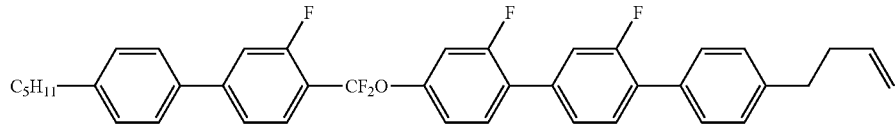
1-2-127
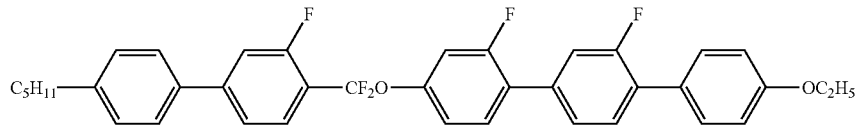
1-2-128
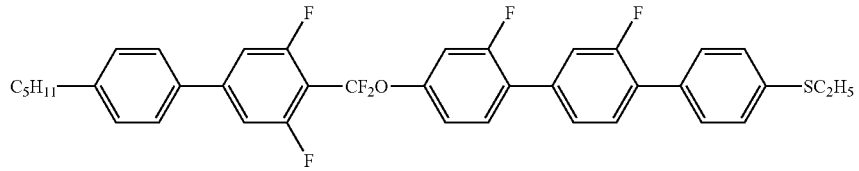
1-2-129
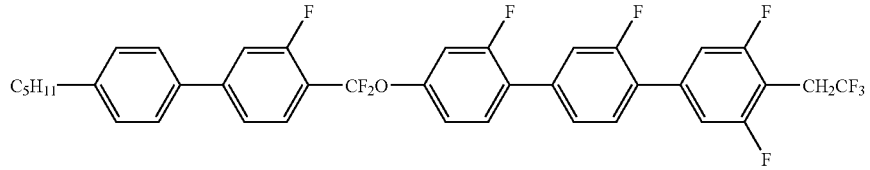
1-2-130
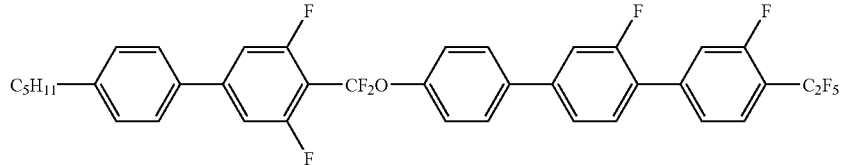
1-2-131
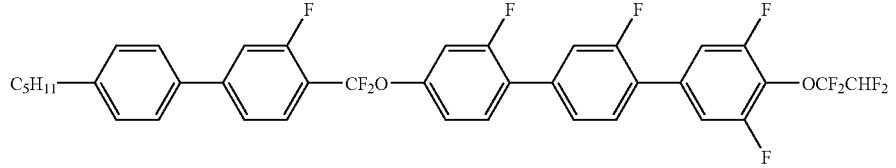
1-2-132
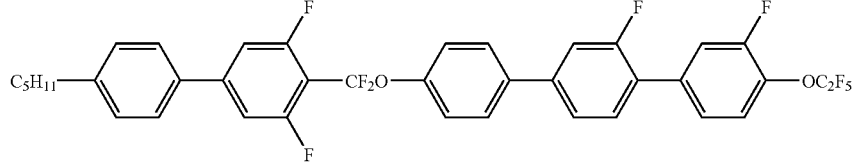
1-2-133
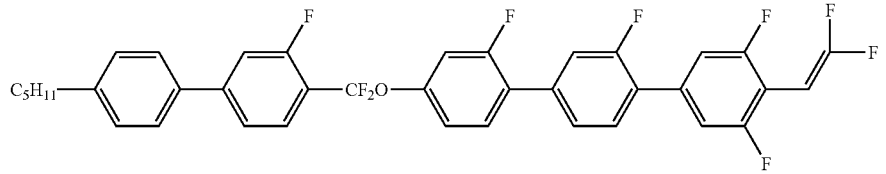
1-2-134

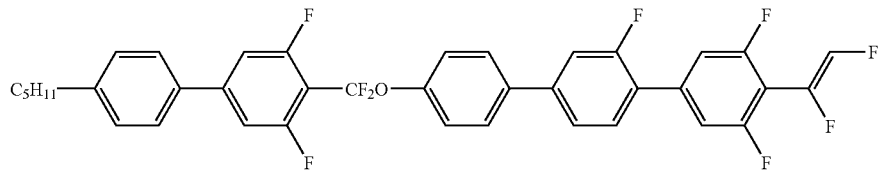
1-2-135
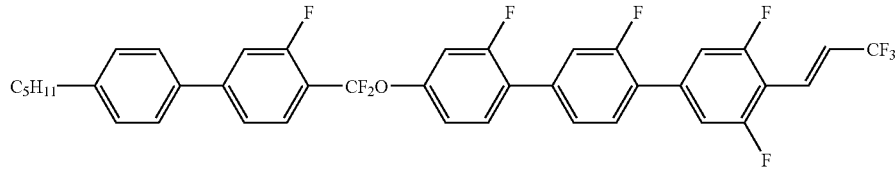
1-2-136
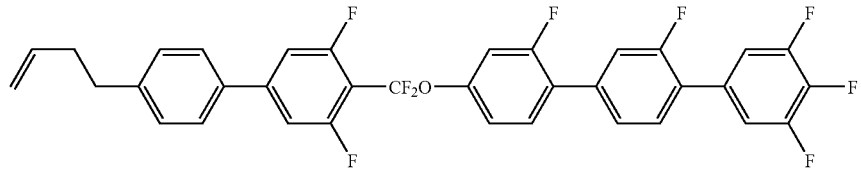
1-2-137
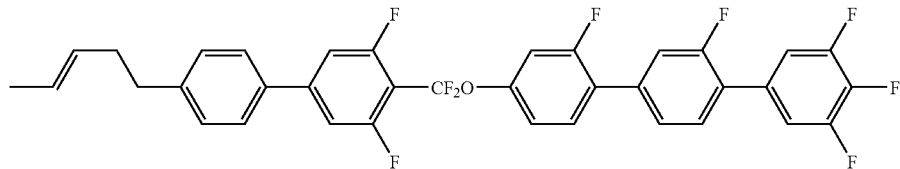
1-2-138
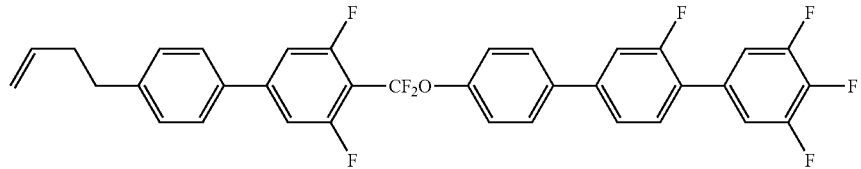
1-2-139
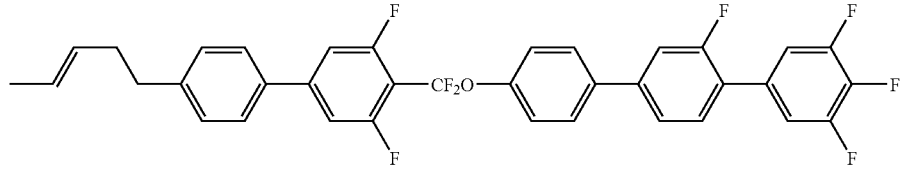
1-2-140
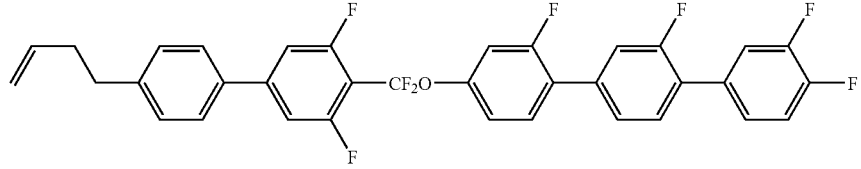
1-2-141
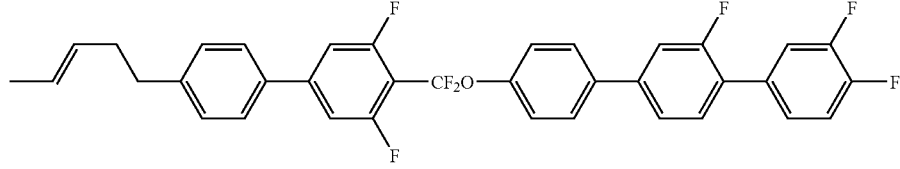
1-2-142
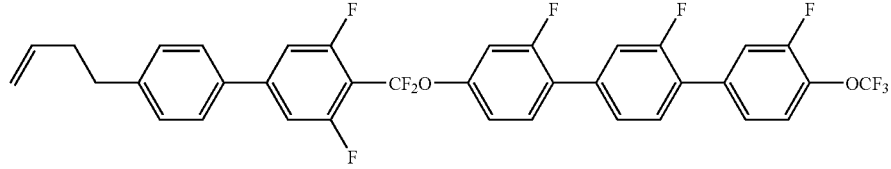
1-2-143

-continued
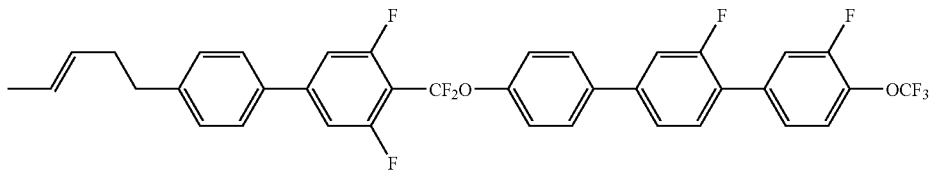
1-2-144
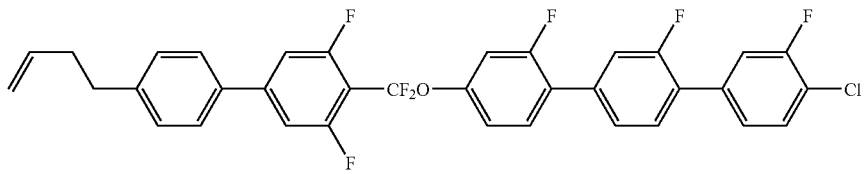
1-2-145
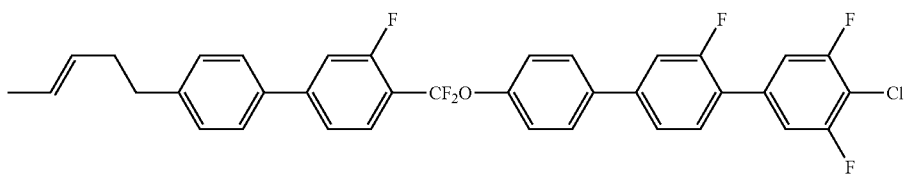
1-2-146
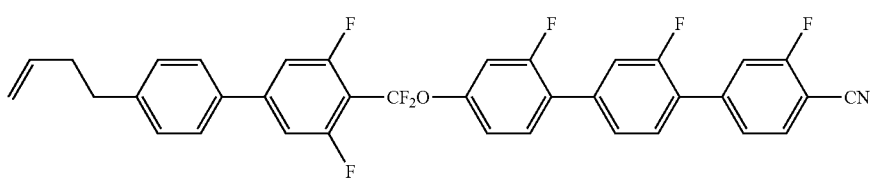
1-2-147
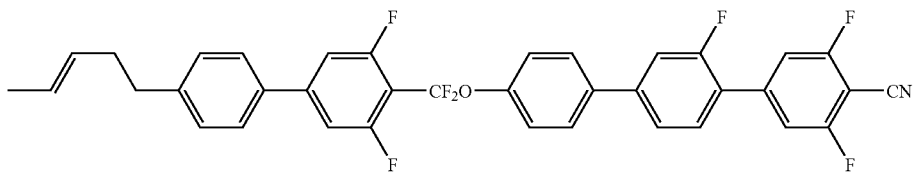
1-2-148
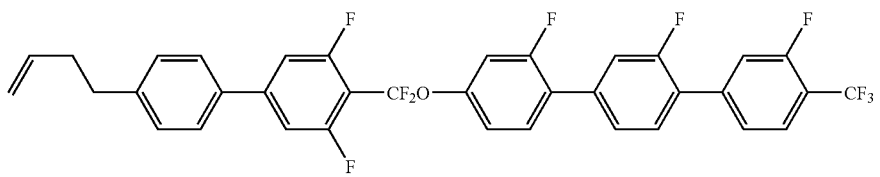
1-2-149
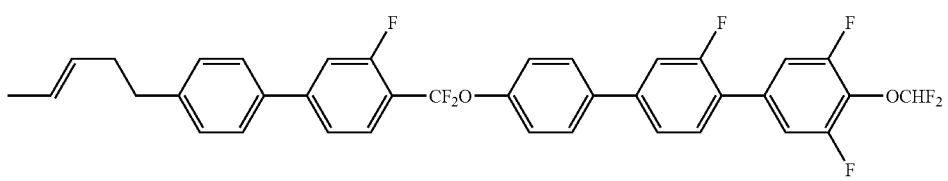
1-2-150
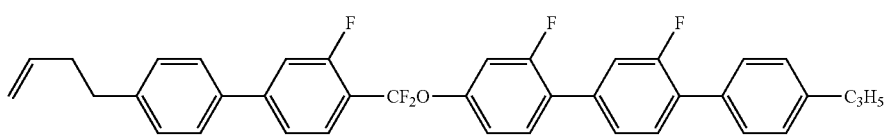
1-2-151
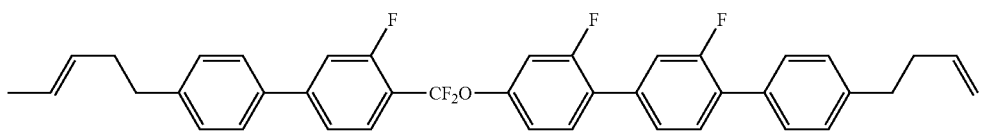
1-2-152

-continued
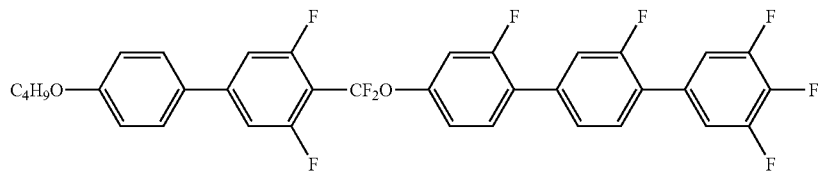
1-2-153
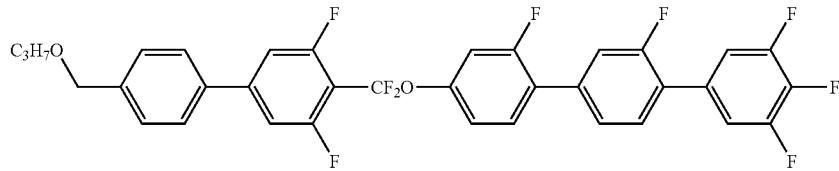
1-2-154
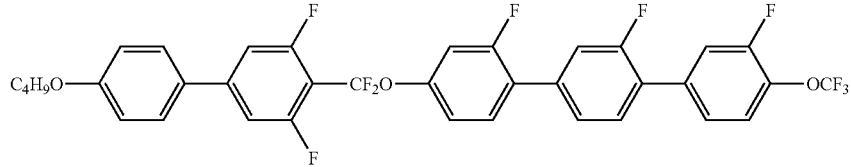
1-2-155
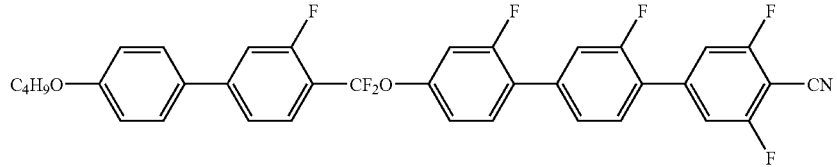
1-2-156
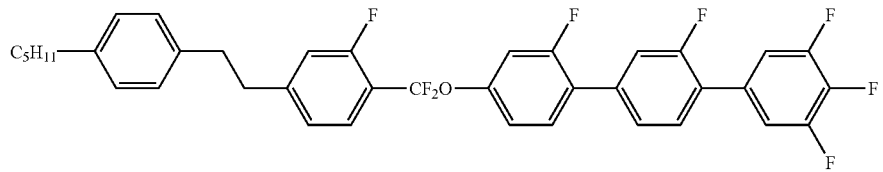
1-2-157
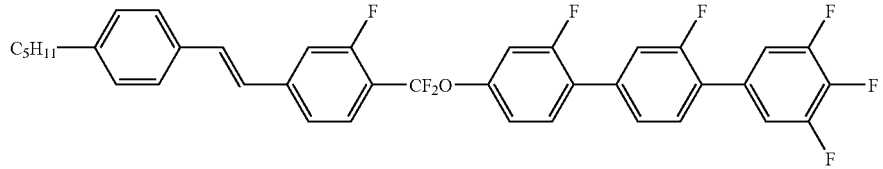
1-2-158
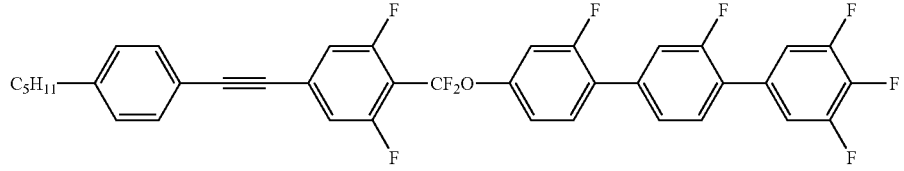
1-2-159
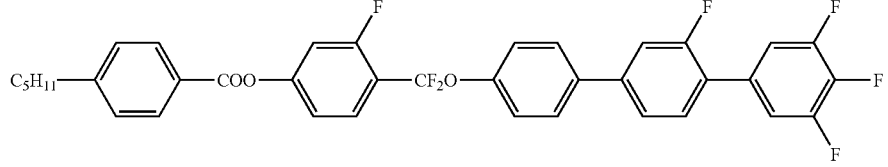
1-2-160
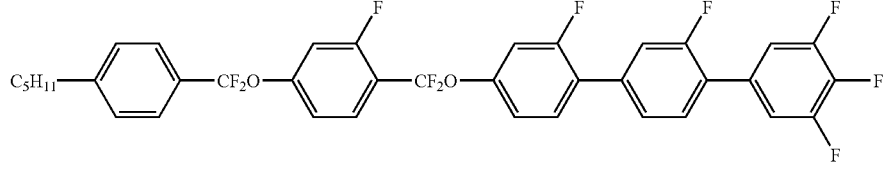
1-2-161

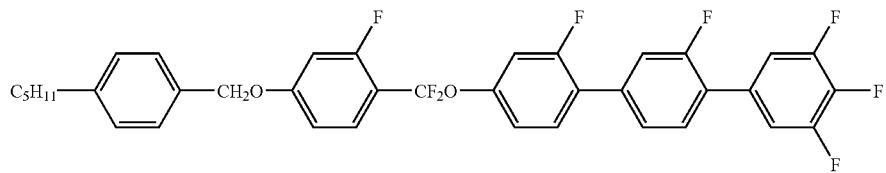
1-2-162
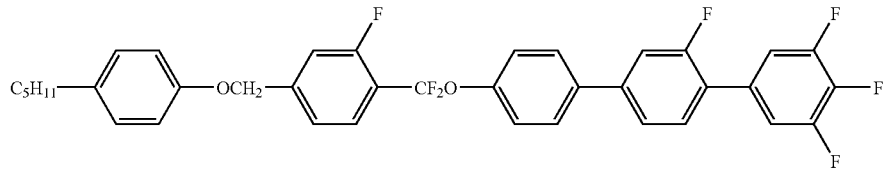
1-2-163
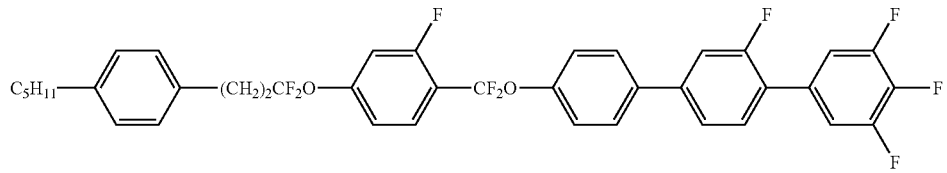
1-2-164
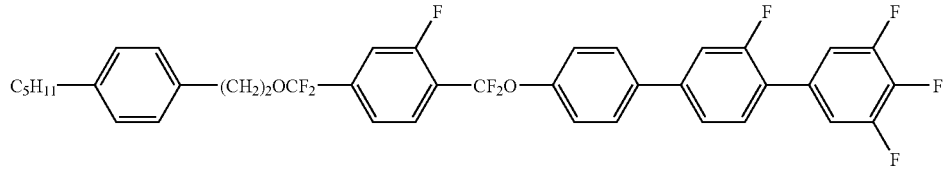
1-2-165
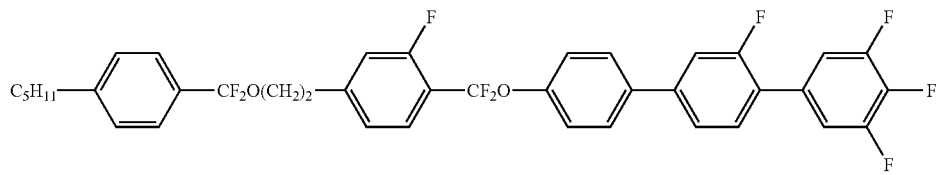
1-2-166
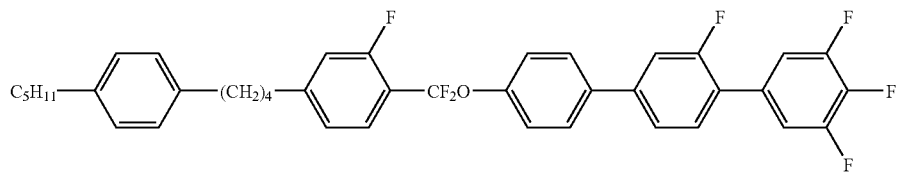
1-2-167
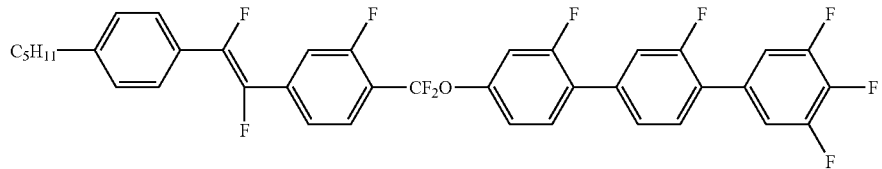
1-2-168
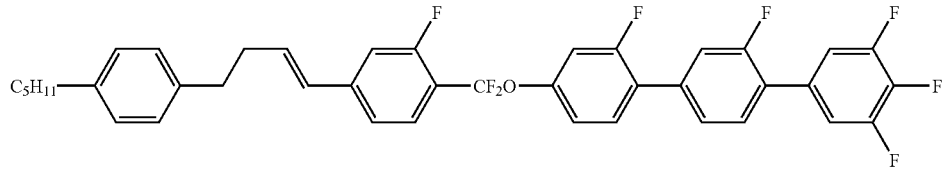
1-2-169
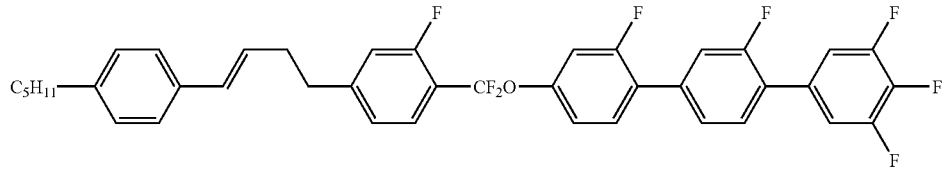
1-2-170

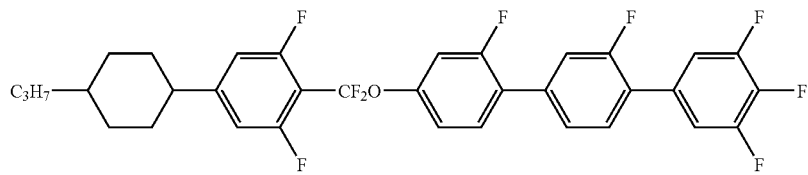
1-2-171
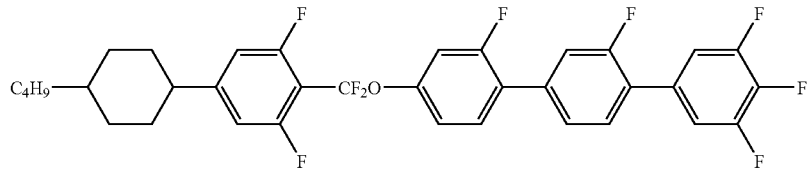
1-2-172
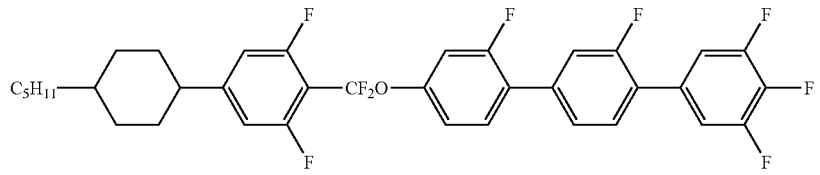
1-2-173
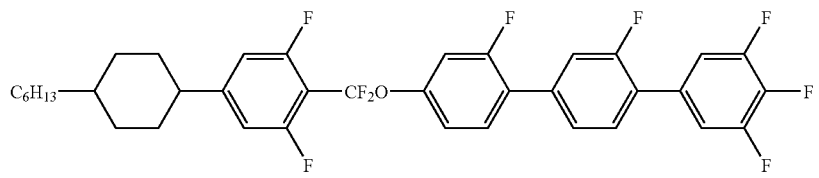
1-2-174
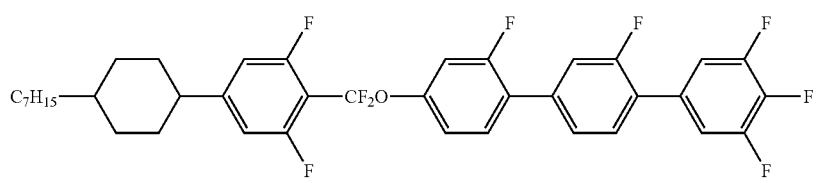
1-2-175
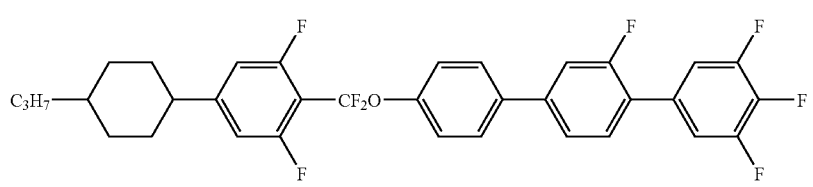
1-2-176
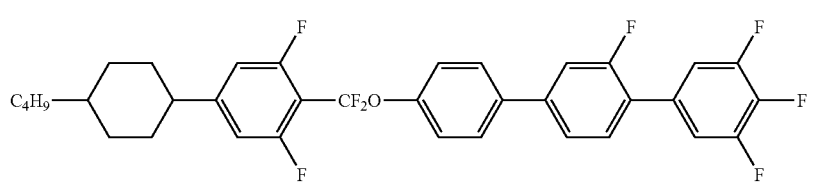
1-2-177
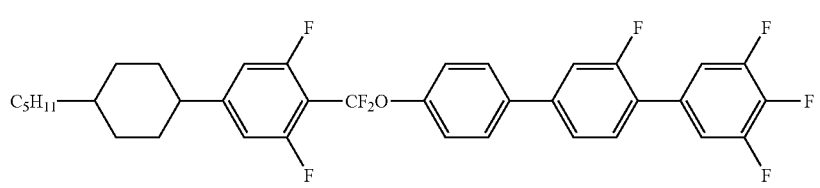
1-2-178
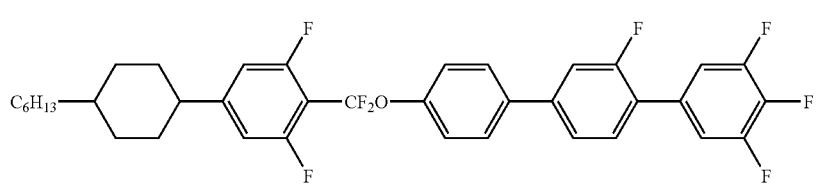
1-2-179

-continued
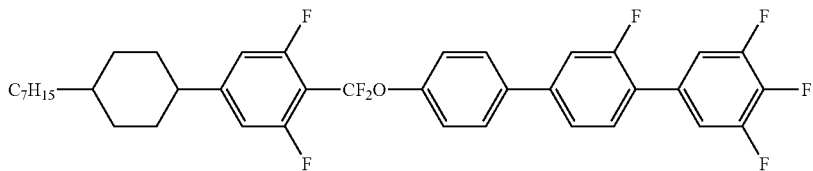
1-2-180
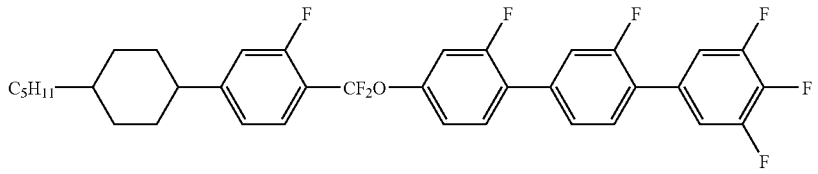
1-2-181
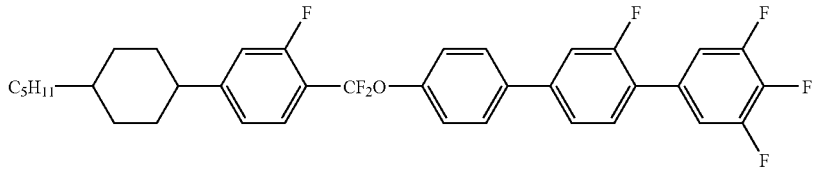
1-2-182
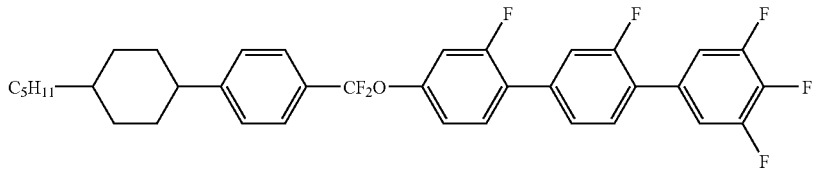
1-2-183
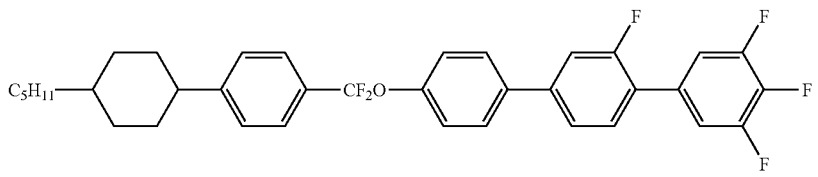
1-2-184
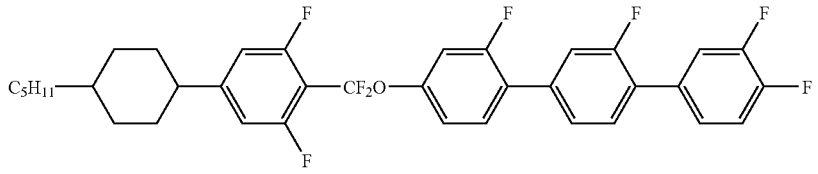
1-2-185
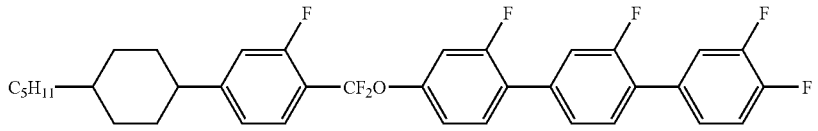
1-2-186
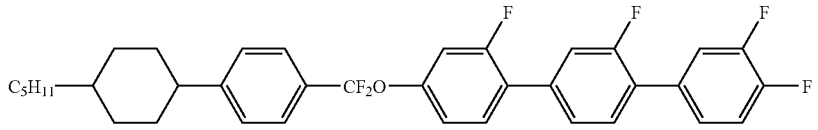
1-2-187
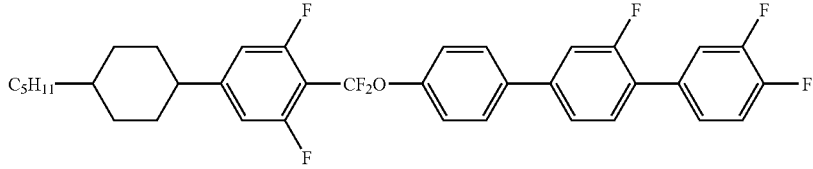
1-2-188

-continued
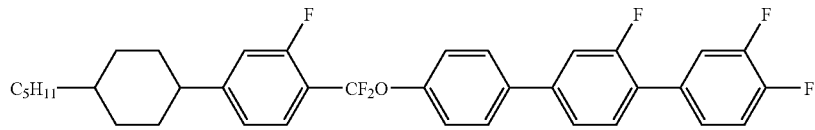
1-2-189
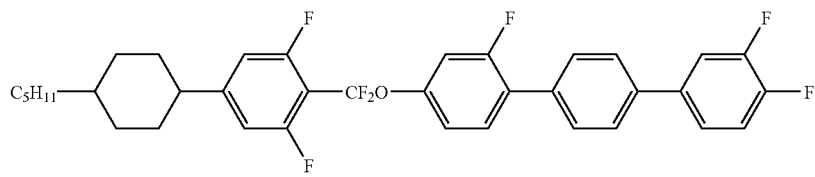
1-2-190
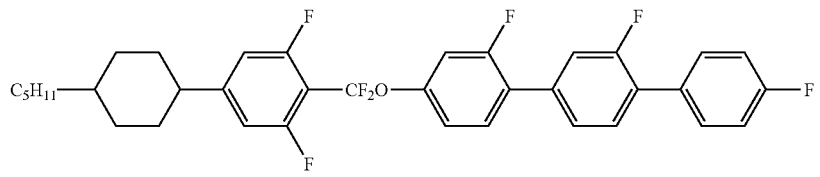
1-2-191
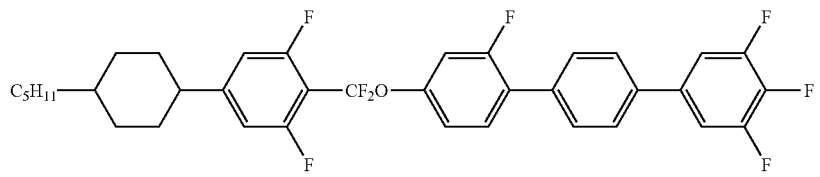
1-2-192
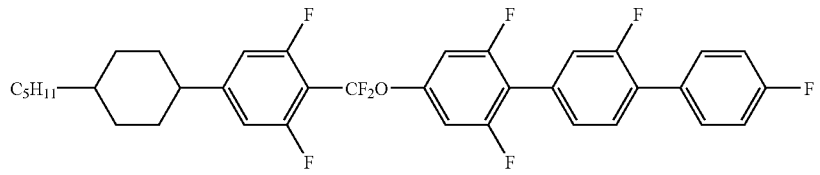
1-2-193
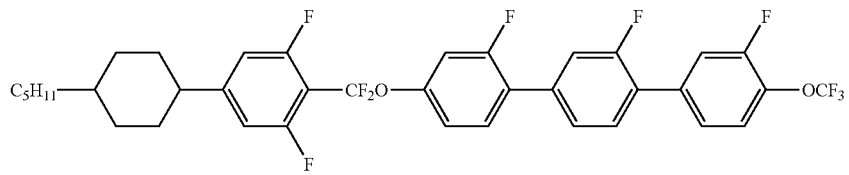
1-2-194
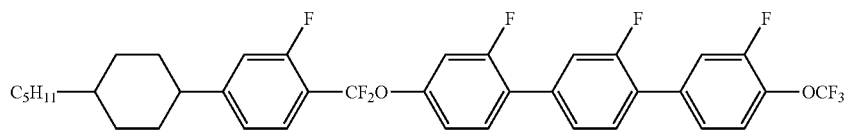
1-2-195
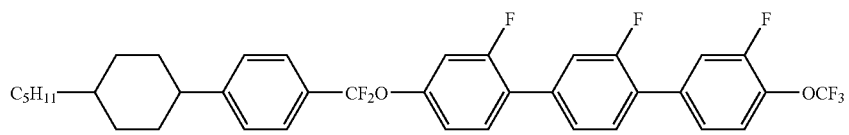
1-2-196
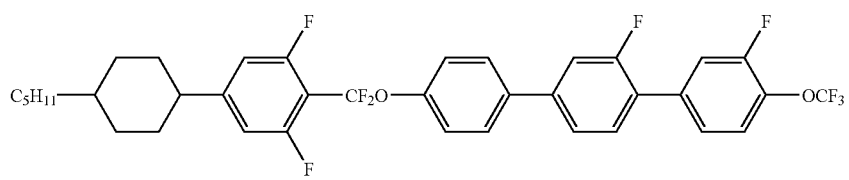
1-2-197
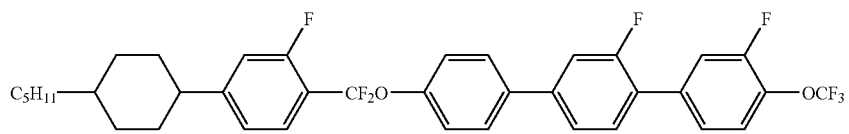
1-2-198

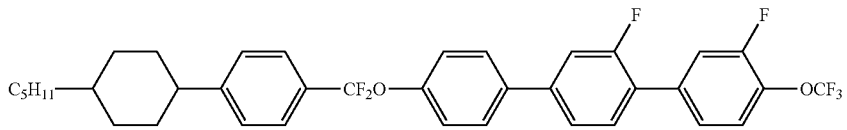
1-2-199
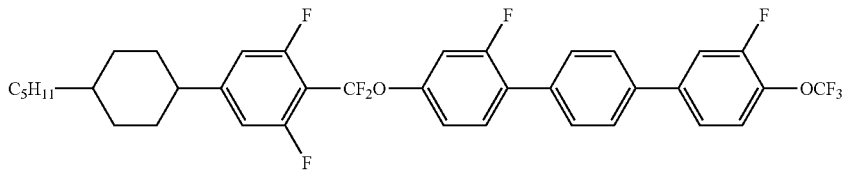
1-2-200
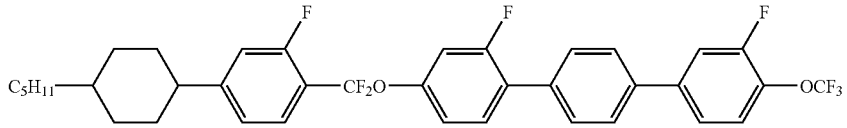
1-2-201
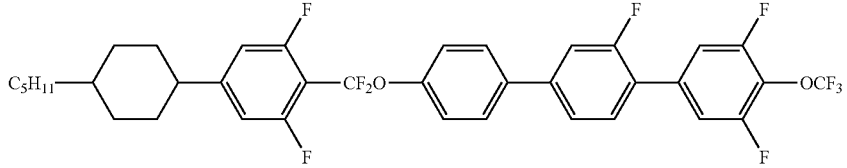
1-2-202
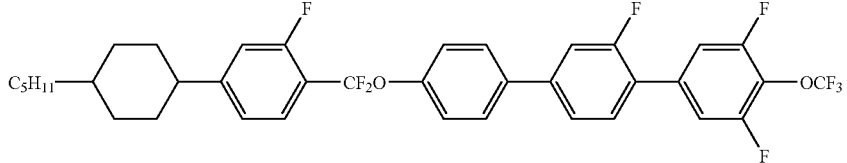
1-2-203
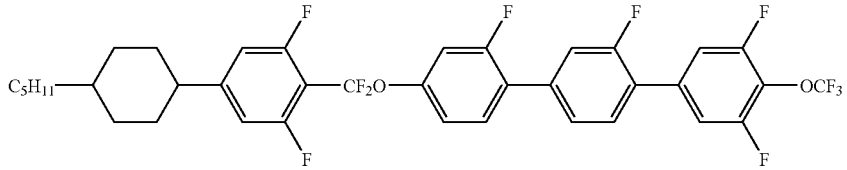
1-2-204
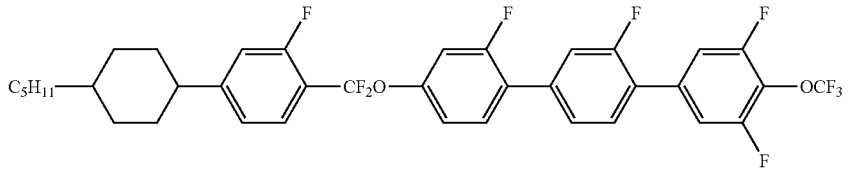
1-2-205
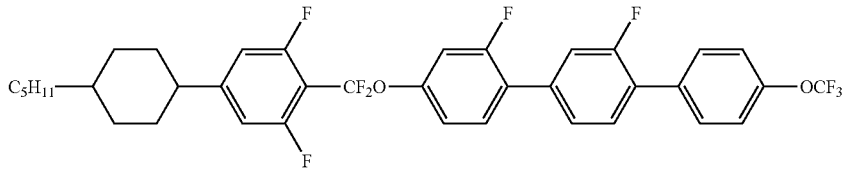
1-2-206
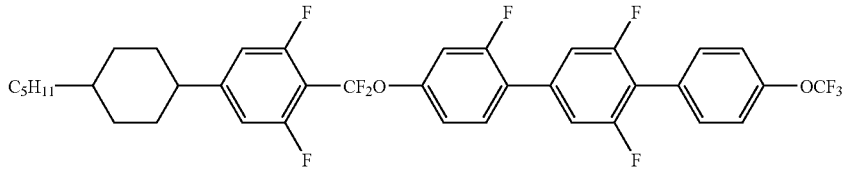
1-2-207

-continued
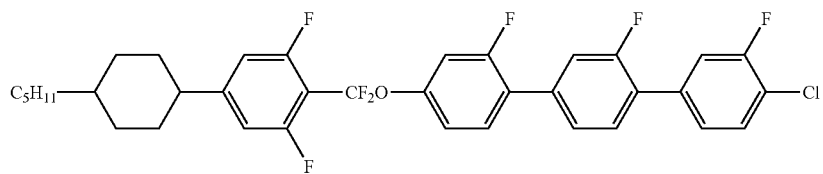
1-2-208
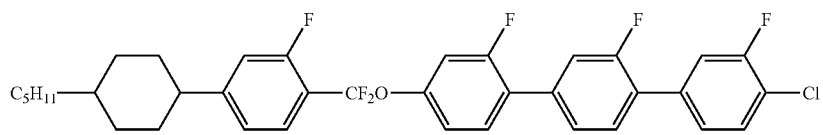
1-2-209
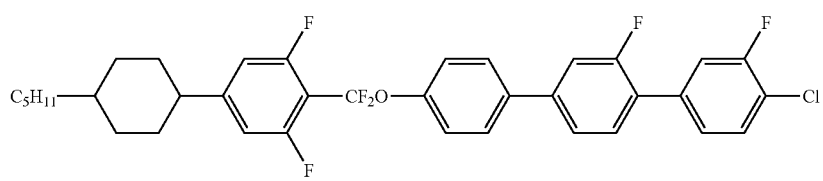
1-2-210
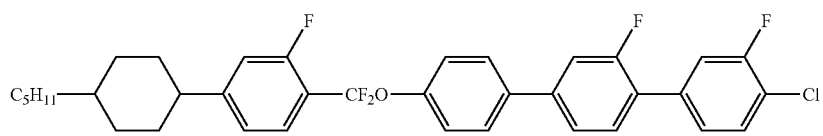
1-2-211
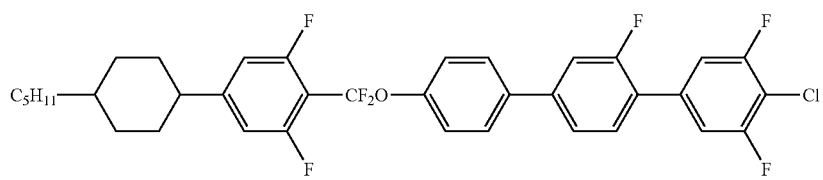
1-2-212
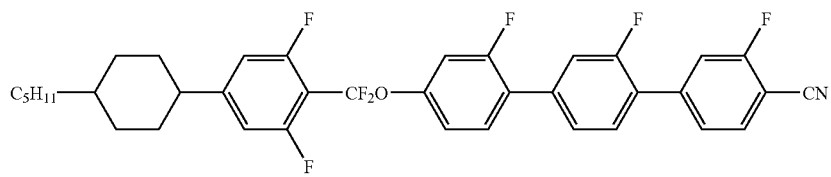
1-2-213
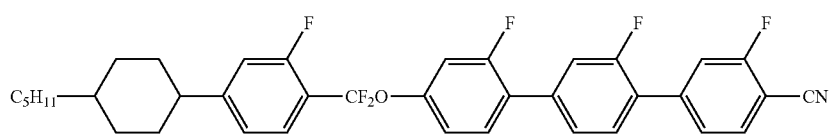
1-2-214
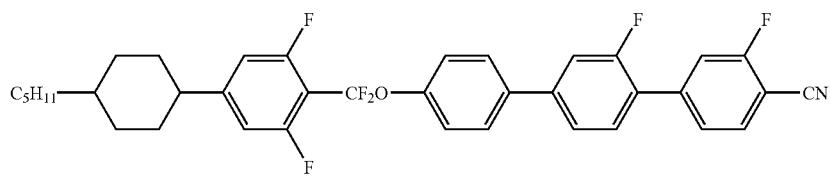
1-2-215
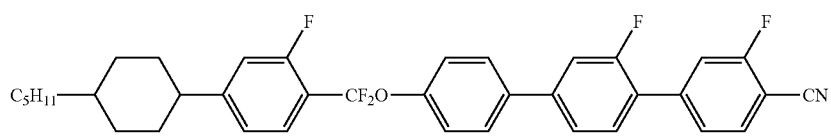
1-2-216
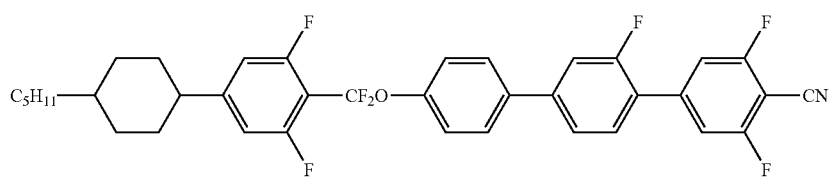
1-2-217

-continued
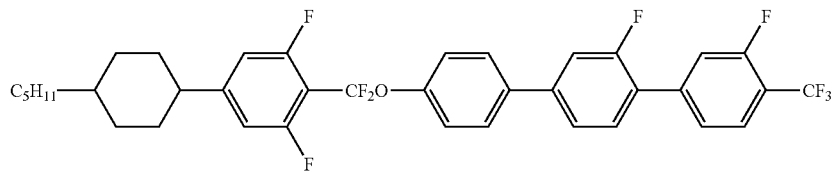
1-2-218
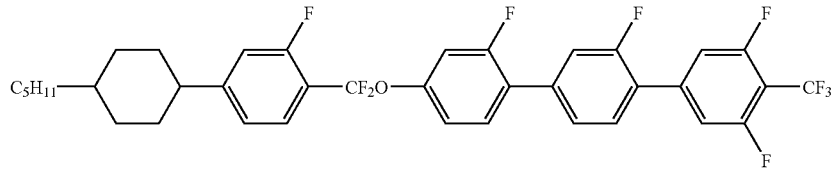
1-2-219
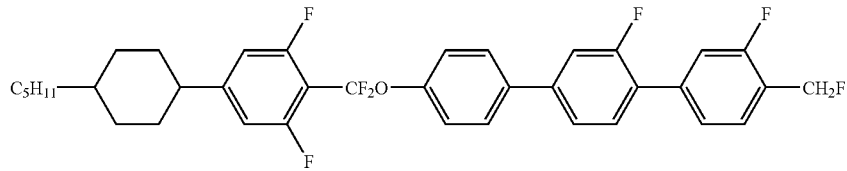
1-2-220
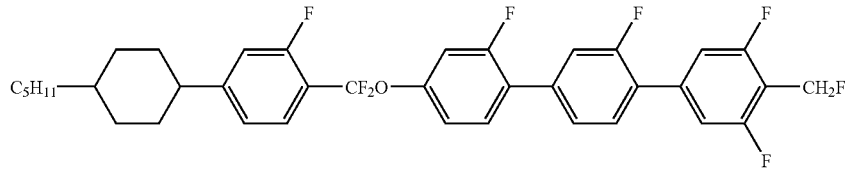
1-2-221
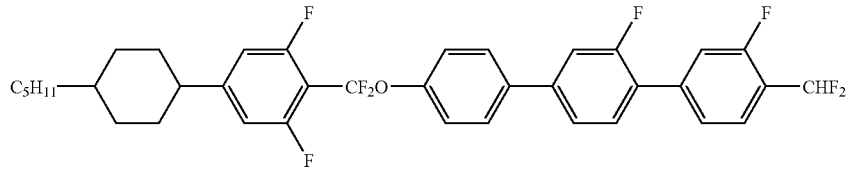
1-2-222
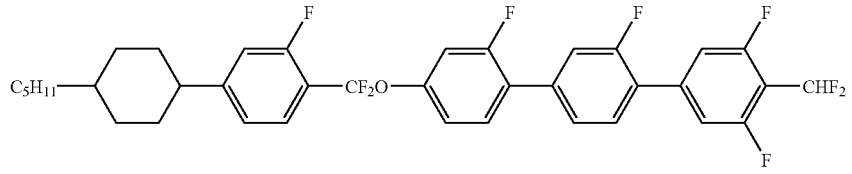
1-2-223
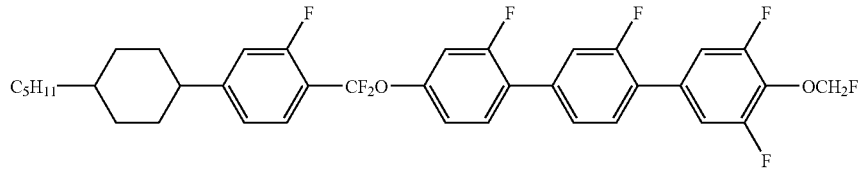
1-2-224
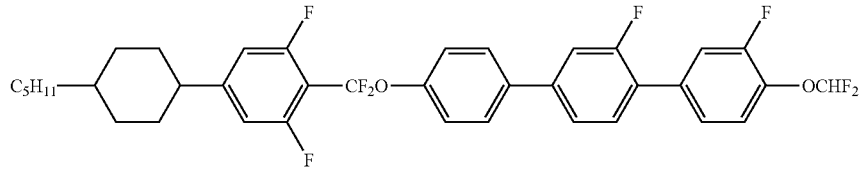
1-2-225
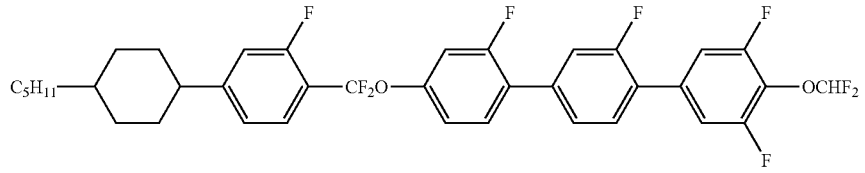
1-2-226

-continued
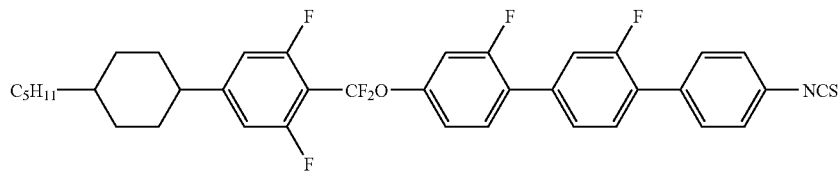
1-2-227
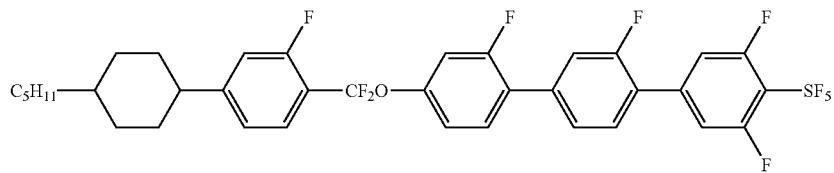
1-2-228
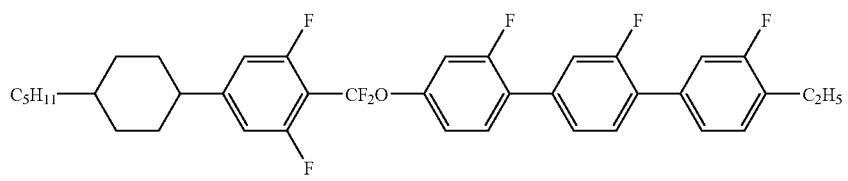
1-2-229
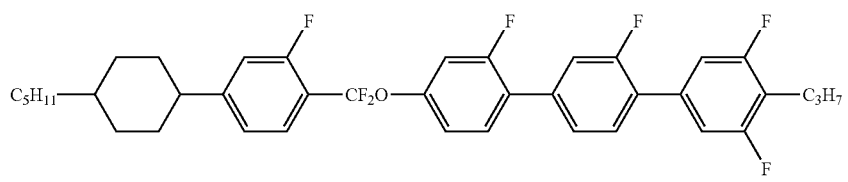
1-2-230
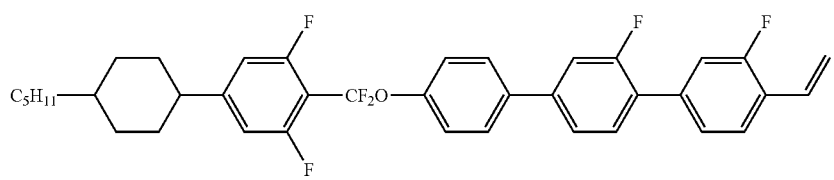
1-2-231
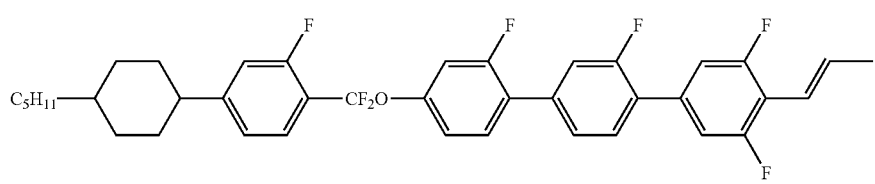
1-2-232
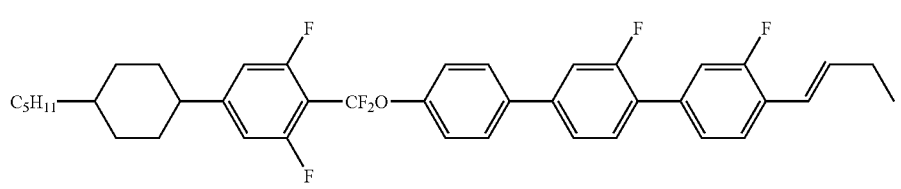
1-2-233
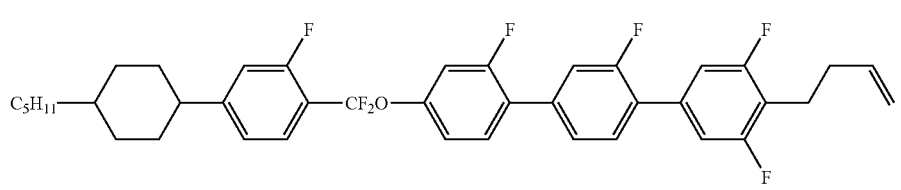
1-2-234
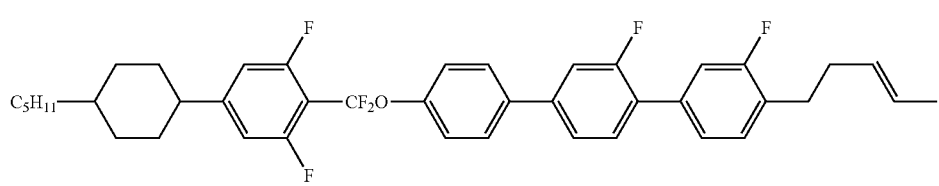
1-2-235

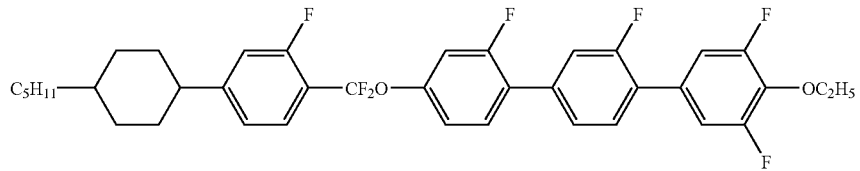
1-2-236
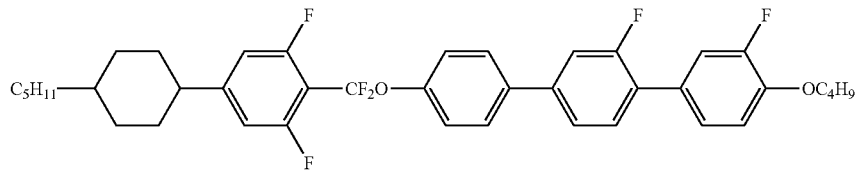
1-2-237
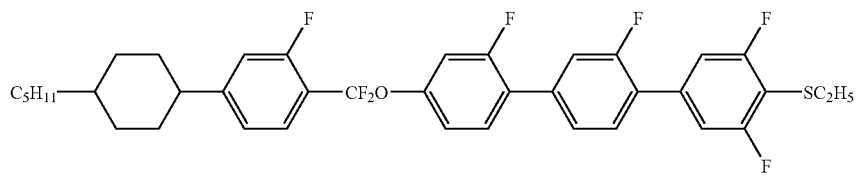
1-2-238
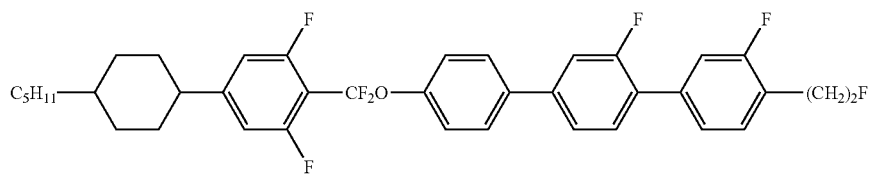
1-2-239
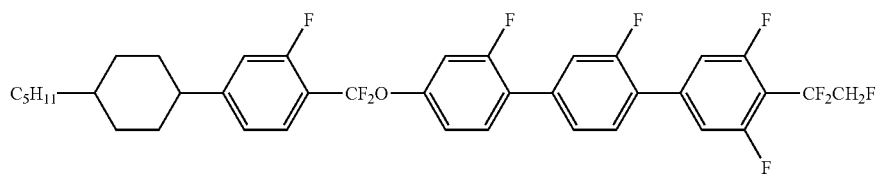
1-2-240
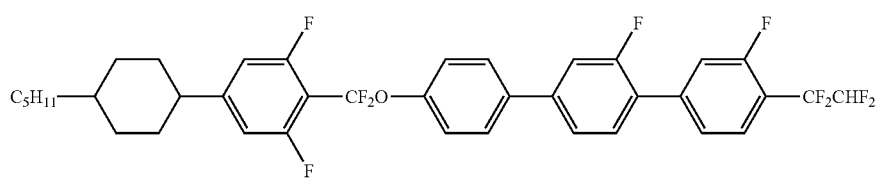
1-2-241
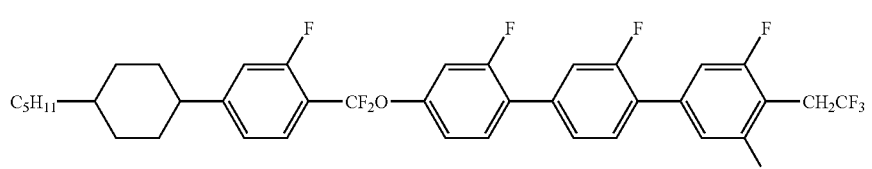
1-2-242
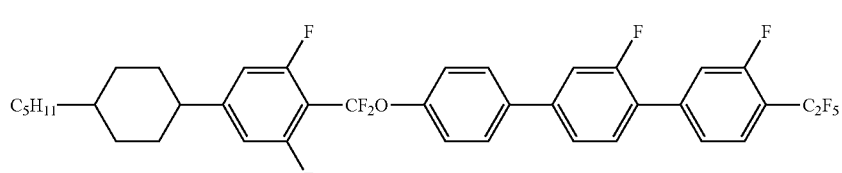
1-2-243
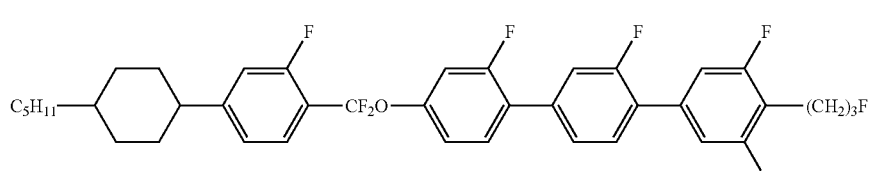
1-2-244

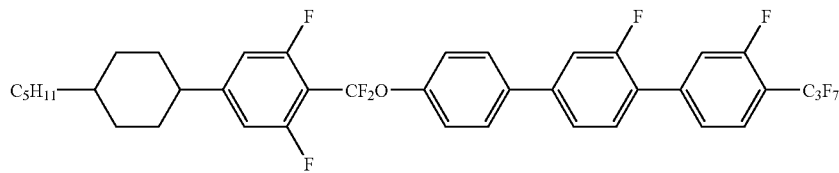
1-2-245
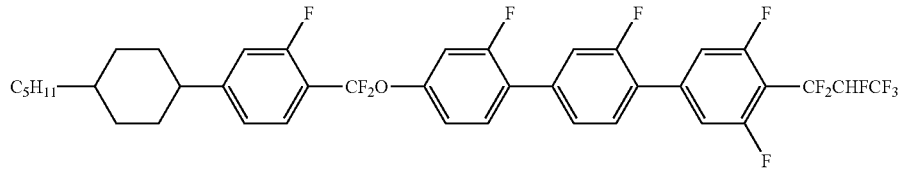
1-2-246
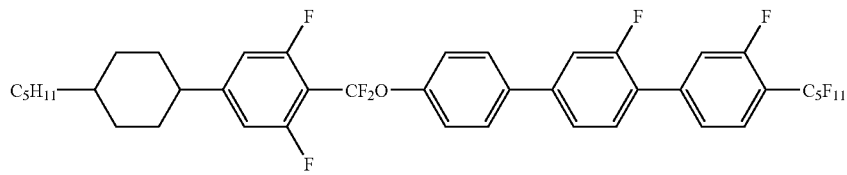
1-2-247
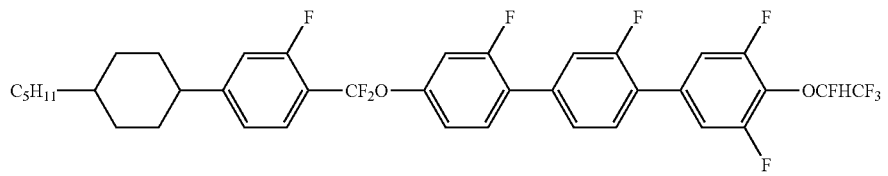
1-2-248
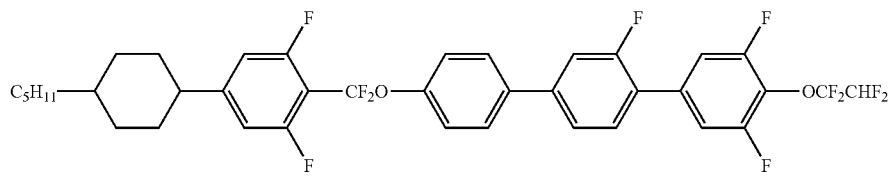
1-2-249
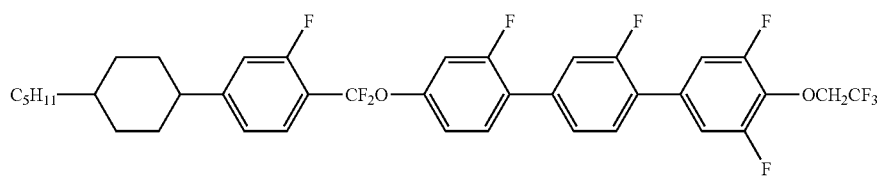
1-2-250
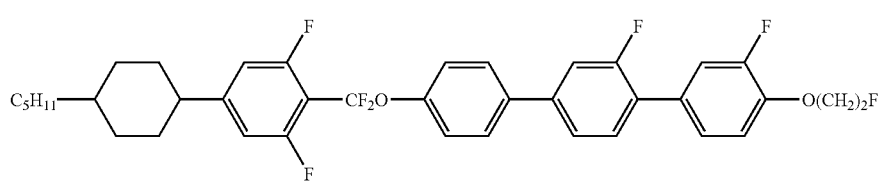
1-2-251
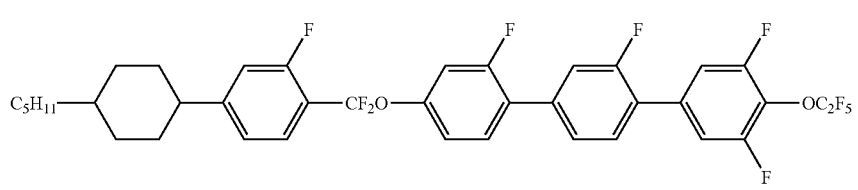
1-2-252
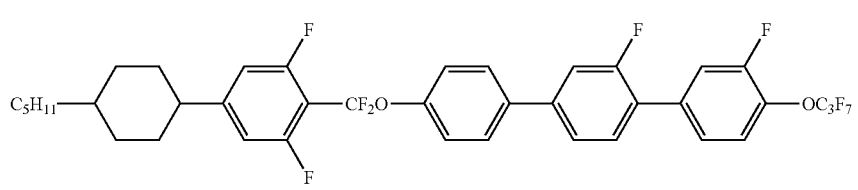
1-2-253

-continued
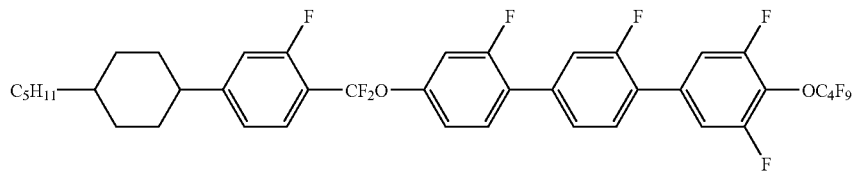
1-2-254
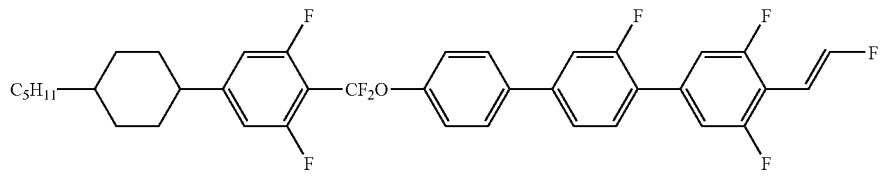
1-2-255
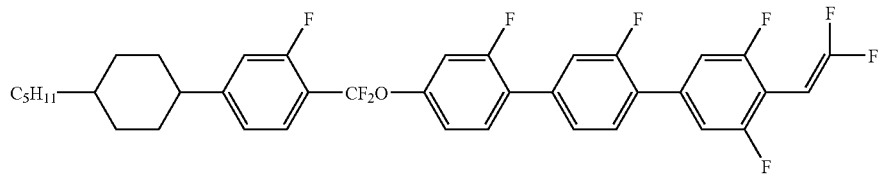
1-2-256
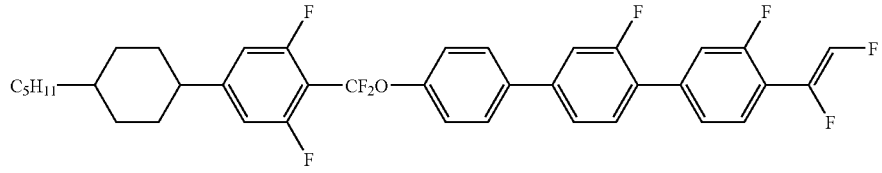
1-2-257
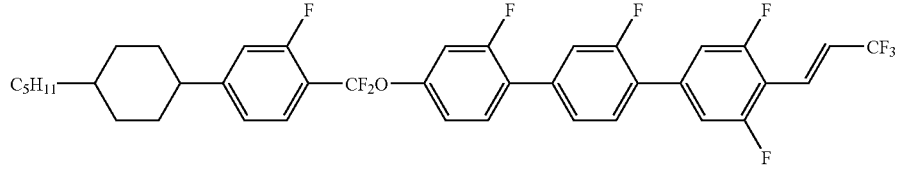
1-2-258
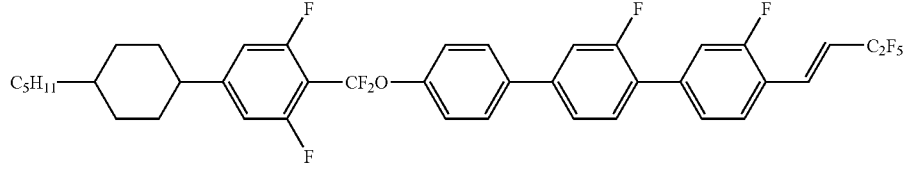
1-2-259
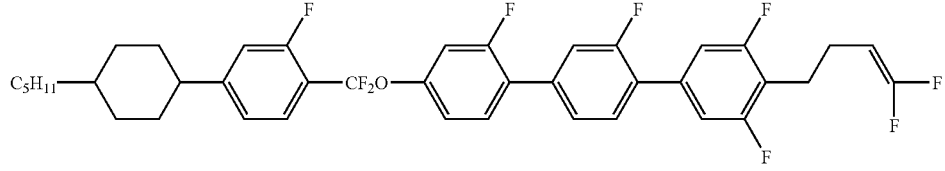
1-2-260
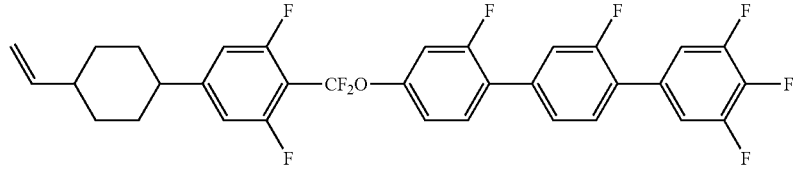
1-2-261
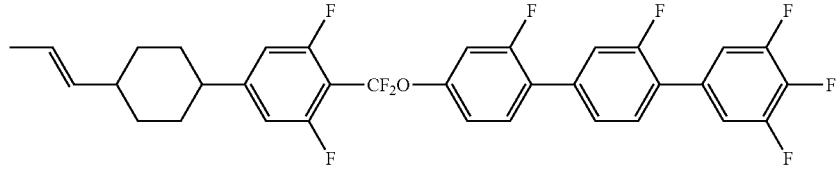
1-2-262

-continued
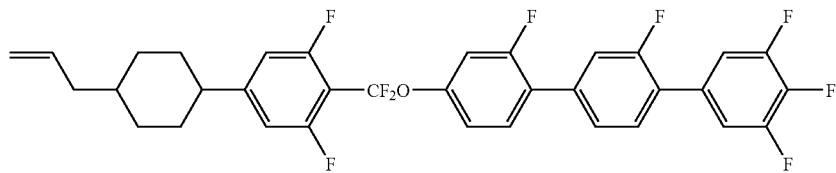
1-2-263
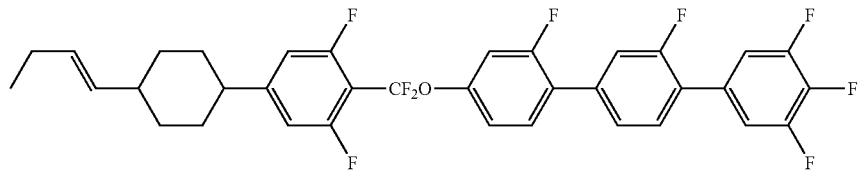
1-2-264
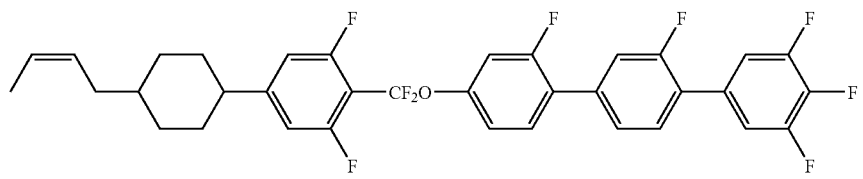
1-2-265
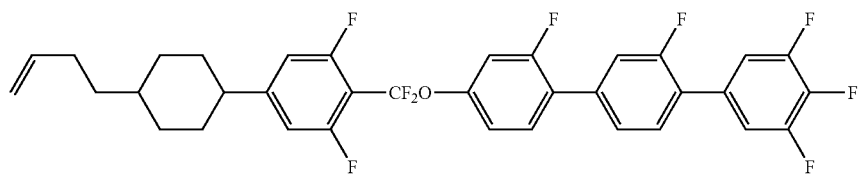
1-2-266
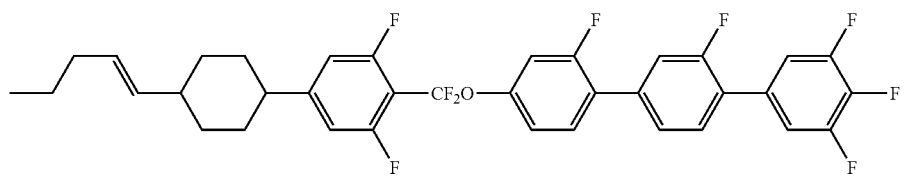
1-2-267
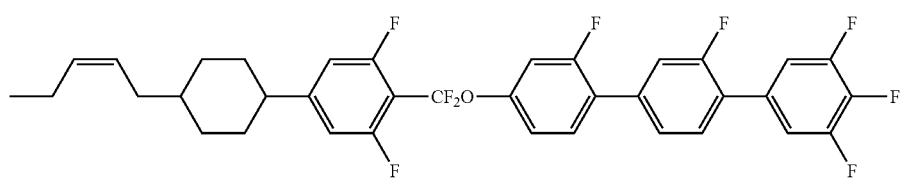
1-2-268
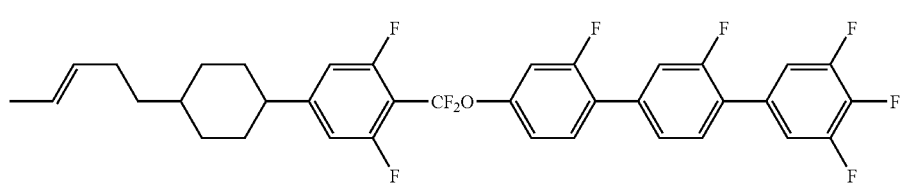
1-2-269
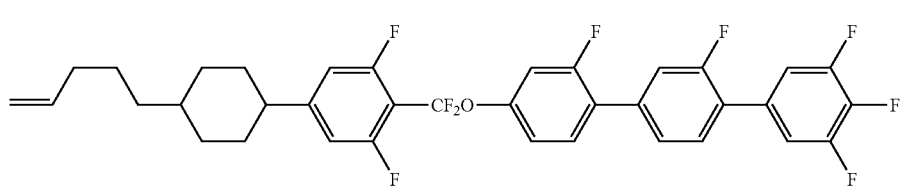
1-2-270
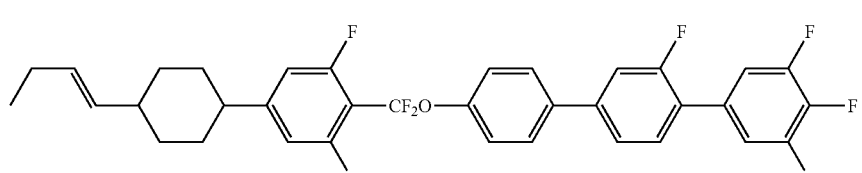
1-2-271

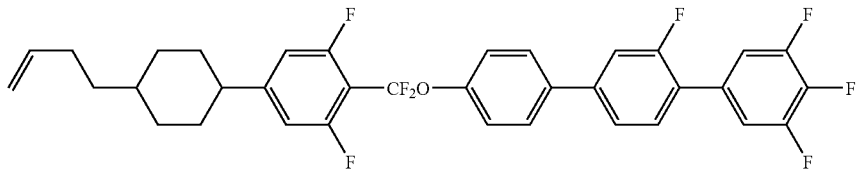 1-2-272
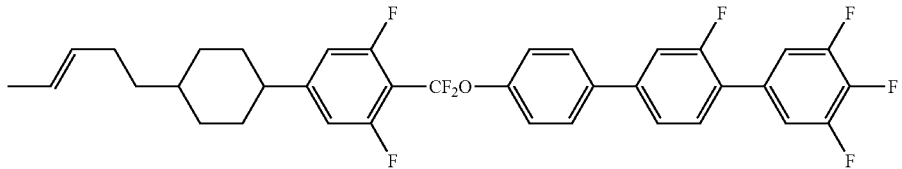 1-2-273
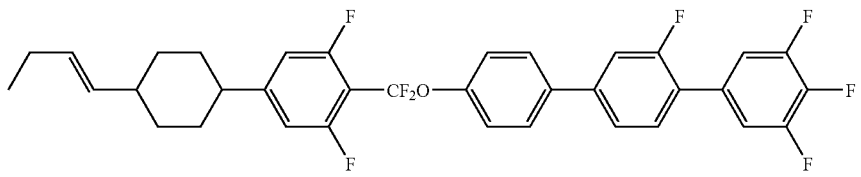 1-2-274
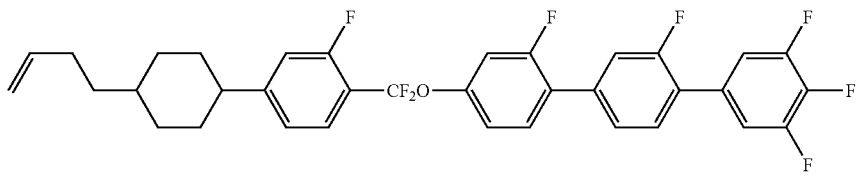 1-2-275
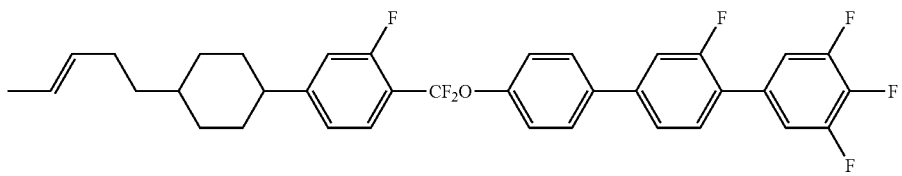 1-2-276
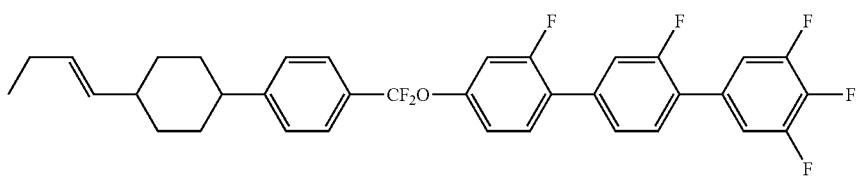 1-2-277
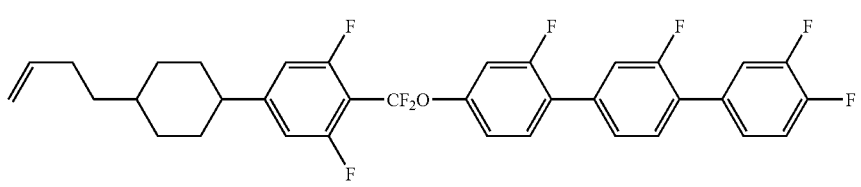 1-2-278
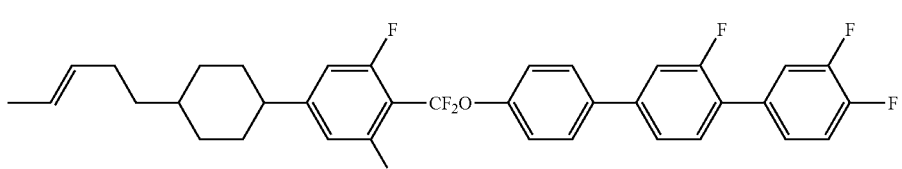 1-2-279
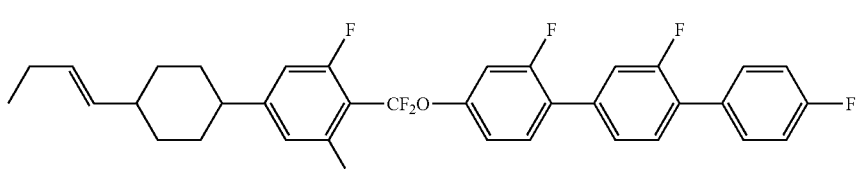 1-2-280

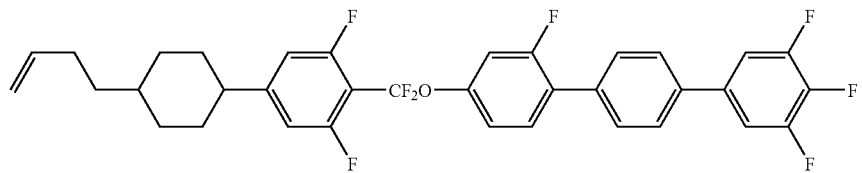
1-2-281
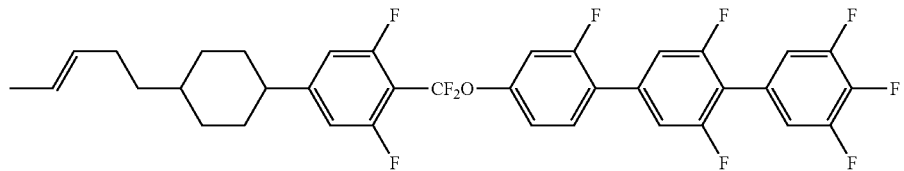
1-2-282
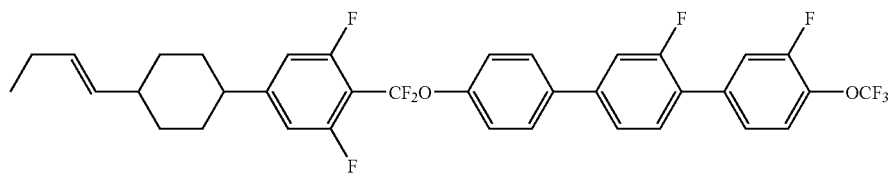
1-2-283
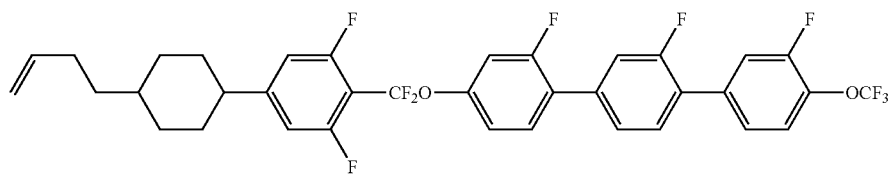
1-2-284
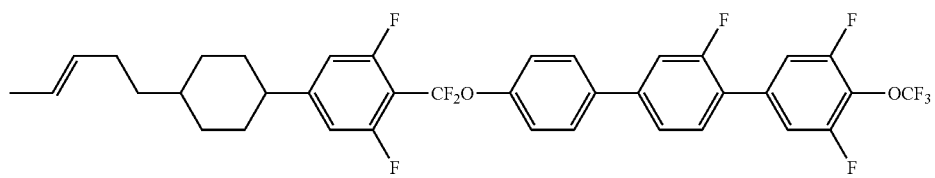
1-2-285
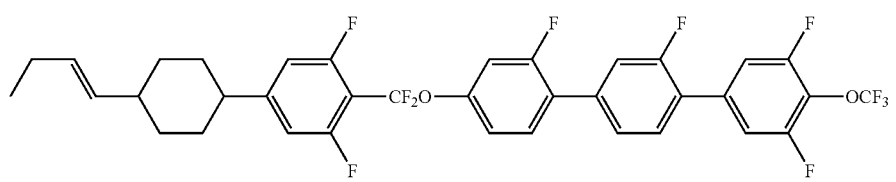
1-2-286
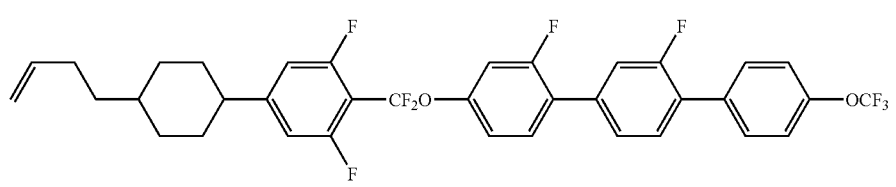
1-2-287
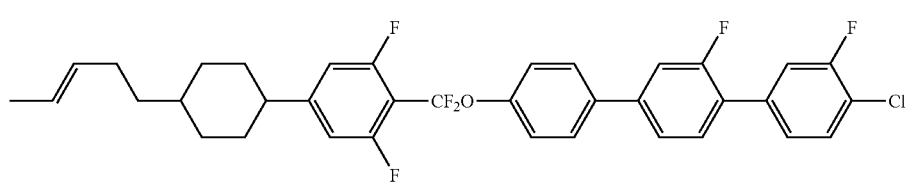
1-2-288
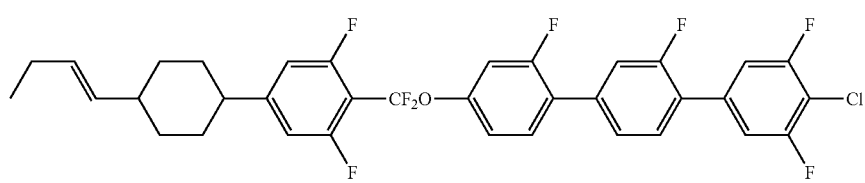
1-2-289

-continued
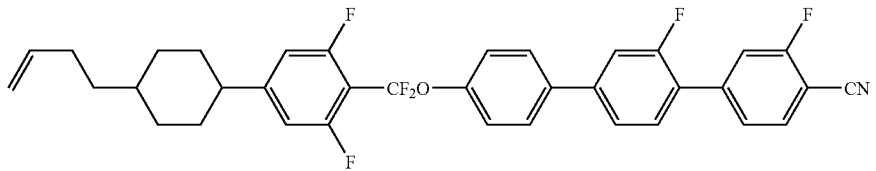
1-2-290
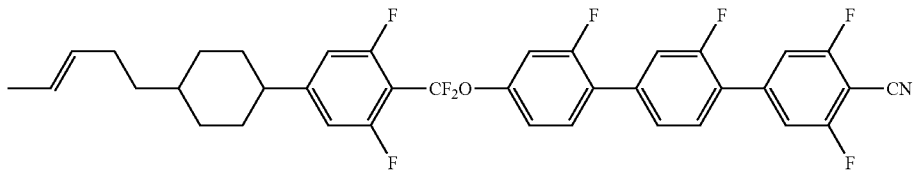
1-2-291
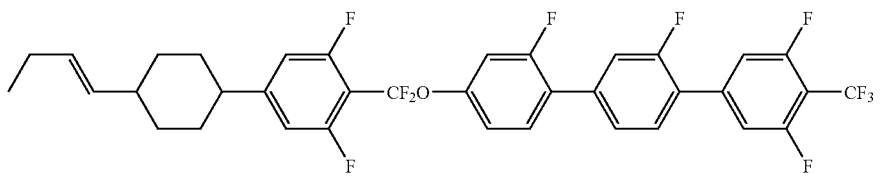
1-2-292
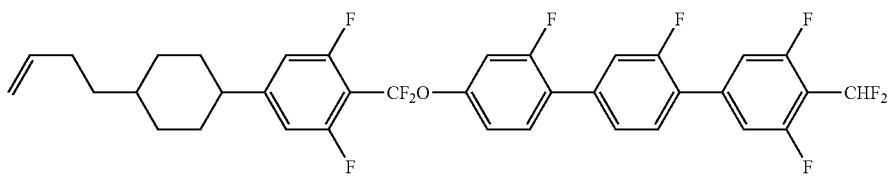
1-2-293
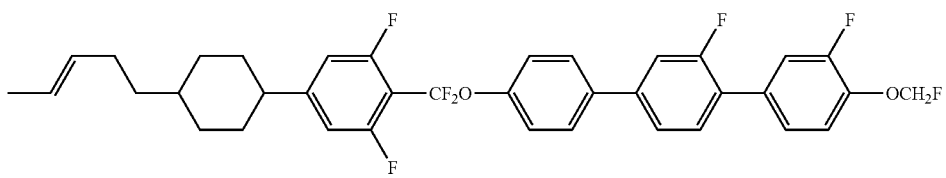
1-2-294
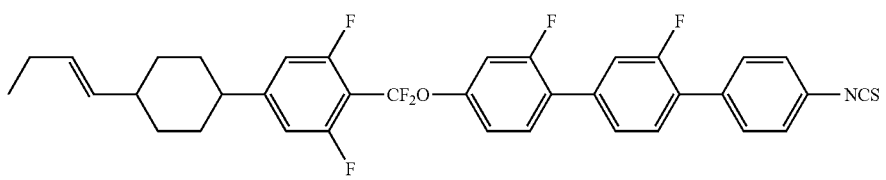
1-2-295
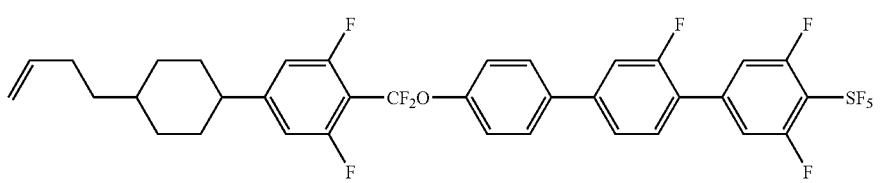
1-2-296
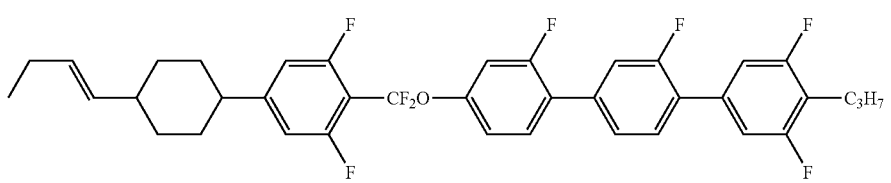
1-2-297
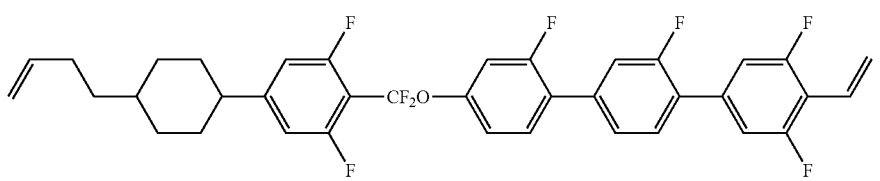
1-2-298

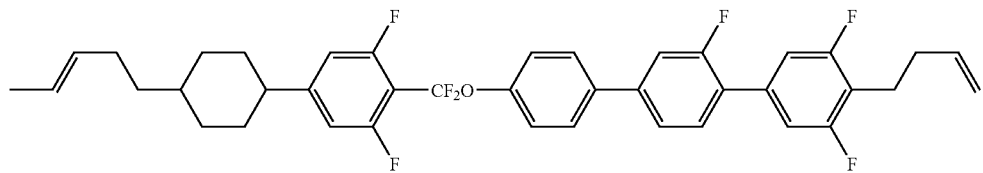
1-2-299
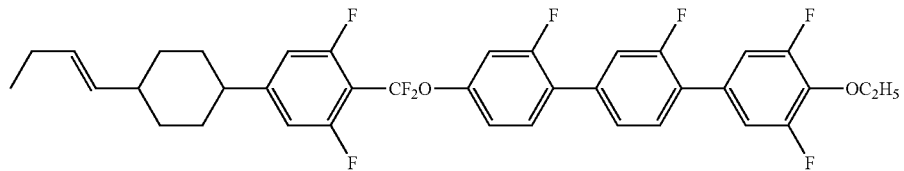
1-2-300
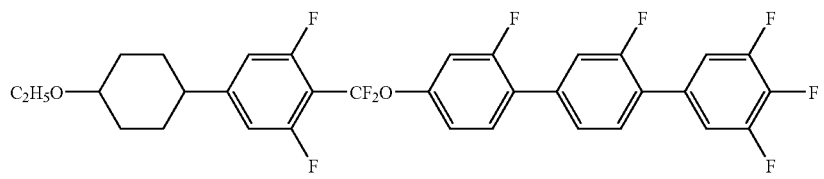
1-2-301
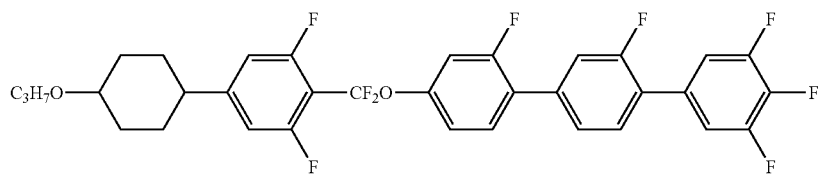
1-2-302
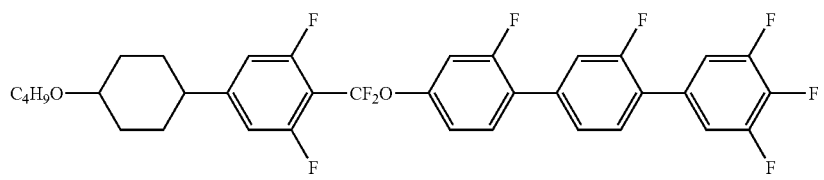
1-2-303
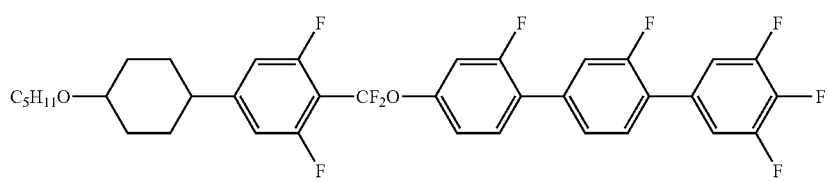
1-2-304
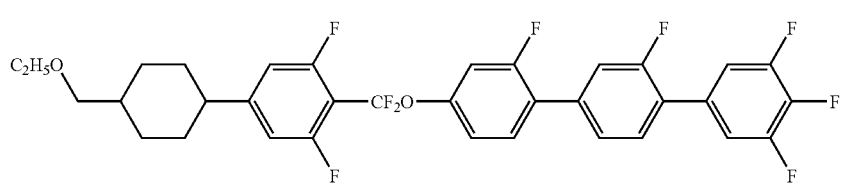
1-2-305
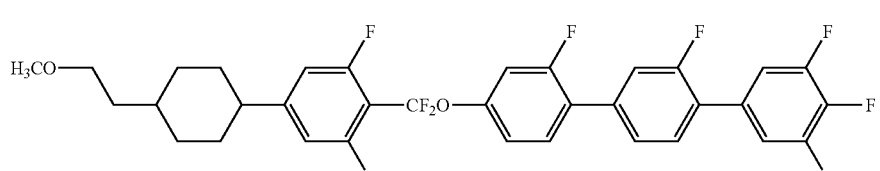
1-2-306
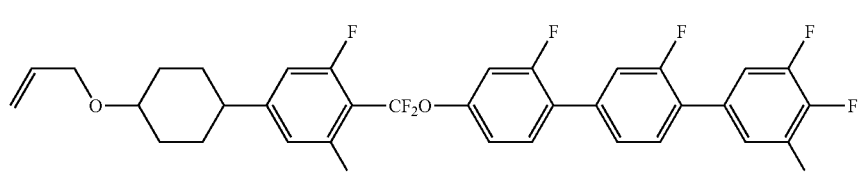
1-2-307

-continued
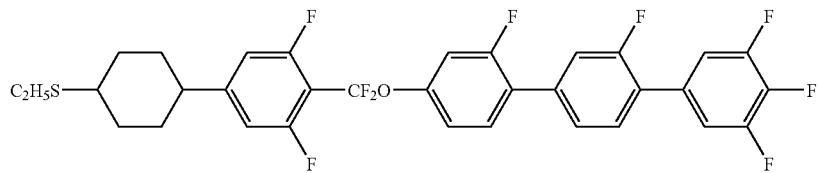
1-2-308
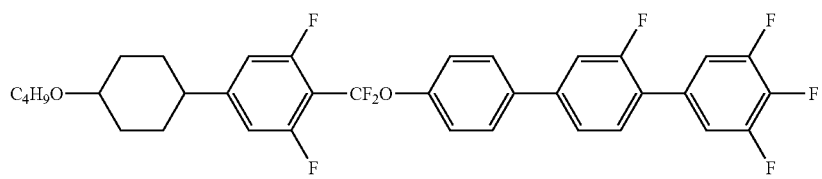
1-2-309
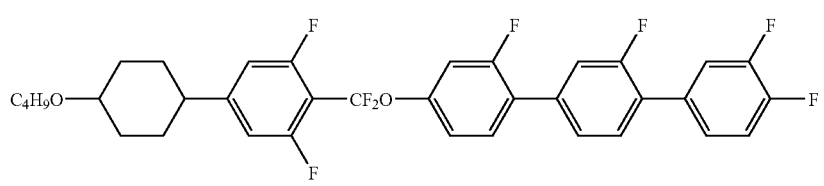
1-2-310
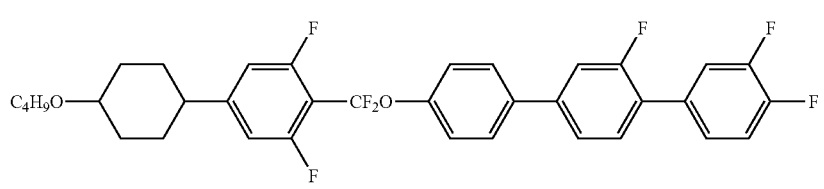
1-2-311
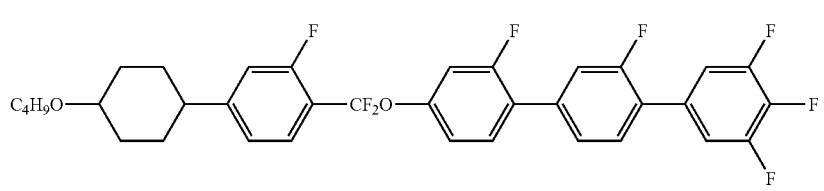
1-2-312
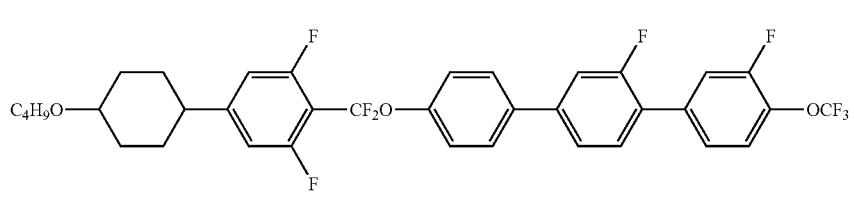
1-2-313
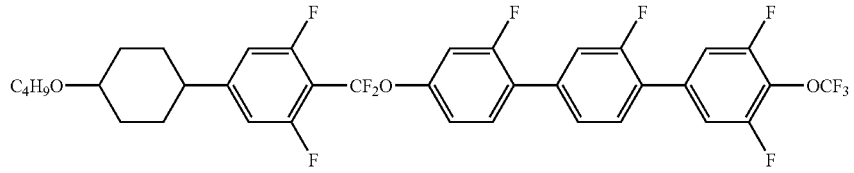
1-2-314
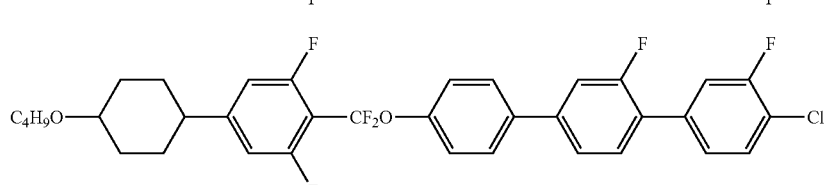
1-2-315
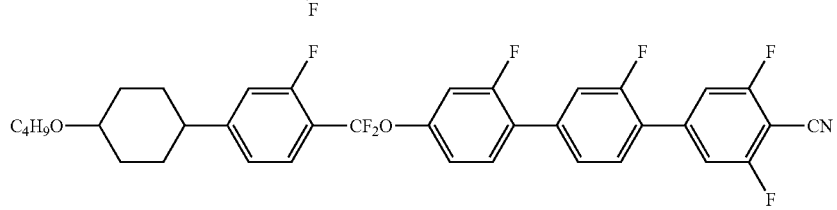
1-2-316

-continued
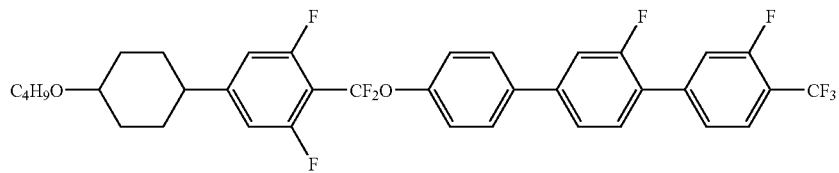
1-2-317
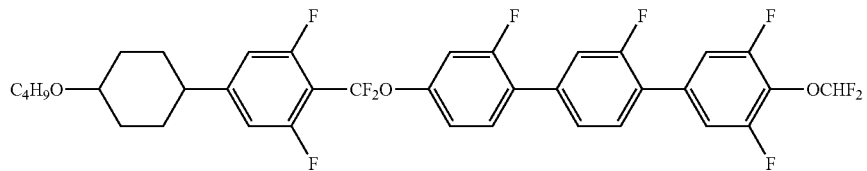
1-2-318
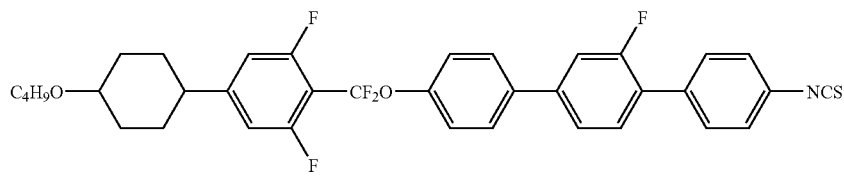
1-2-319
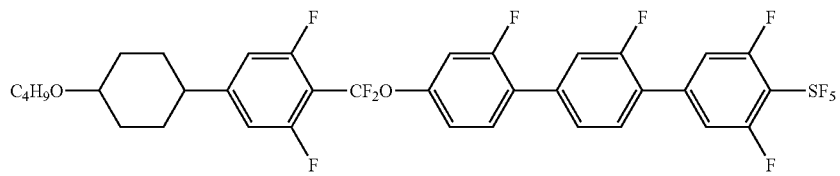
1-2-320
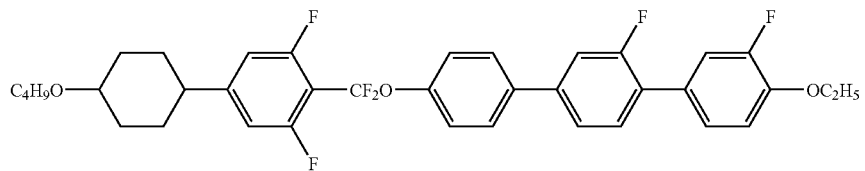
1-2-321
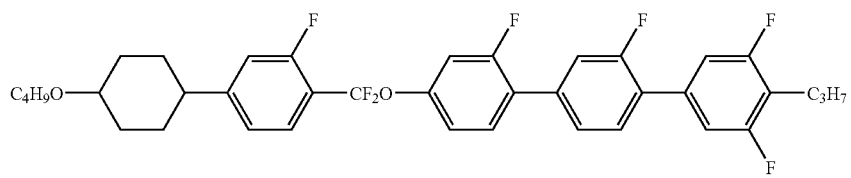
1-2-322
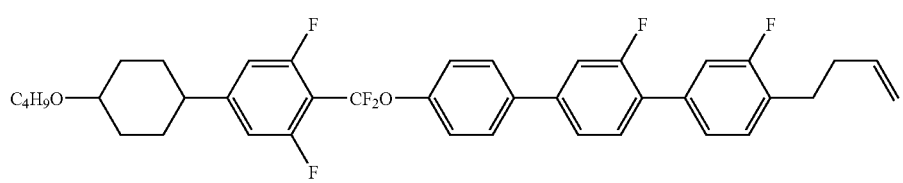
1-2-323
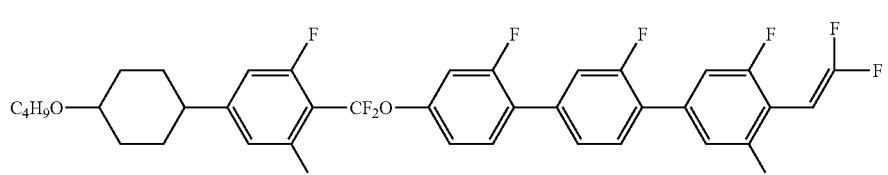
1-2-324
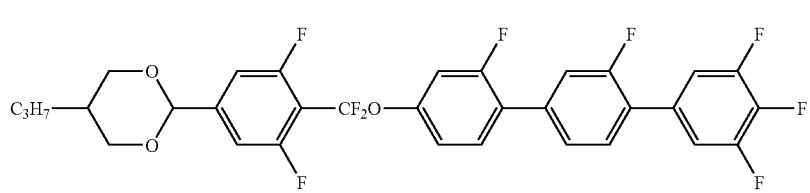
1-2-325

-continued
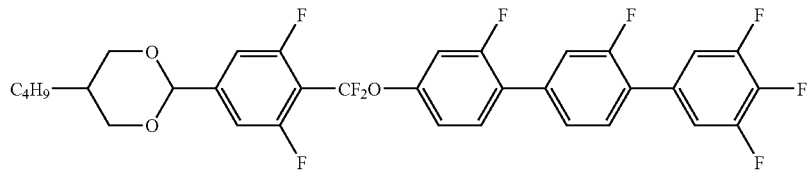
1-2-326
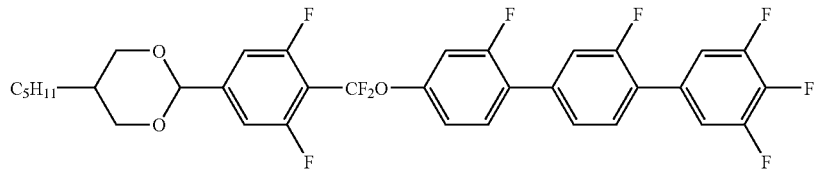
1-2-327
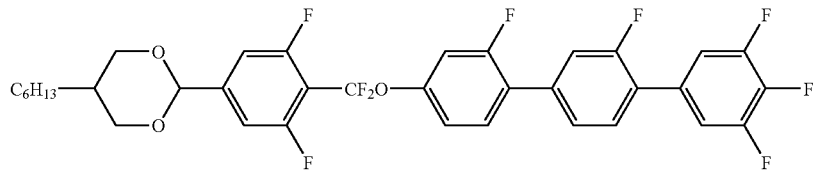
1-2-328
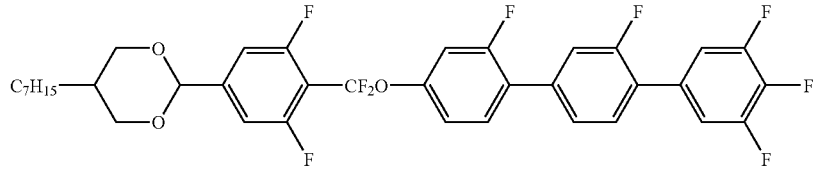
1-2-329
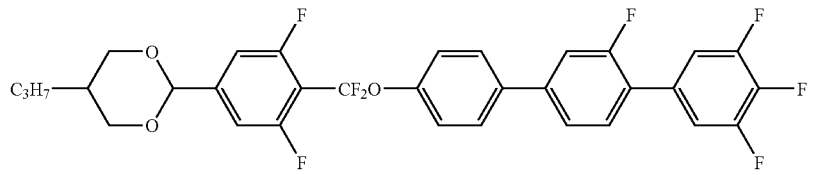
1-2-330
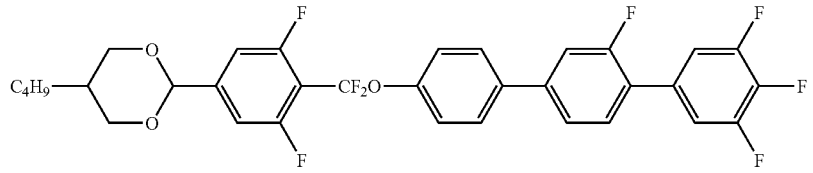
1-2-331
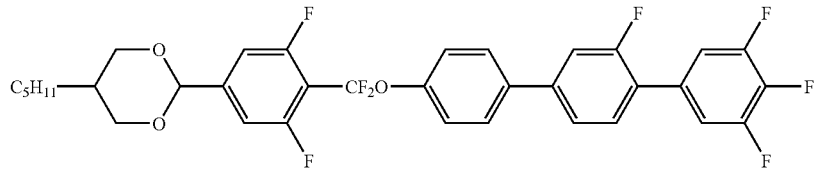
1-2-332
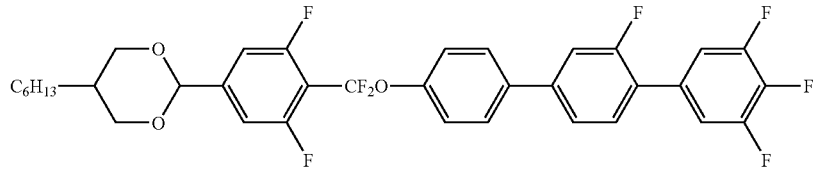
1-2-333
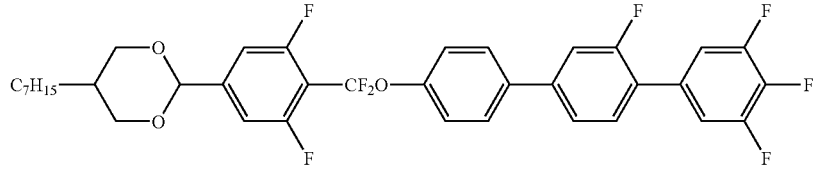
1-2-334

-continued
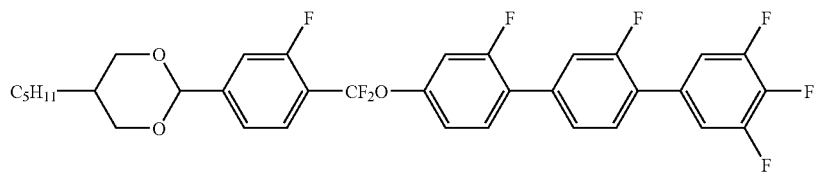
1-2-335
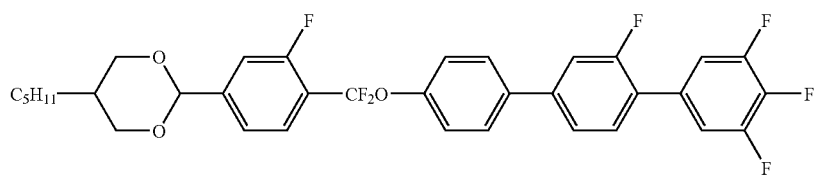
1-2-336
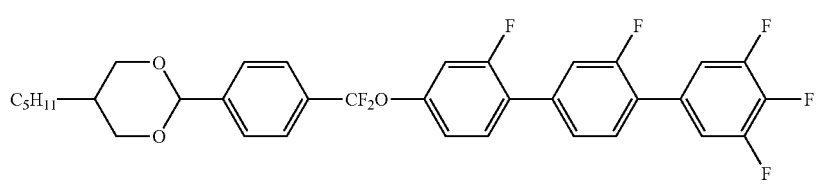
1-2-337
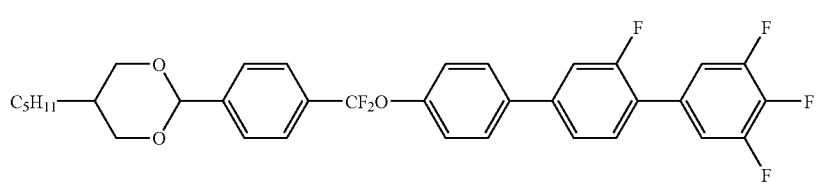
1-2-338
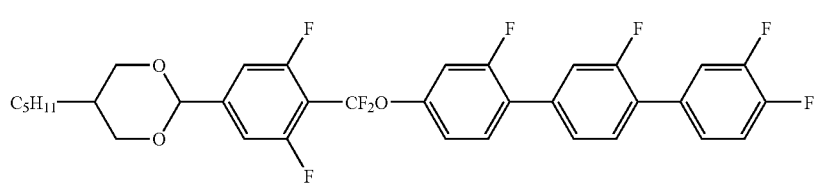
1-2-339
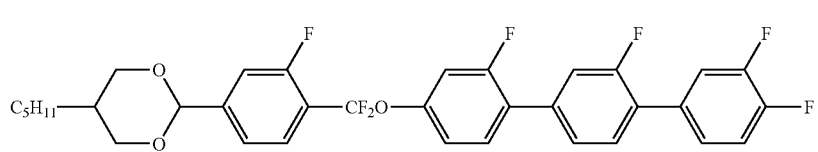
1-2-340
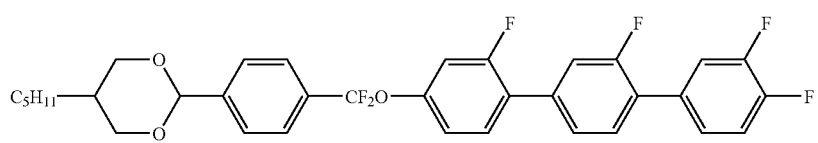
1-2-341
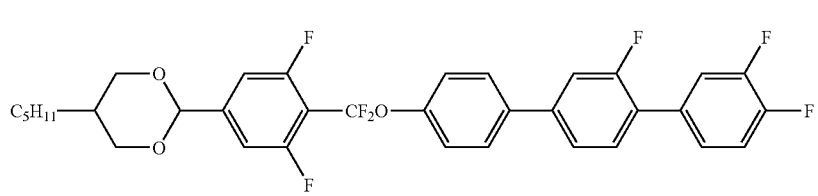
1-2-342
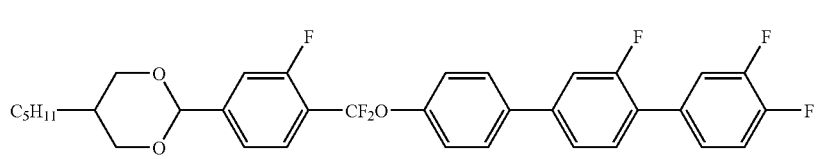
1-2-343

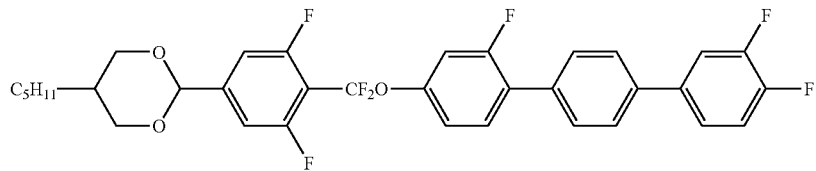
1-2-344
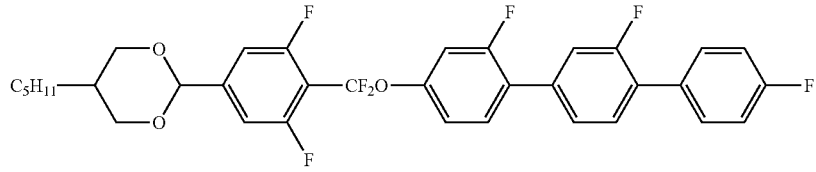
1-2-345
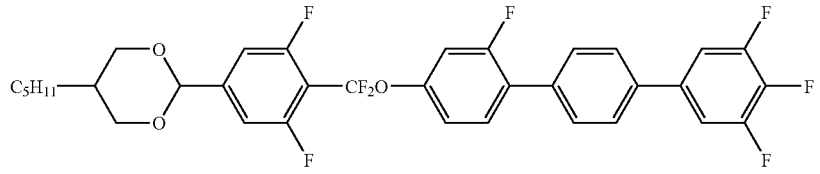
1-2-346
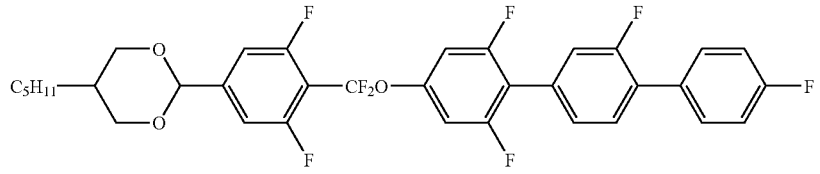
1-2-347
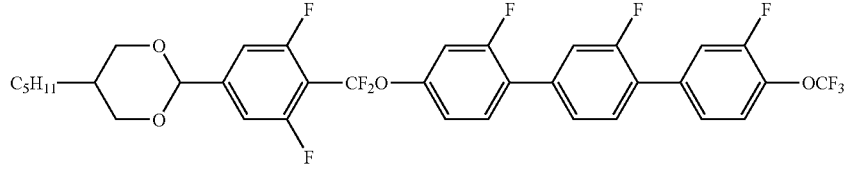
1-2-348
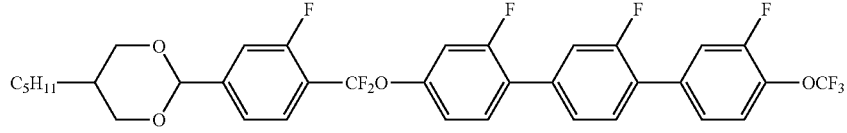
1-2-349
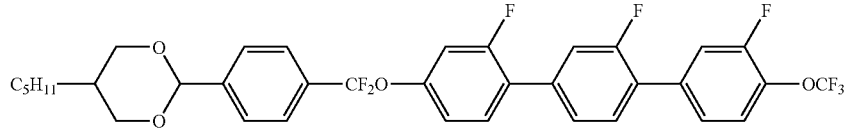
1-2-350
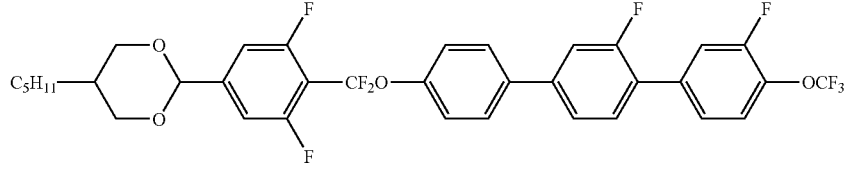
1-2-351
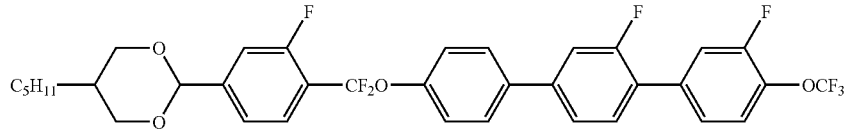
1-2-352

-continued
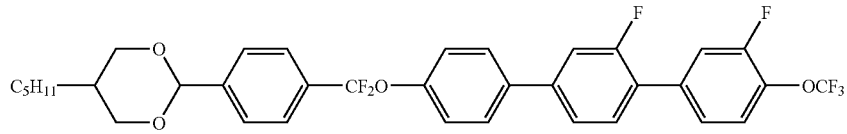
1-2-353
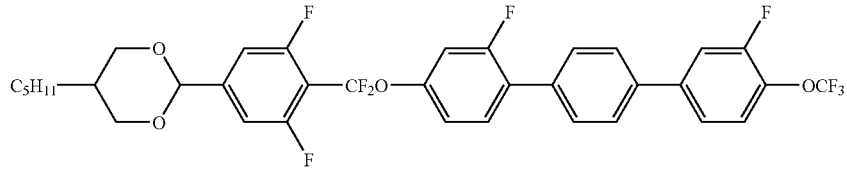
1-2-354
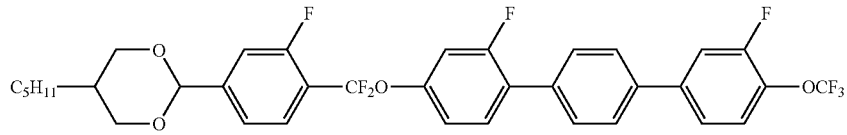
1-2-355
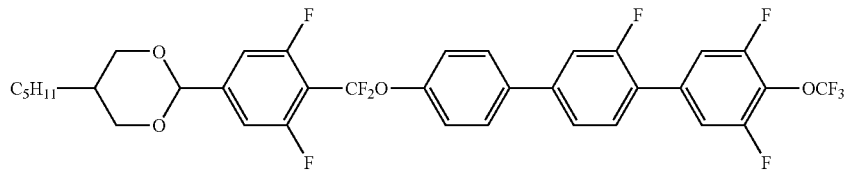
1-2-356
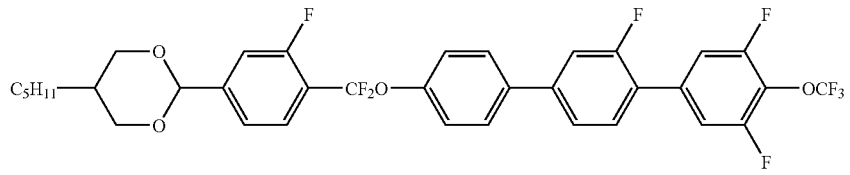
1-2-357
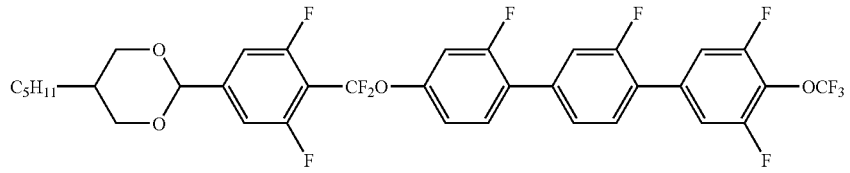
1-2-358
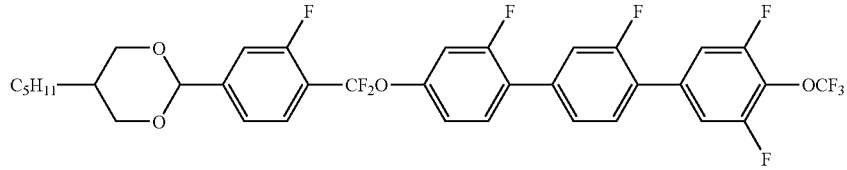
1-2-359
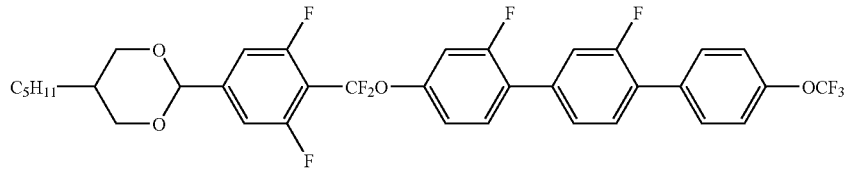
1-2-360
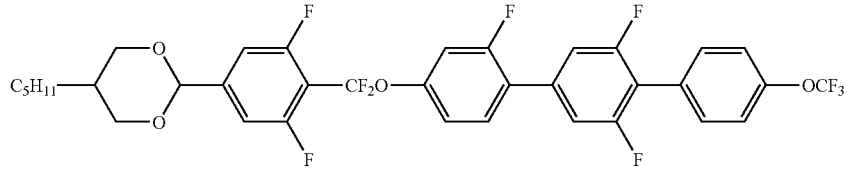
1-2-361

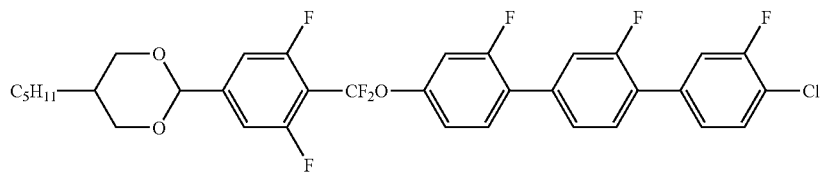
1-2-362
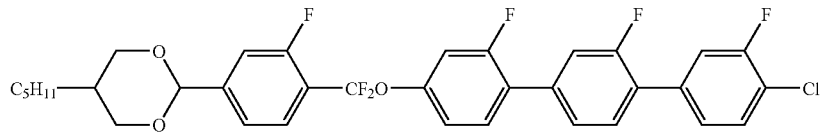
1-2-363
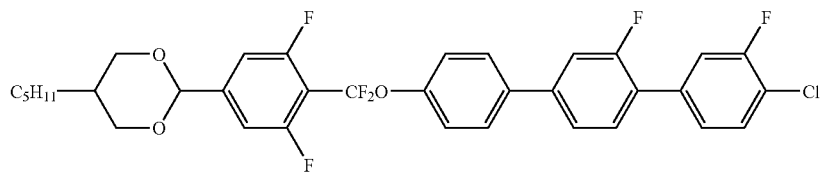
1-2-364
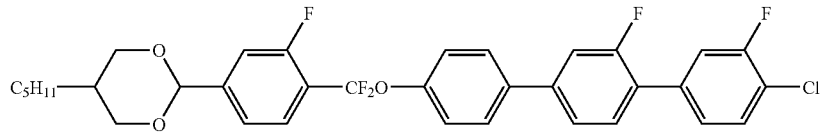
1-2-365
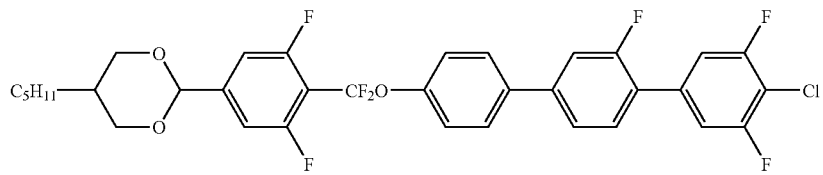
1-2-366
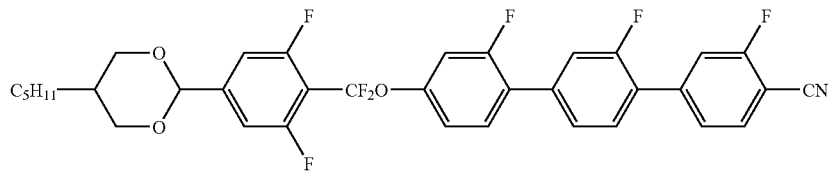
1-2-367
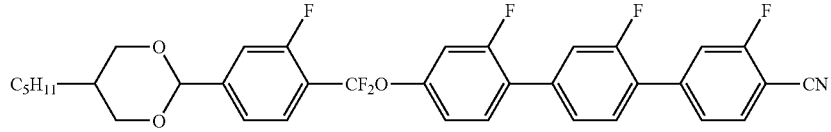
1-2-368
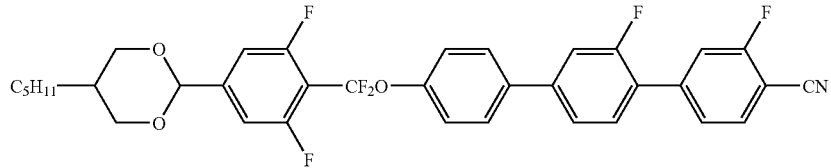
1-2-369
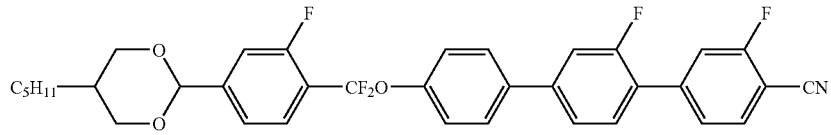
1-2-370

-continued
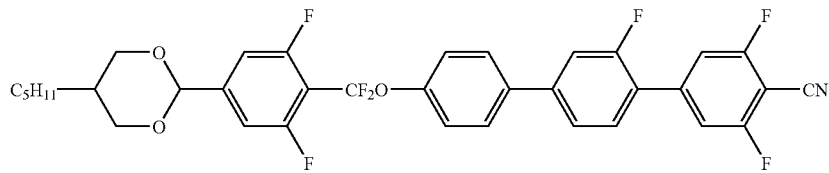 1-2-371
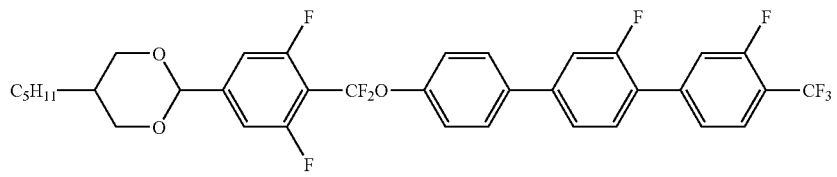 1-2-372
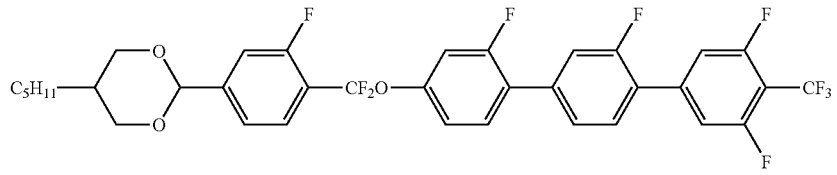 1-2-373
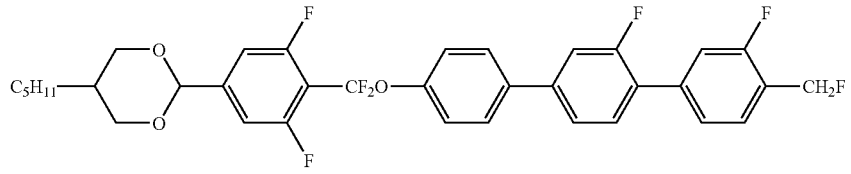 1-2-374
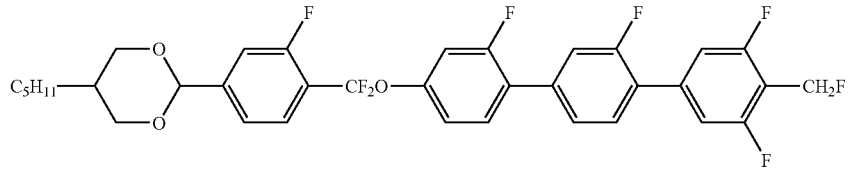 1-2-375
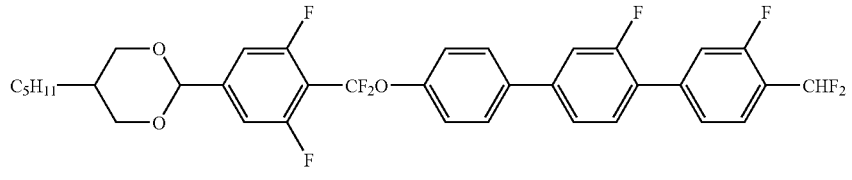 1-2-376
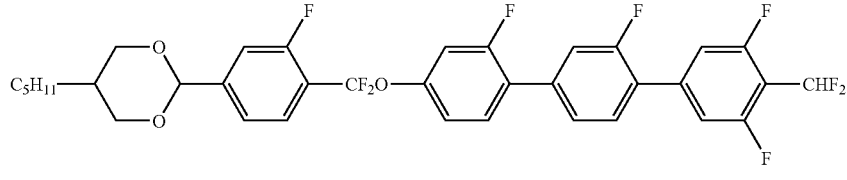 1-2-377
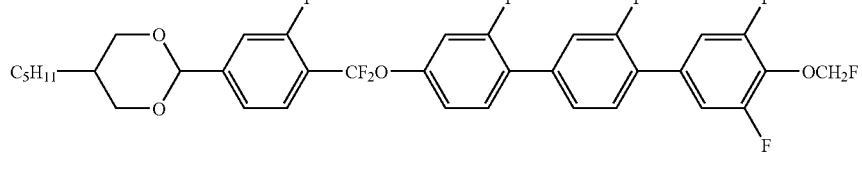 1-2-378
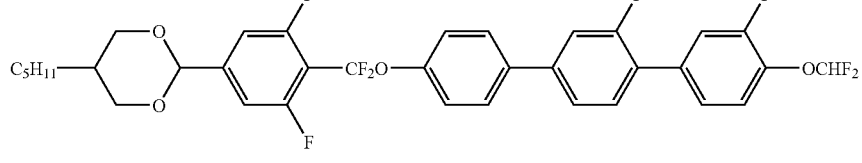 1-2-379

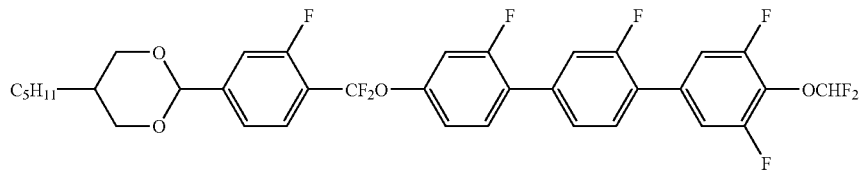
1-2-380
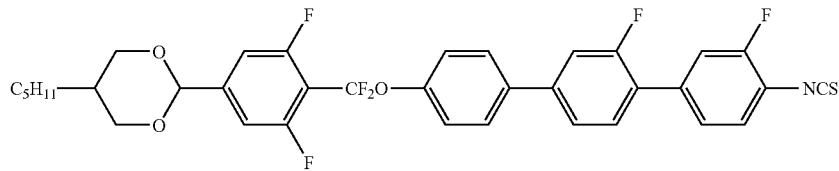
1-2-381
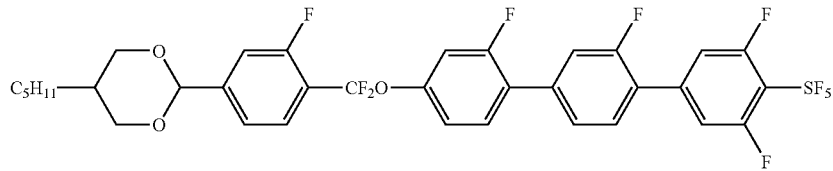
1-2-382
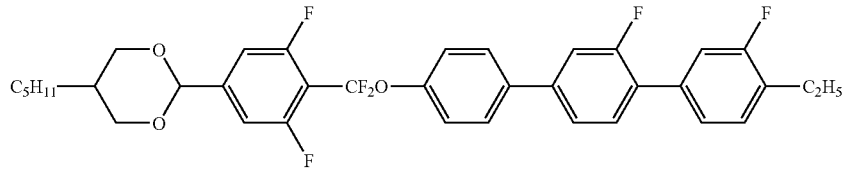
1-2-383
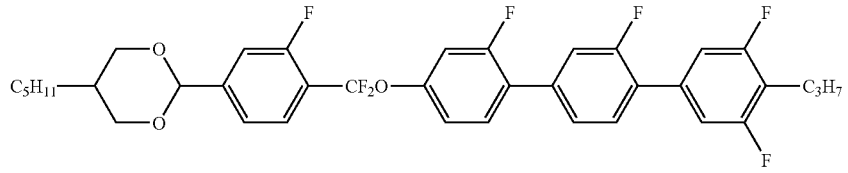
1-2-384
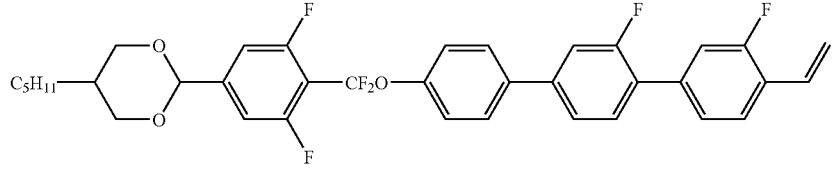
1-2-385
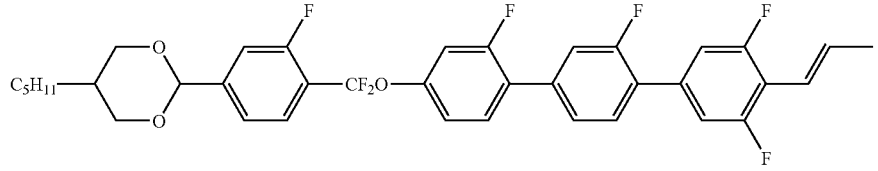
1-2-386
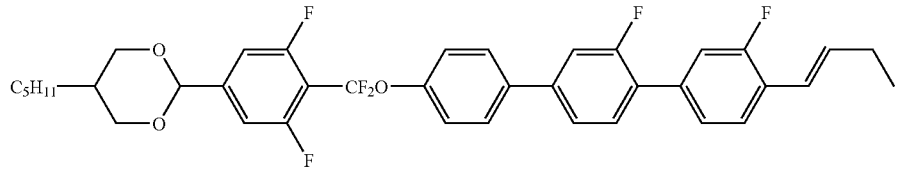
1-2-387
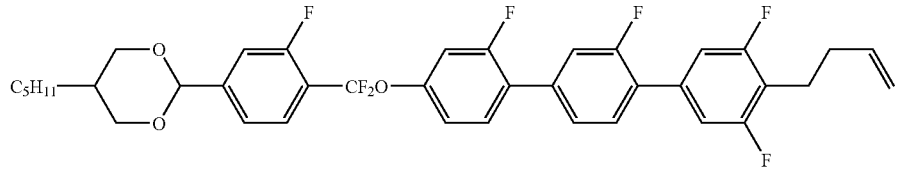
1-2-388

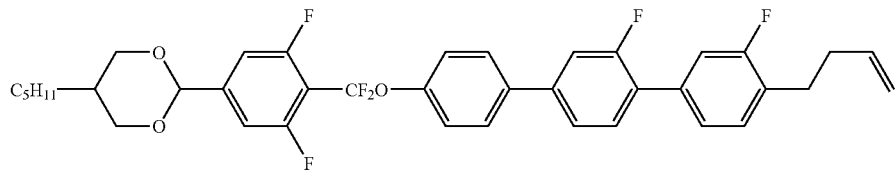
1-2-389
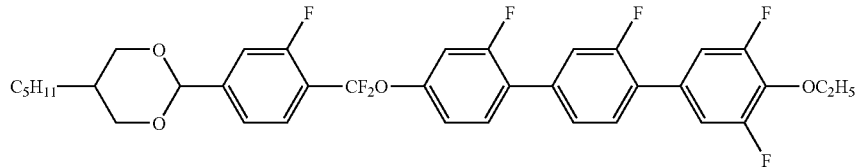
1-2-390
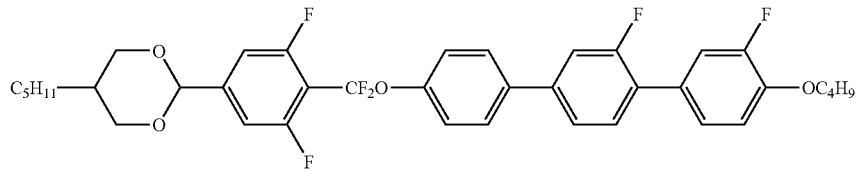
1-2-391
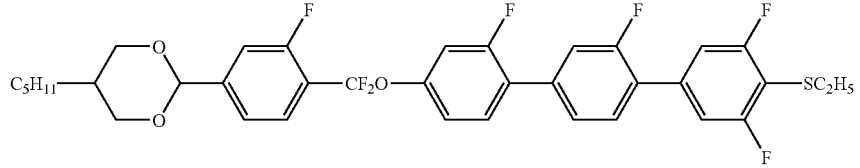
1-2-392
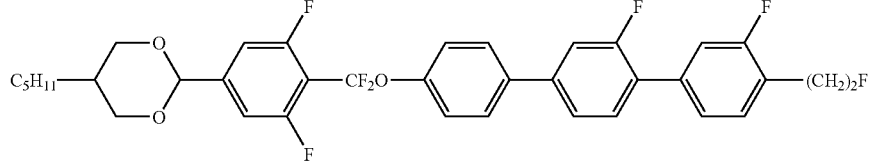
1-2-393
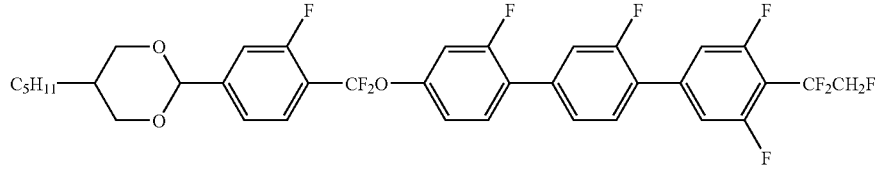
1-2-394
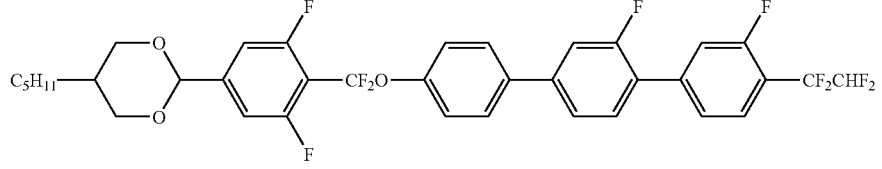
1-2-395
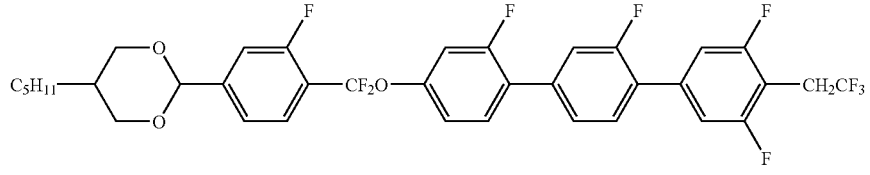
1-2-396
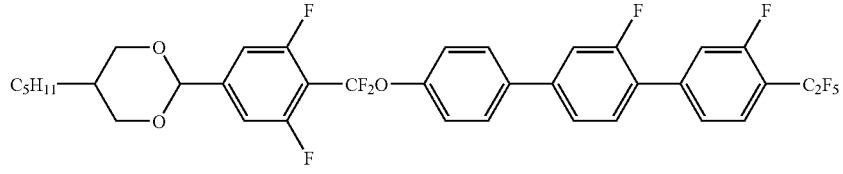
1-2-397

-continued
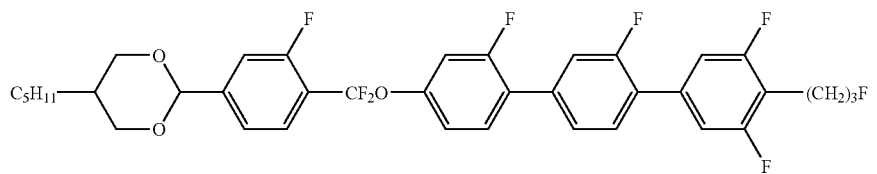
1-2-398
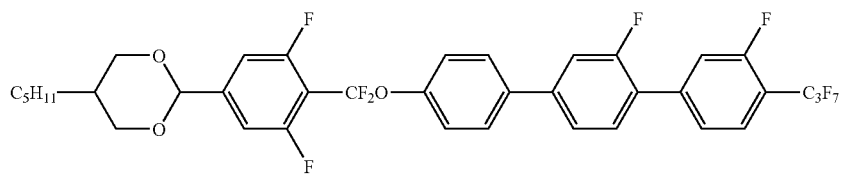
1-2-399
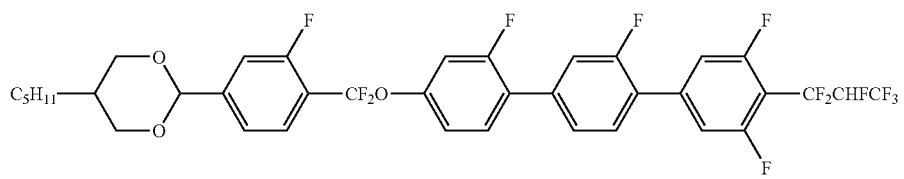
1-2-400
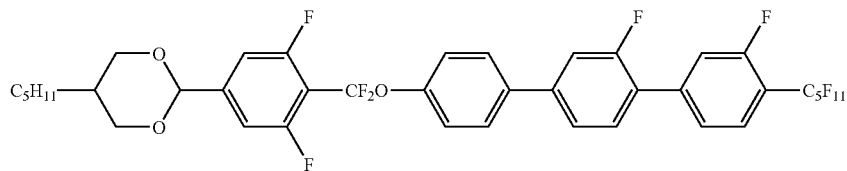
1-2-401
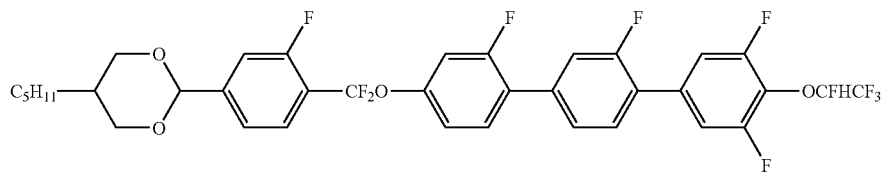
1-2-402
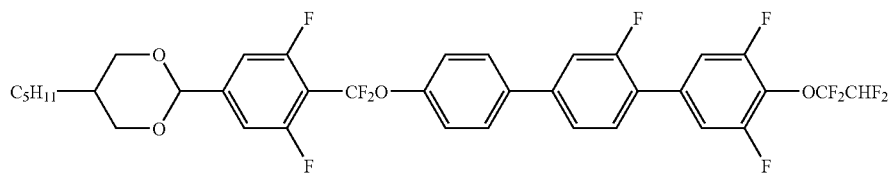
1-2-403
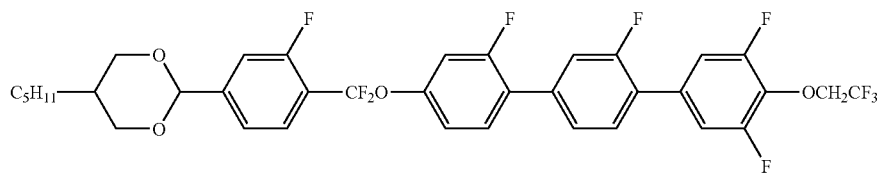
1-2-404
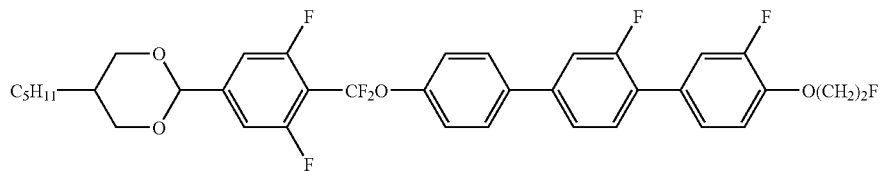
1-2-405
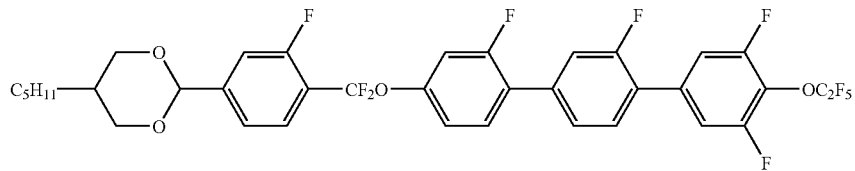
1-2-406

-continued
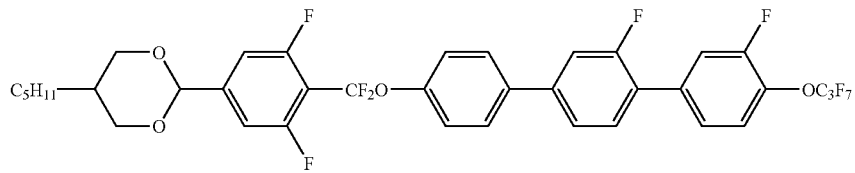
1-2-407
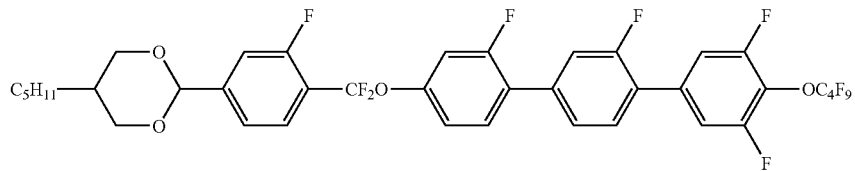
1-2-408
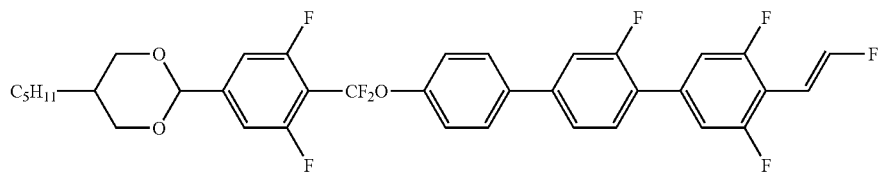
1-2-409
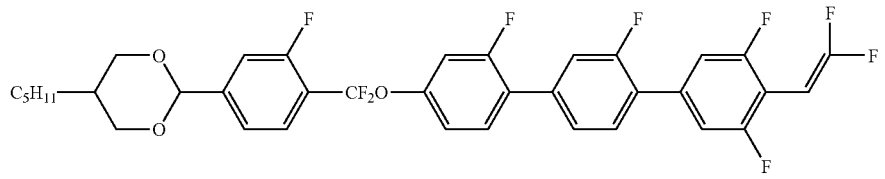
1-2-410
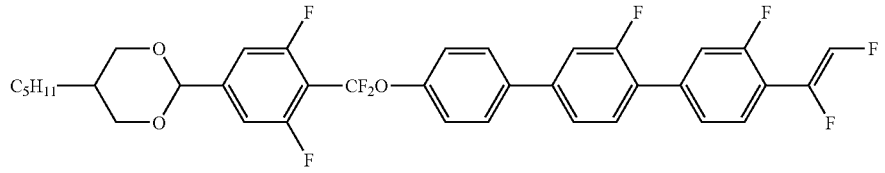
1-2-411
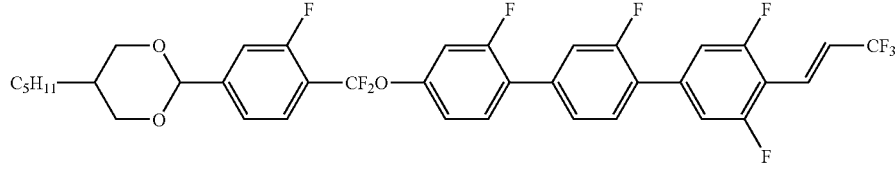
1-2-412
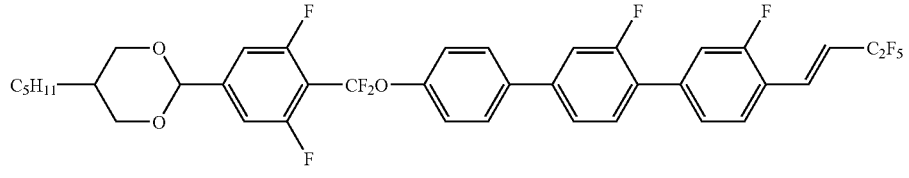
1-2-413
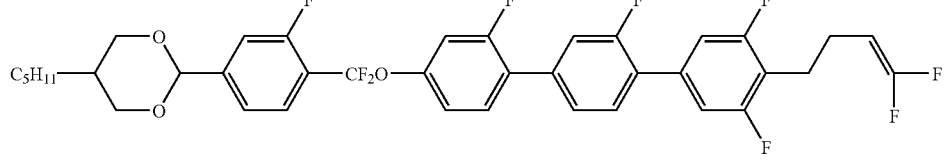
1-2-414
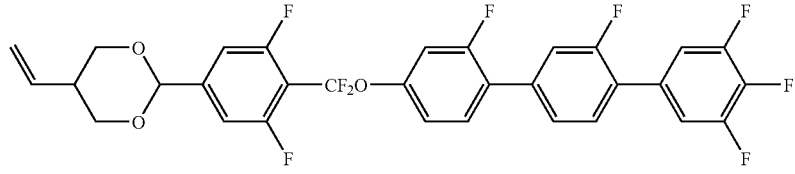
1-2-415

-continued
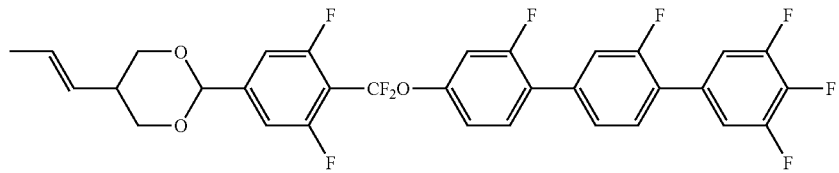
1-2-416
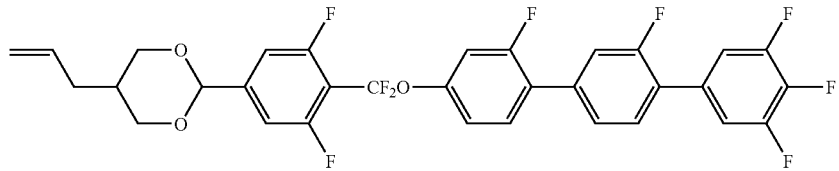
1-2-417
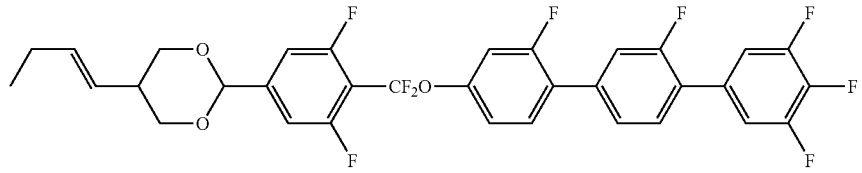
1-2-418
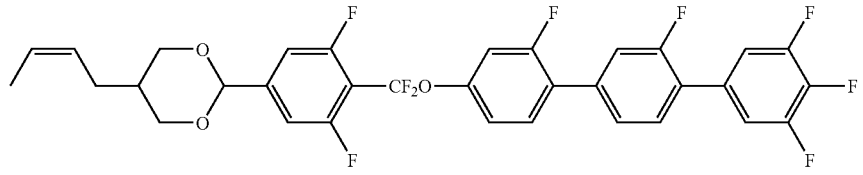
1-2-419
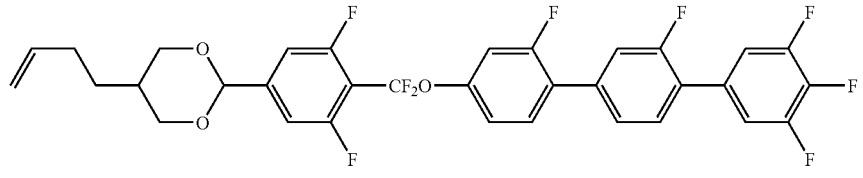
1-2-420
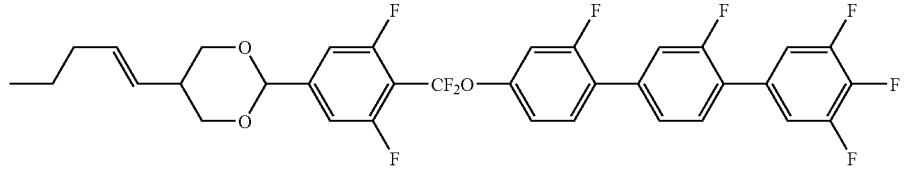
1-2-421
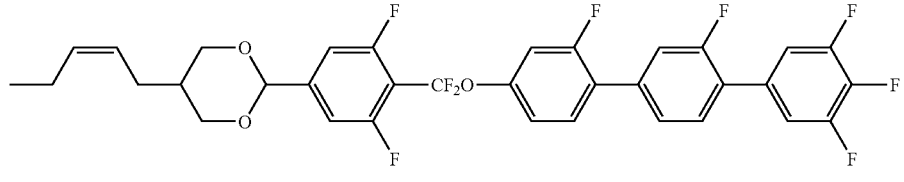
1-2-422
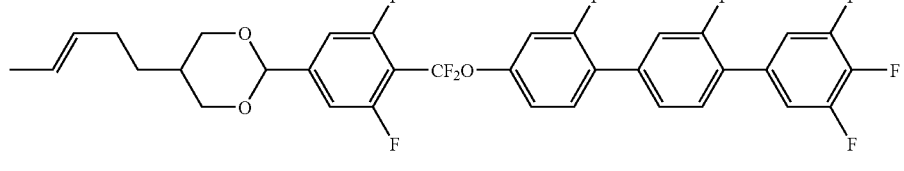
1-2-423
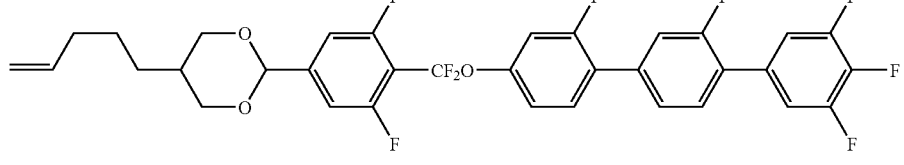
1-2-424

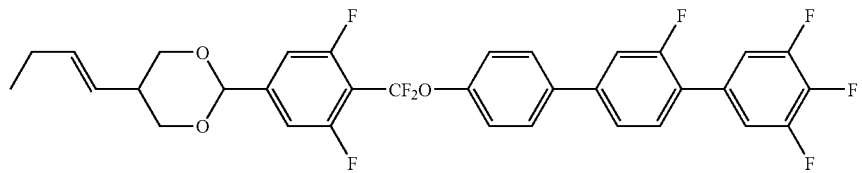
1-2-425
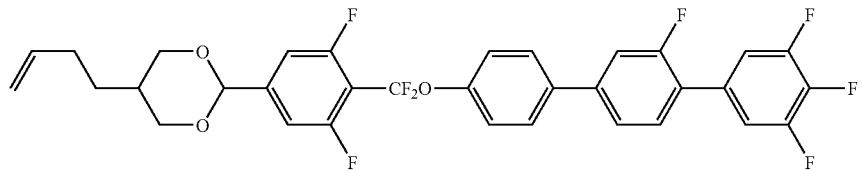
1-2-426
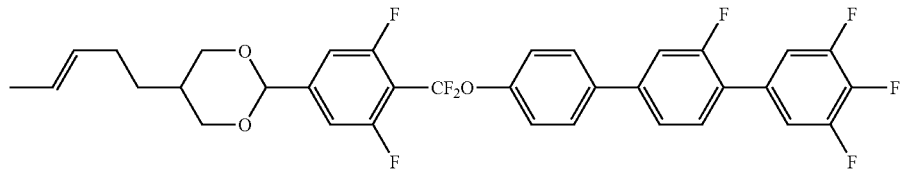
1-2-427
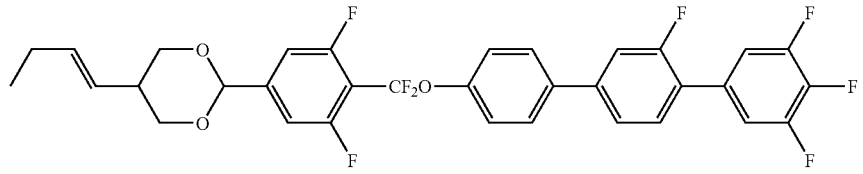
1-2-428
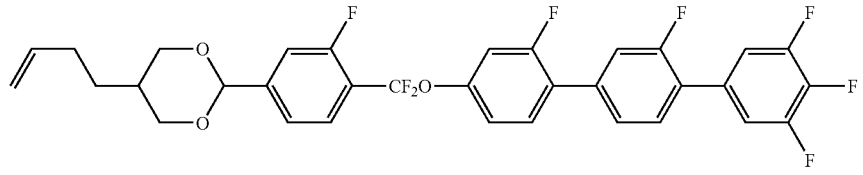
1-2-429
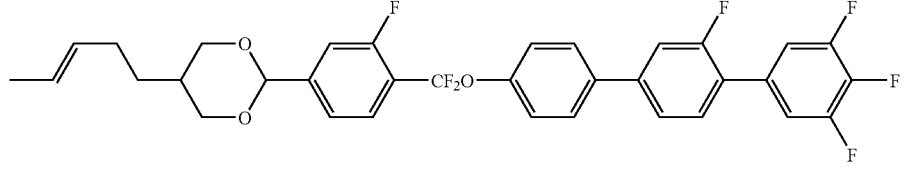
1-2-430
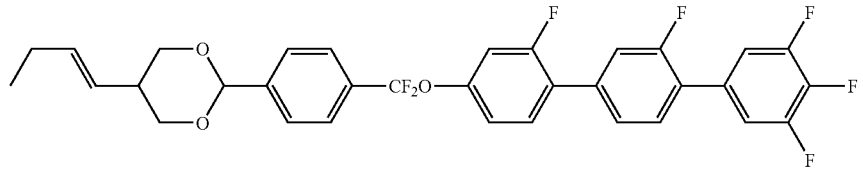
1-2-431
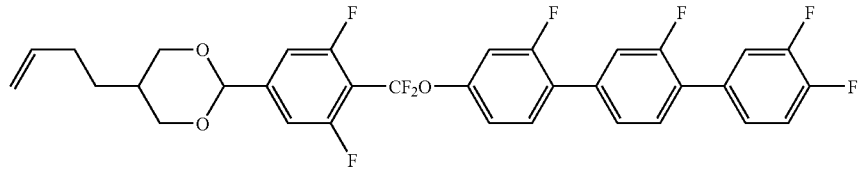
1-2-432
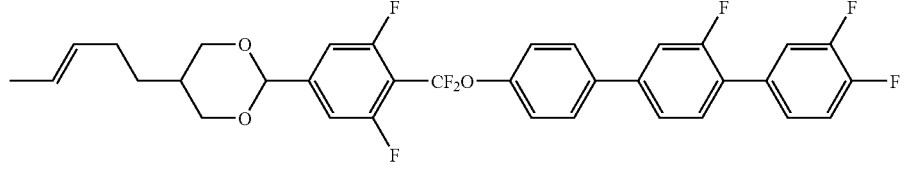
1-2-433

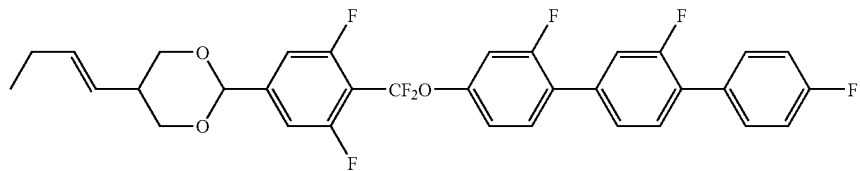 1-2-434
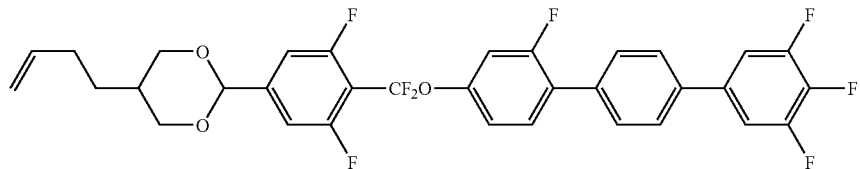 1-2-435
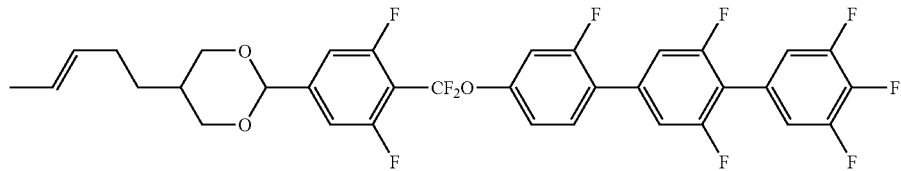 1-2-436
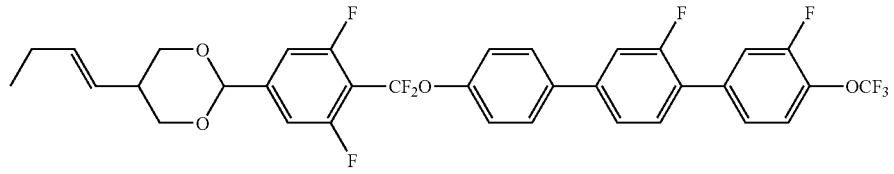 1-2-437
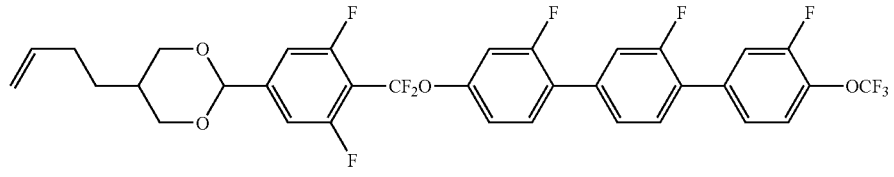 1-2-438
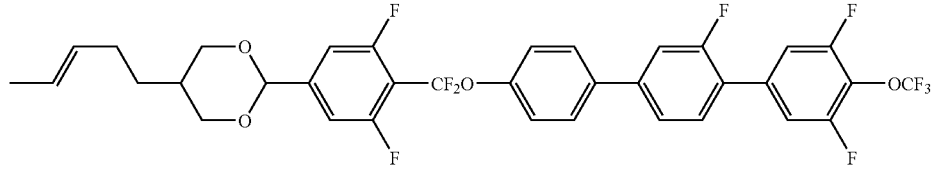 1-2-439
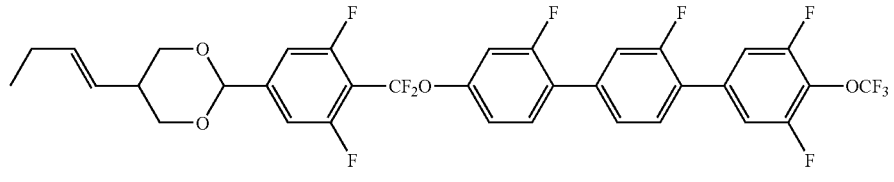 1-2-440
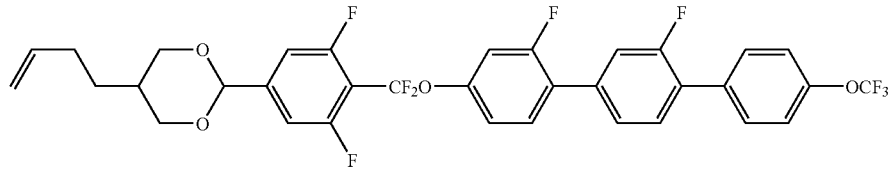 1-2-441
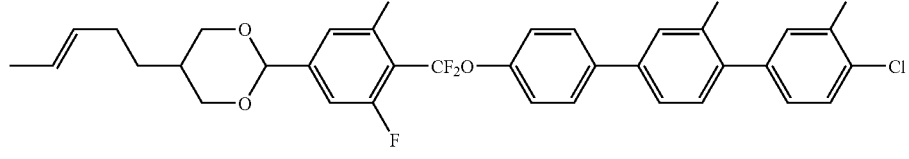 1-2-442

-continued
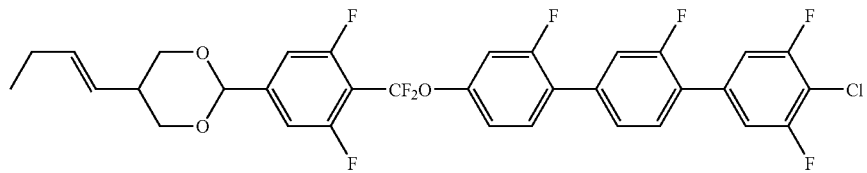
1-2-443
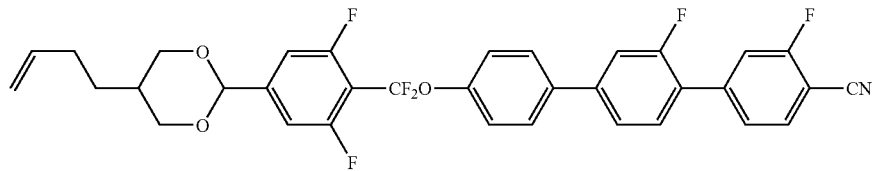
1-2-444
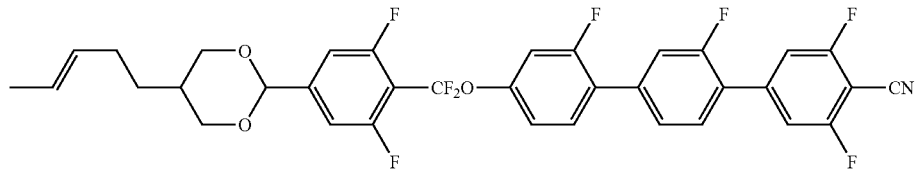
1-2-445
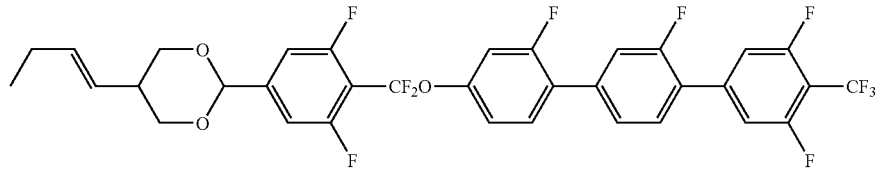
1-2-446
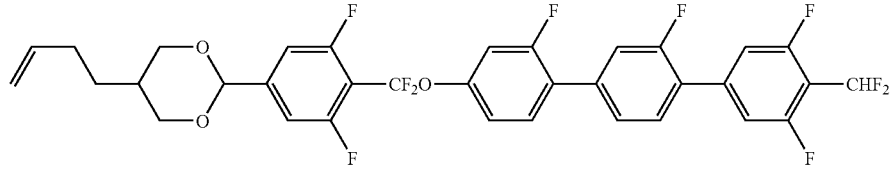
1-2-447
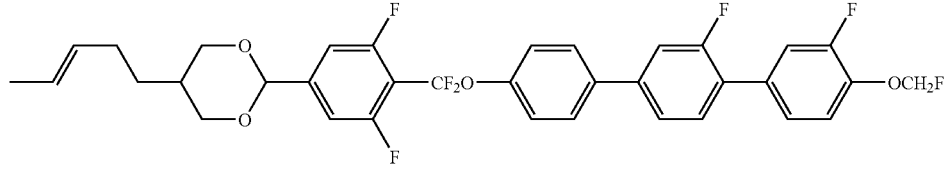
1-2-448
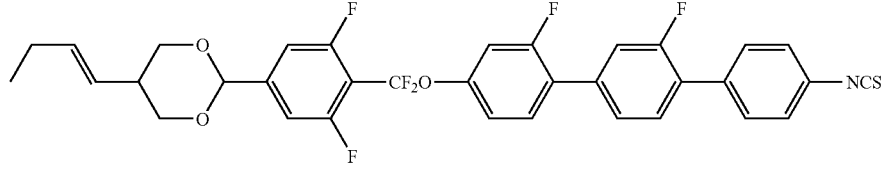
1-2-449
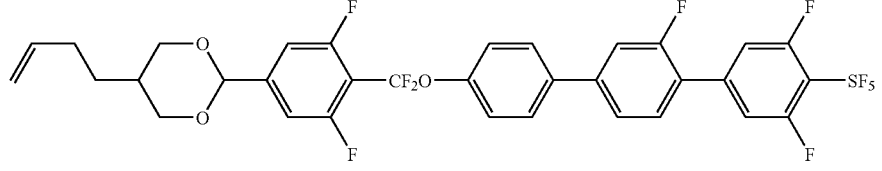
1-2-450
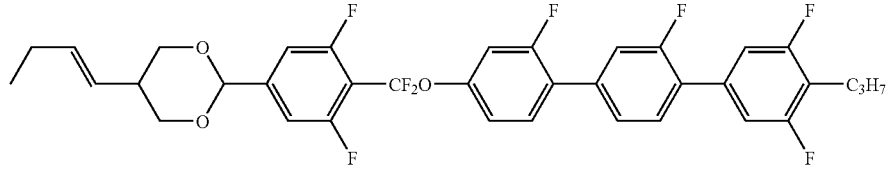
1-2-451

-continued
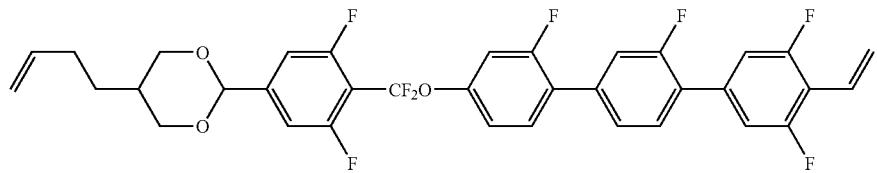 1-2-452
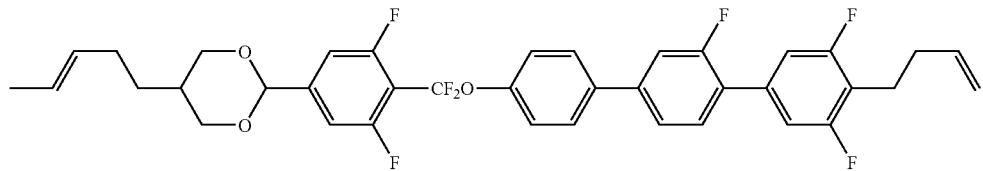 1-2-453
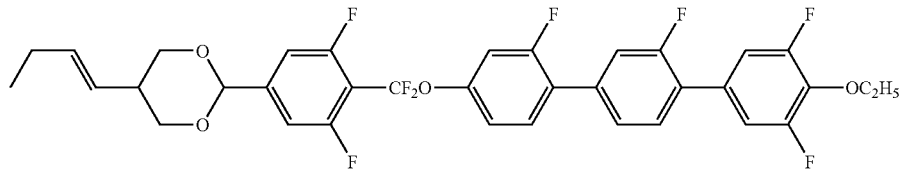 1-2-454
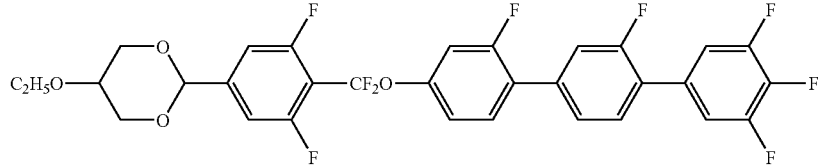 1-2-455
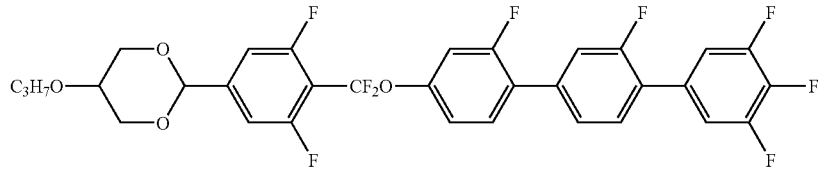 1-2-456
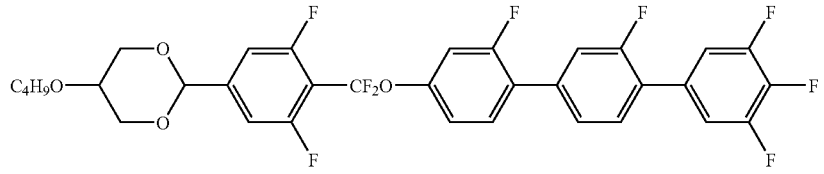 1-2-457
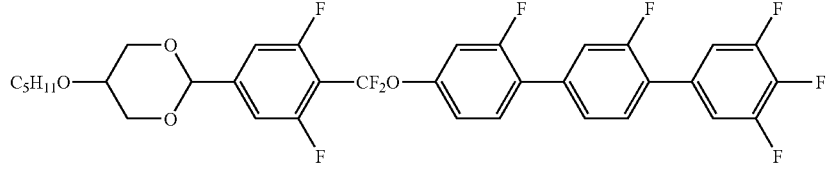 1-2-458
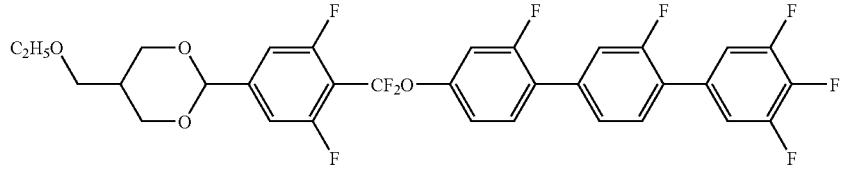 1-2-459
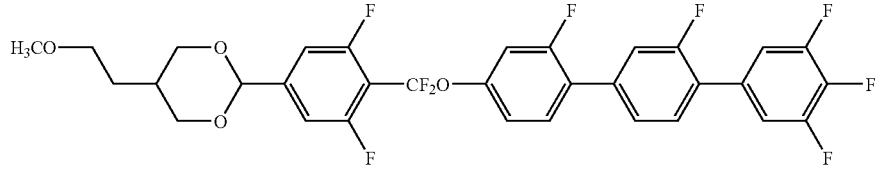 1-2-460

-continued
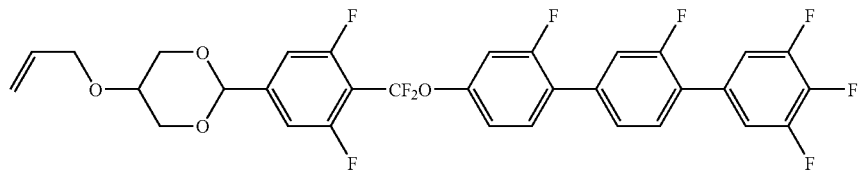
1-2-461
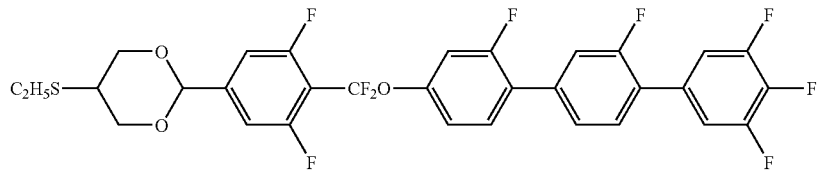
1-2-462
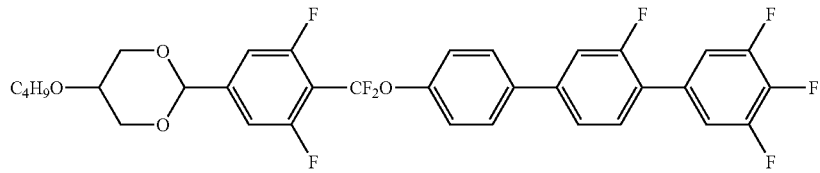
1-2-463
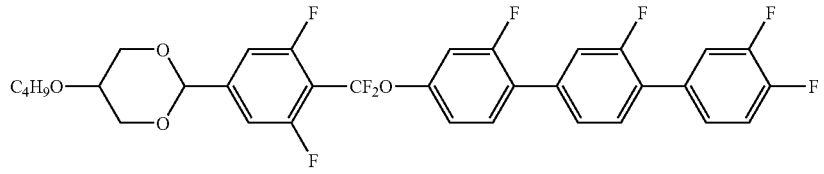
1-2-464
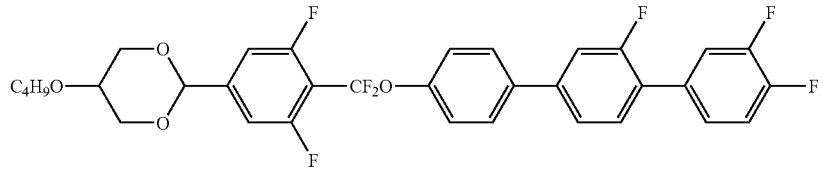
1-2-465
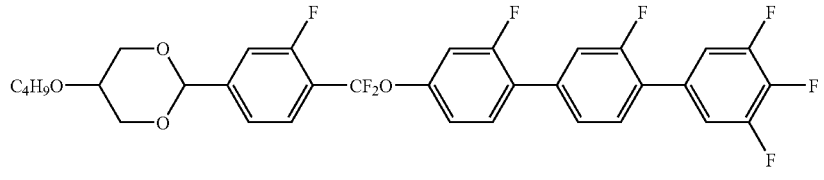
1-2-466
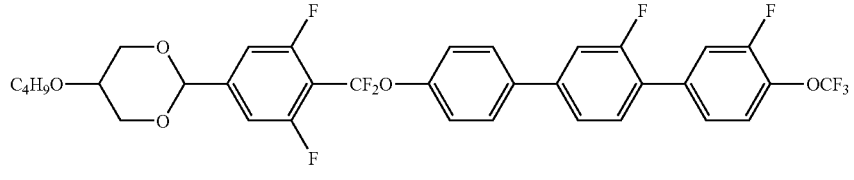
1-2-467
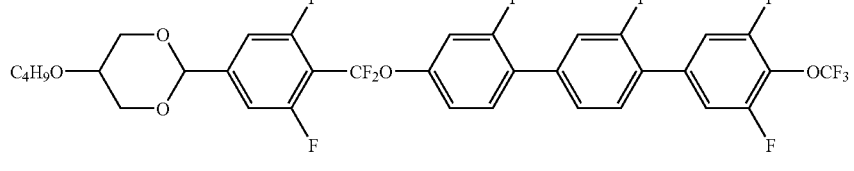
1-2-468
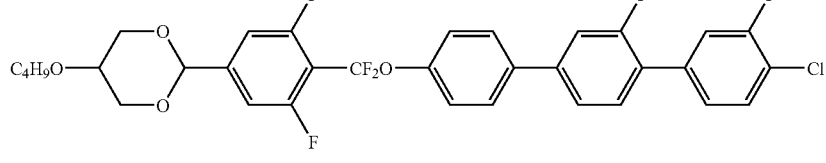
1-2-469

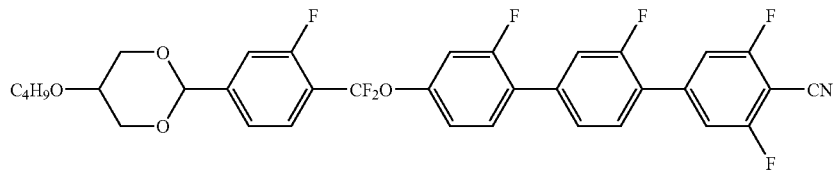 1-2-470
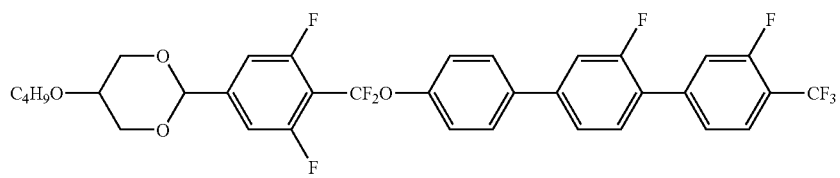 1-2-471
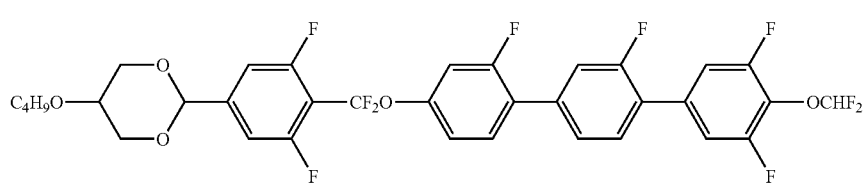 1-2-472
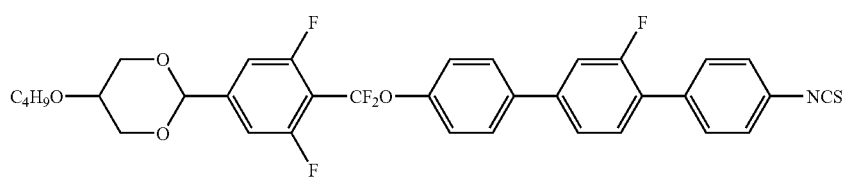 1-2-473
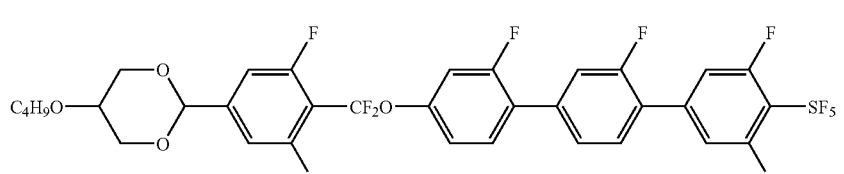 1-2-474
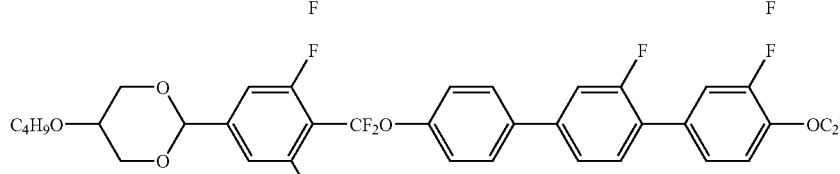 1-2-475
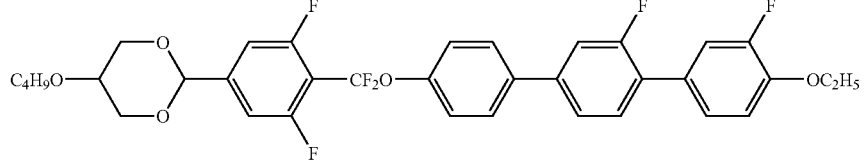 1-2-476
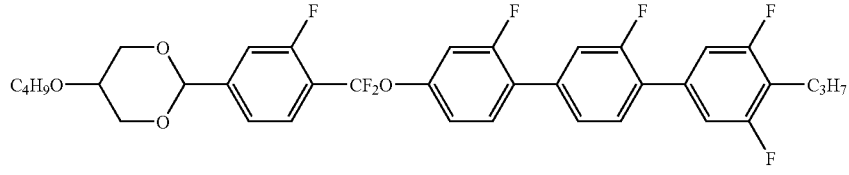 1-2-477
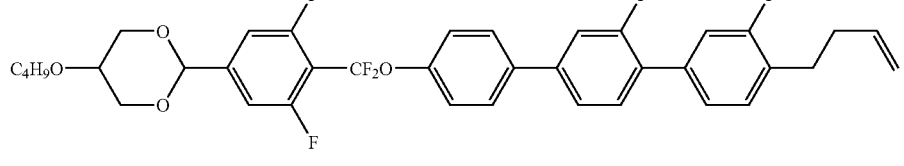 1-2-478
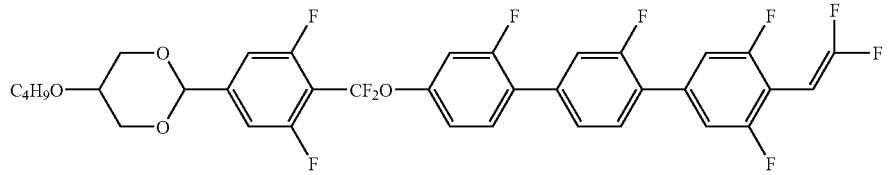

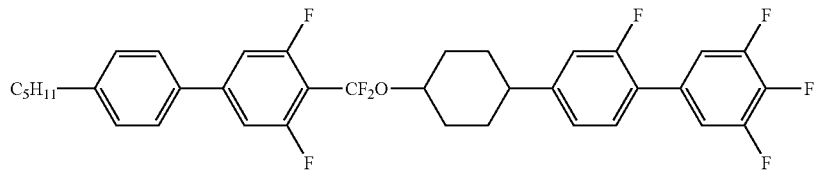 1-2-479
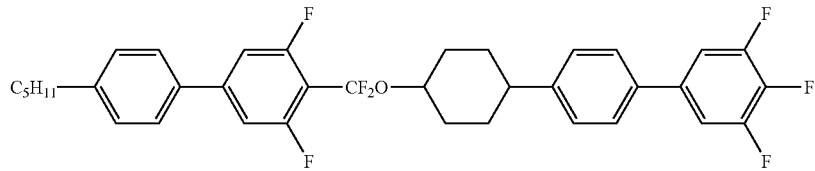 1-2-480
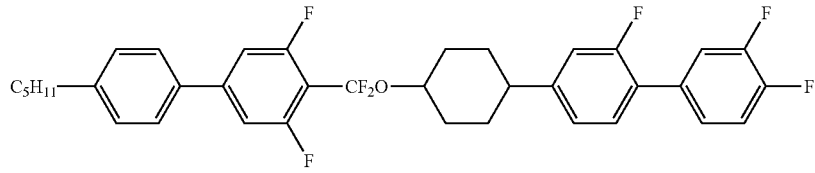 1-2-481
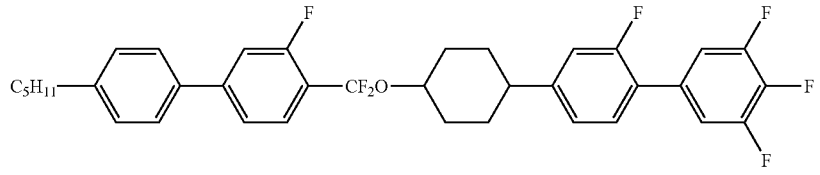 1-2-482
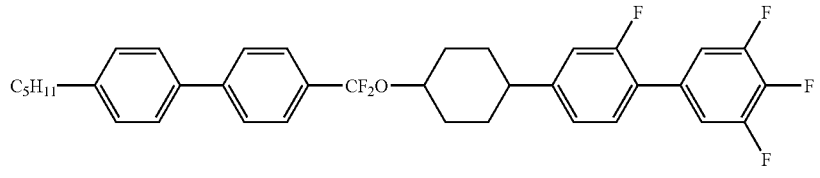 1-2-483
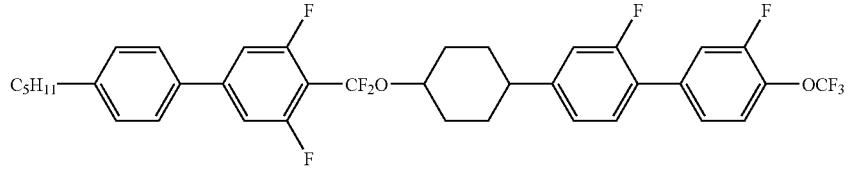 1-2-484
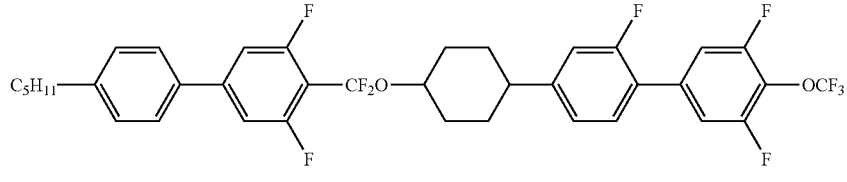 1-2-485
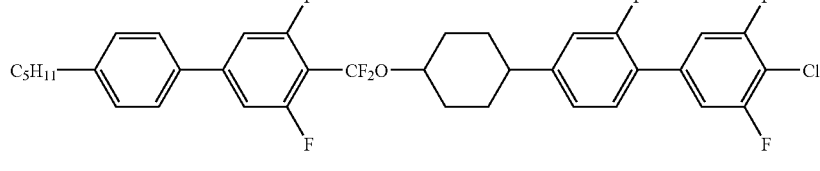 1-2-486
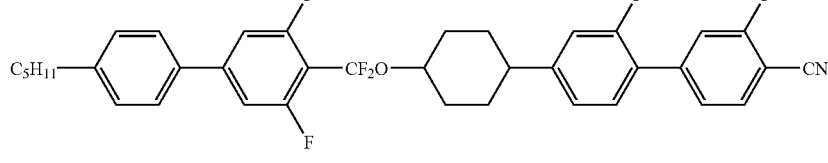 1-2-487

-continued
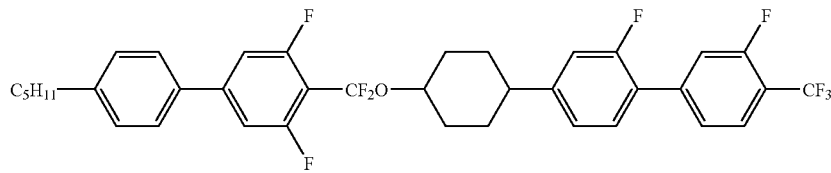
1-2-488
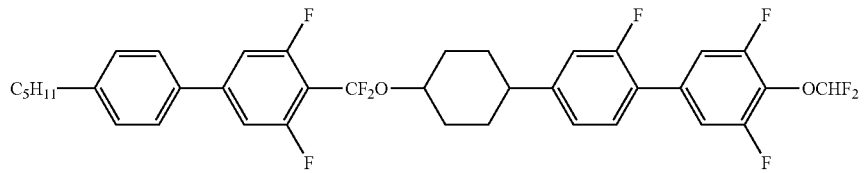
1-2-489
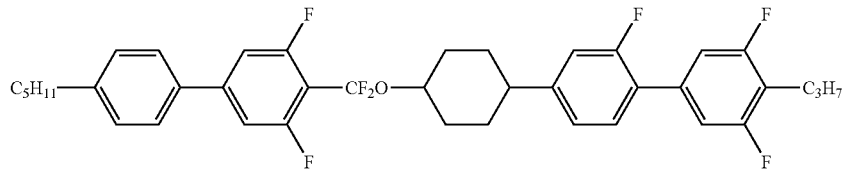
1-2-490
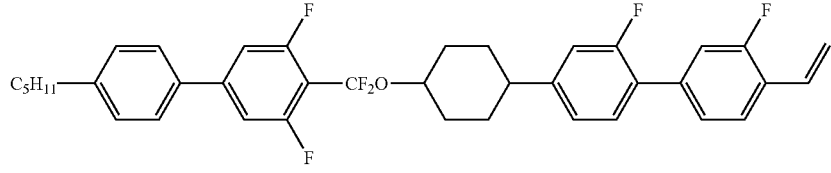
1-2-491
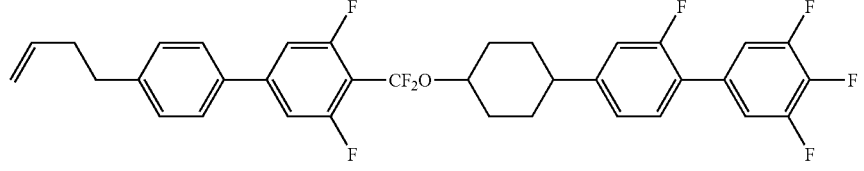
1-2-492
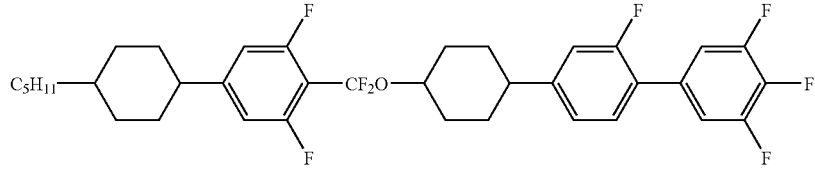
1-2-493
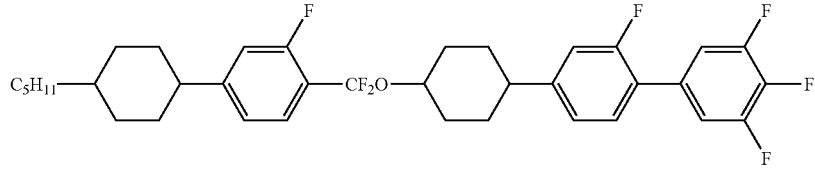
1-2-494
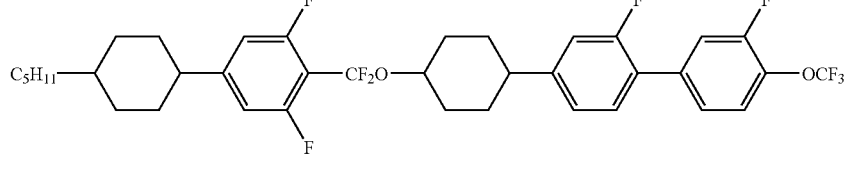
1-2-495
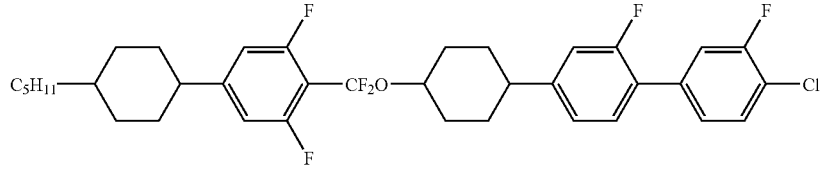
1-2-496

-continued
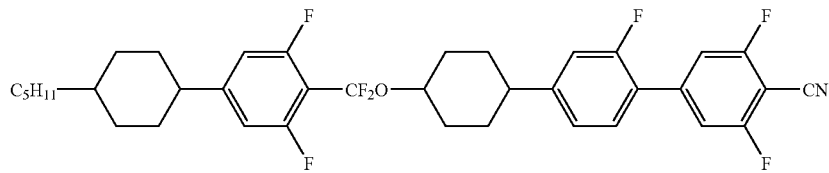
1-2-497
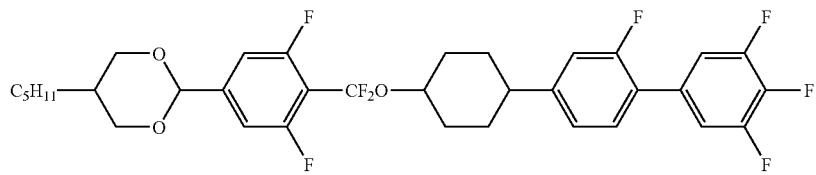
1-2-498
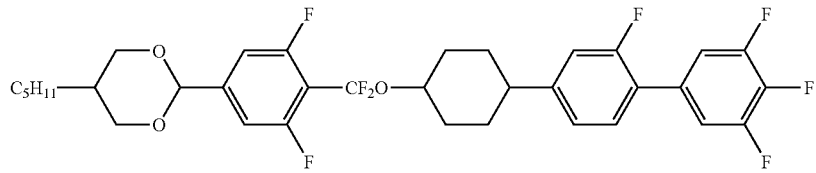
1-2-499
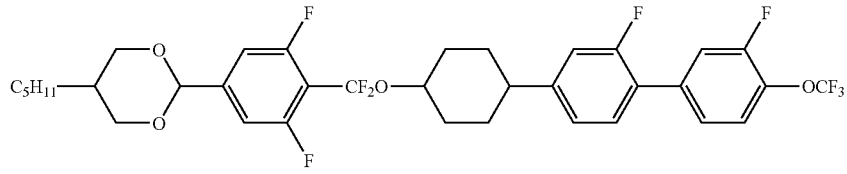
1-2-500
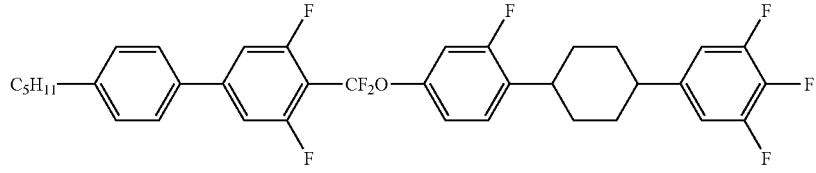
1-2-501
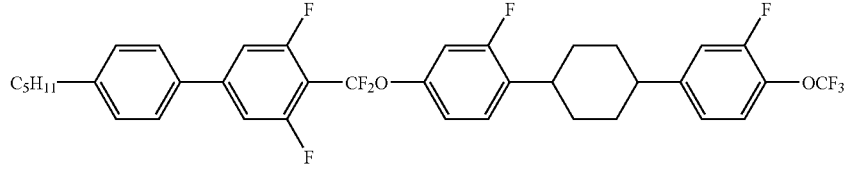
1-2-502
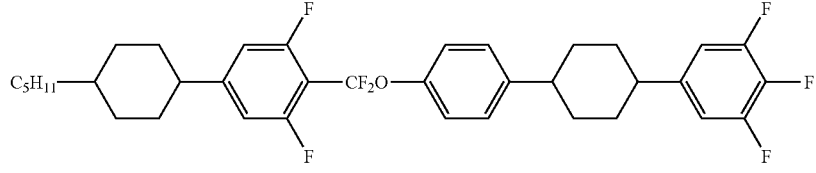
1-2-503
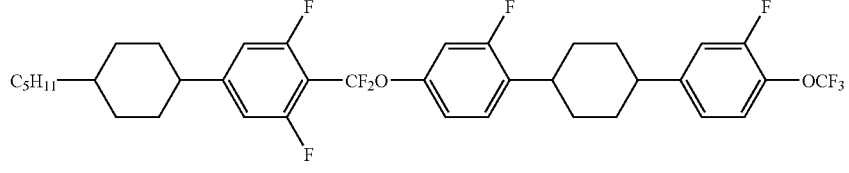
1-2-504
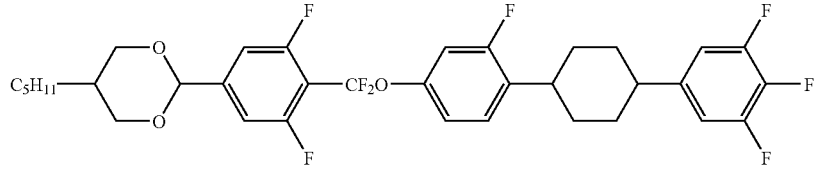
1-2-505

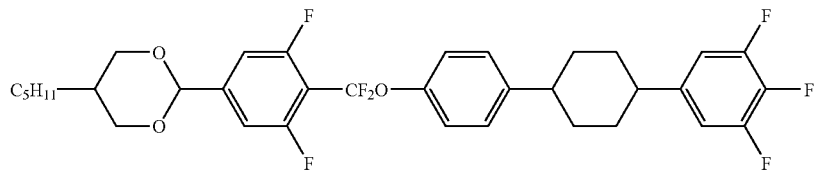
1-2-506
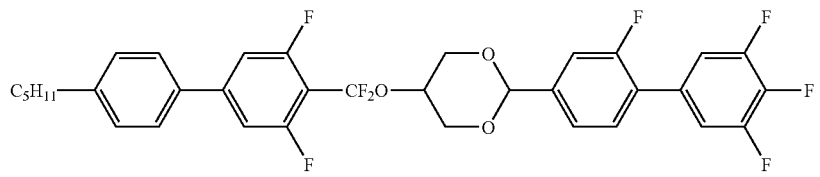
1-2-507
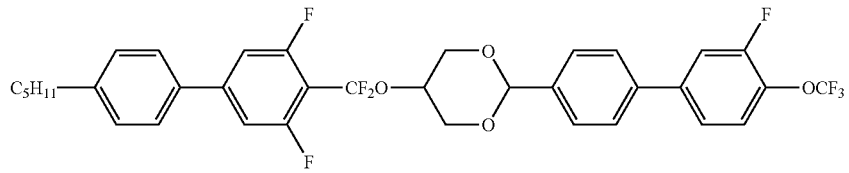
1-2-508
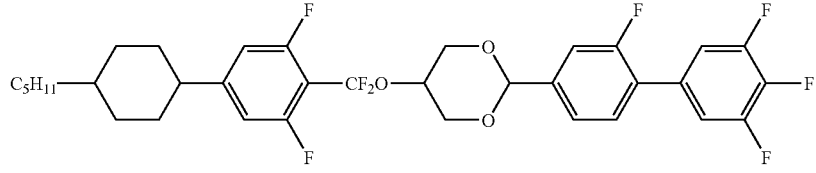
1-2-509
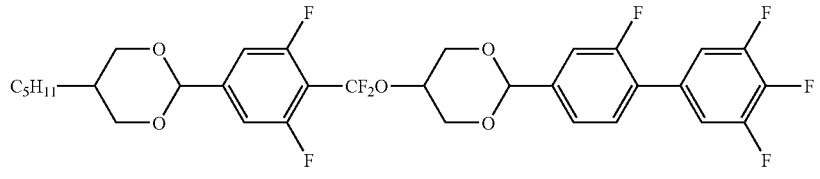
1-2-510
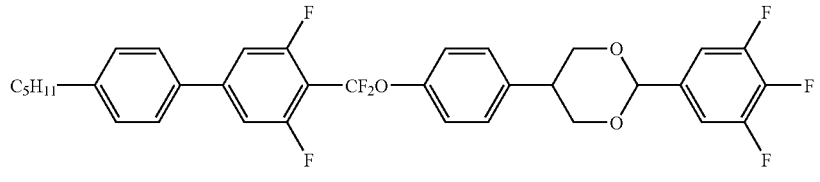
1-2-511
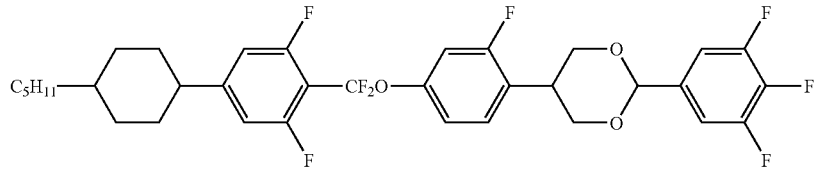
1-2-512
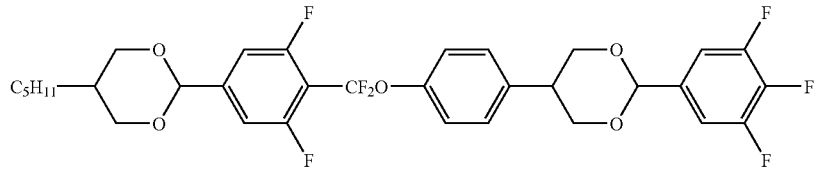
1-2-513
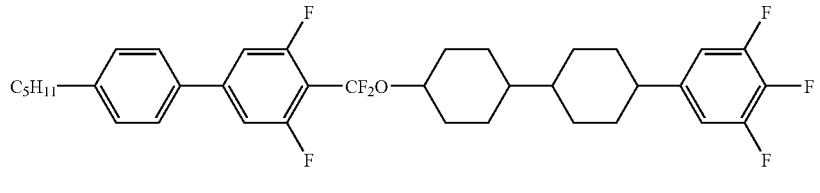
1-2-514

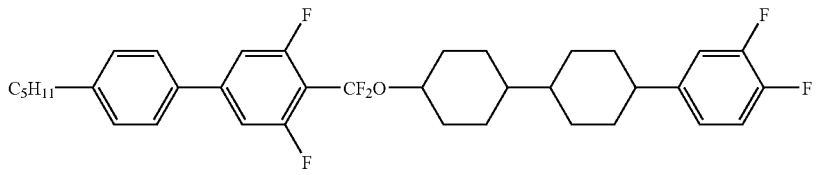
1-2-515
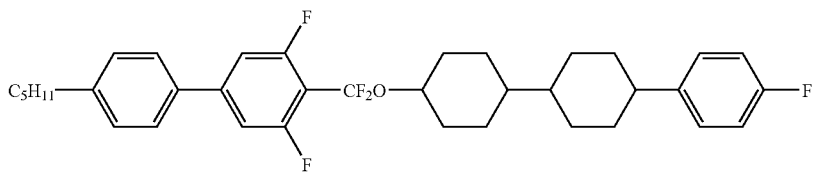
1-2-516
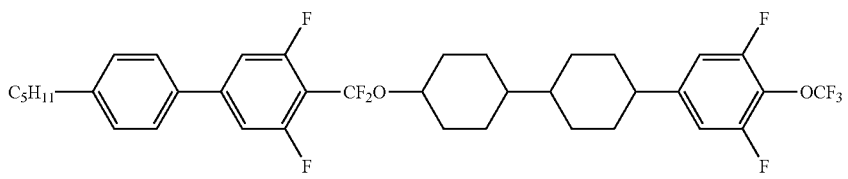
1-2-517
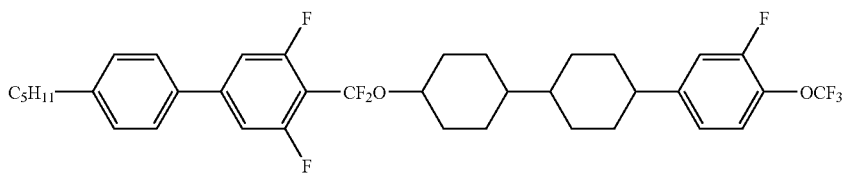
1-2-518
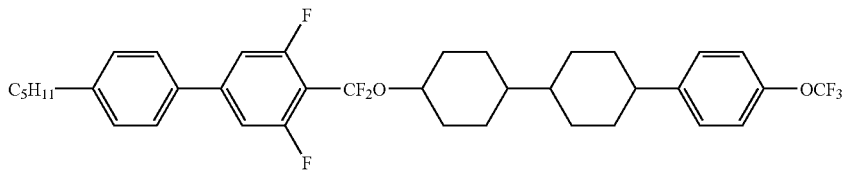
1-2-519
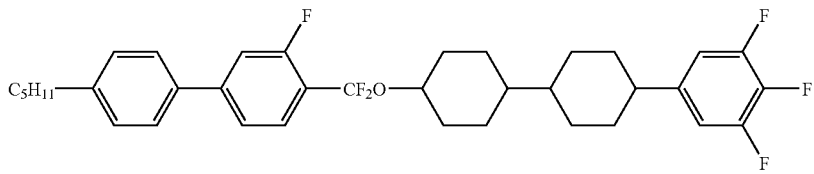
1-2-520
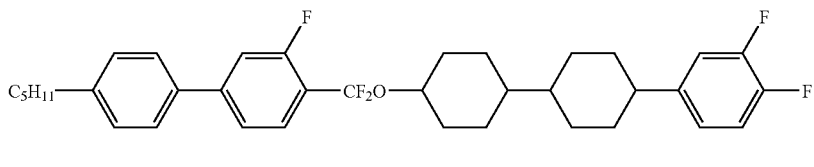
1-2-521
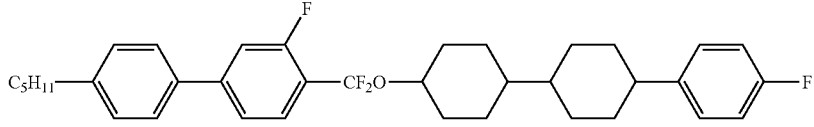
1-2-522
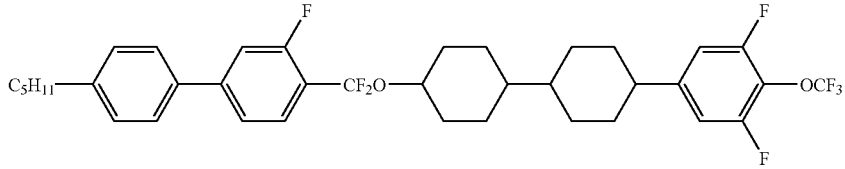
1-2-523

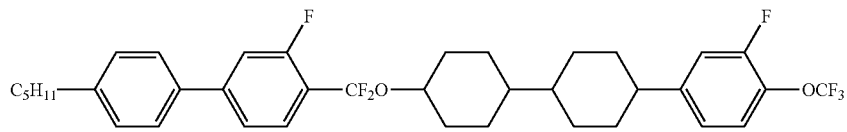 1-2-524
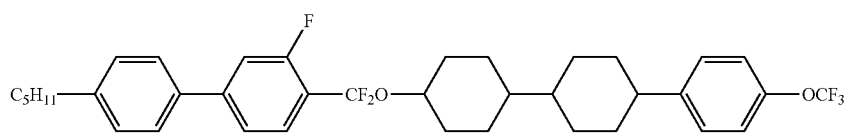 1-2-525
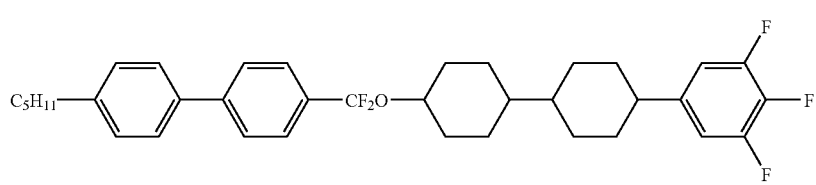 1-2-526
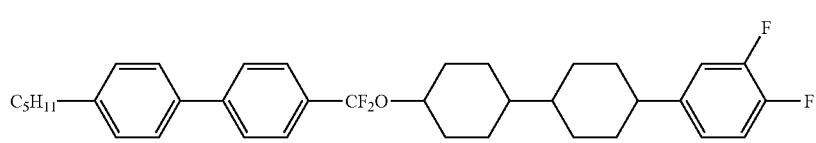 1-2-527
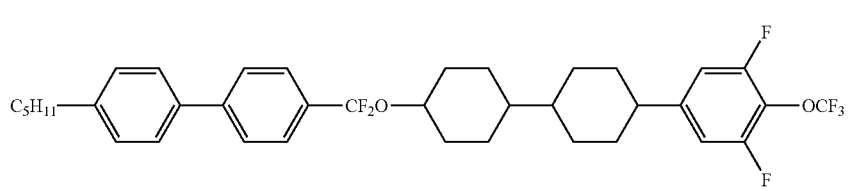 1-2-528
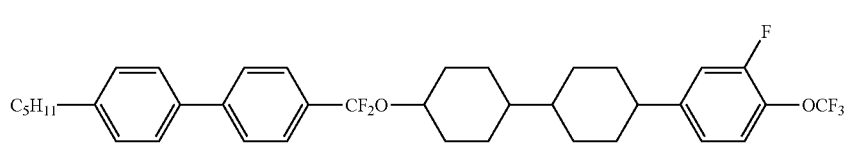 1-2-529
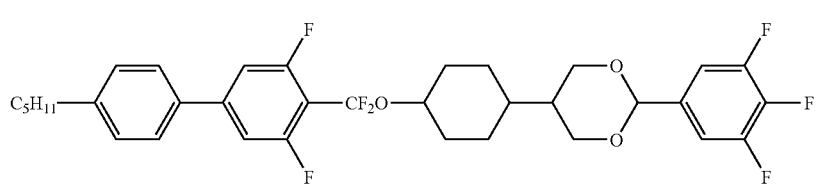 1-2-530
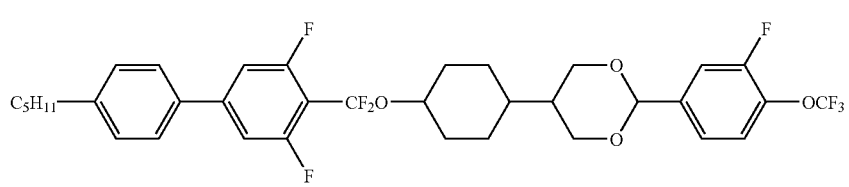 1-2-531
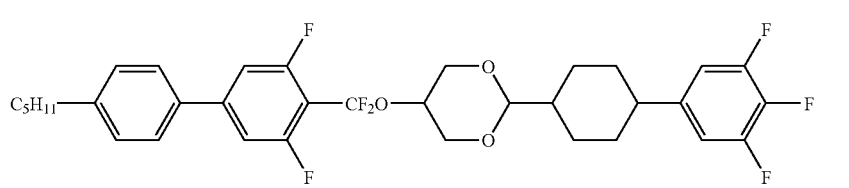 1-2-532
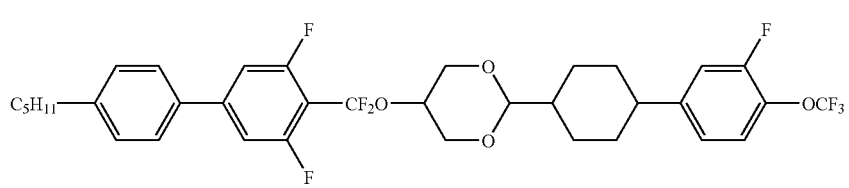 1-2-533

-continued
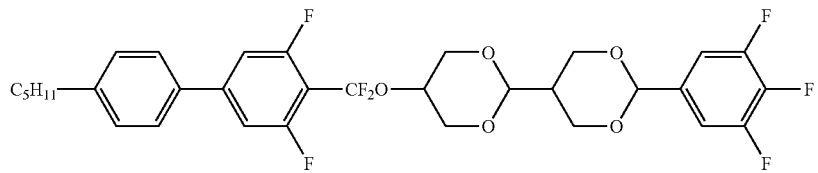
1-2-534
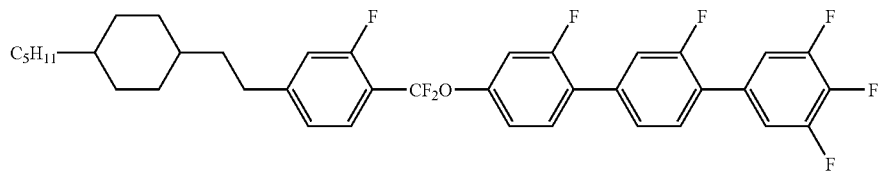
1-2-535
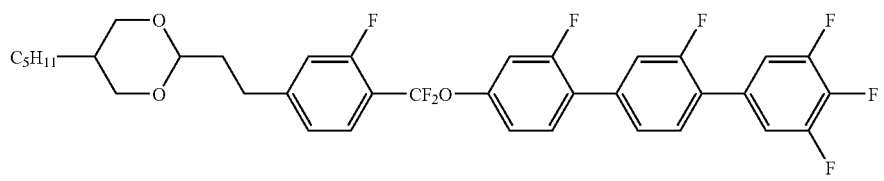
1-2-536
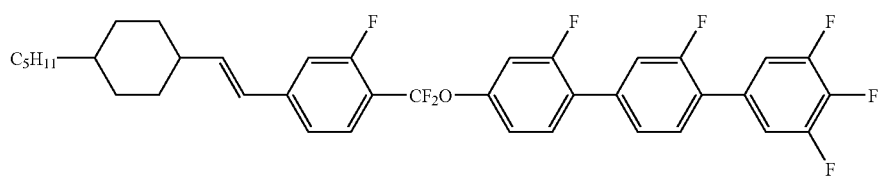
1-2-537
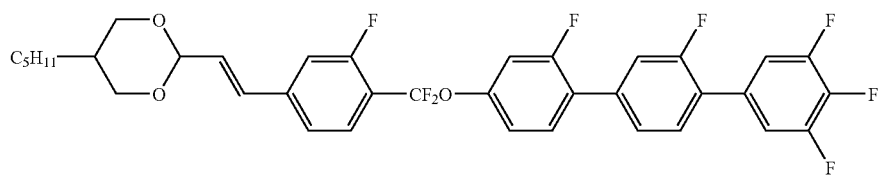
1-2-538
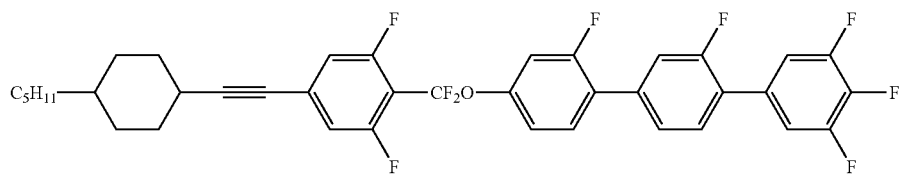
1-2-539
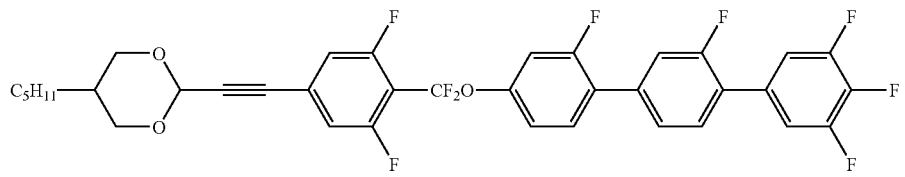
1-2-540
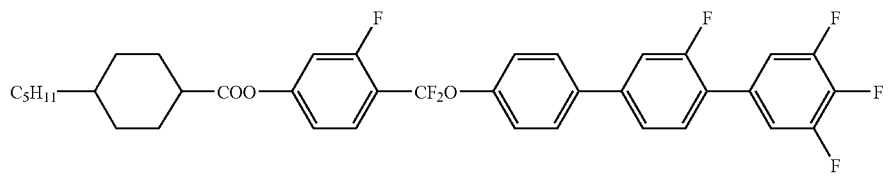
1-2-541
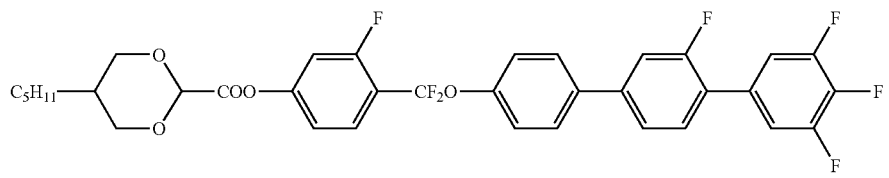
1-2-542

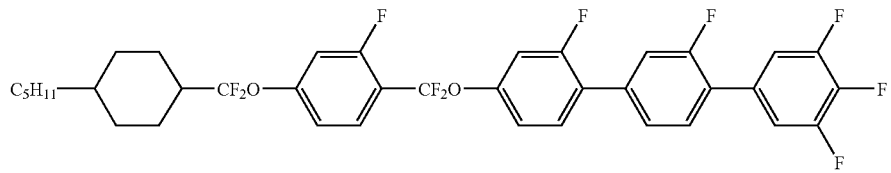
1-2-543
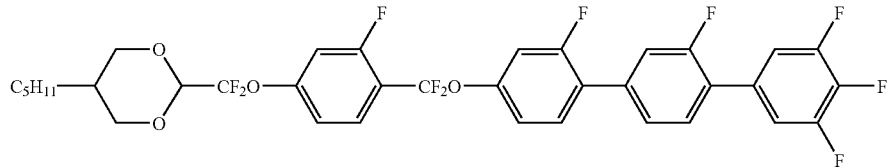
1-2-544
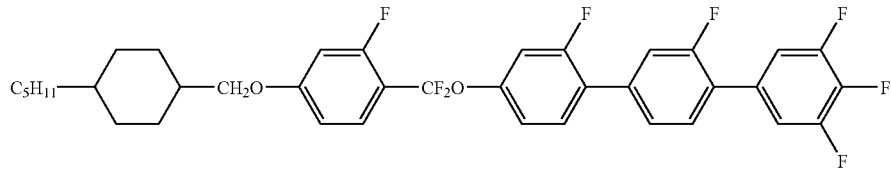
1-2-545
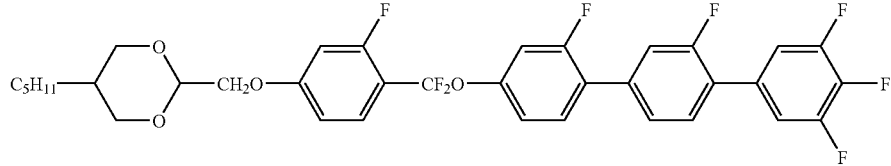
1-2-546
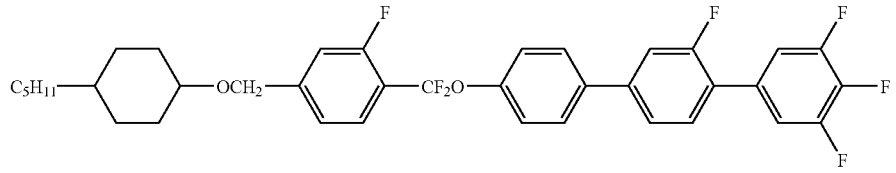
1-2-547
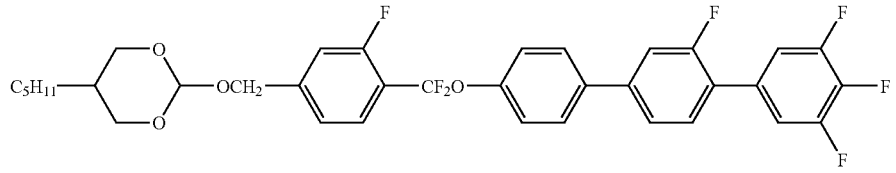
1-2-548
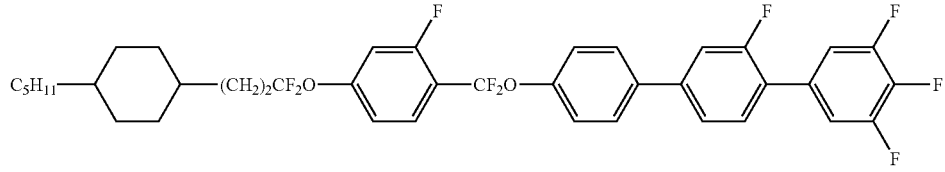
1-2-549

1-2-550
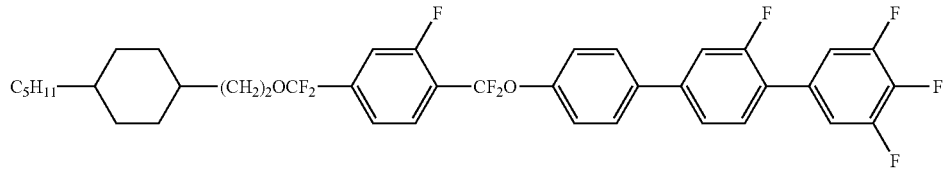
1-2-551

-continued
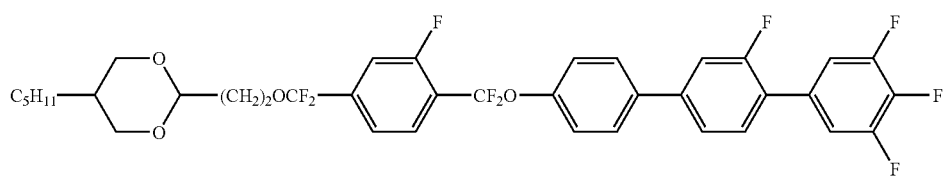
1-2-552
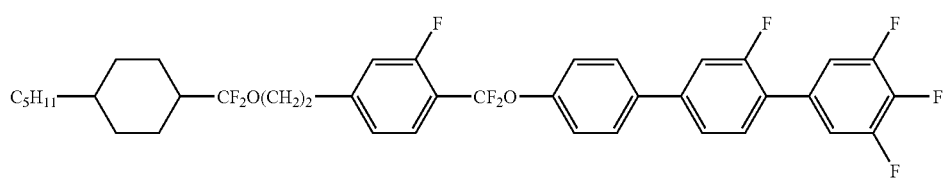
1-2-553
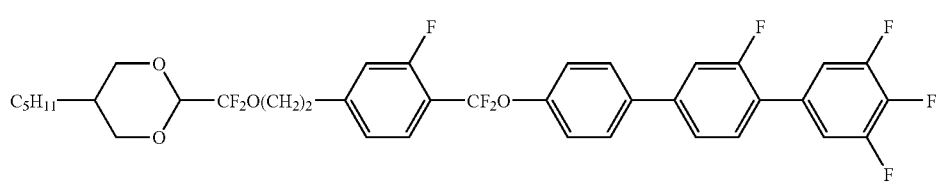
1-2-554
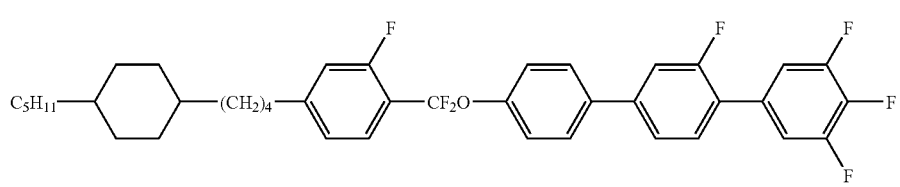
1-2-555
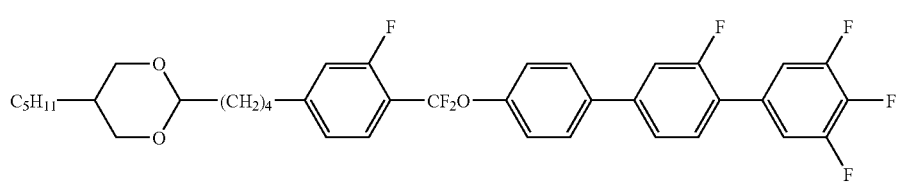
1-2-556
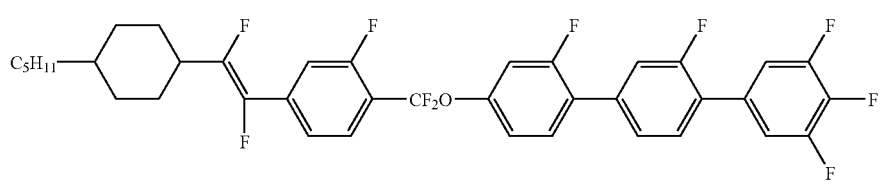
1-2-557
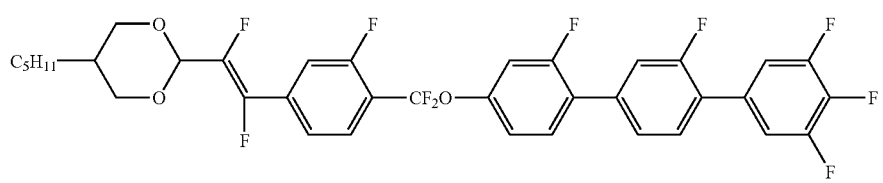
1-2-558
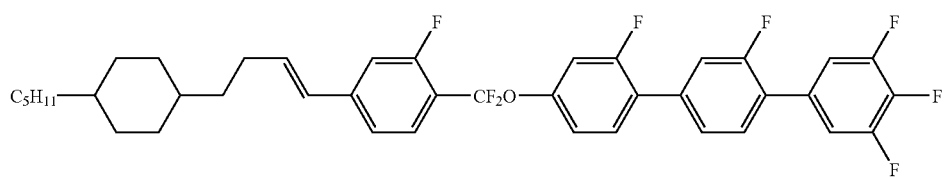
1-2-559
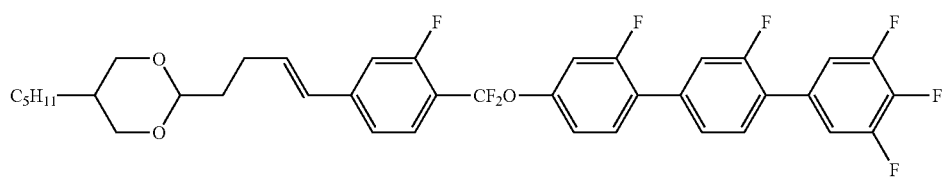
1-2-560

-continued
1-2-561
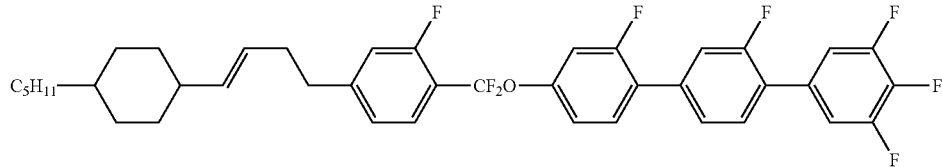
1-2-562
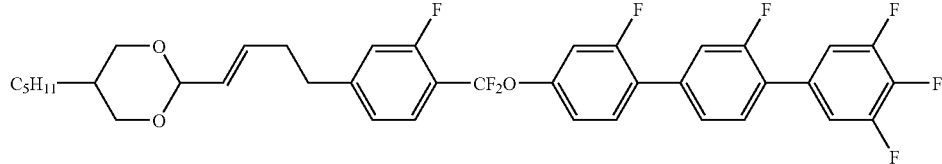
1-3-1
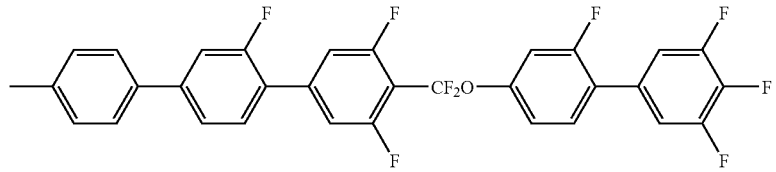
1-3-2
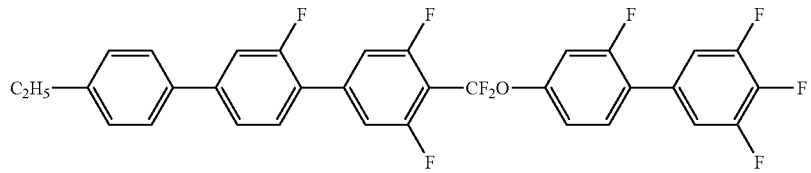
1-3-3
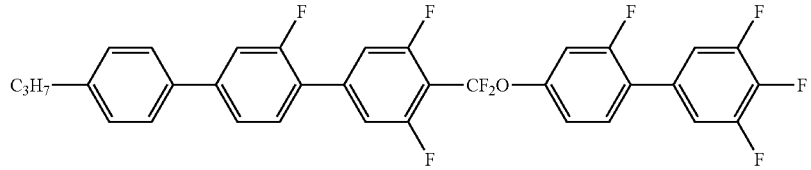
$T_{NI} = 148°$ C., $\Delta n = 0.244$, $\Delta \varepsilon = 45.2$
1-3-4
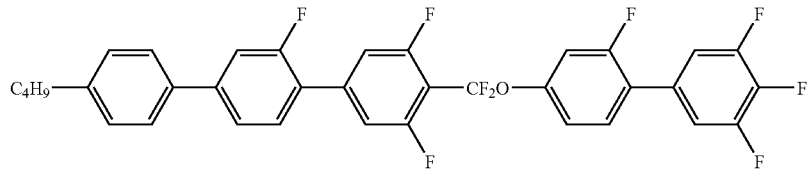
1-3-5
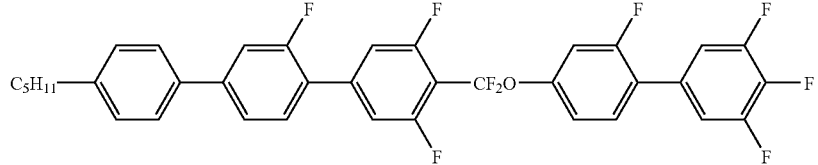
$T_{NI} = 146°$ C., $\Delta n = 0.237$, $\Delta \varepsilon = 39.0$
1-3-6
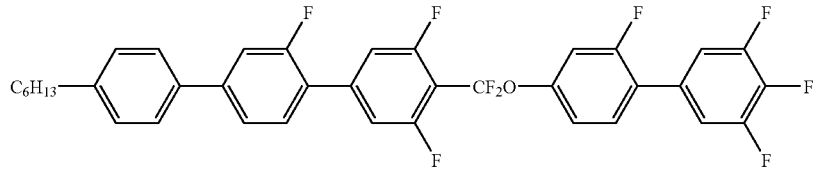

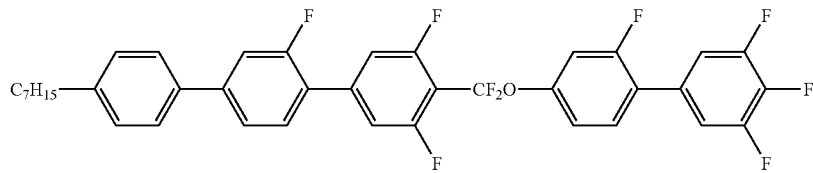
1-3-7
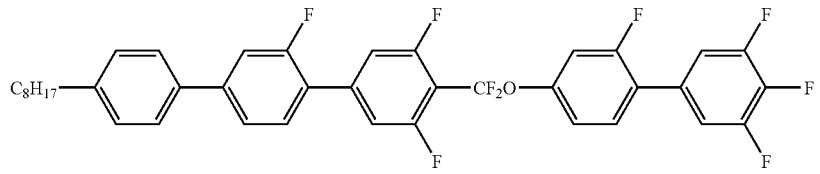
1-3-8
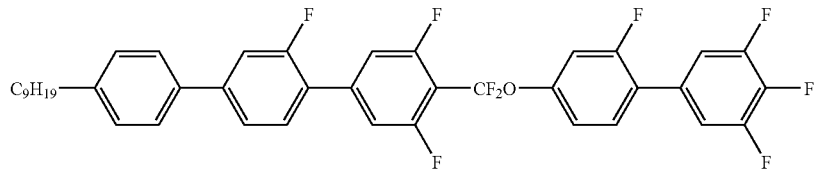
1-3-9
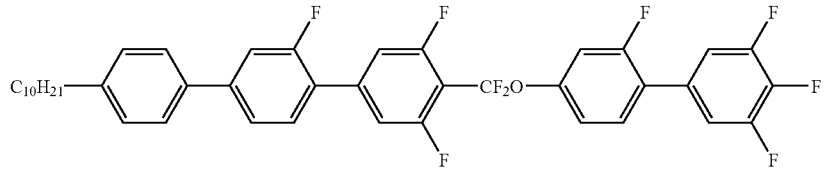
1-3-10
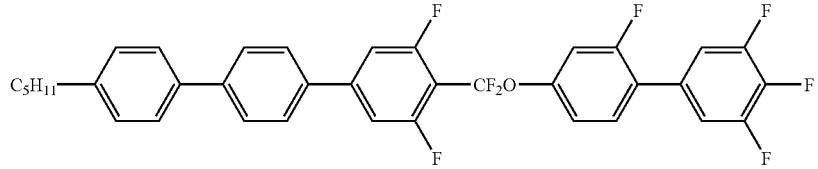
1-3-11
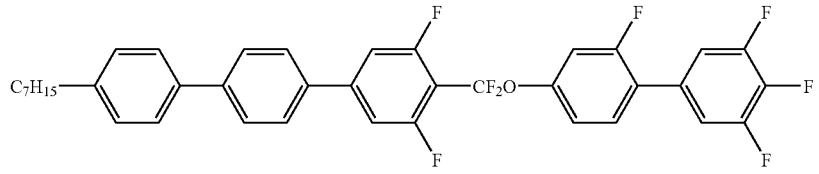
1-3-12
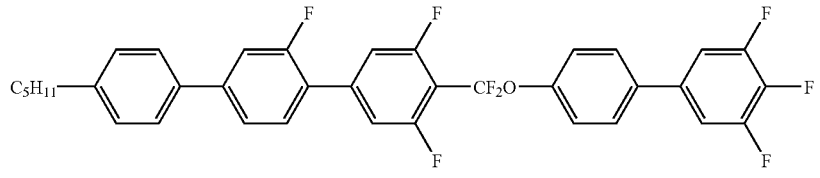
1-3-13
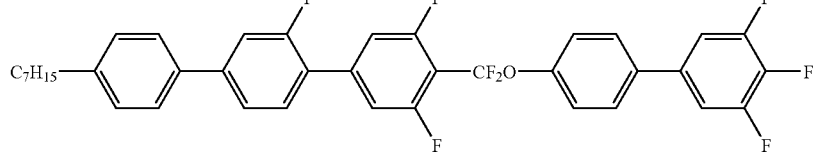
1-3-14
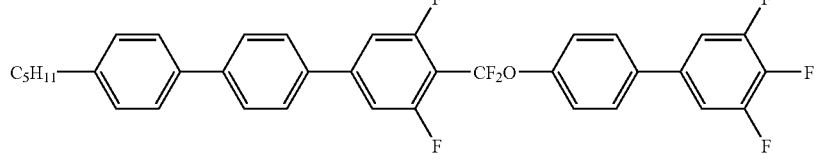
1-3-15

-continued
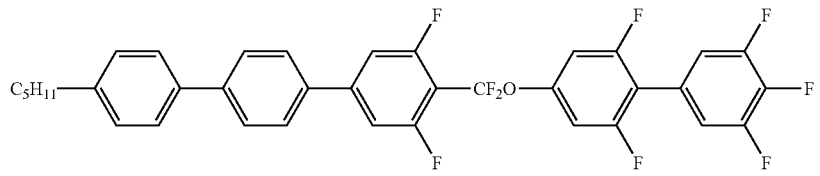
1-3-16
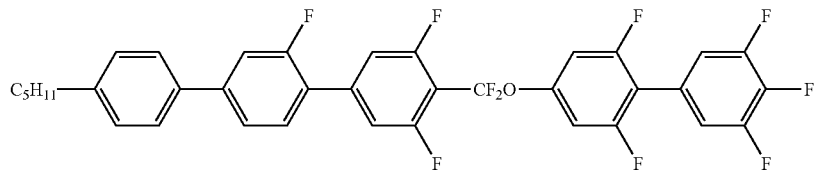
1-3-17
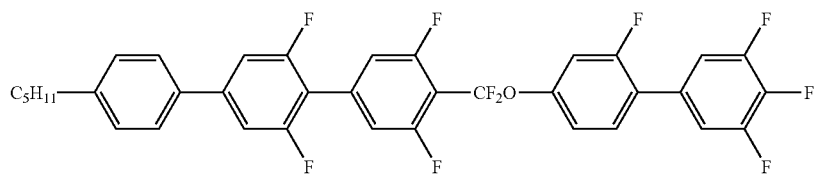
1-3-18
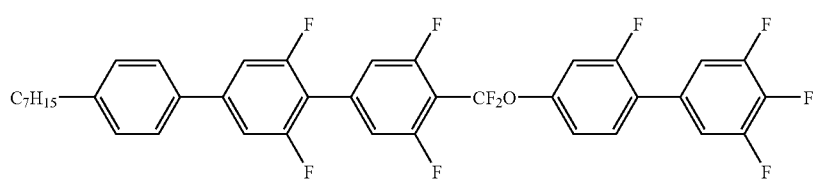
1-3-19
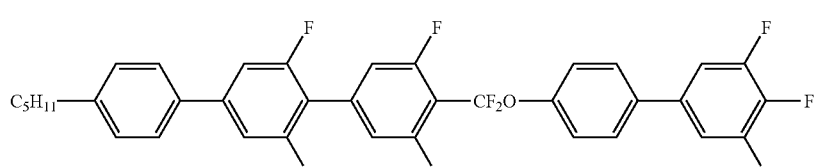
1-3-20
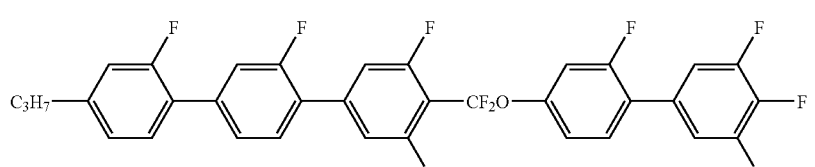
1-3-21
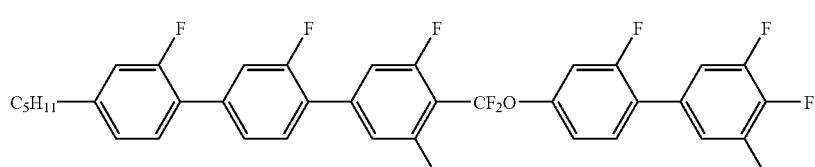
1-3-22
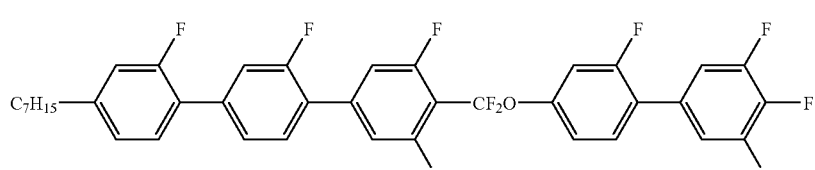
1-3-23
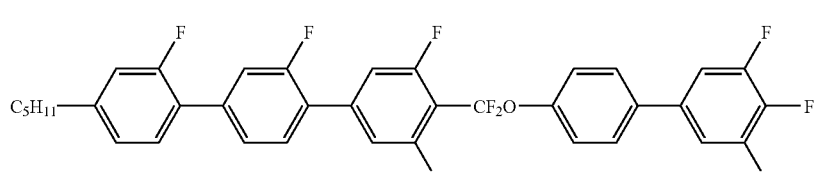
1-3-24

-continued
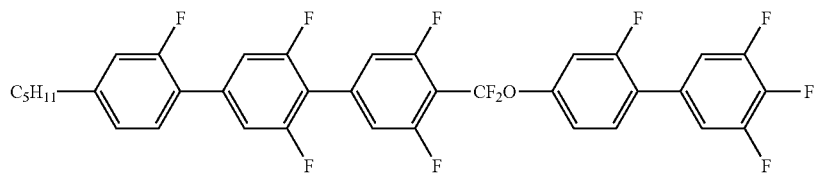
1-3-25
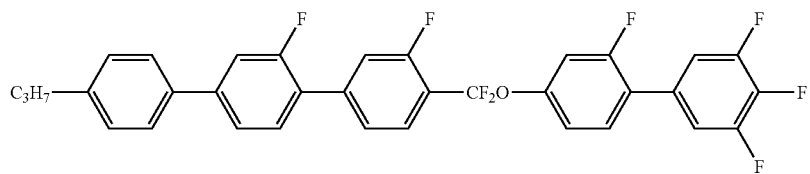
1-3-26
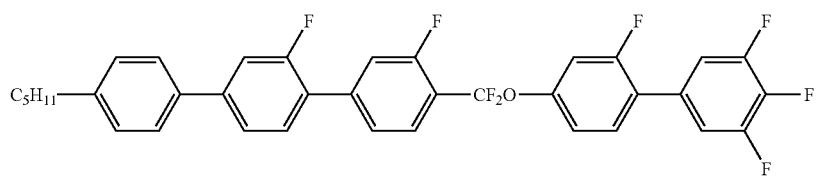
1-3-27
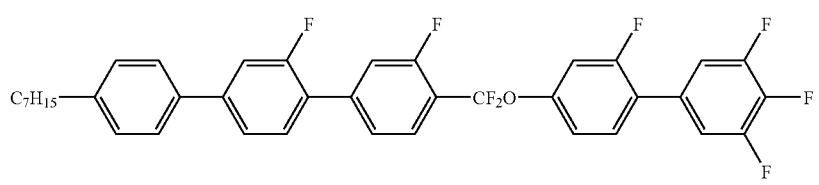
1-3-28
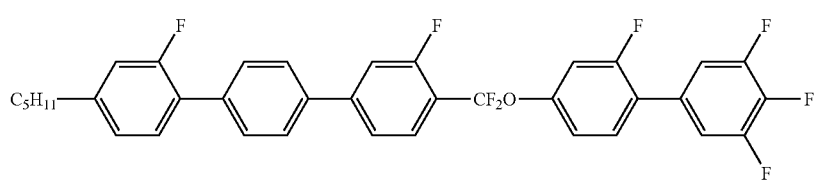
1-3-29
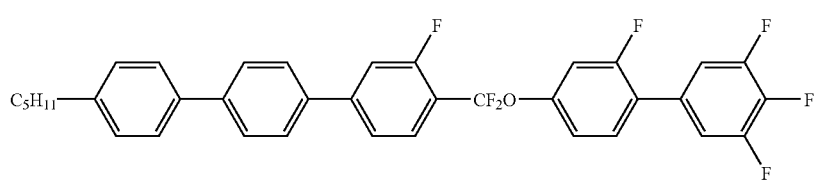
1-3-30
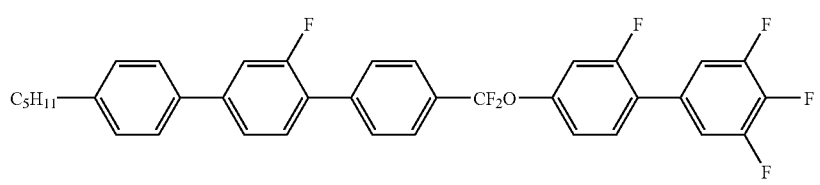
1-3-31
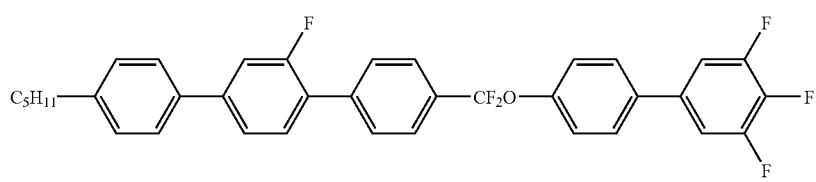
1-3-32
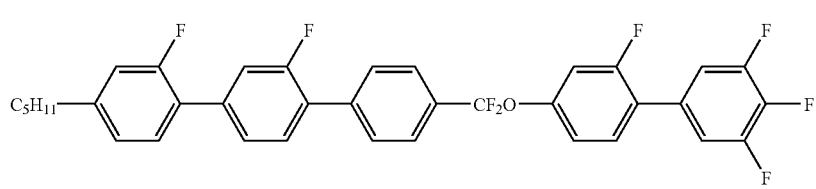
1-3-33

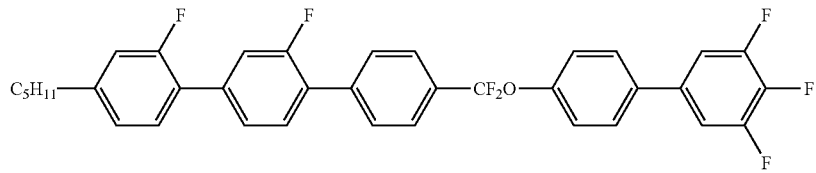
1-3-34
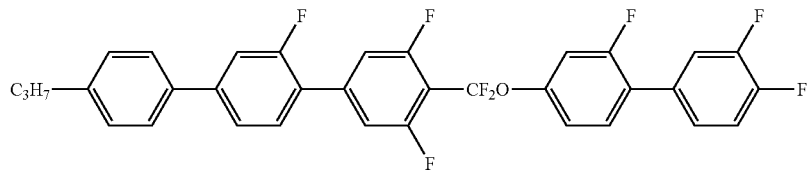
1-3-35
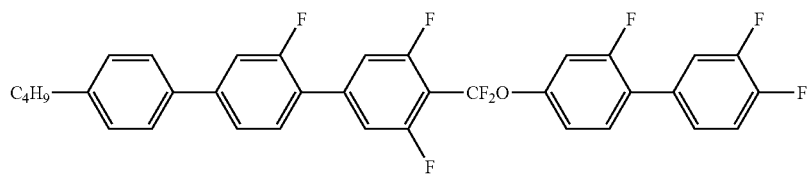
1-3-36
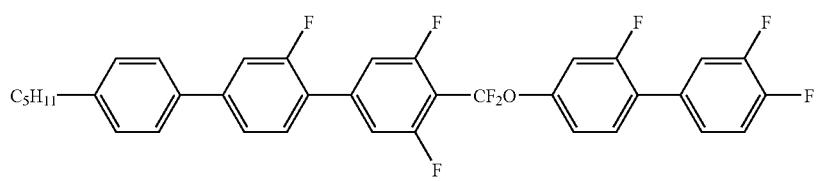
1-3-37
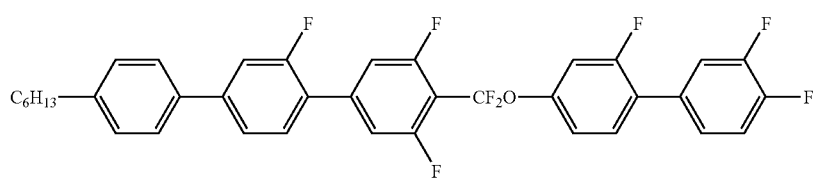
1-3-38
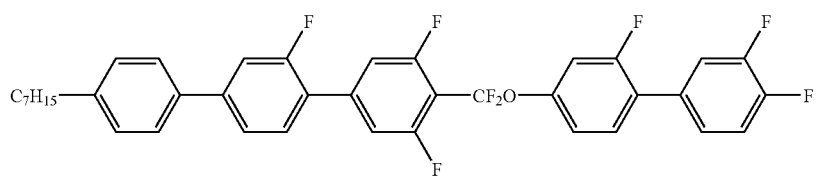
1-3-39
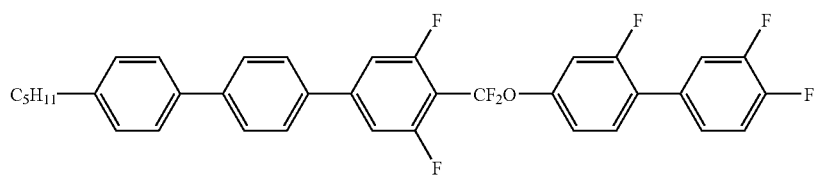
1-3-40
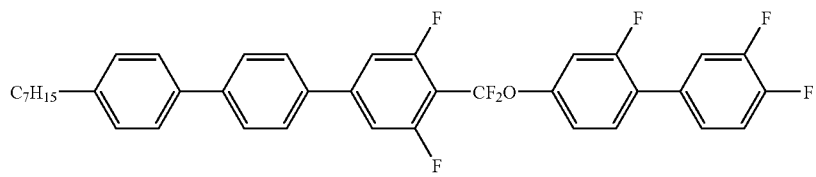
1-3-41
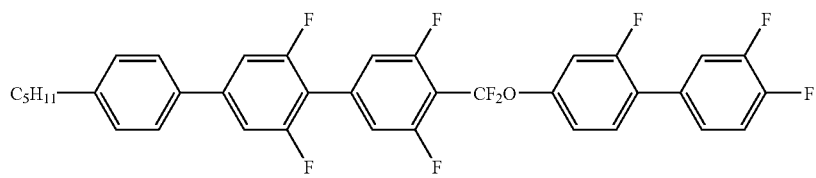
1-3-42

-continued
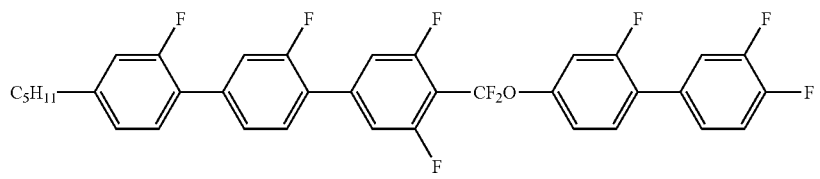
1-3-43
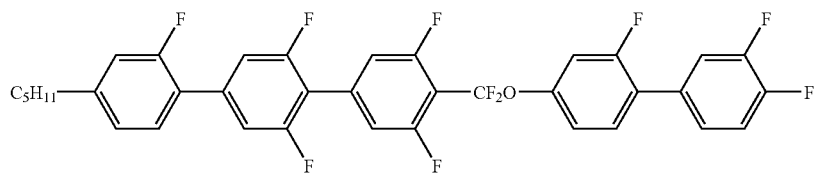
1-3-44
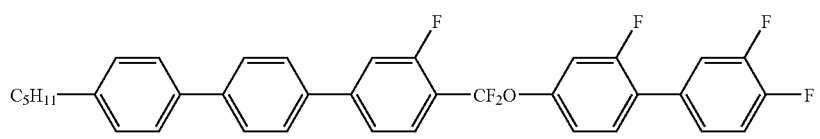
1-3-45
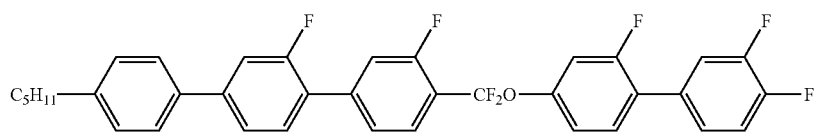
1-3-46
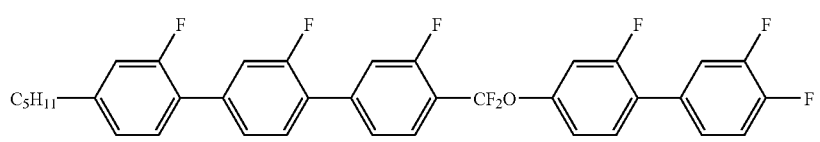
1-3-47
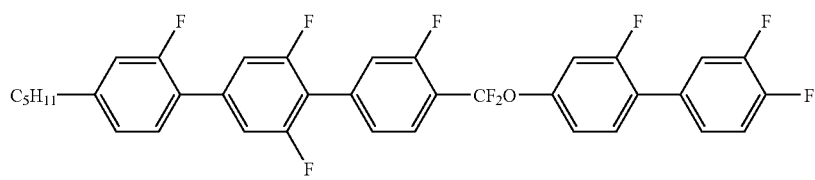
1-3-48
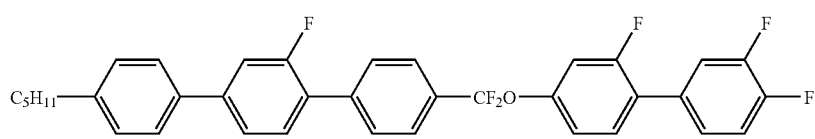
1-3-49
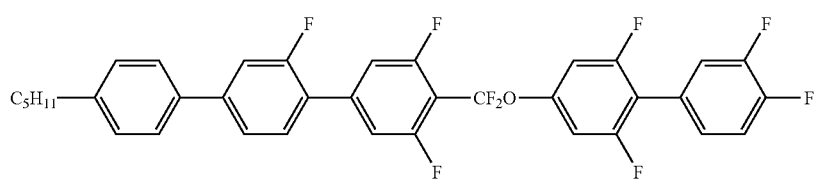
1-3-50
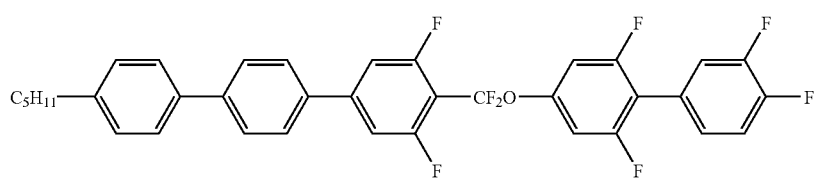
1-3-51
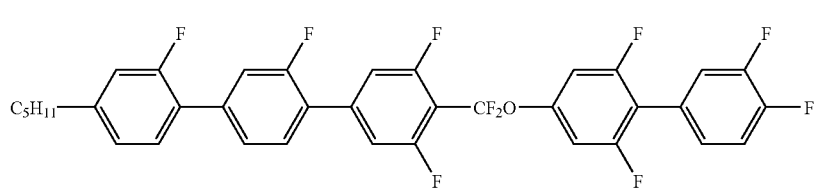
1-3-52

-continued
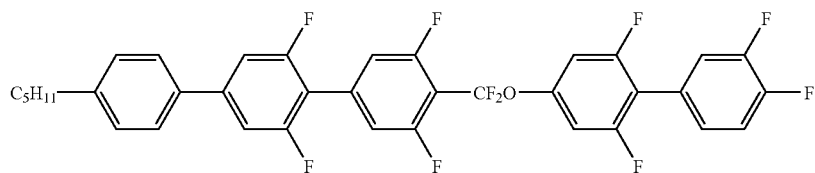
1-3-53
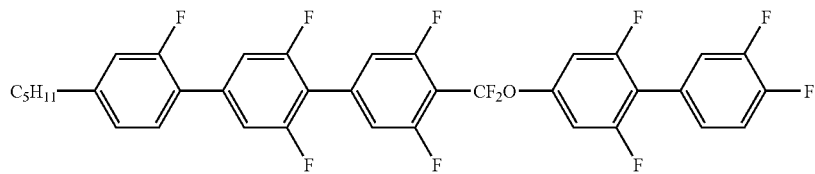
1-3-54
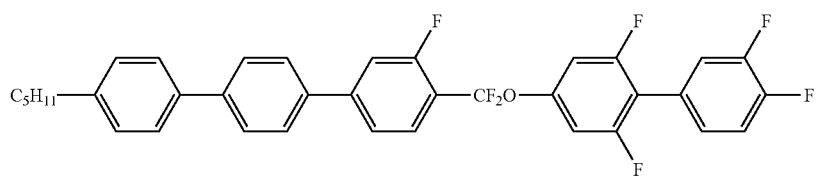
1-3-55
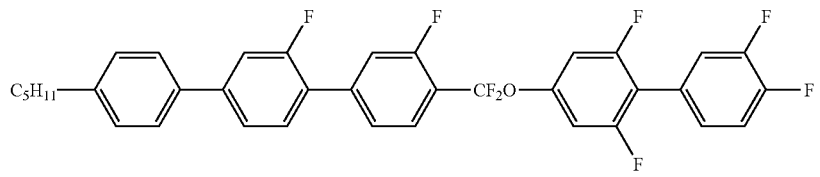
1-3-56
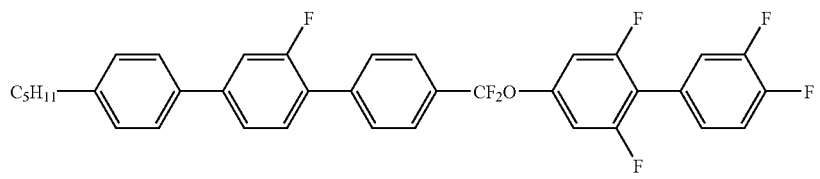
1-3-57
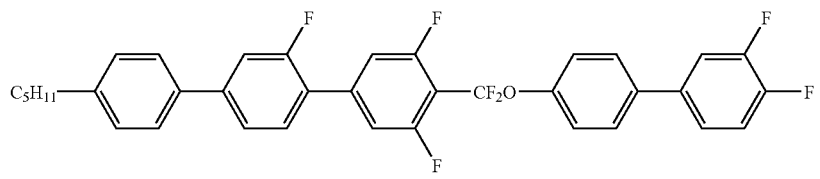
1-3-58
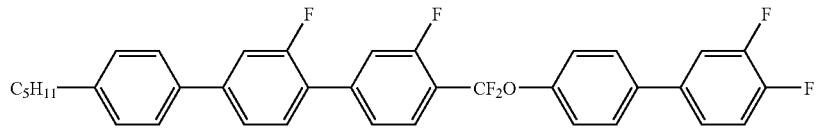
1-3-59
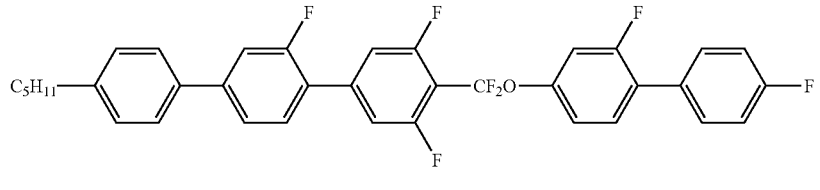
1-3-60
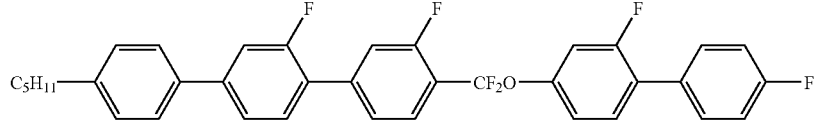
1-3-61

-continued
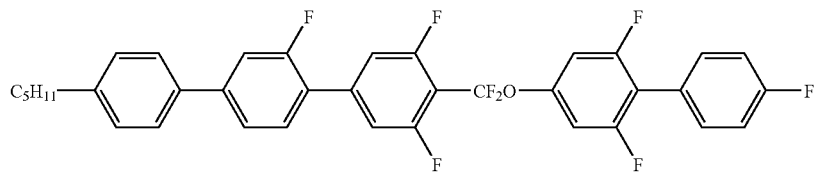
1-3-62
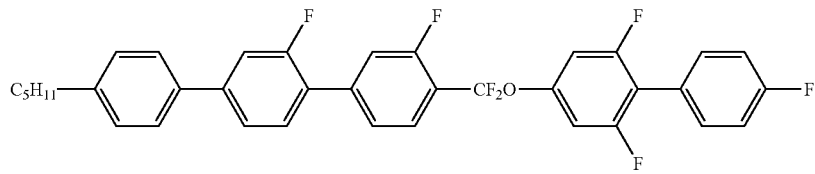
1-3-63
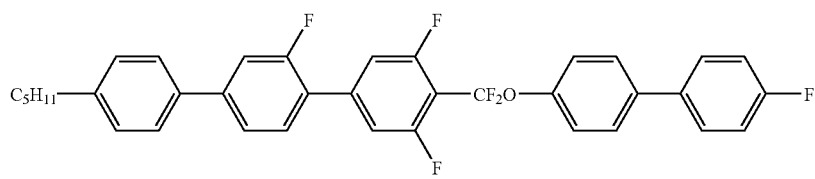
1-3-64
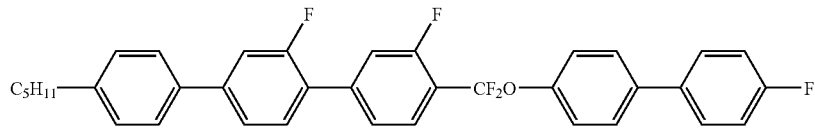
1-3-65
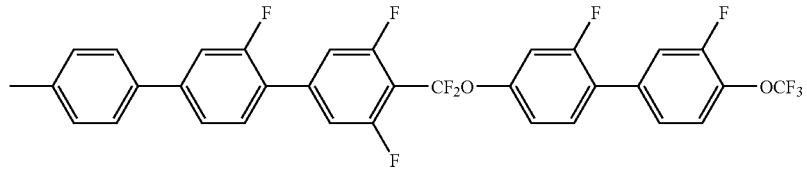
1-3-66
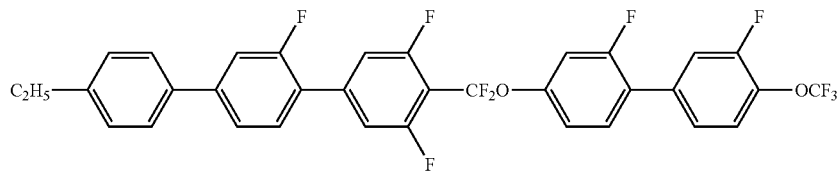
1-3-67
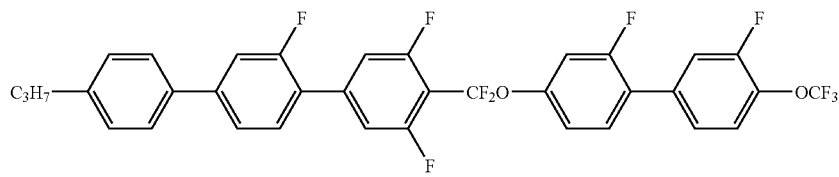
1-3-68
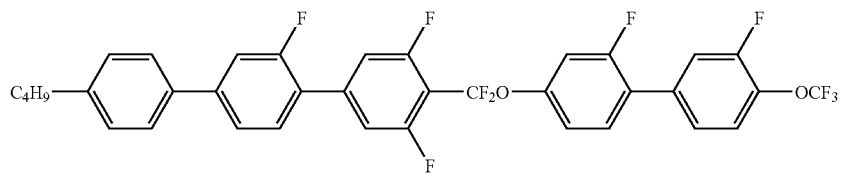
1-3-69
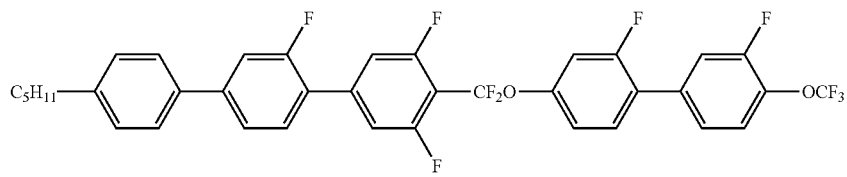
1-3-70
$T_{NI} = 155°$ C., $\Delta n = 0.230$, $\Delta \varepsilon\ 30.9$ -continued
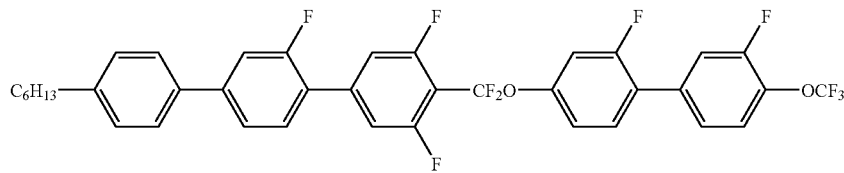
1-3-71
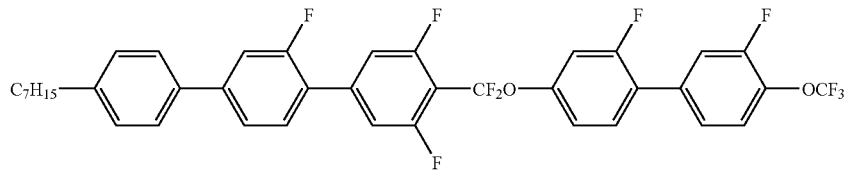
1-3-72
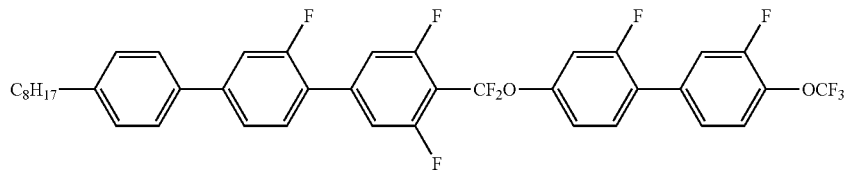
1-3-73
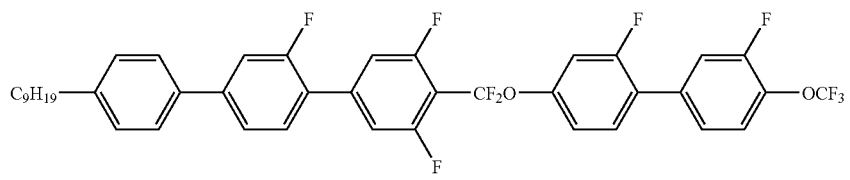
1-3-74
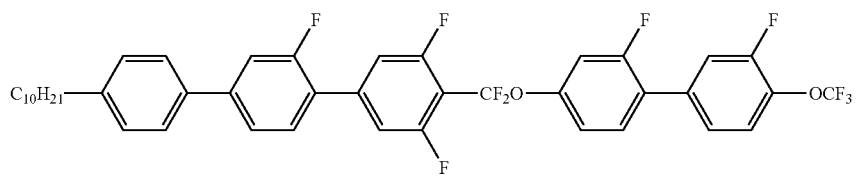
1-3-75
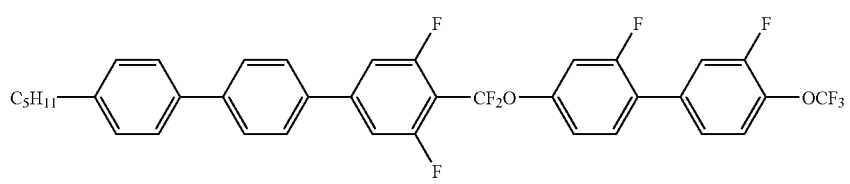
1-3-76
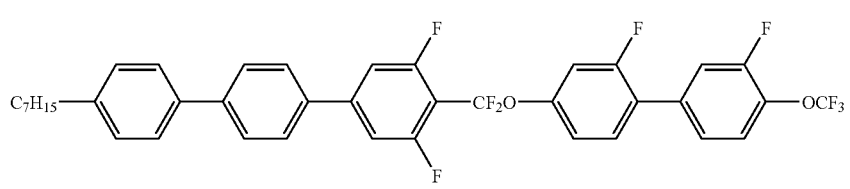
1-3-77
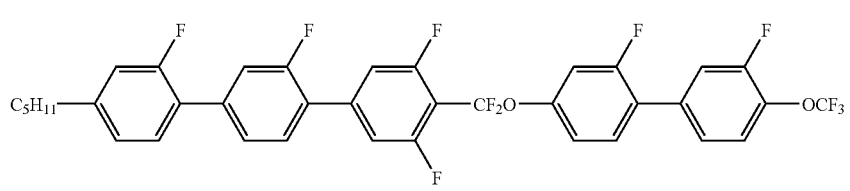
1-3-78
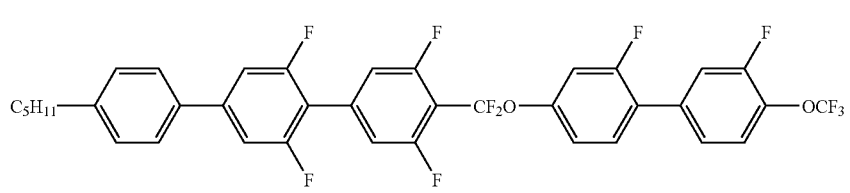
1-3-79

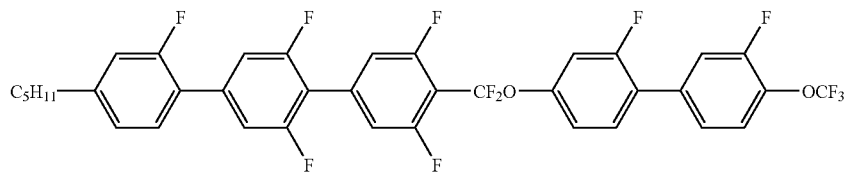
1-3-80
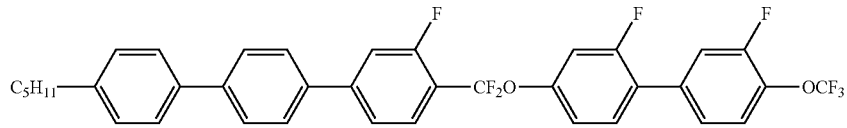
1-3-81
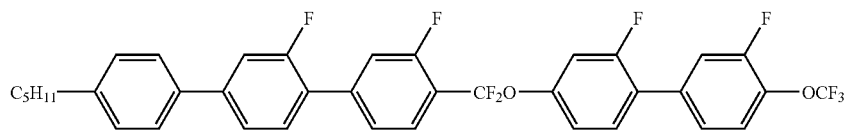
1-3-82
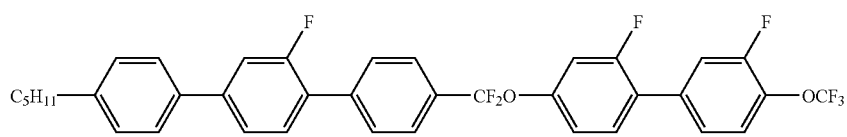
1-3-83
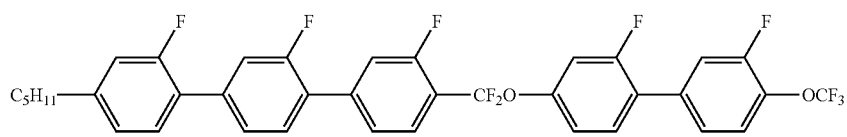
1-3-84
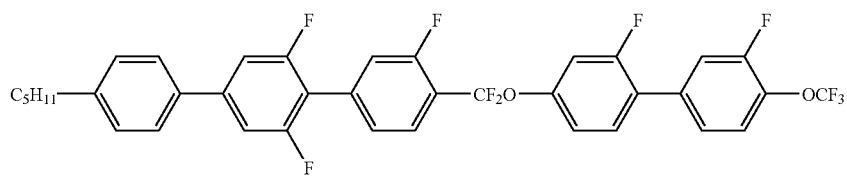
1-3-85
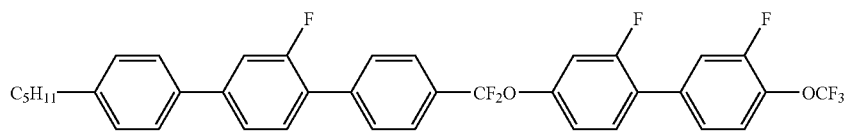
1-3-86
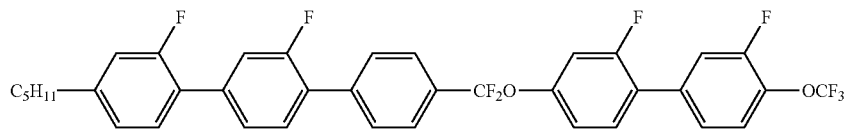
1-3-87
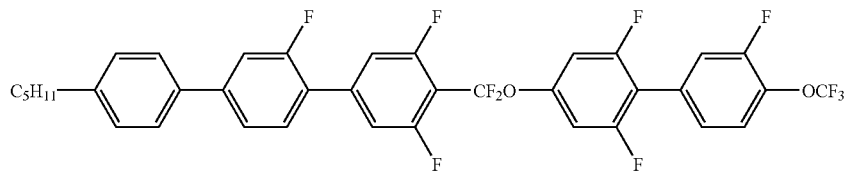
1-3-88
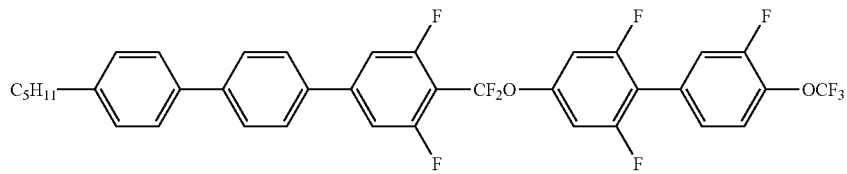
1-3-89

-continued
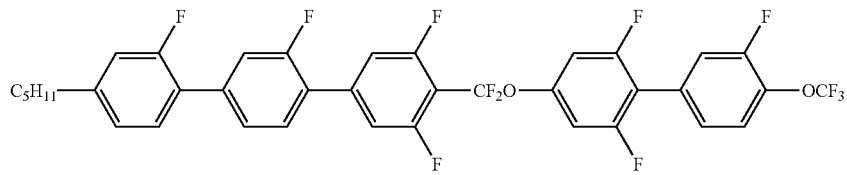
1-3-90
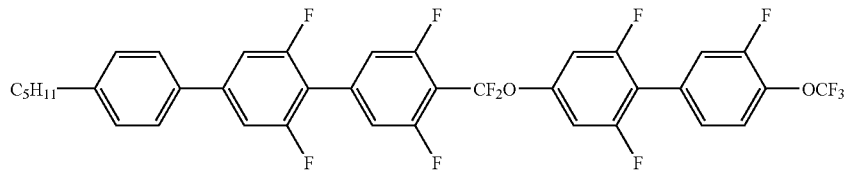
1-3-91
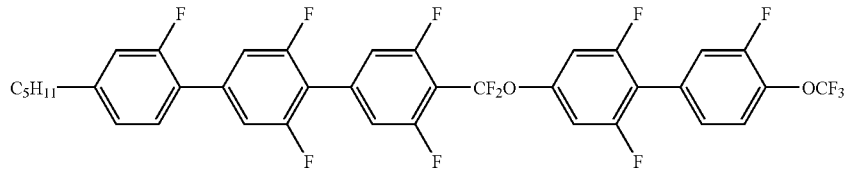
1-3-92
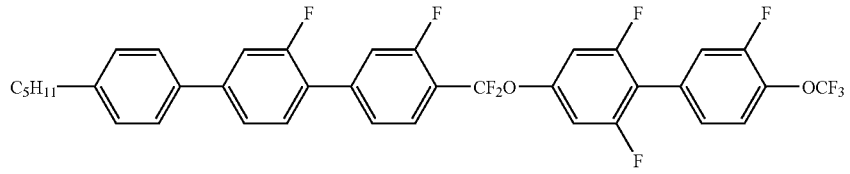
1-3-93
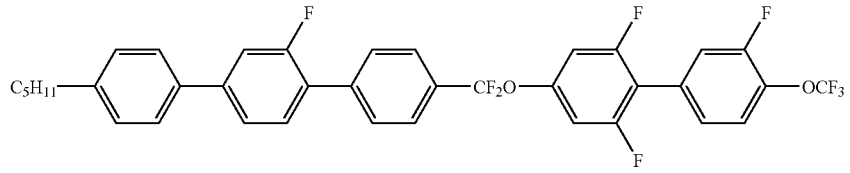
1-3-94
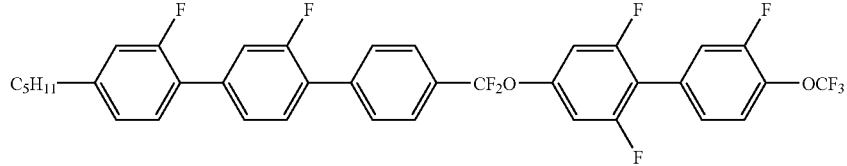
1-3-95
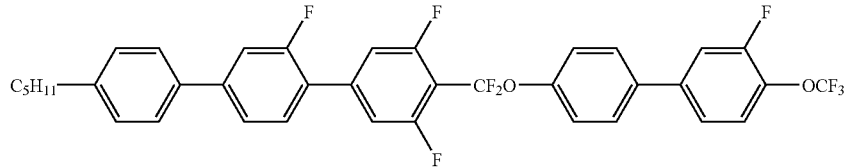
1-3-96
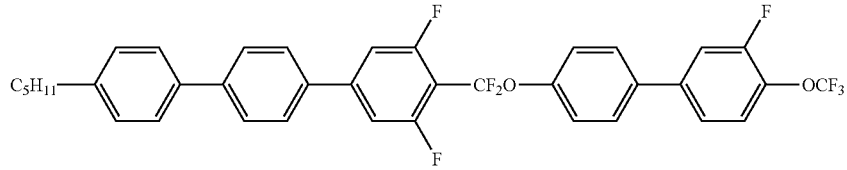
1-3-97
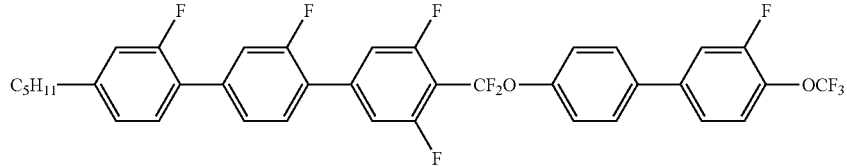
1-3-98

-continued
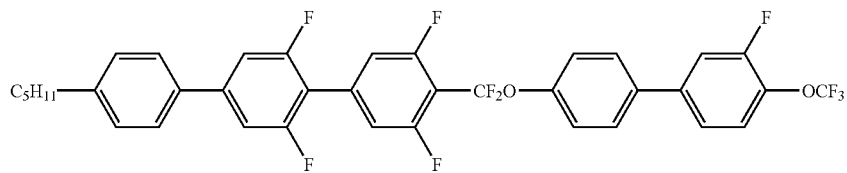
1-3-99
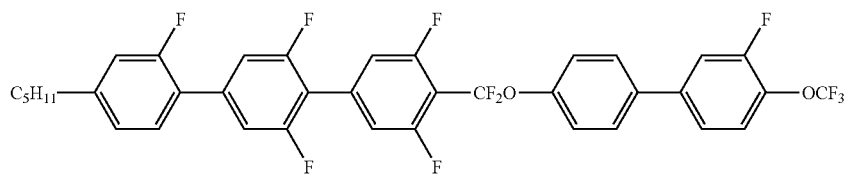
1-3-100
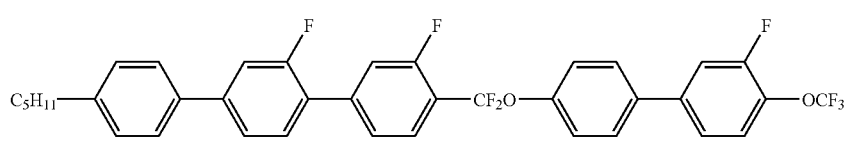
1-3-101
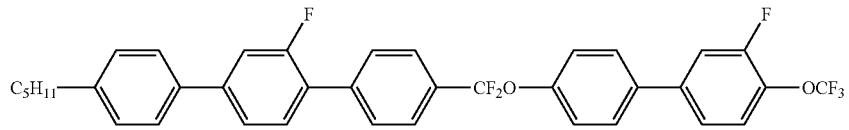
1-3-102
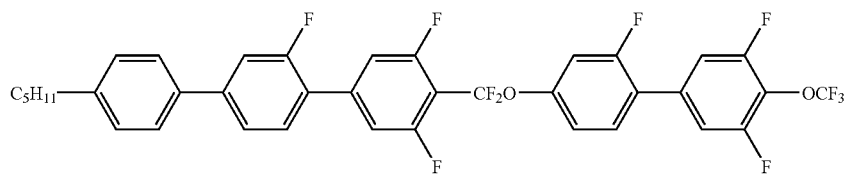
1-3-103
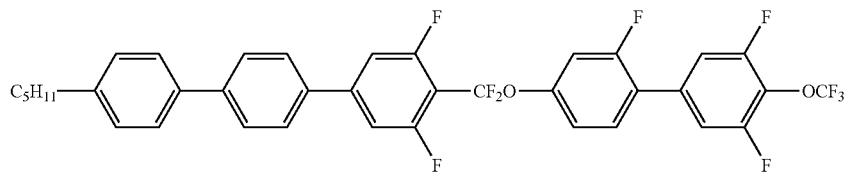
1-3-104
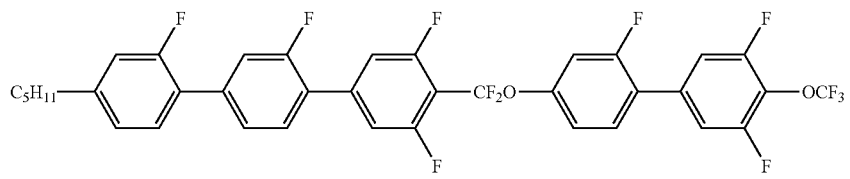
1-3-105
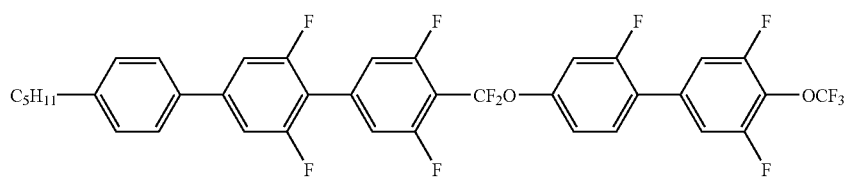
1-3-106
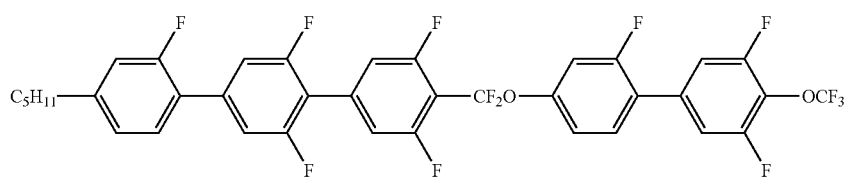
1-3-107

-continued
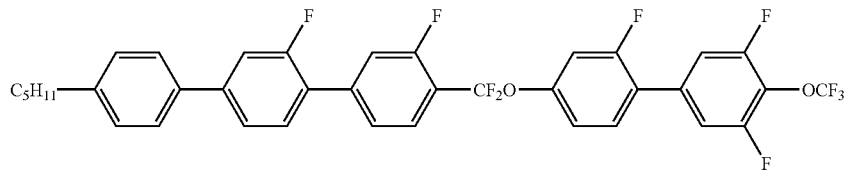
1-3-108
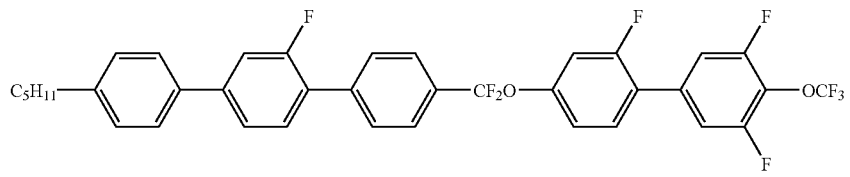
1-3-109
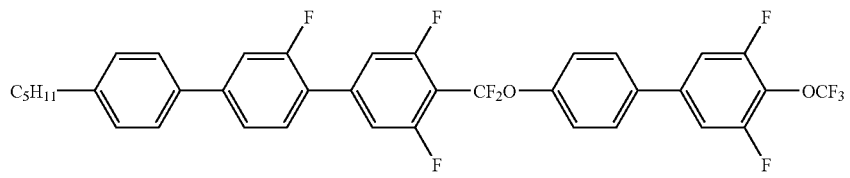
1-3-110
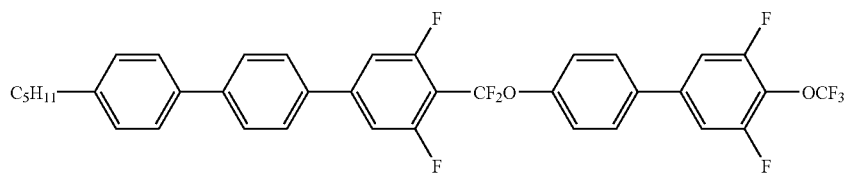
1-3-111
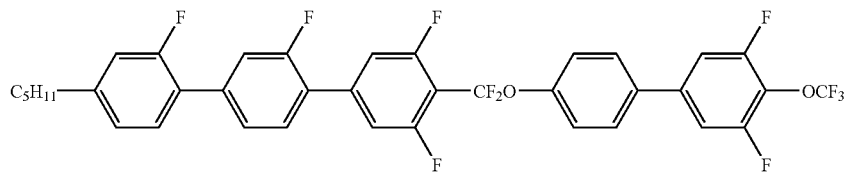
1-3-112
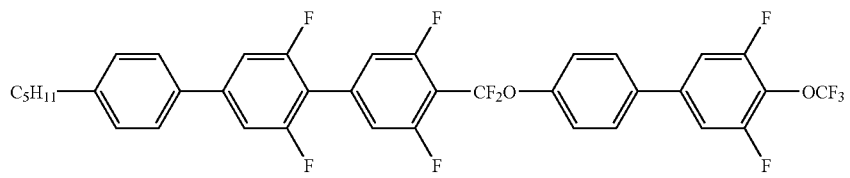
1-3-113
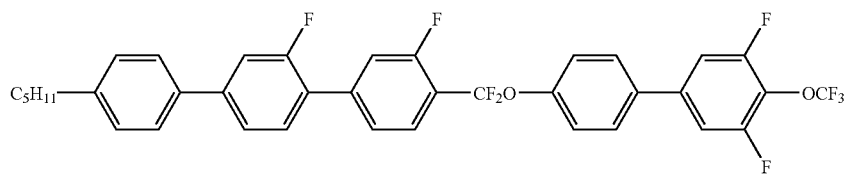
1-3-114
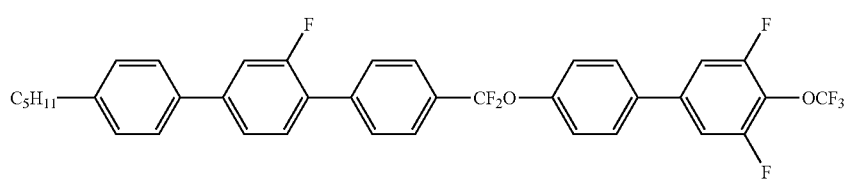
1-3-115
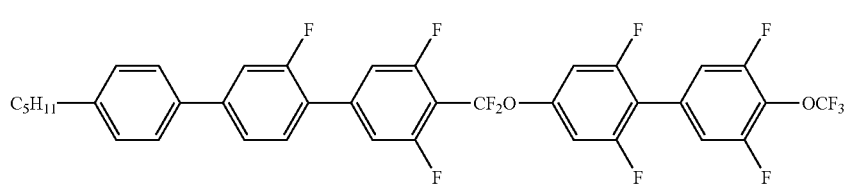
1-3-116

-continued
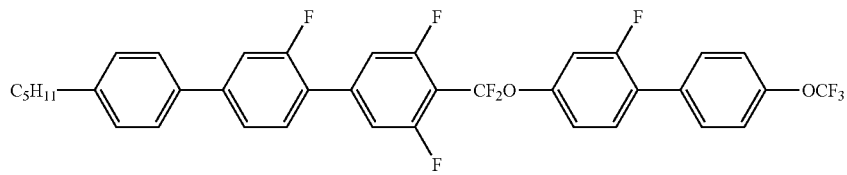
1-3-117
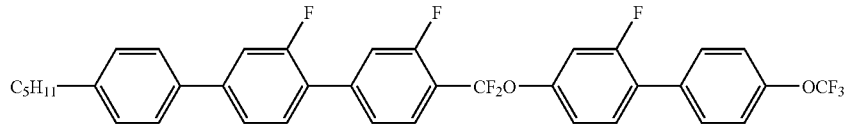
1-3-118
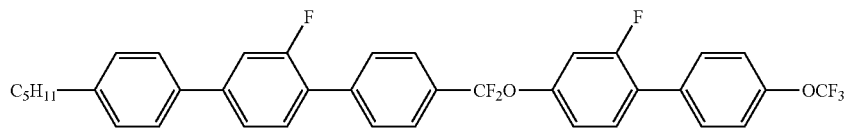
1-3-119
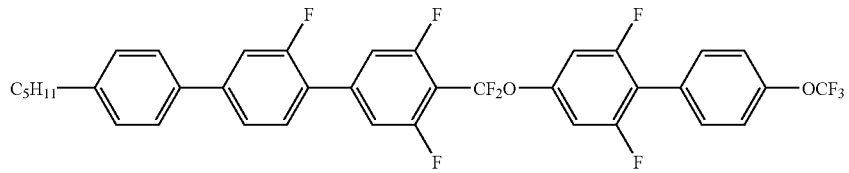
1-3-120
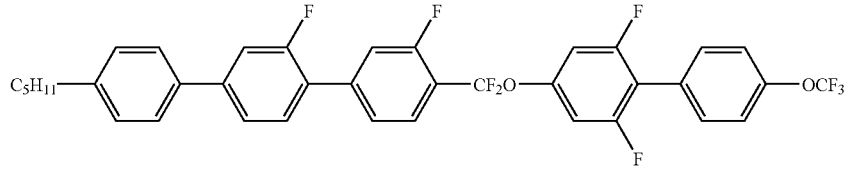
1-3-121
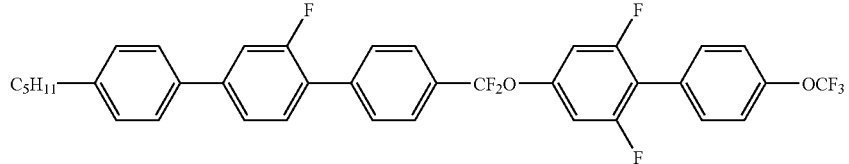
1-3-122
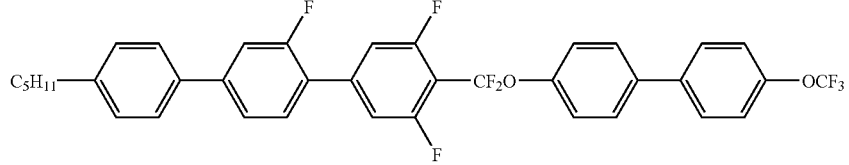
1-3-123
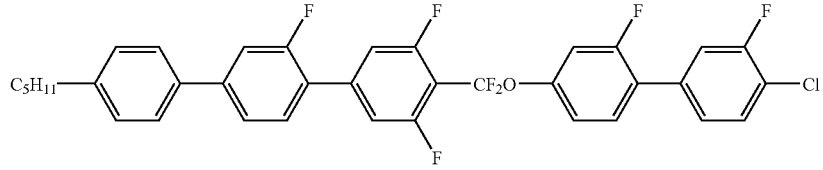
1-3-124
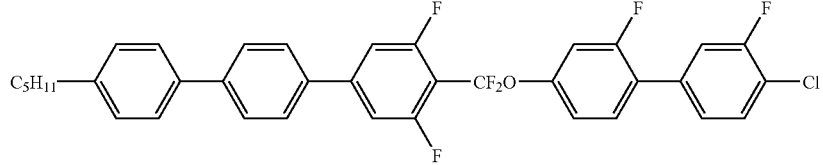
1-3-125

-continued
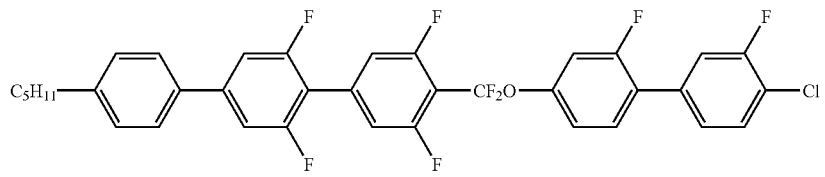
1-3-126
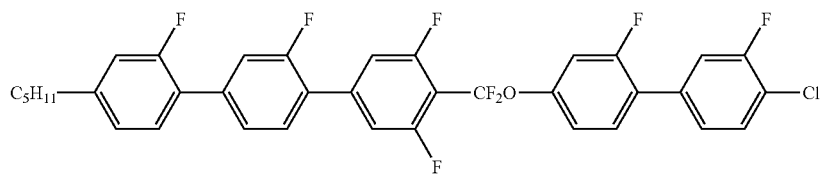
1-3-127
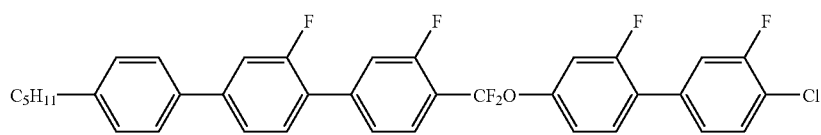
1-3-128
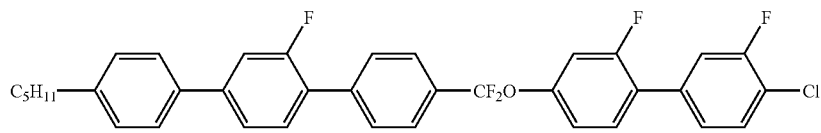
1-3-129
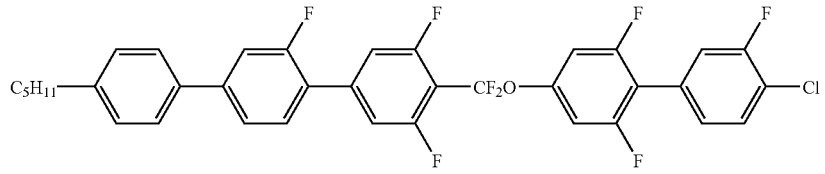
1-3-130
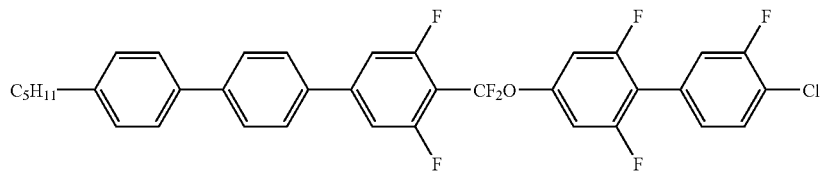
1-3-131
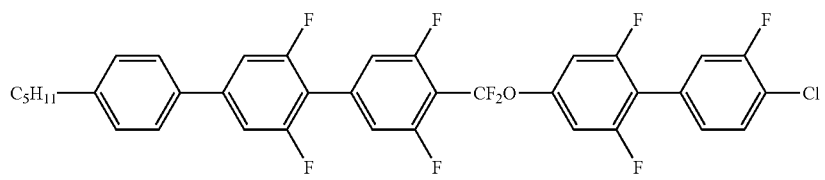
1-3-132
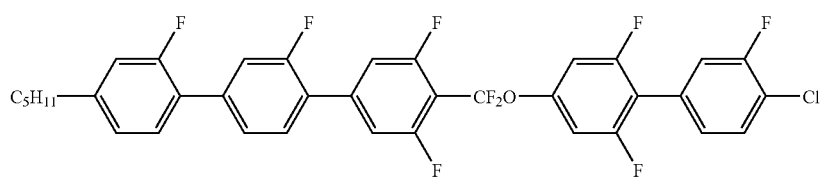
1-3-133
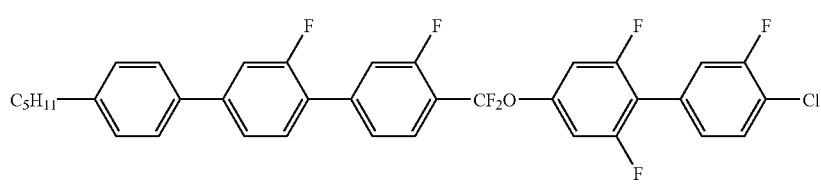
1-3-134

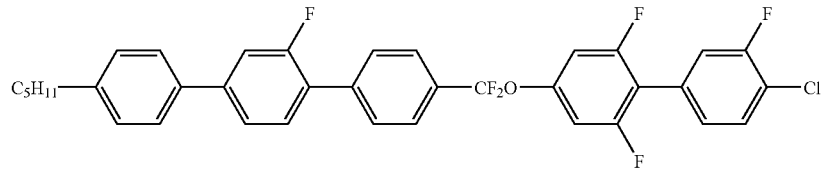 1-3-135
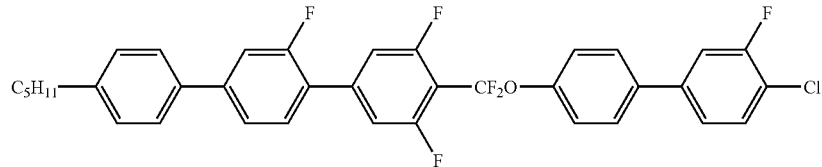 1-3-136
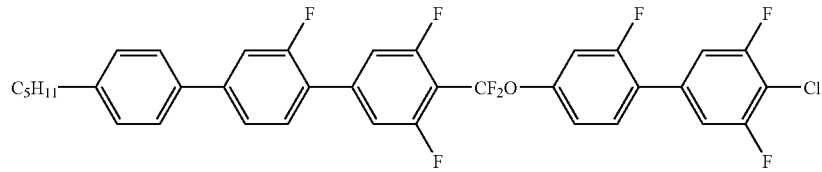 1-3-137
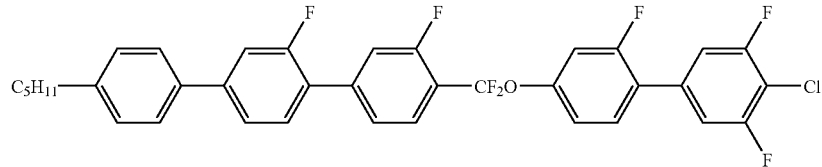 1-3-138
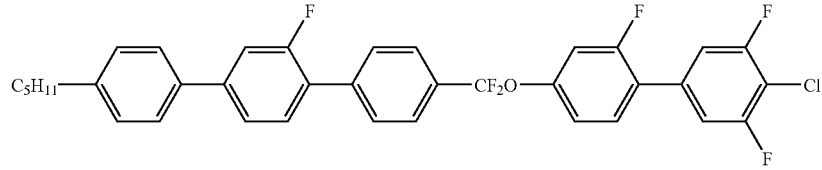 1-3-139
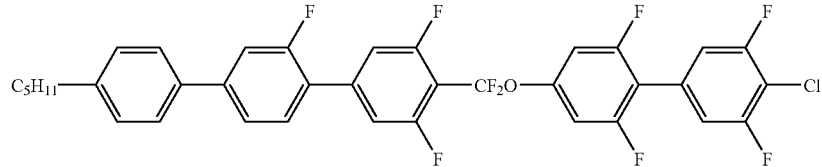 1-3-140
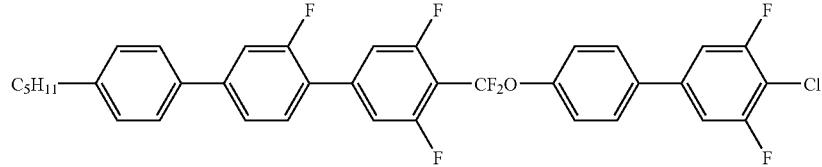 1-3-141
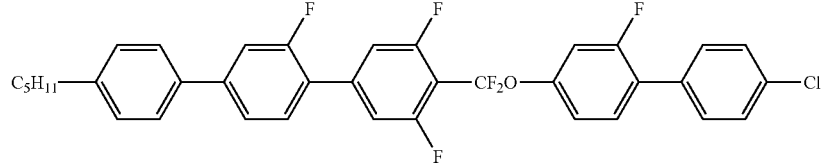 1-3-142
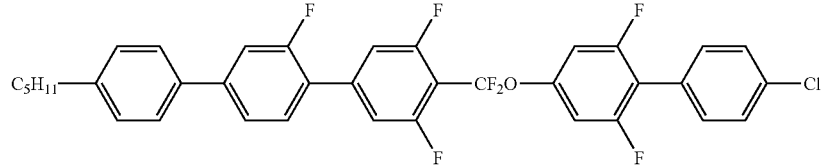 1-3-143

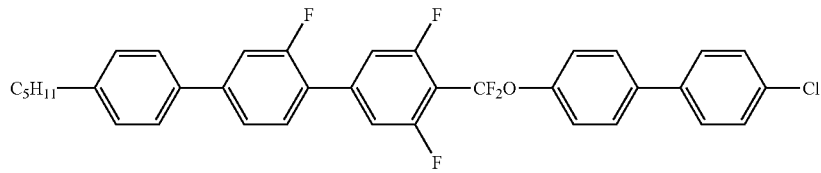
1-3-144
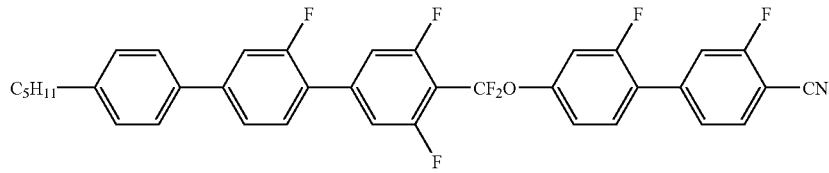
1-3-145
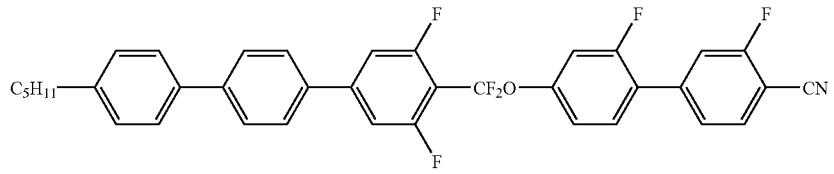
1-3-146
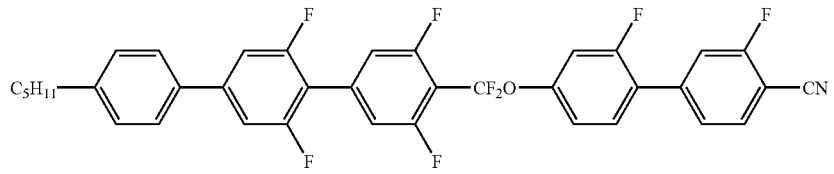
1-3-147
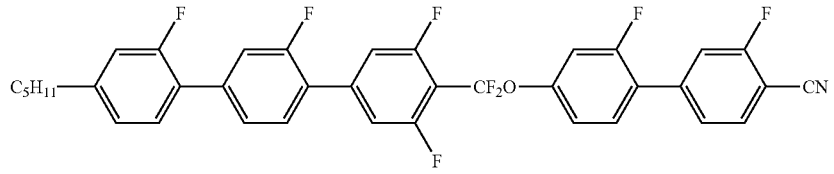
1-3-148
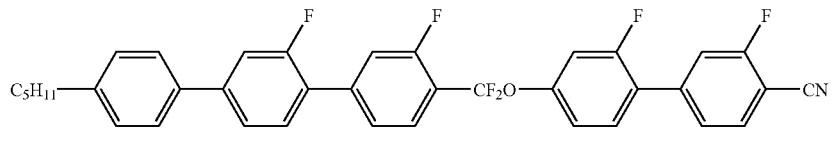
1-3-149

1-3-150
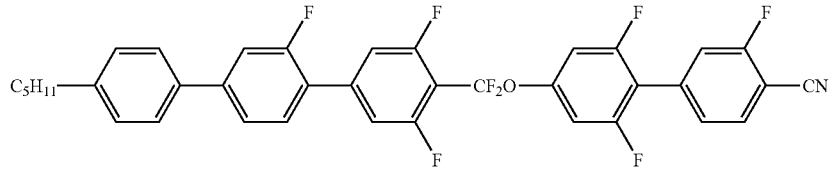
1-3-151
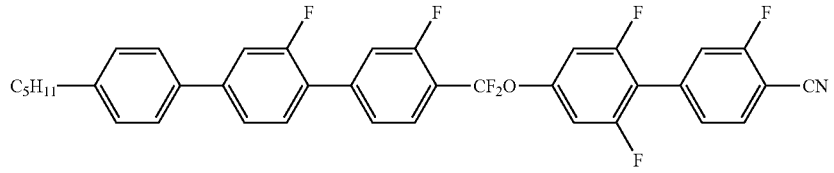
1-3-152

-continued
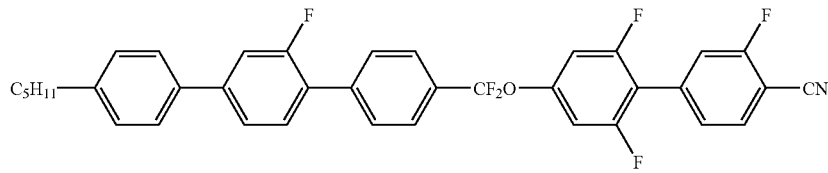
1-3-153
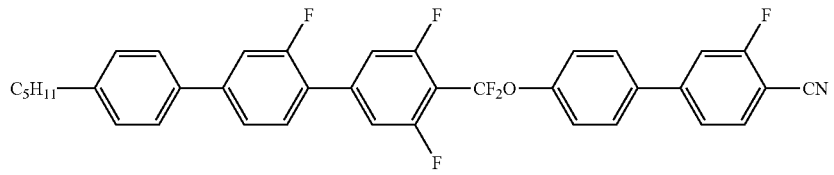
1-3-154
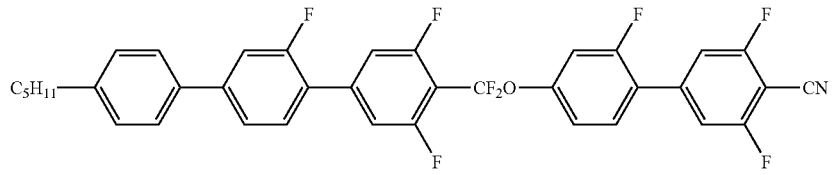
1-3-155
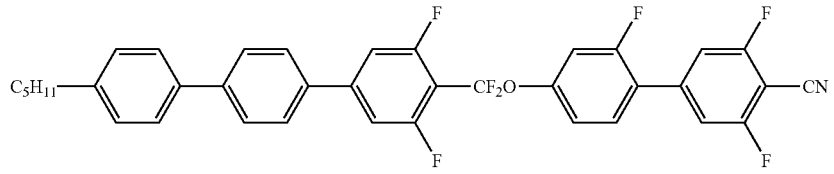
1-3-156
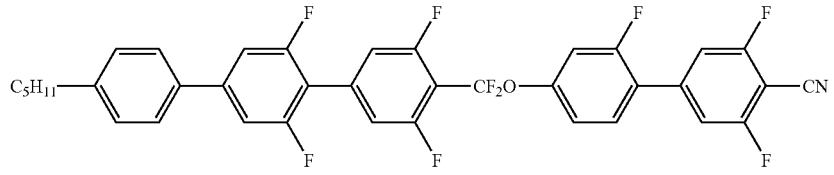
1-3-157
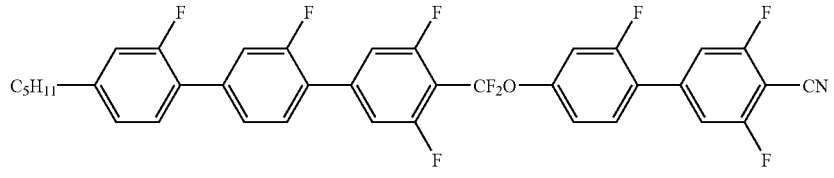
1-3-158
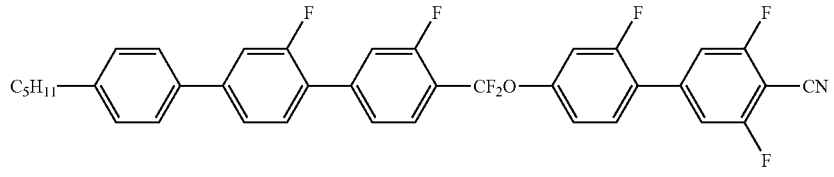
1-3-159
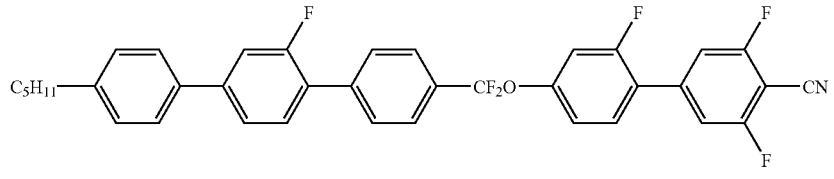
1-3-160
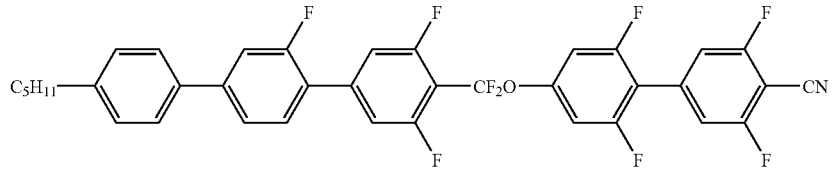
1-3-161

-continued
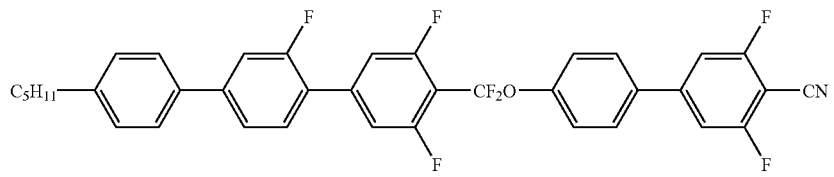
1-3-162

1-3-163
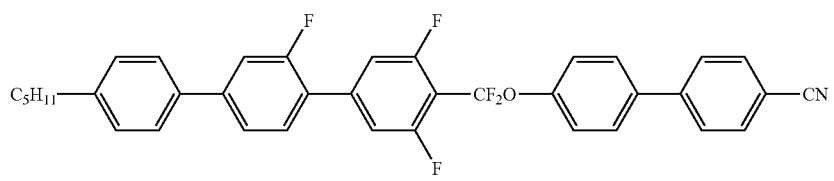
1-3-164
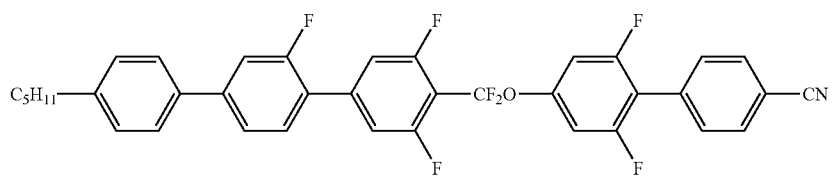
1-3-165
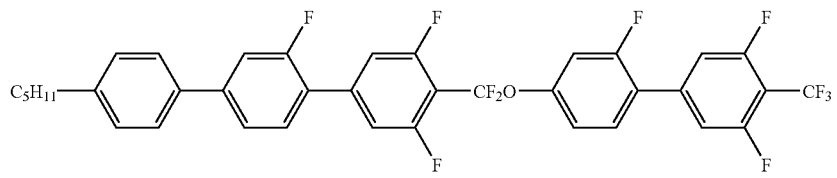
1-3-166

1-3-167
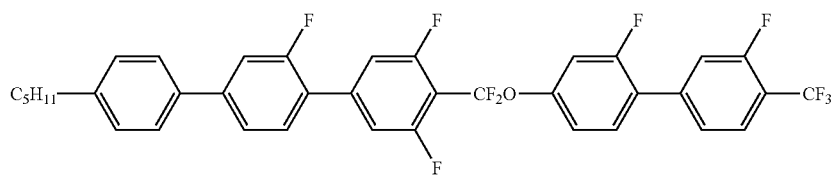
1-3-168
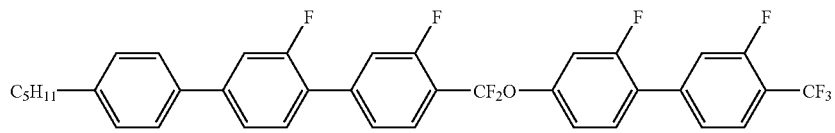
1-3-169
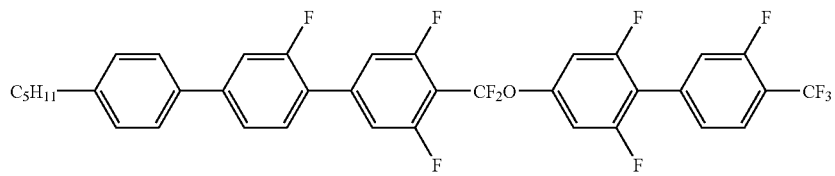
1-3-170

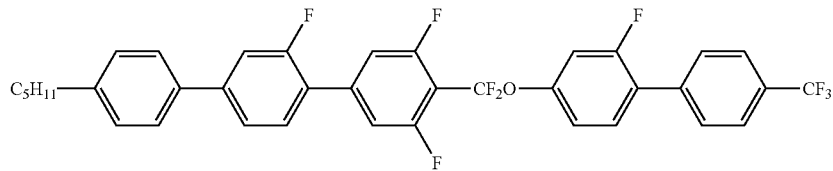 1-3-171
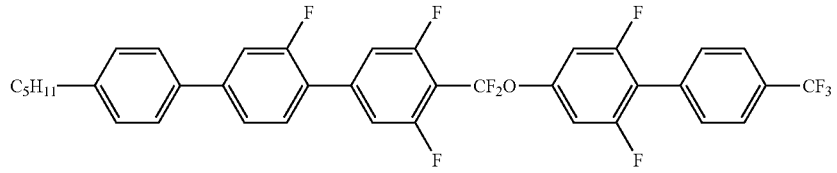 1-3-172
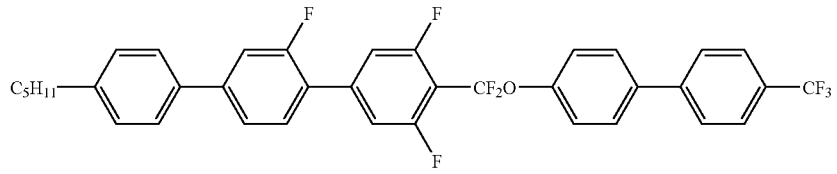 1-3-173
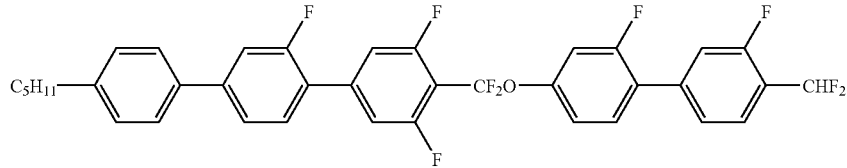 1-3-174
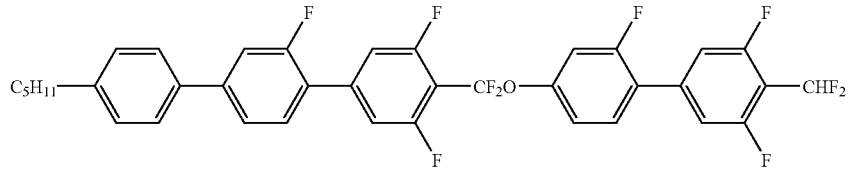 1-3-175
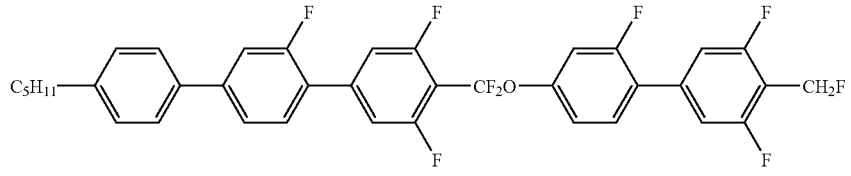 1-3-176
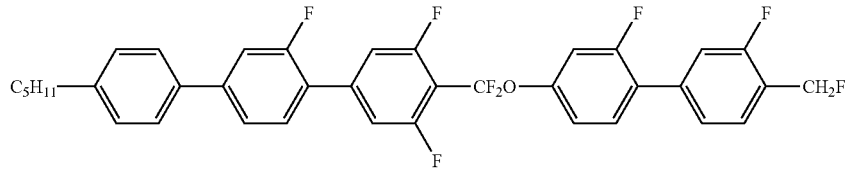 1-3-177
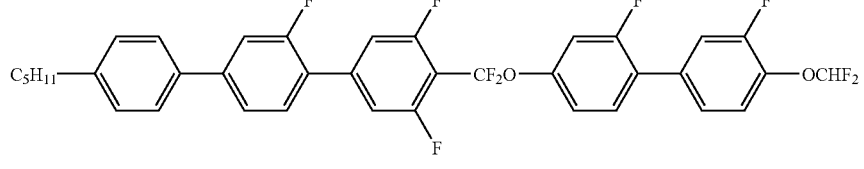 1-3-178
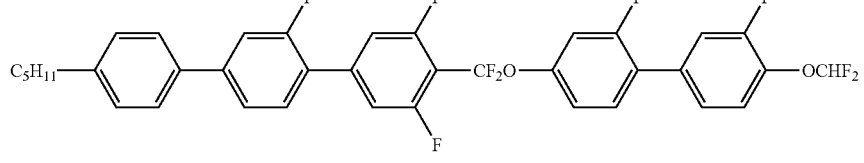 1-3-179

-continued
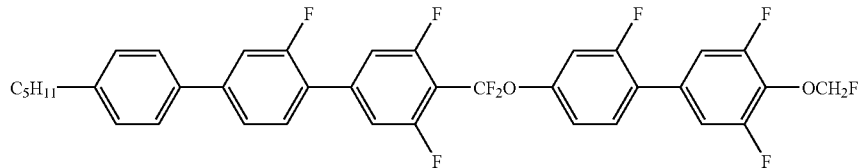
1-3-180
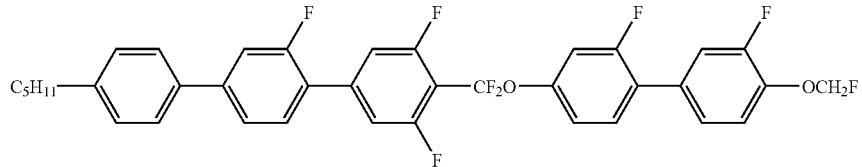
1-3-181
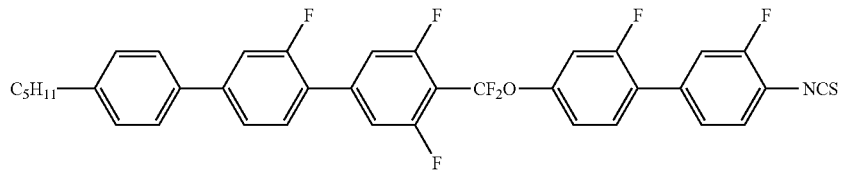
1-3-182
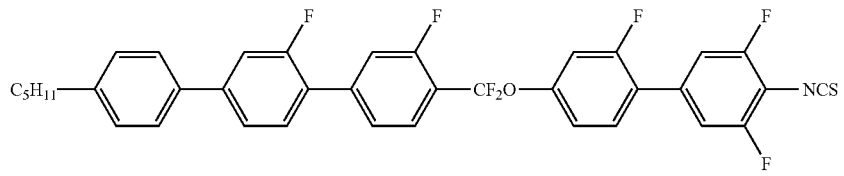
1-3-183
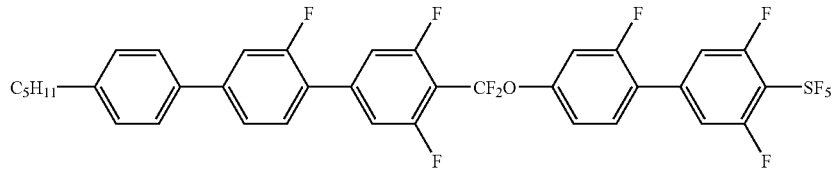
1-3-184
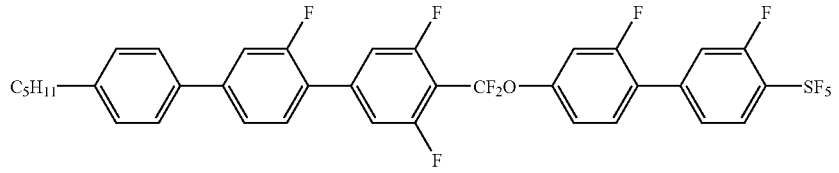
1-3-185
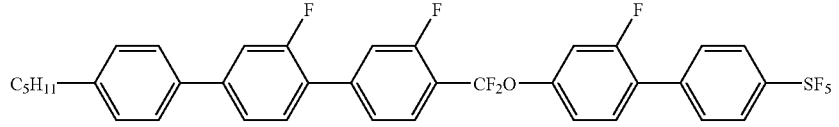
1-3-186
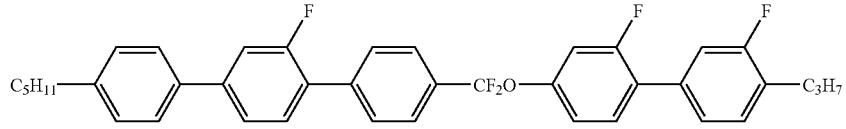
1-3-187
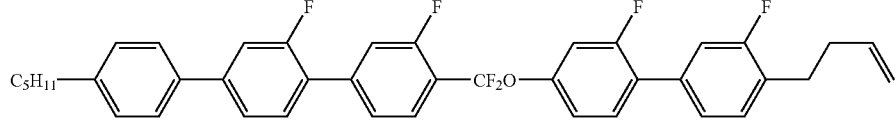
1-3-188
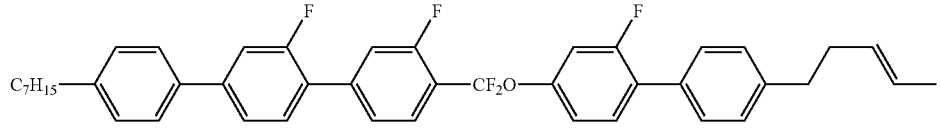
1-3-189

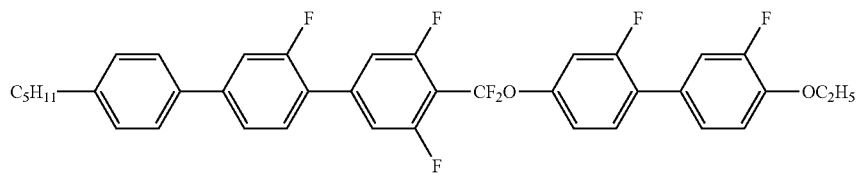
1-3-190
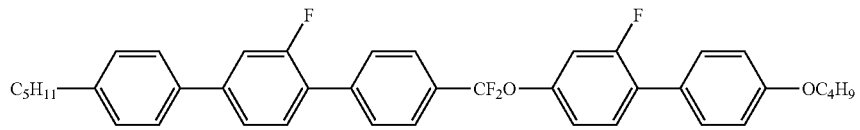
1-3-191
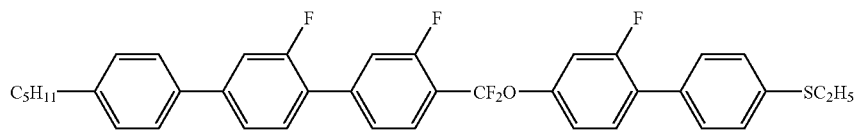
1-3-192
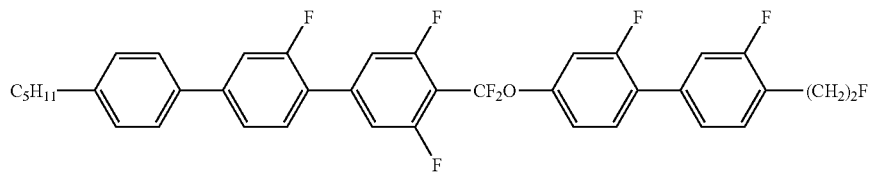
1-3-193
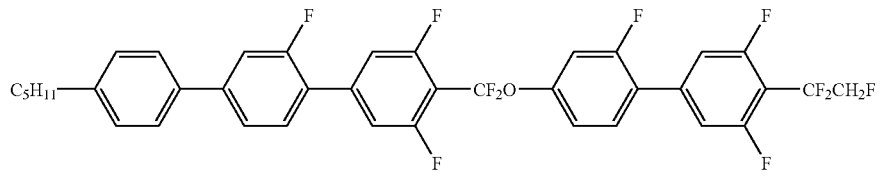
1-3-194
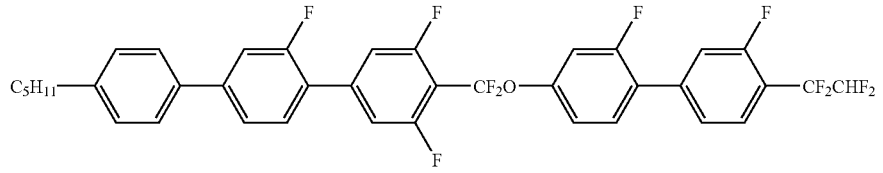
1-3-195
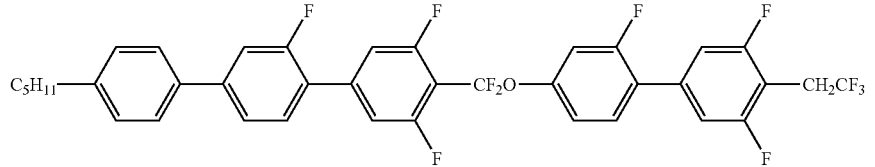
1-3-196
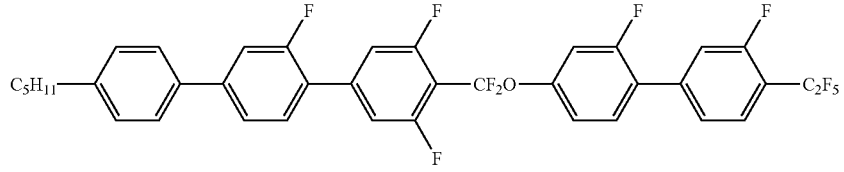
1-3-197
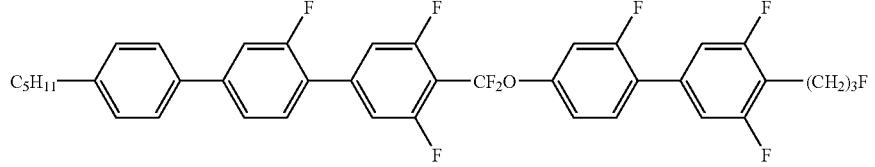
1-3-198

-continued
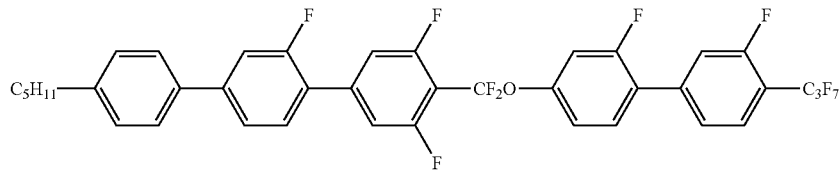
1-3-199
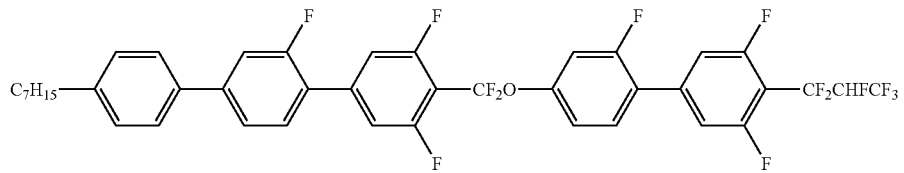
1-3-200
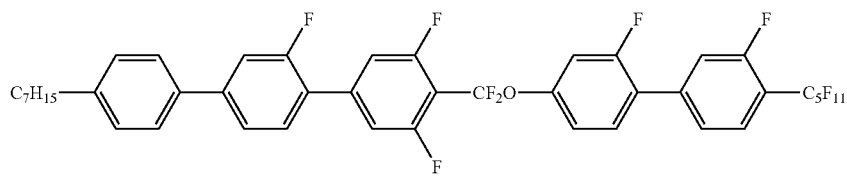
1-3-201
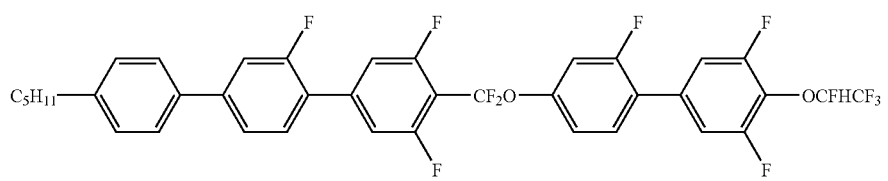
1-3-202
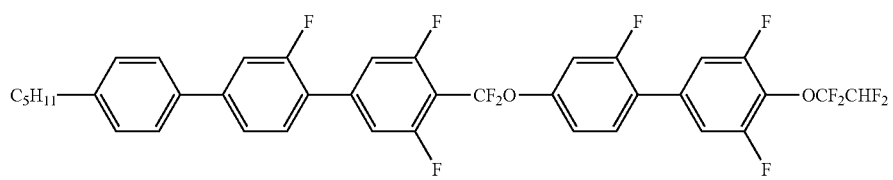
1-3-203
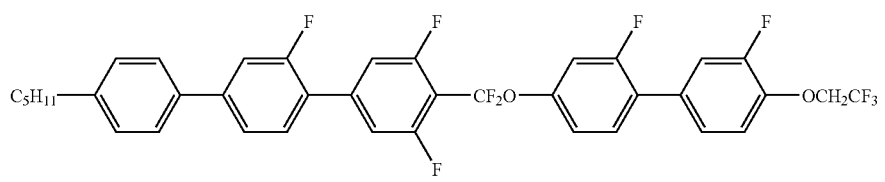
1-3-204
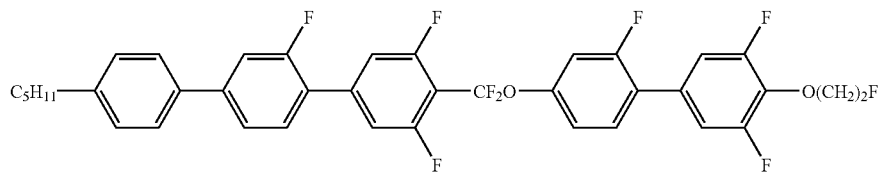
1-3-205
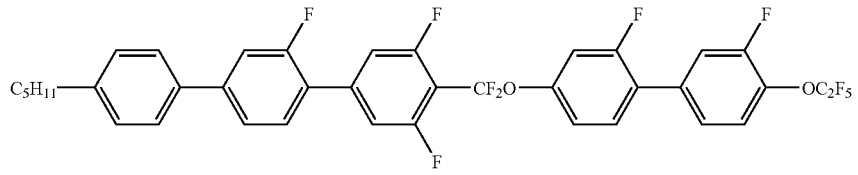
1-3-206
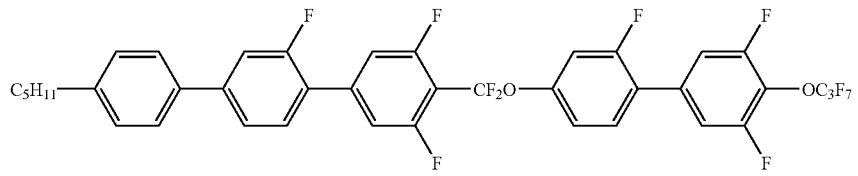
1-3-207

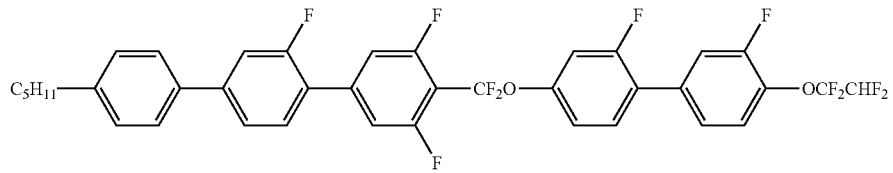
1-3-208
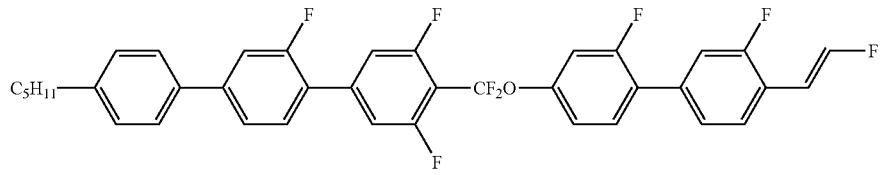
1-3-209
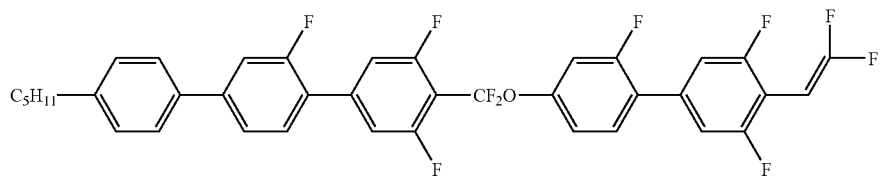
1-3-210
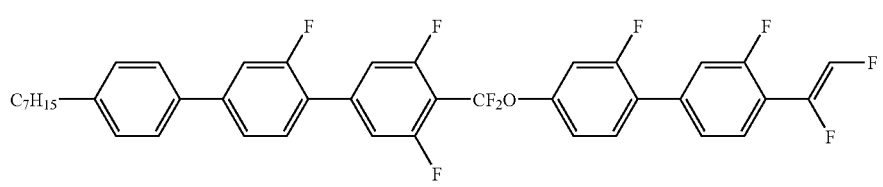
1-3-211
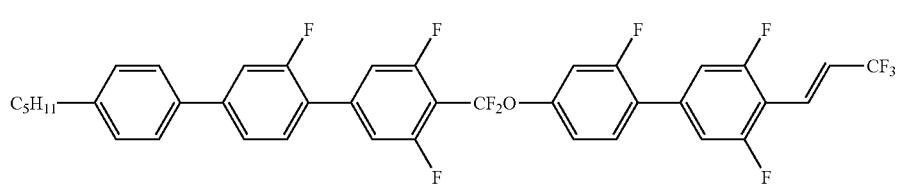
1-3-212
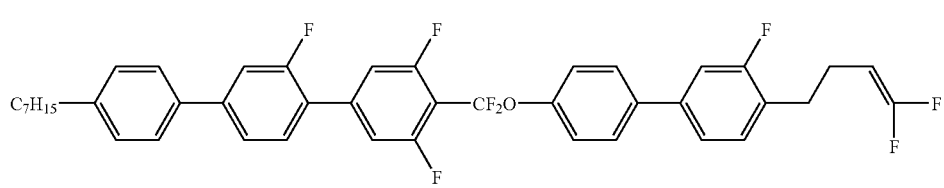
1-3-213
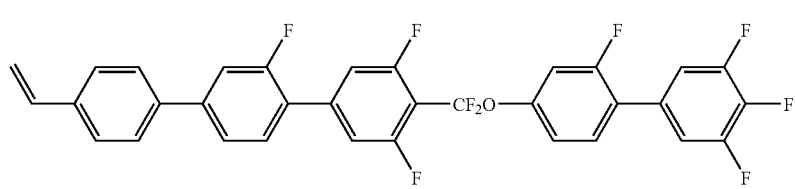
1-3-214
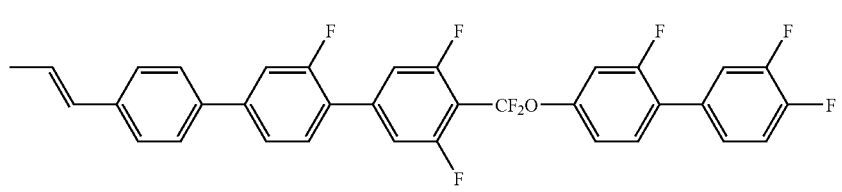
1-3-215
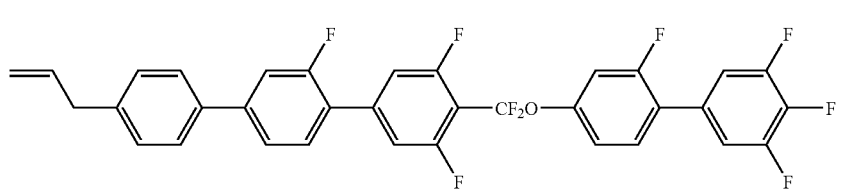
1-3-216

-continued
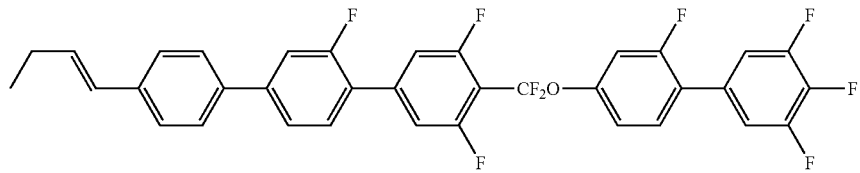
1-3-217
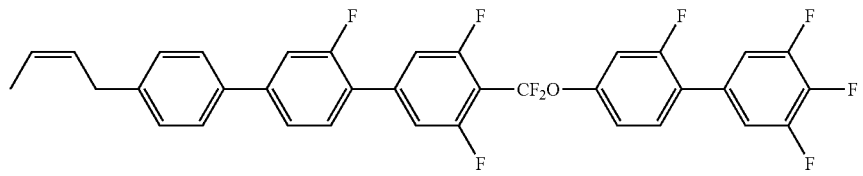
1-3-218
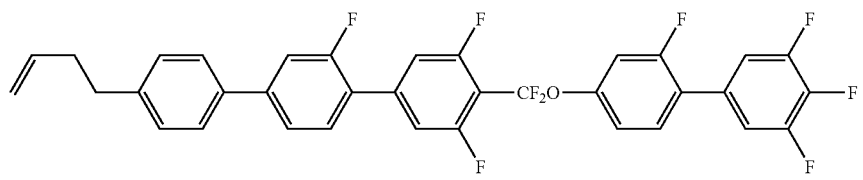
1-3-219
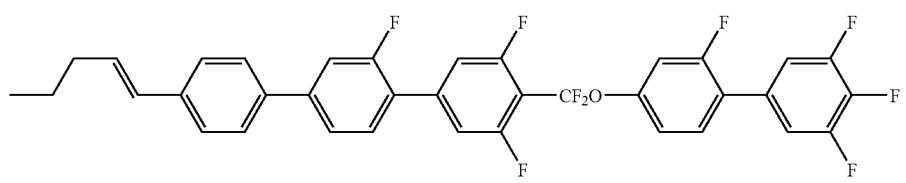
1-3-220
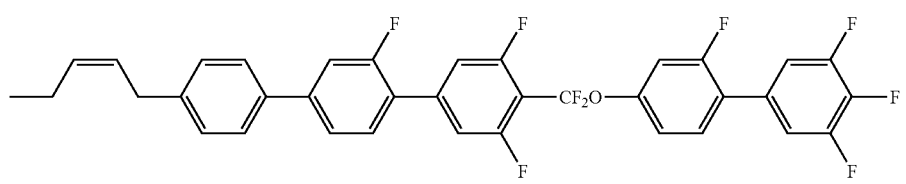
1-3-221
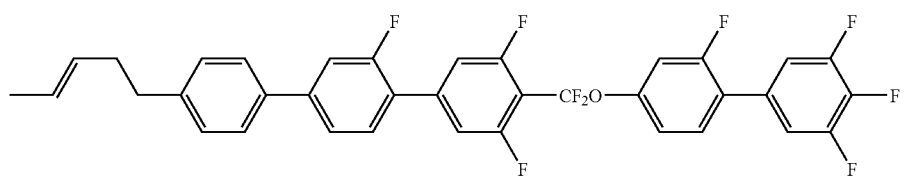
1-3-222
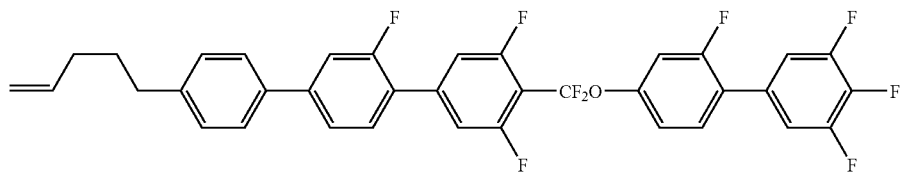
1-3-223
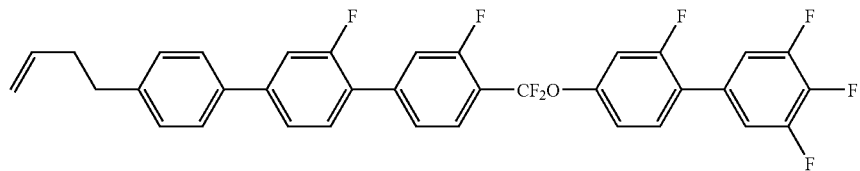
1-3-224
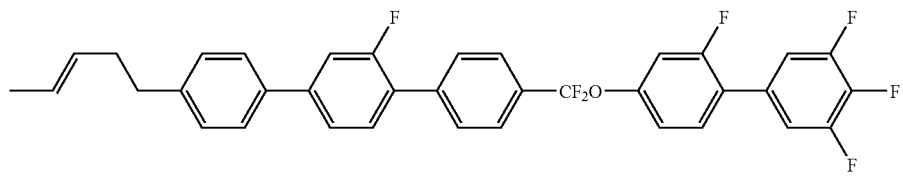
1-3-225

-continued
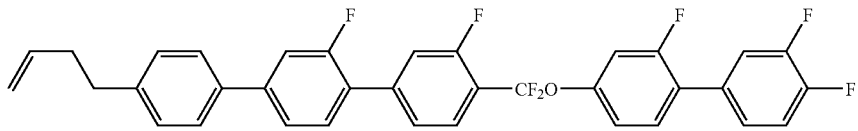
1-3-226
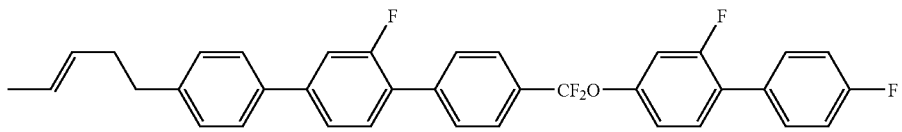
1-3-227
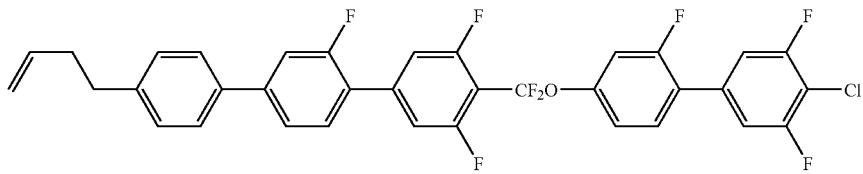
1-3-228
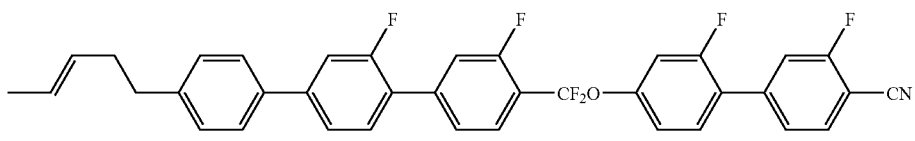
1-3-229
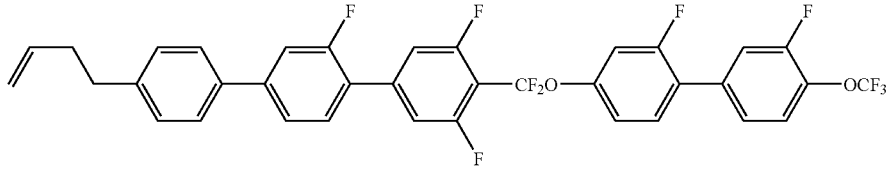
1-3-230
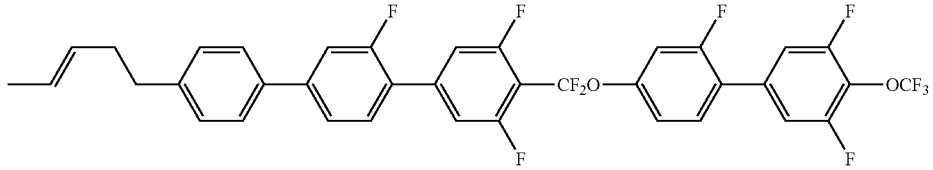
1-3-231
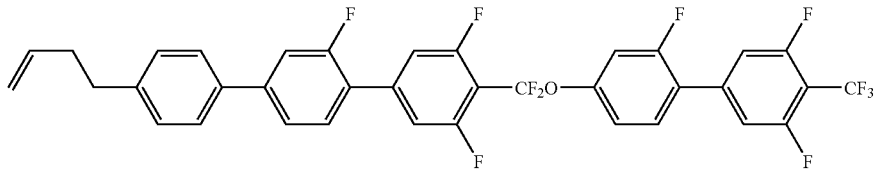
1-3-232
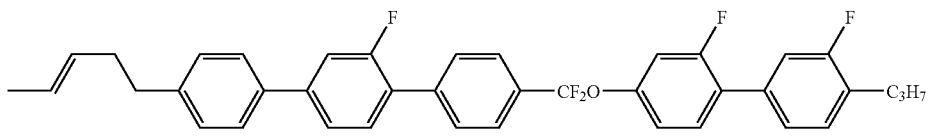
1-3-233
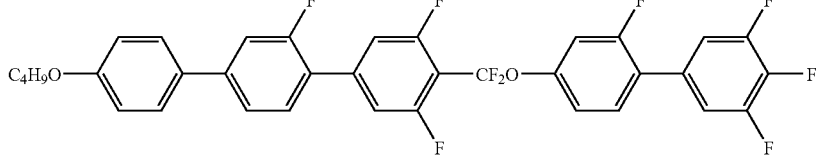
1-3-234
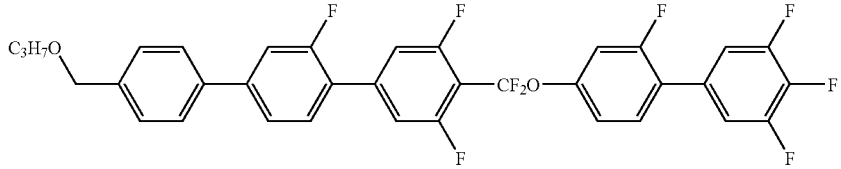
1-3-235

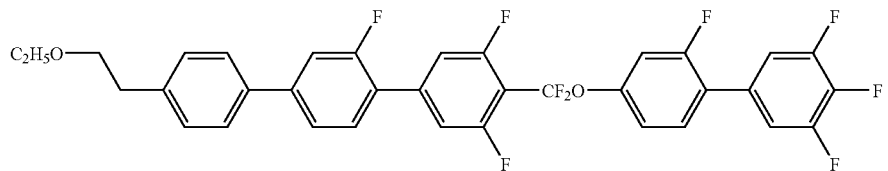
1-3-236
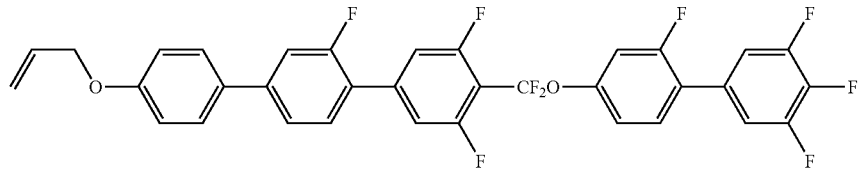
1-3-237
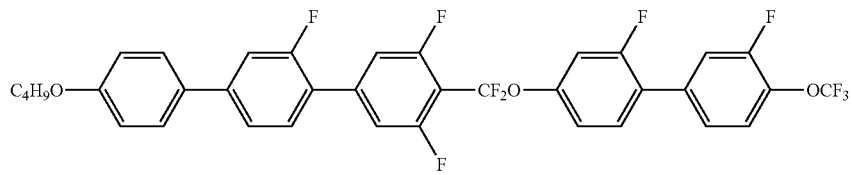
1-3-238
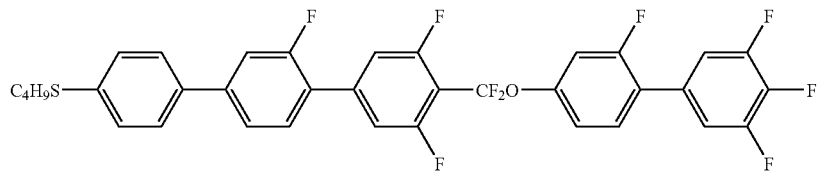
1-3-239
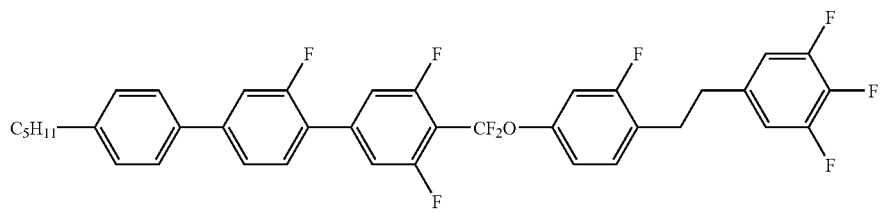
1-3-240
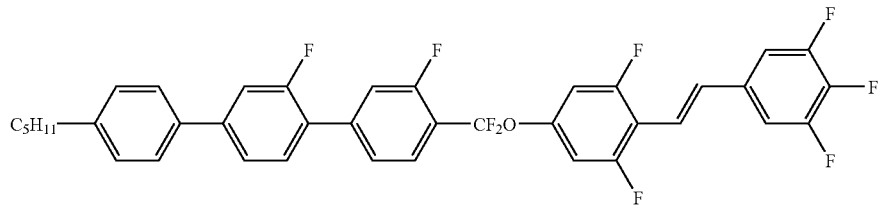
1-3-241
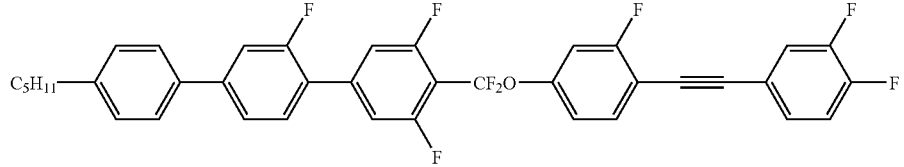
1-3-242
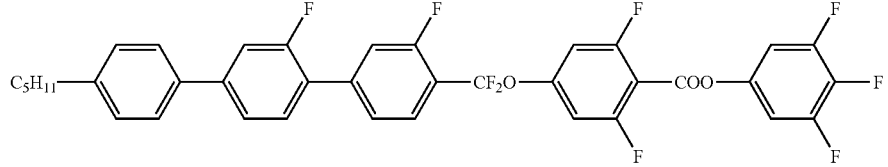
1-3-243

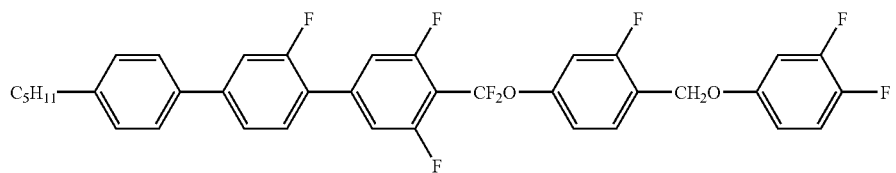 1-3-244
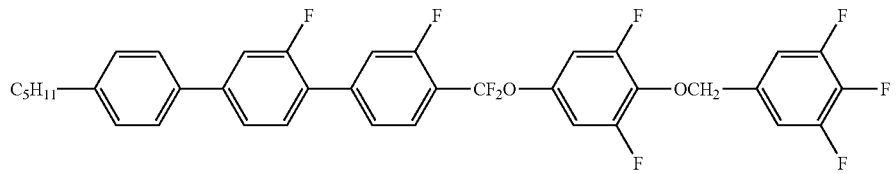 1-3-245
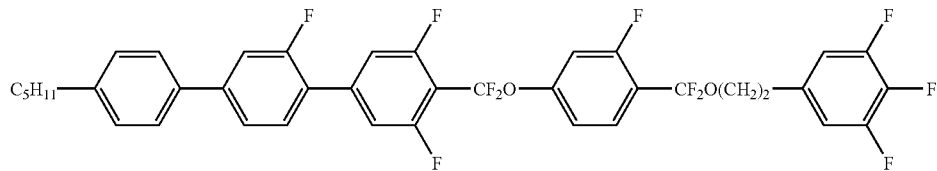 1-3-246
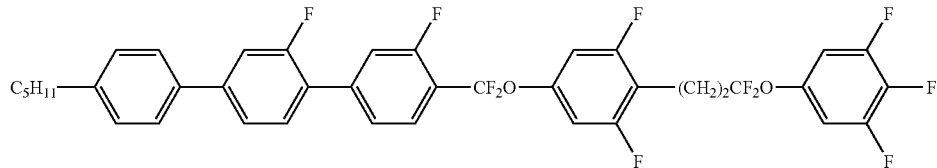 1-3-247
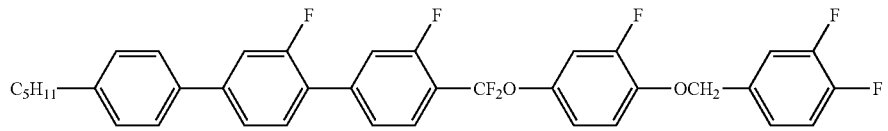 1-3-248
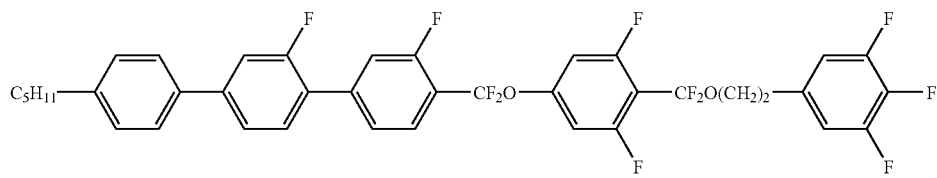 1-3-249
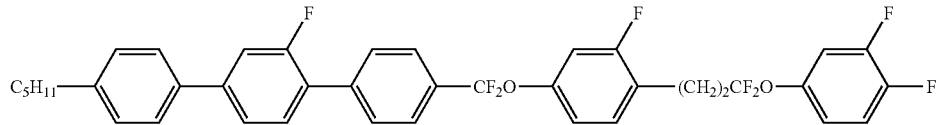 1-3-250
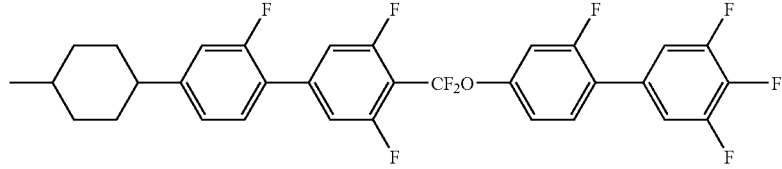 1-3-251
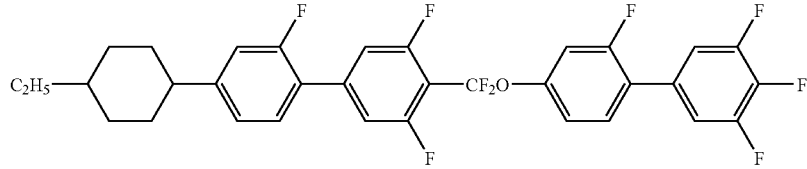 1-3-252

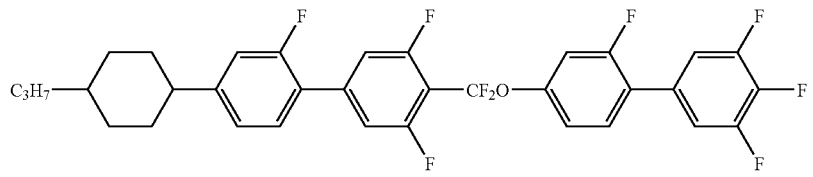
1-3-253
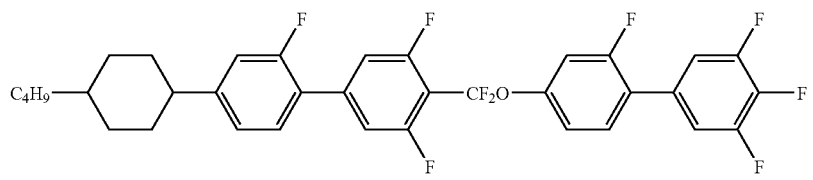
1-3-254
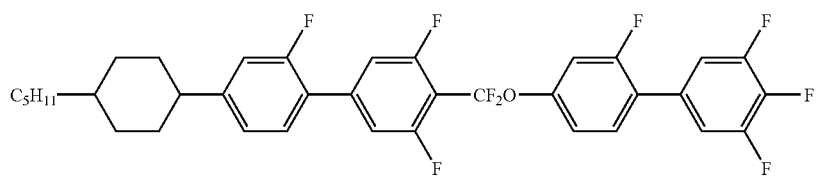
$T_{NI} = 146°$ C., $\Delta n = 0.184$, $\Delta \varepsilon = 34.3$
1-3-255
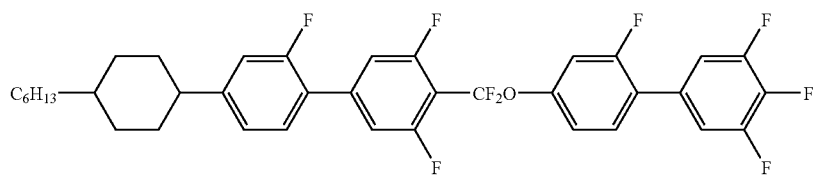
1-3-256
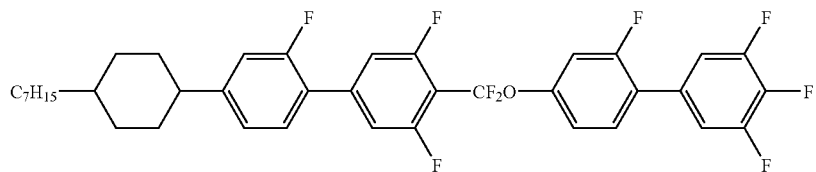
1-3-257
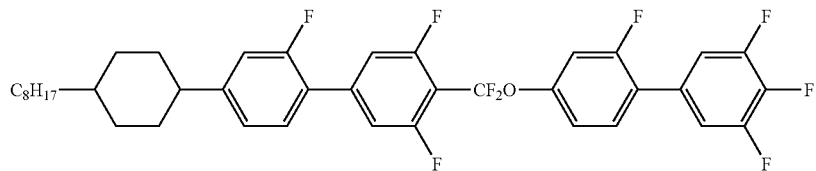
1-3-258
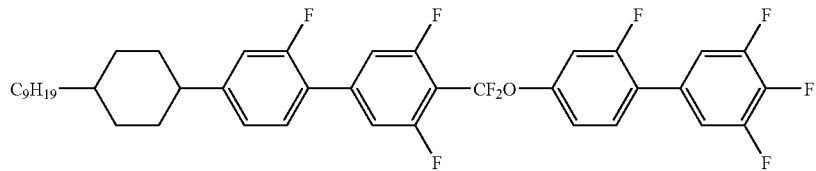
1-3-259
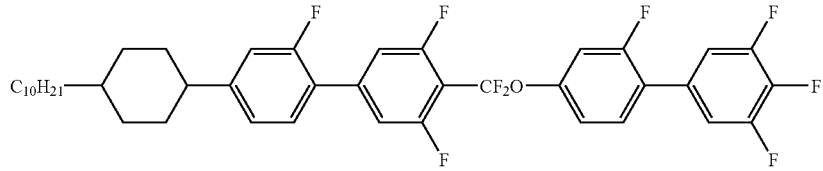
1-3-260

-continued
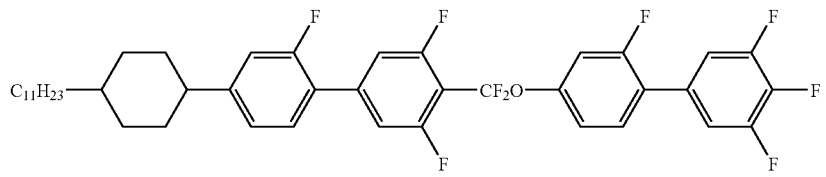
1-3-261
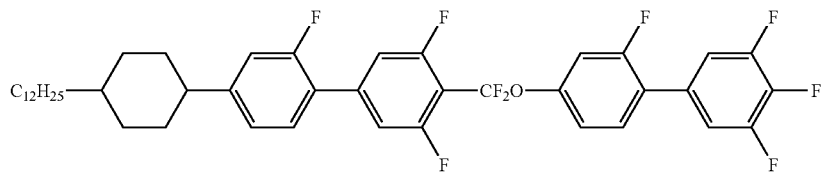
1-3-262
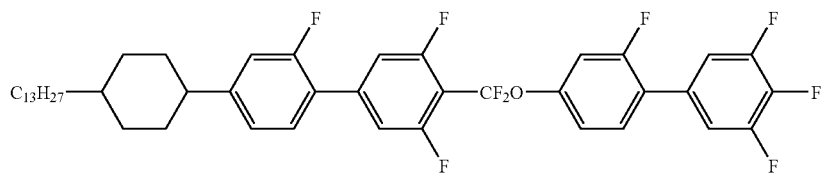
1-3-263
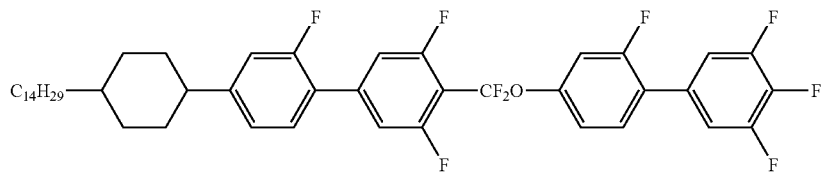
1-3-264
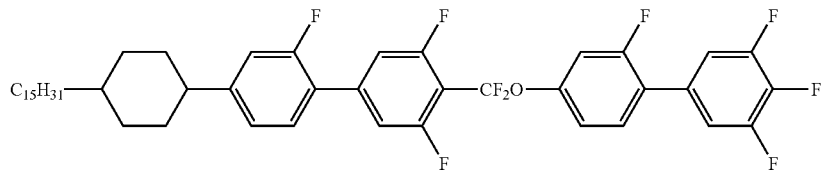
1-3-265
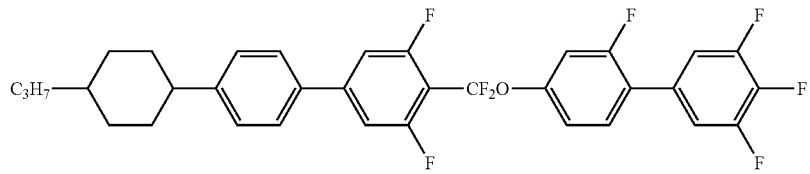
1-3-266
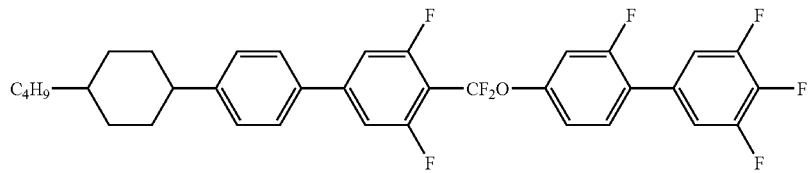
1-3-267
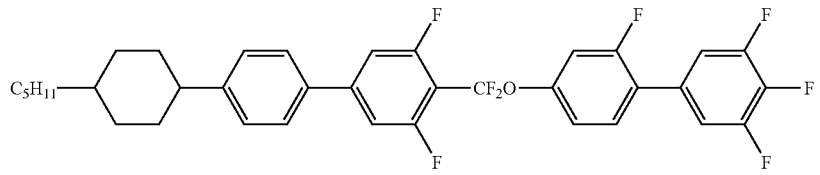
1-3-268
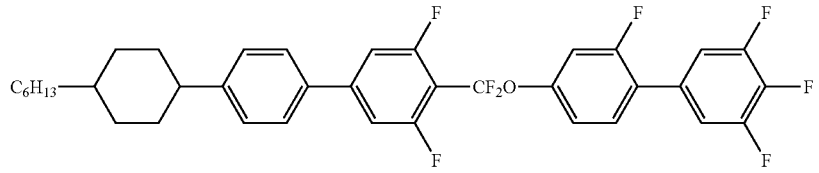
1-3-269

-continued
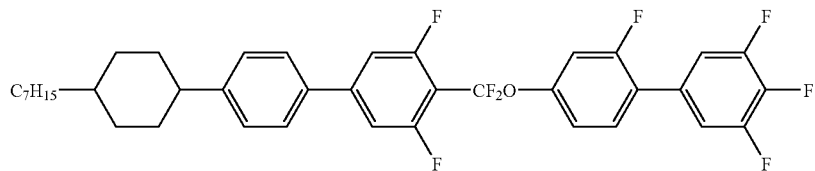
1-3-270
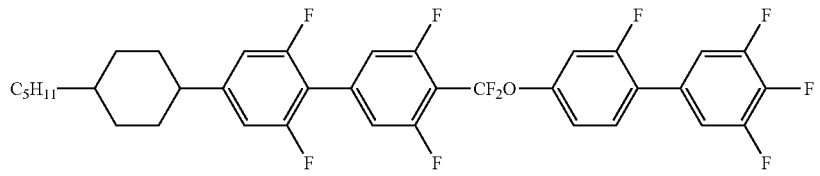
1-3-271
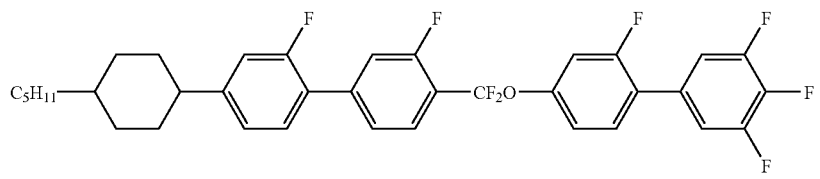
1-3-272
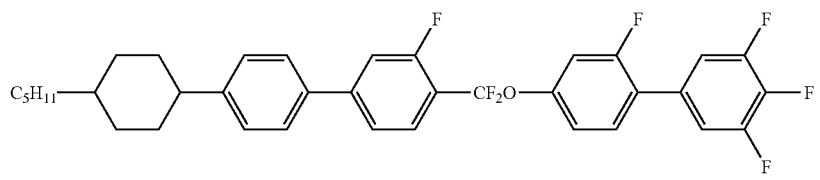
1-3-273
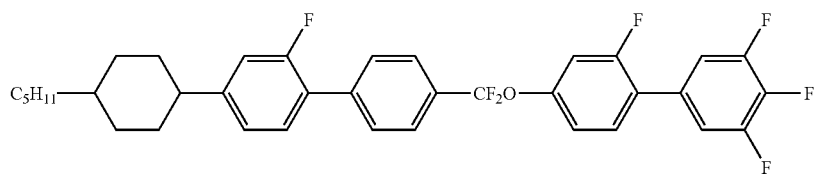
1-3-274
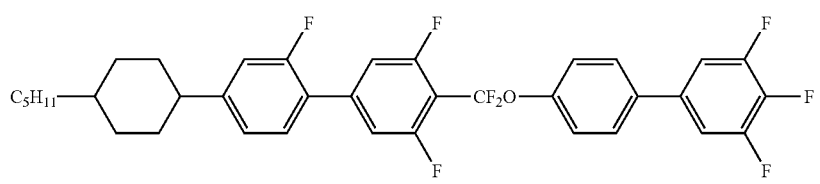
1-3-275
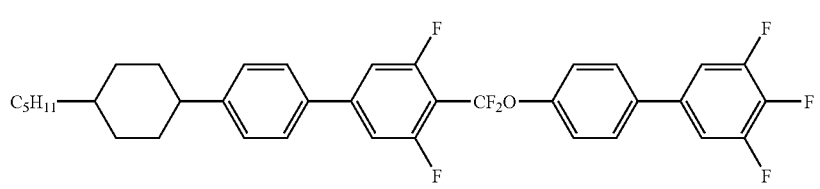
1-3-276
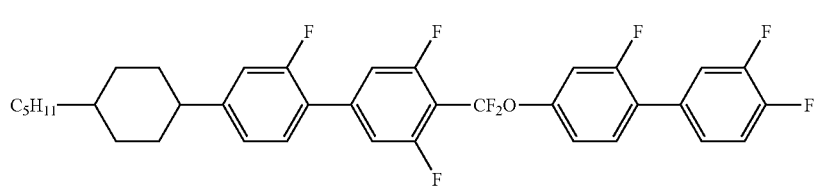
1-3-277
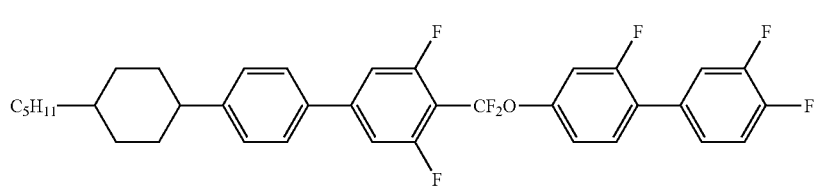
1-3-278

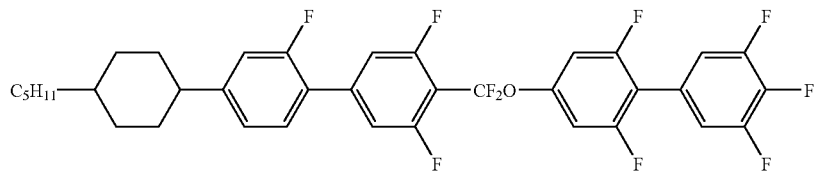
1-3-279
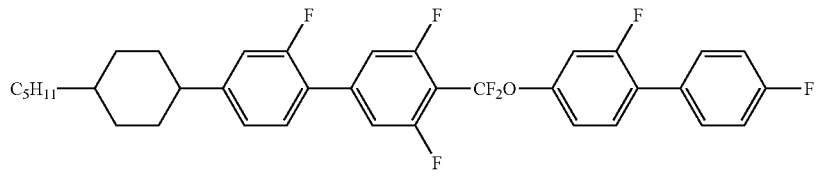
1-3-280
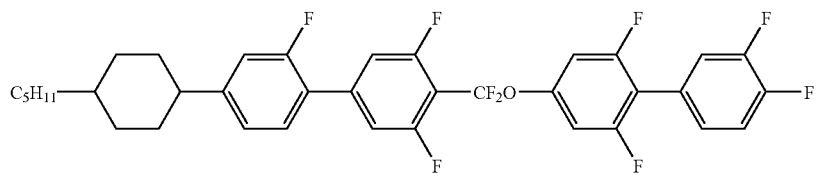
1-3-281
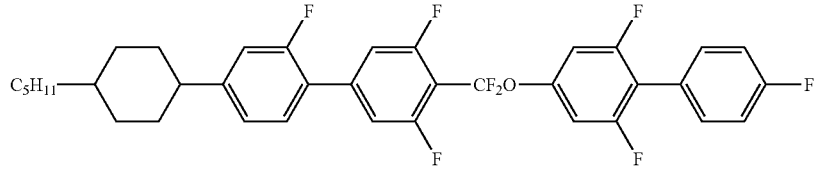
1-3-282
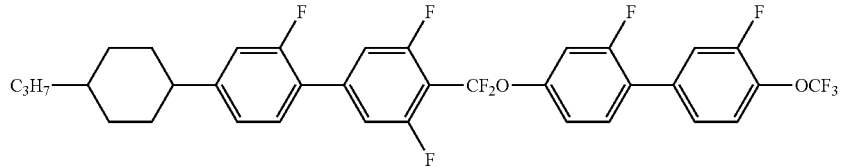
1-3-283
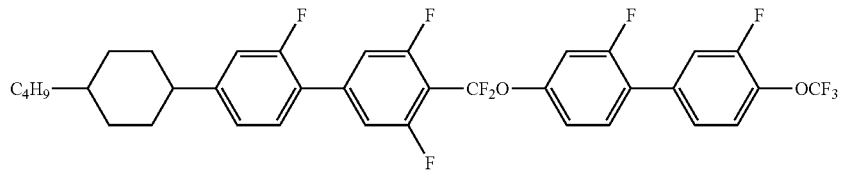
1-3-284
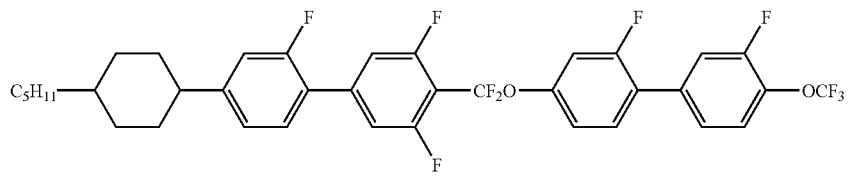
1-3-285
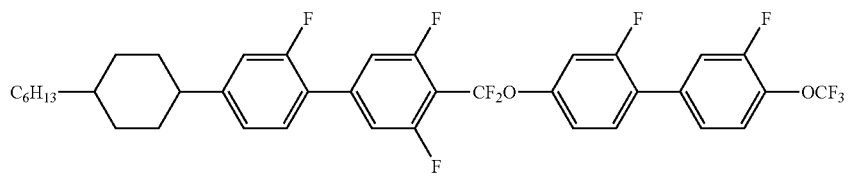
1-3-286
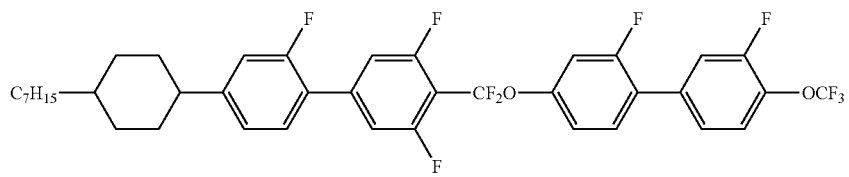
1-3-287

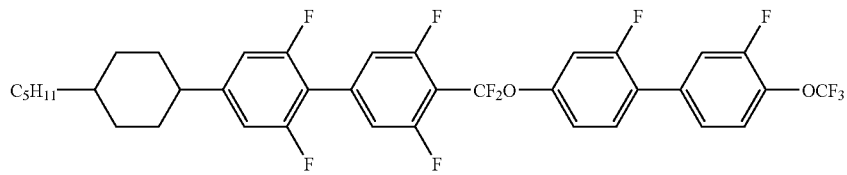
1-3-288
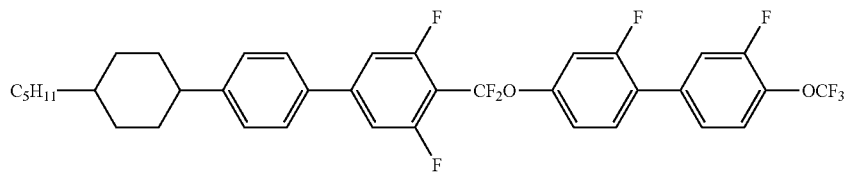
1-3-289
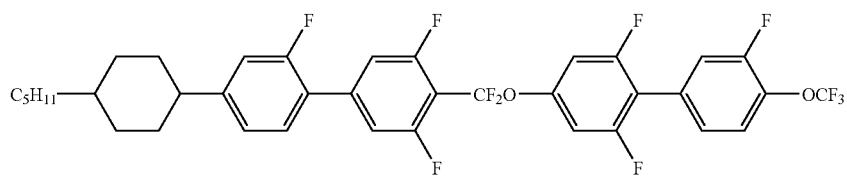
1-3-290
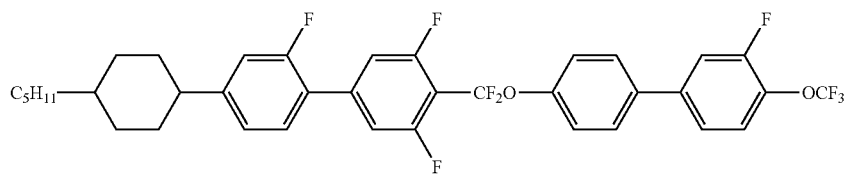
1-3-291
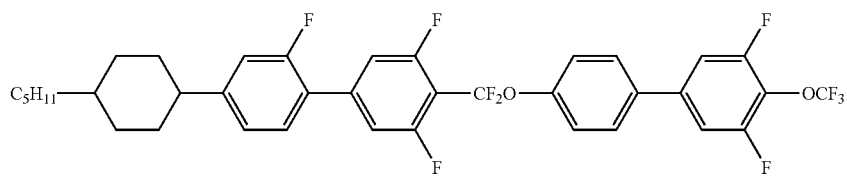
1-3-292
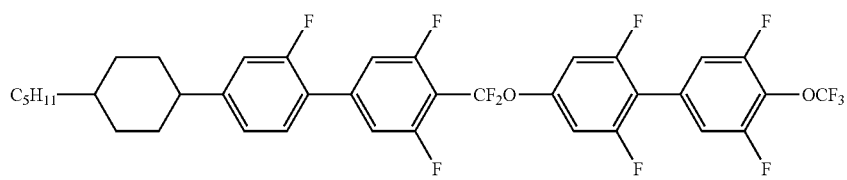
1-3-293
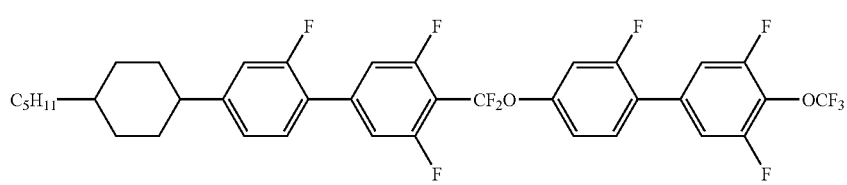
1-3-294
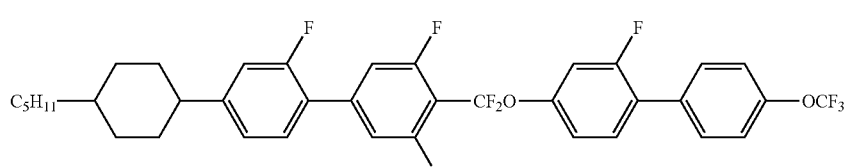
1-3-295
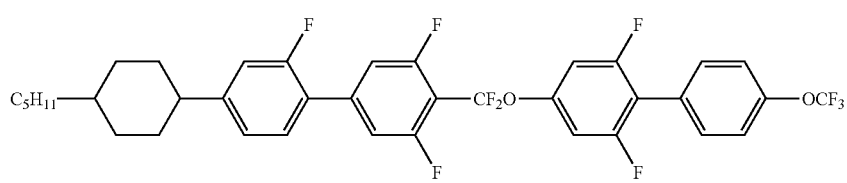
1-3-296

-continued
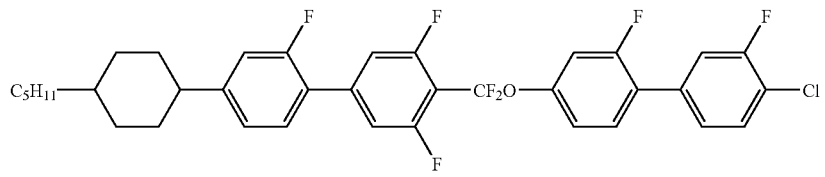
1-3-297
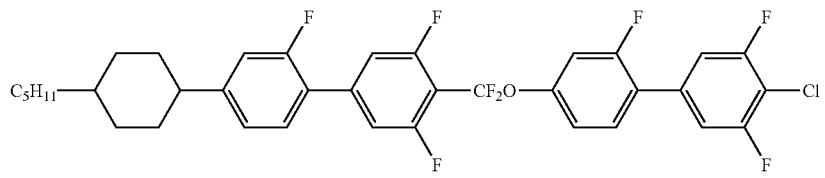
1-3-298
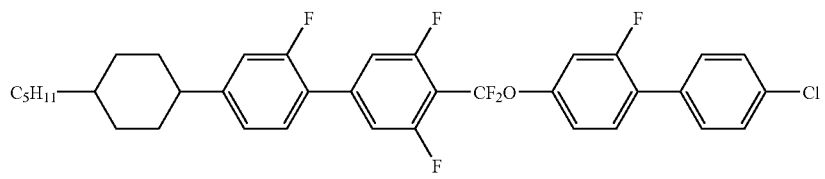
1-3-299
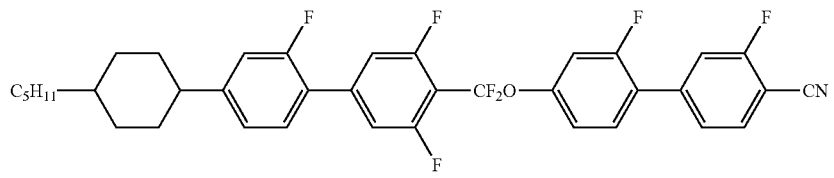
1-3-300
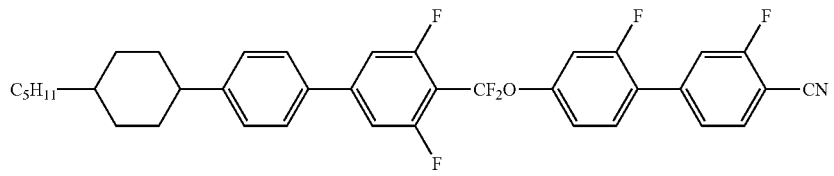
1-3-301
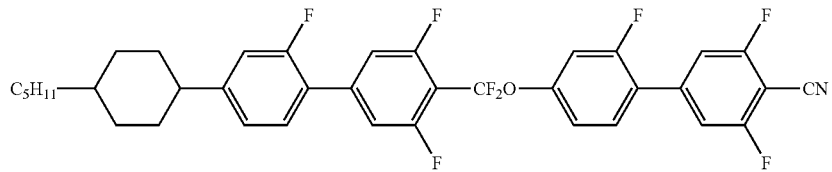
1-3-302
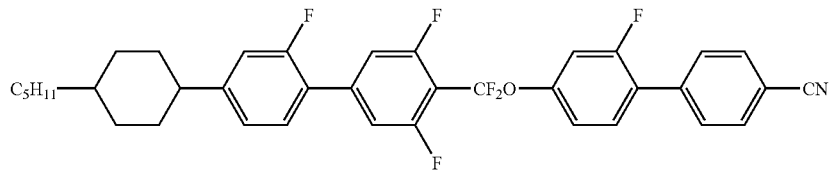
1-3-303
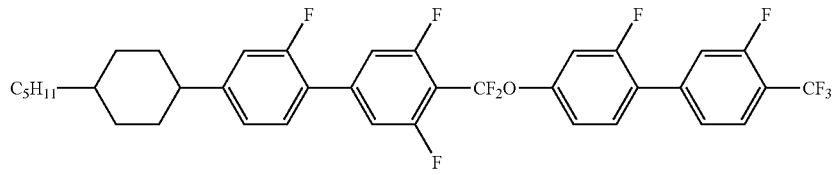
1-3-304
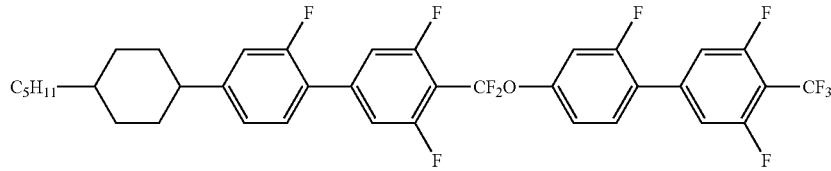
1-3-305

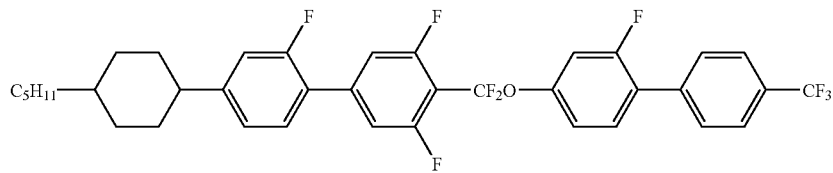
1-3-306
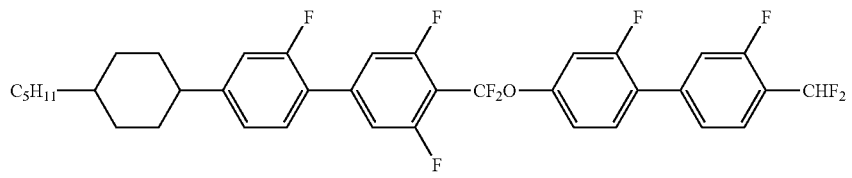
1-3-307
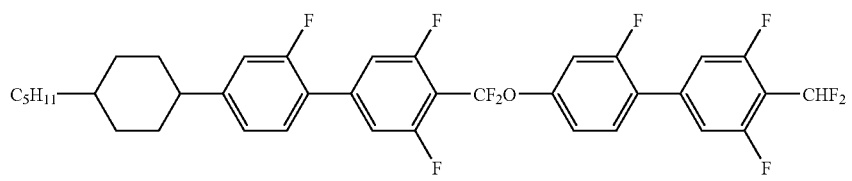
1-3-308
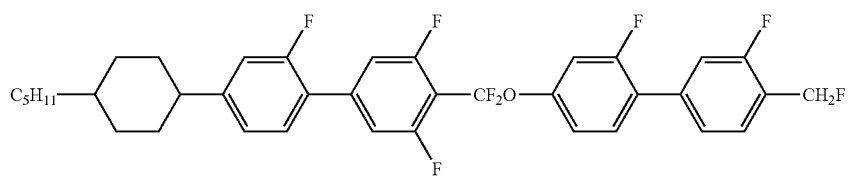
1-3-309
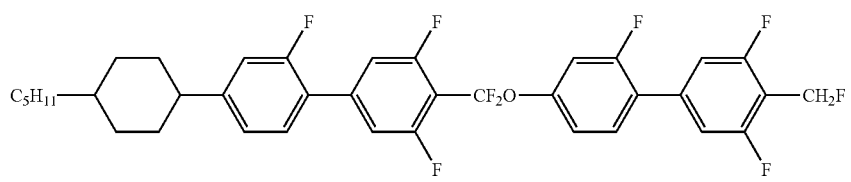
1-3-310
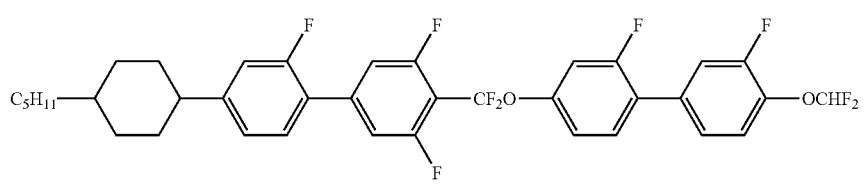
1-3-311
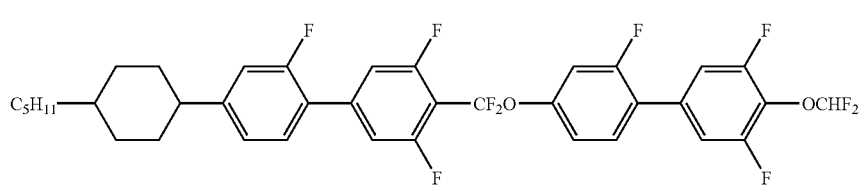
1-3-312
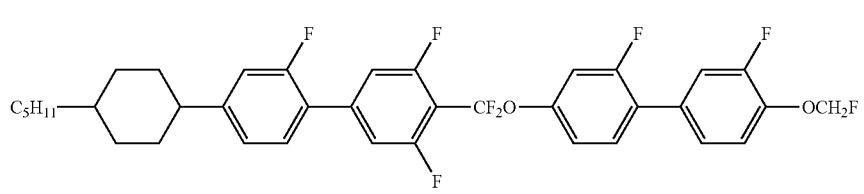
1-3-313
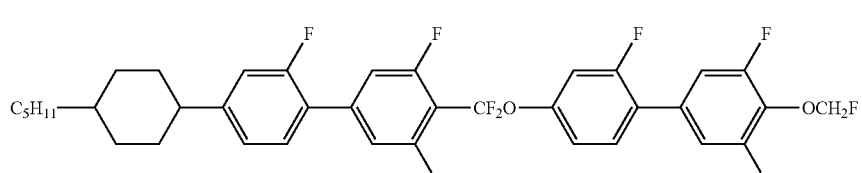
1-3-314

-continued
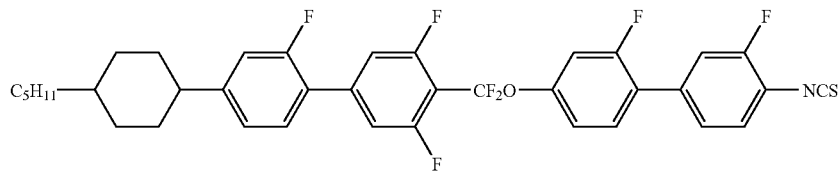
1-3-315
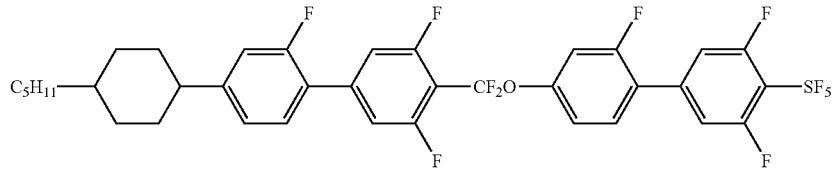
1-3-316
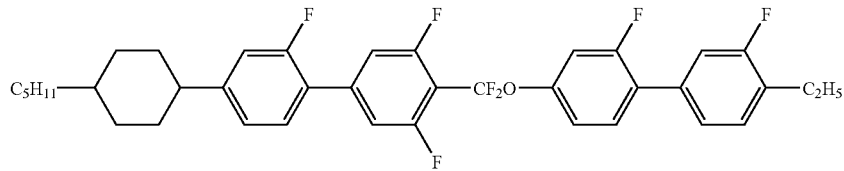
1-3-317
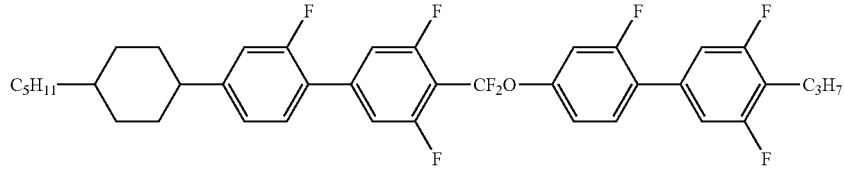
1-3-318
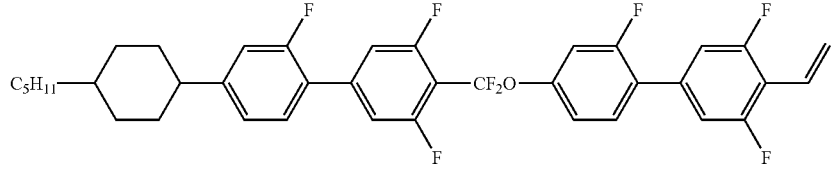
1-3-319
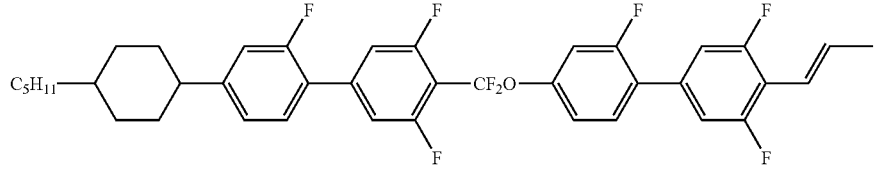
1-3-320
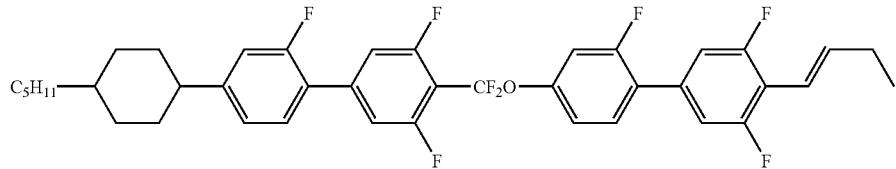
1-3-321
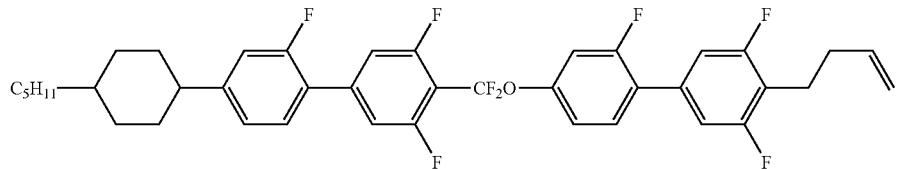
1-3-322
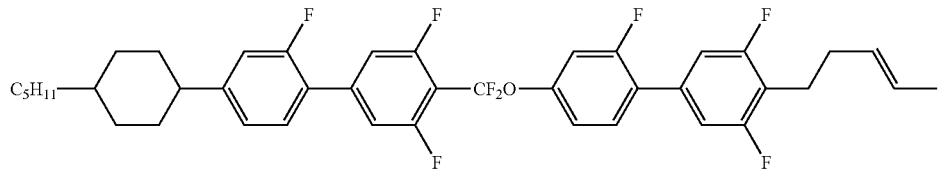
1-3-323

-continued
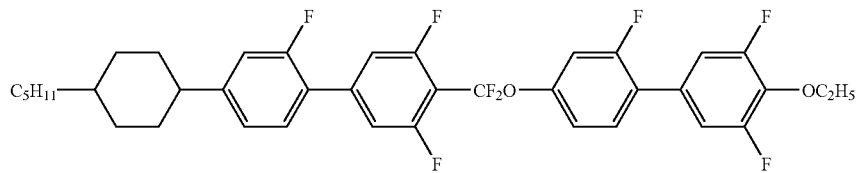
1-3-324
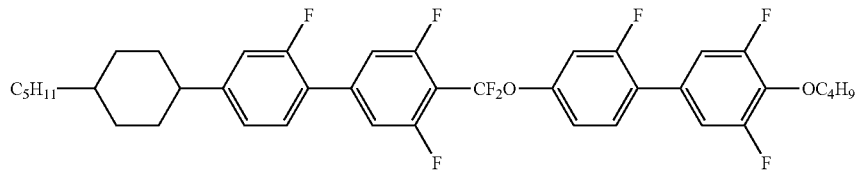
1-3-325
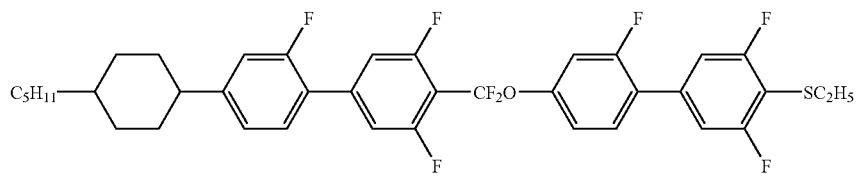
1-3-326
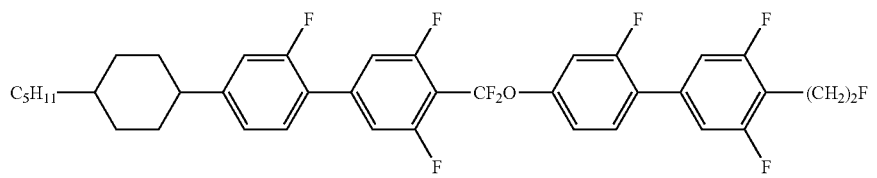
1-3-327
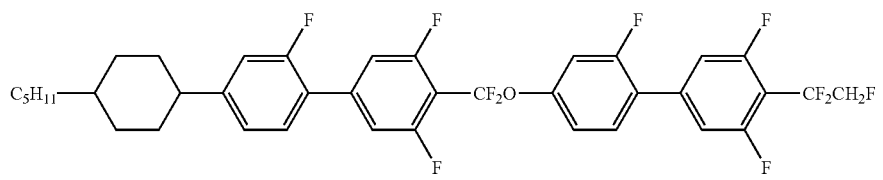
1-3-328
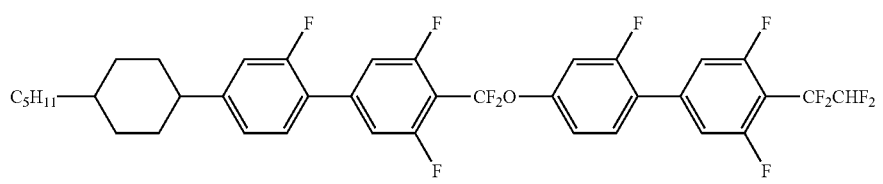
1-3-329
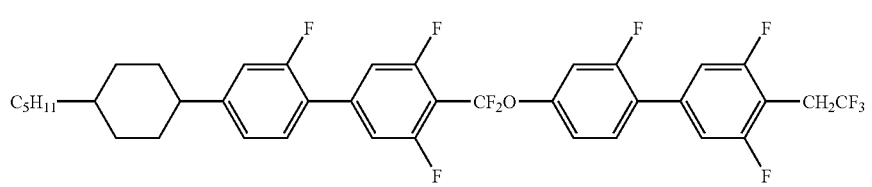
1-3-330
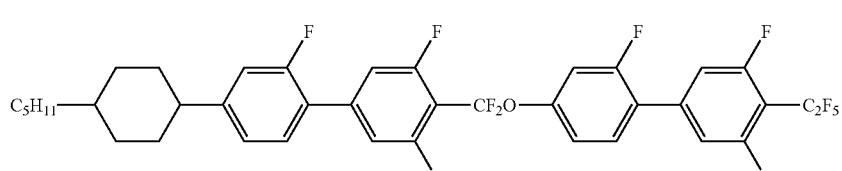
1-3-331
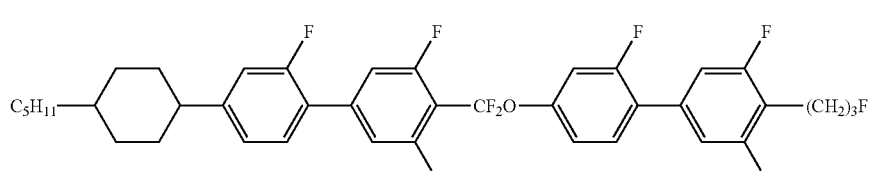
1-3-332

-continued
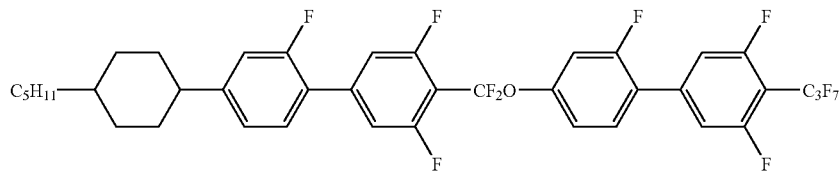
1-3-333
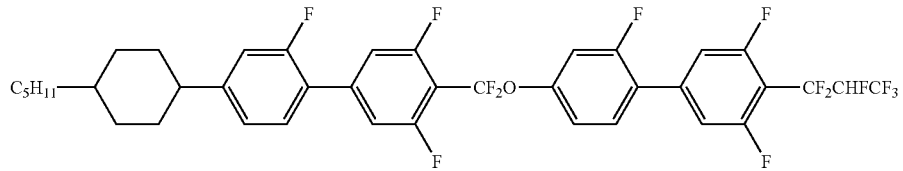
1-3-334
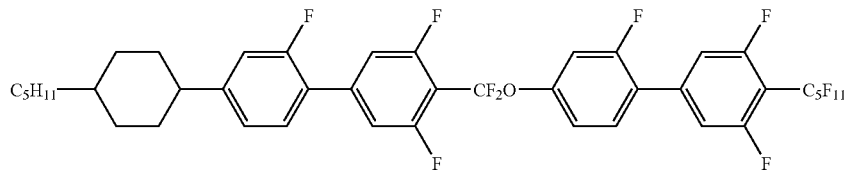
1-3-335
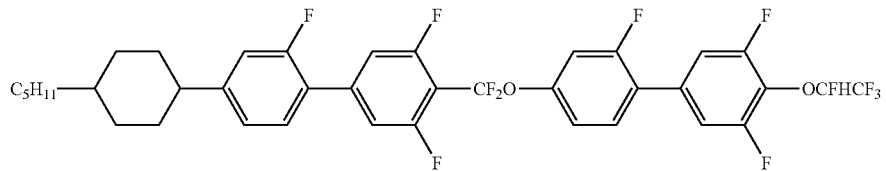
1-3-336
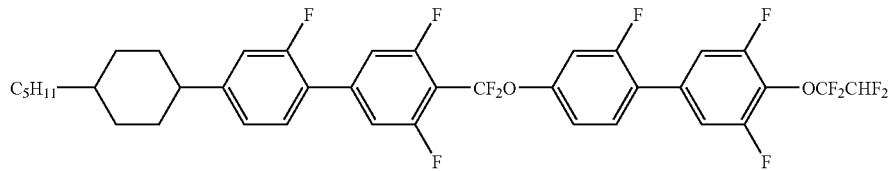
1-3-337
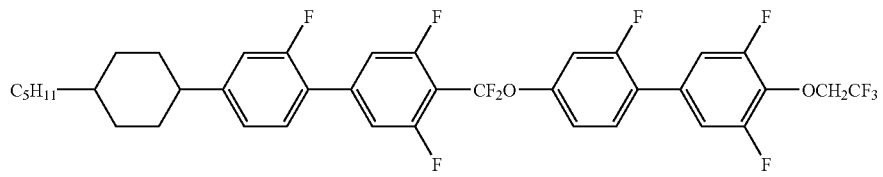
1-3-338
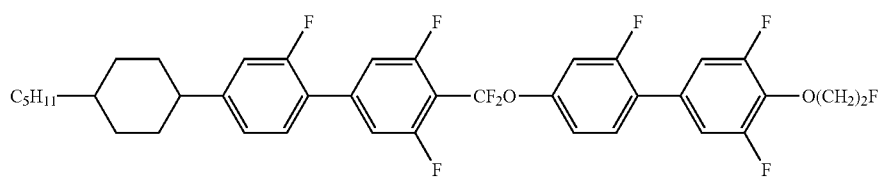
1-3-339
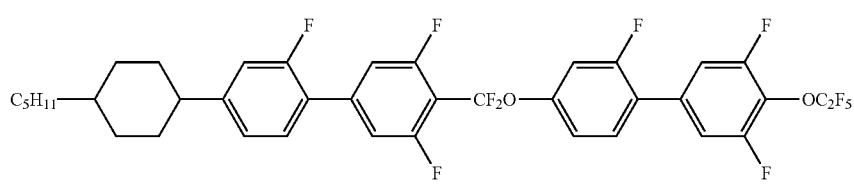
1-3-340
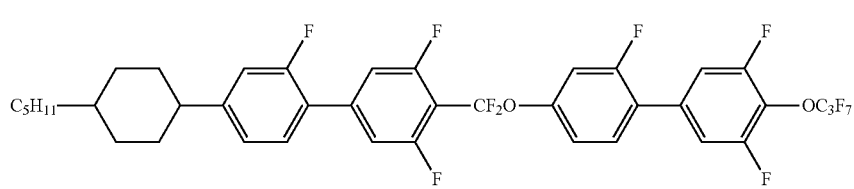
1-3-341

-continued
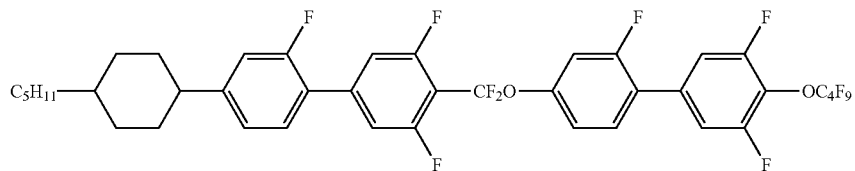 1-3-342
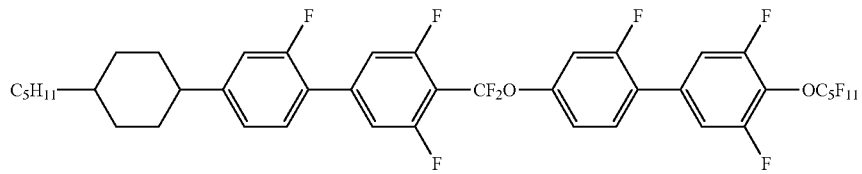 1-3-343
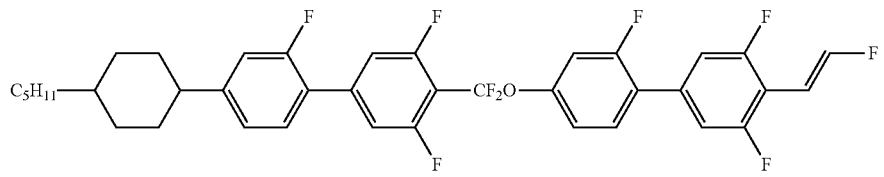 1-3-344
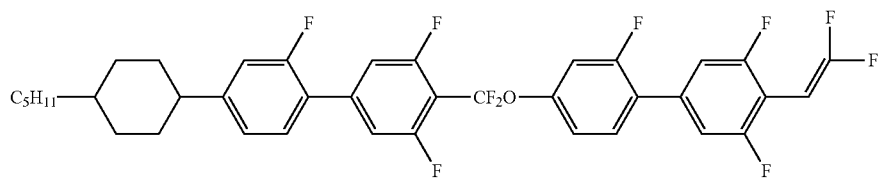 1-3-345
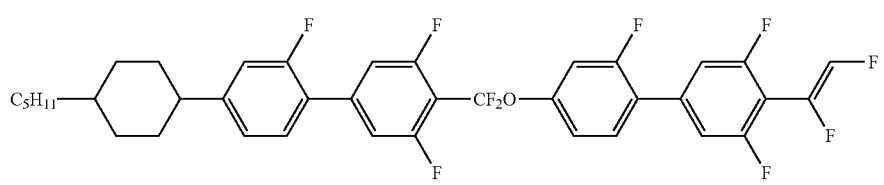 1-3-346
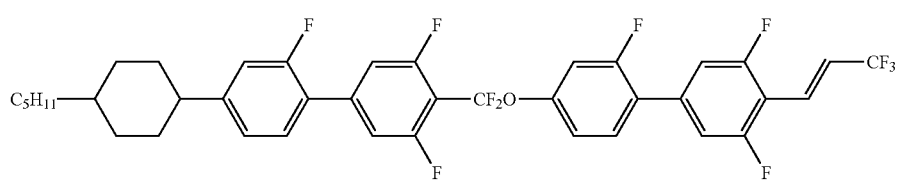 1-3-347
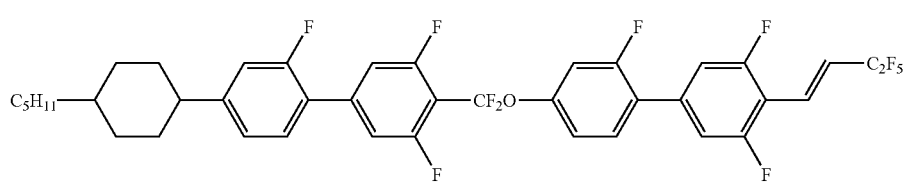 1-3-348
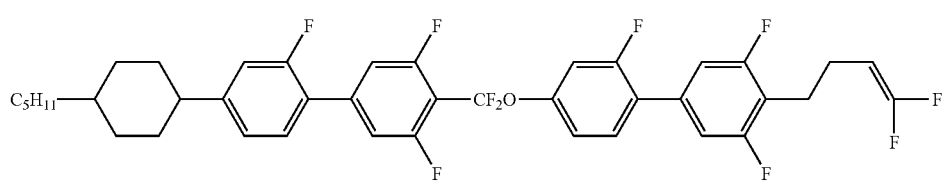 1-3-349
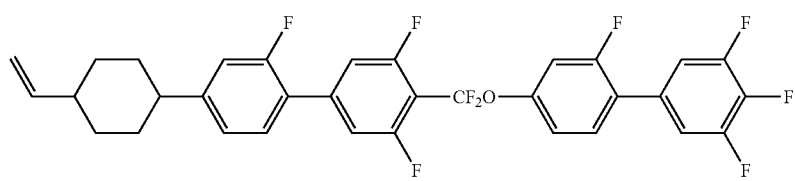 1-3-350

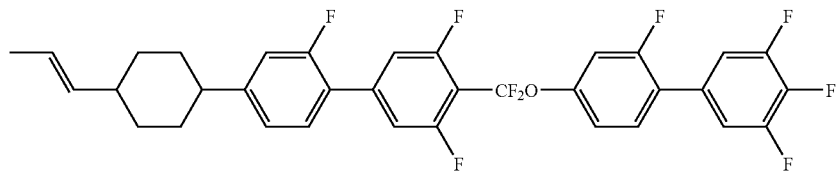
1-3-351
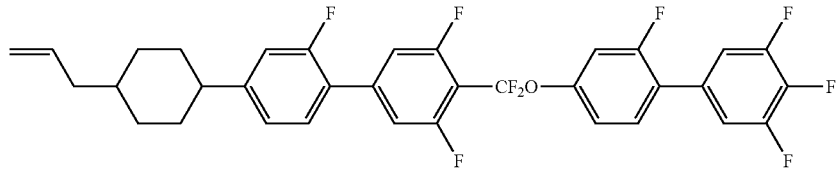
1-3-352
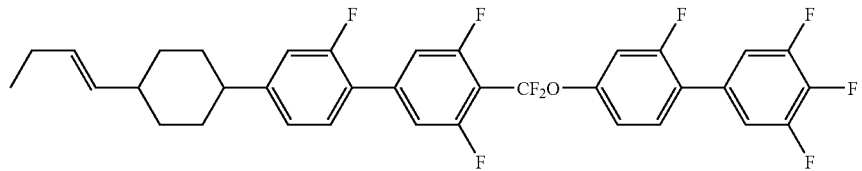
1-3-353
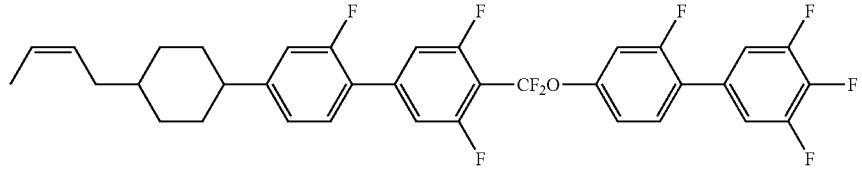
1-3-354
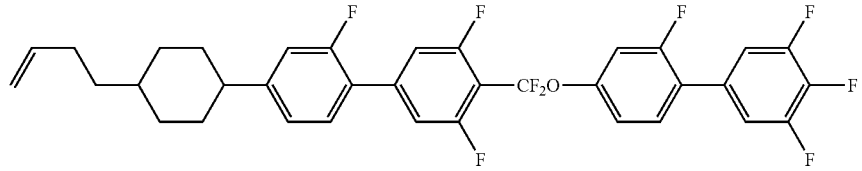
1-3-355
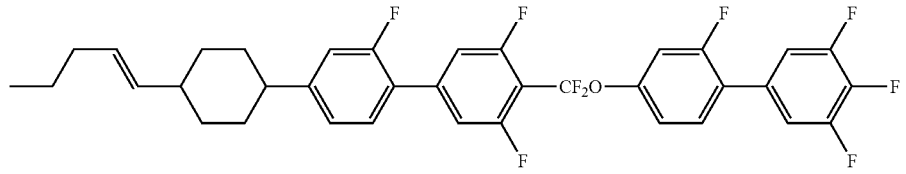
1-3-356
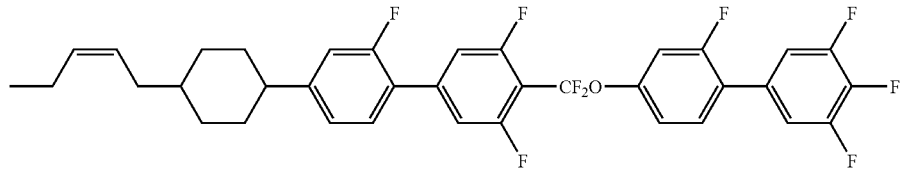
1-3-357
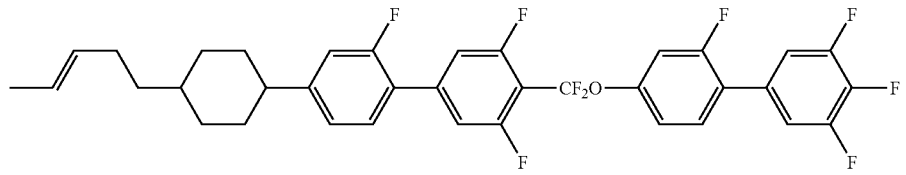
1-3-358
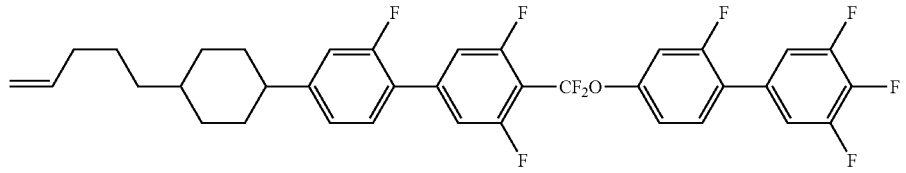
1-3-359

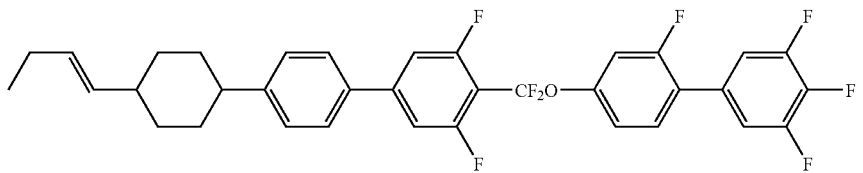
1-3-360
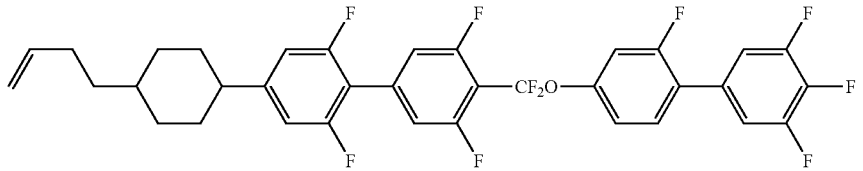
1-3-361
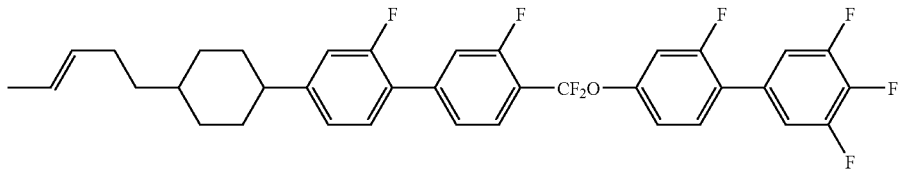
1-3-362
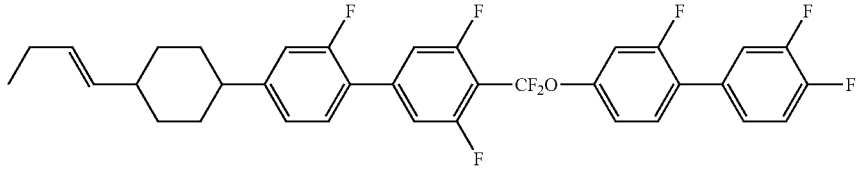
1-3-363
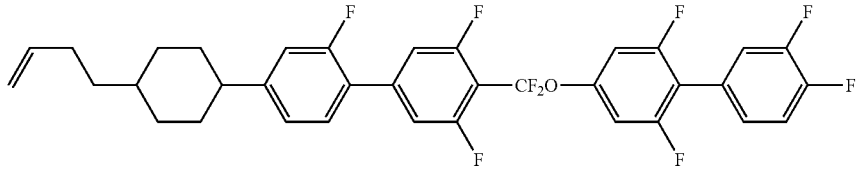
1-3-364
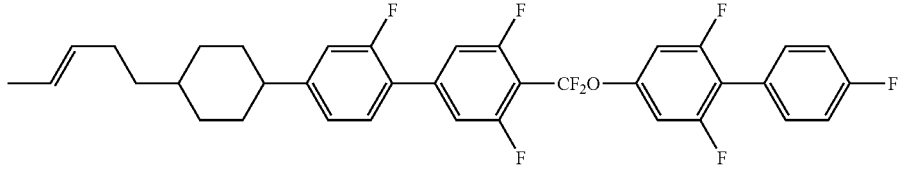
1-3-365
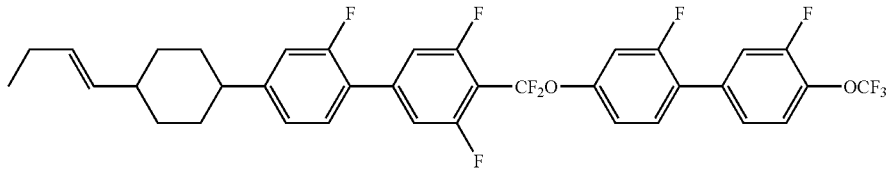
1-3-366
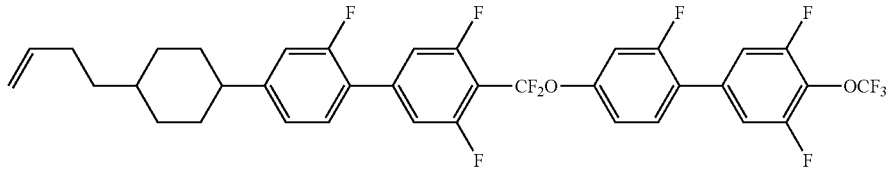
1-3-367
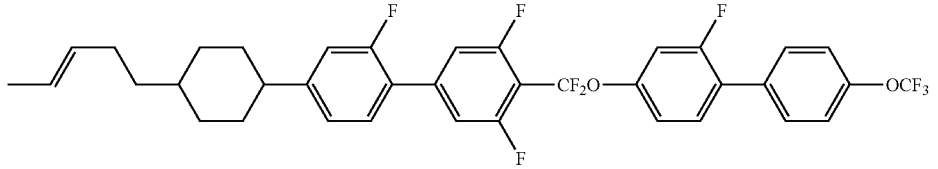
1-3-368

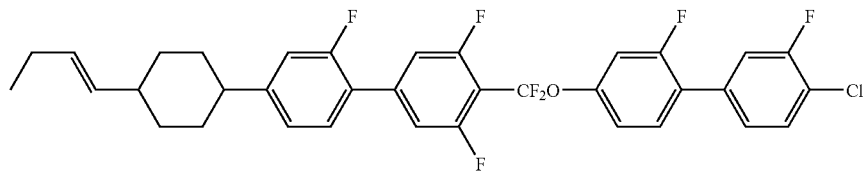
1-3-369
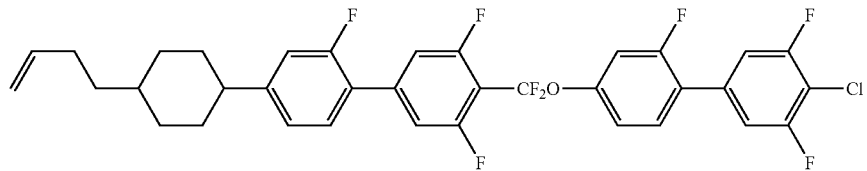
1-3-370
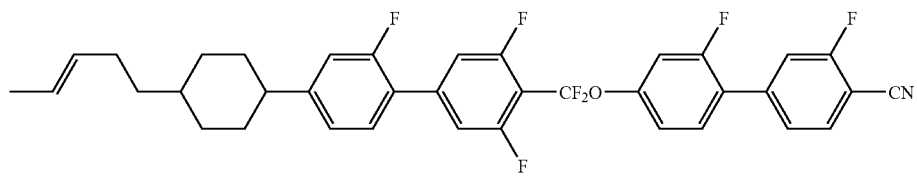
1-3-371
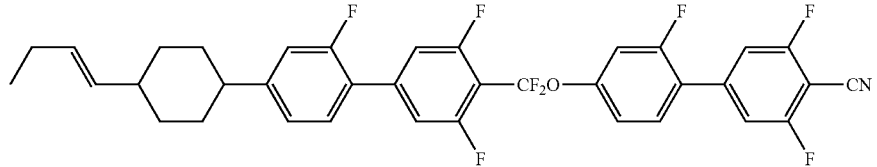
1-3-372
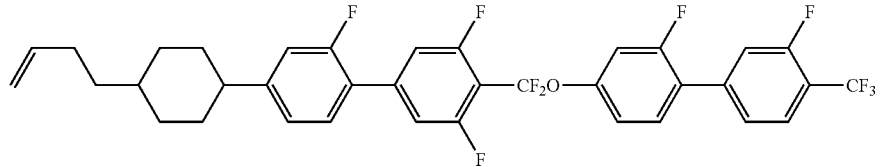
1-3-373
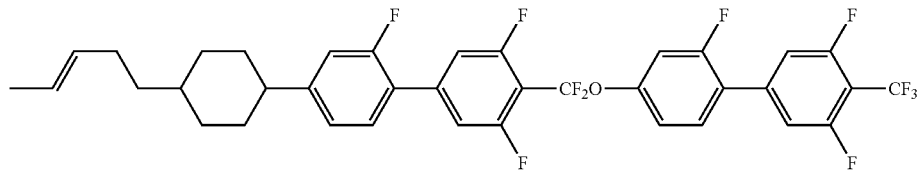
1-3-374
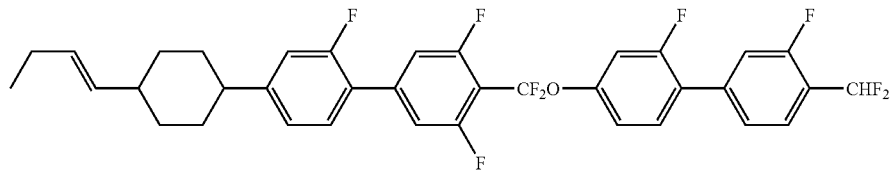
1-3-375
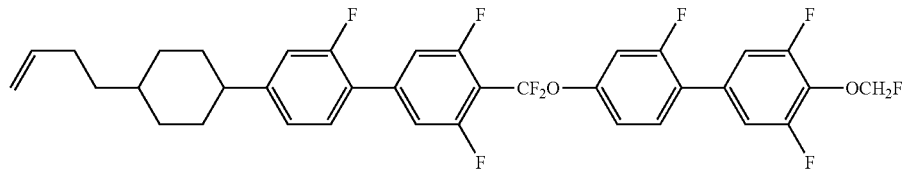
1-3-376
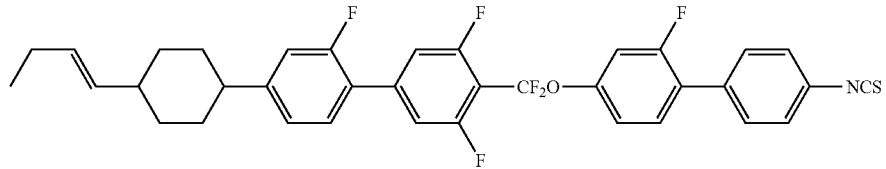
1-3-377

-continued
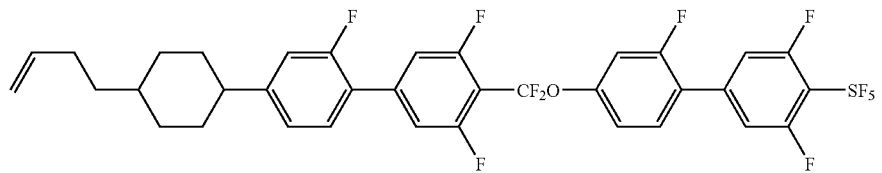
1-3-378
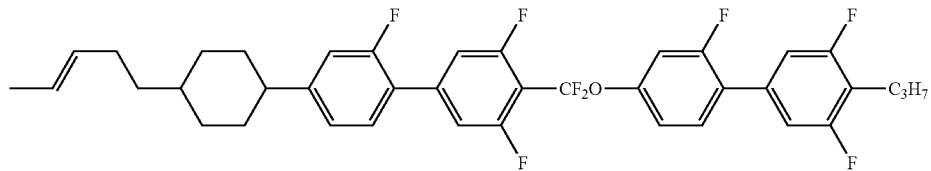
1-3-379
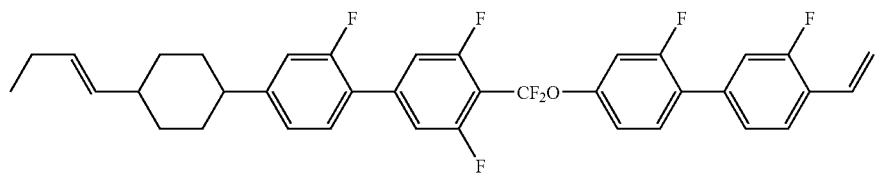
1-3-380
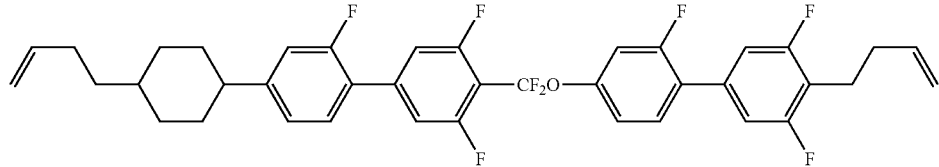
1-3-381
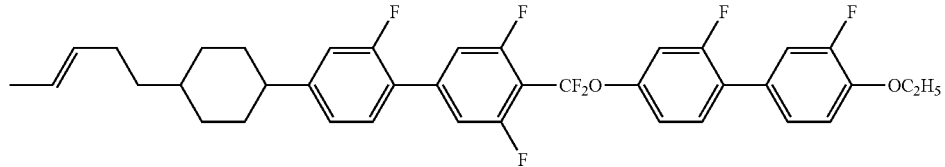
1-3-382
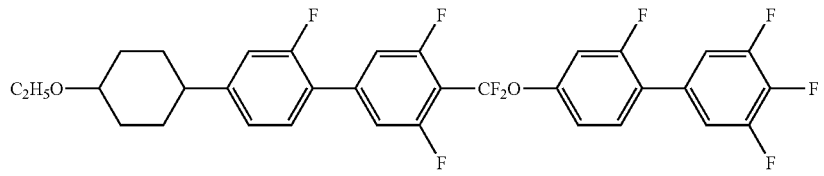
1-3-383
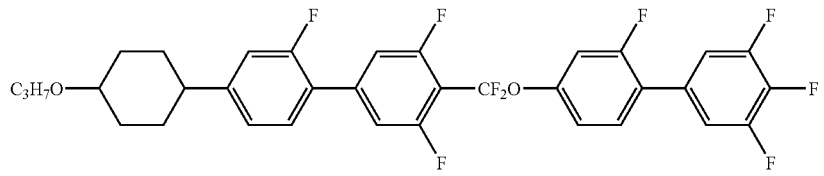
1-3-384
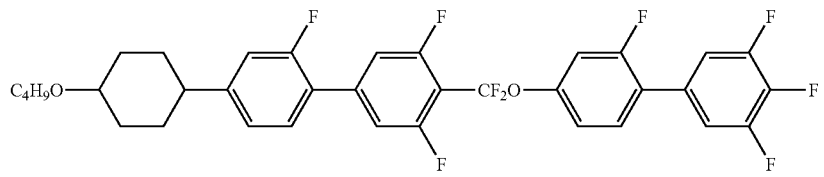
1-3-385
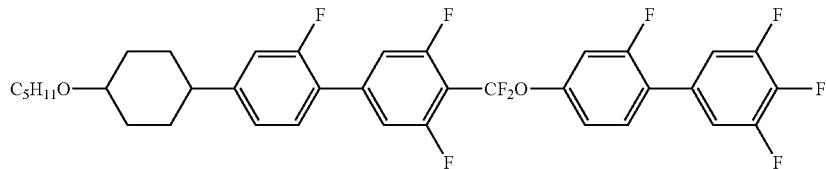
1-3-386

-continued
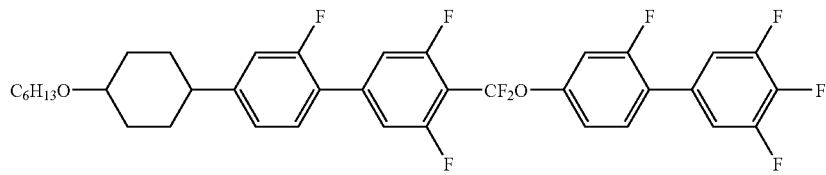 1-3-387
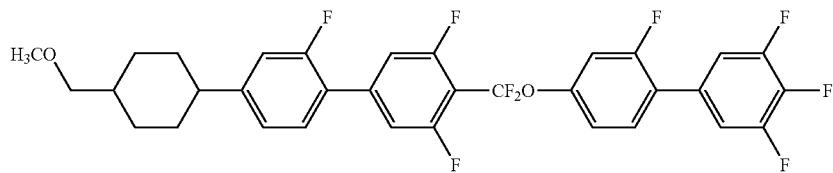 1-3-388
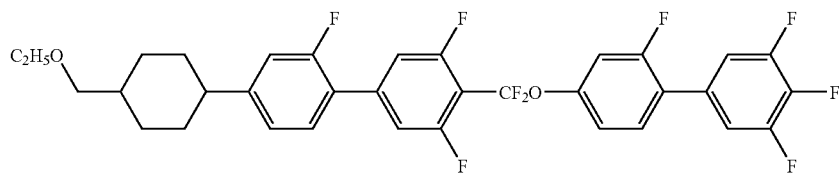 1-3-389
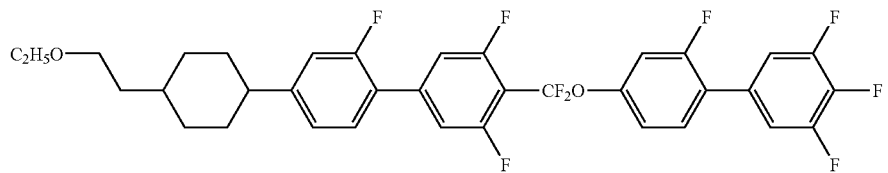 1-3-390
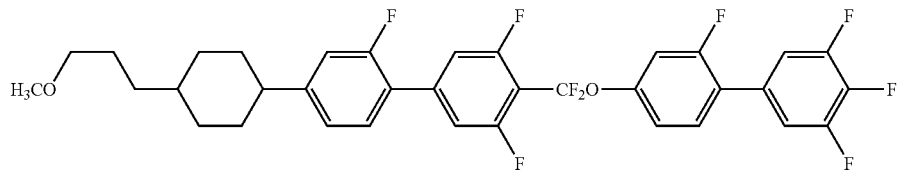 1-3-391
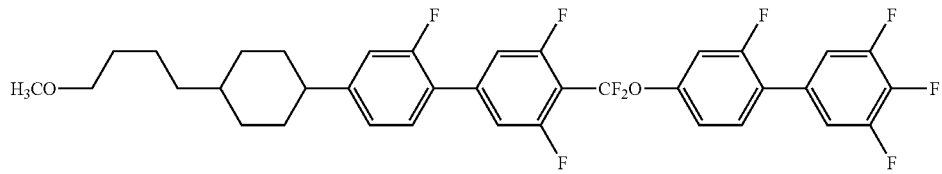 1-3-392
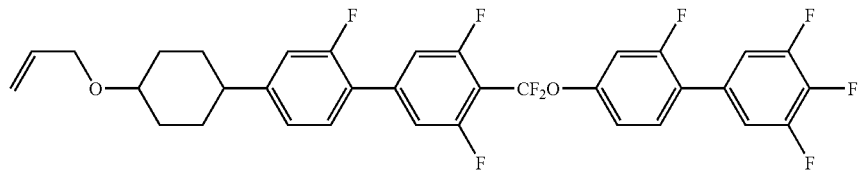 1-3-393
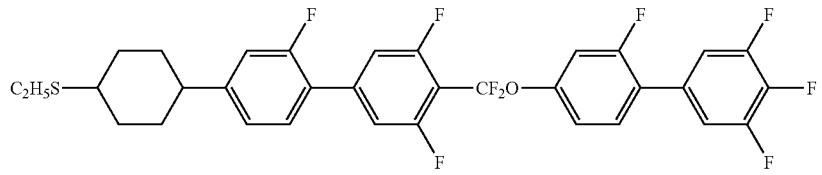 1-3-394
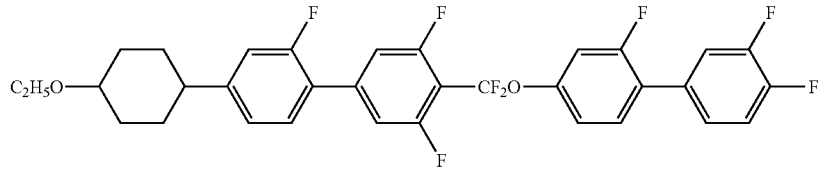 1-3-395

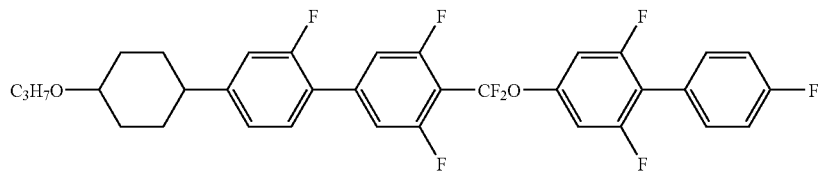
1-3-396
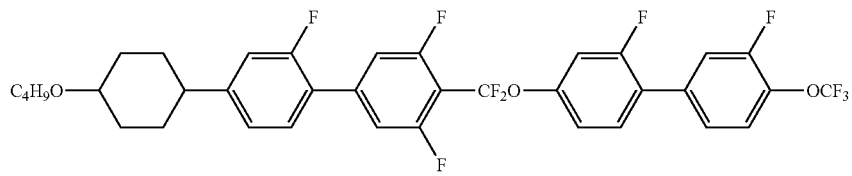
1-3-397
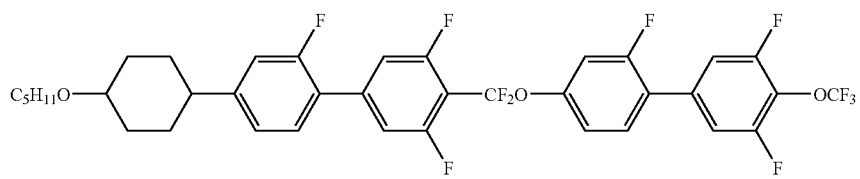
1-3-398
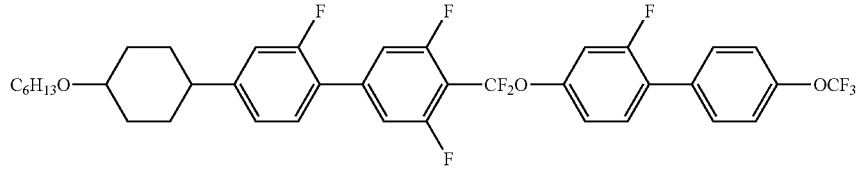
1-3-399
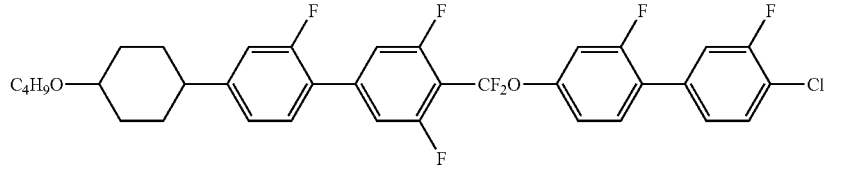
1-3-400
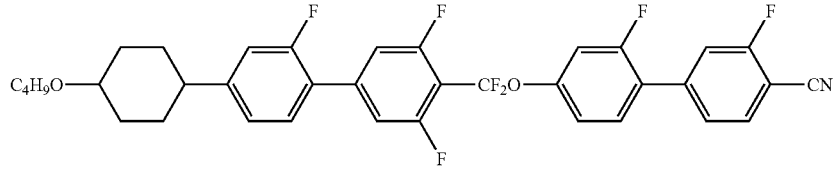
1-3-401
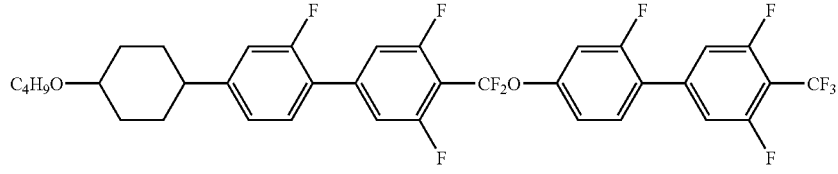
1-3-402
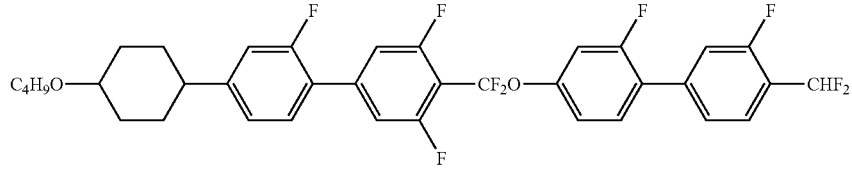
1-3-403
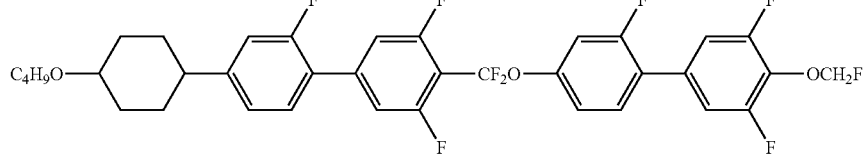
1-3-404

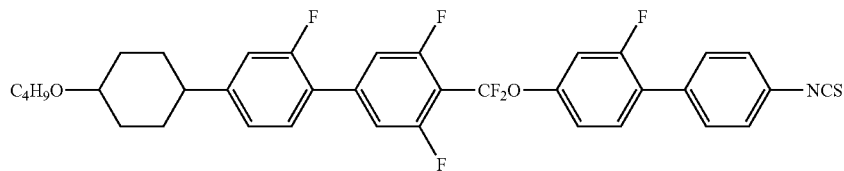
1-3-405
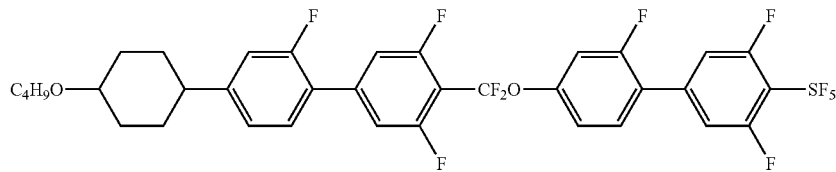
1-3-406
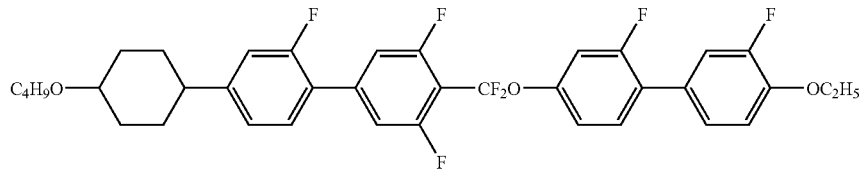
1-3-407
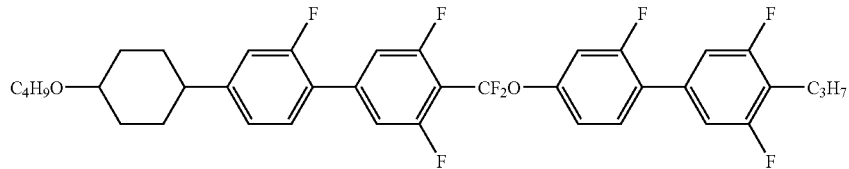
1-3-408
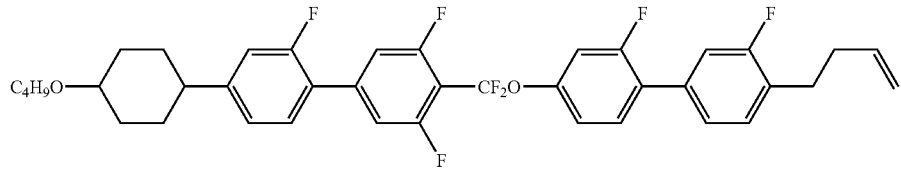
1-3-409
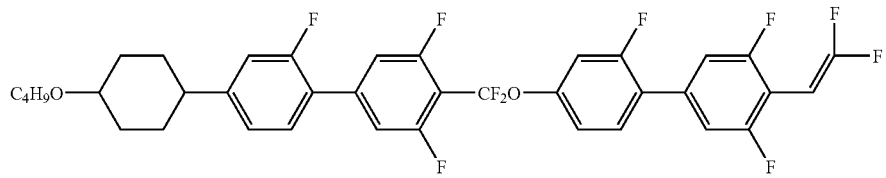
1-3-410
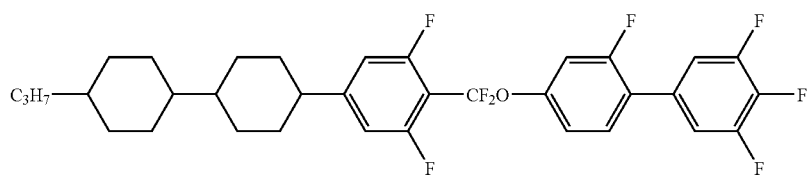
1-3-411
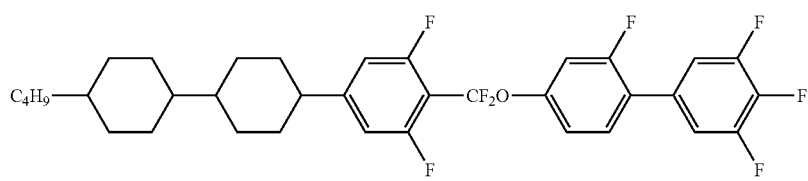
1-3-412

-continued
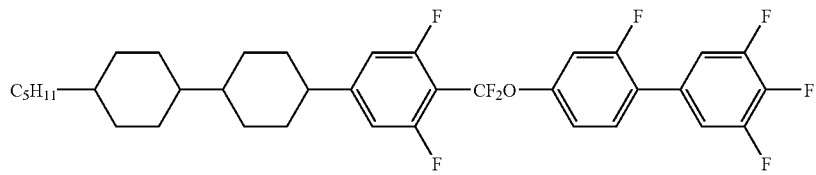
$T_{NI}$ = 167° C., Δn = 0.157, Δε = 22.6
1-3-413
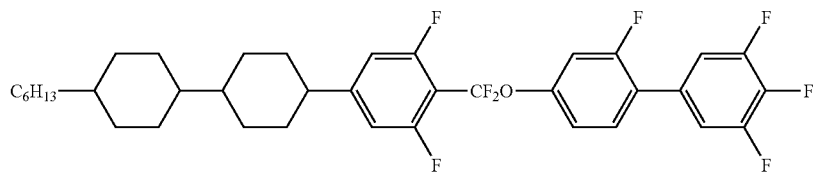
1-3-414
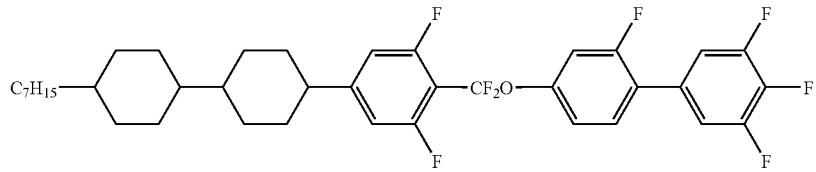
1-3-415
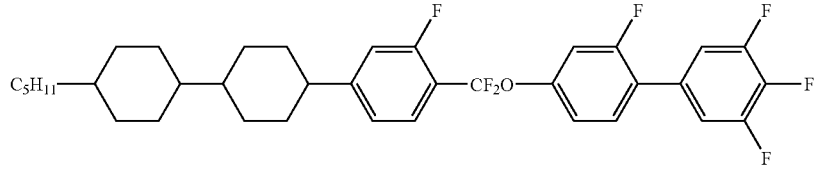
1-3-416
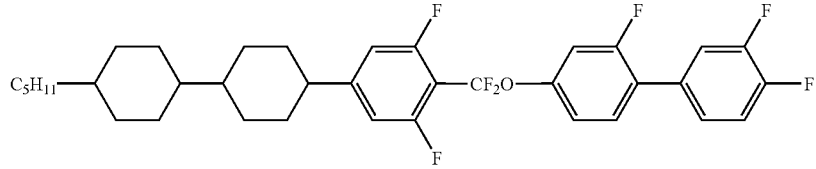
1-3-417
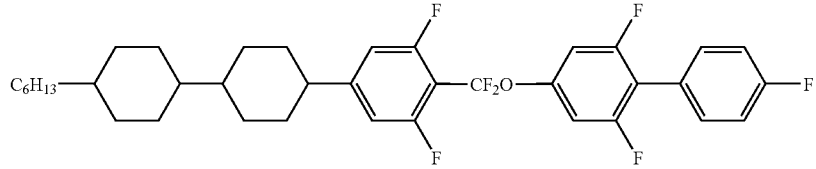
1-3-418
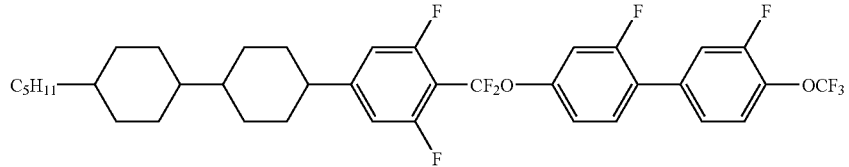
1-3-419
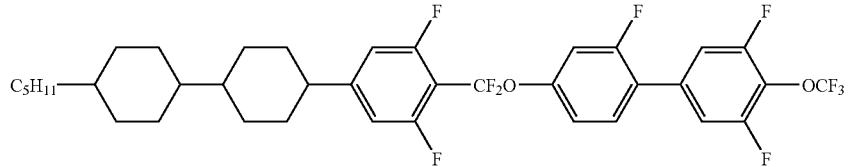
1-3-420
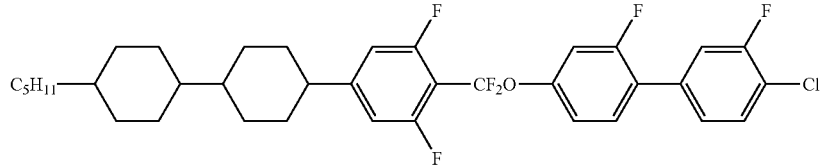
1-3-421

-continued
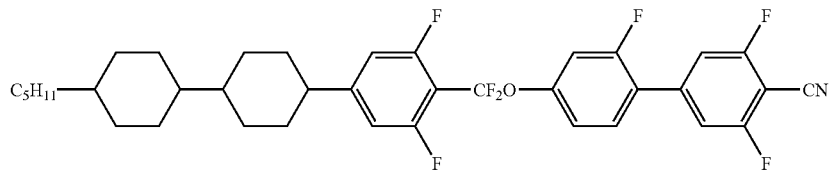
1-3-422
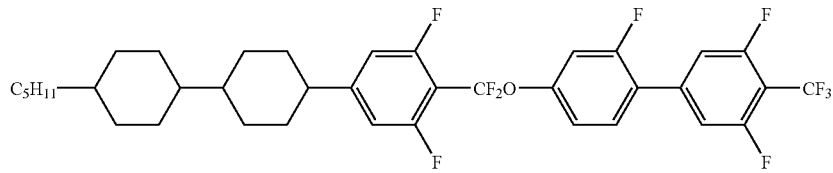
1-3-423
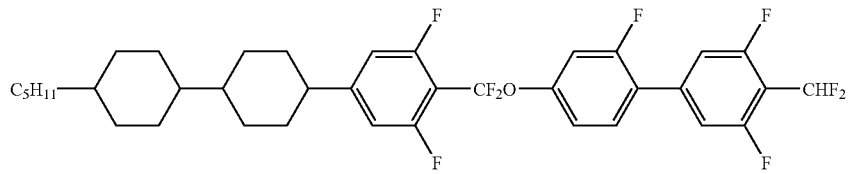
1-3-424
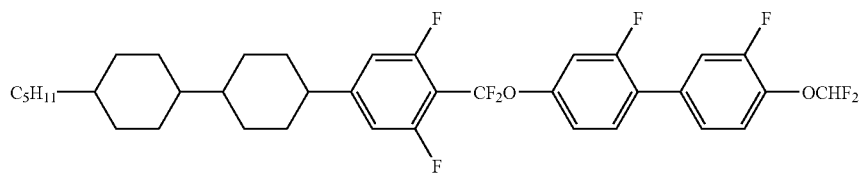
1-3-425
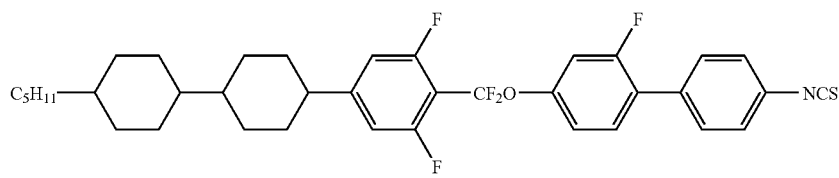
1-3-426
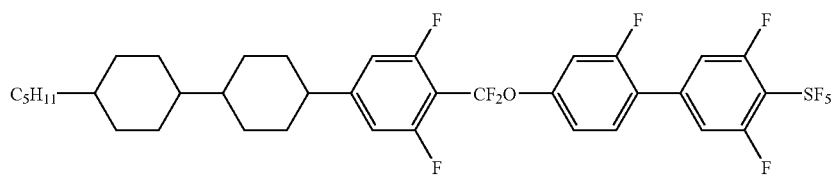
1-3-427
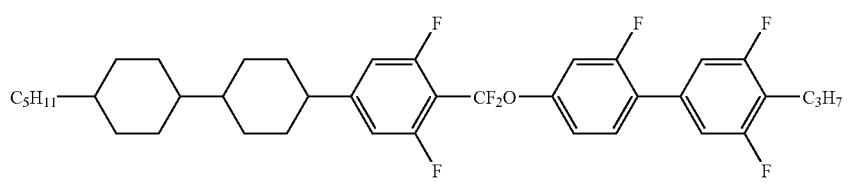
1-3-428
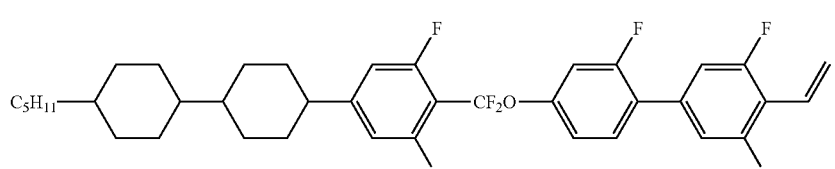
1-3-429
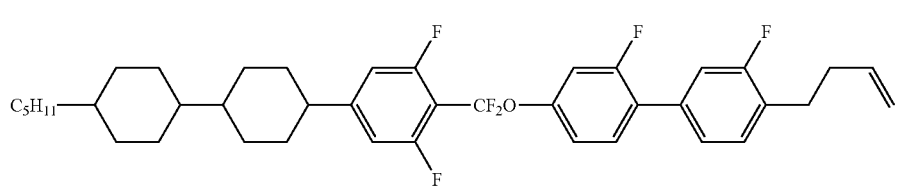
1-3-430

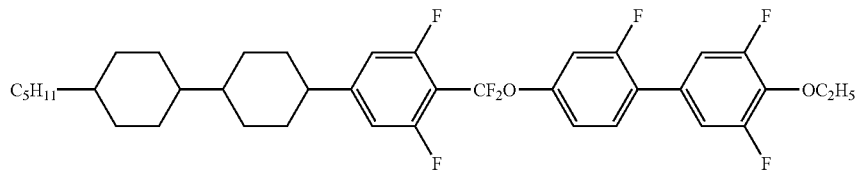
1-3-431
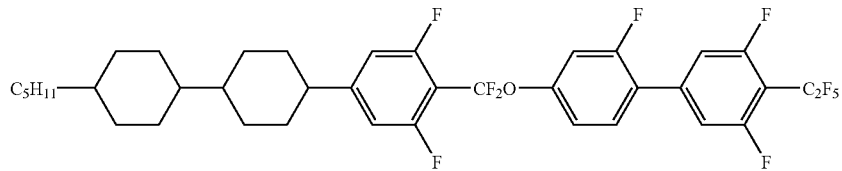
1-3-432
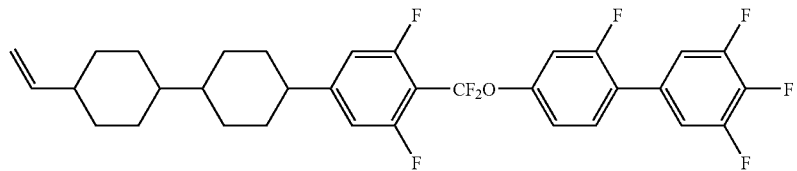
1-3-433
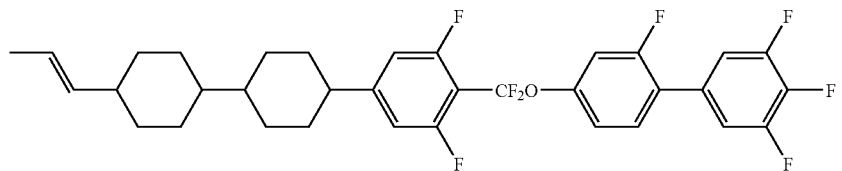
1-3-434
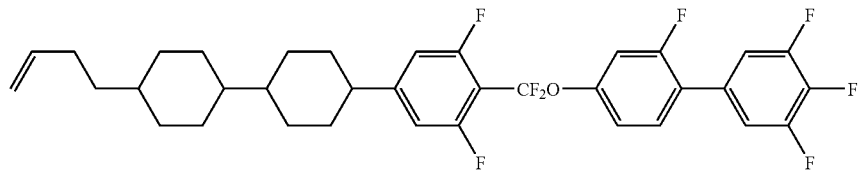
1-3-435
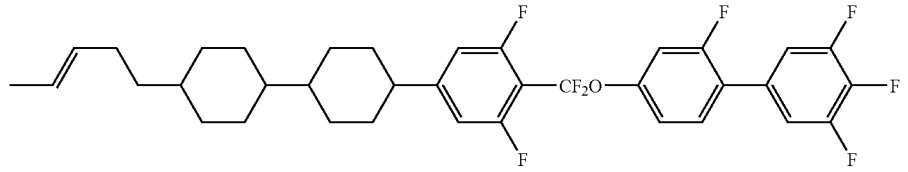
1-3-436
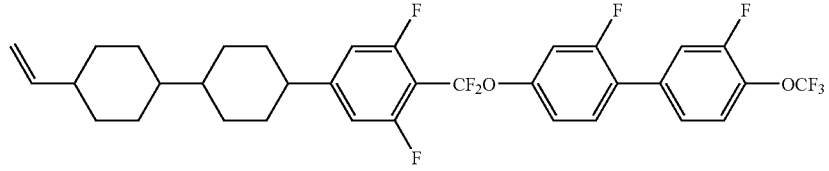
1-3-437
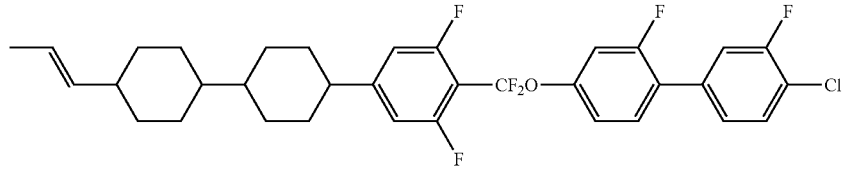
1-3-438
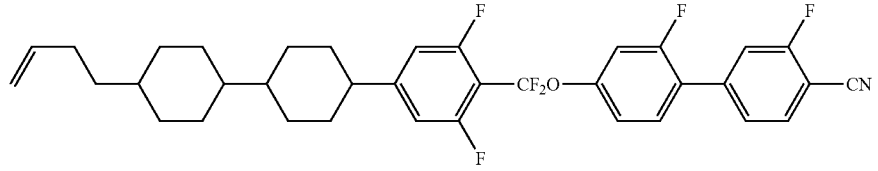
1-3-439

-continued
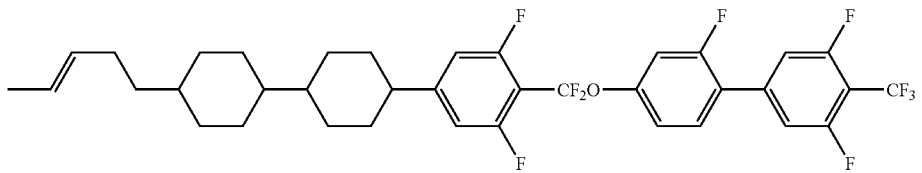 1-3-440
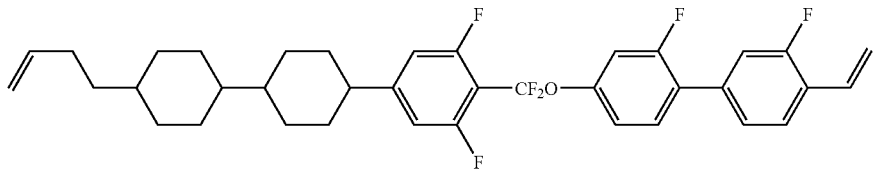 1-3-441
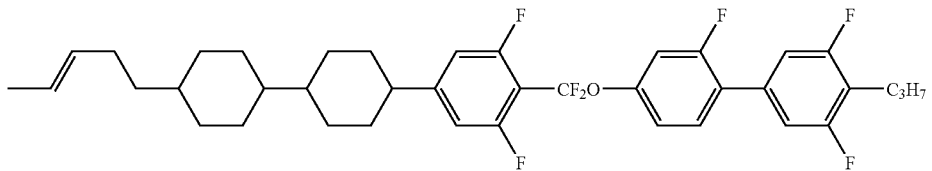 1-3-442
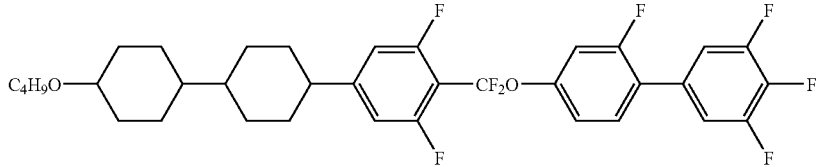 1-3-443
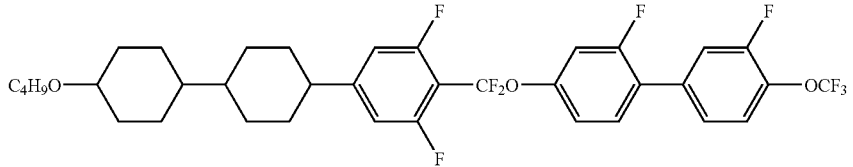 1-3-444
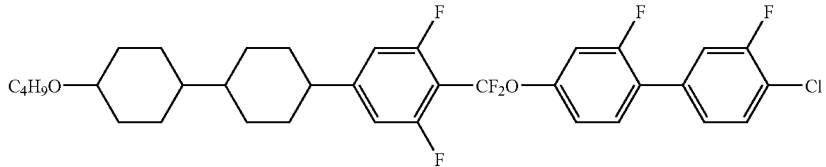 1-3-445
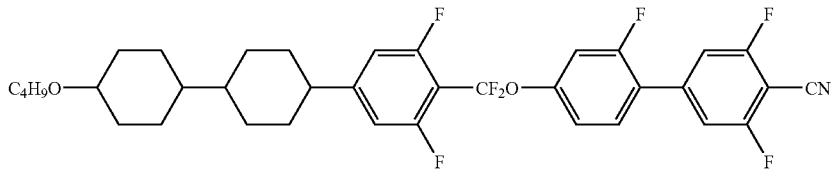 1-3-446
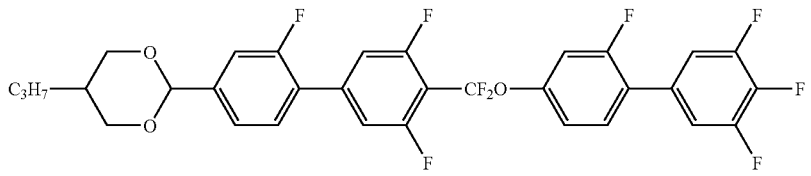 1-3-447
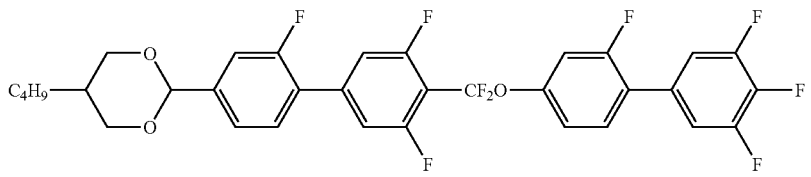 1-3-448

-continued
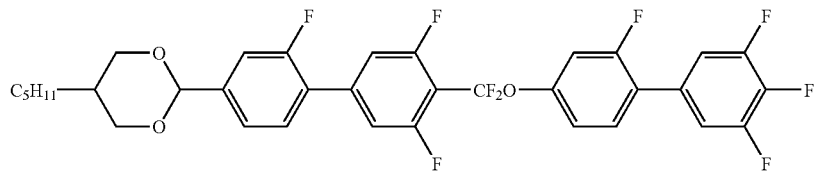
$T_{NI} = 141°$ C., $\Delta n = 0.184$, $\Delta \varepsilon = 44.1$
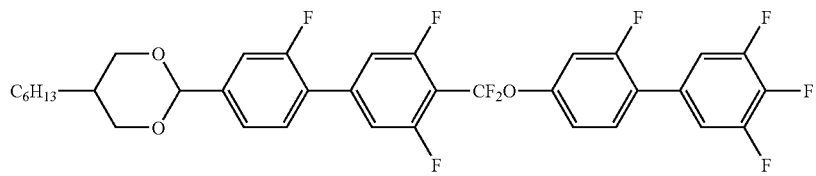
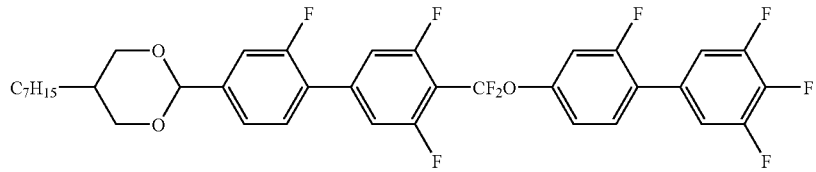
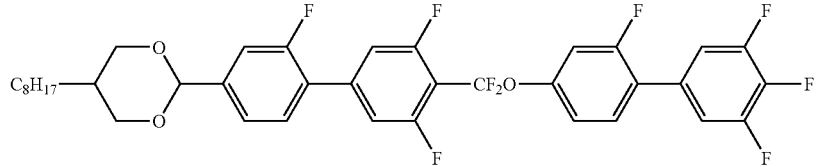
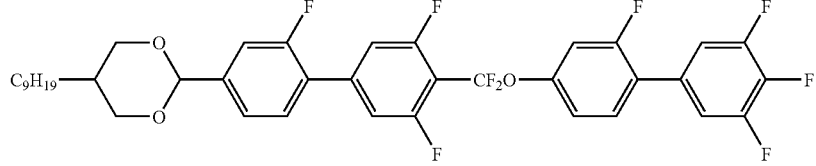
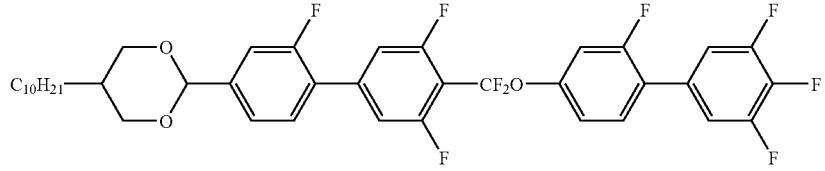
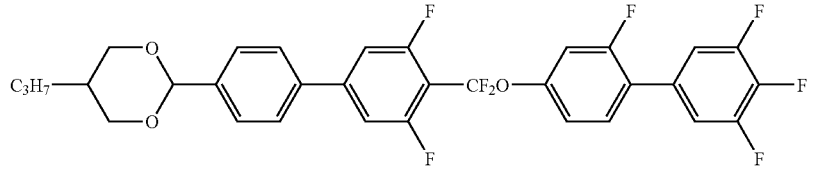
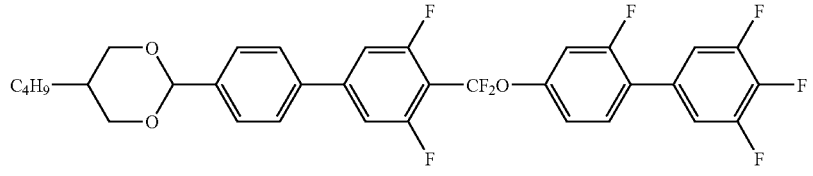
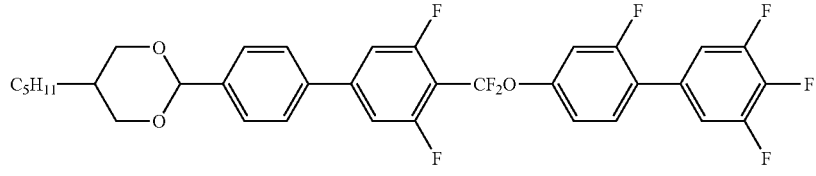
1-3-449
1-3-450
1-3-451
1-3-452
1-3-453
1-3-454
1-3-455
1-3-456
1-3-457

-continued
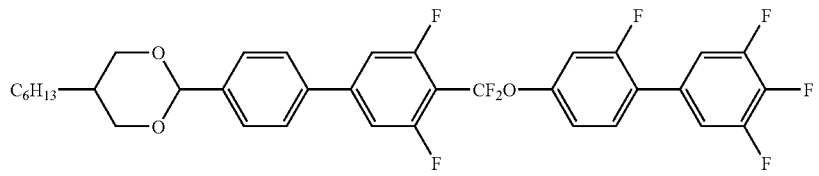
1-3-458

1-3-459
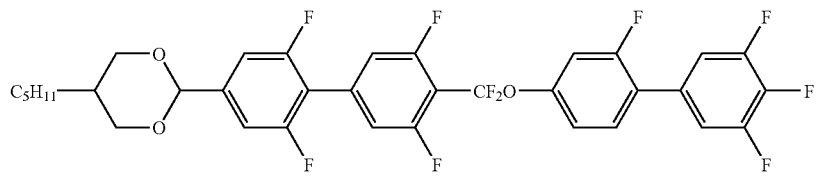
1-3-460
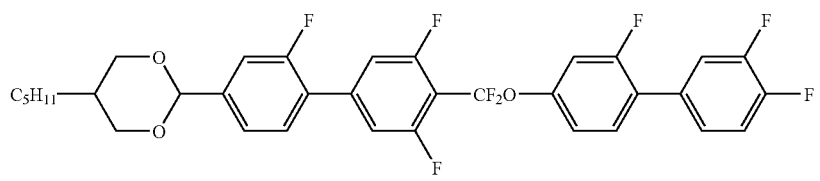
1-3-461
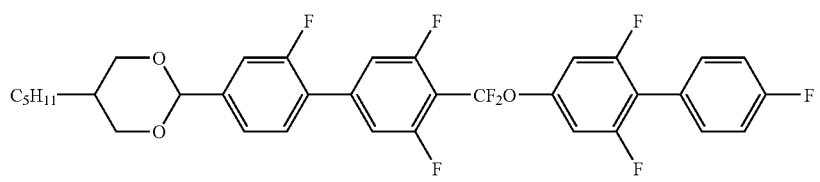
1-3-462
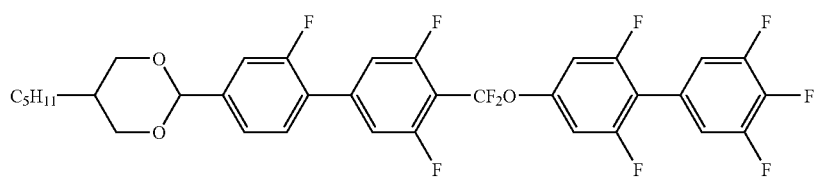
1-3-463
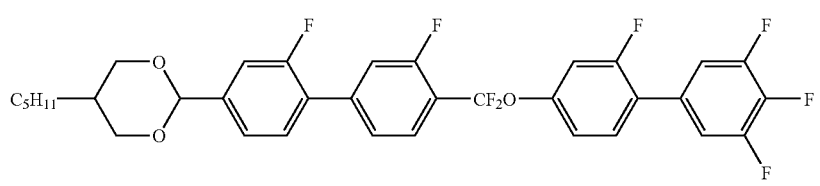
1-3-464
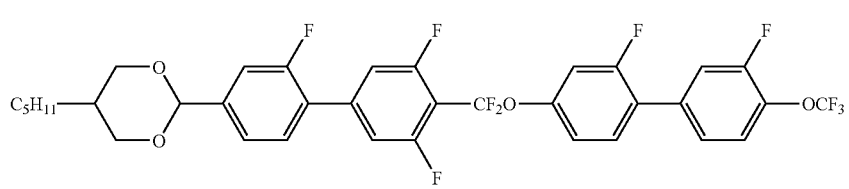
1-3-465
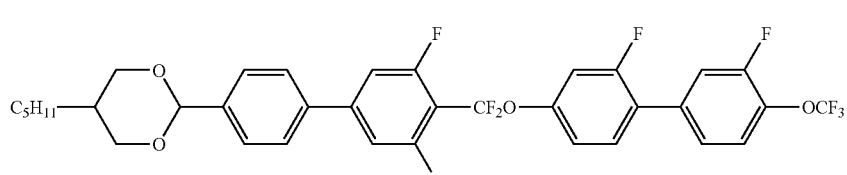
1-3-466

-continued
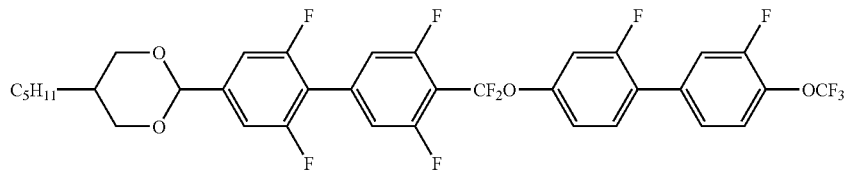
1-3-467

1-3-468
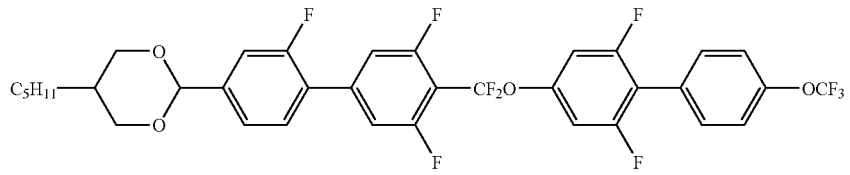
1-3-469
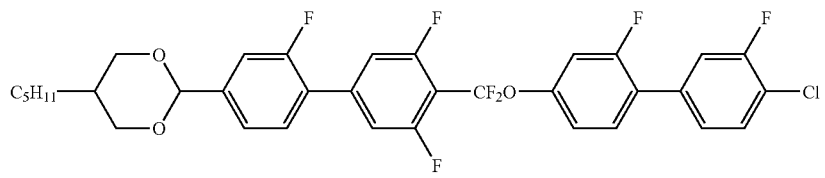
1-3-470
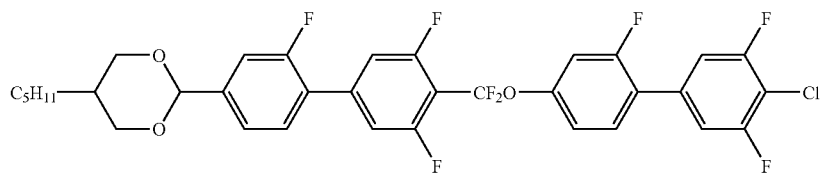
1-3-471
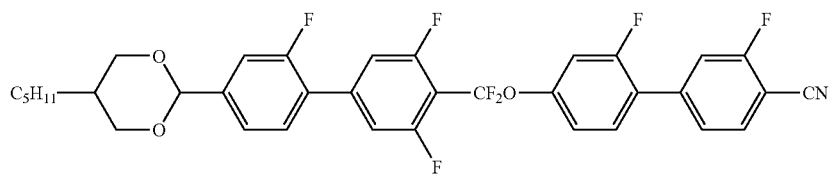
1-3-472
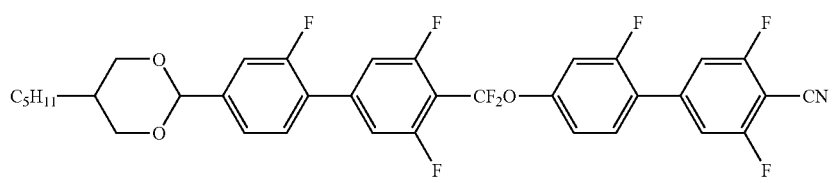
1-3-473
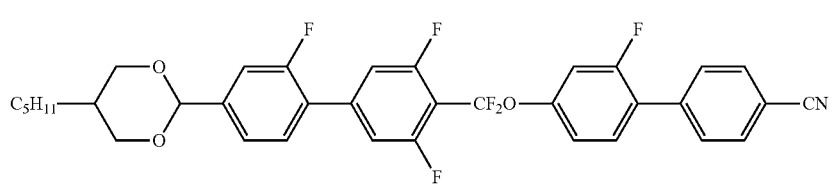
1-3-474
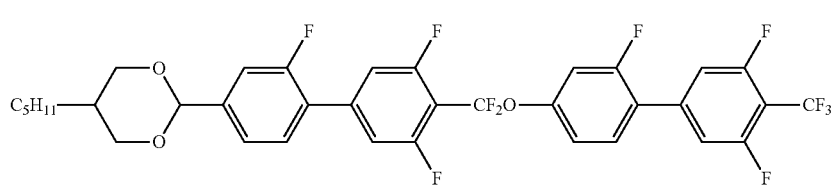
1-3-475

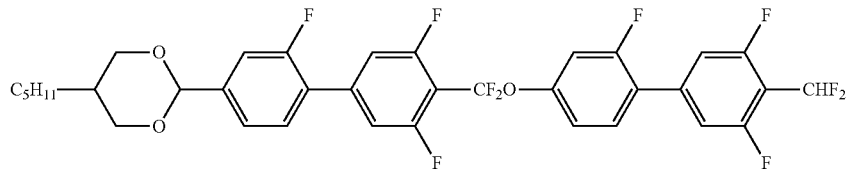
1-3-476
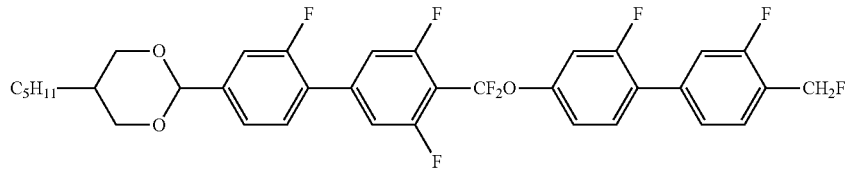
1-3-477
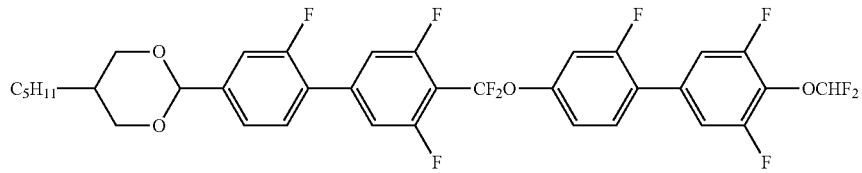
1-3-478
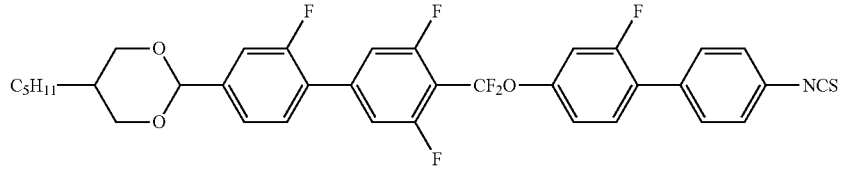
1-3-479
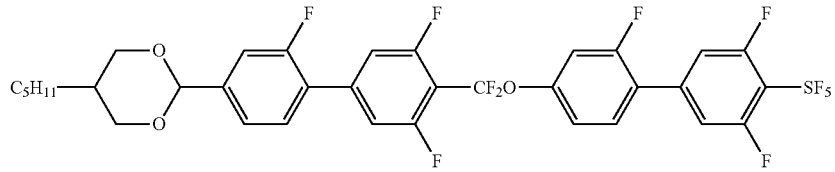
1-3-480
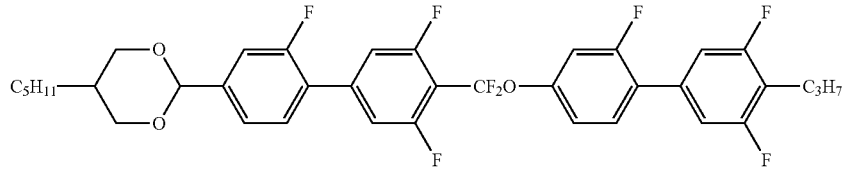
1-3-481
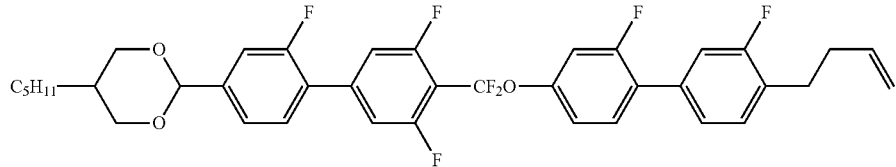
1-3-482
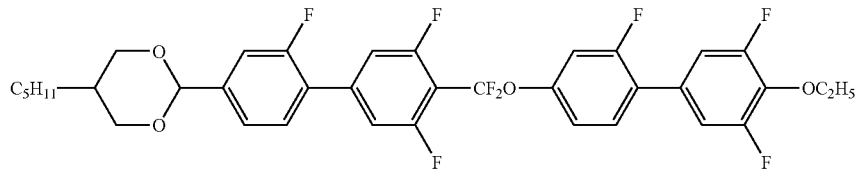
1-3-483
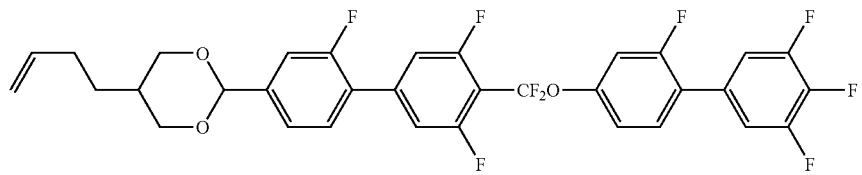
1-3-484

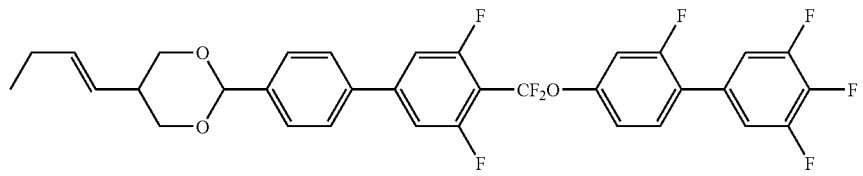
1-3-485
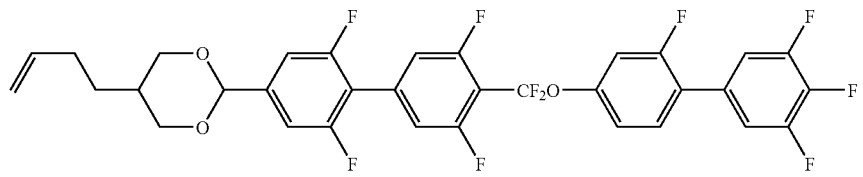
1-3-486
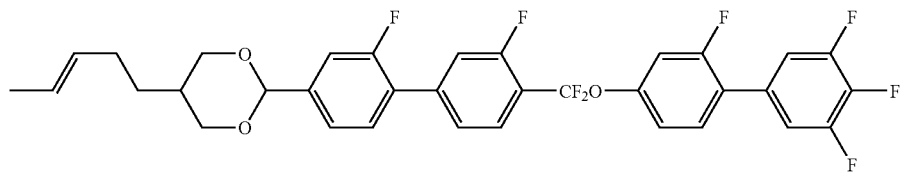
1-3-487
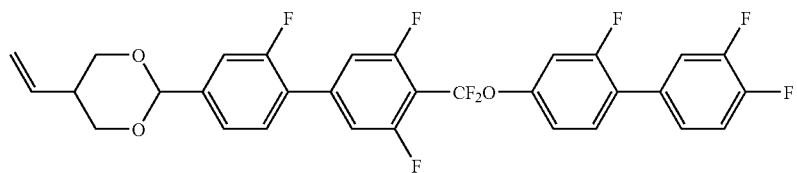
1-3-488
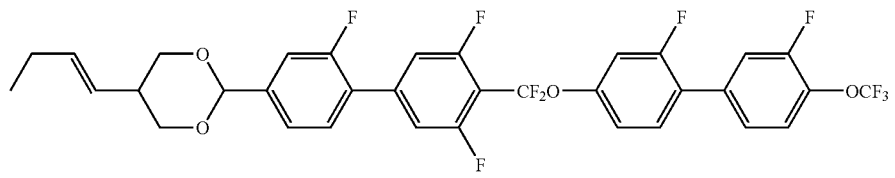
1-3-489
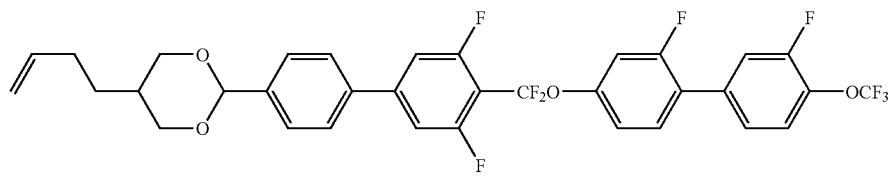
1-3-490
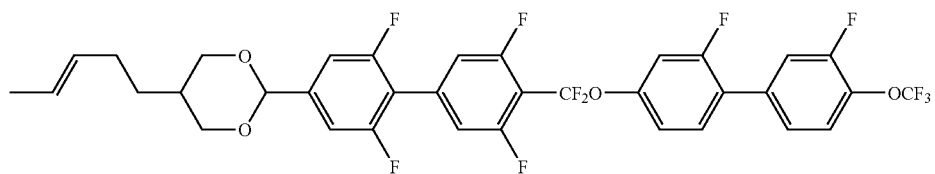
1-3-491
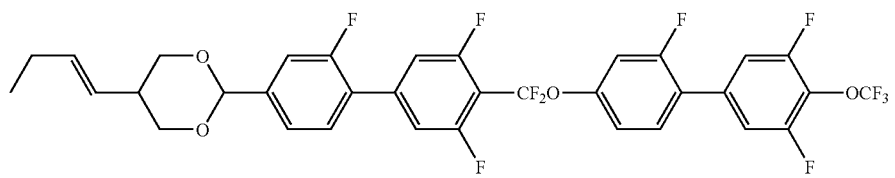
1-3-492
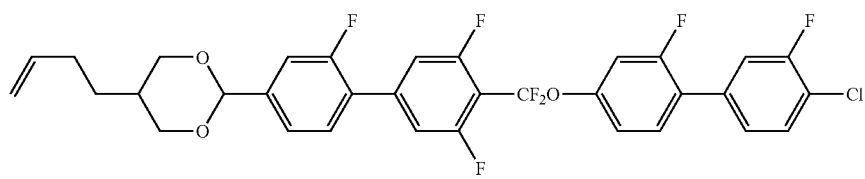
1-3-493

-continued
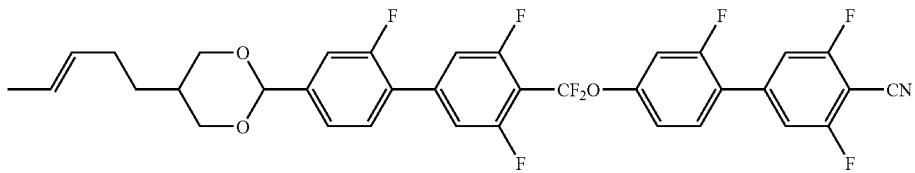
1-3-494
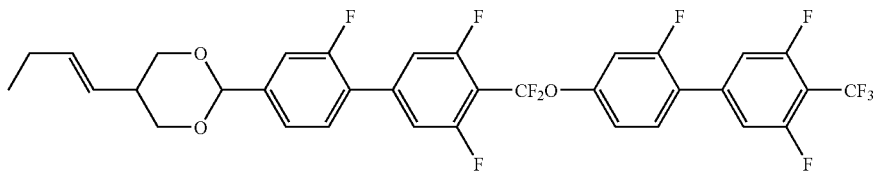
1-3-495
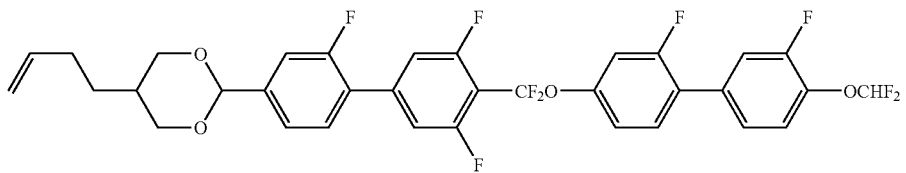
1-3-496
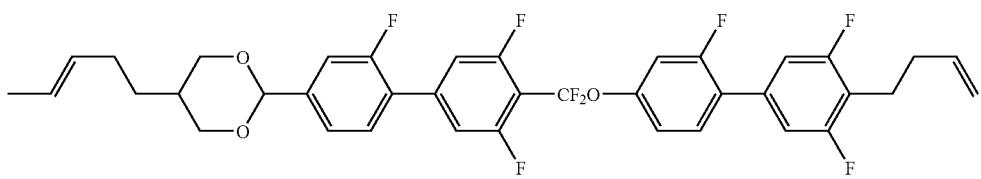
1-3-497
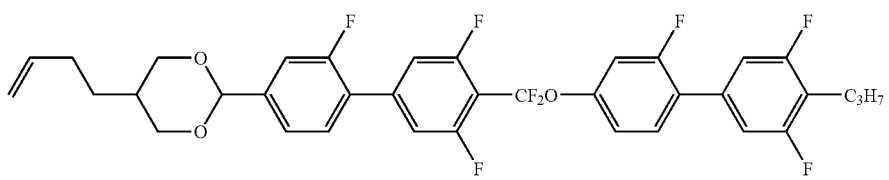
1-3-498
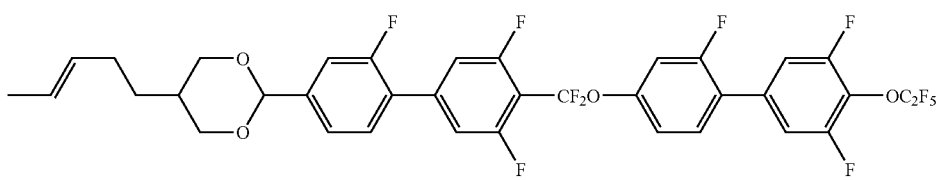
1-3-499
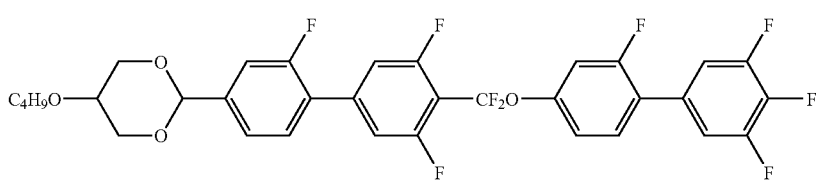
1-3-500
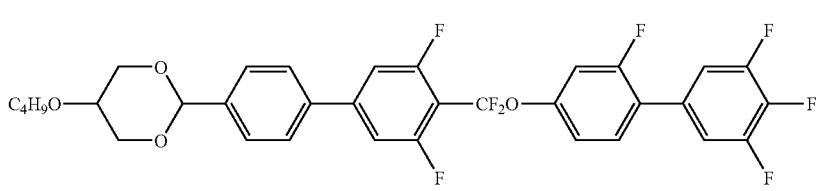
1-3-501
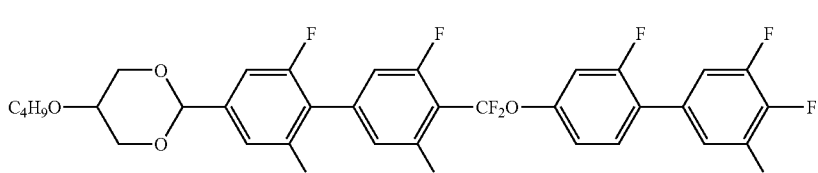
1-3-502

-continued
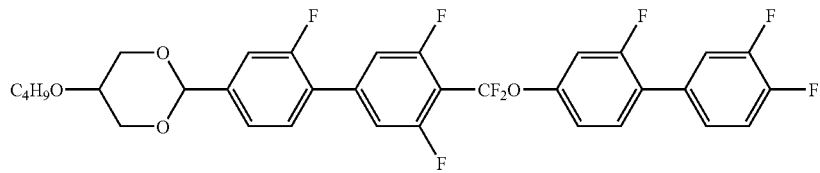
1-3-503
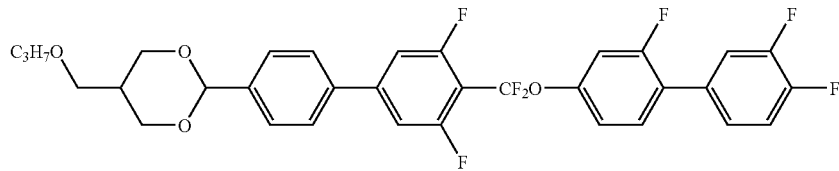
1-3-504
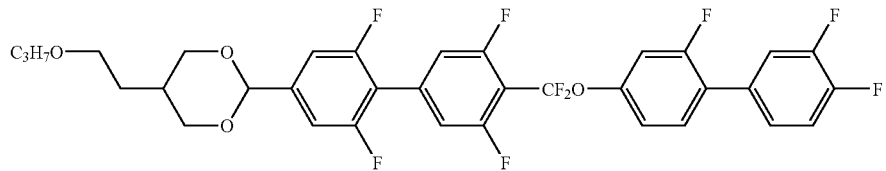
1-3-505
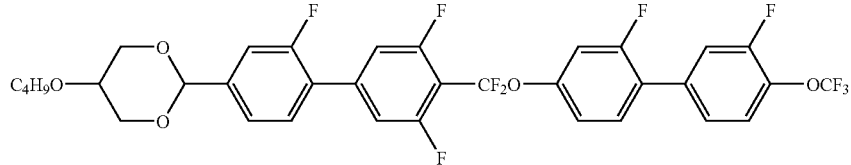
1-3-506
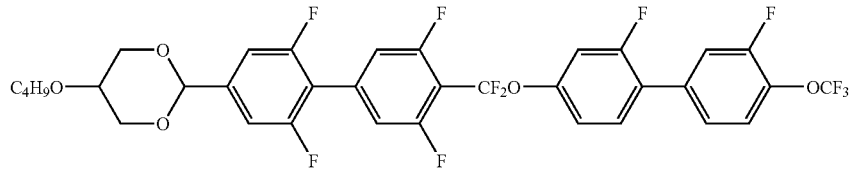
1-3-507
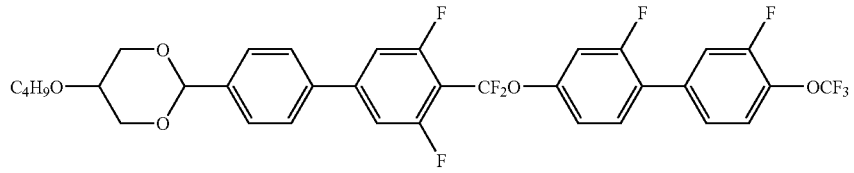
1-3-508
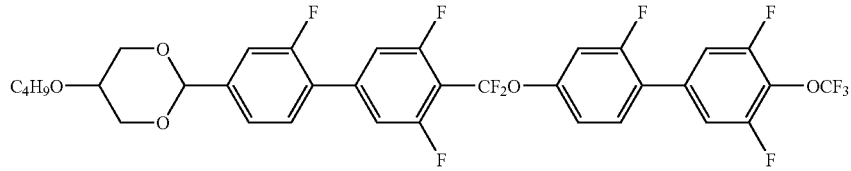
1-3-509
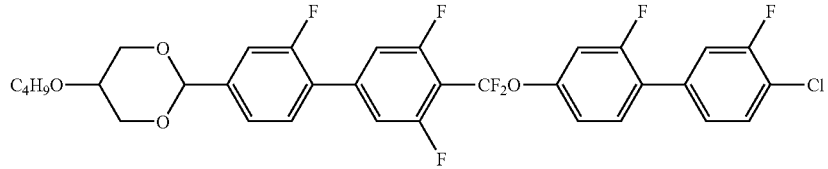
1-3-510
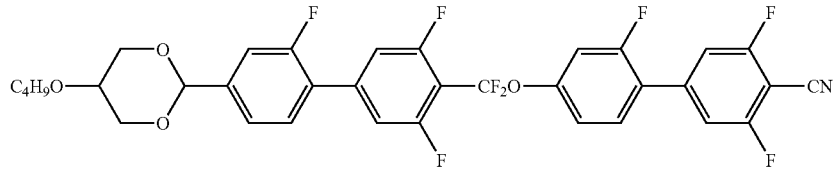
1-3-511

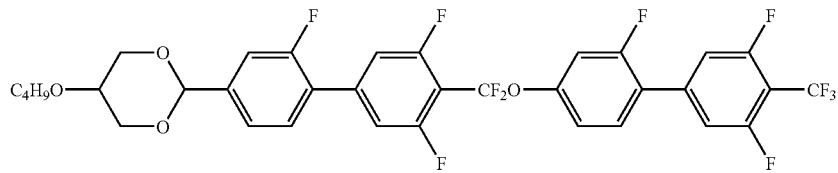 1-3-512
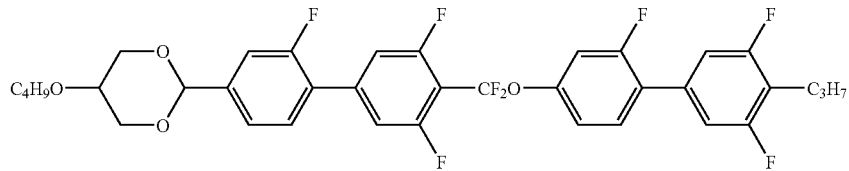 1-3-513
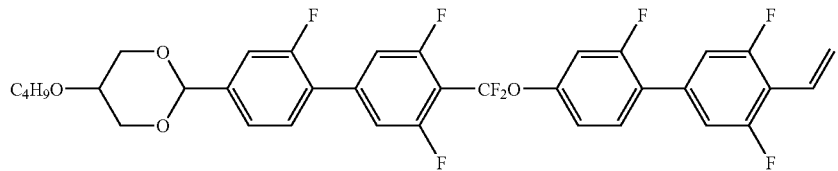 1-3-514
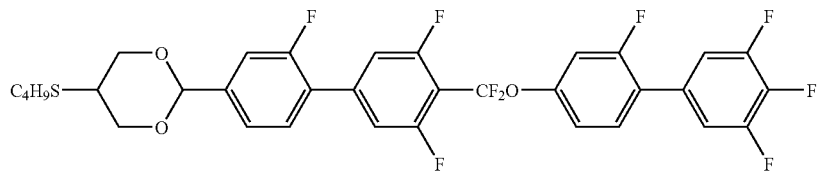 1-3-515
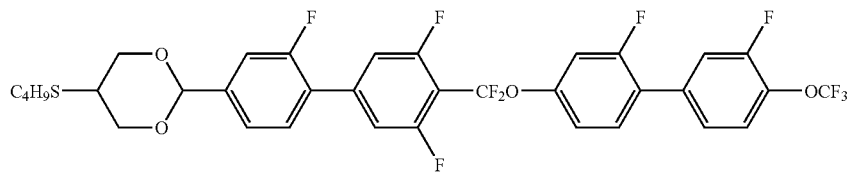 1-3-516
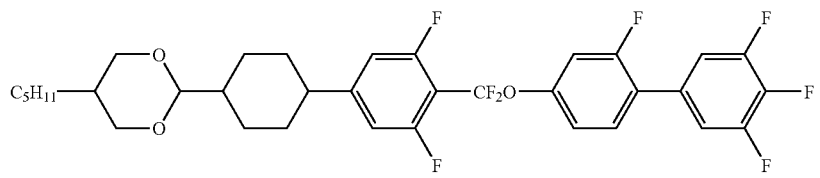 1-3-517
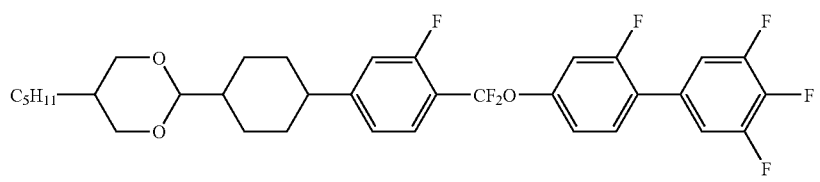 1-3-518
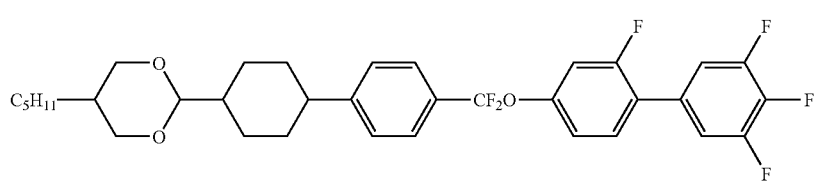 1-3-519
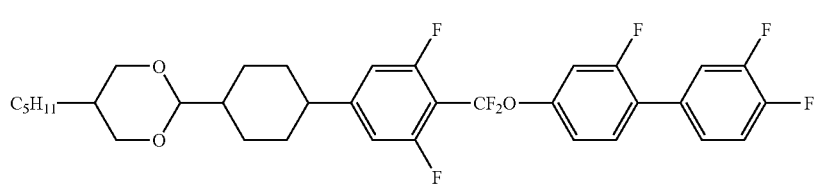 1-3-520

-continued
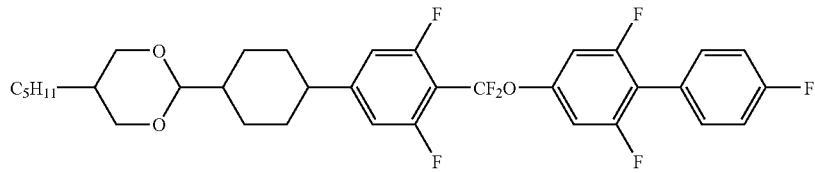
1-3-521
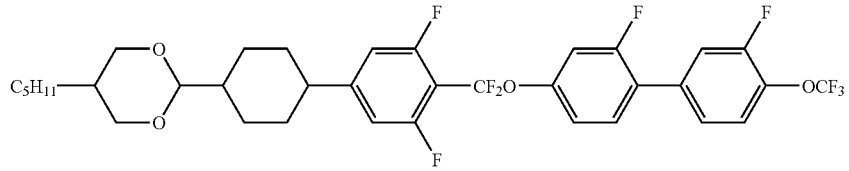
1-3-522
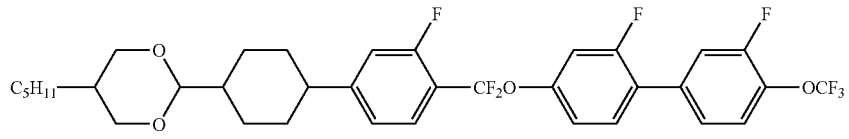
1-3-523
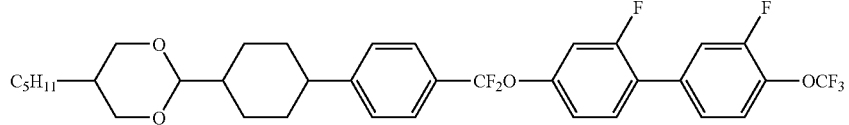
1-3-524
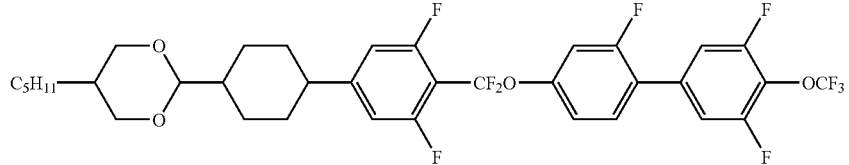
1-3-525
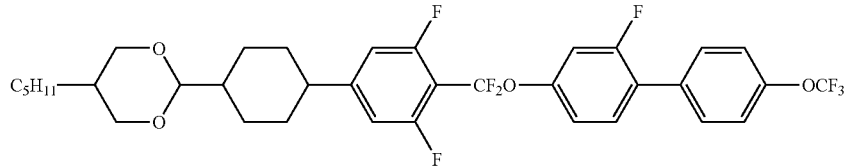
1-3-526
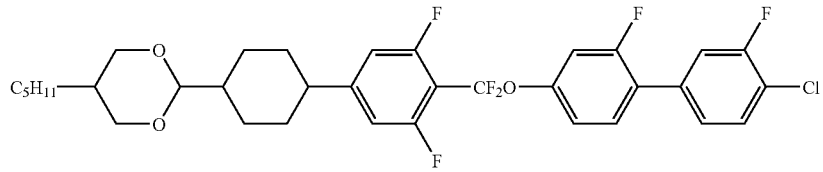
1-3-527
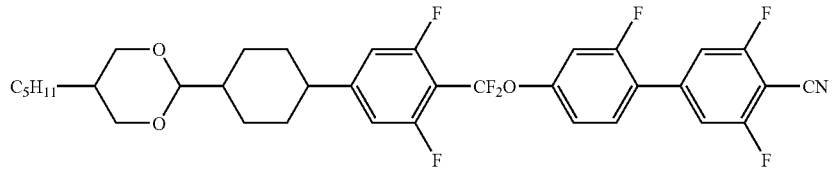
1-3-528
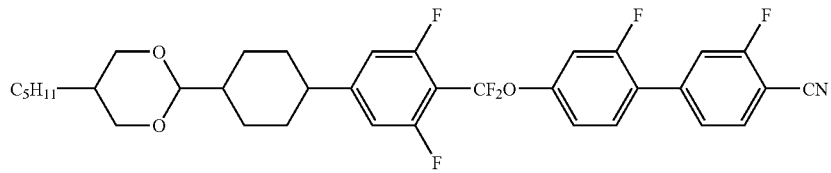
1-3-529

-continued
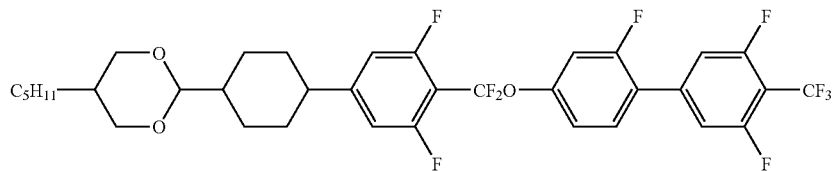
1-3-530
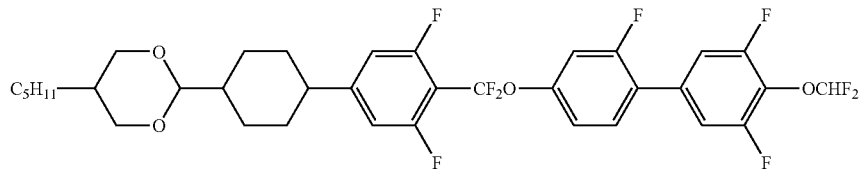
1-3-531
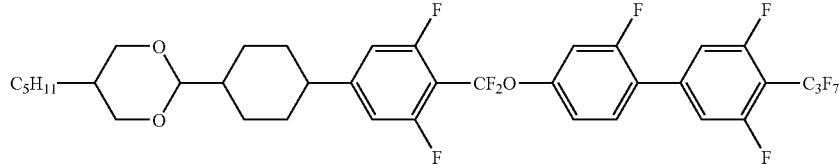
1-3-532
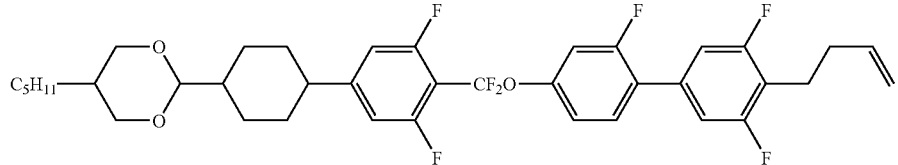
1-3-533
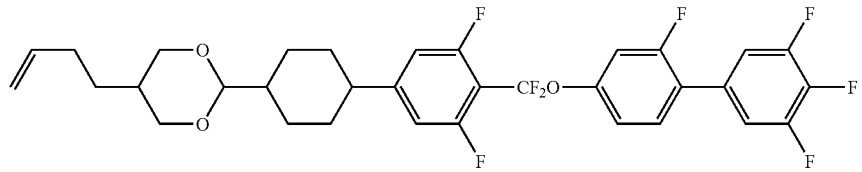
1-3-534
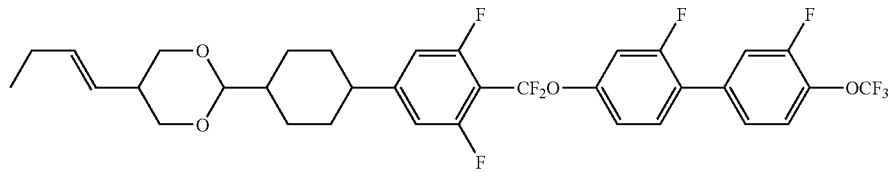
1-3-535
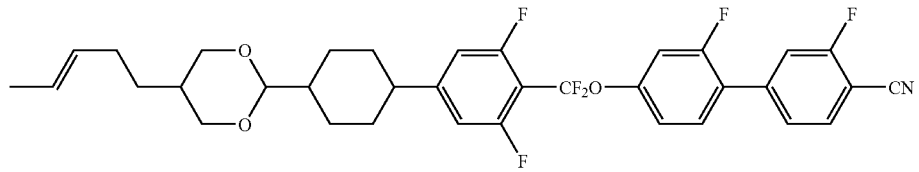
1-3-536
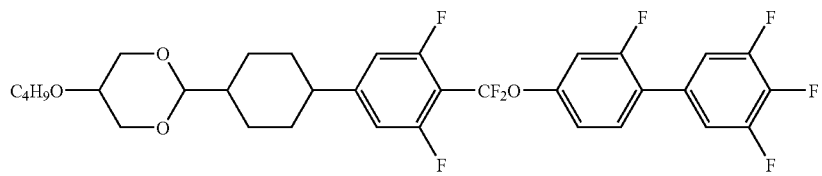
1-3-537
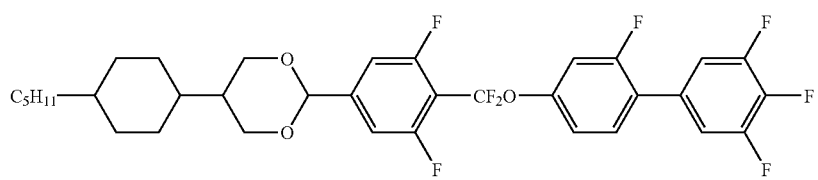
1-3-538

-continued
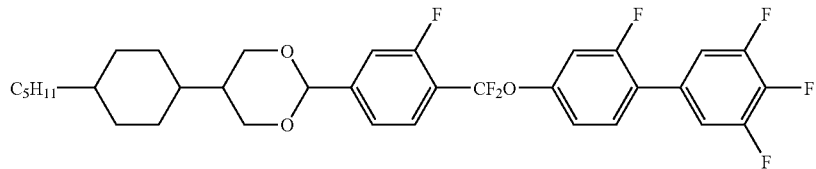
1-3-539
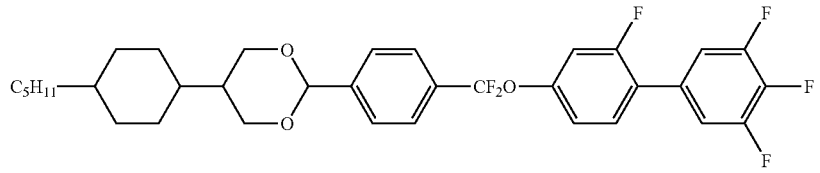
1-3-540
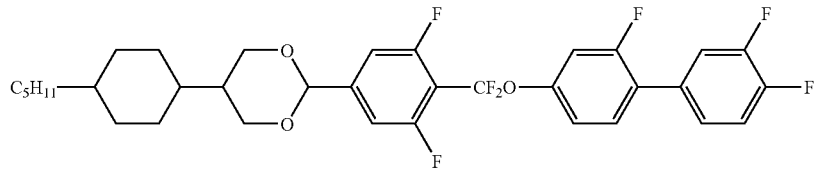
1-3-541
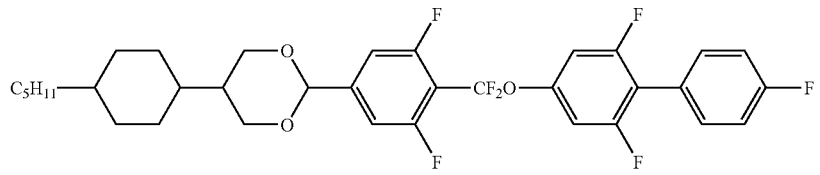
1-3-542
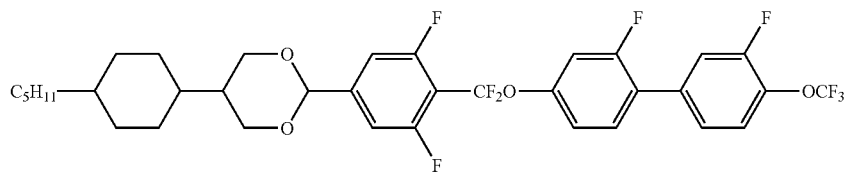
1-3-543
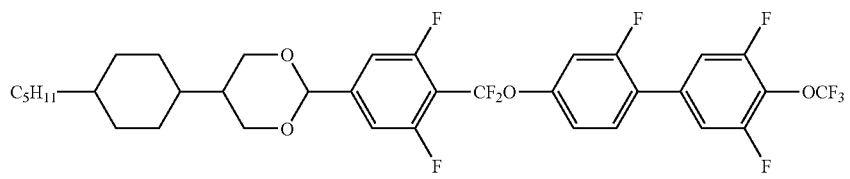
1-3-544
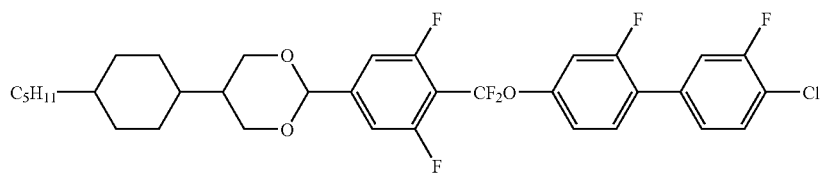
1-3-545
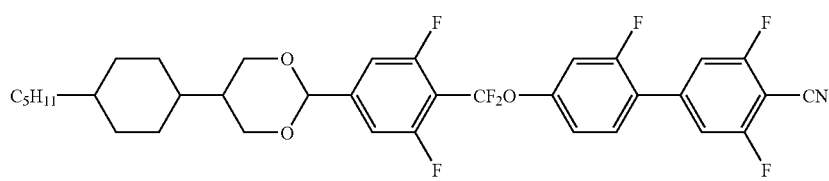
1-3-546
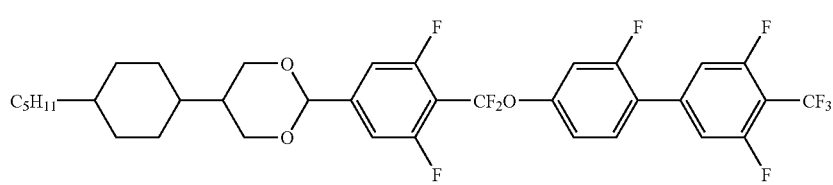
1-3-547

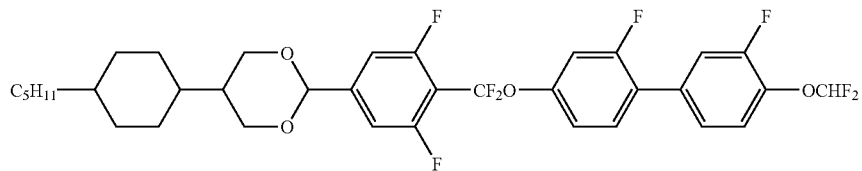
1-3-548
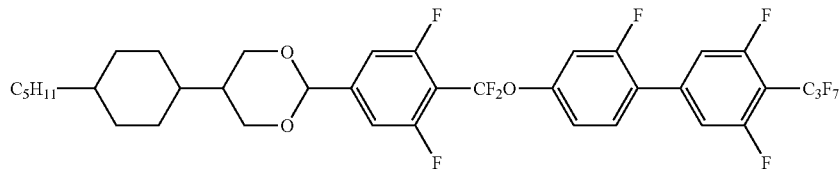
1-3-549
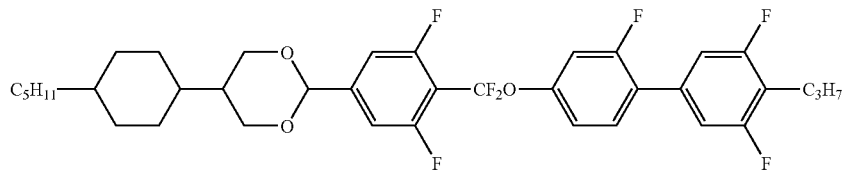
1-3-550
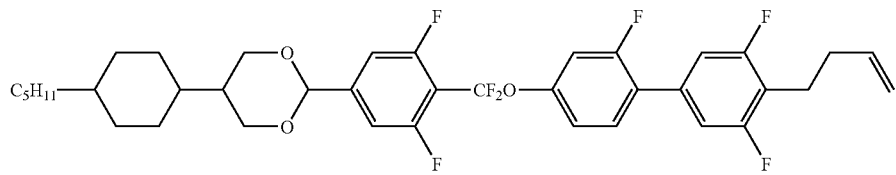
1-3-551
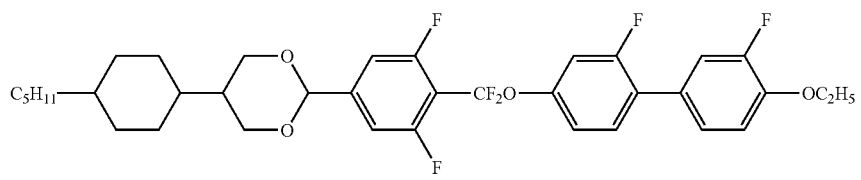
1-3-552
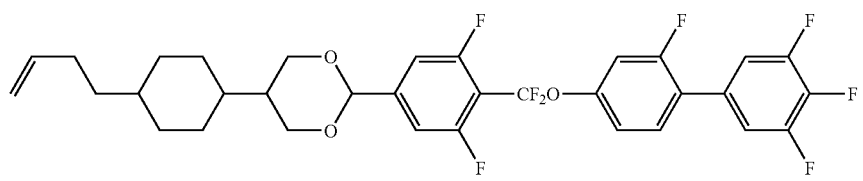
1-3-553
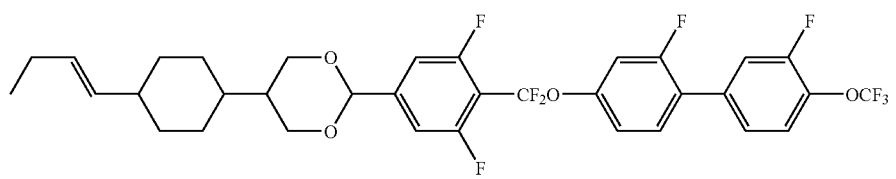
1-3-554
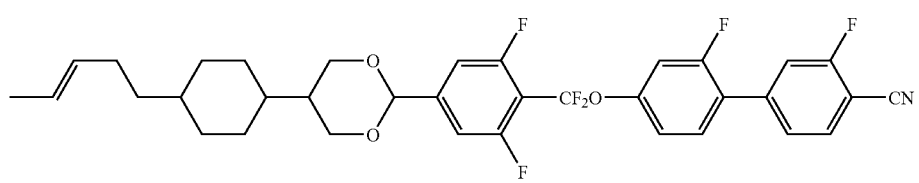
1-3-555
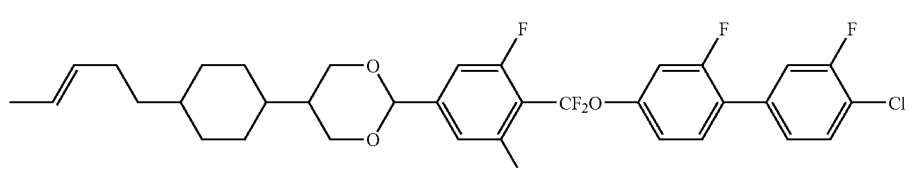
1-3-556

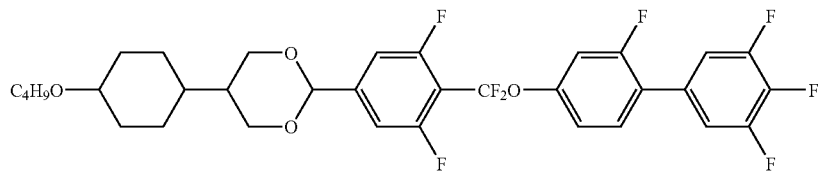
1-3-557
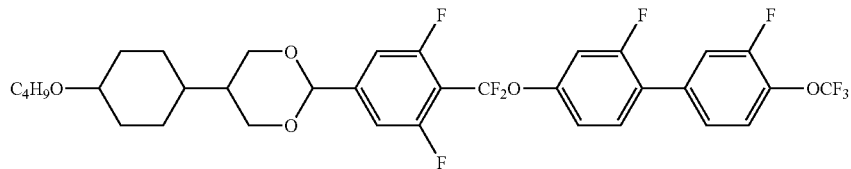
1-3-558
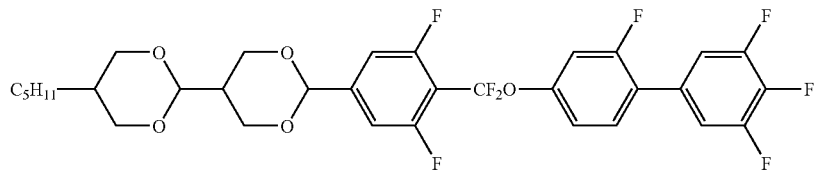
1-3-559
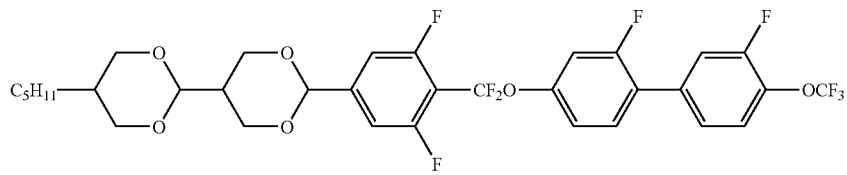
1-3-560
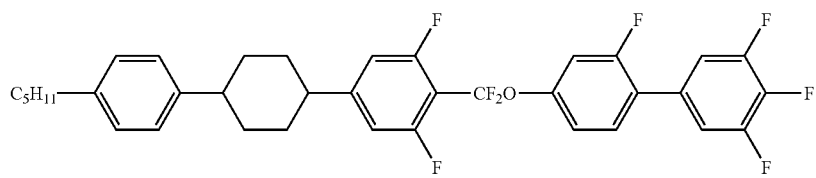
1-3-561
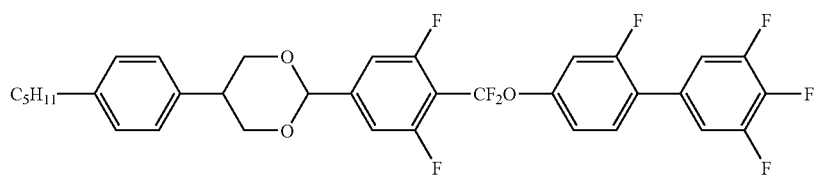
1-3-562
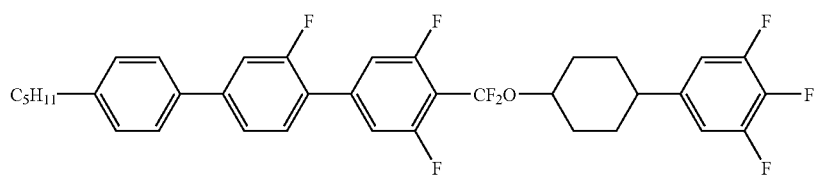
1-3-563
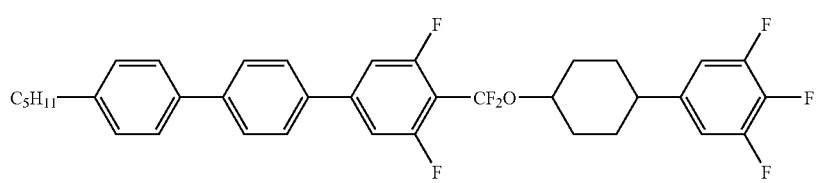
1-3-564
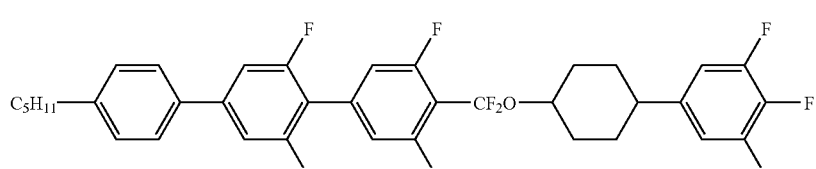
1-3-565

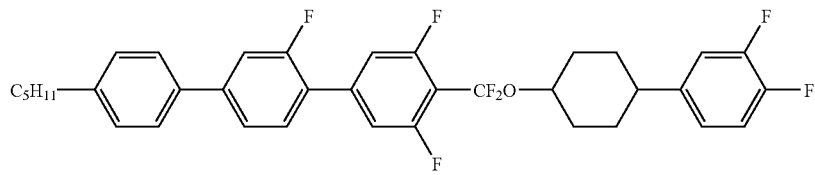
1-3-566
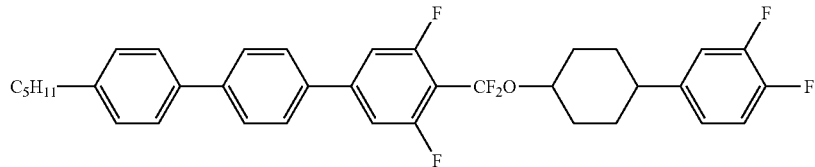
1-3-567
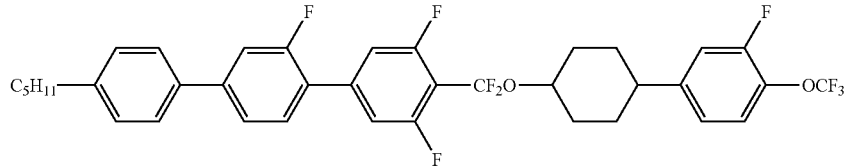
1-3-568
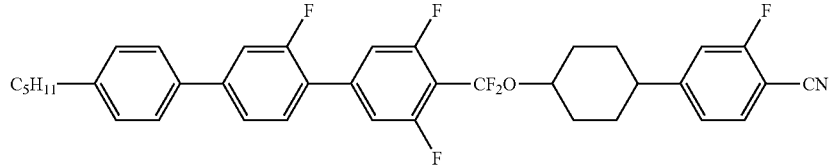
1-3-569
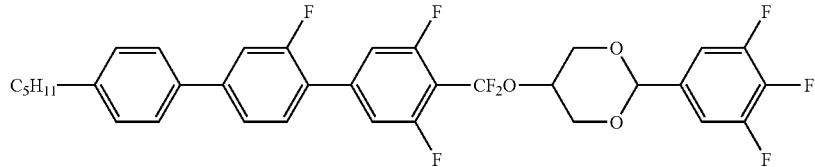
1-3-570
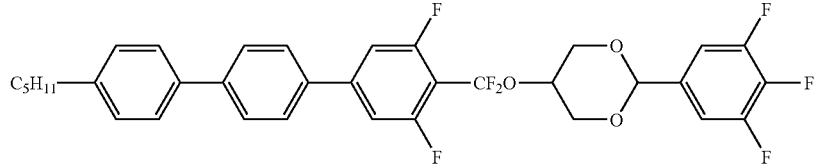
1-3-571
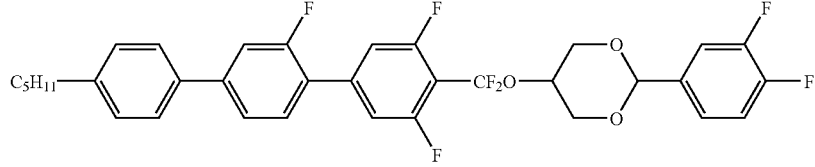
1-3-572
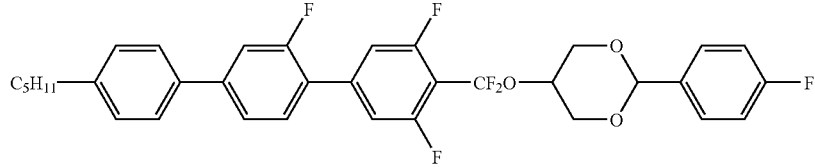
1-3-573
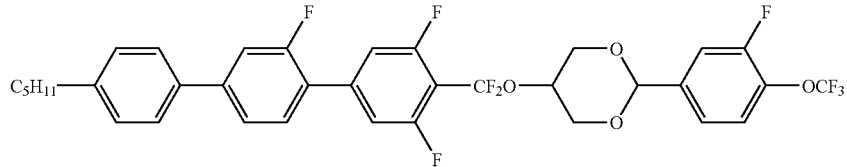
1-3-574

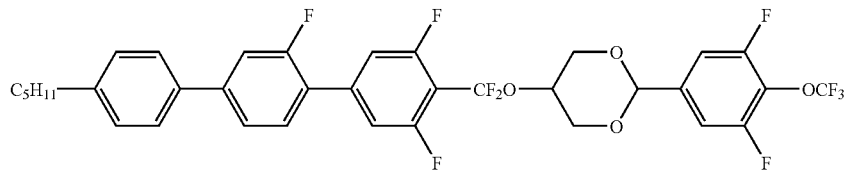
1-3-575
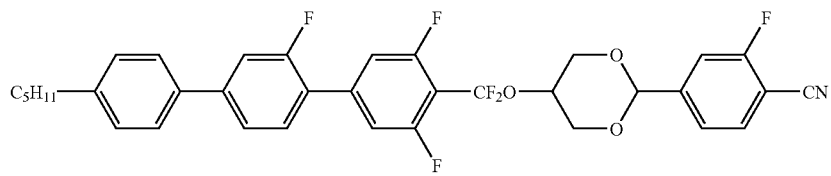
1-3-576
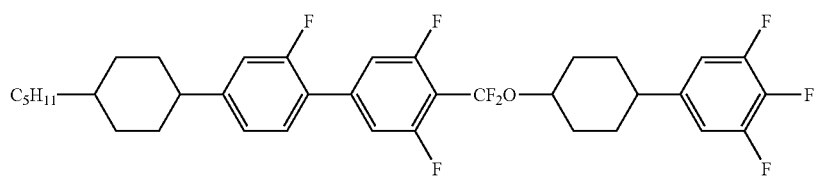
1-3-577
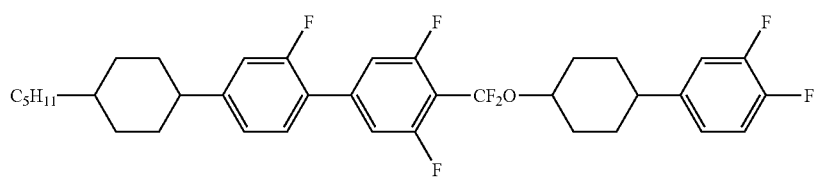
1-3-578
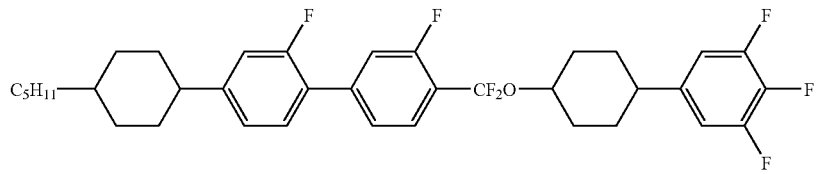
1-3-579
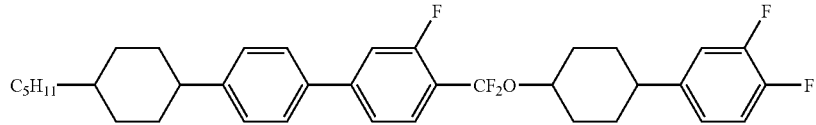
1-3-580
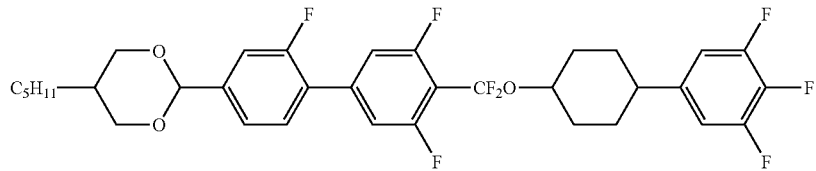
1-3-581
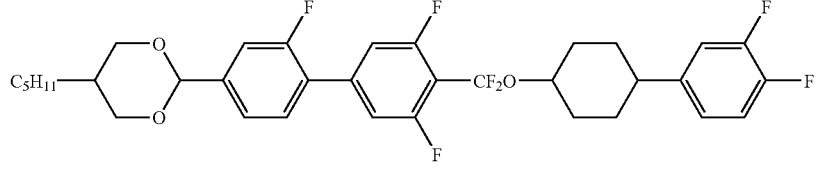
1-3-582
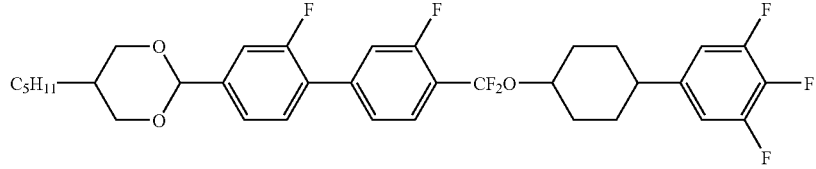
1-3-583

-continued
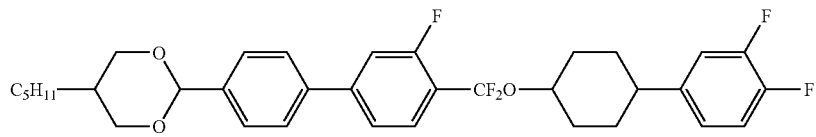
1-3-584
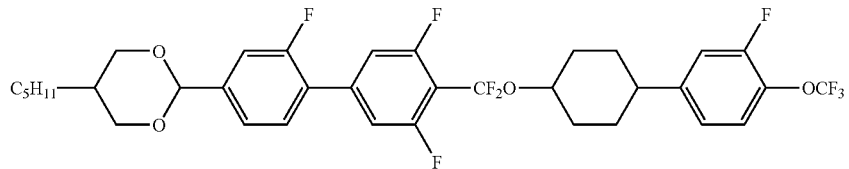
1-3-585
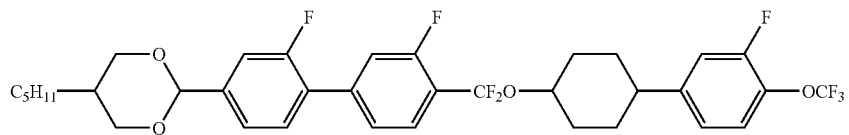
1-3-586
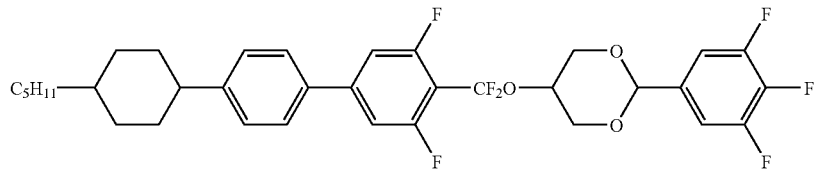
1-3-587
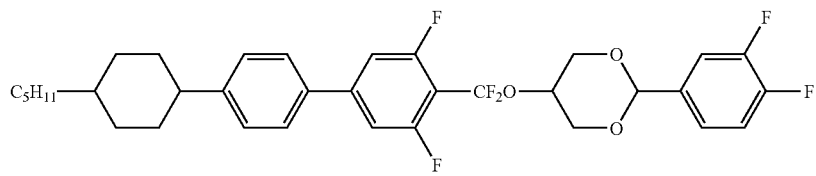
1-3-588
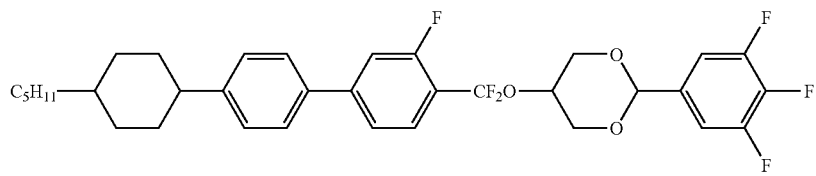
1-3-589
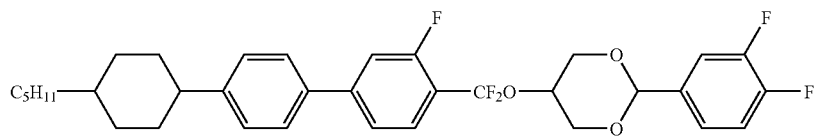
1-3-590
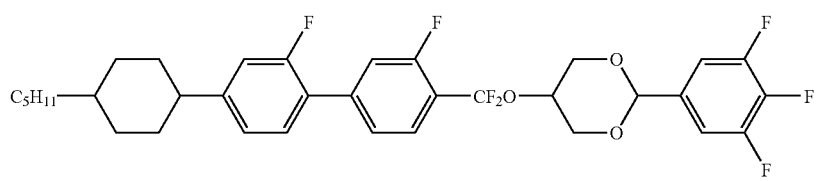
1-3-591
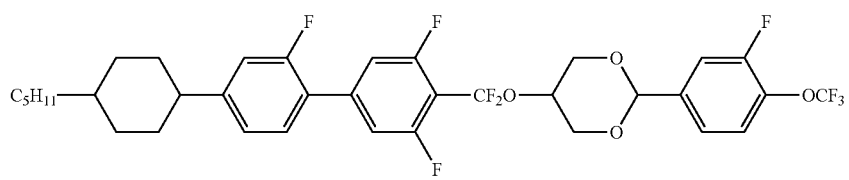
1-3-592

-continued
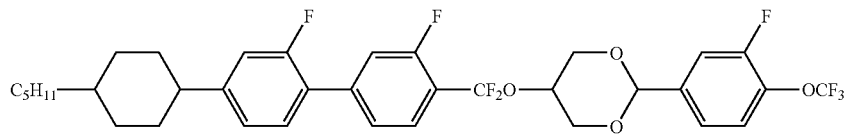
1-3-593
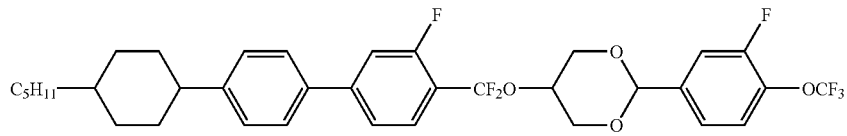
1-3-594
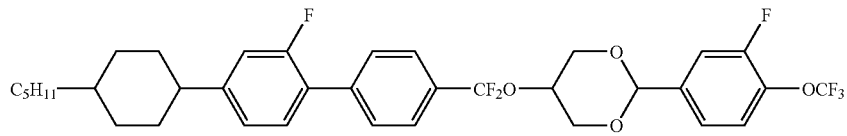
1-3-595
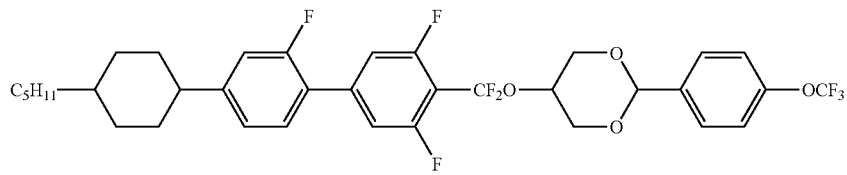
1-3-596
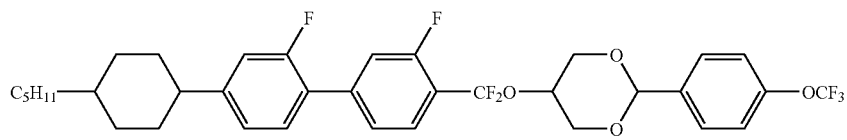
1-3-597
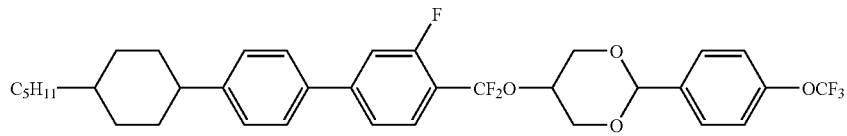
1-3-598
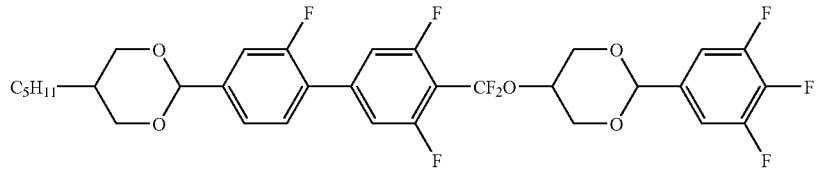
1-3-599
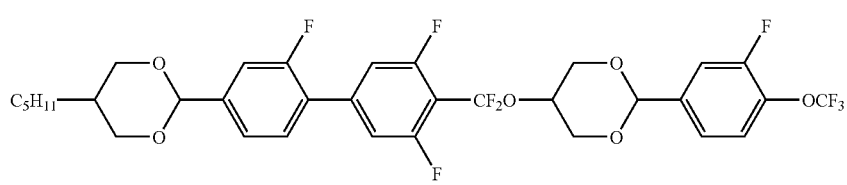
1-3-600
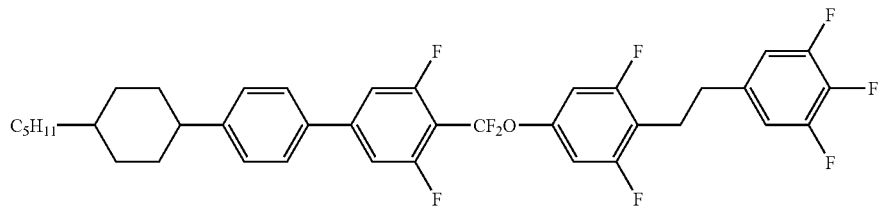
1-3-601

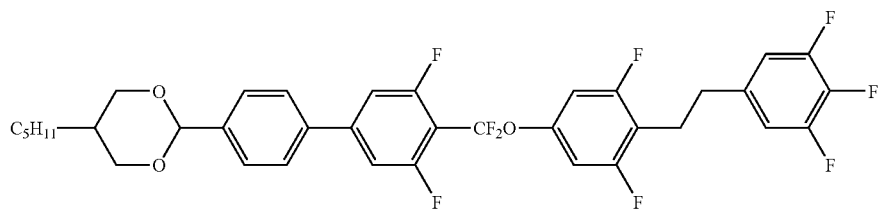
1-3-602
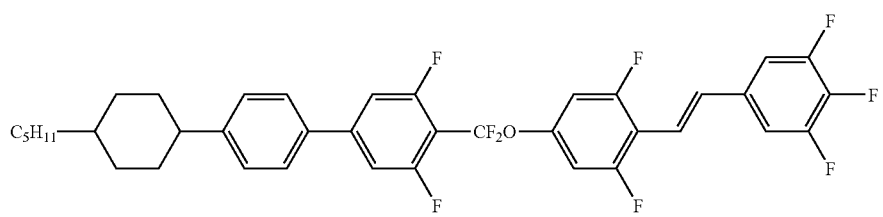
1-3-603
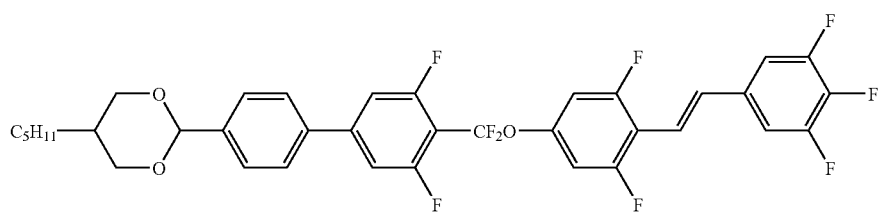
1-3-604
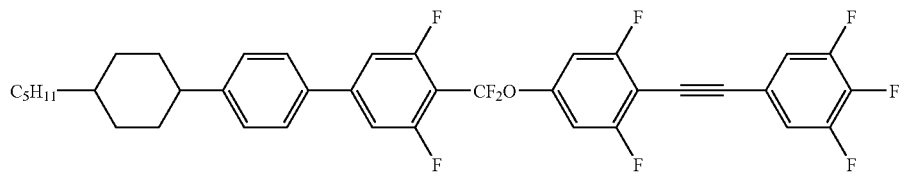
1-3-605
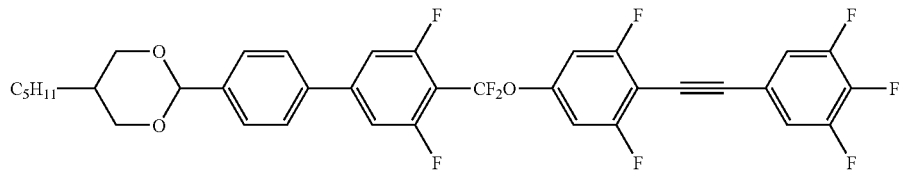
1-3-606
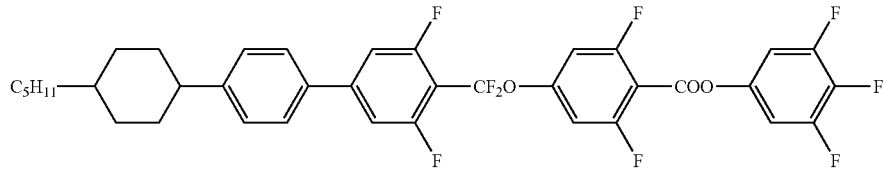
1-3-607
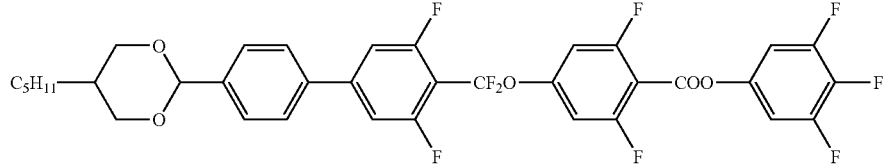
1-3-608
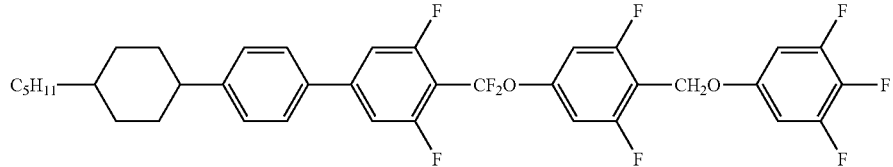
1-3-609

-continued
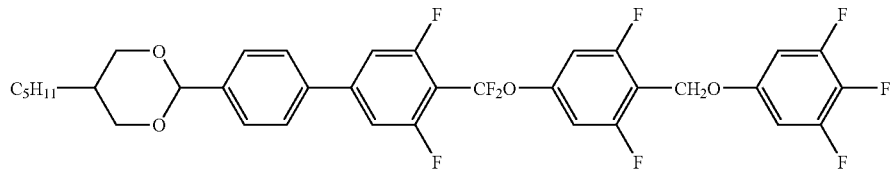 1-3-610
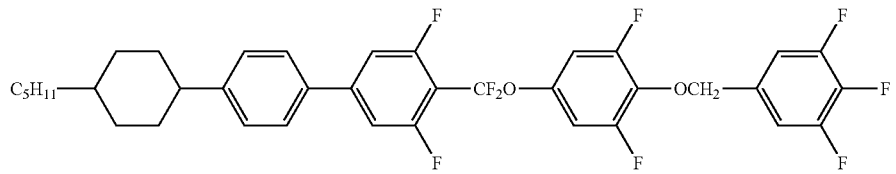 1-3-611
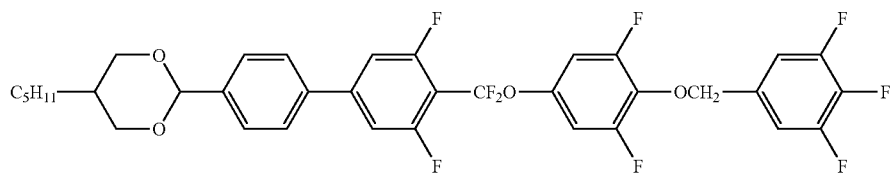 1-3-612
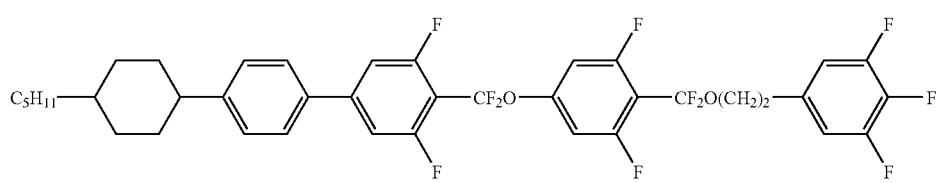 1-3-613
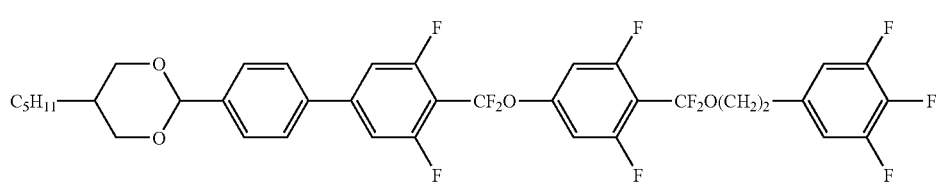 1-3-614
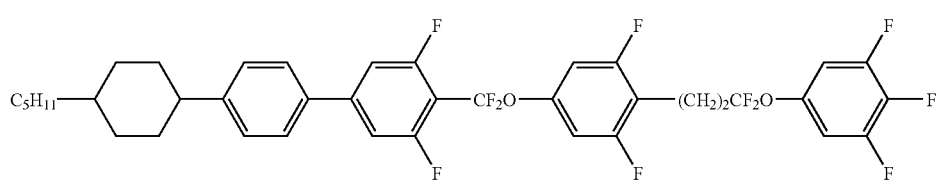 1-3-615
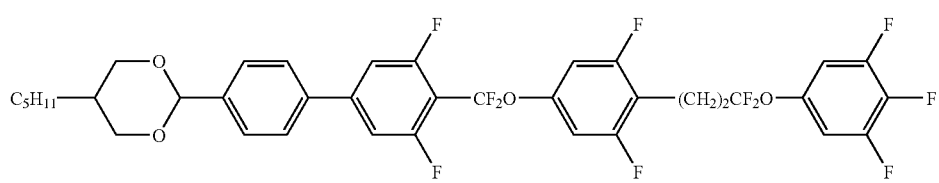 1-3-616
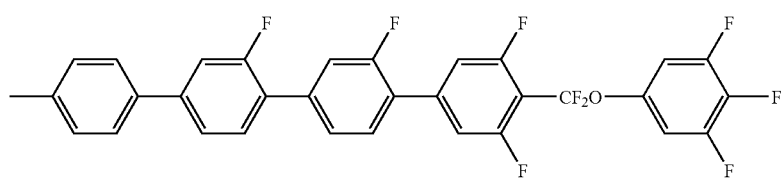 1-4-1
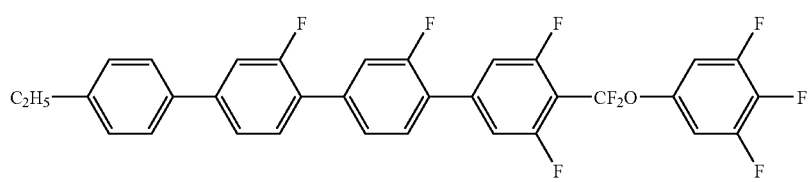 1-4-2

1-4-3
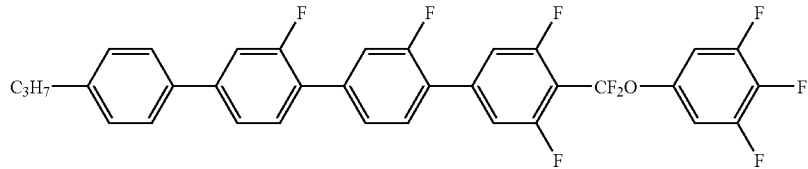
1-4-4
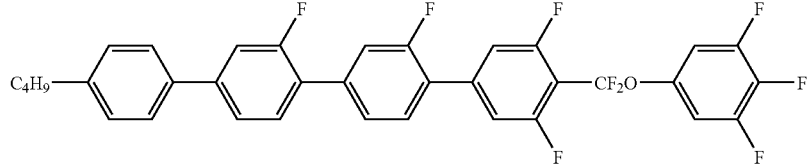
1-4-5
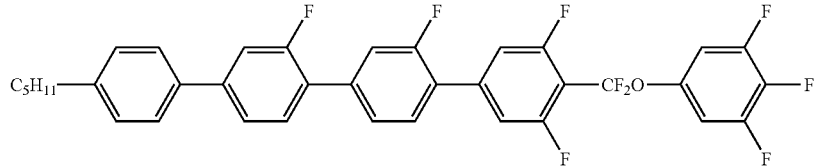
$T_{NI} = 169°$ C., $\Delta n = 0.257$, $\Delta \varepsilon = 36.7$
1-4-6
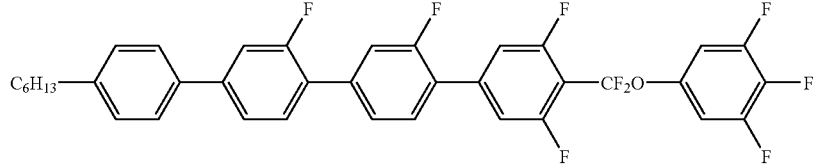
1-4-7
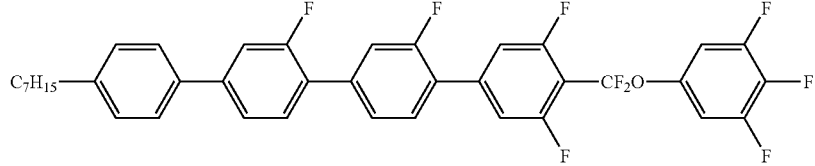
$T_{NI} = 165°$ C., $\Delta n = 0.244$, $\Delta \varepsilon = 31.4$
1-4-8
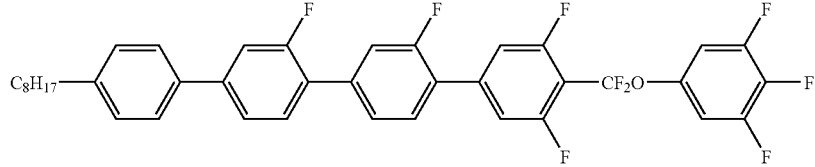
1-4-9
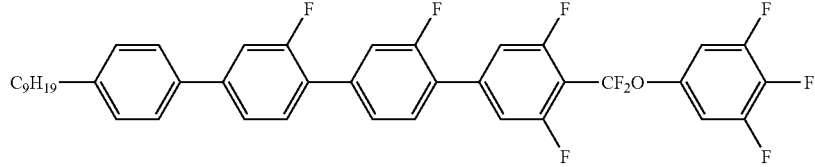
1-4-10
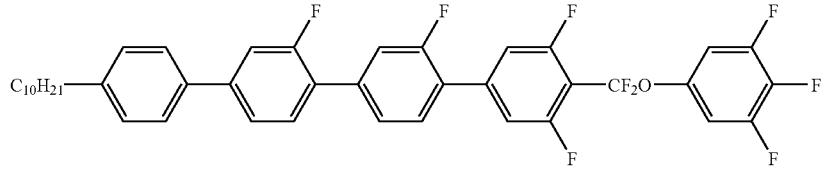

-continued
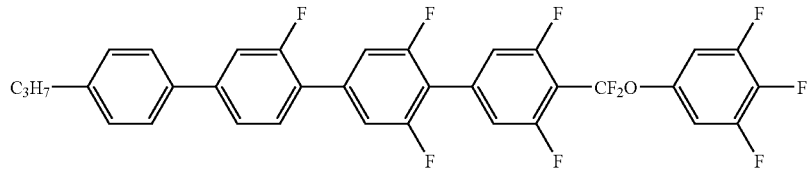
1-4-11
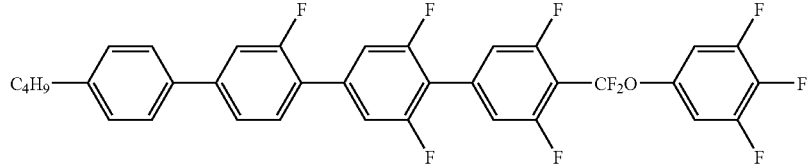
1-4-12
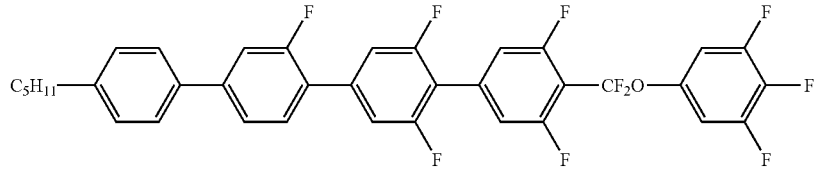
1-4-13
$T_{NI} = 156°$ C., $\Delta n = 0.257$, $\Delta \varepsilon = 43.6$
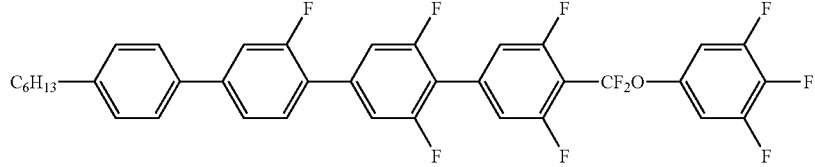
1-4-14
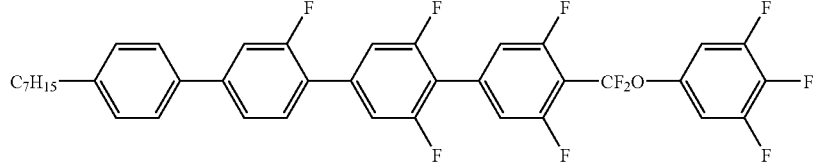
1-4-15
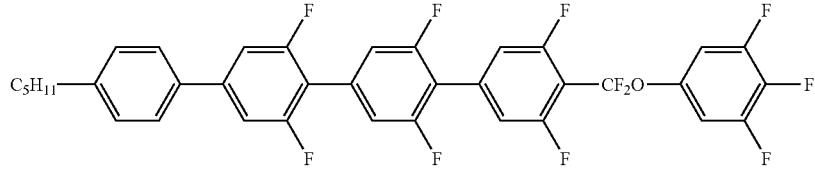
1-4-16
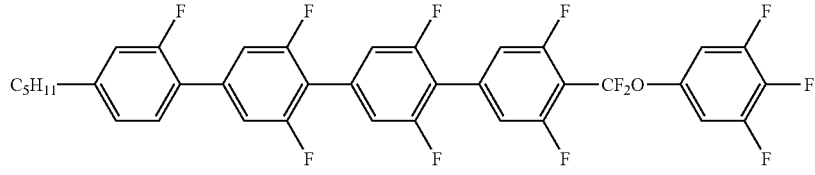
1-4-17
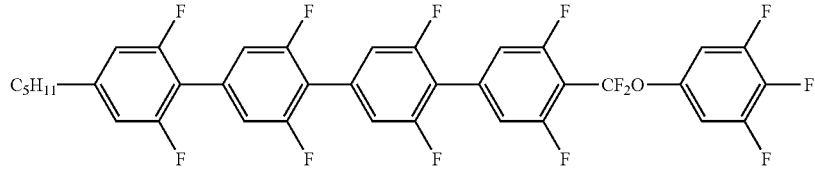
1-4-18

-continued
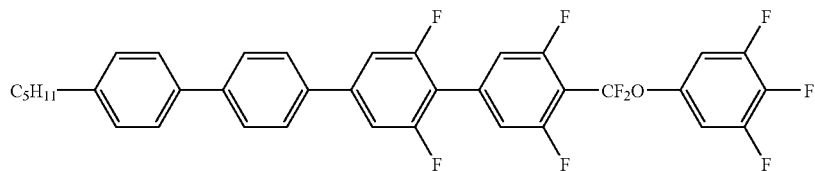
1-4-19
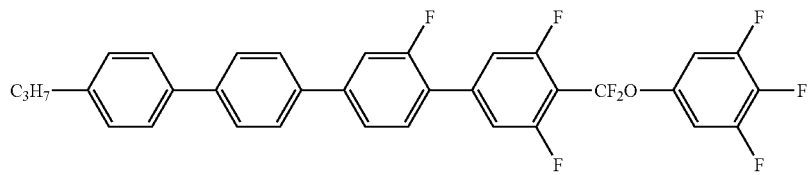
1-4-20
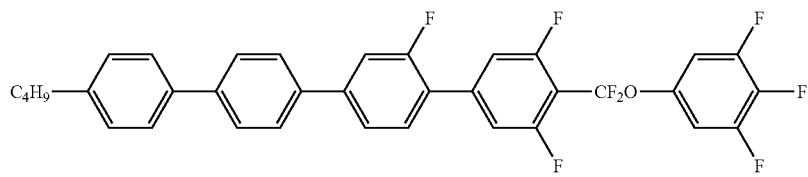
1-4-21
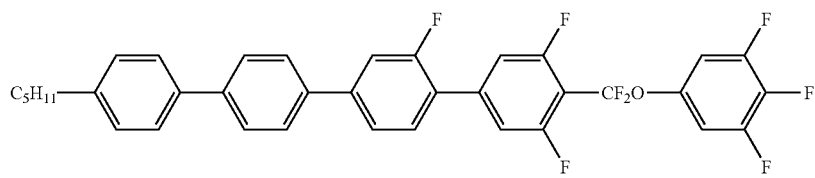
1-4-22
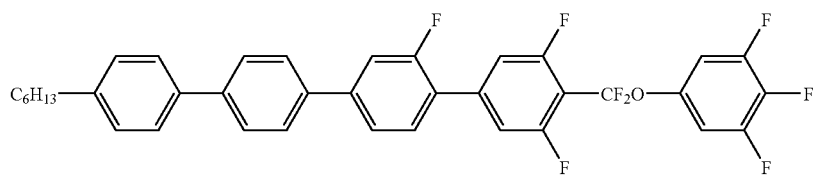
1-4-23
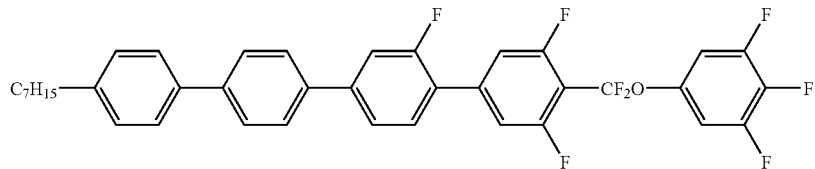
1-4-24
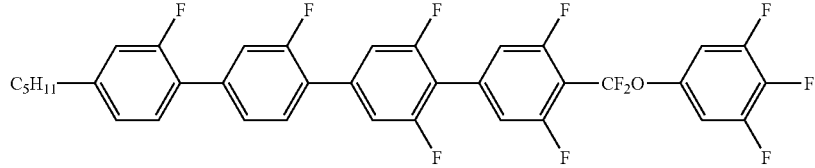
1-4-25
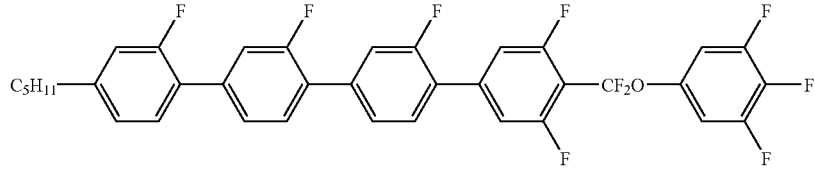
1-4-26

-continued
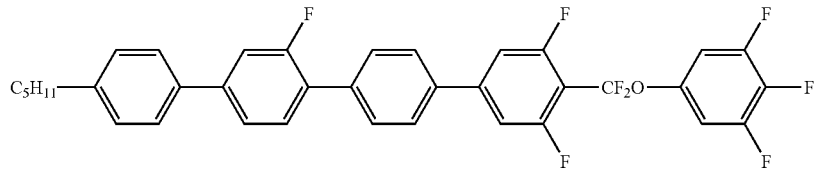
$T_{NI}$ = 174° C., Δn = 0.277, Δε = 29.7
1-4-27
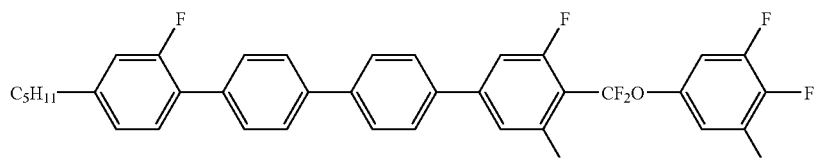
1-4-28
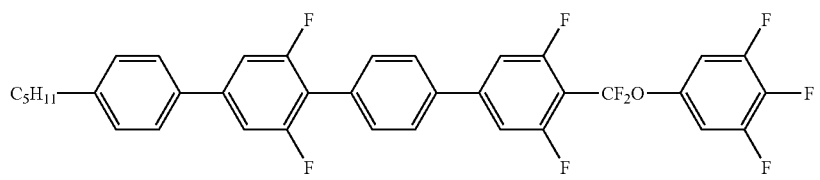
1-4-29
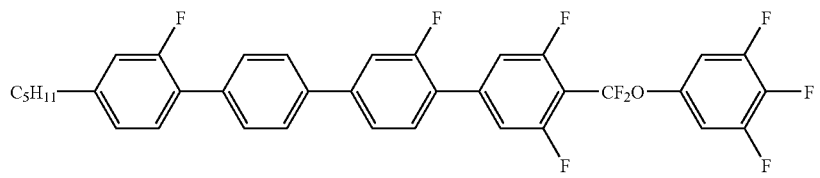
1-4-30
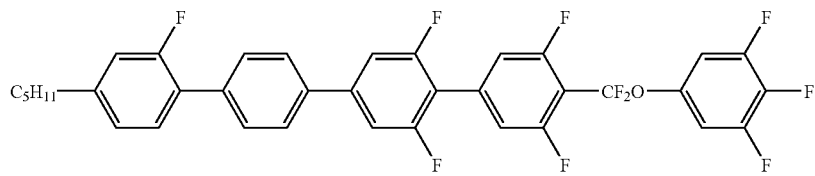
1-4-31
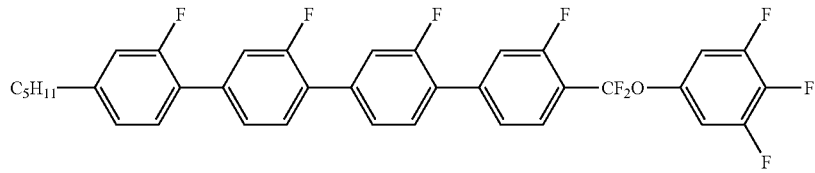
1-4-32
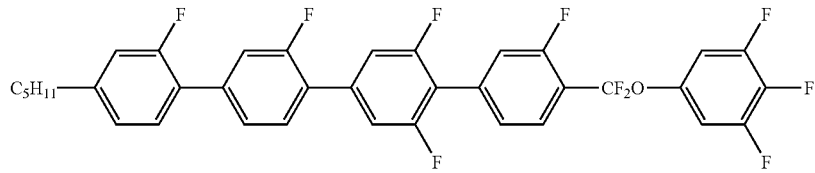
1-4-33
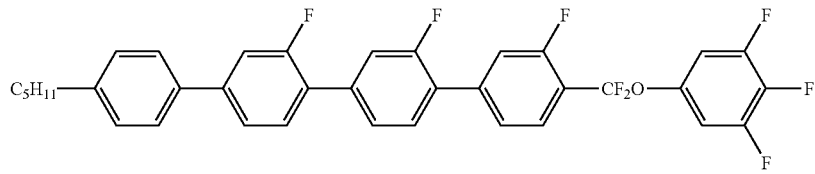
1-4-34
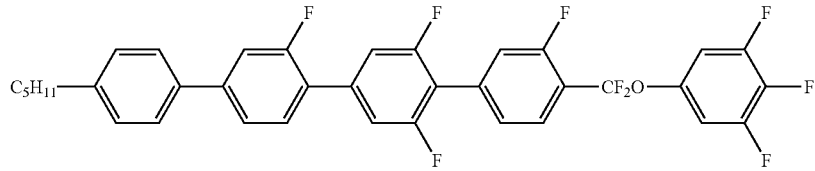
1-4-35

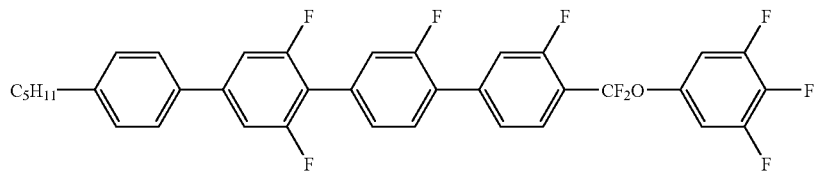 1-4-36
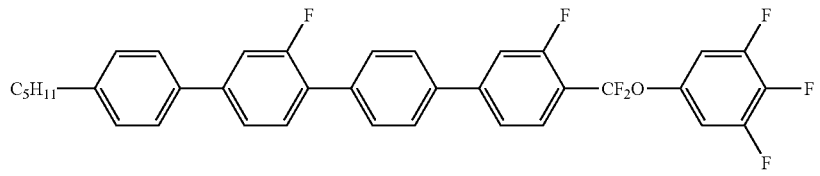 1-4-37
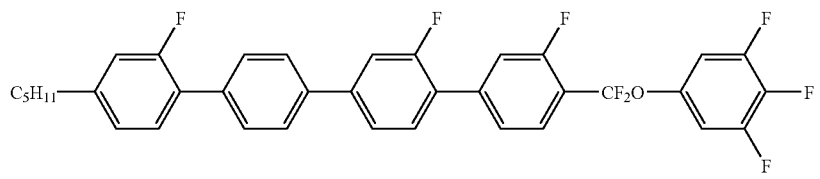 1-4-38
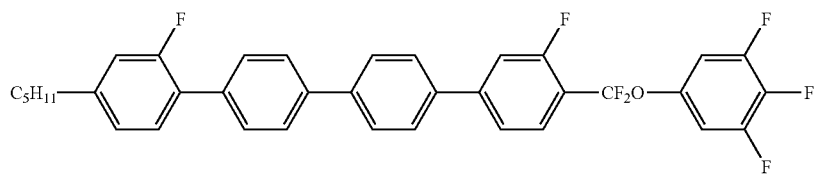 1-4-39
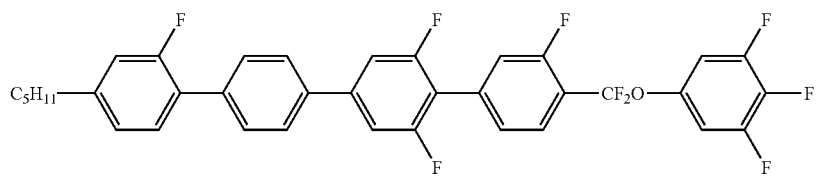 1-4-40
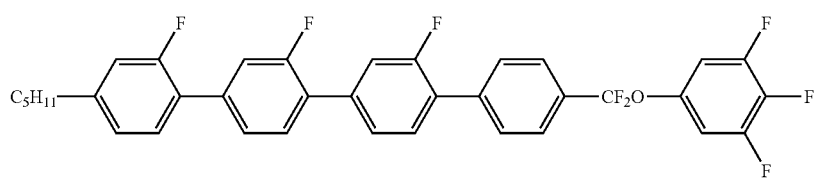 1-4-41
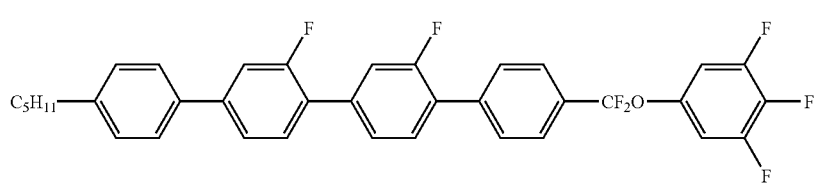 1-4-42
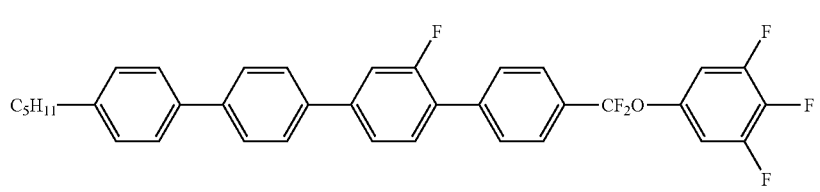 1-4-43
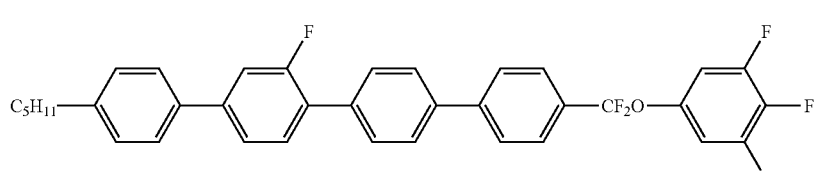 1-4-44

-continued
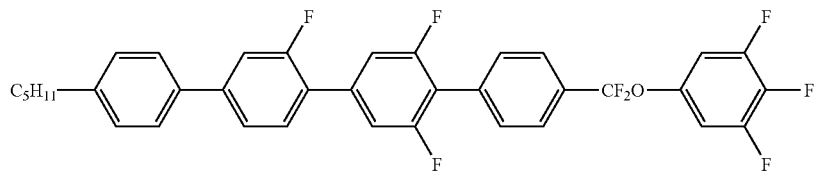
1-4-45
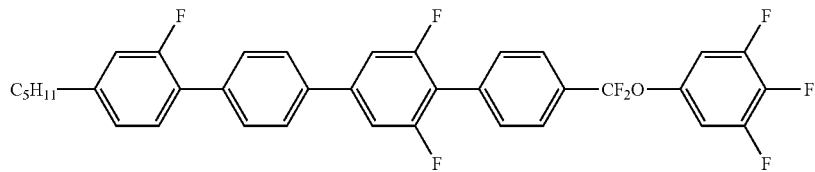
1-4-46
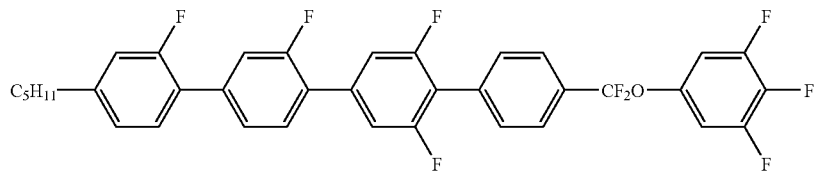
1-4-47
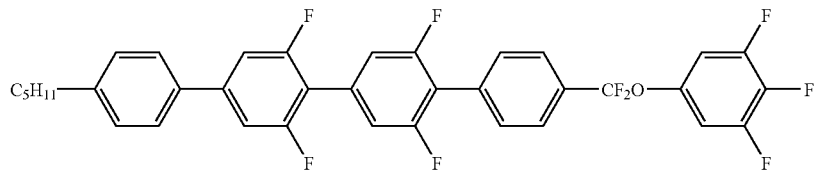
1-4-48
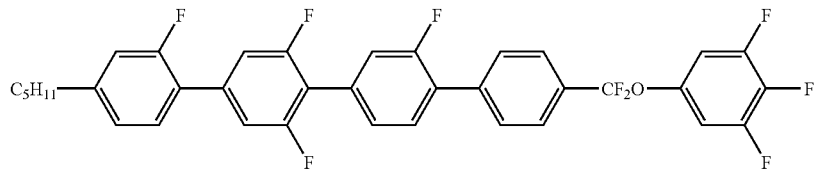
1-4-49
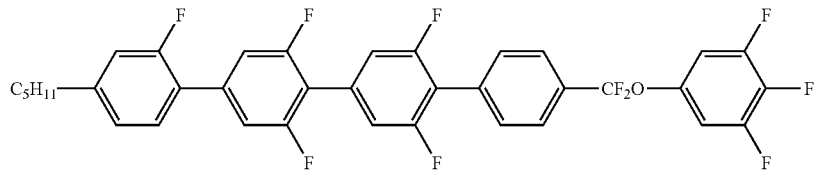
1-4-50
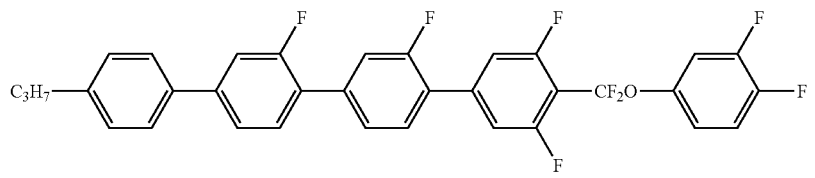
1-4-51
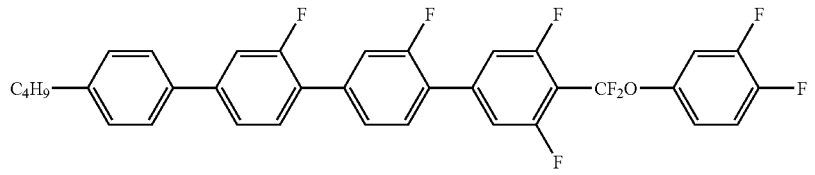
1-4-52

-continued
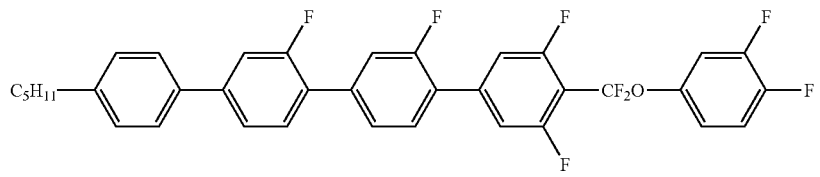
$T_{NI}$ = 175° C., Δn = 0.270, Δε = 26.5
1-4-53
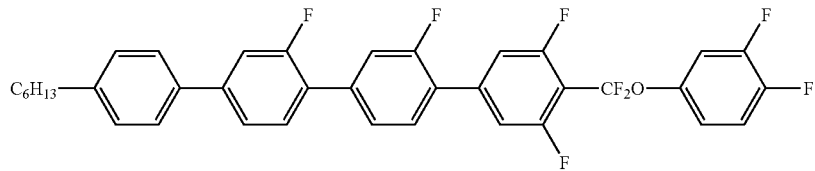
1-4-54
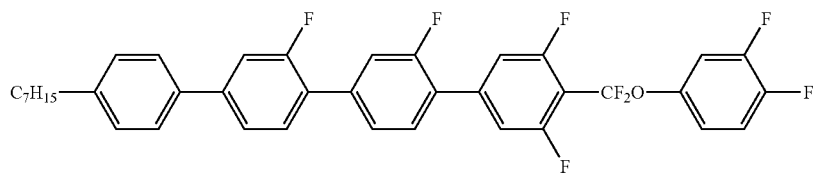
1-4-55
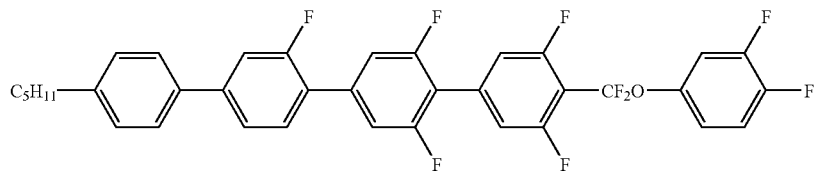
1-4-56
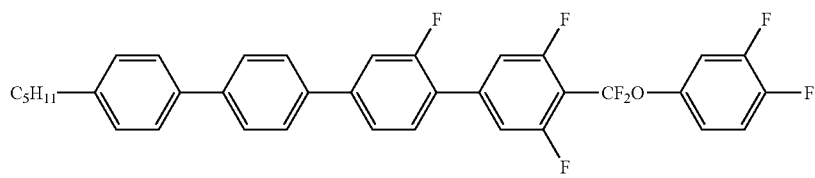
1-4-57
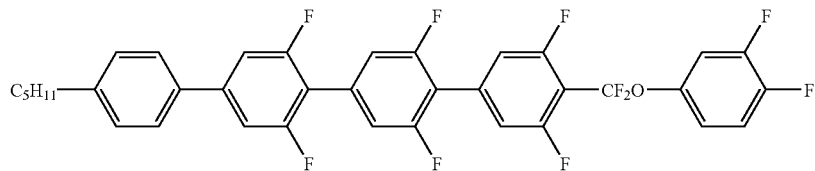
1-4-58
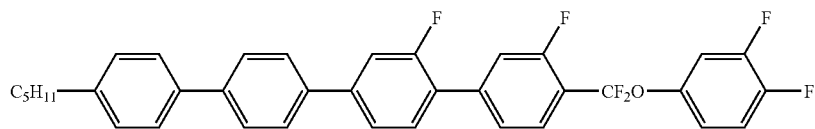
1-4-59
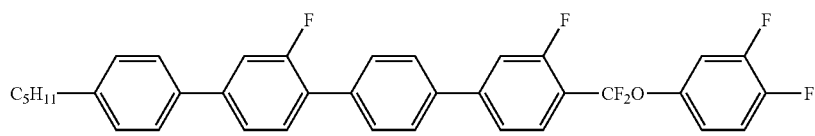
1-4-60
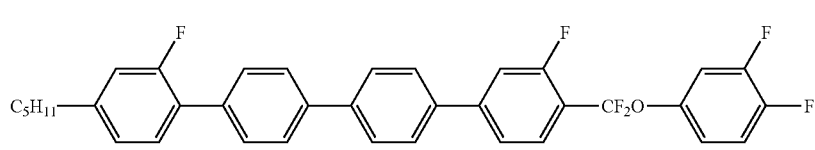
1-4-61

-continued
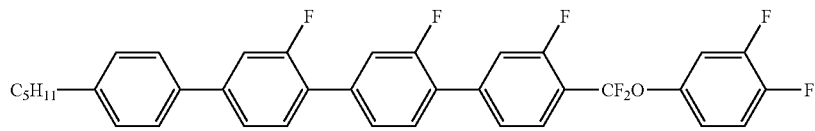
1-4-62
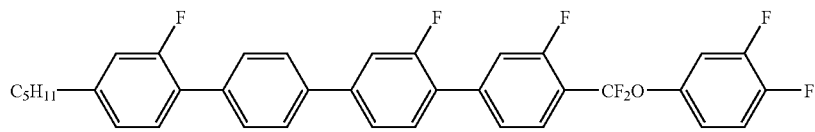
1-4-63
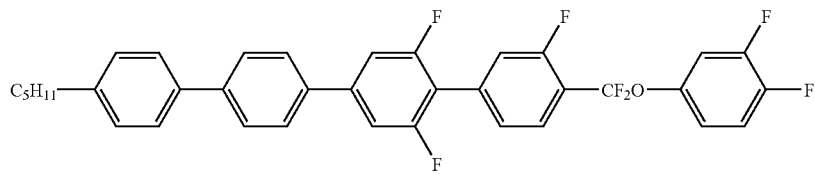
1-4-64
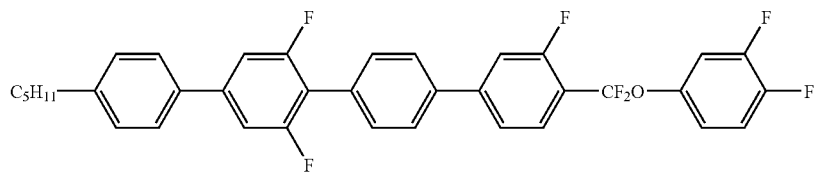
1-4-65
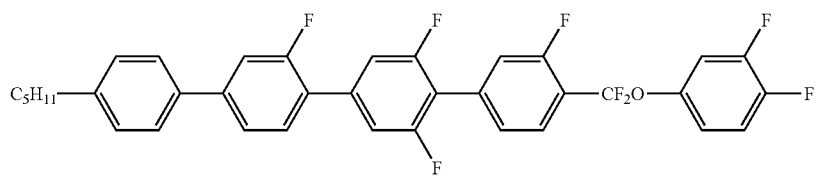
1-4-66
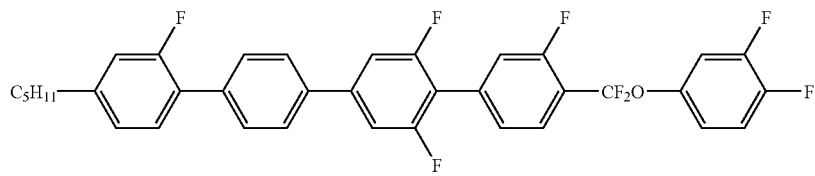
1-4-67
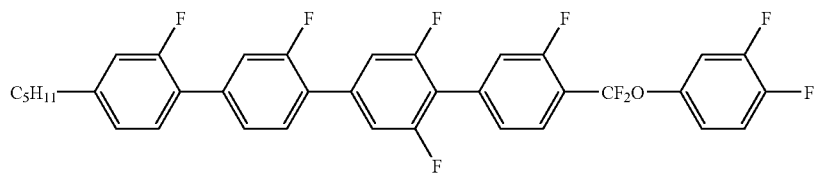
1-4-68
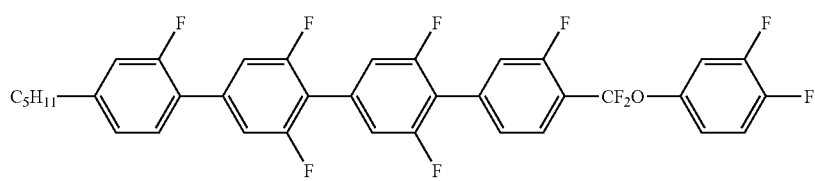
1-4-69
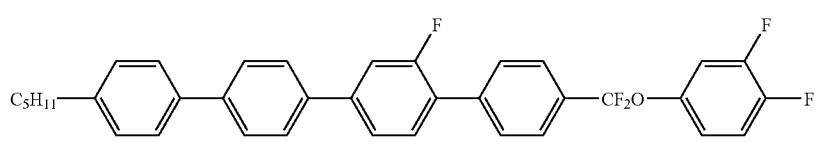
1-4-70
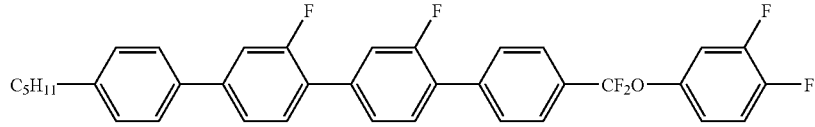
1-4-71

-continued
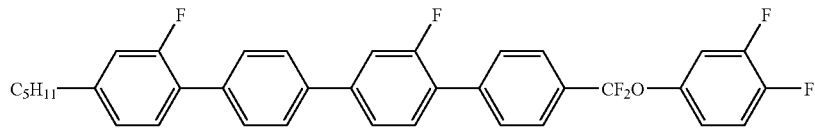
1-4-72
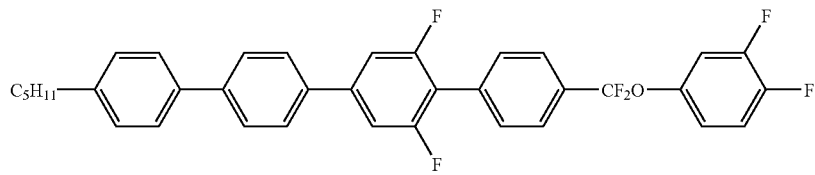
1-4-73
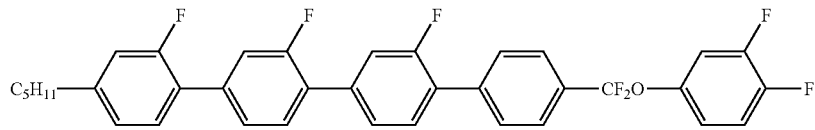
1-4-74
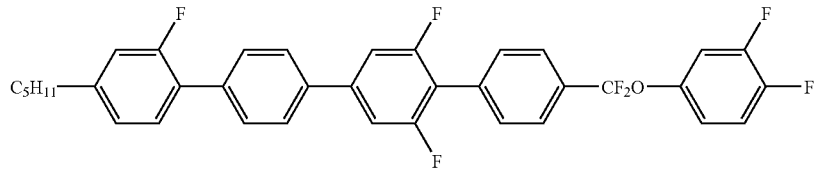
1-4-75
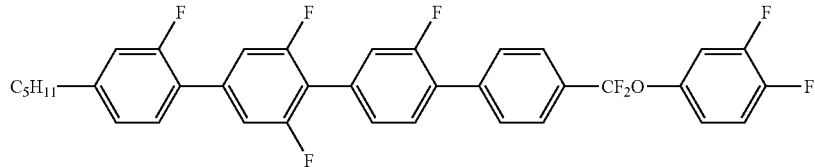
1-4-76
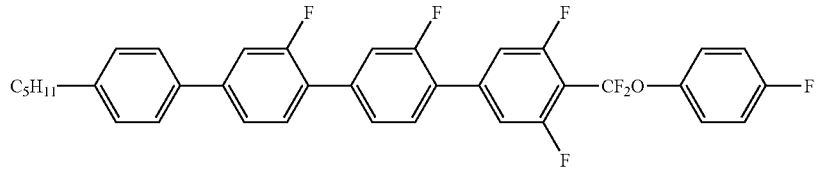
1-4-77
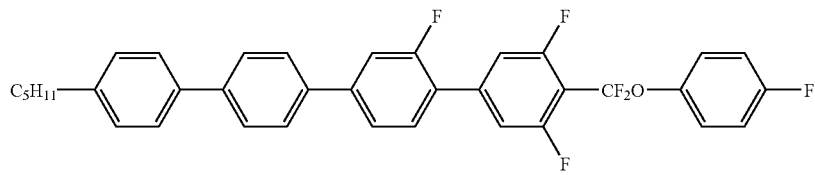
1-4-78
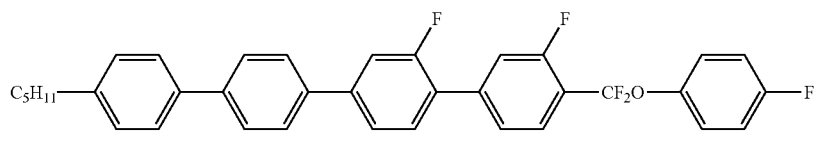
1-4-79
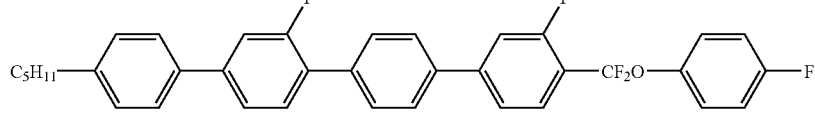
1-4-80
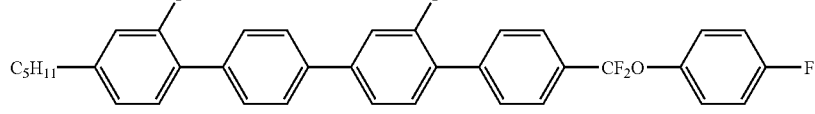
1-4-81

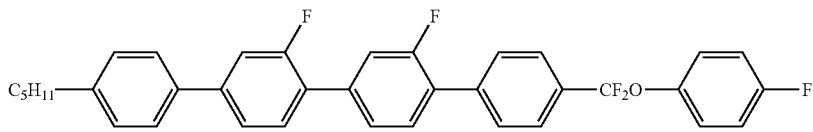
1-4-82
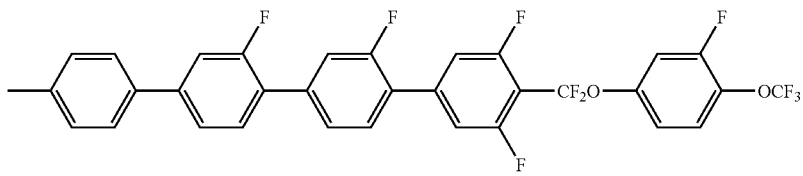
1-4-83
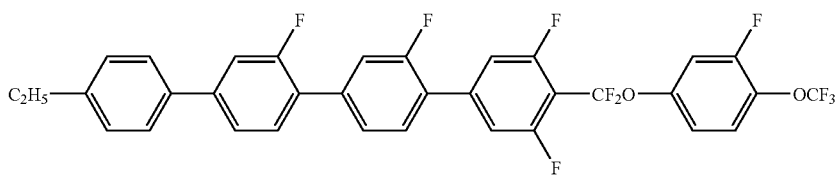
1-4-84
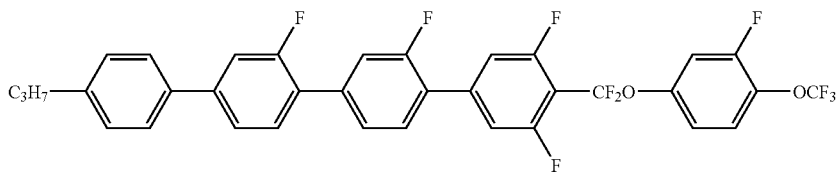
1-4-85
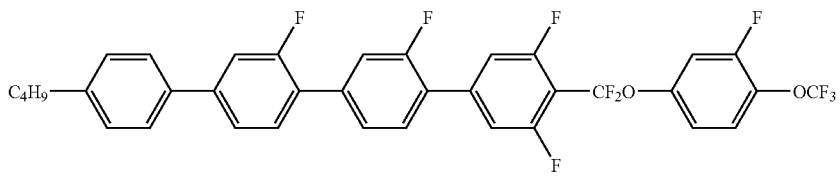
1-4-86
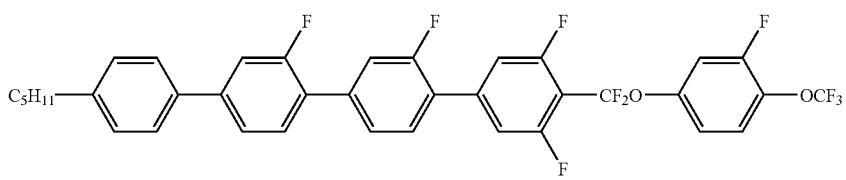
1-4-87
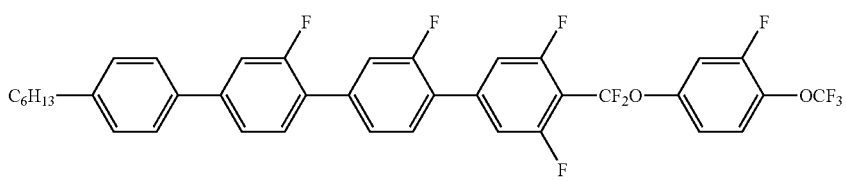
1-4-88
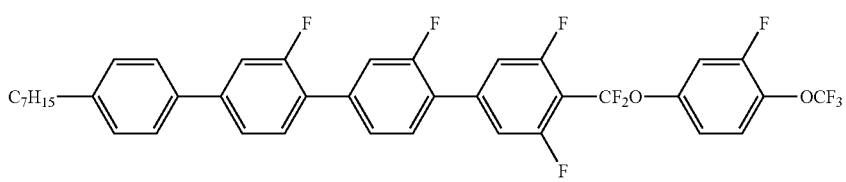
1-4-89
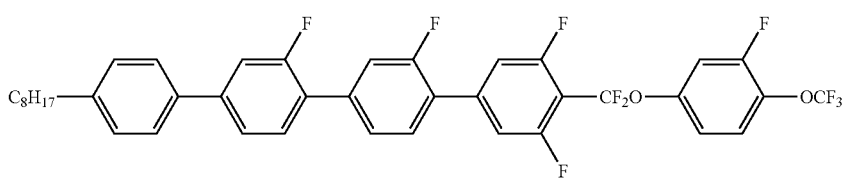
1-4-90

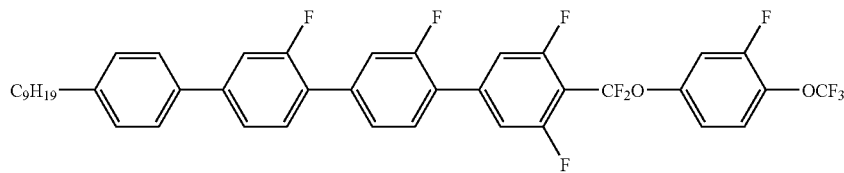
1-4-91
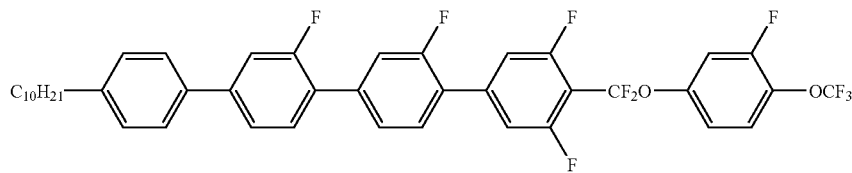
1-4-92
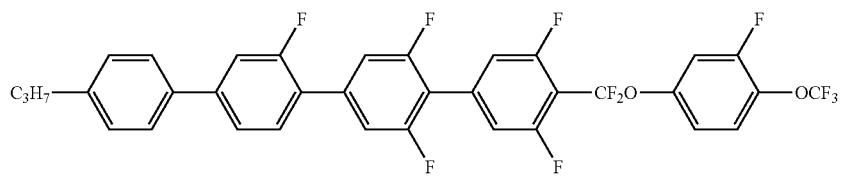
1-4-93
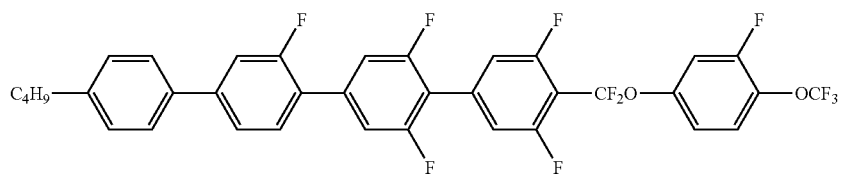
1-4-94
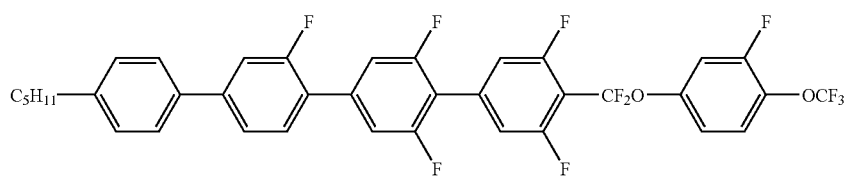
1-4-95
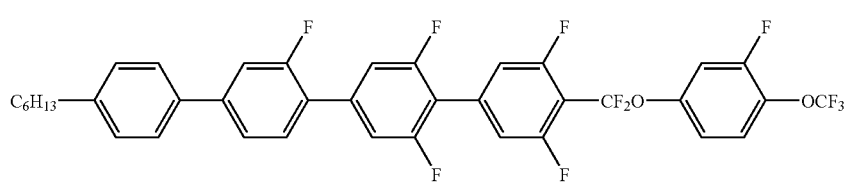
1-4-96
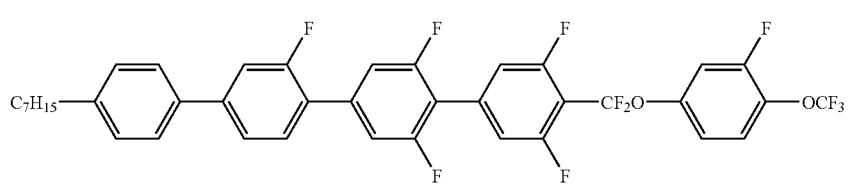
1-4-97
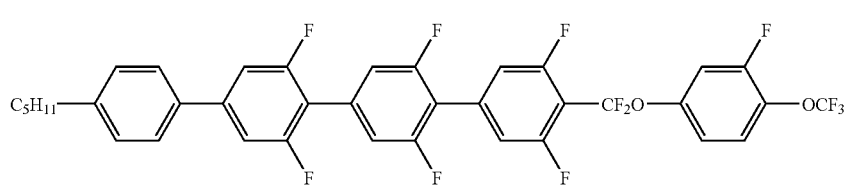
1-4-98
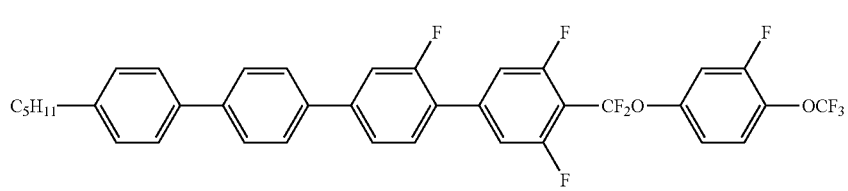
1-4-99

-continued
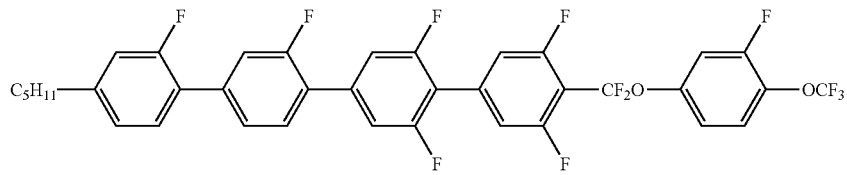
1-4-100
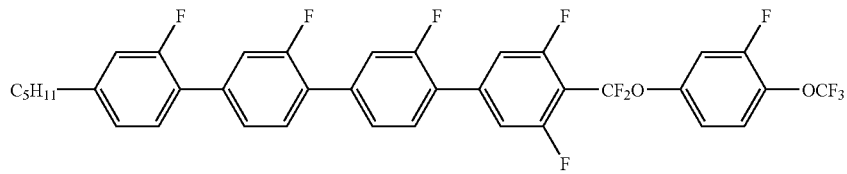
1-4-101
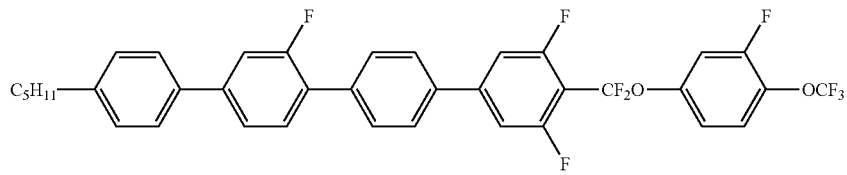
1-4-102
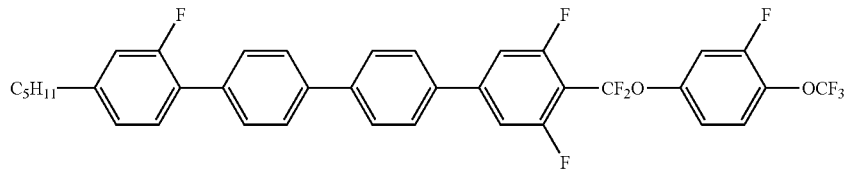
1-4-103
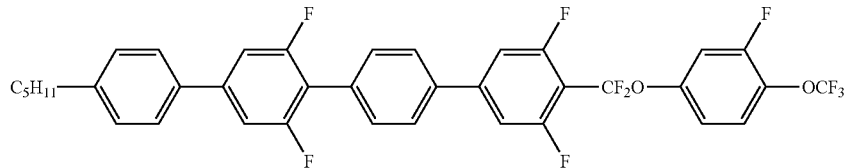
1-4-104
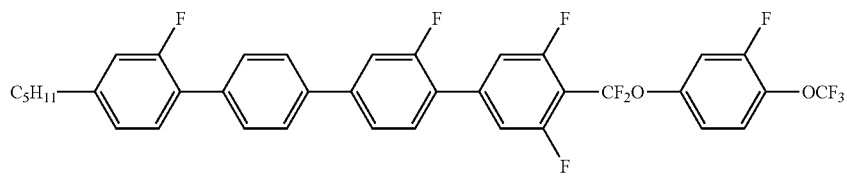
1-4-105
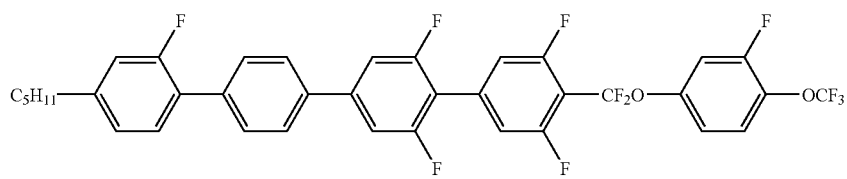
1-4-106
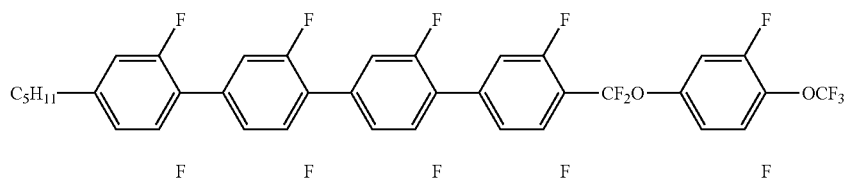
1-4-107
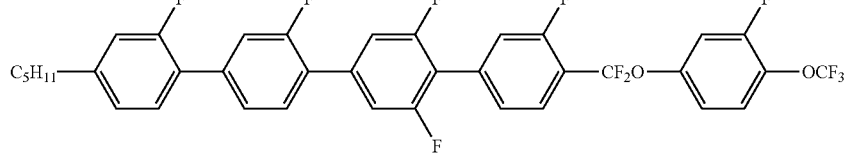
1-4-108

-continued
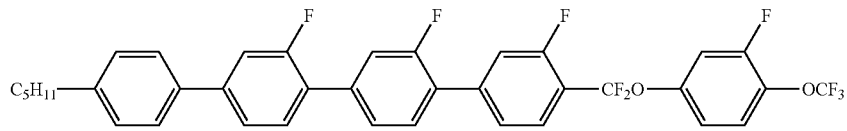
1-4-109
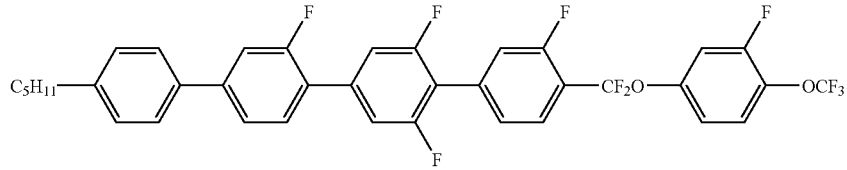
1-4-110
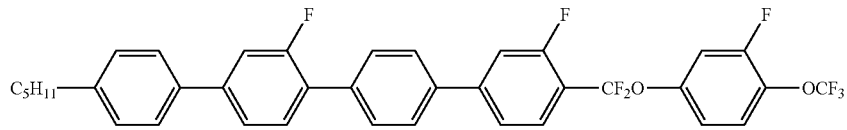
1-4-111
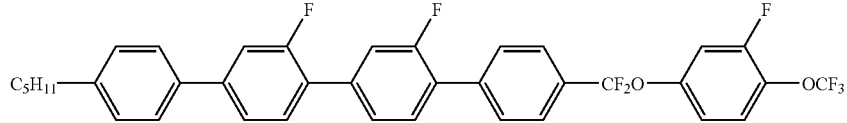
1-4-112
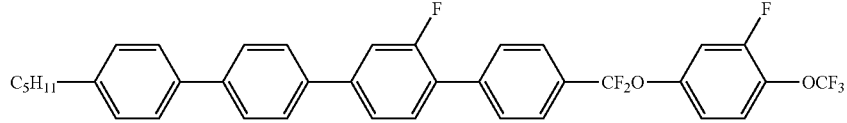
1-4-113
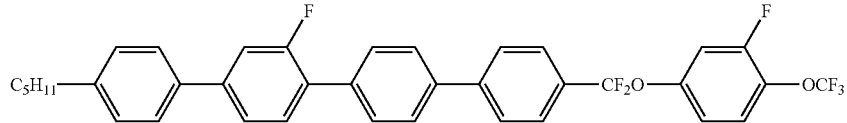
1-4-114
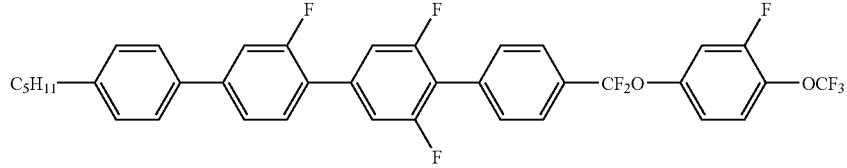
1-4-115
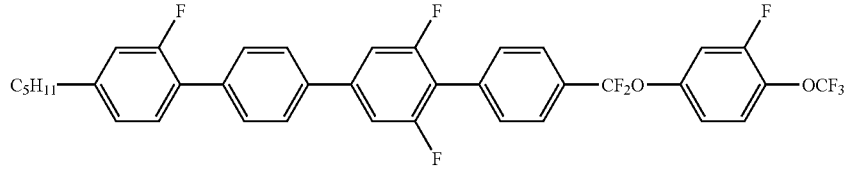
1-4-116
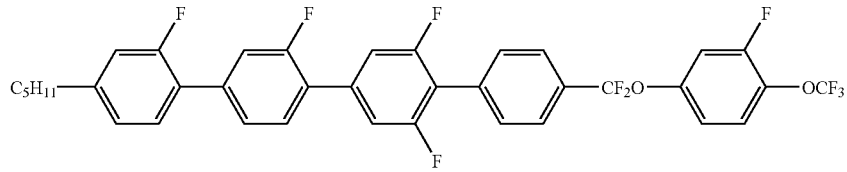
1-4-117
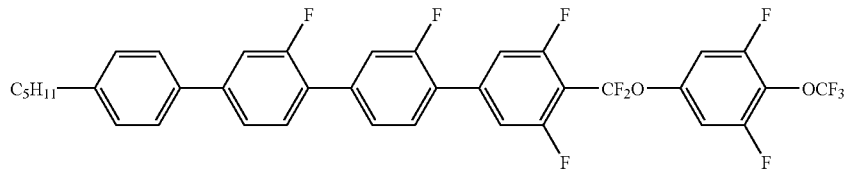
1-4-118

-continued
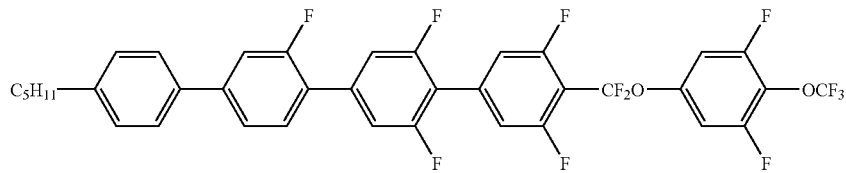
1-4-119
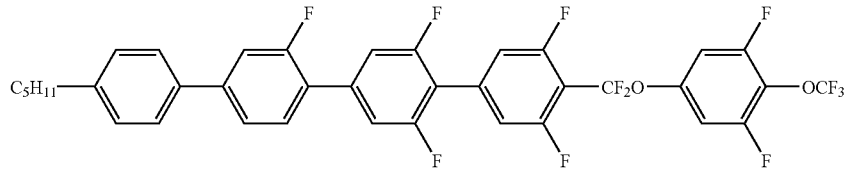
1-4-120
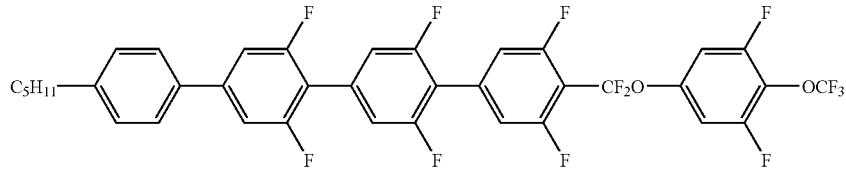
1-4-121
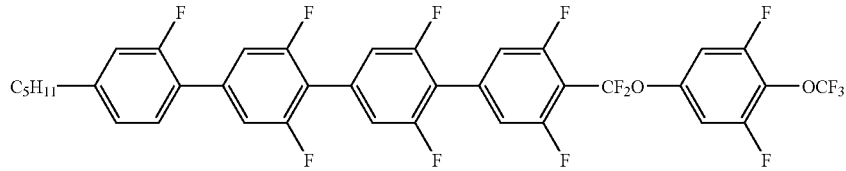
1-4-122
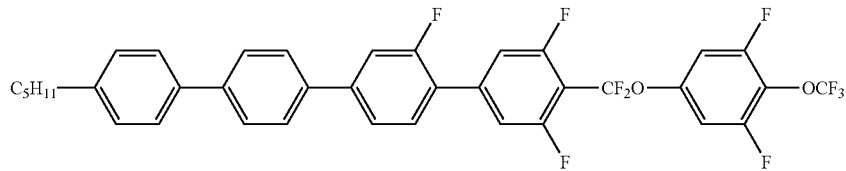
1-4-123
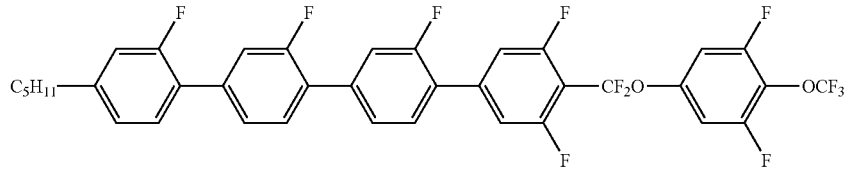
1-4-124
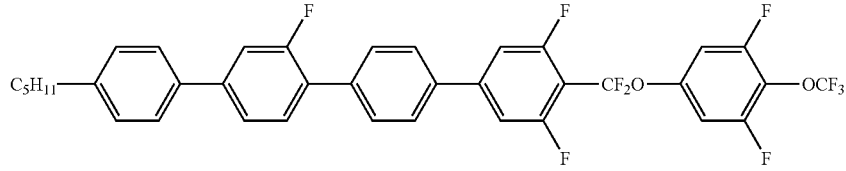
1-4-125
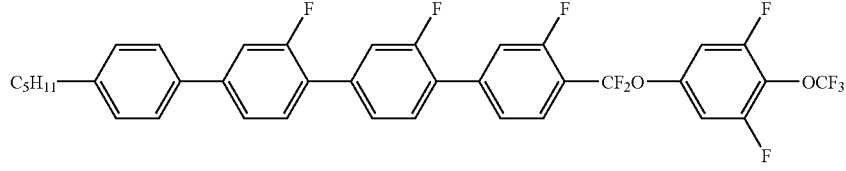
1-4-126
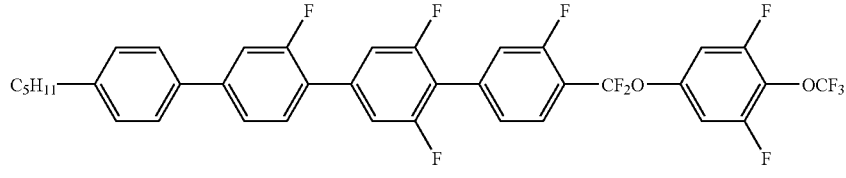
1-4-127

-continued
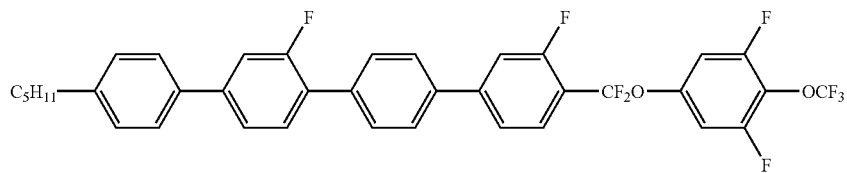
1-4-128
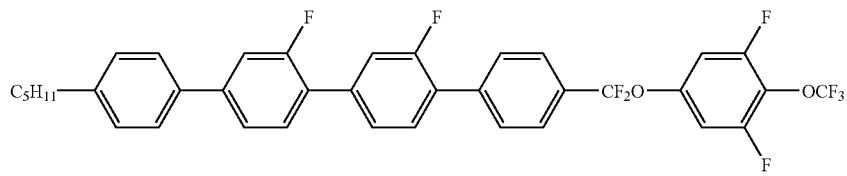
1-4-129
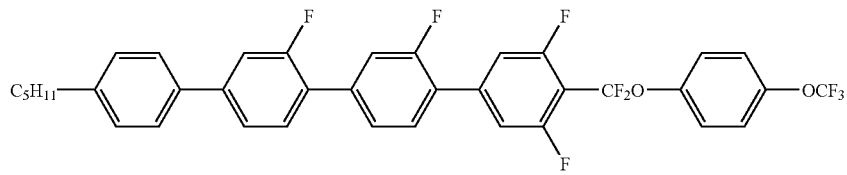
1-4-130
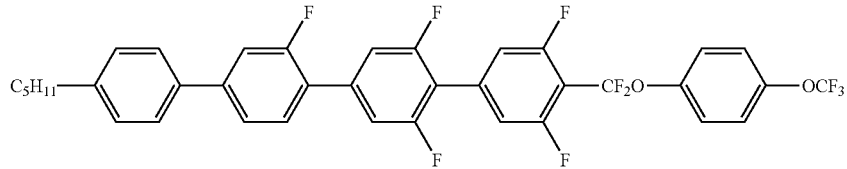
1-4-131
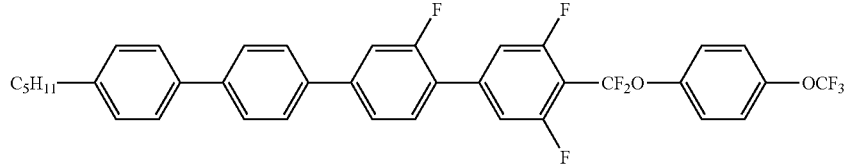
1-4-132
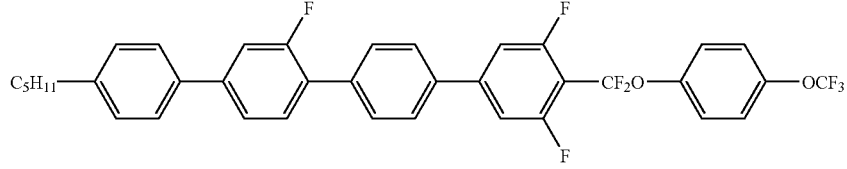
1-4-133
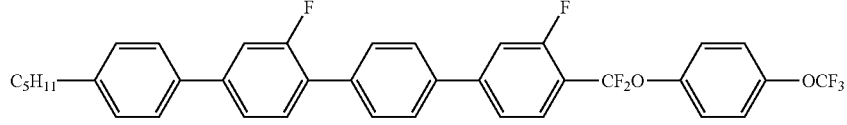
1-4-134
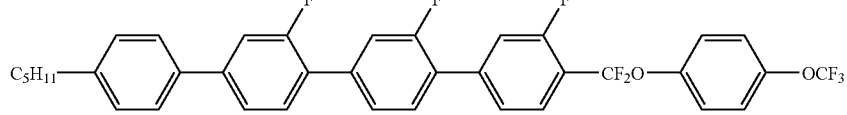
1-4-135
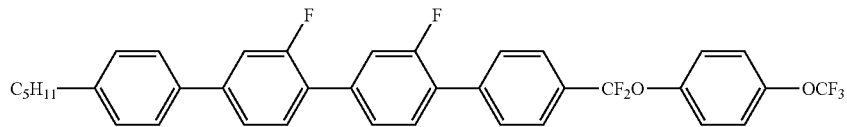
1-4-136

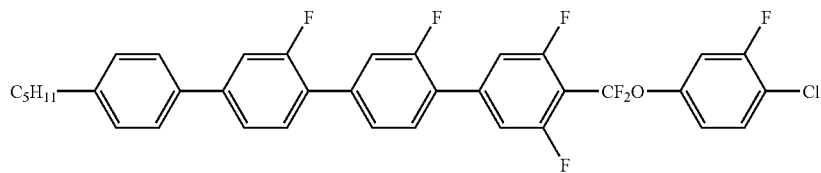
1-4-137
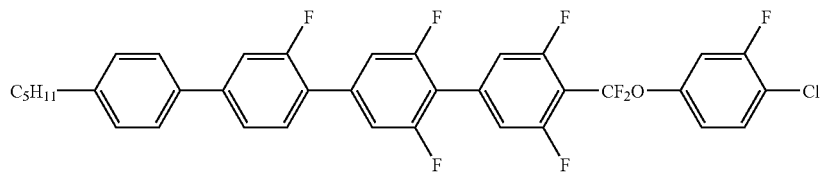
1-4-138
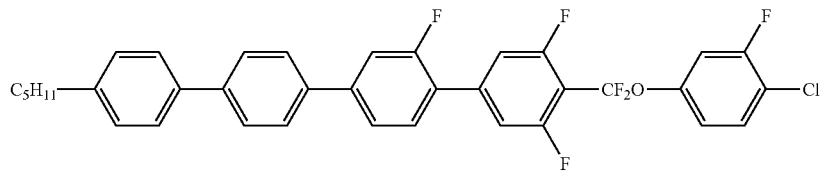
1-4-139
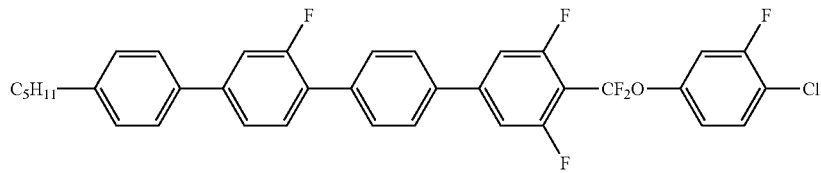
1-4-140
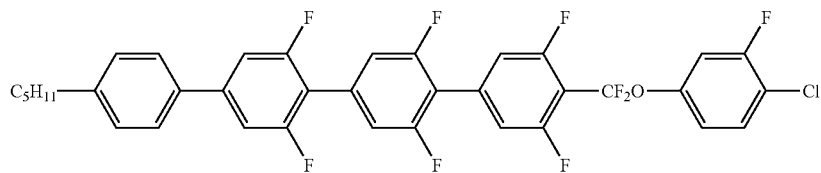
1-4-141
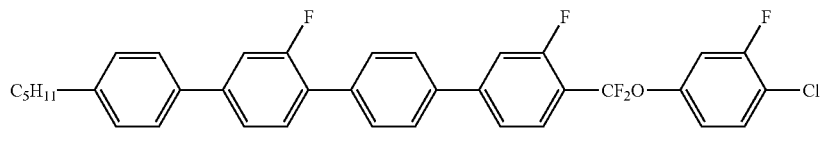
1-4-142
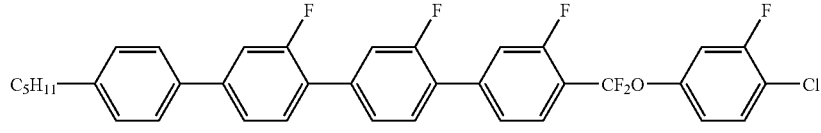
1-4-143
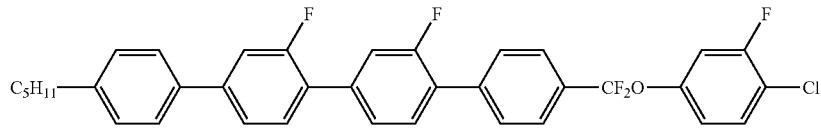
1-4-144
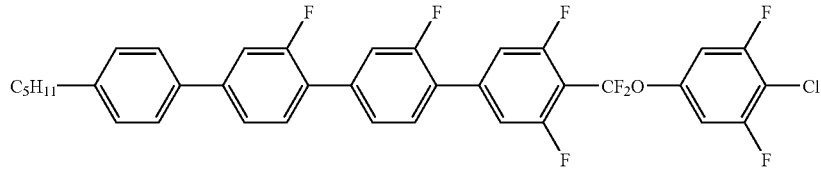
1-4-145

-continued
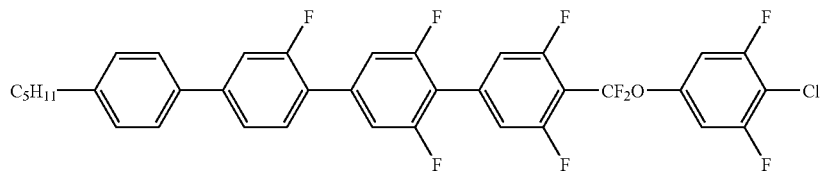
1-4-146
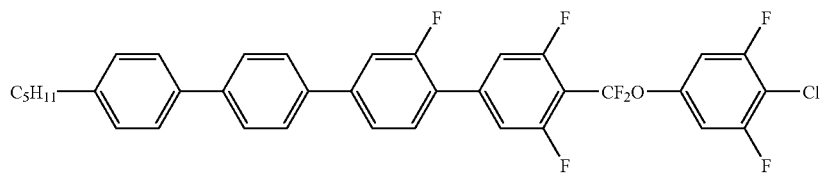
1-4-147
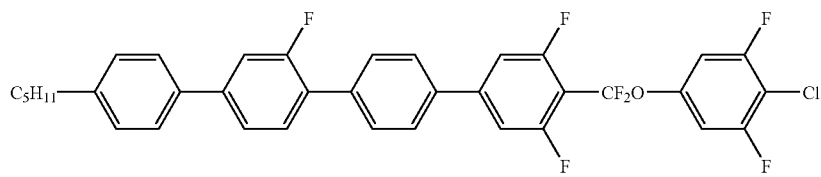
1-4-148
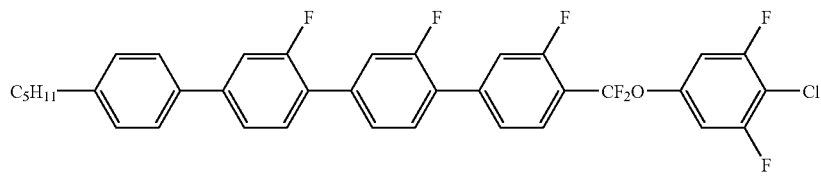
1-4-149
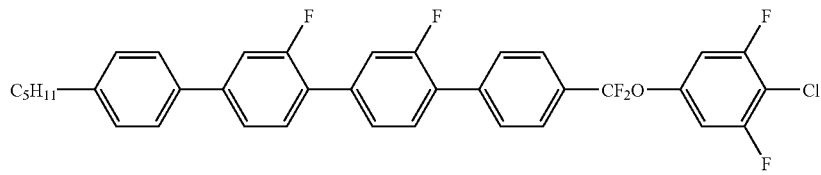
1-4-150
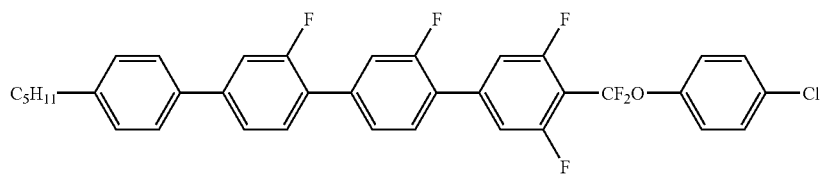
1-4-151
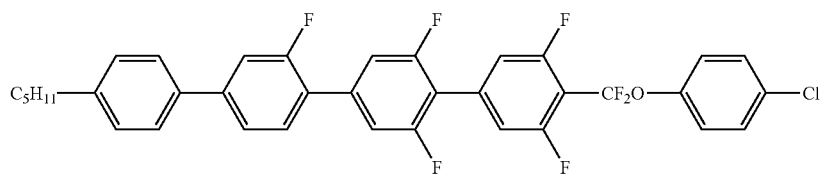
1-4-152
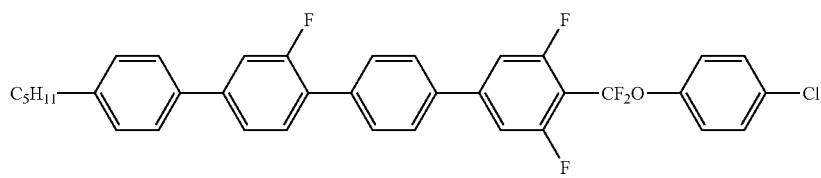
1-4-153
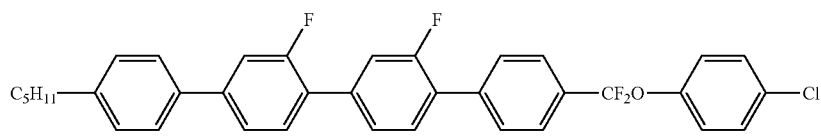
1-4-154

-continued
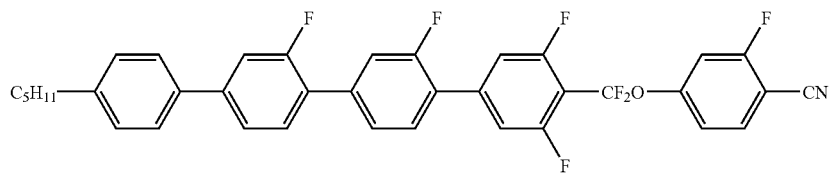
1-4-155
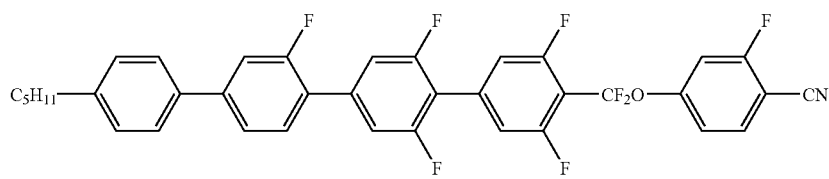
1-4-156
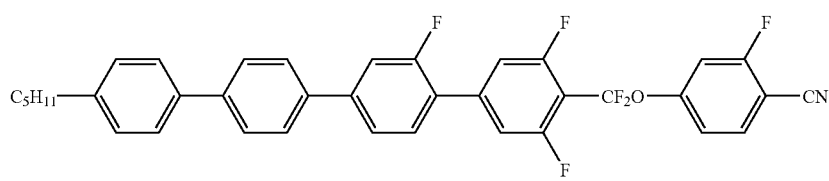
1-4-157
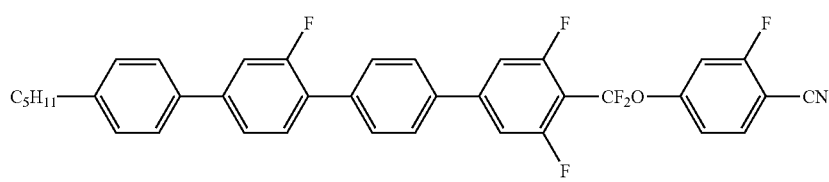
1-4-158
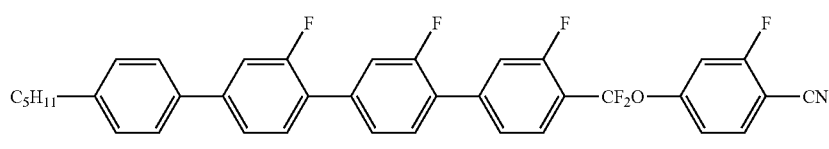
1-4-159
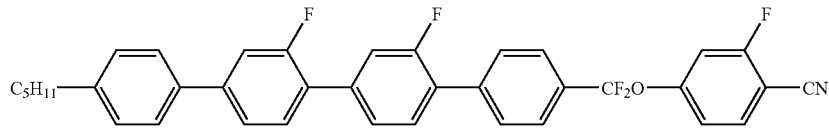
1-4-160
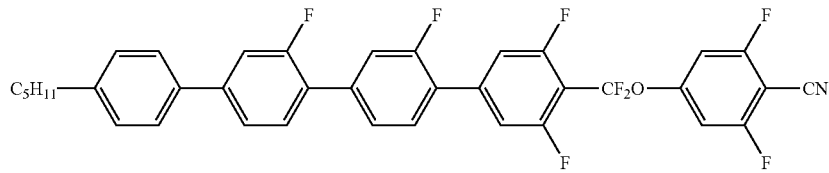
1-4-161
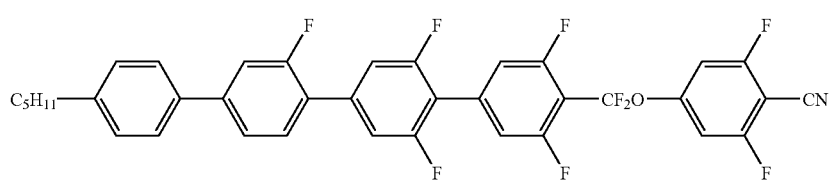
1-4-162
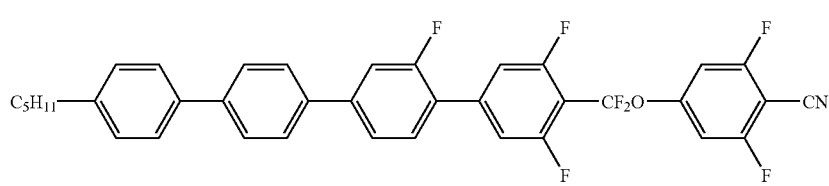
1-4-163

-continued
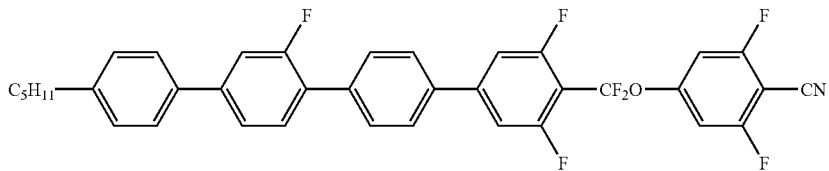
1-4-164
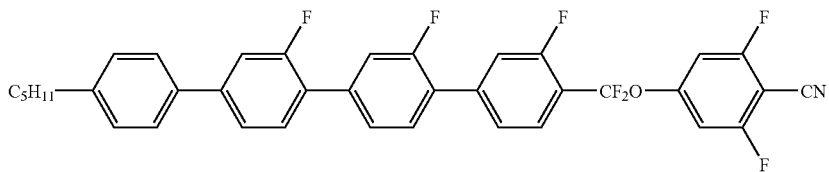
1-4-165
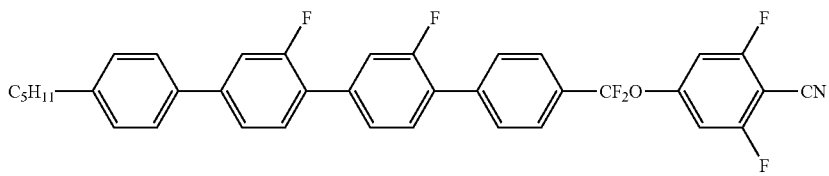
1-4-166
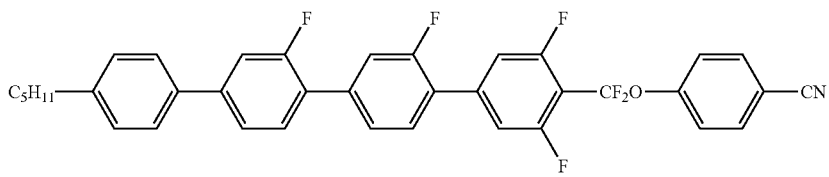
1-4-167
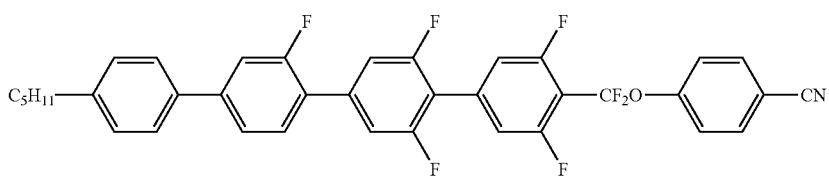
1-4-168
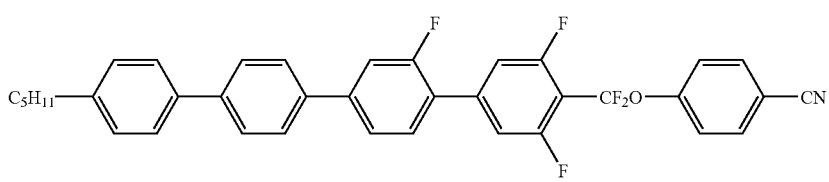
1-4-169
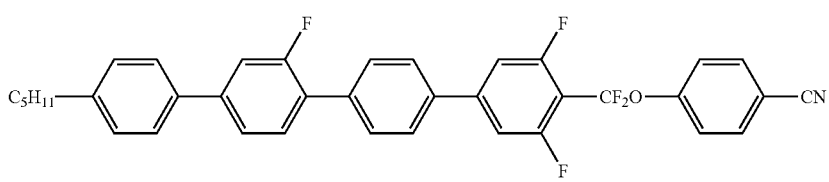
1-4-170
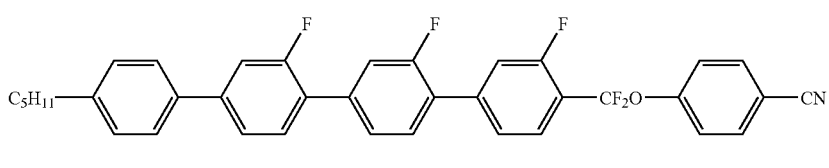
1-4-171
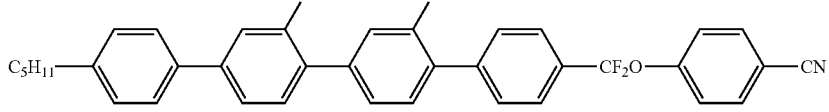
1-4-172

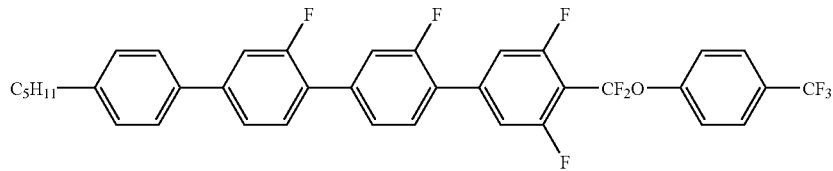
1-4-173
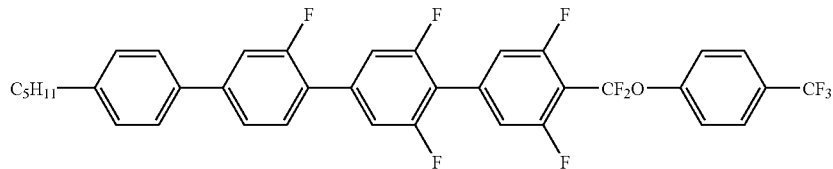
1-4-174
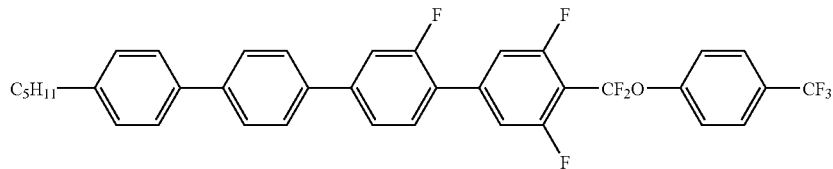
1-4-175
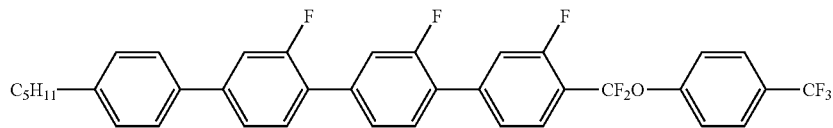
1-4-176
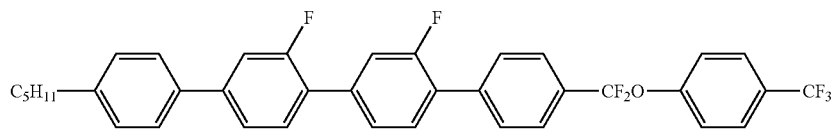
1-4-177
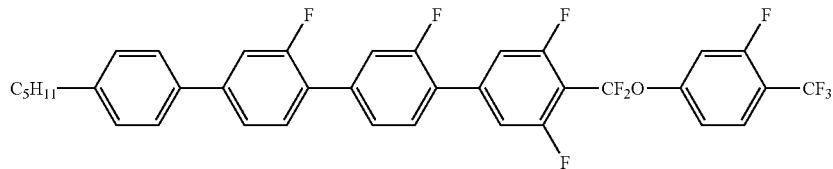
1-4-178
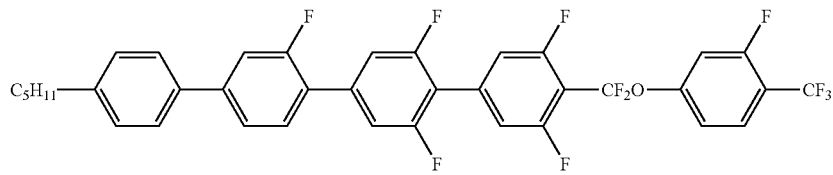
1-4-179
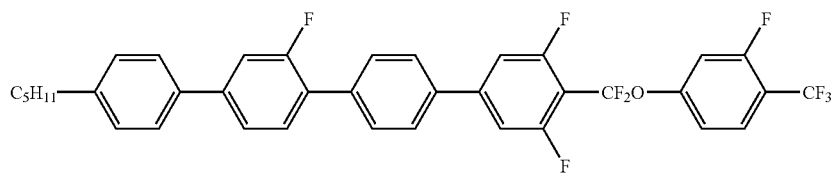
1-4-180
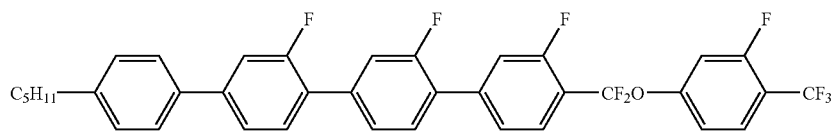
1-4-181
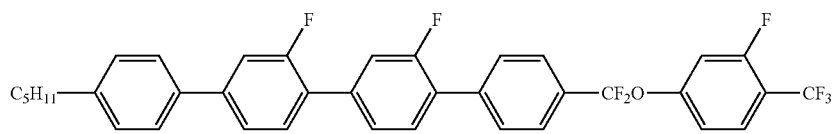
1-4-182

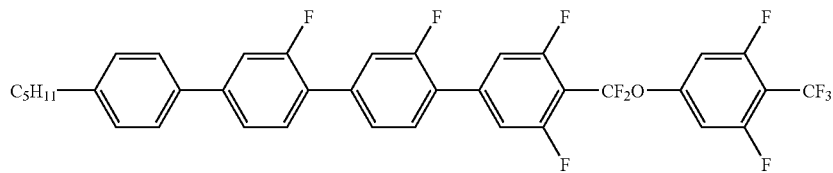 1-4-183
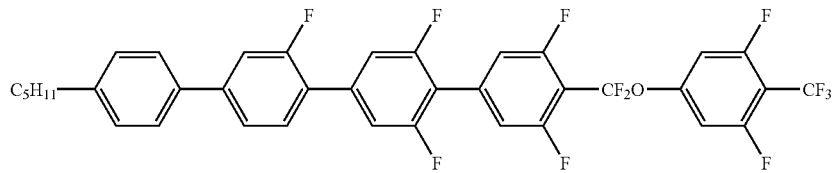 1-4-184
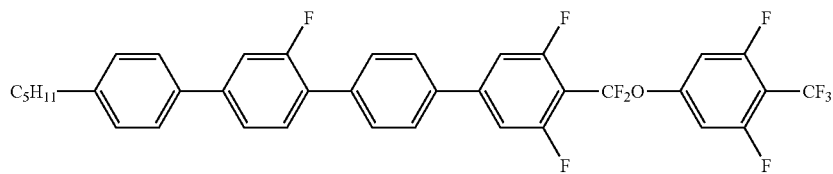 1-4-185
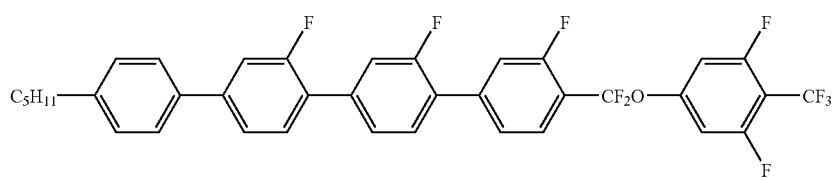 1-4-186
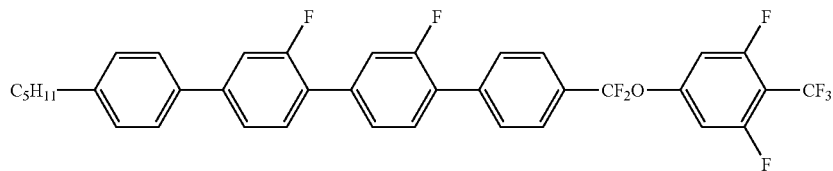 1-4-187
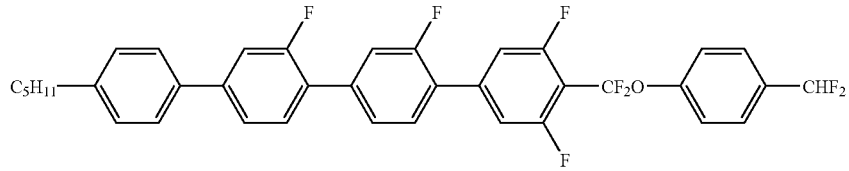 1-4-188
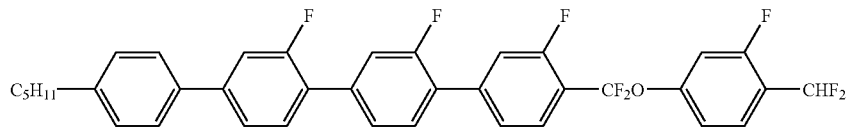 1-4-189
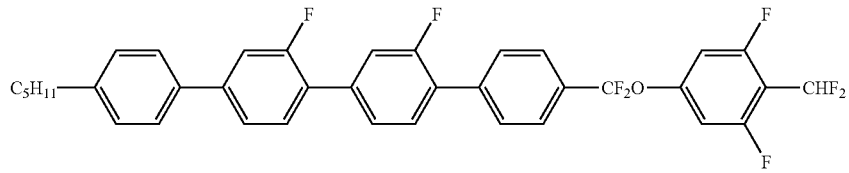 1-4-190
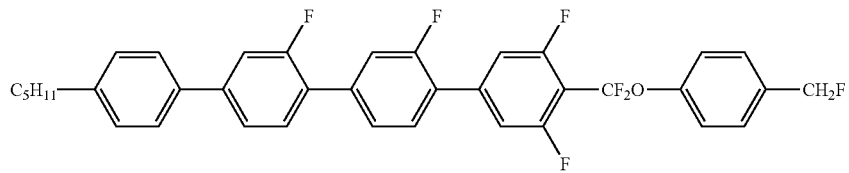 1-4-191

-continued
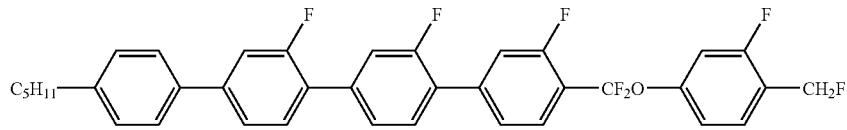
1-4-192
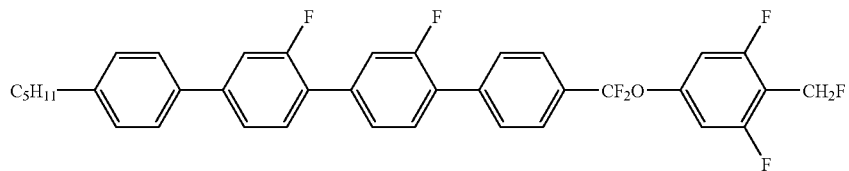
1-4-193
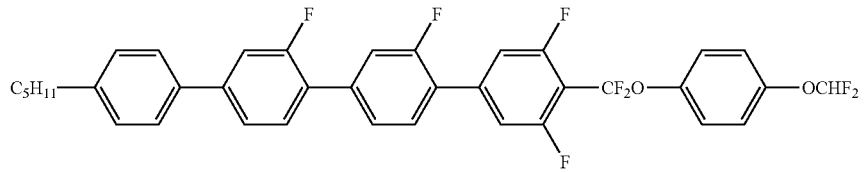
1-4-194
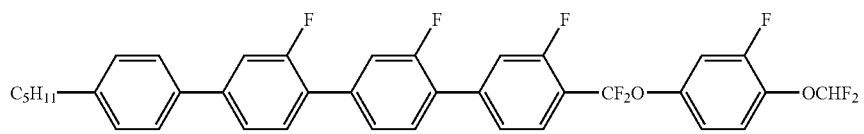
1-4-195
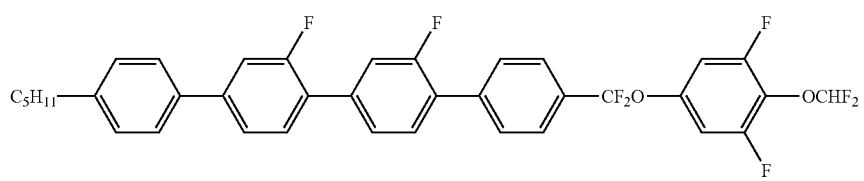
1-4-196
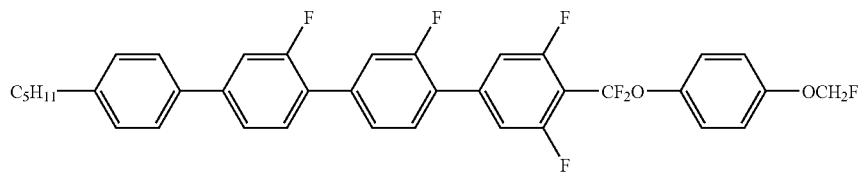
1-4-197
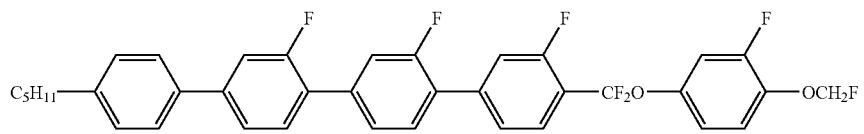
1-4-198
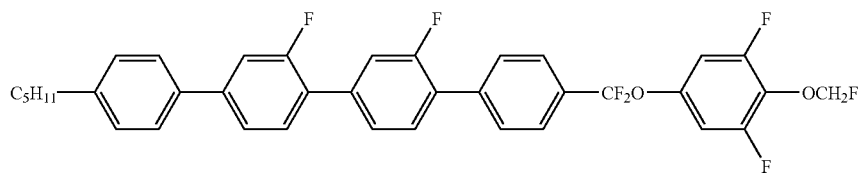
1-4-199
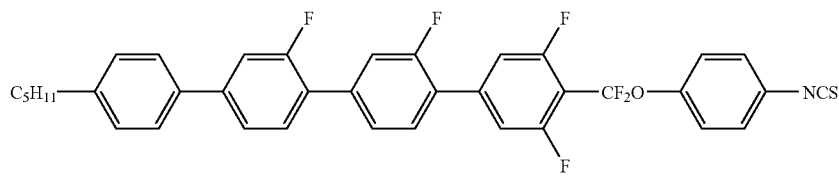
1-4-200
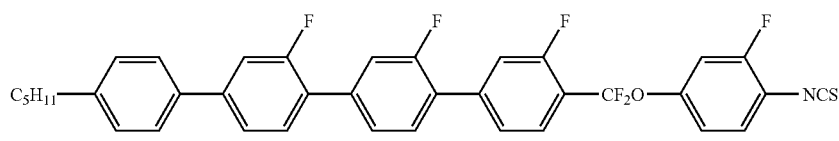
1-4-201

-continued
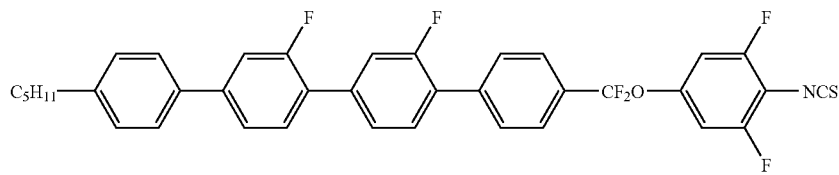
1-4-202
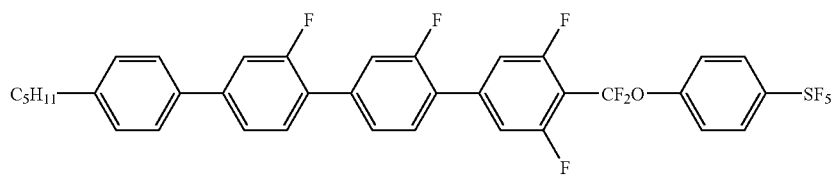
1-4-203
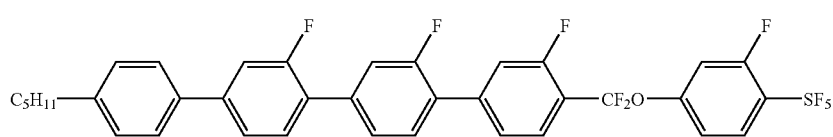
1-4-204
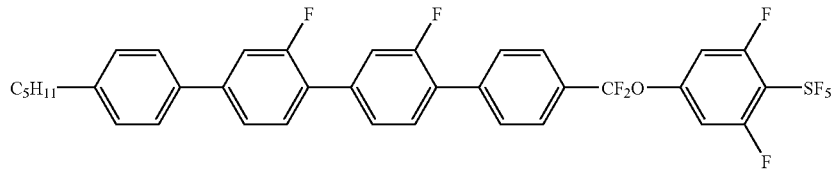
1-4-205
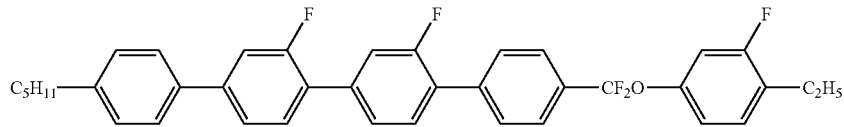
1-4-206
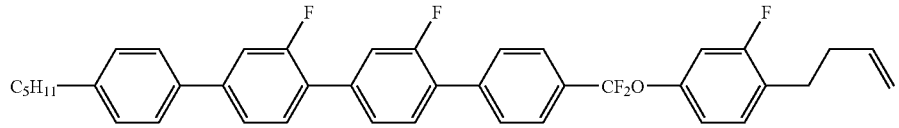
1-4-207
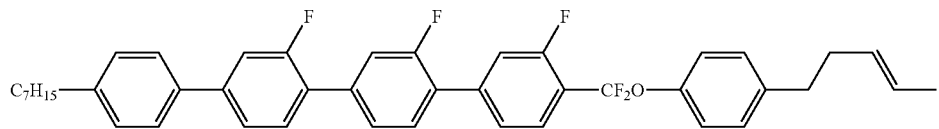
1-4-208
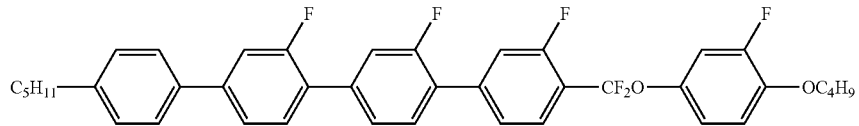
1-4-209
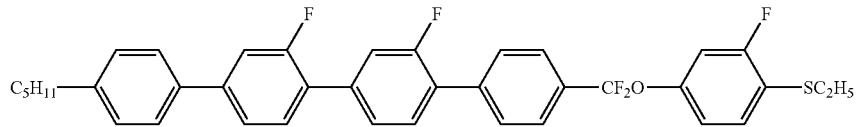
1-4-210
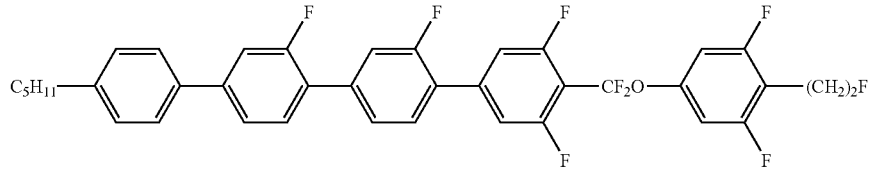
1-4-211

-continued
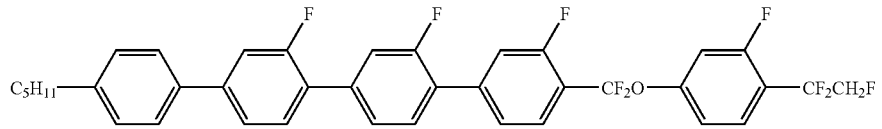
1-4-212
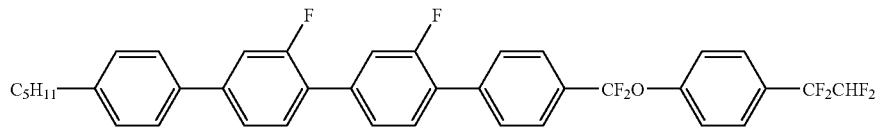
1-4-213
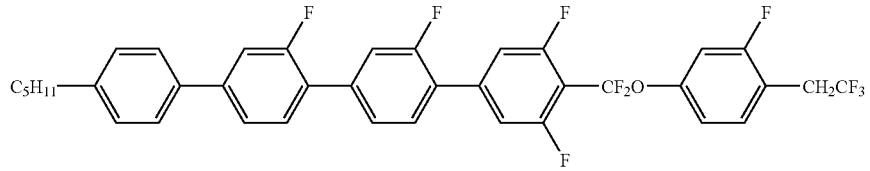
1-4-214
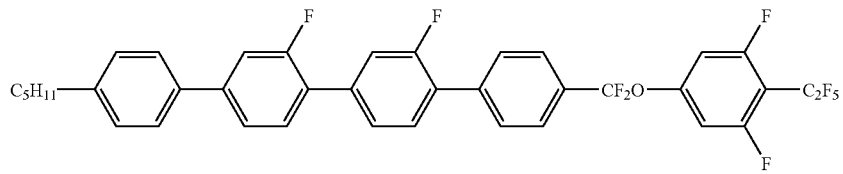
1-4-215
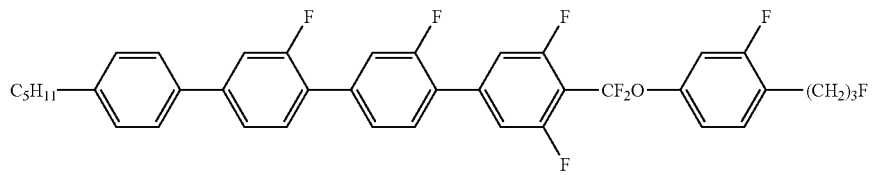
1-4-216
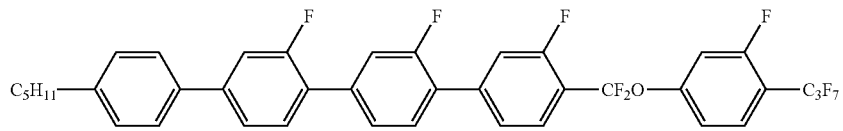
1-4-217
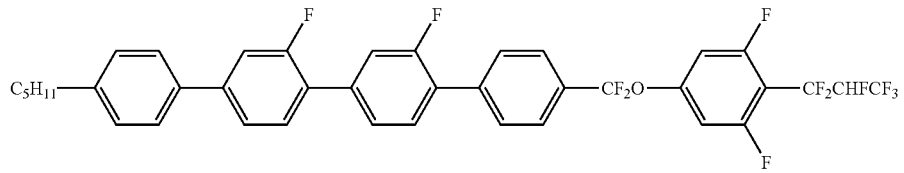
1-4-218
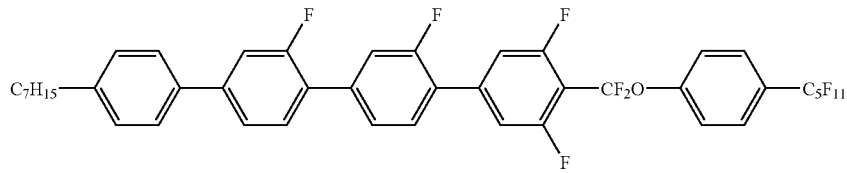
1-4-219
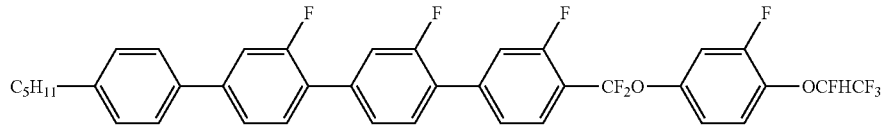
1-4-220
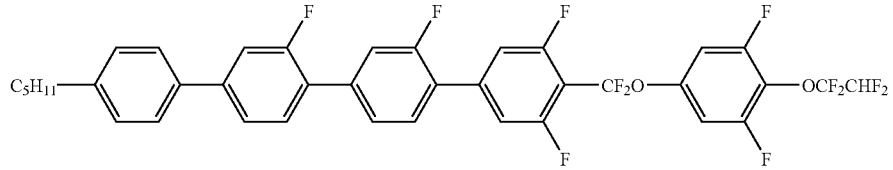
1-4-221

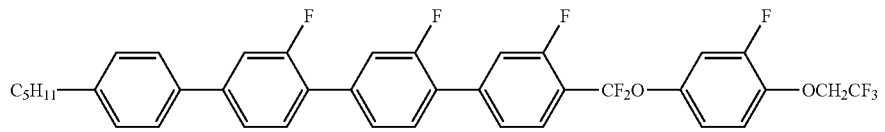
1-4-222
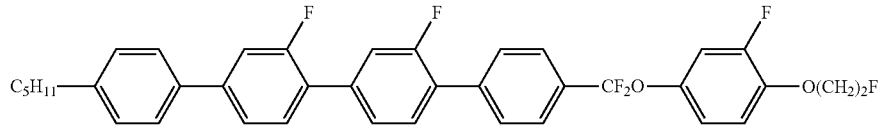
1-4-223
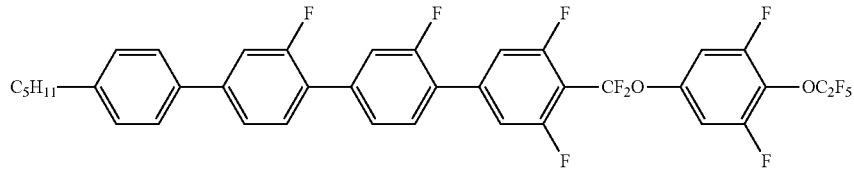
1-4-224
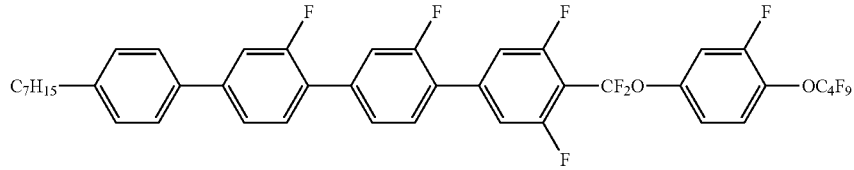
1-4-225
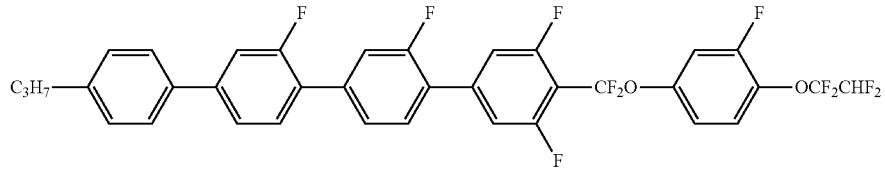
1-4-226
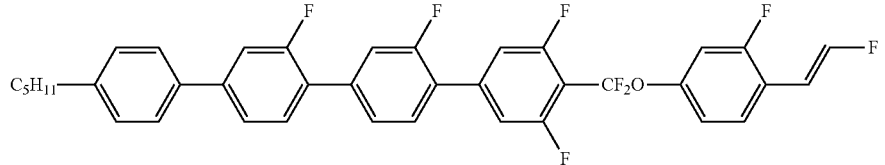
1-4-227
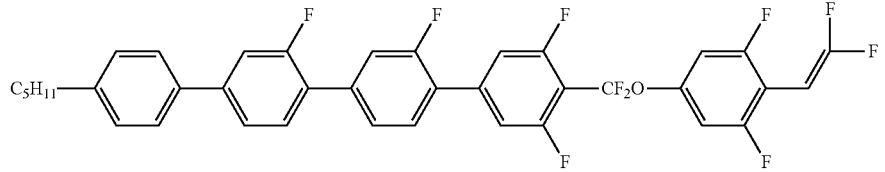
1-4-228
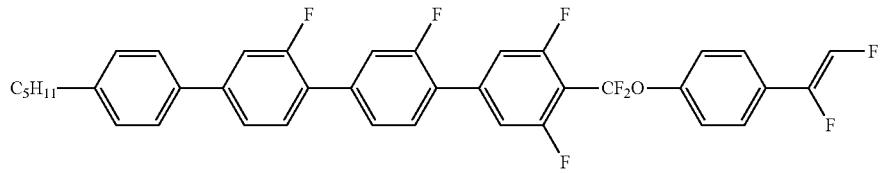
1-4-229
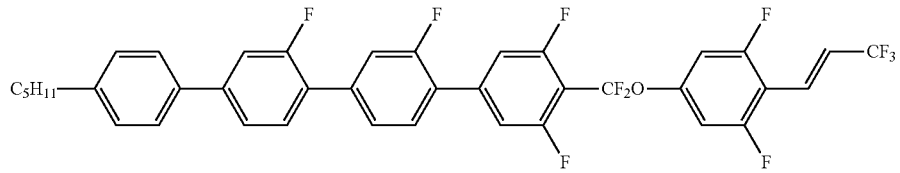
1-4-230

-continued
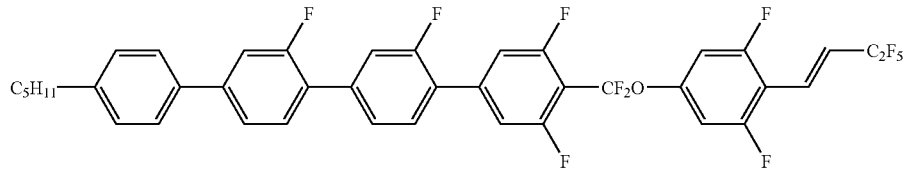
1-4-231
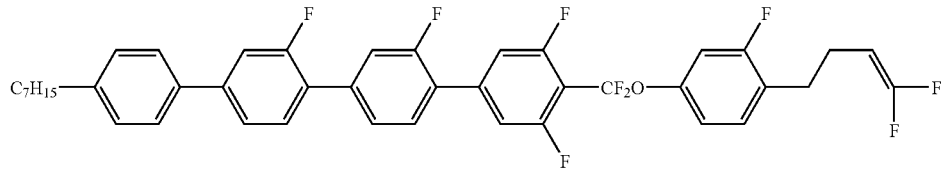
1-4-232
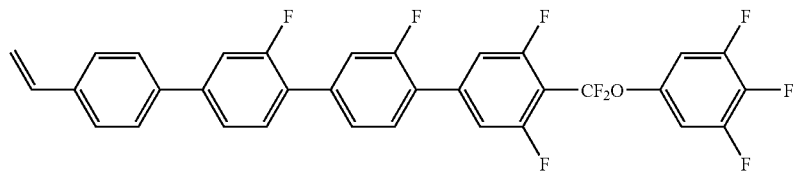
1-4-233
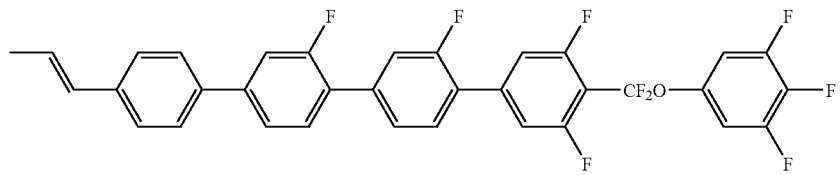
1-4-234
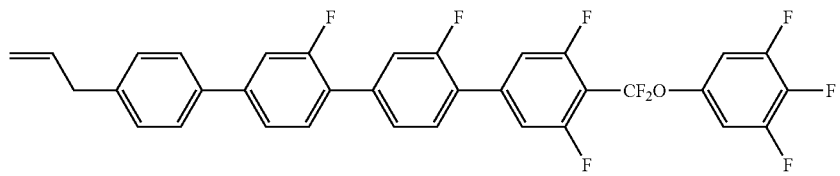
1-4-235
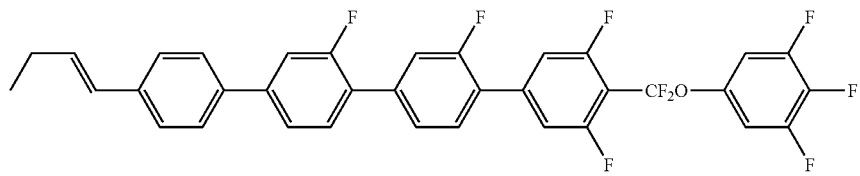
1-4-236
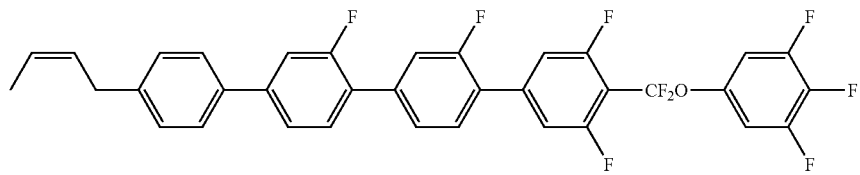
1-4-237
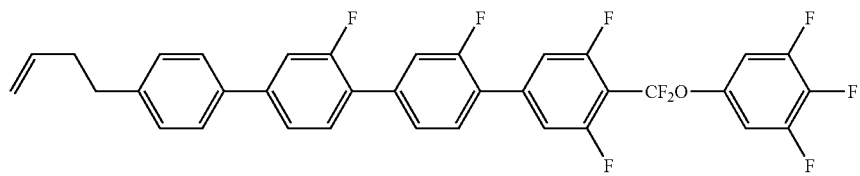
1-4-238
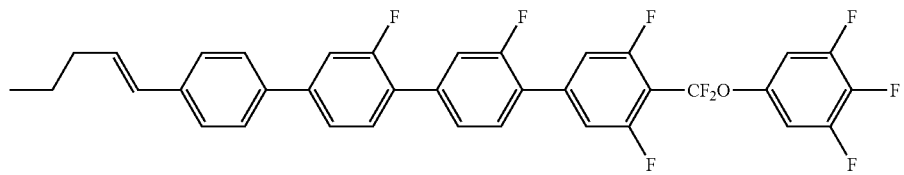
1-4-239

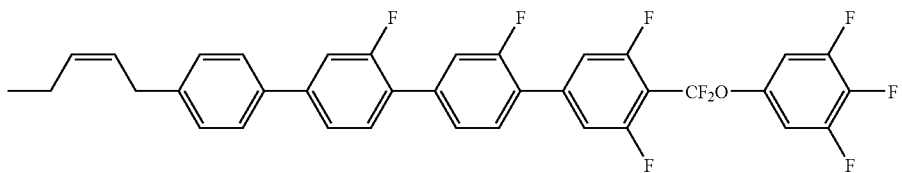 1-4-240
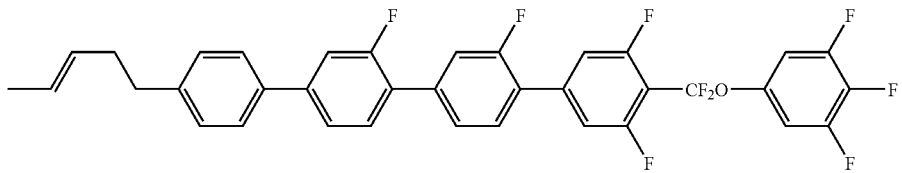 1-4-241
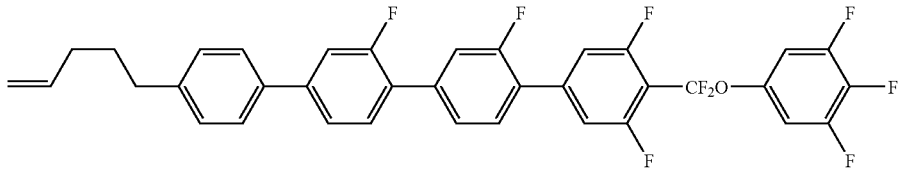 1-4-242
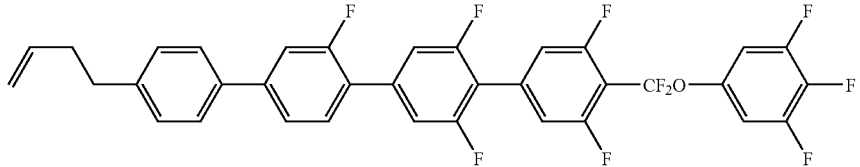 1-4-243
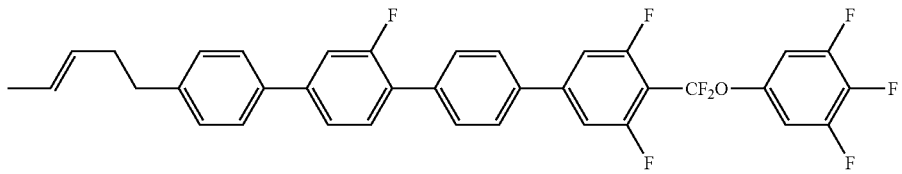 1-4-244
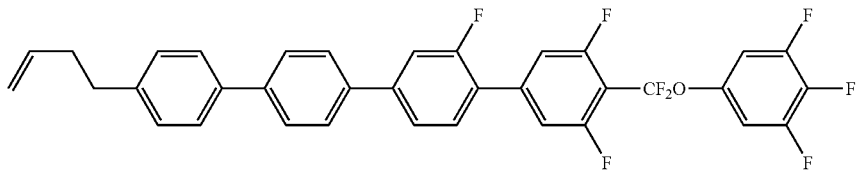 1-4-245
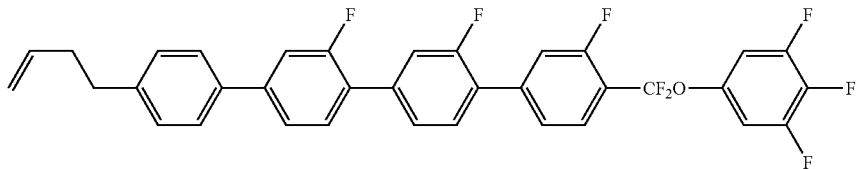 1-4-246
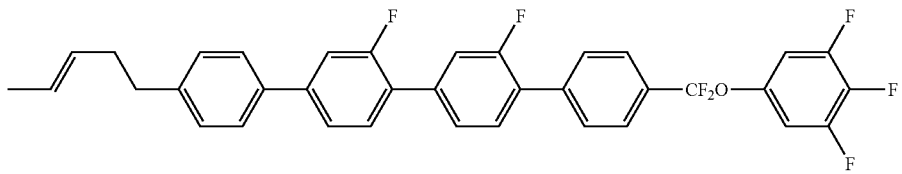 1-4-247
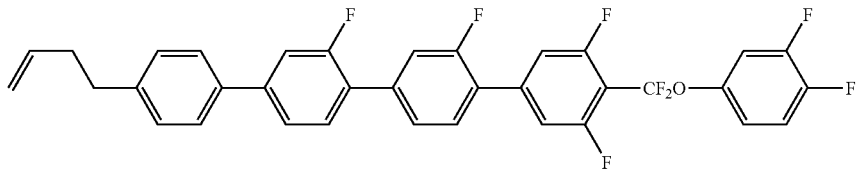 1-4-248

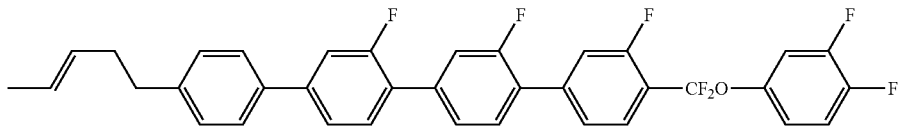
1-4-249
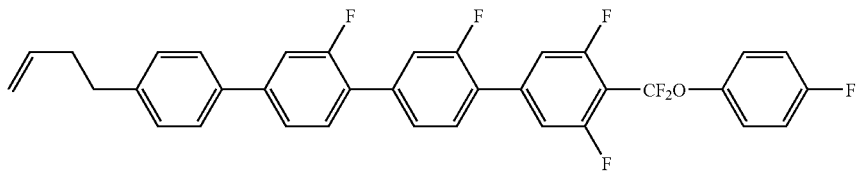
1-4-250
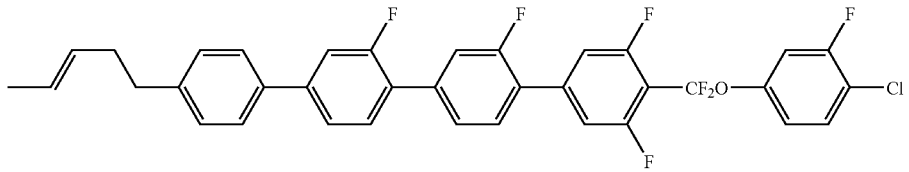
1-4-251
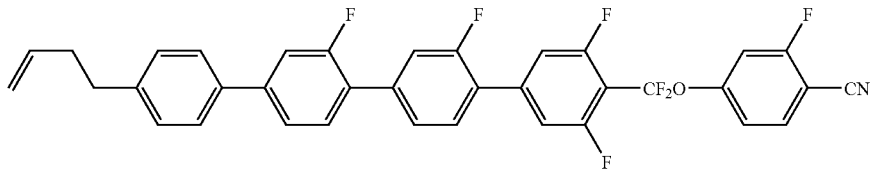
1-4-252
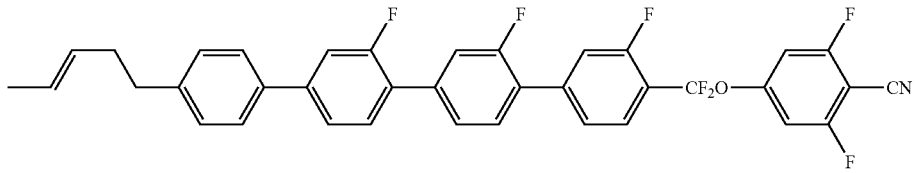
1-4-253
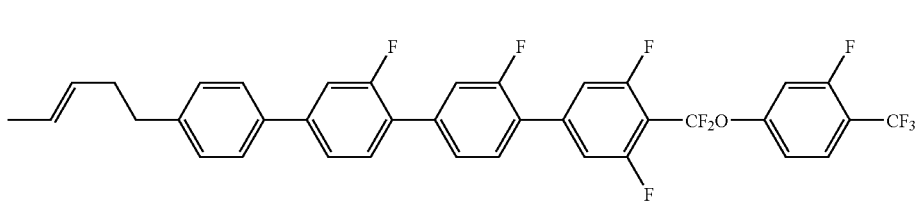
1-4-254
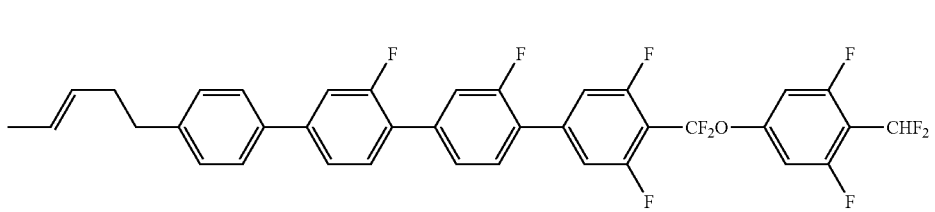
1-4-255
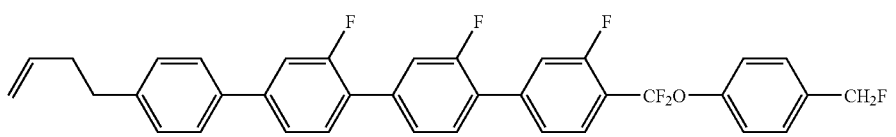
1-4-256
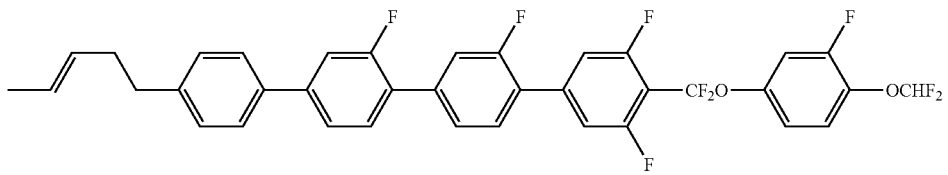
1-4-257

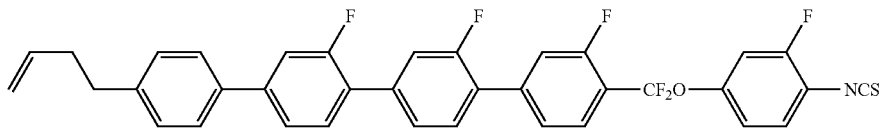
1-4-258
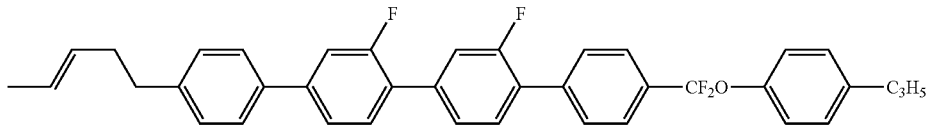
1-4-259
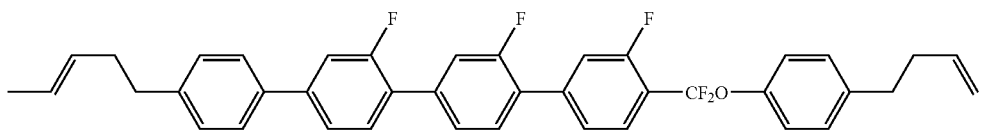
1-4-260
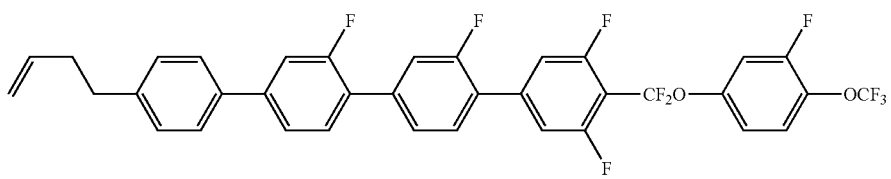
1-4-261
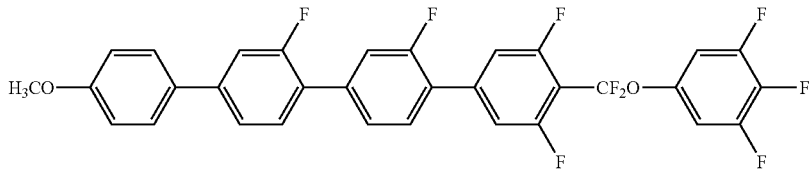
1-4-262
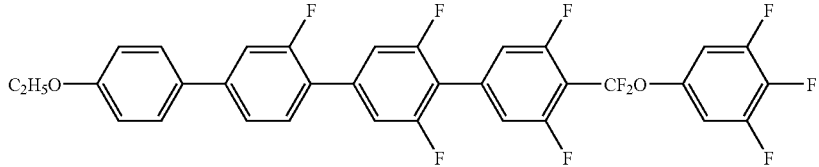
1-4-263
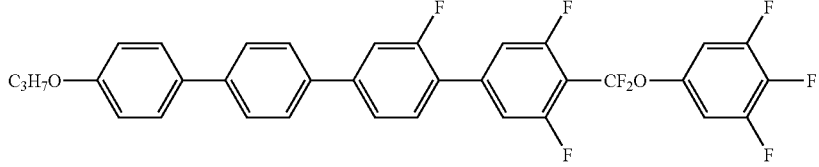
1-4-264
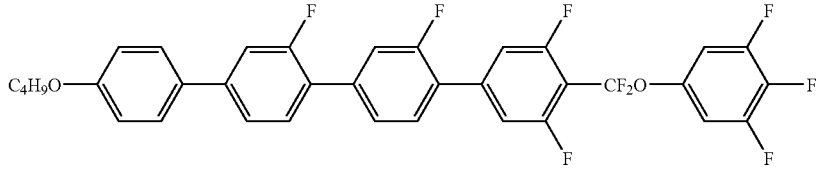
1-4-265
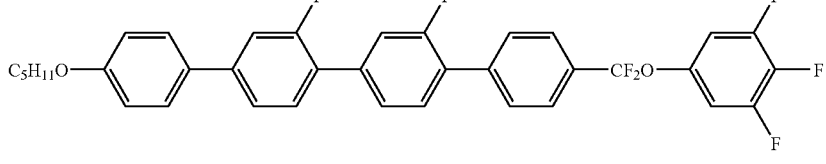
1-4-266

-continued
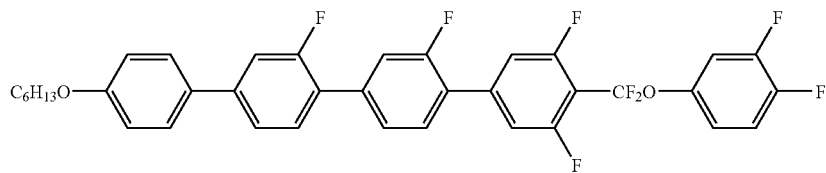
1-4-267
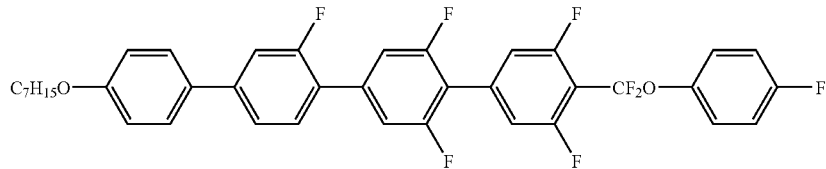
1-4-268
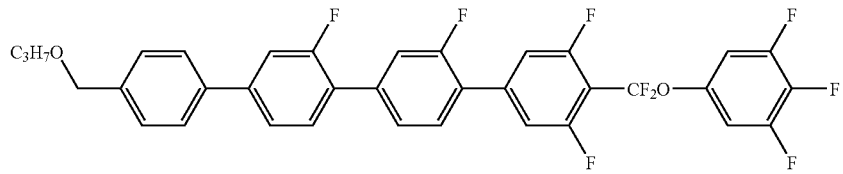
1-4-269
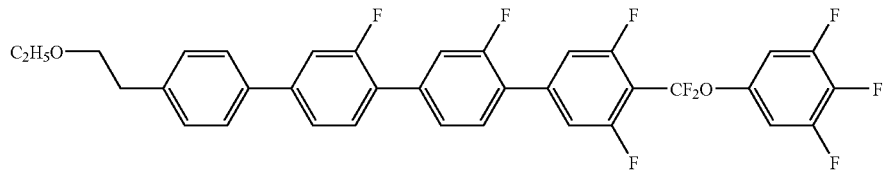
1-4-270
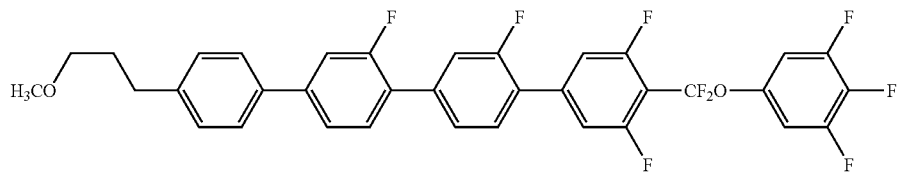
1-4-271
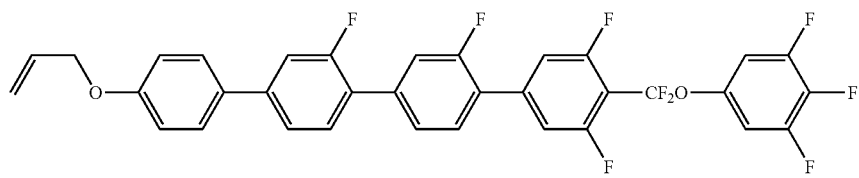
1-4-272
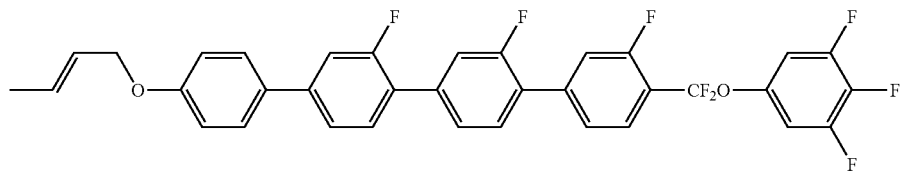
1-4-273
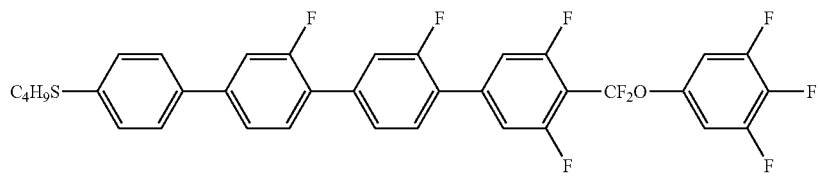
1-4-274
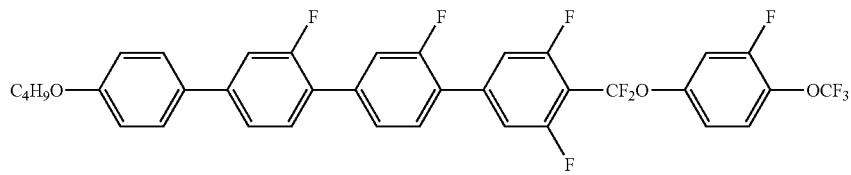
1-4-275

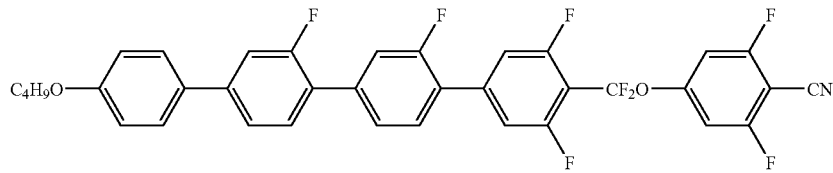 1-4-276
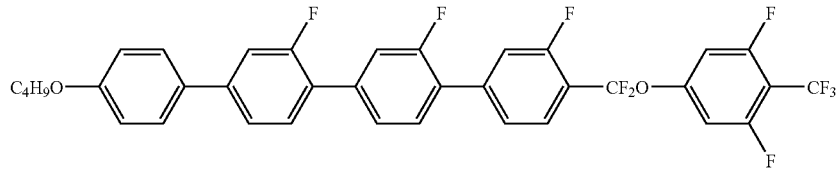 1-4-277
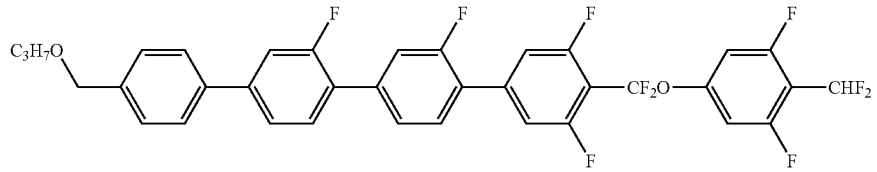 1-4-278
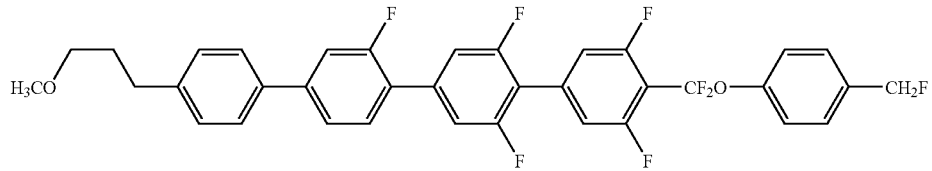 1-4-279
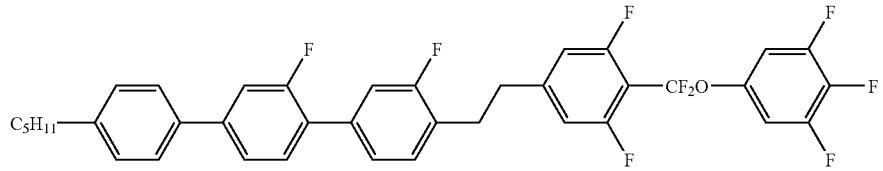 1-4-280
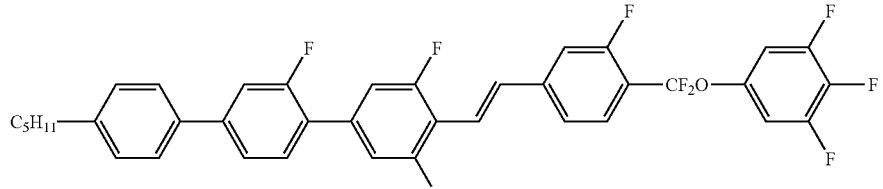 1-4-281
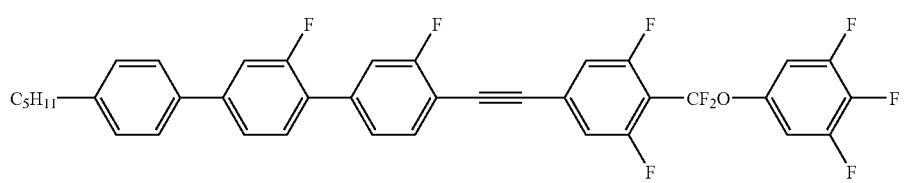 1-4-282
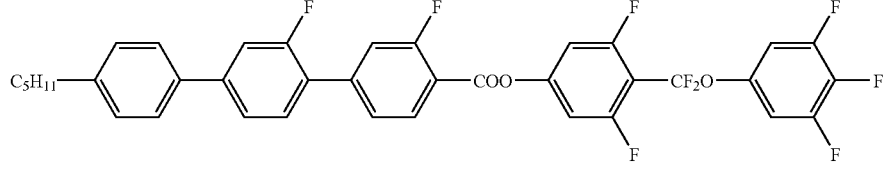 1-4-283
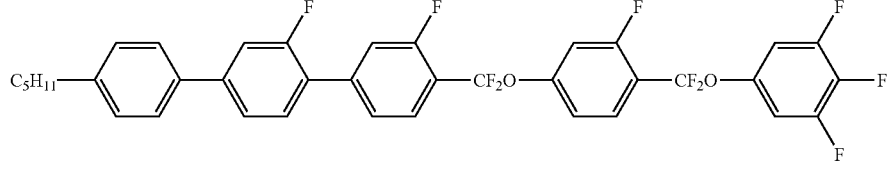 1-4-284

-continued
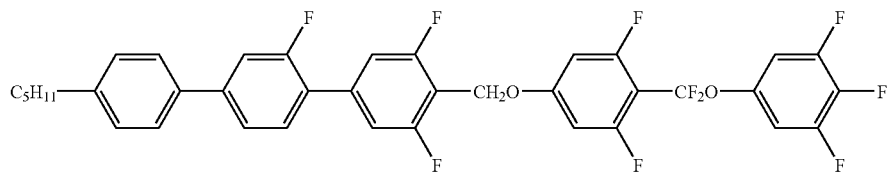
1-4-285
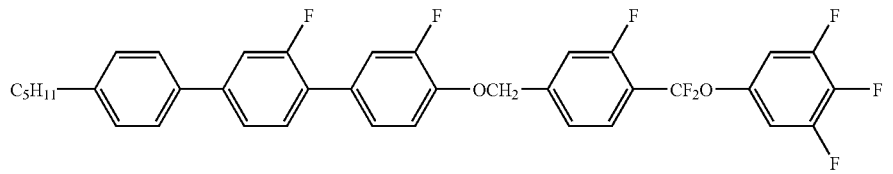
1-4-286
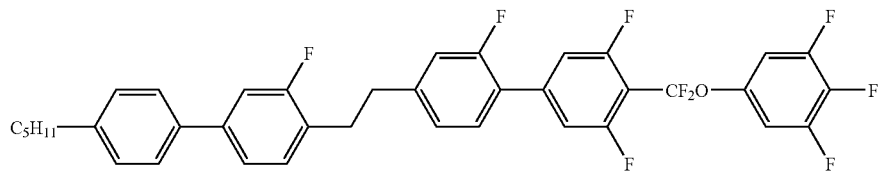
1-4-287
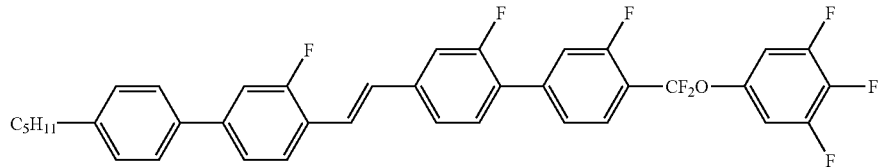
1-4-288
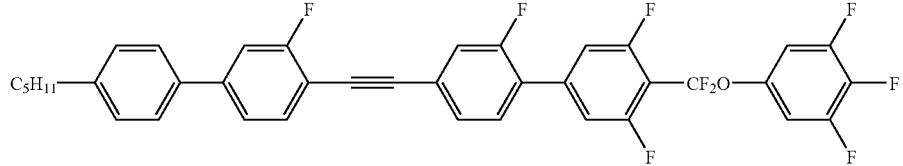
1-4-289
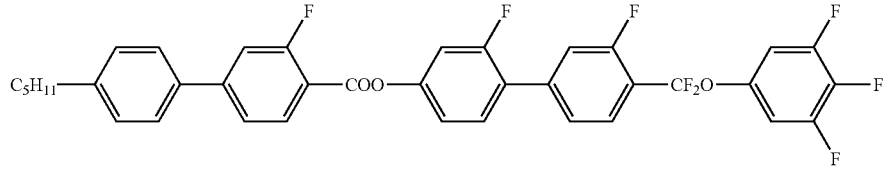
1-4-290
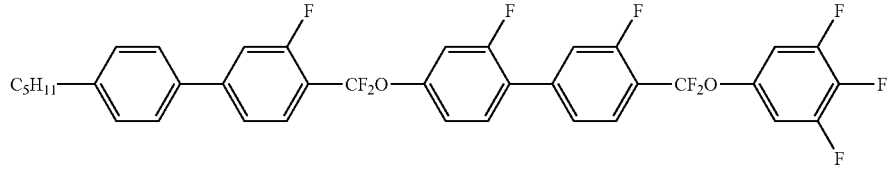
1-4-291
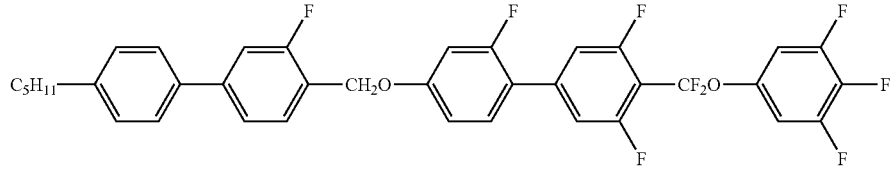
1-4-292
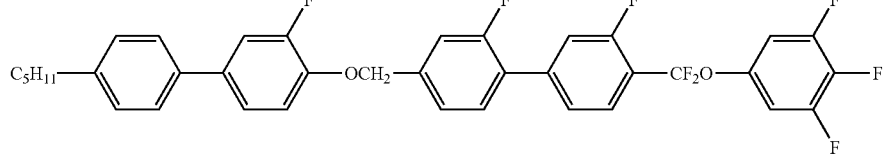
1-4-293

-continued
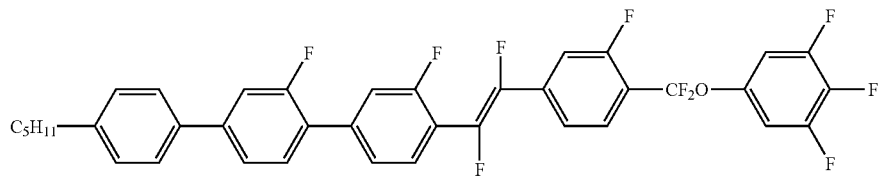
1-4-294
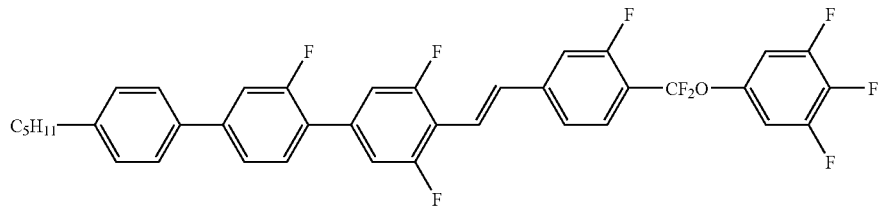
1-4-295
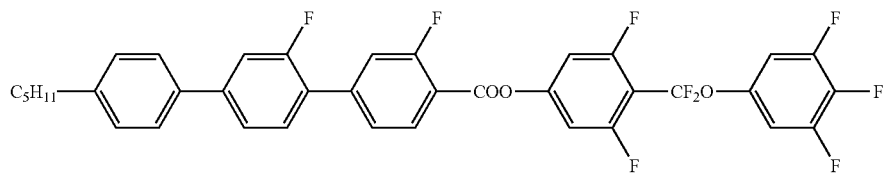
1-4-296
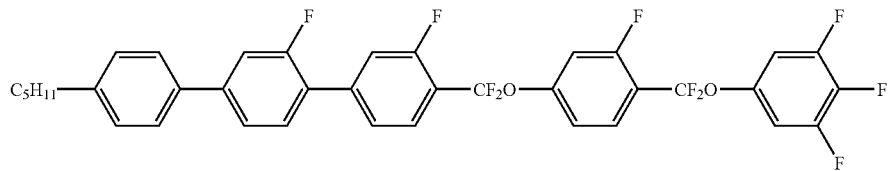
1-4-297
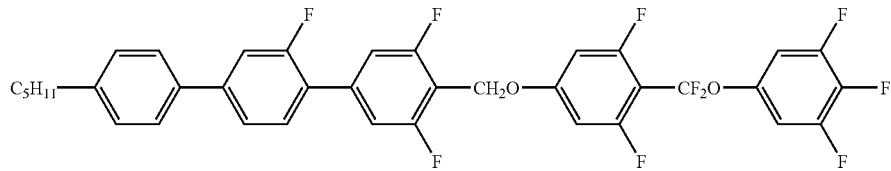
1-4-298
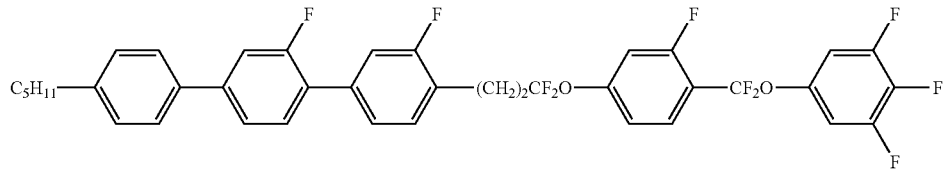
1-4-299
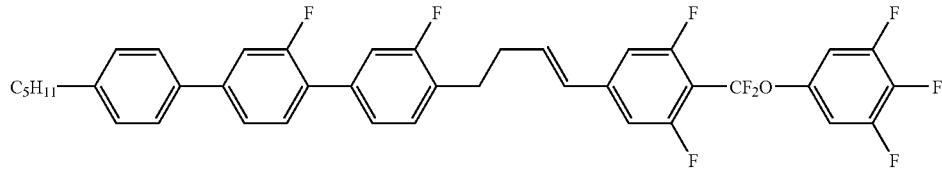
1-4-300
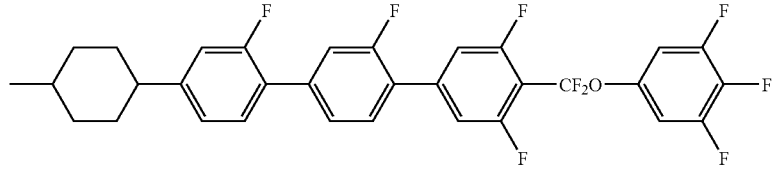
1-4-301

-continued
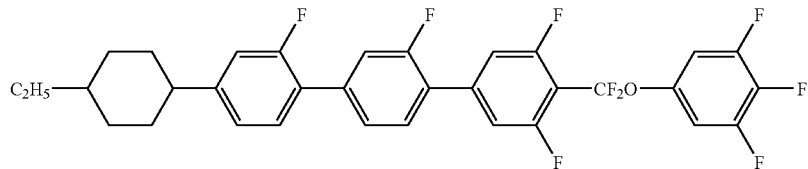
1-4-302
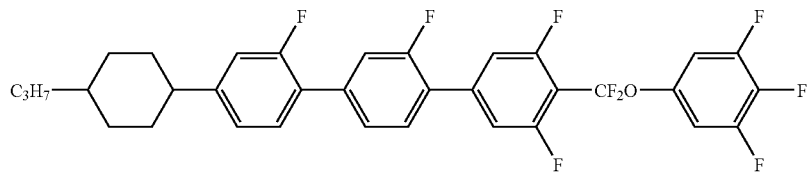
1-4-303
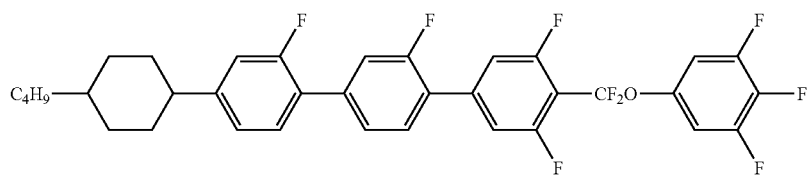
1-4-304
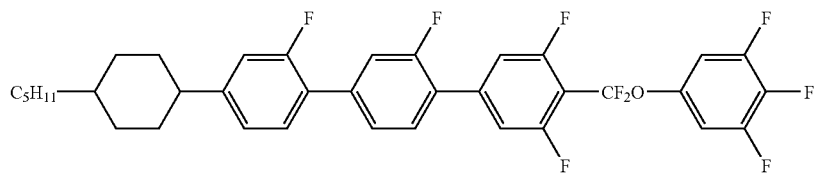
1-4-305
$T_{NI} = 166°$ C., $\Delta n = 0.204$, $\Delta\varepsilon = 30.3$
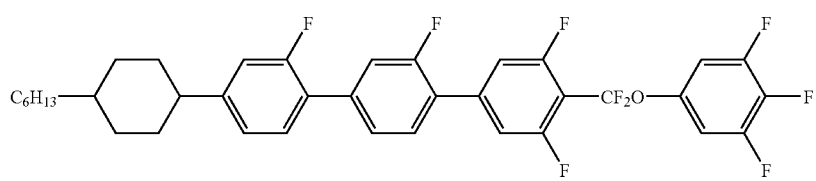
1-4-306
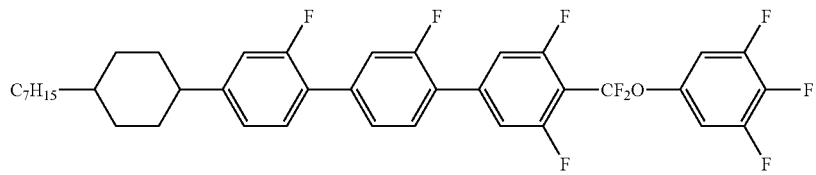
1-4-307
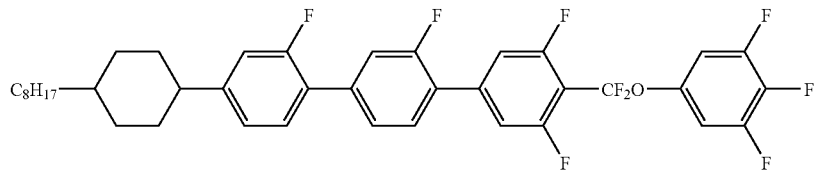
1-4-308
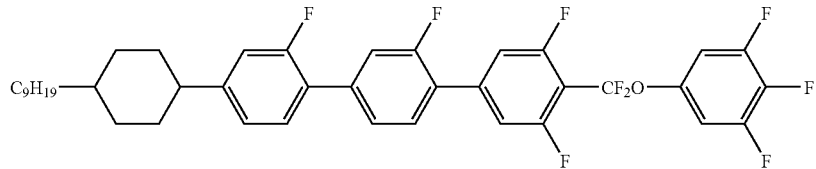
1-4-309

-continued
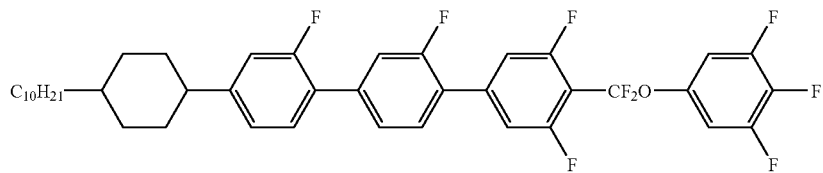
1-4-310
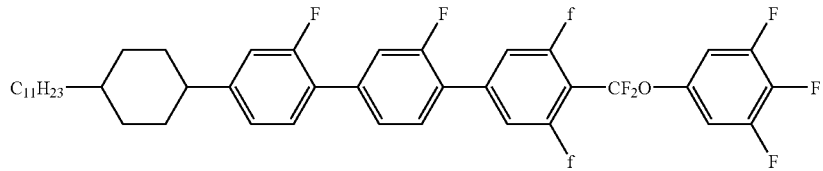
1-4-311
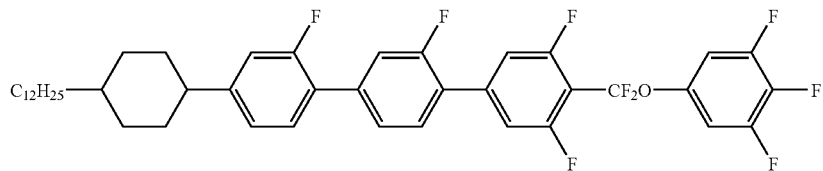
1-4-312
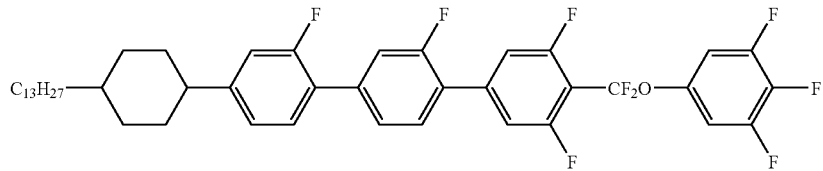
1-4-313
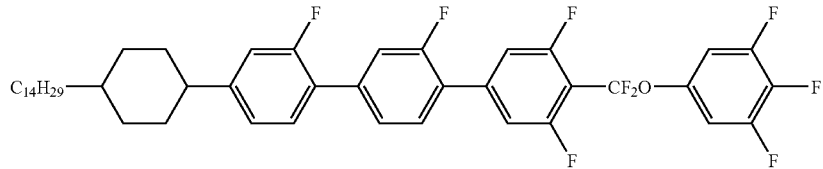
1-4-314
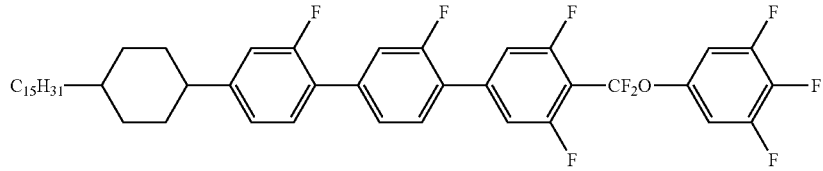
1-4-315
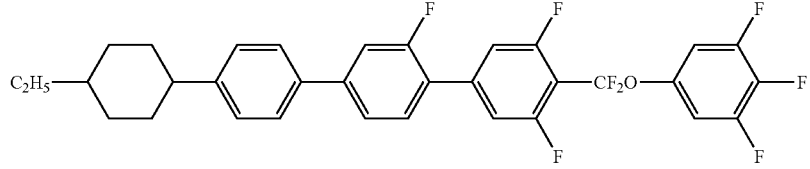
1-4-316
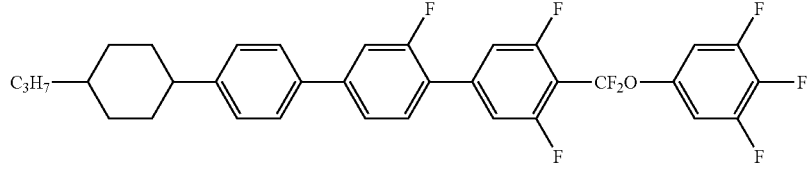
1-4-317
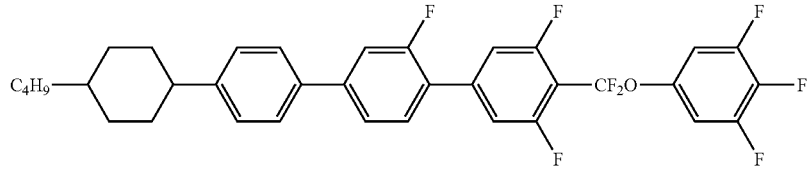
1-4-318

-continued
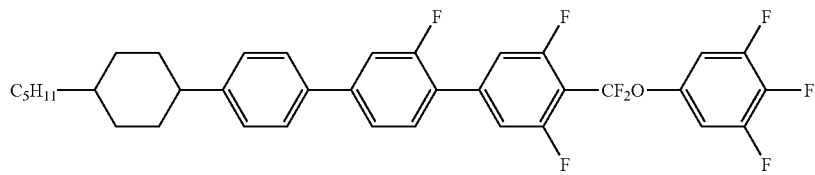
$T_{NI} = 189°$ C., $\Delta n = 0.210$, $\Delta\epsilon = 22.9$
1-4-319
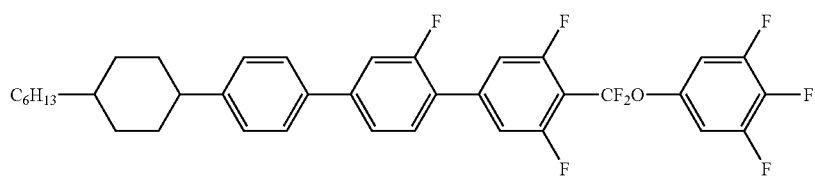
1-4-320
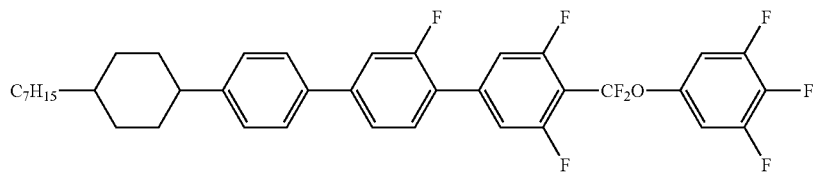
1-4-321
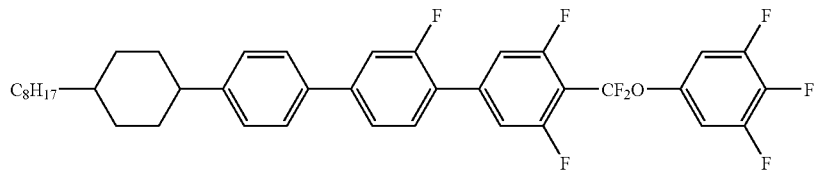
1-4-322
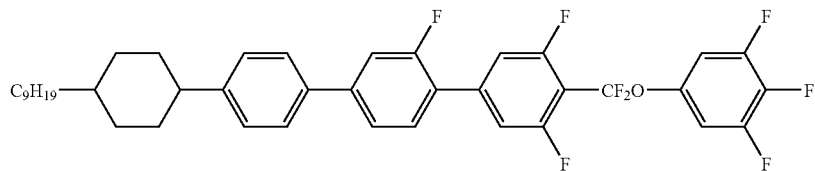
1-4-323
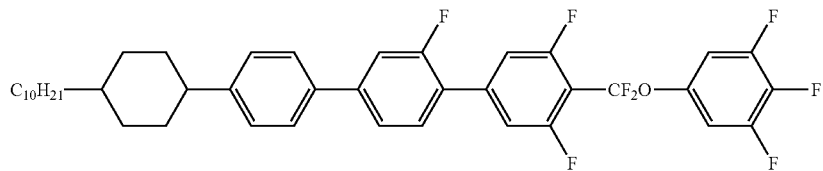
1-4-324
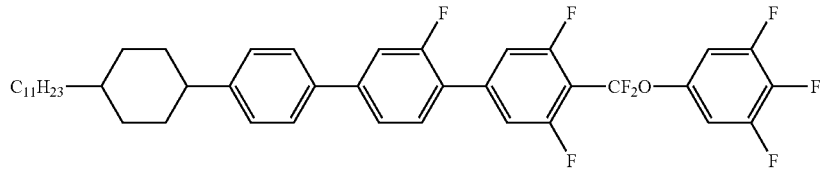
1-4-325
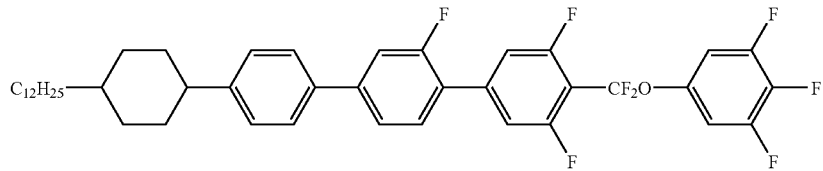
1-4-326

-continued
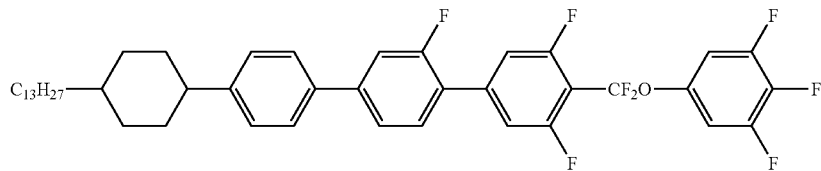
1-4-327
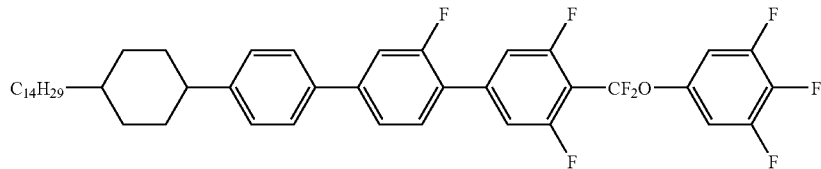
1-4-328
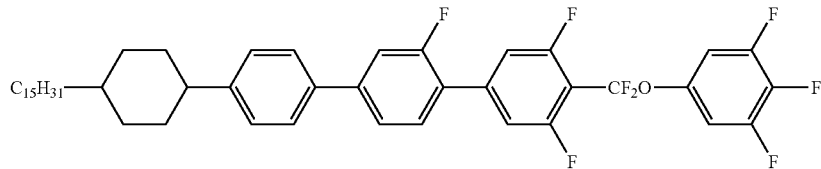
1-4-329
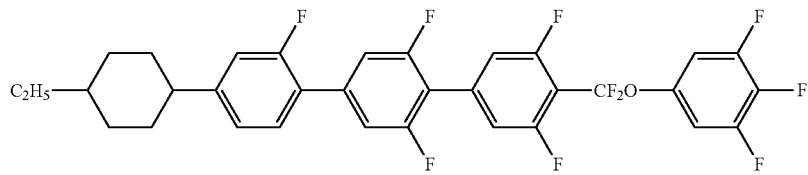
1-4-330
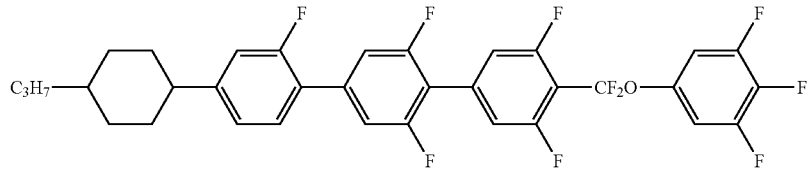
1-4-331
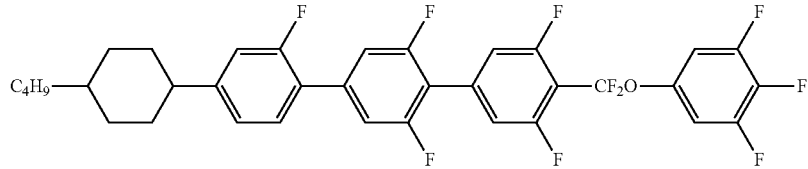
1-4-332
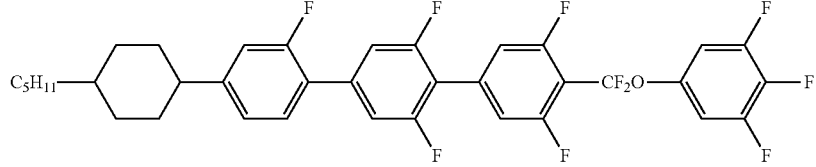
1-4-333
$T_{NI}$ = 146° C., $\Delta$ n = 0.197, $\Delta\varepsilon$ = 39.6
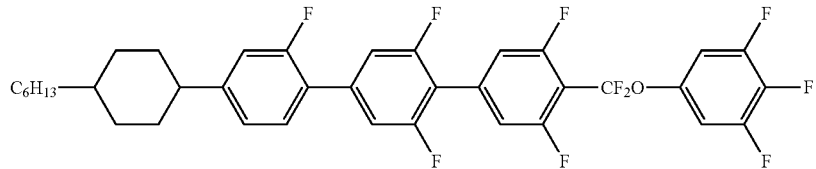
1-4-334

-continued
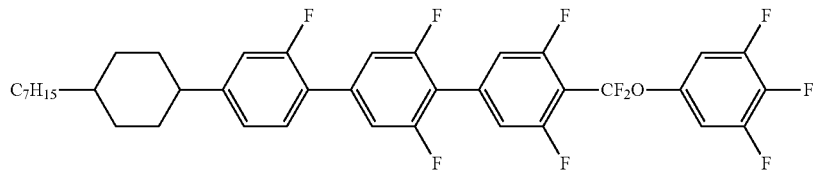
1-4-335
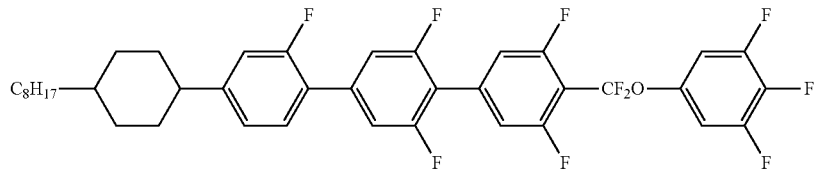
1-4-336
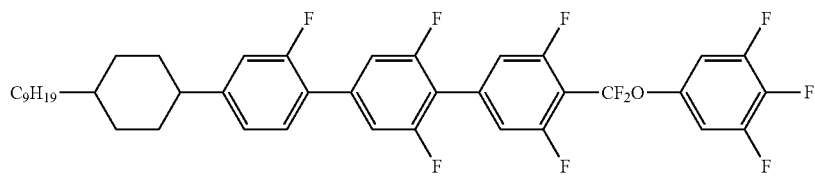
1-4-337
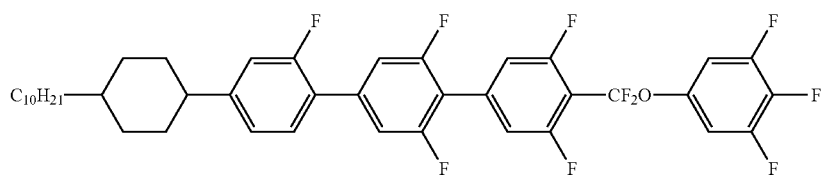
1-4-338
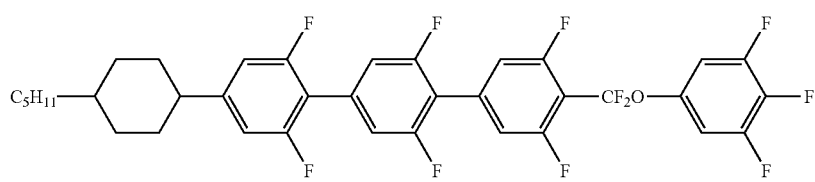
1-4-339
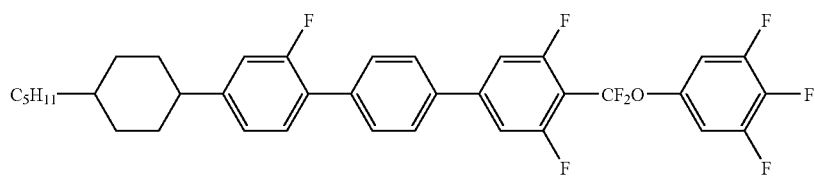
1-4-340
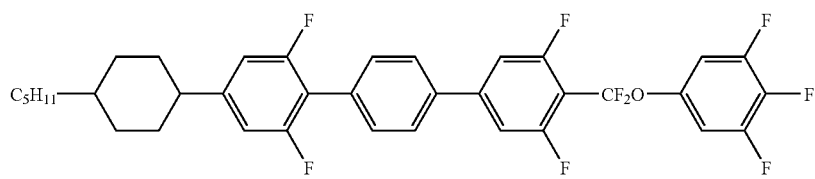
1-4-341
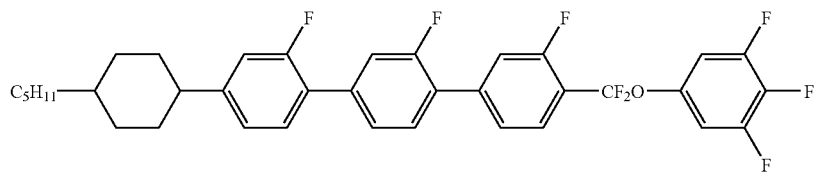
1-4-342

-continued
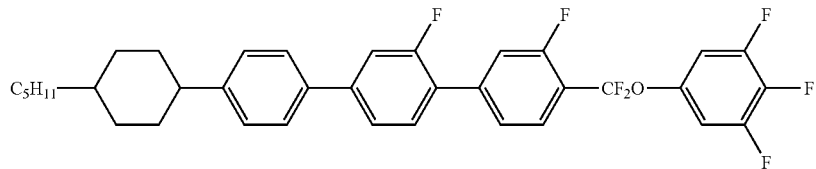
$T_{NI}$ = 210° C., Δ n = 0.217, Δε = 16.4
1-4-343
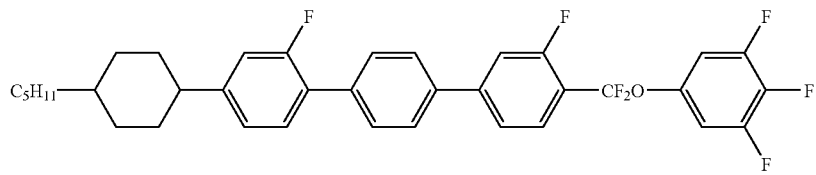
1-4-344
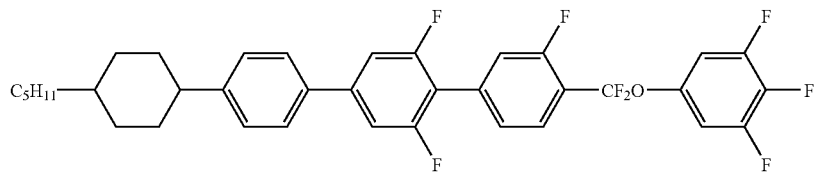
1-4-345
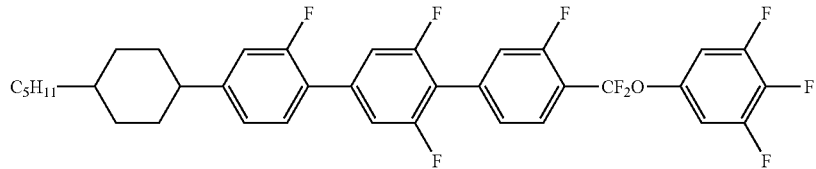
1-4-346
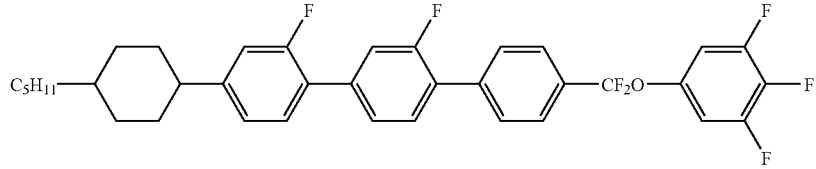
1-4-347
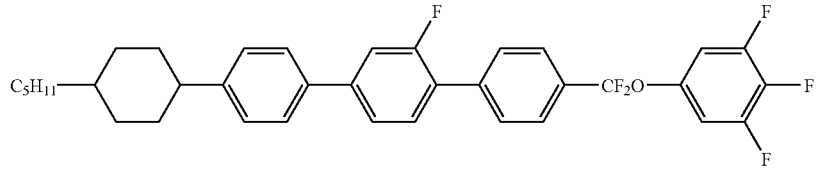
$T_{NI}$ = 218° C., Δ n = 0.224, Δε = 11.7
1-4-348
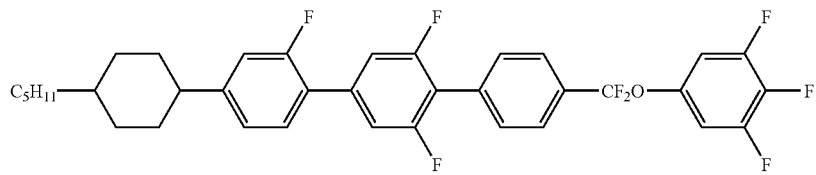
1-4-349
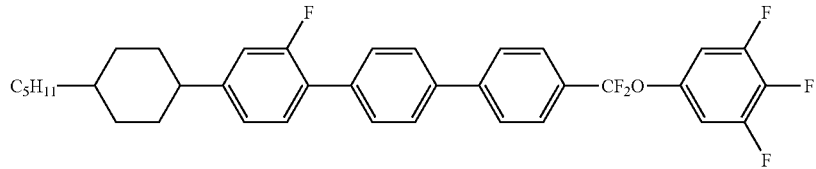
1-4-350

-continued
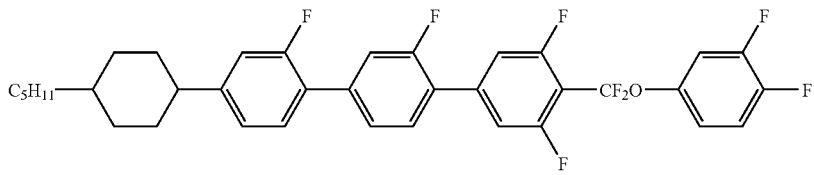
1-4-351
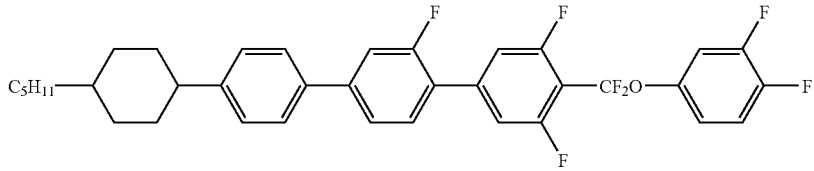
1-4-352
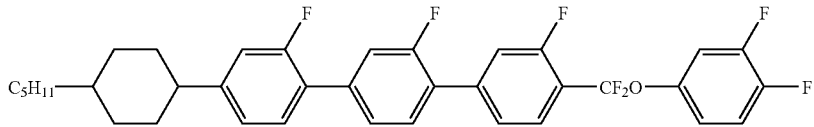
1-4-353
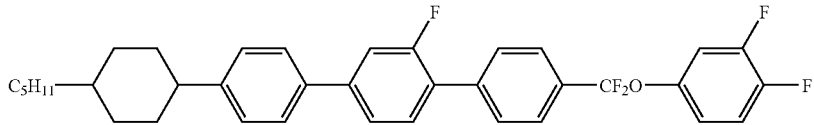
1-4-354
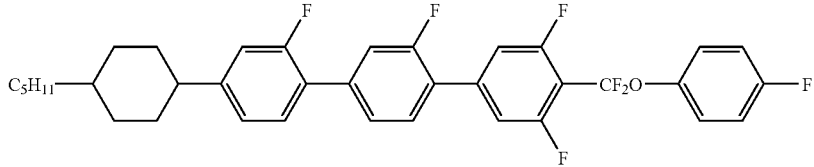
1-4-355
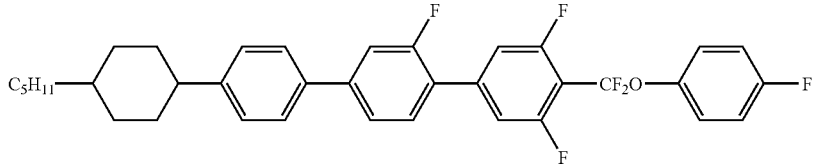
1-4-356
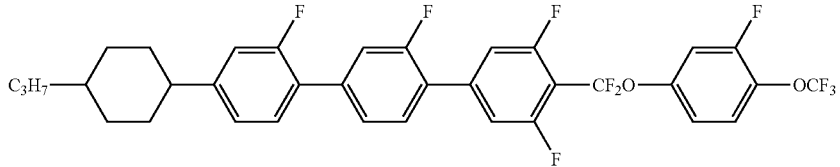
1-4-357
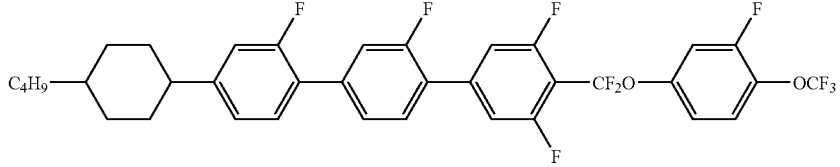
1-4-358
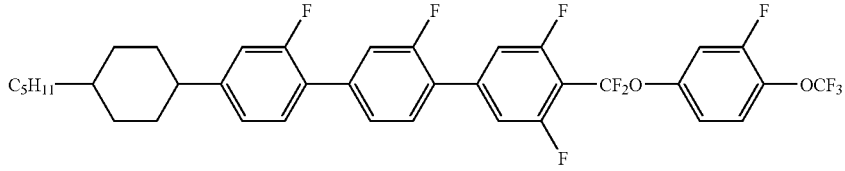
1-4-359

-continued
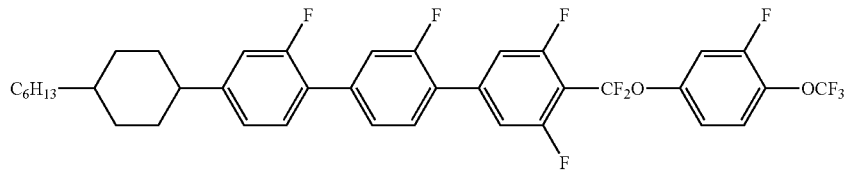
1-4-360
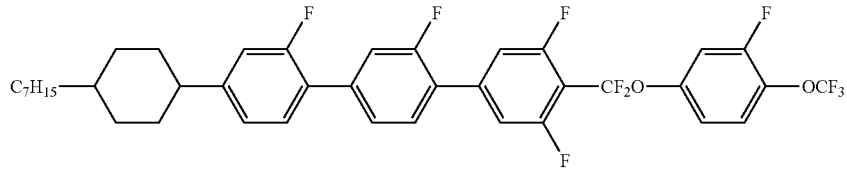
1-4-361
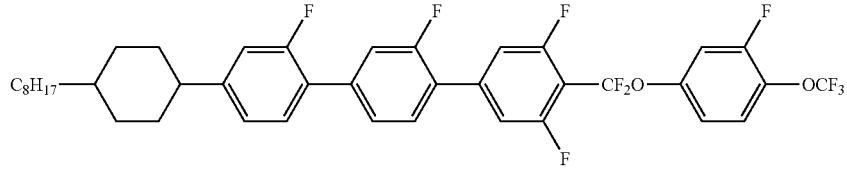
1-4-362
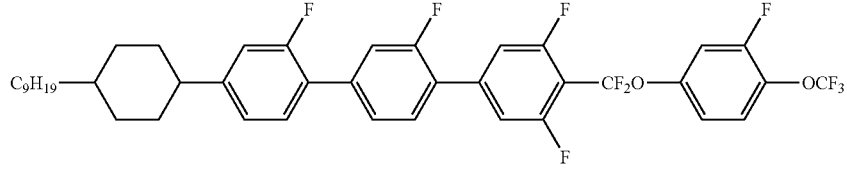
1-4-363
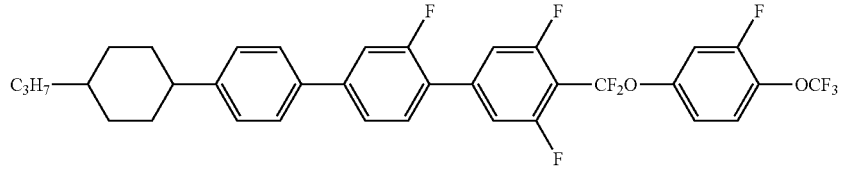
1-4-364
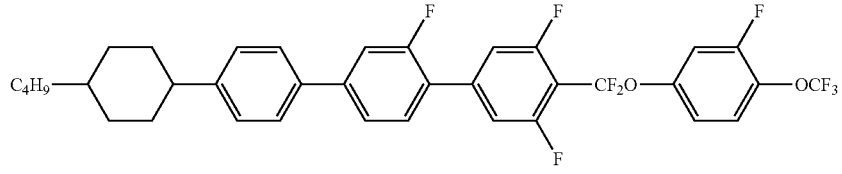
1-4-365
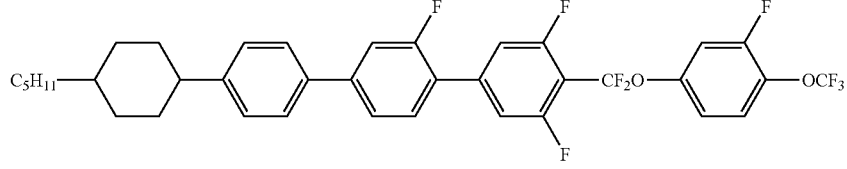
1-4-366
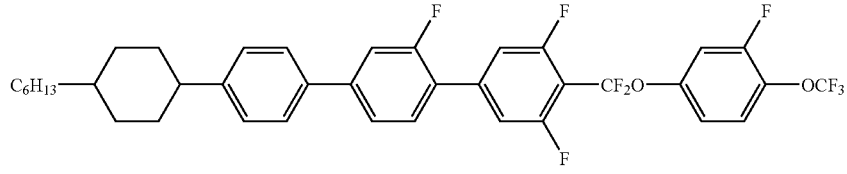
1-4-367
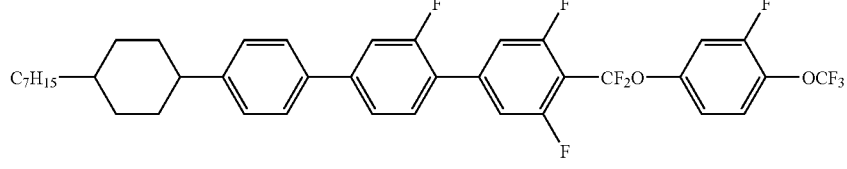
1-4-368

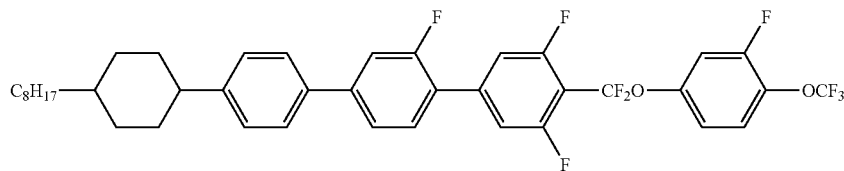 1-4-369
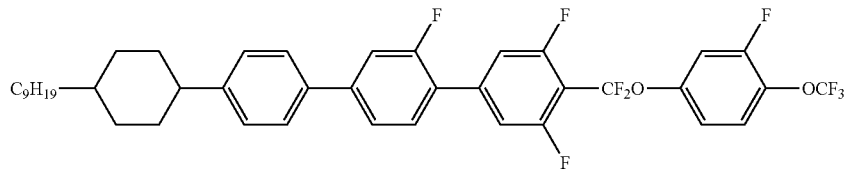 1-4-370
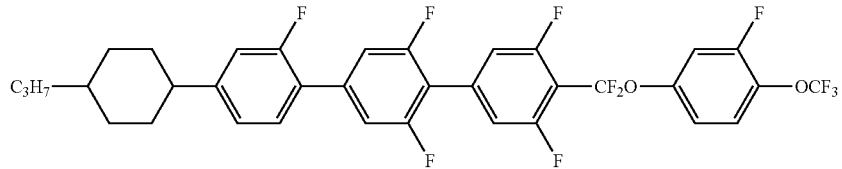 1-4-371
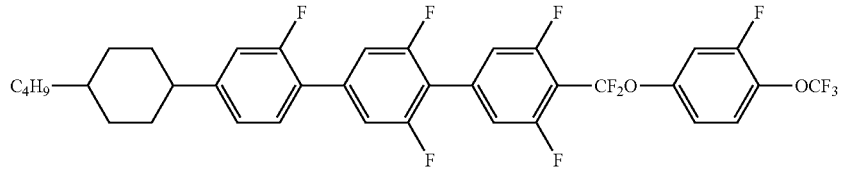 1-4-372
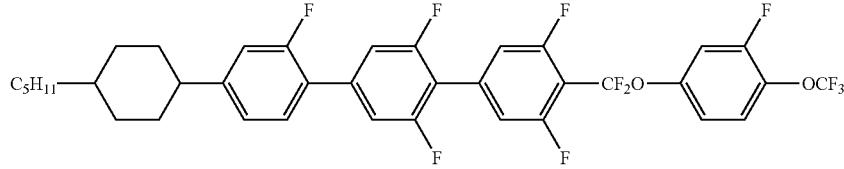 1-4-373
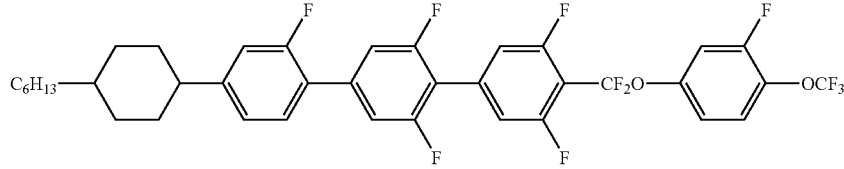 1-4-374
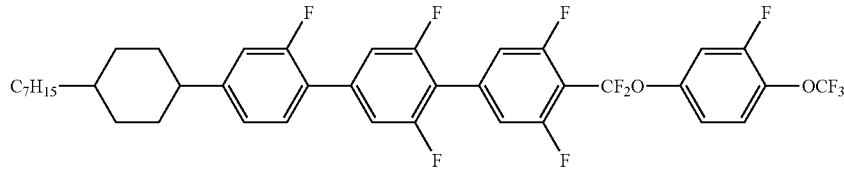 1-4-375
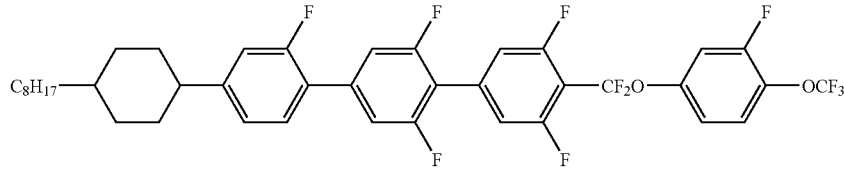 1-4-376
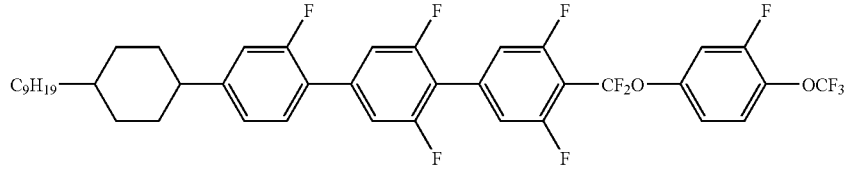 1-4-377

-continued
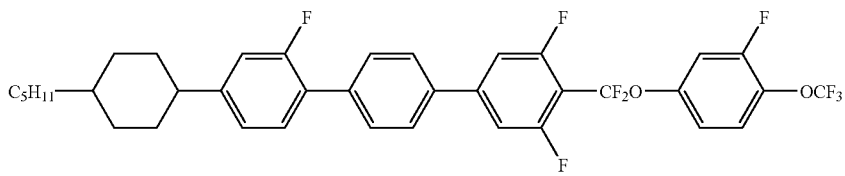
1-4-378
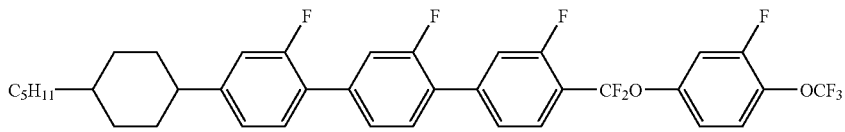
1-4-379
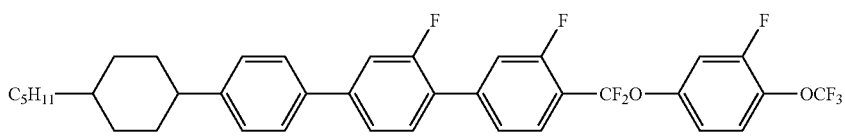
1-4-380
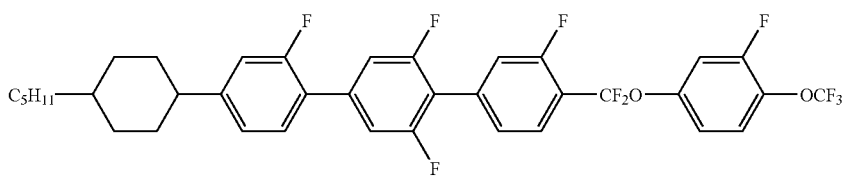
1-4-381
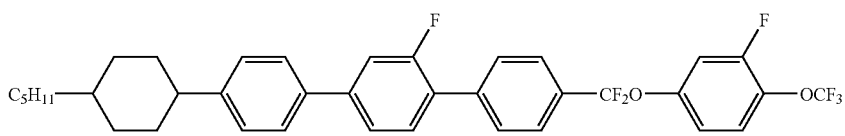
1-4-382
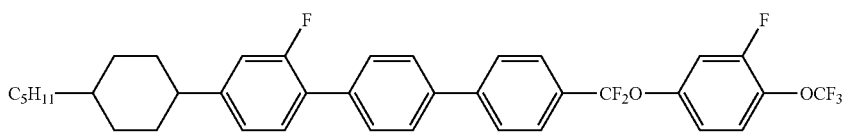
1-4-383
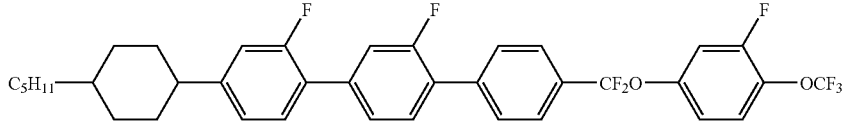
1-4-384
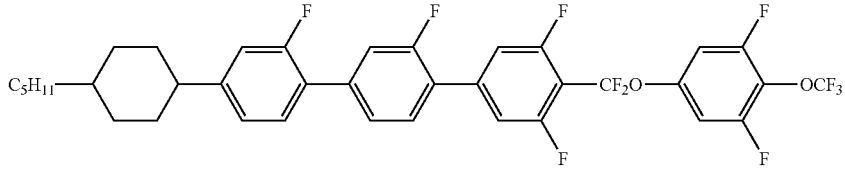
1-4-385
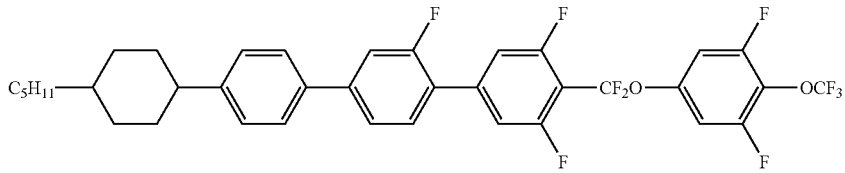
1-4-386
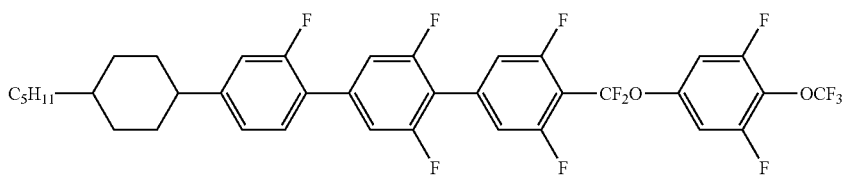
1-4-387

-continued
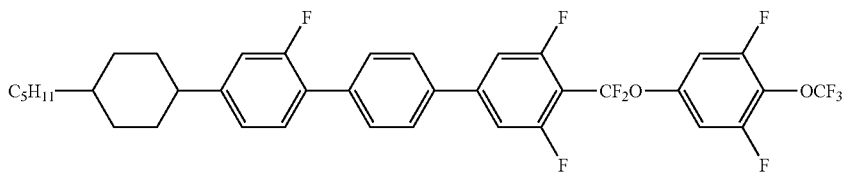
1-4-388
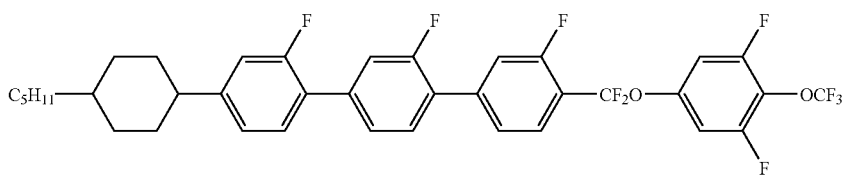
1-4-389
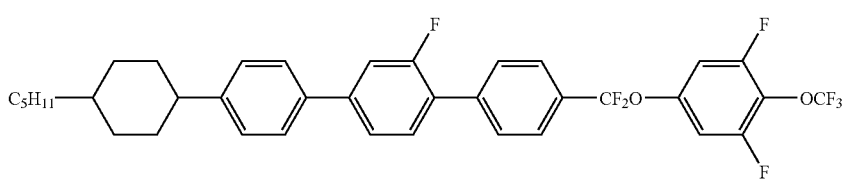
1-4-390
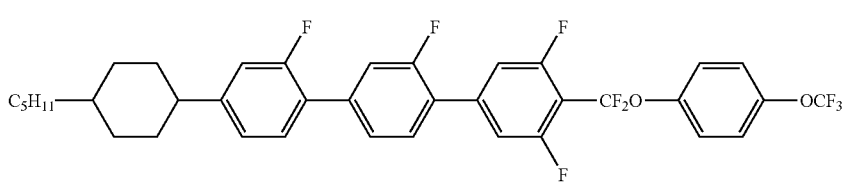
1-4-391
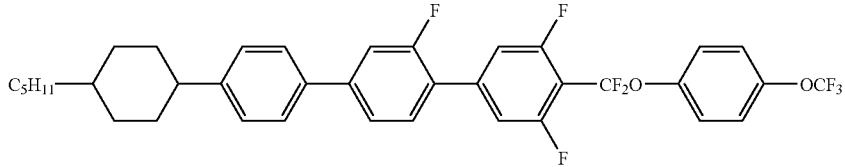
1-4-392
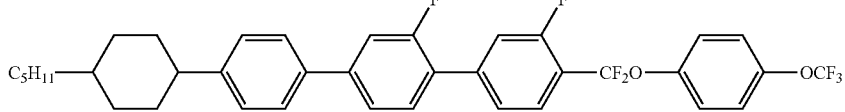
1-4-393
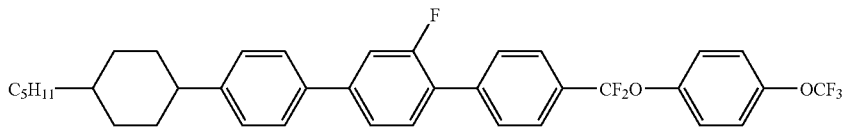
1-4-394
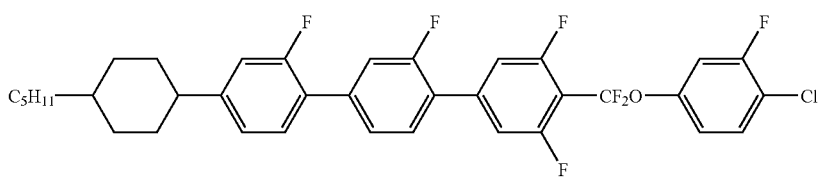
1-4-395
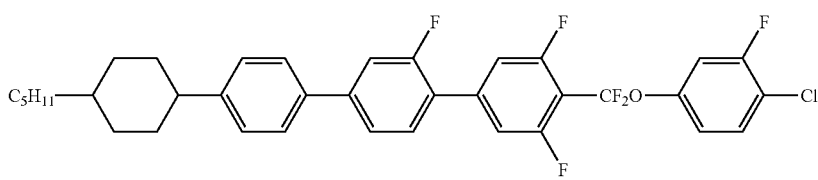
1-4-396

-continued
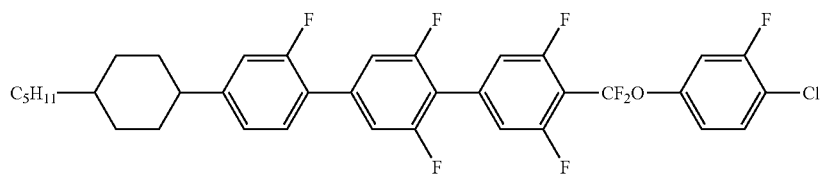
1-4-397
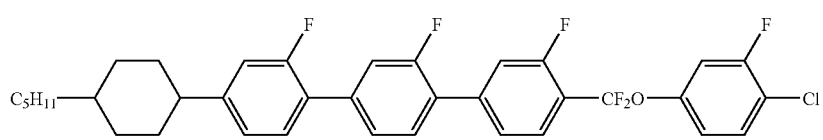
1-4-398
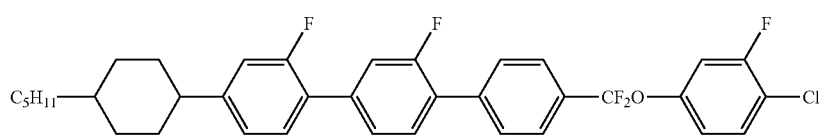
1-4-399
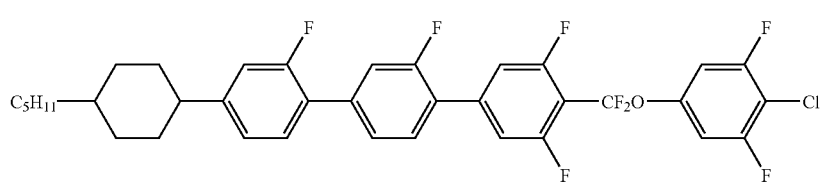
1-4-400
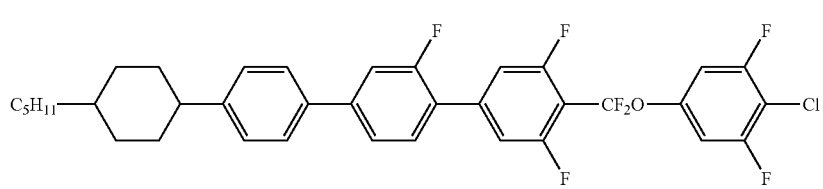
1-4-401
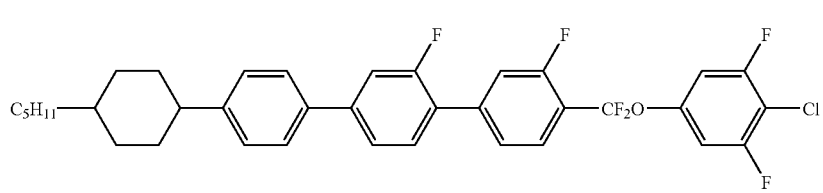
1-4-402
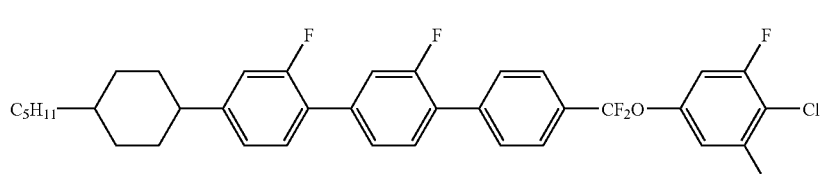
1-4-403
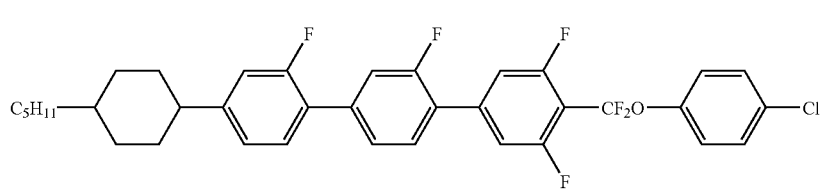
1-4-404
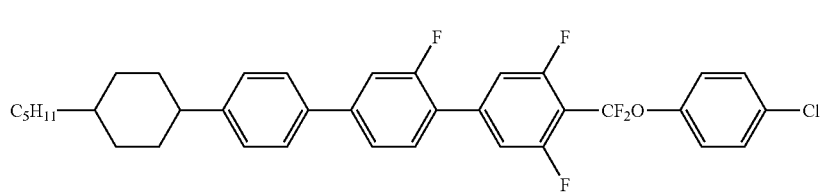
1-4-405

-continued
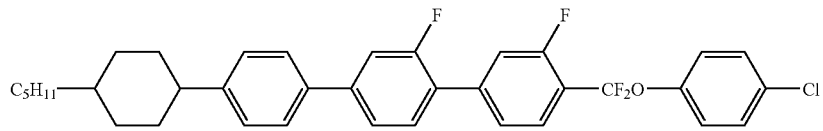
1-4-406
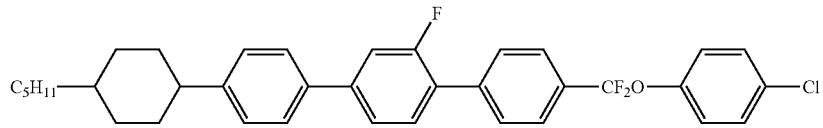
1-4-407
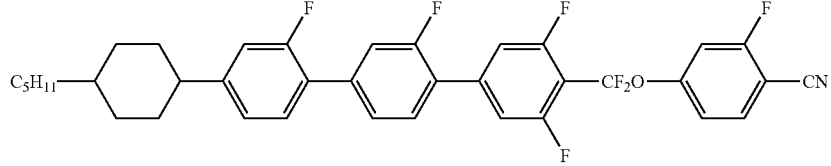
1-4-408
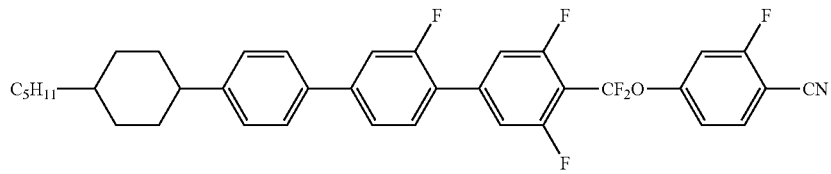
1-4-409
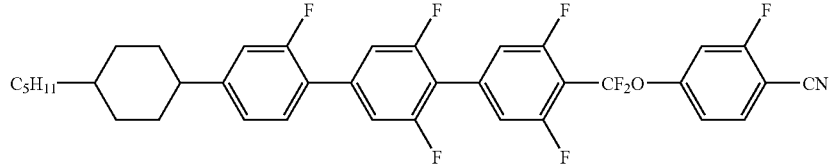
1-4-410
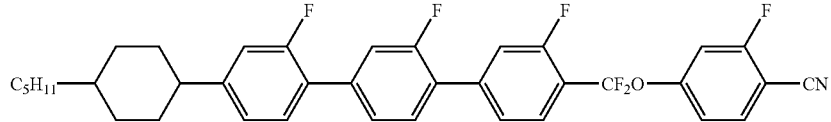
1-4-411
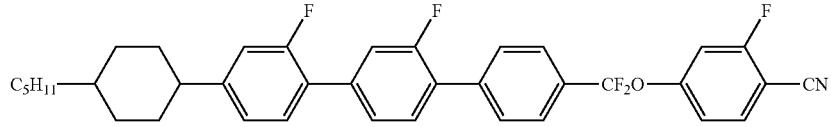
1-4-412
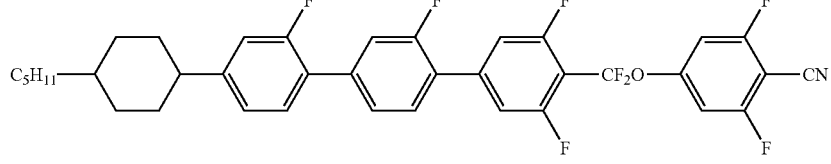
1-4-413
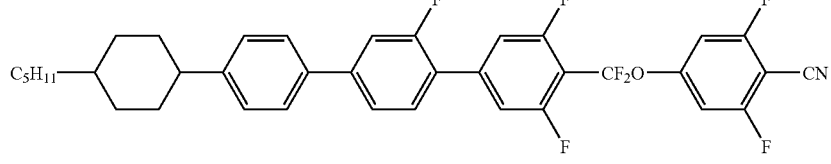
1-4-414
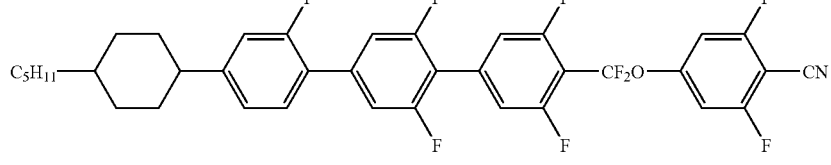
1-4-415

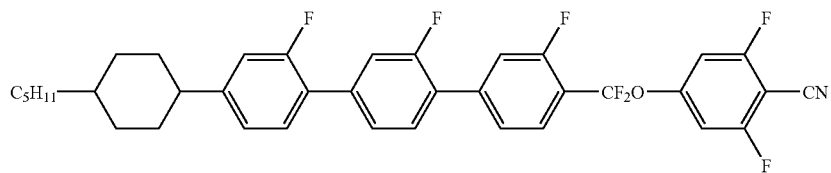
1-4-416
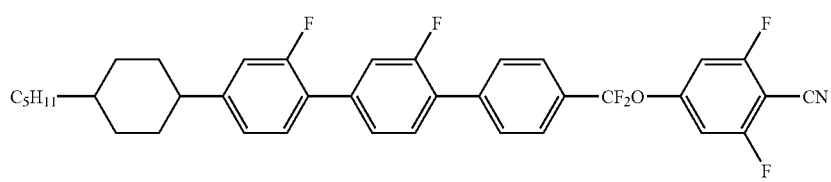
1-4-417
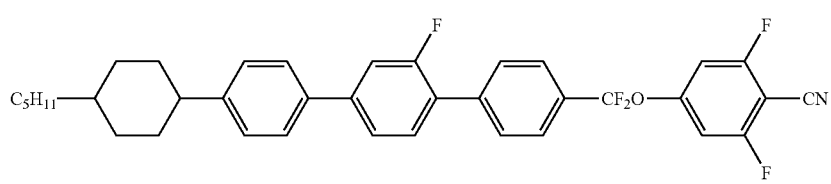
1-4-418
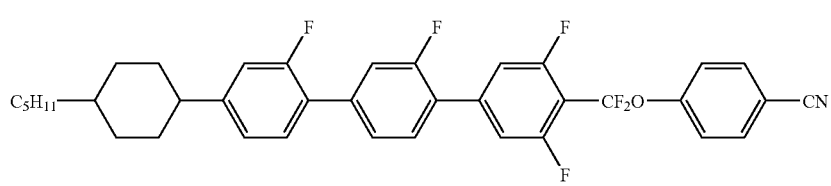
1-4-419
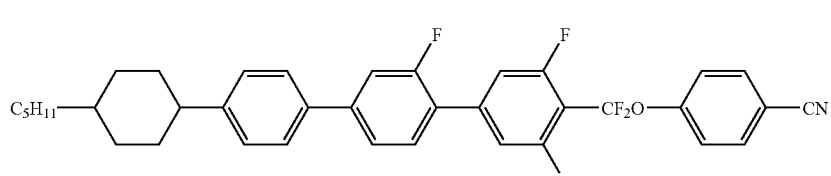
1-4-420
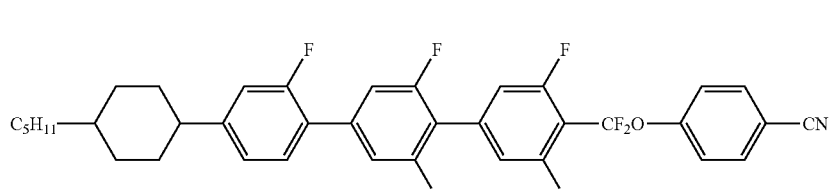
1-4-421
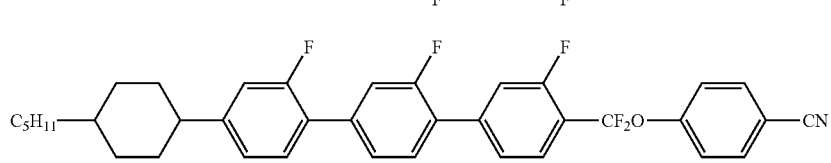
1-4-422
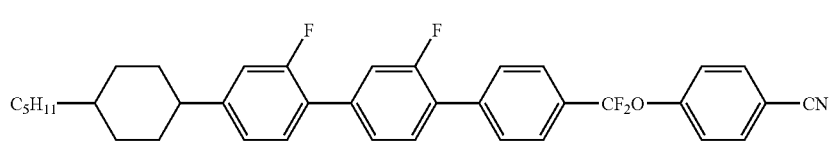
1-4-423
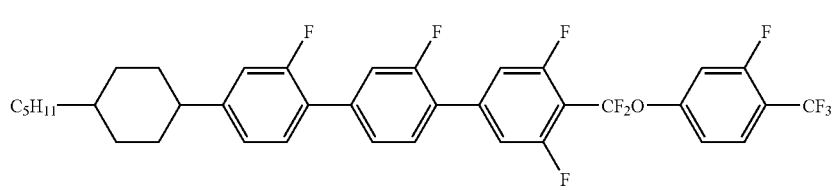
1-4-424

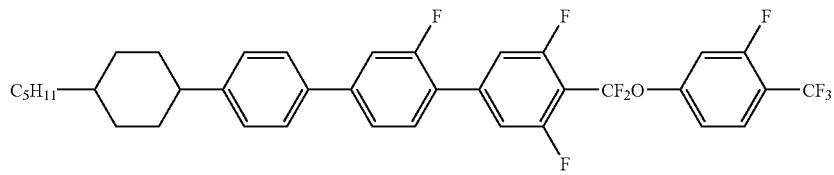 1-4-425
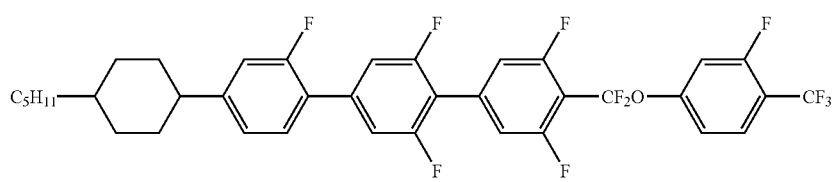 1-4-426
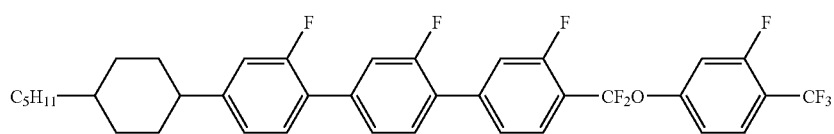 1-4-427
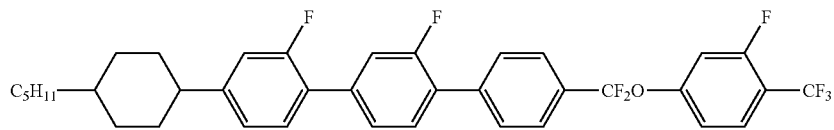 1-4-428
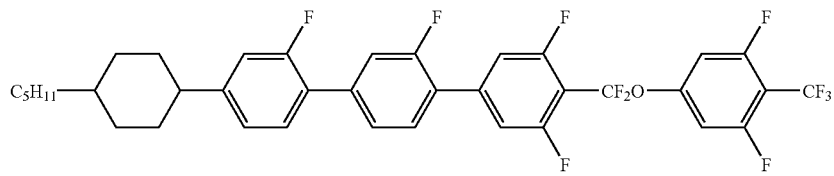 1-4-429
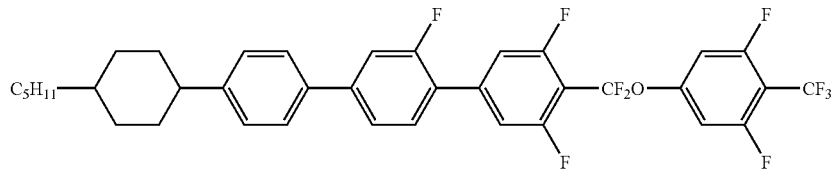 1-4-430
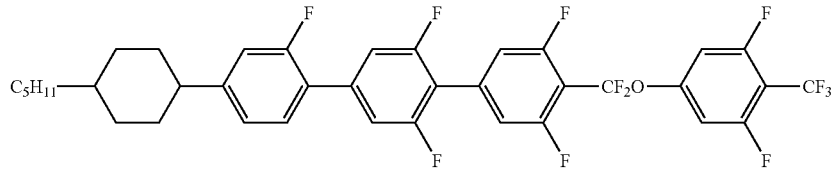 1-4-431
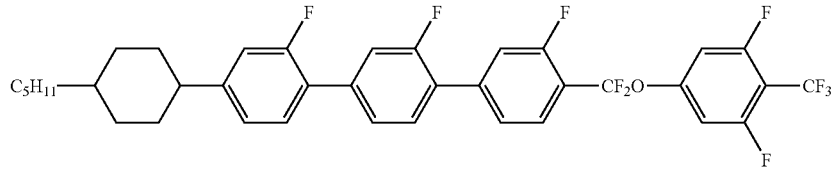 1-4-432
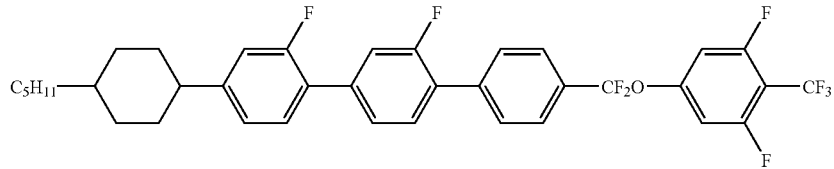 1-4-433

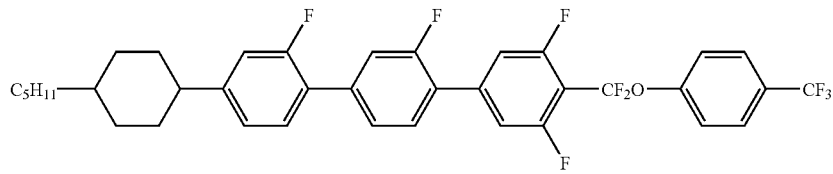
1-4-434
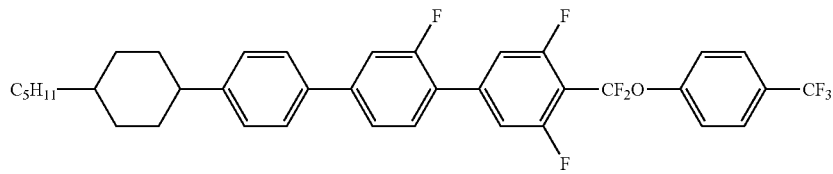
1-4-435
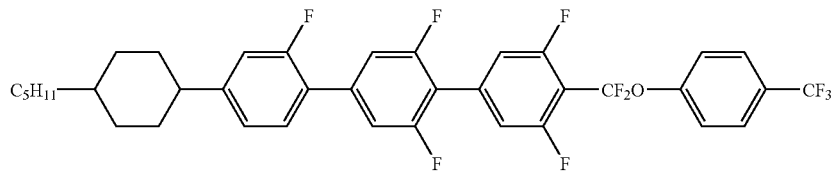
1-4-436
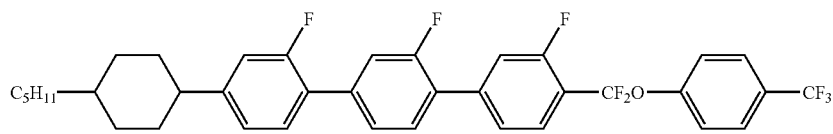
1-4-437
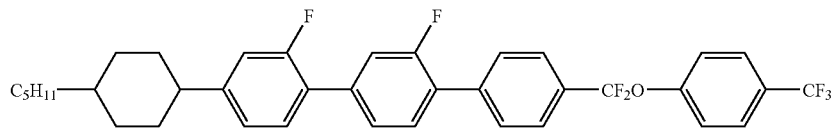
1-4-438
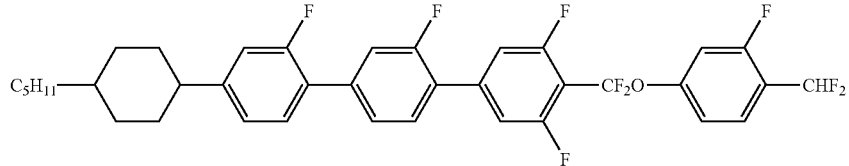
1-4-439
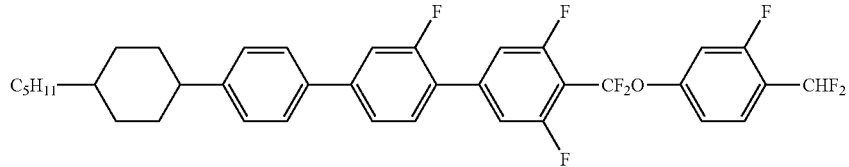
1-4-440
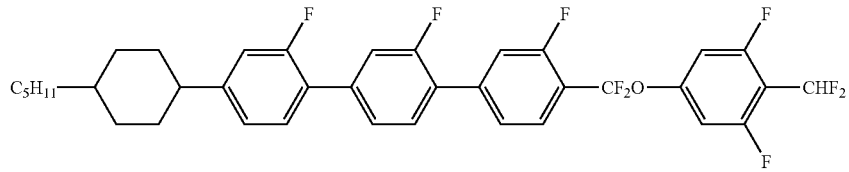
1-4-441
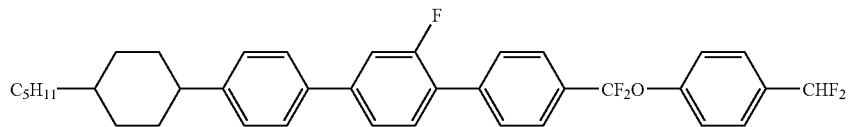
1-4-442

-continued
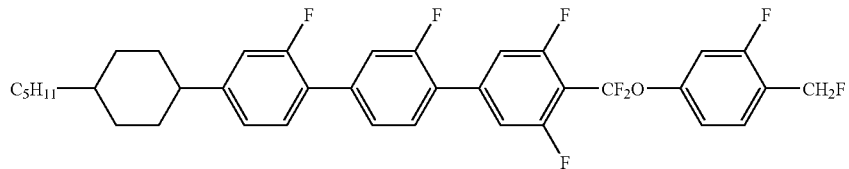
1-4-443
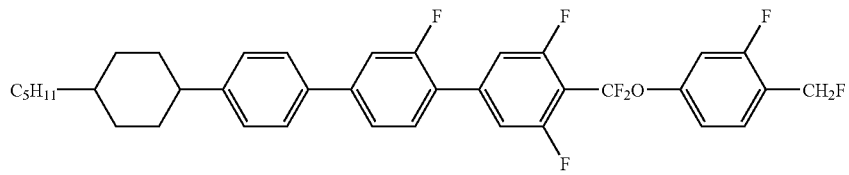
1-4-444
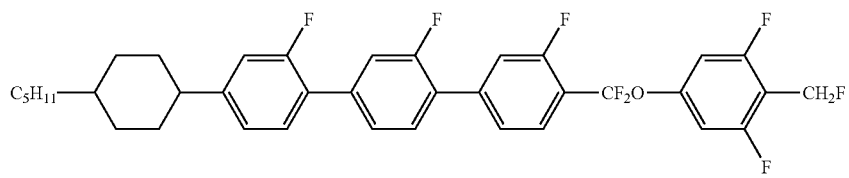
1-4-445
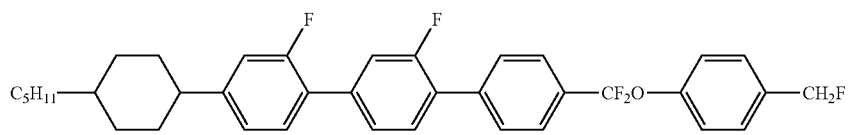
1-4-446
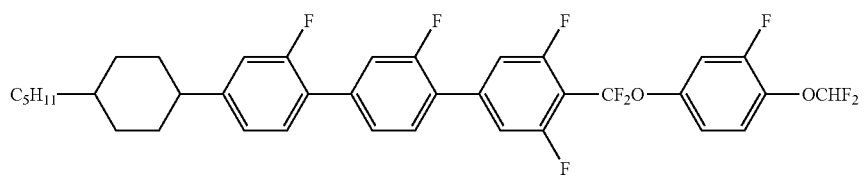
1-4-447
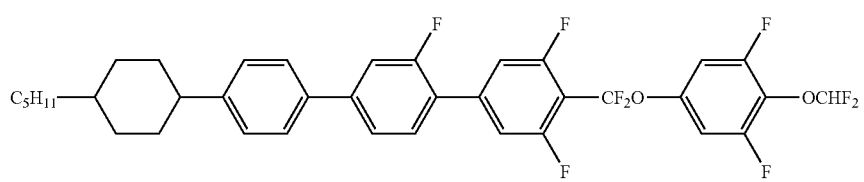
1-4-448
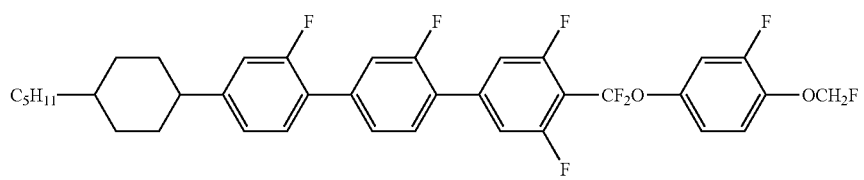
1-4-449
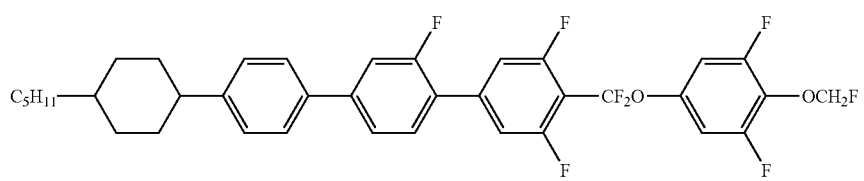
1-4-450
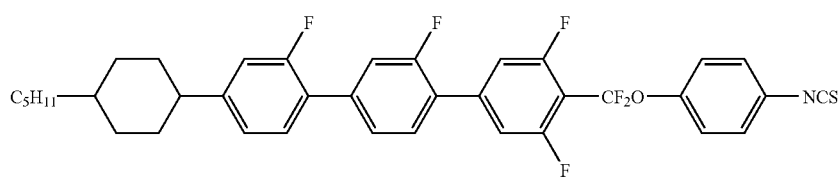
1-4-451

-continued
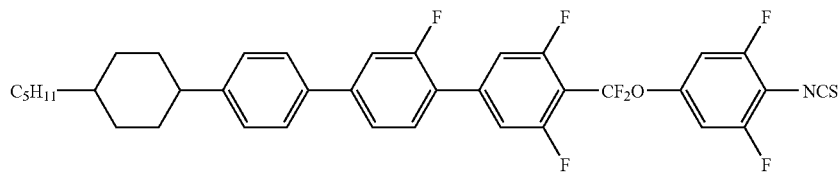
1-4-452
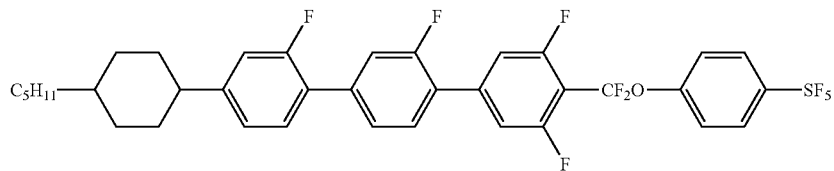
1-4-453
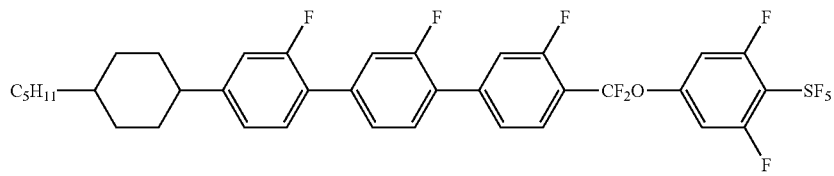
1-4-454
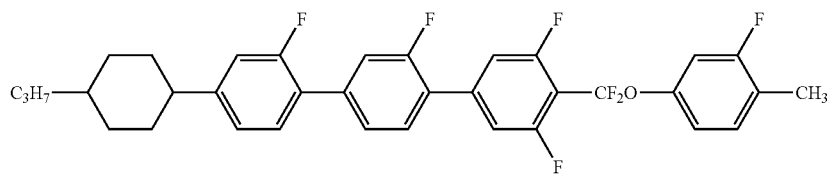
1-4-455
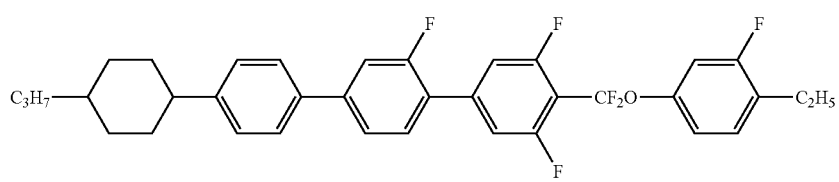
1-4-456
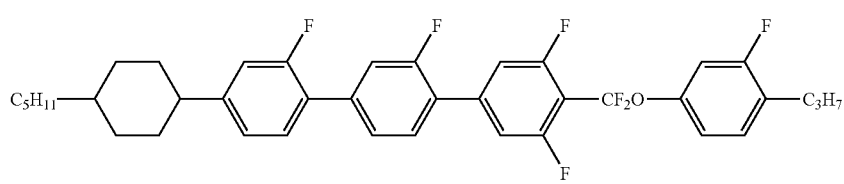
1-4-457
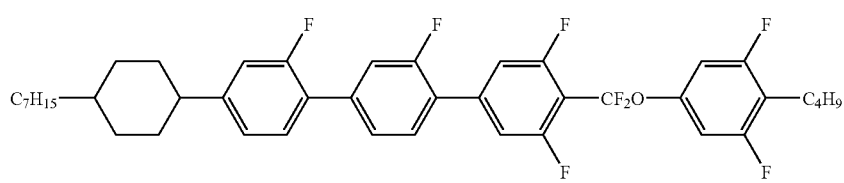
1-4-458
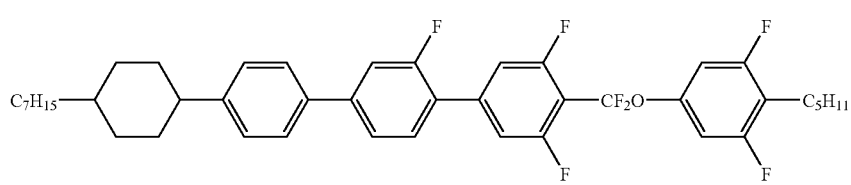
1-4-459
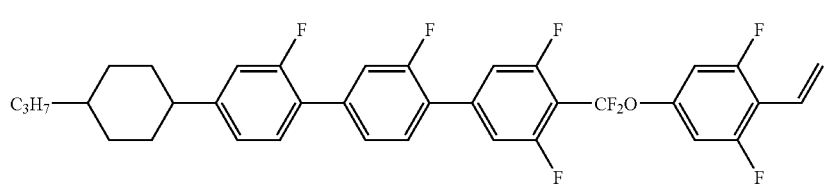
1-4-460

-continued
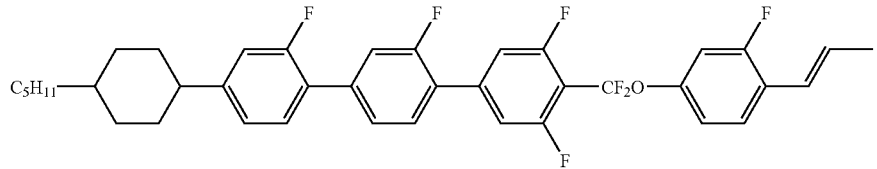 1-4-461
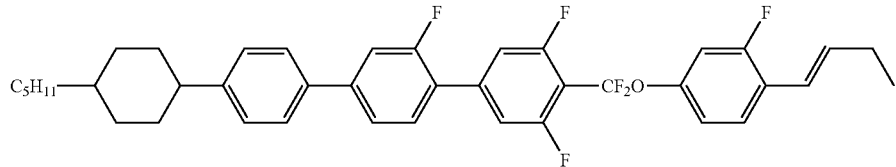 1-4-462
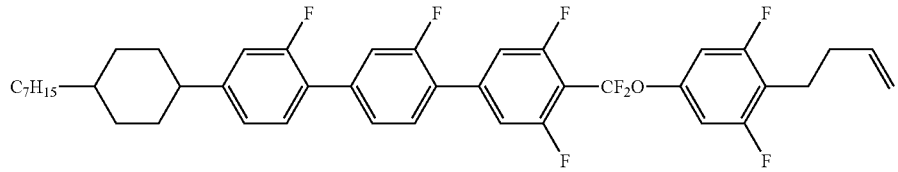 1-4-463
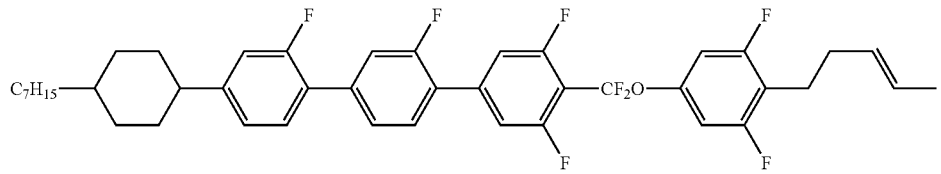 1-4-464
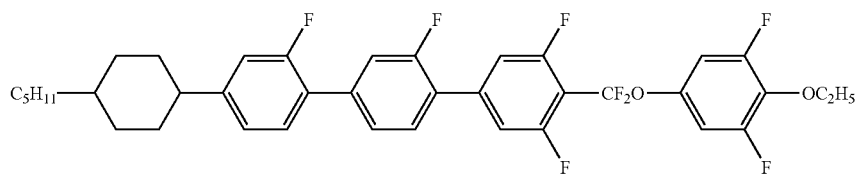 1-4-465
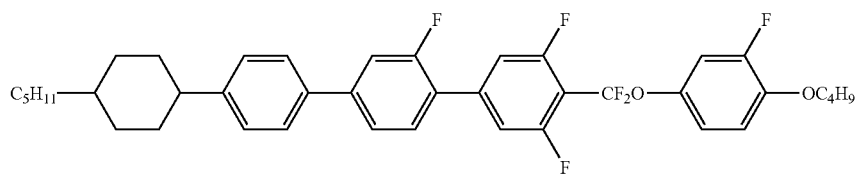 1-4-466
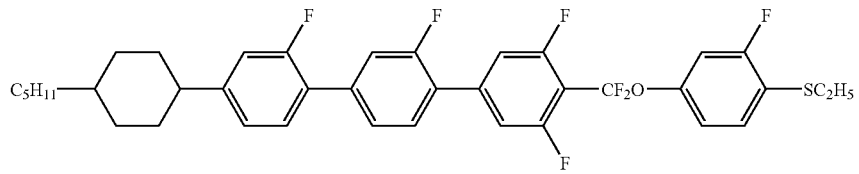 1-4-467
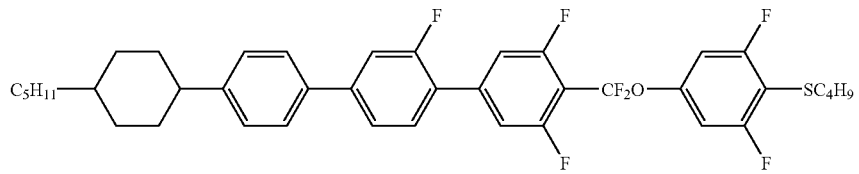 1-4-468
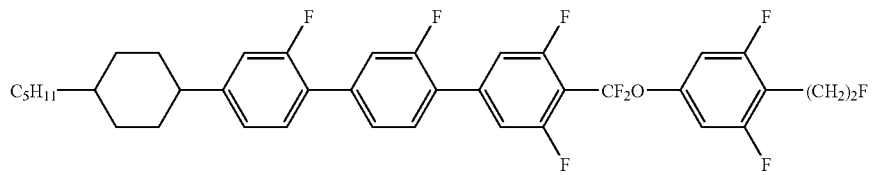 1-4-469

-continued
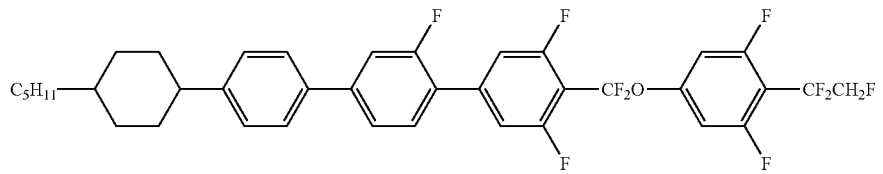 1-4-470
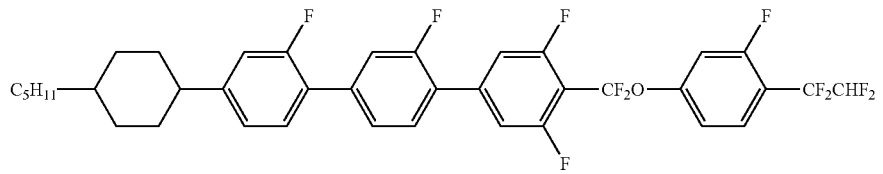 1-4-471
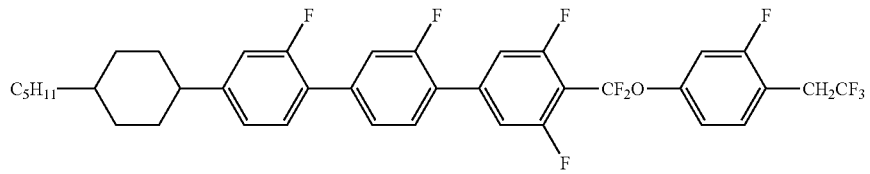 1-4-472
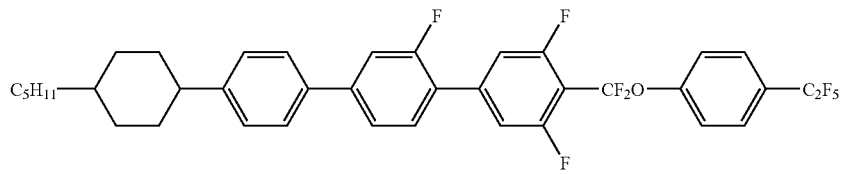 1-4-473
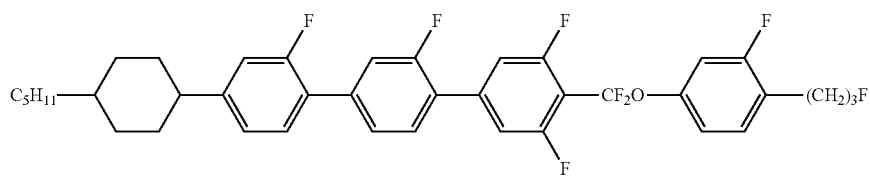 1-4-474
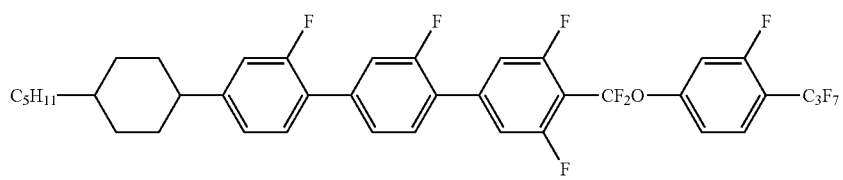 1-4-475
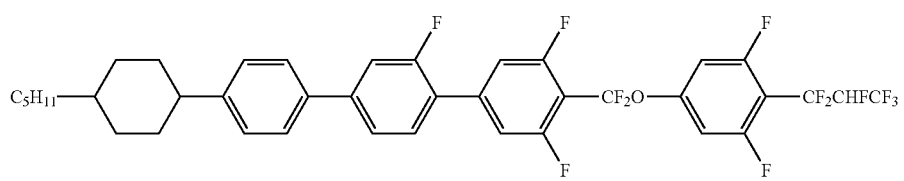 1-4-476
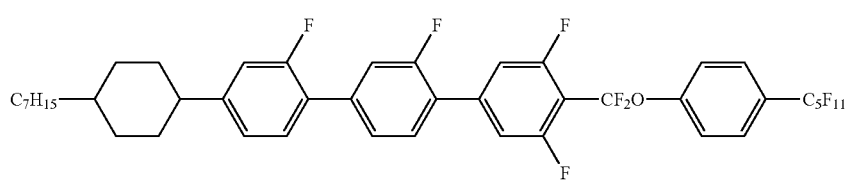 1-4-477
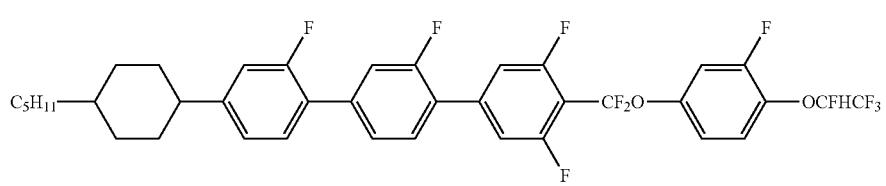 1-4-478

-continued
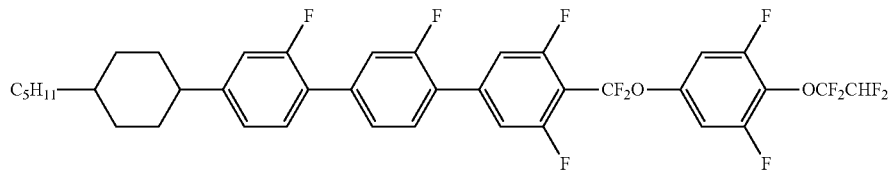
1-4-479
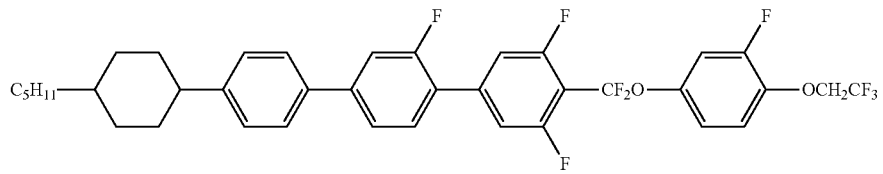
1-4-480
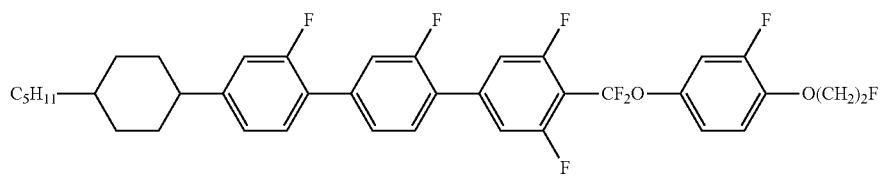
1-4-481
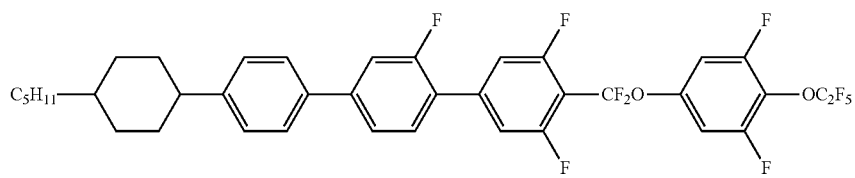
1-4-482
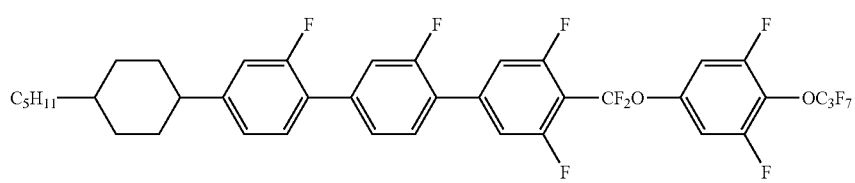
1-4-483
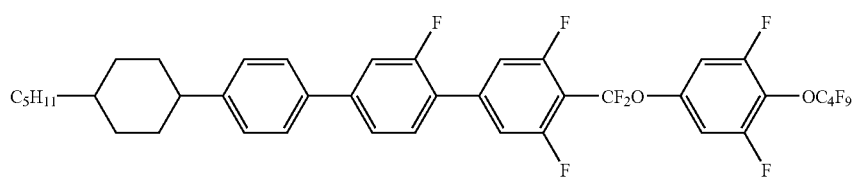
1-4-484
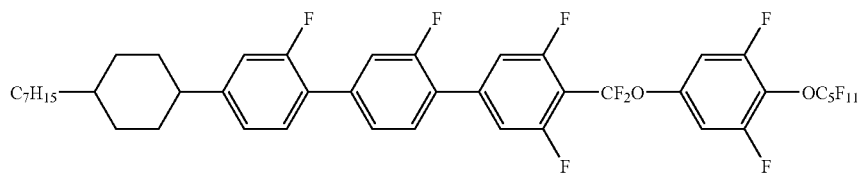
1-4-485
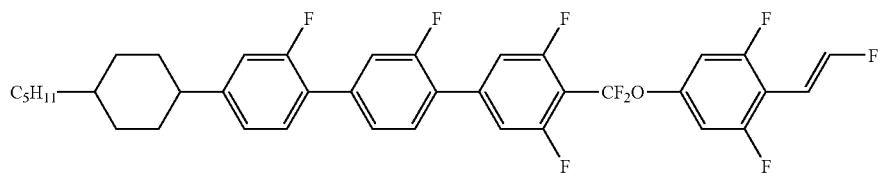
1-4-486
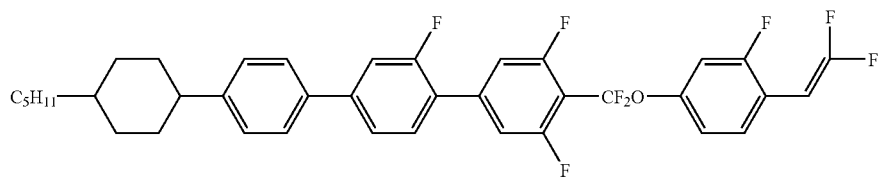
1-4-487

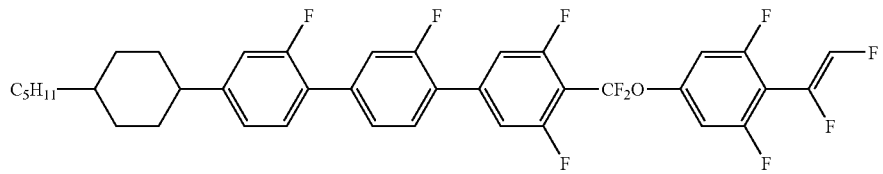
1-4-488
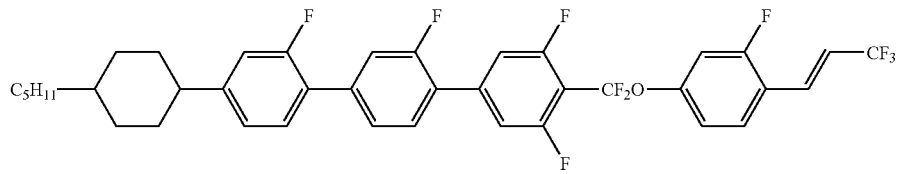
1-4-489
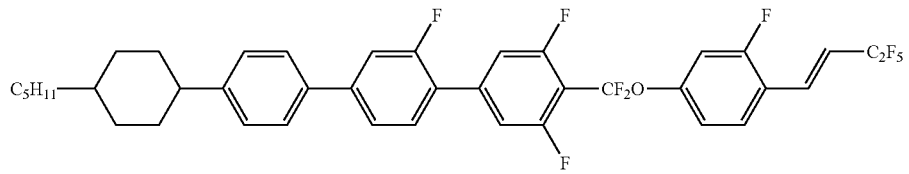
1-4-490
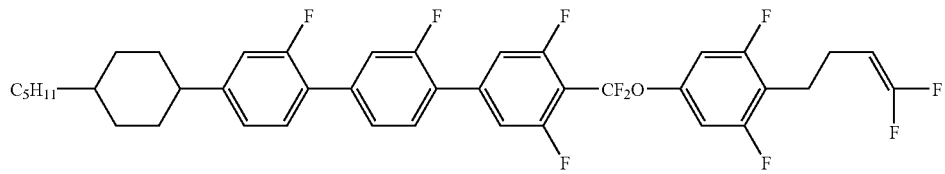
1-4-491
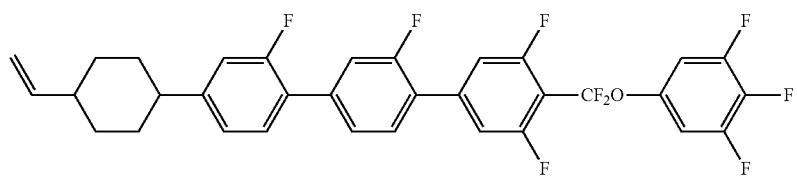
1-4-492
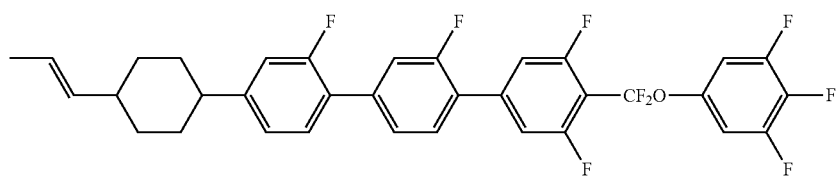
1-4-493
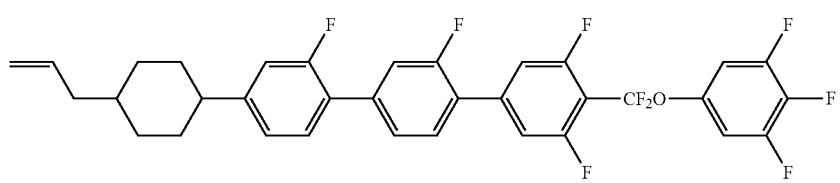
1-4-494
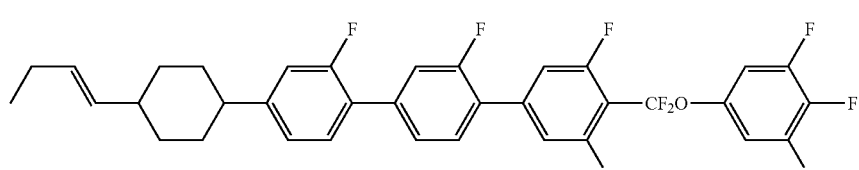
1-4-495
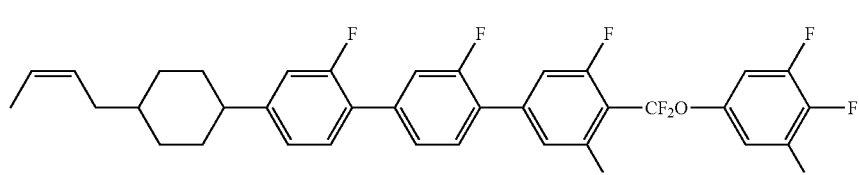
1-4-496

-continued
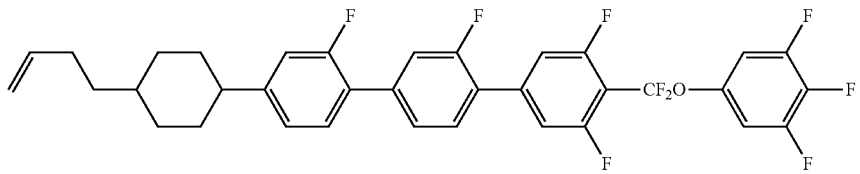
1-4-497
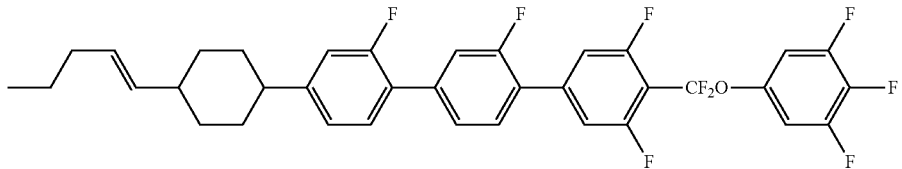
1-4-498
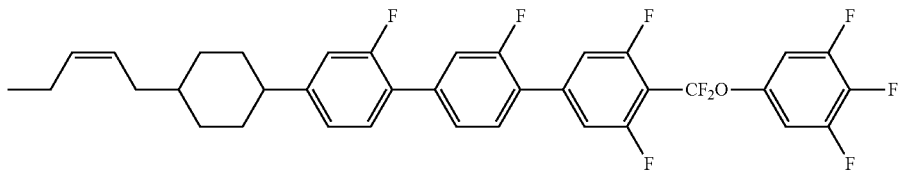
1-4-499
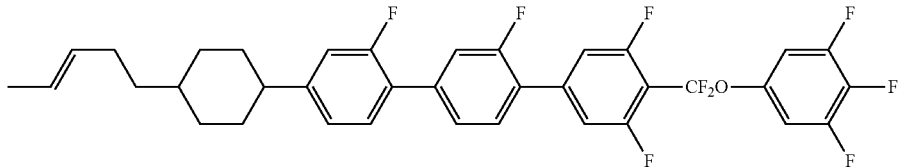
1-4-500
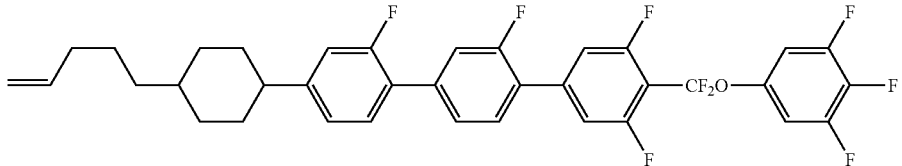
1-4-501
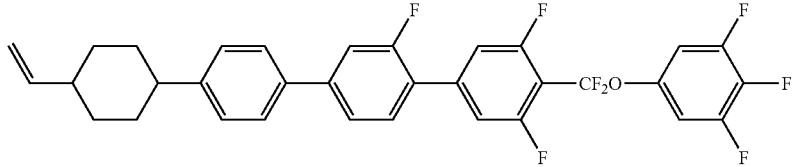
1-4-502
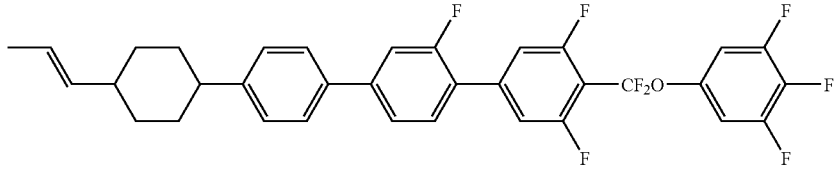
1-4-503
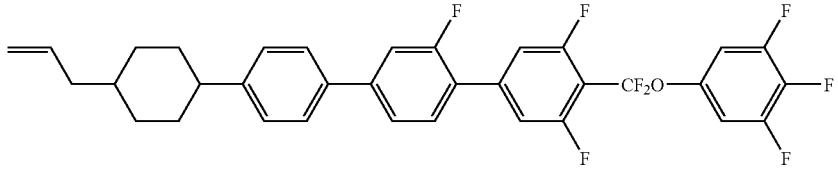
1-4-504
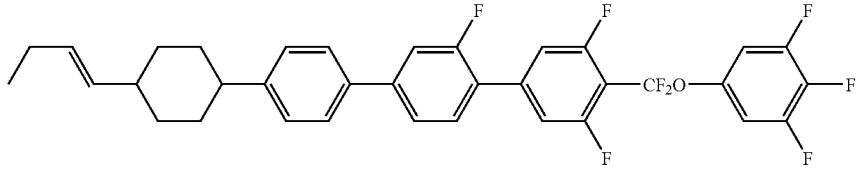
1-4-505

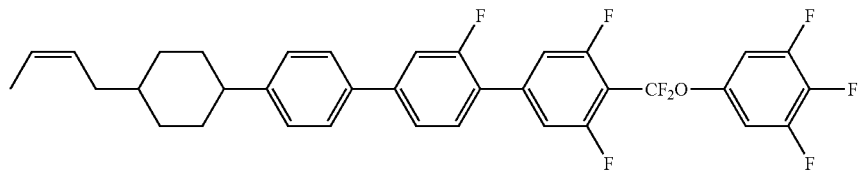
1-4-506
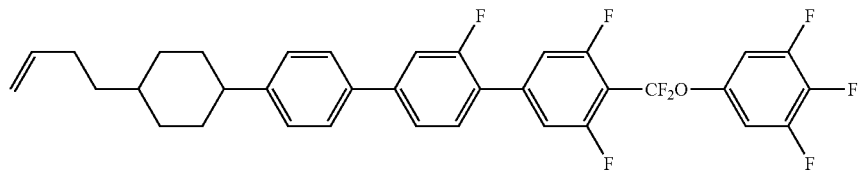
1-4-507
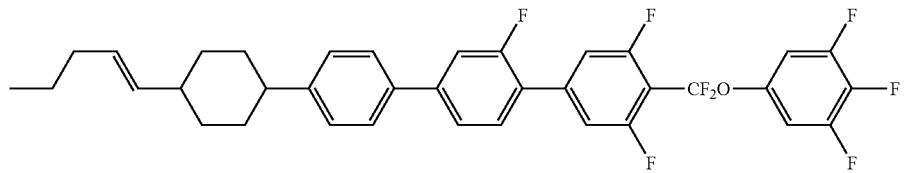
1-4-508
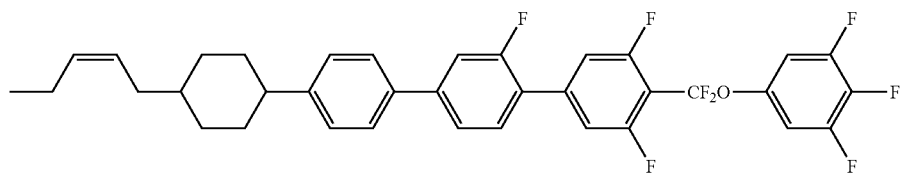
1-4-509
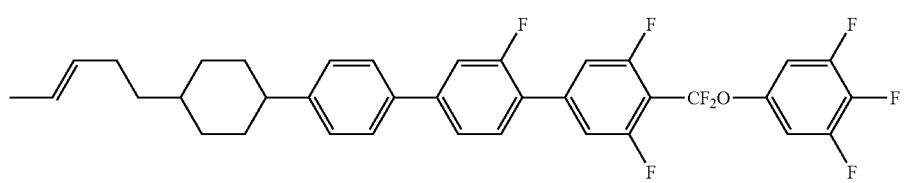
1-4-510
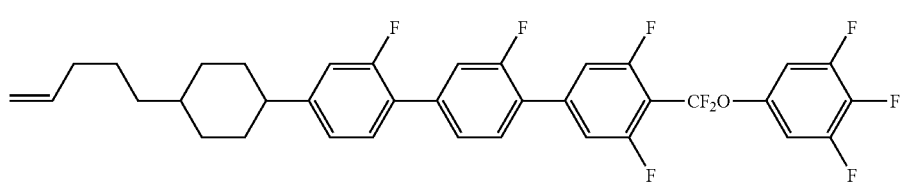
1-4-511
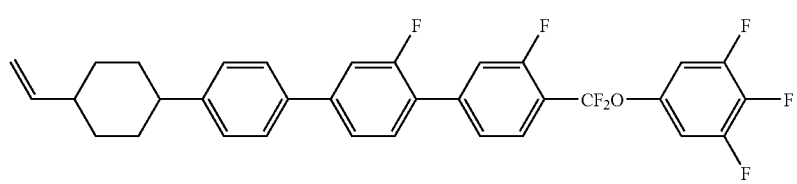
1-4-512
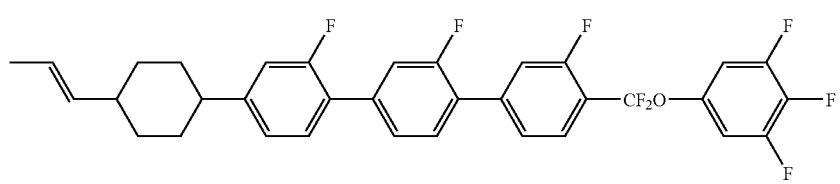
1-4-513
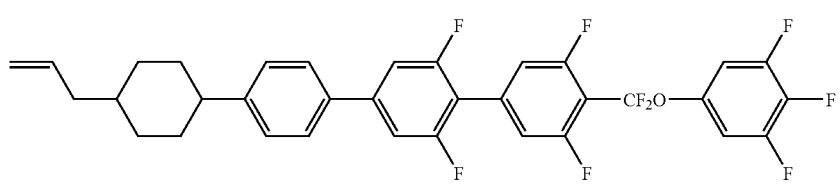
1-4-514

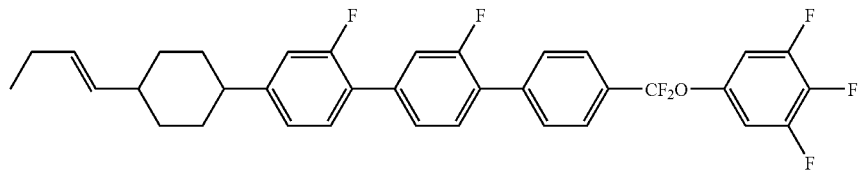 1-4-515
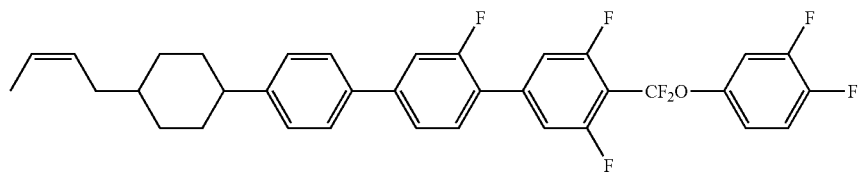 1-4-516
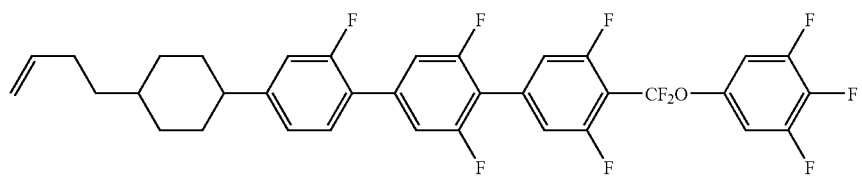 1-4-517
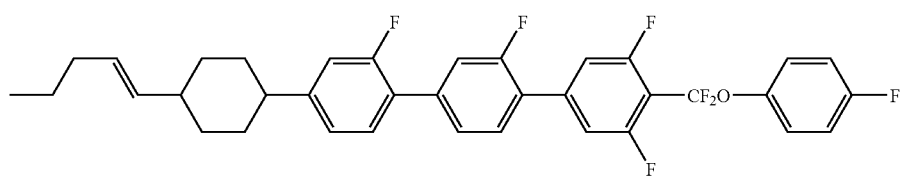 1-4-518
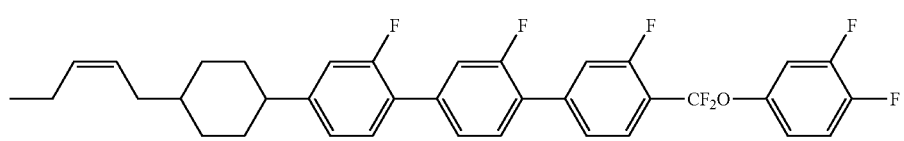 1-4-519
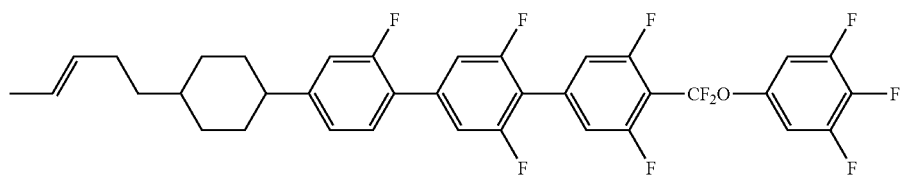 1-4-520
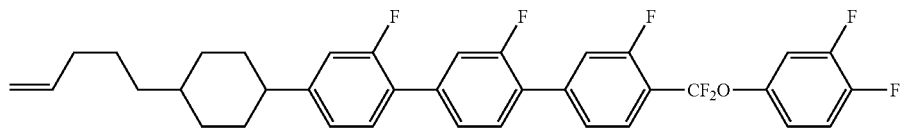 1-4-521
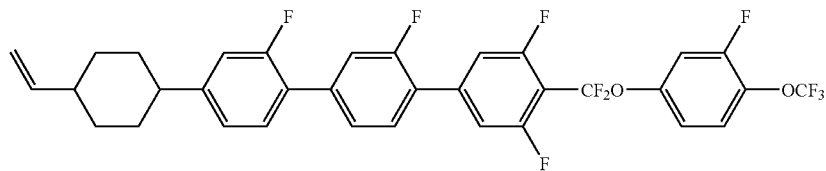 1-4-522
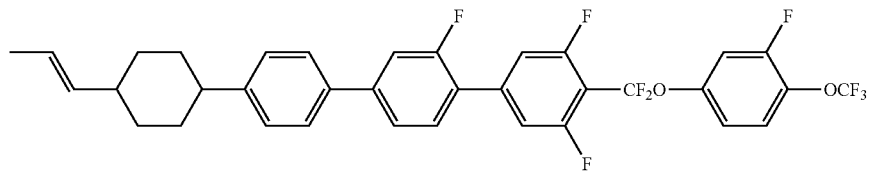 1-4-523

-continued
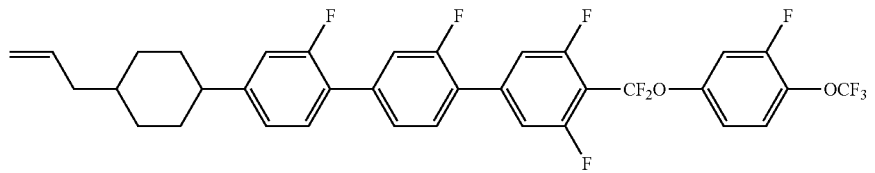
1-4-524
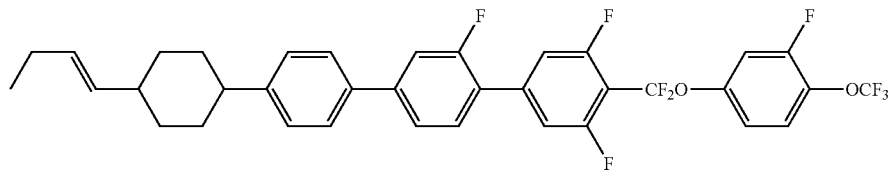
1-4-525
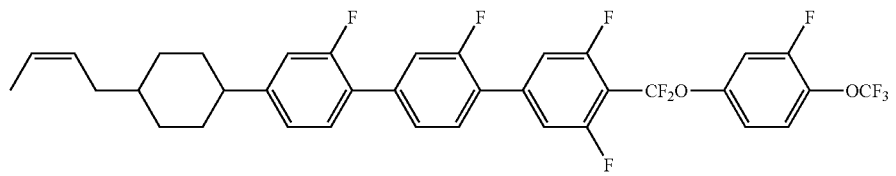
1-4-526
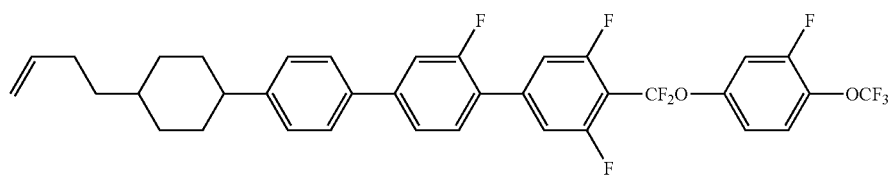
1-4-527
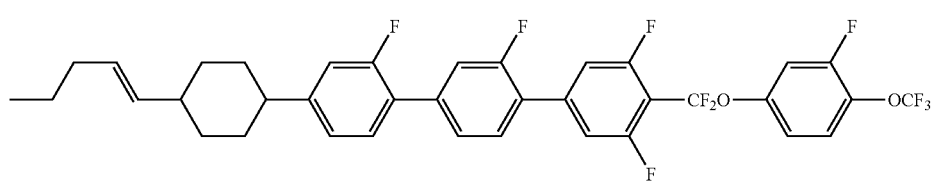
1-4-528
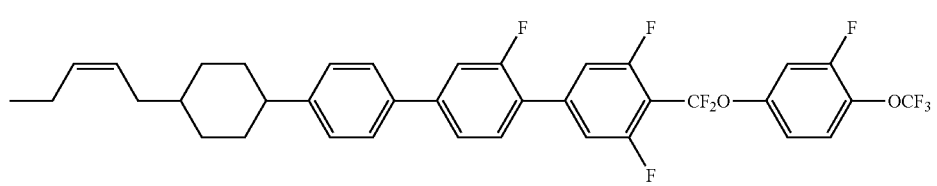
1-4-529
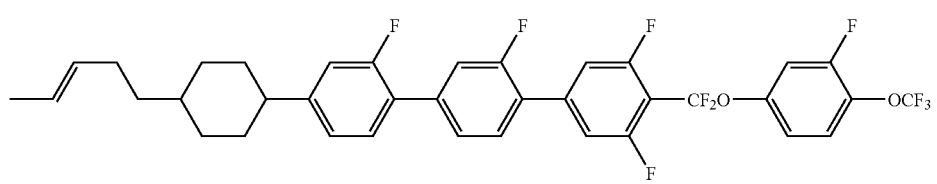
1-4-530
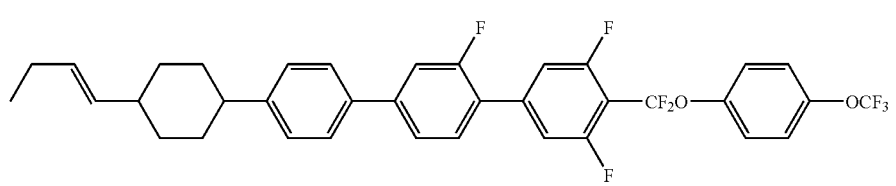
1-4-531
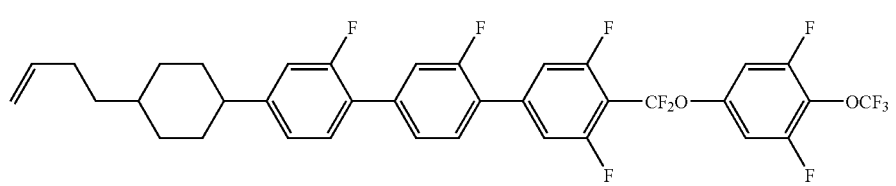
1-4-532

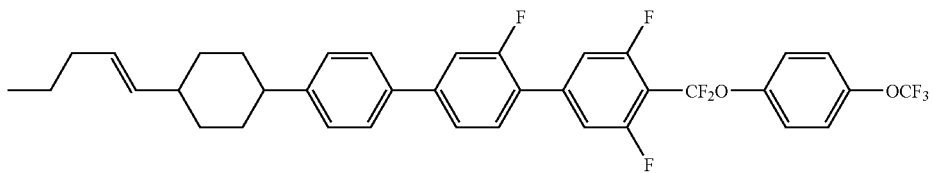
1-4-533
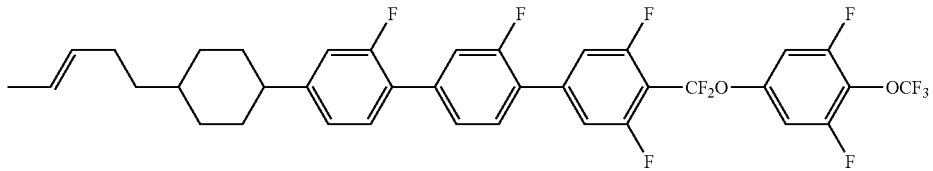
1-4-534
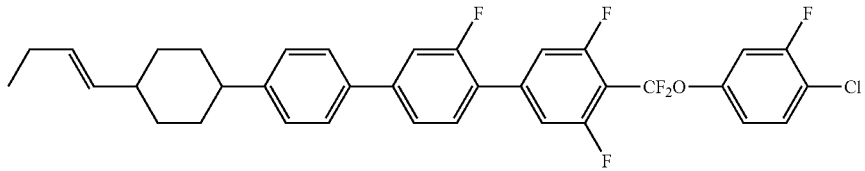
1-4-535
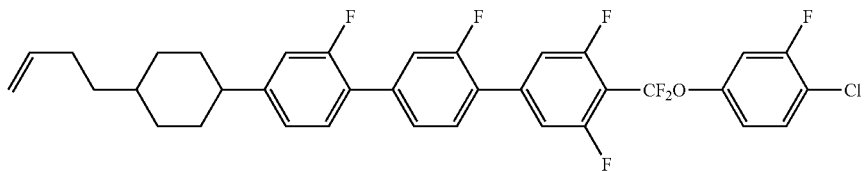
1-4-536
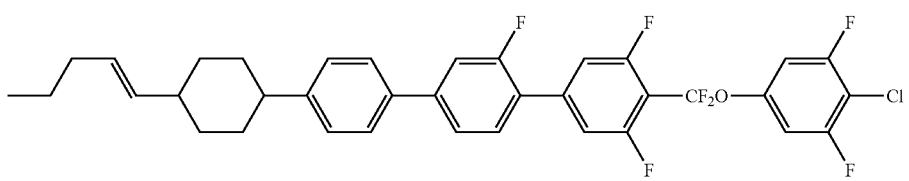
1-4-537
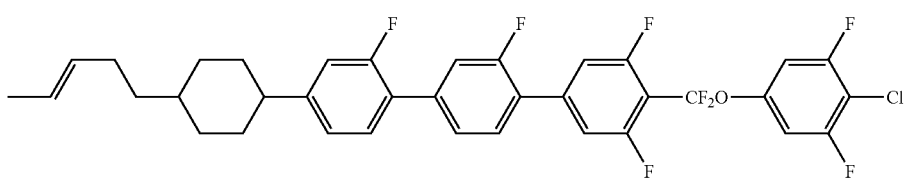
1-4-538
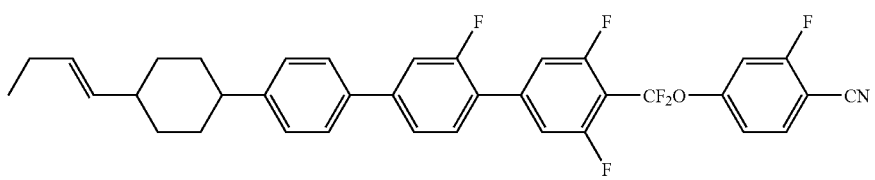
1-4-539
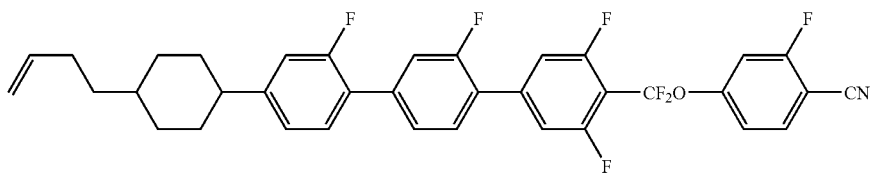
1-4-540
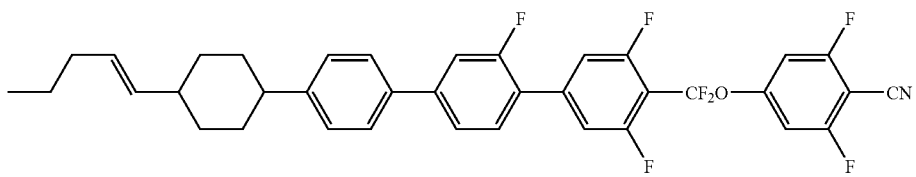
1-4-541

1-4-542
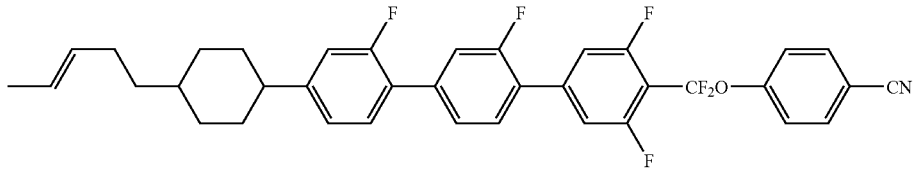
1-4-543
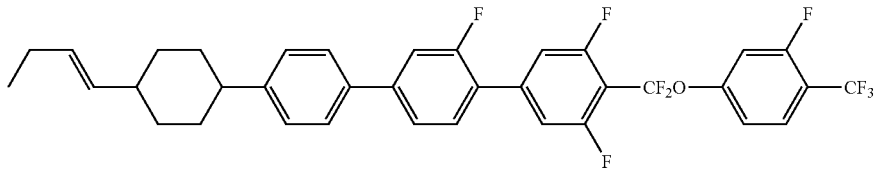
1-4-544
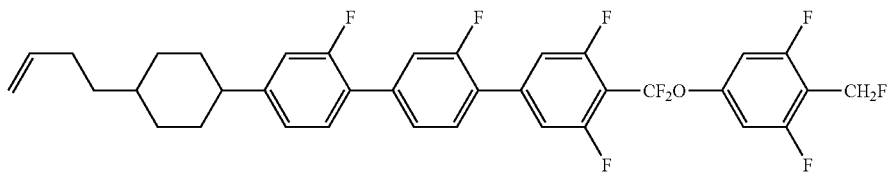
1-4-545
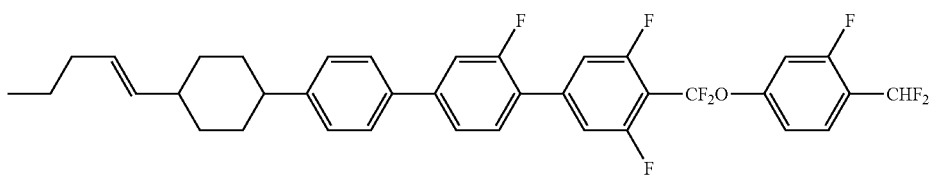
1-4-546
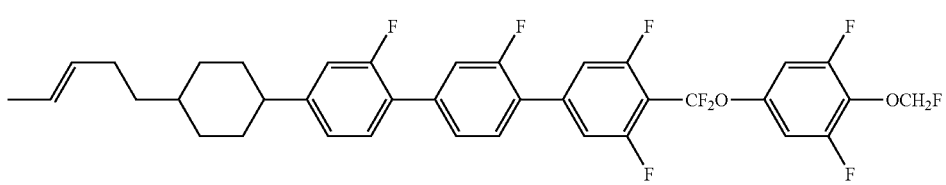
1-4-547
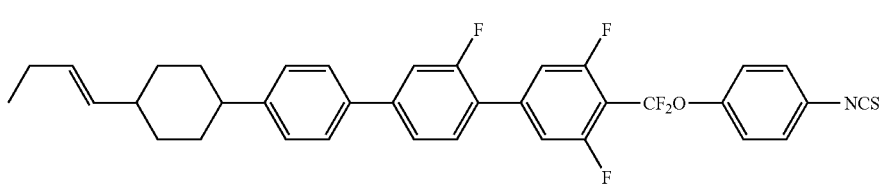
1-4-548
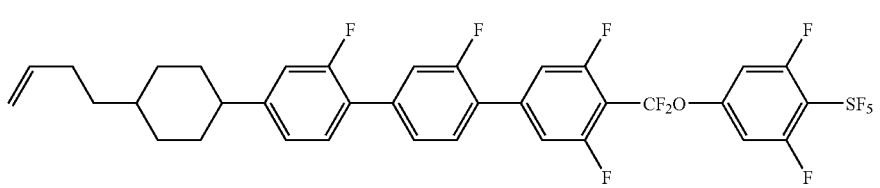
1-4-549
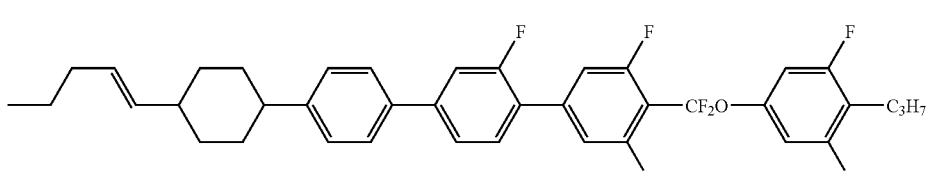
1-4-550
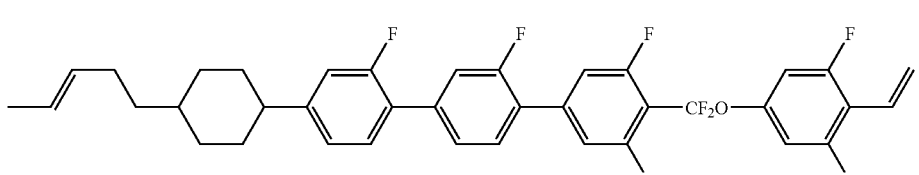

-continued
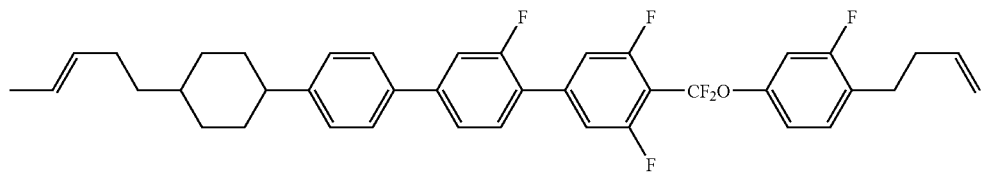
1-4-551
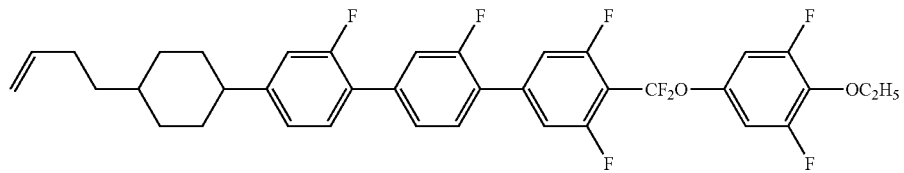
1-4-552
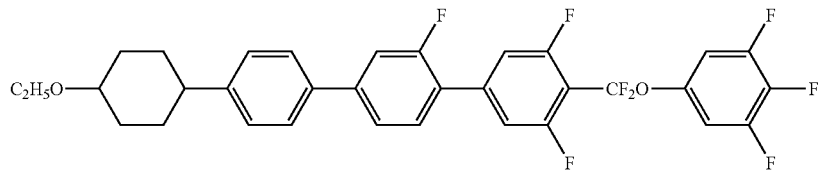
1-4-553
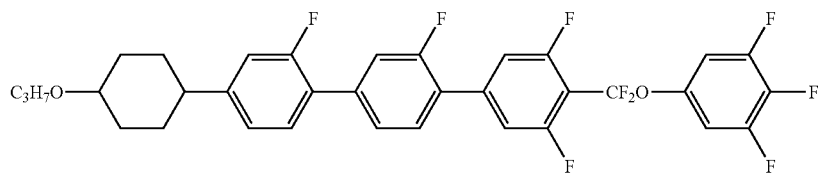
1-4-554
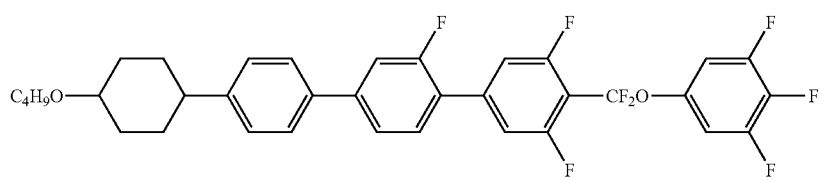
1-4-555
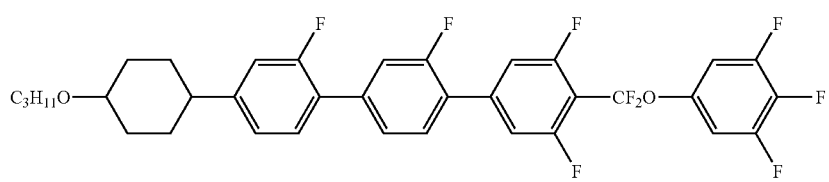
1-4-556
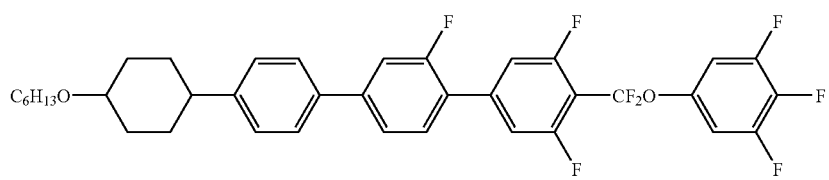
1-4-557
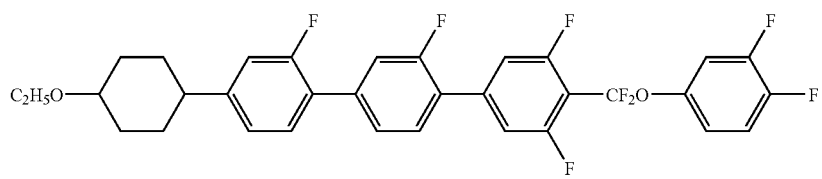
1-4-558
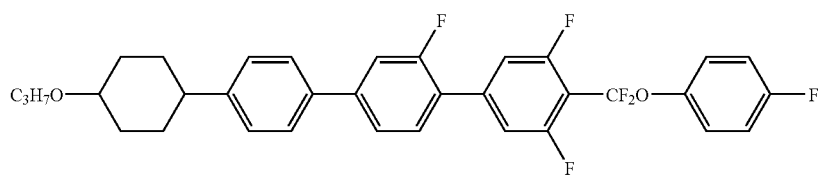
1-4-559

-continued
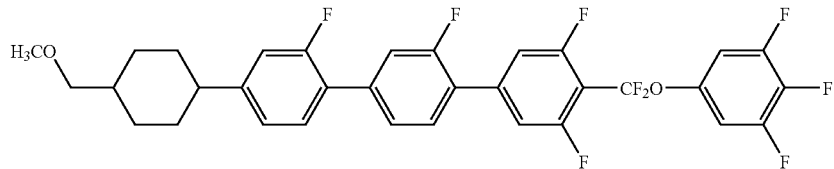
1-4-560
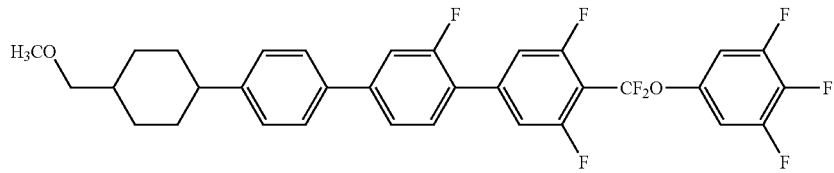
1-4-561
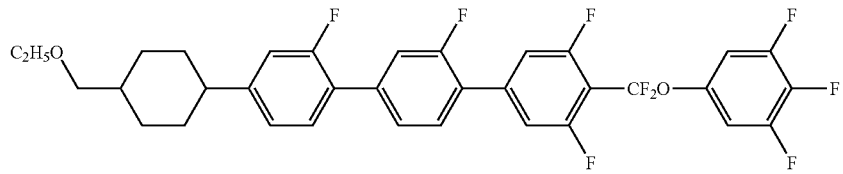
1-4-562
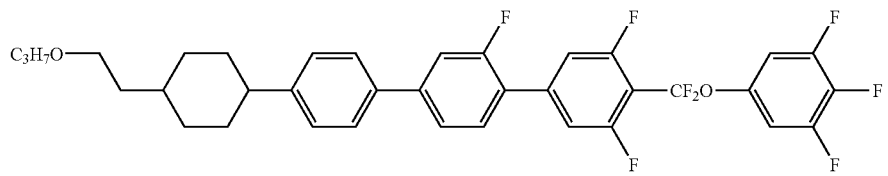
1-4-563
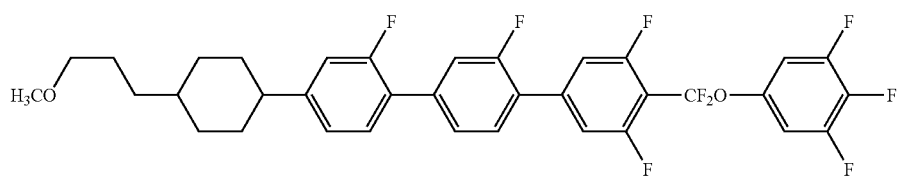
1-4-564
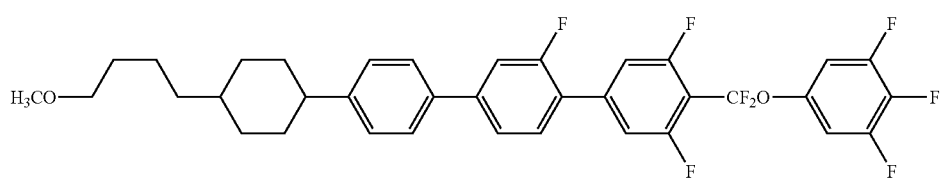
1-4-565
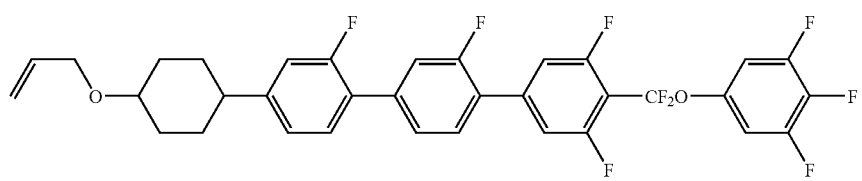
1-4-566
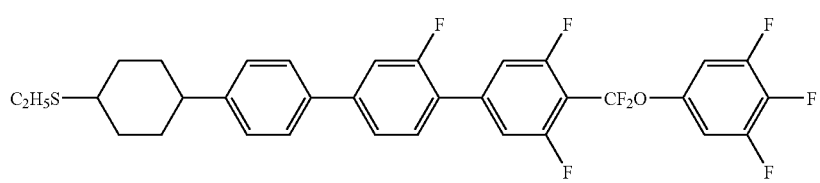
1-4-567
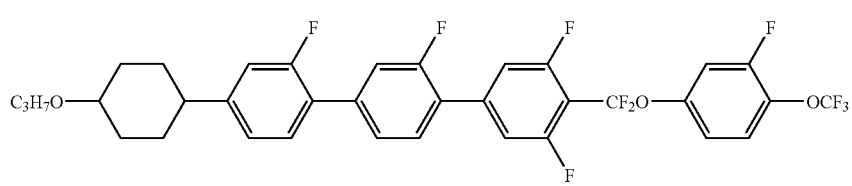
1-4-568

-continued
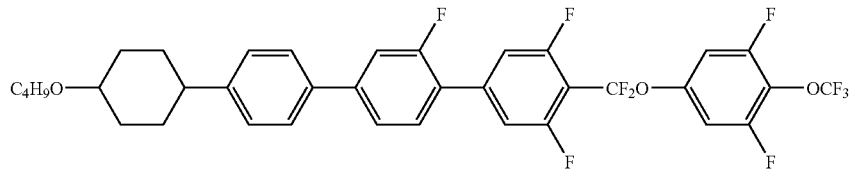 1-4-569
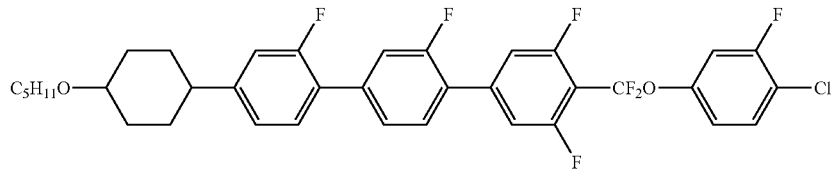 1-4-570
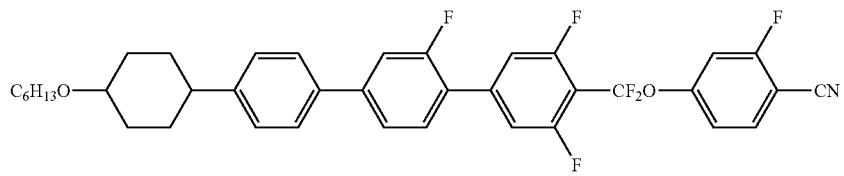 1-4-571
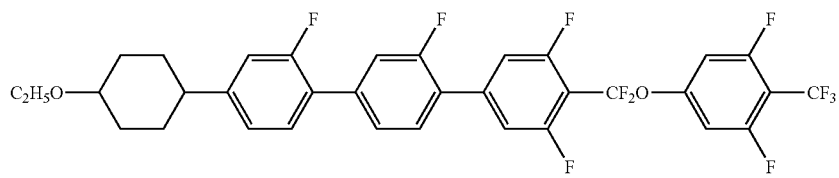 1-4-572
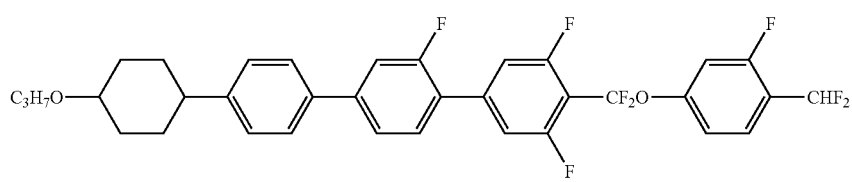 1-4-573
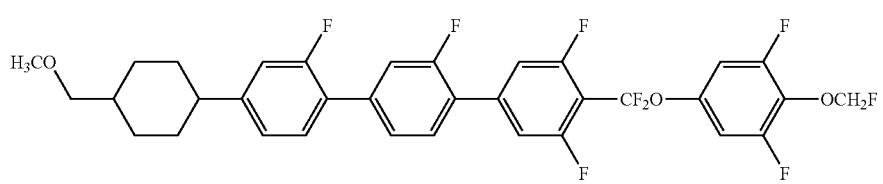 1-4-574
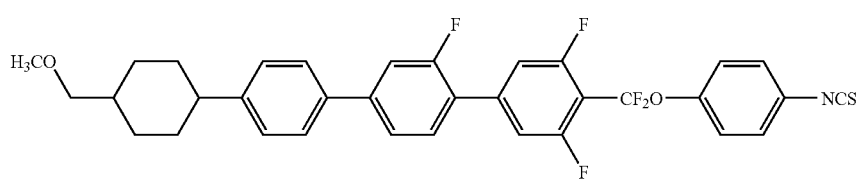 1-4-575
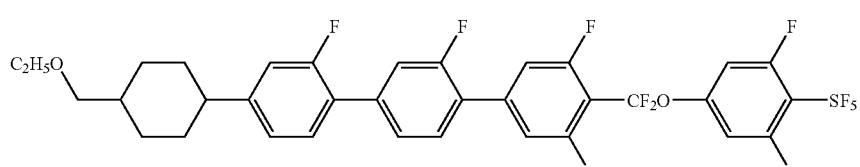 1-4-576
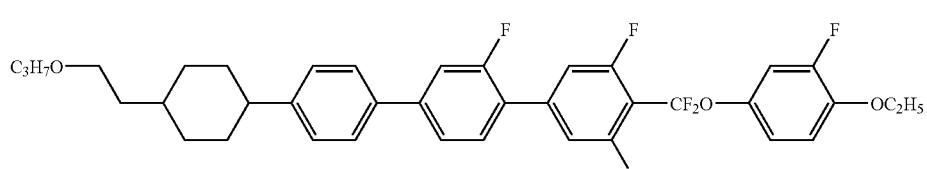 1-4-577

-continued
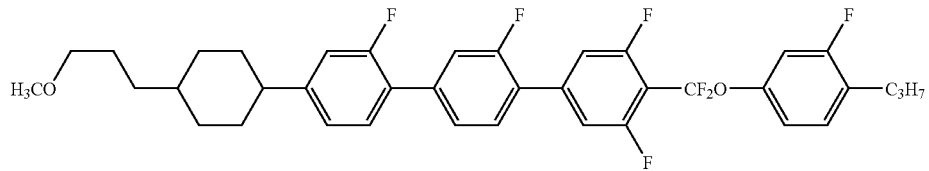
1-4-578
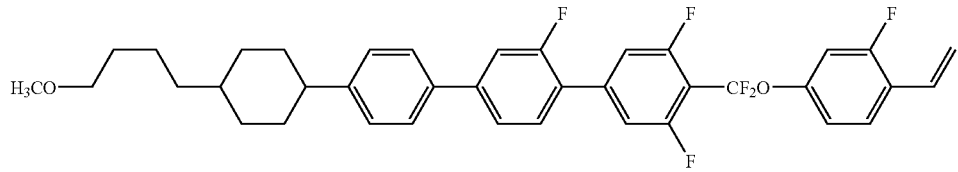
1-4-579
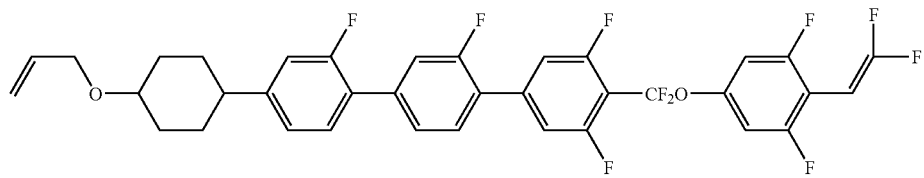
1-4-580
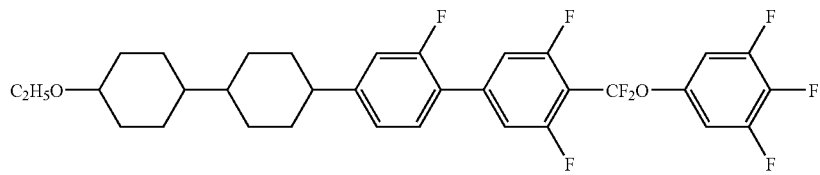
1-4-581
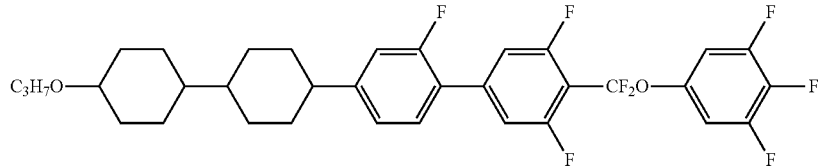
1-4-582
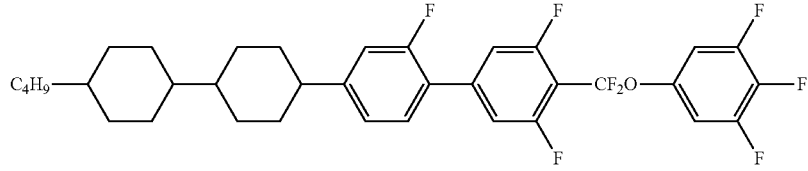
1-4-583
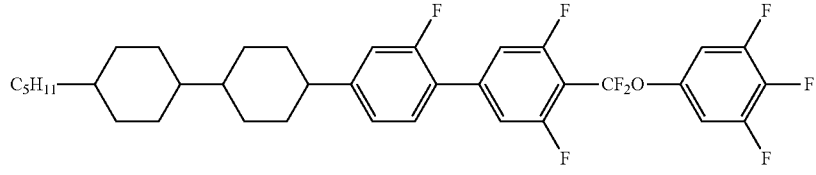
1-4-584
$T_{NI} = 189°$ C., $\Delta n = 0.157$, $\Delta \varepsilon = 21.7$
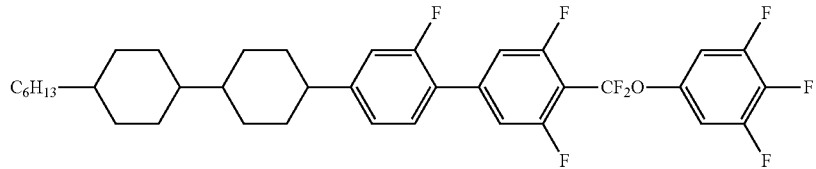
1-4-585

-continued
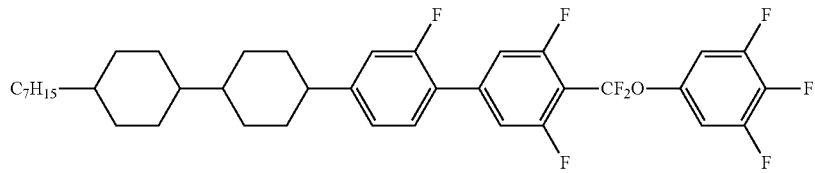
1-4-586
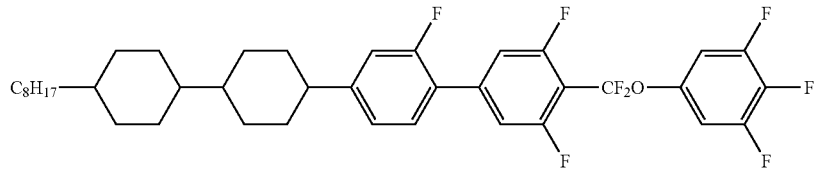
1-4-587
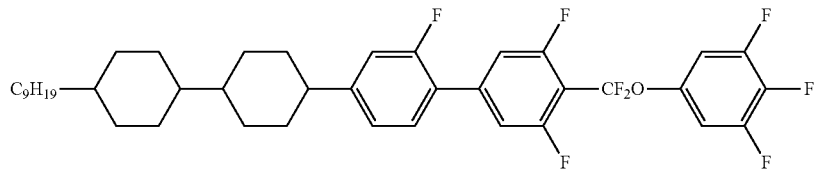
1-4-588
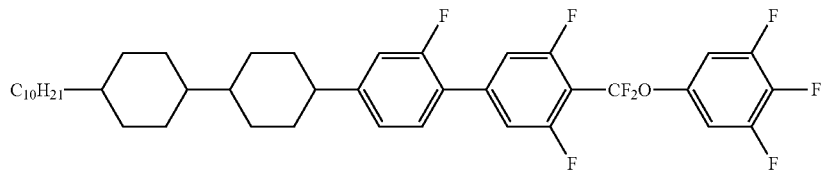
1-4-589
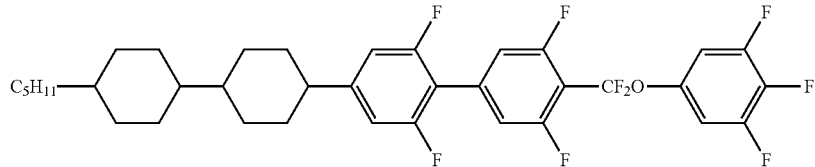
1-4-590
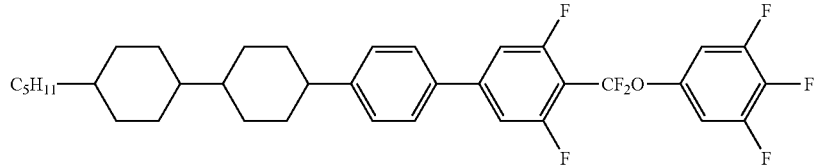
1-4-591
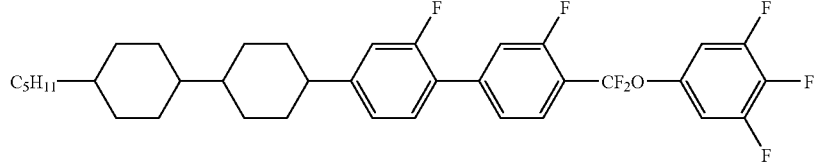
1-4-592
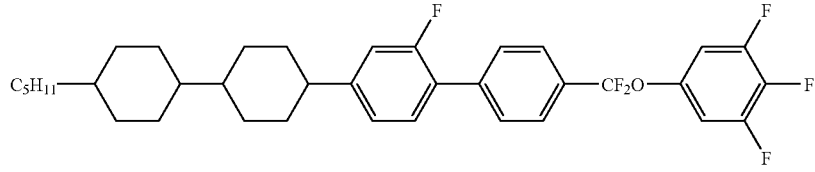
1-4-593

-continued
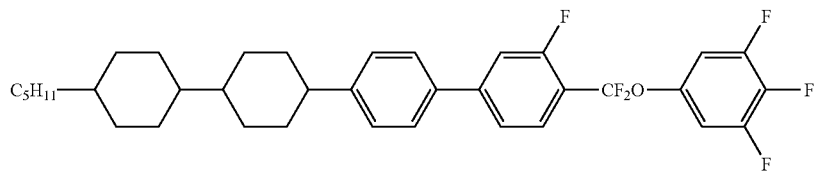
1-4-594
$T_{NI}$ = 220° C., Δn = 0.170, Δε = 6.93
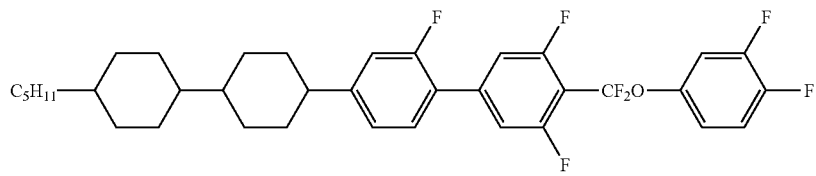
1-4-595
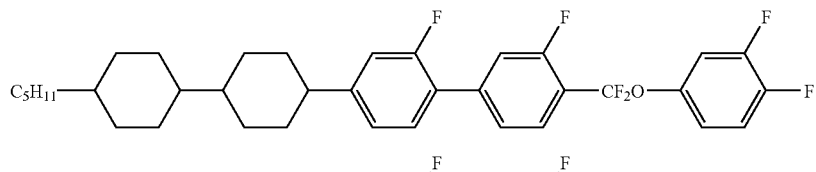
1-4-596
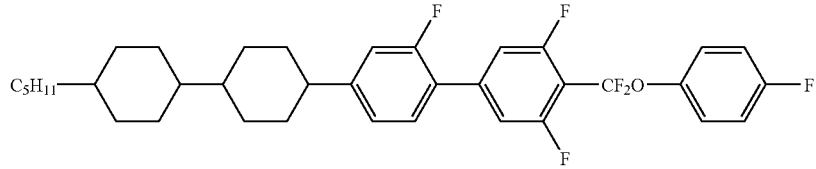
1-4-597
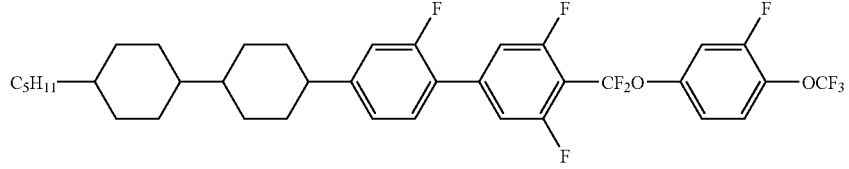
1-4-598
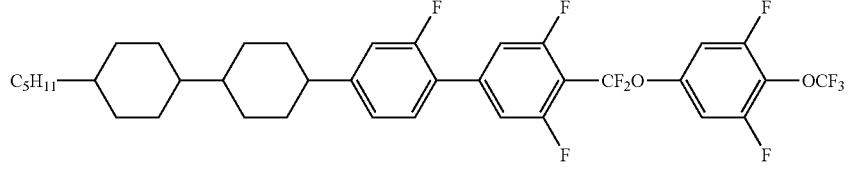
1-4-599
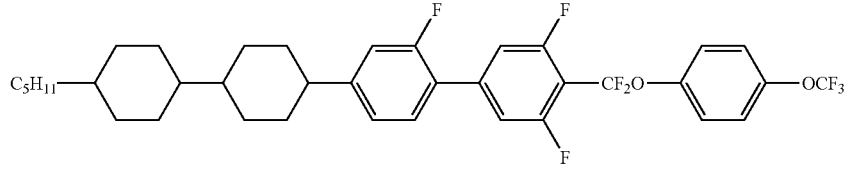
1-4-600
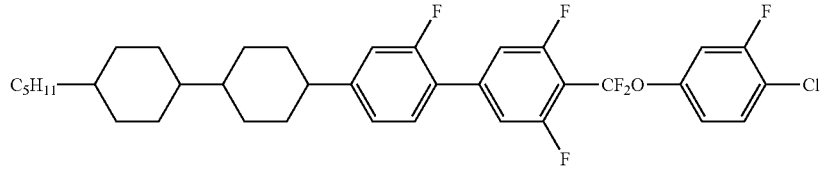
1-4-601
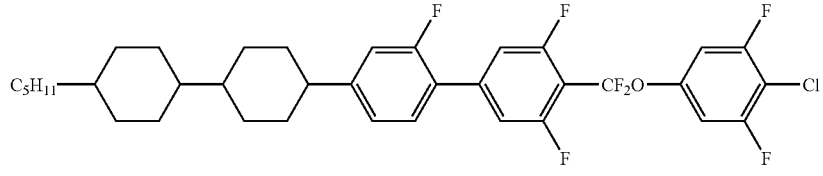
1-4-602

-continued
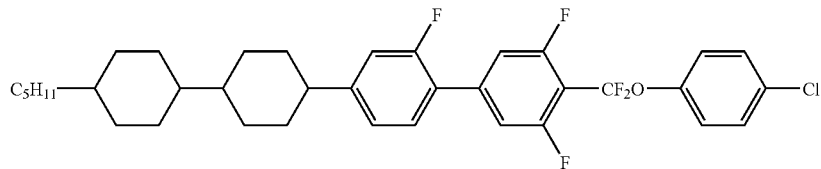
1-4-603
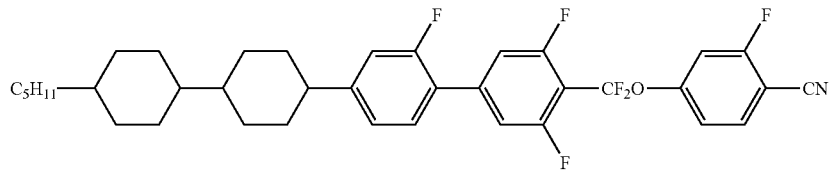
1-4-604
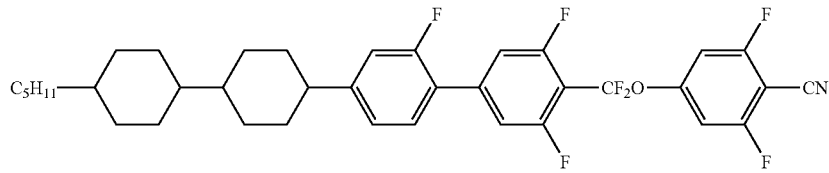
1-4-605
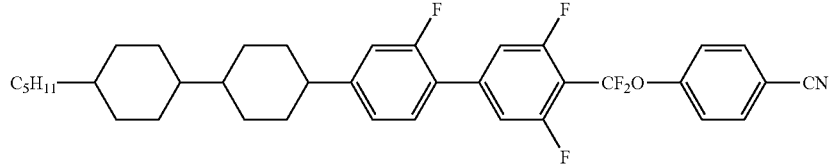
1-4-606
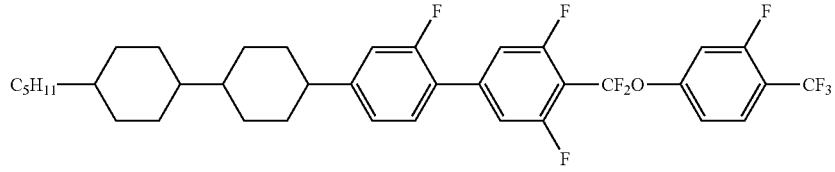
1-4-607
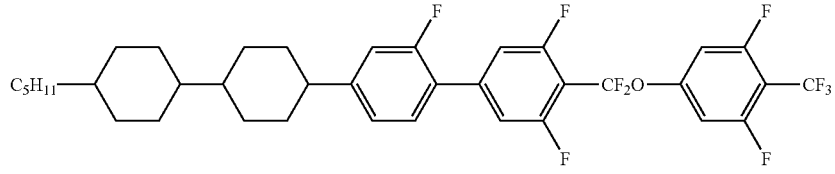
1-4-608
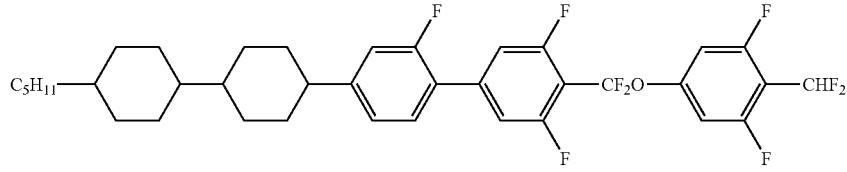
1-4-609
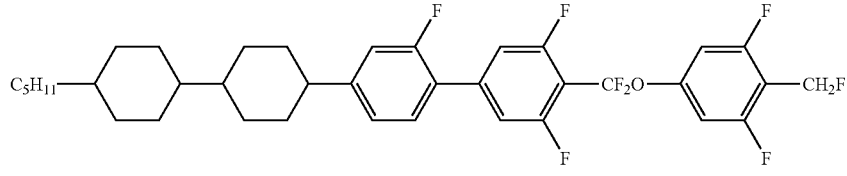
1-4-610
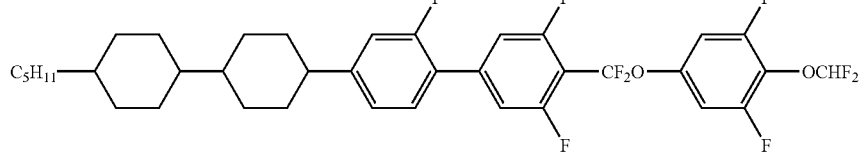
1-4-611

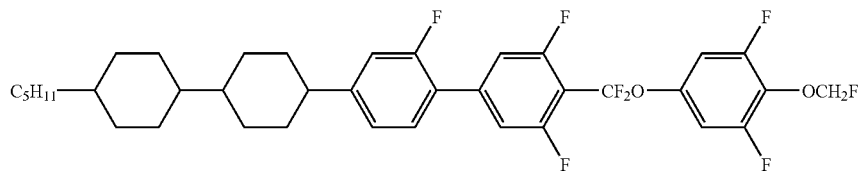
1-4-612
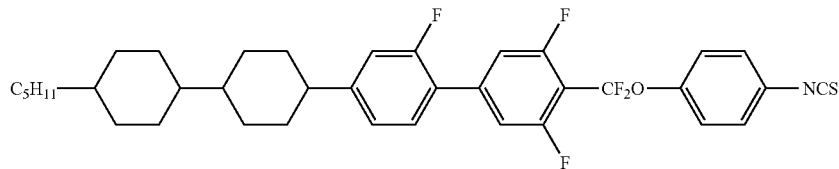
1-4-613
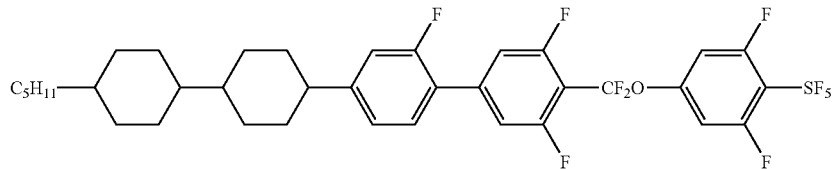
1-4-614
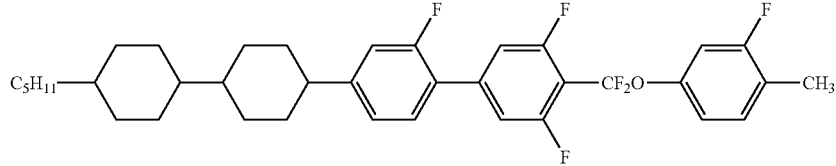
1-4-615
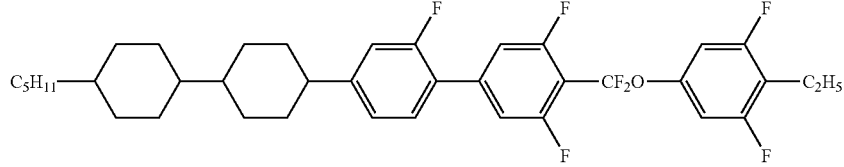
1-4-616
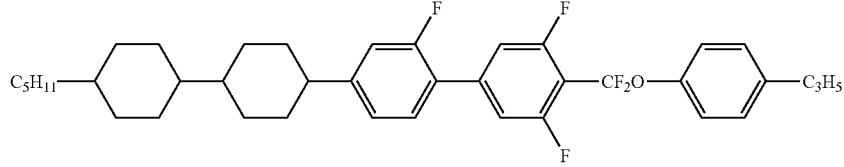
1-4-617
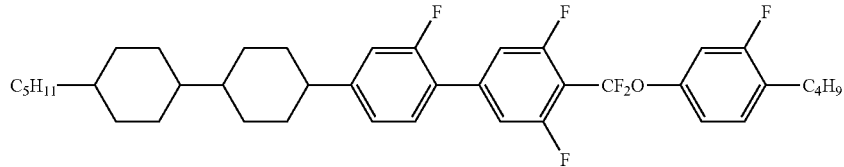
1-4-618
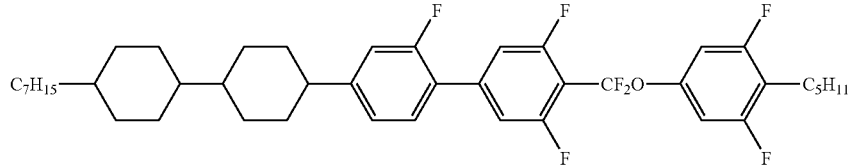
1-4-619
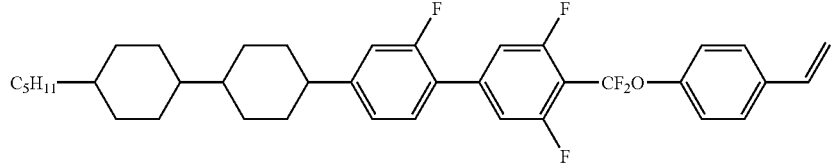
1-4-620

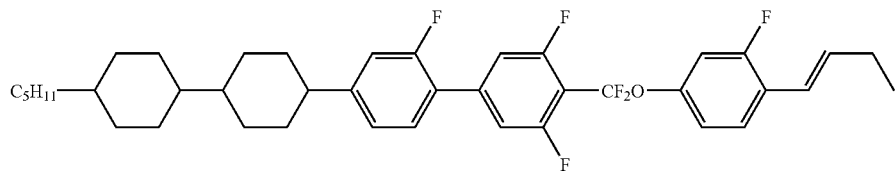
1-4-621
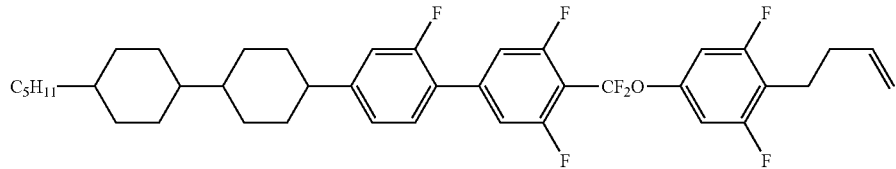
1-4-622
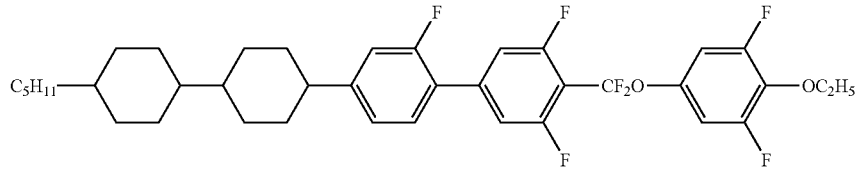
1-4-623
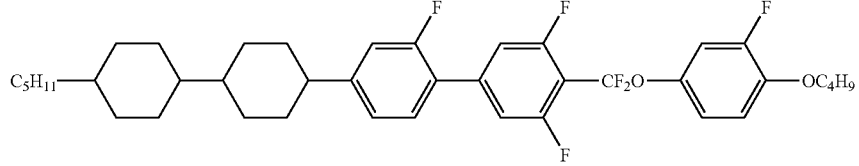
1-4-624
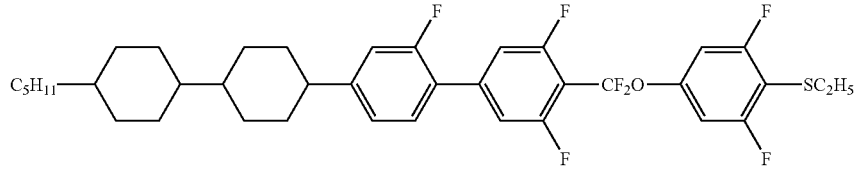
1-4-625
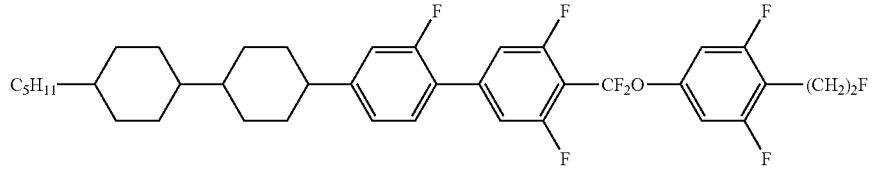
1-4-626
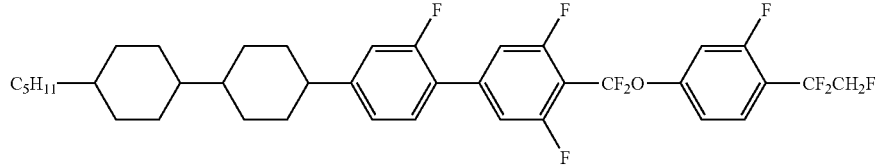
1-4-627
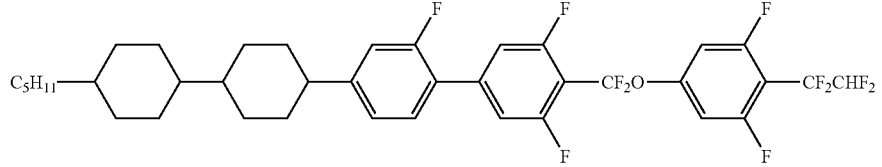
1-4-628
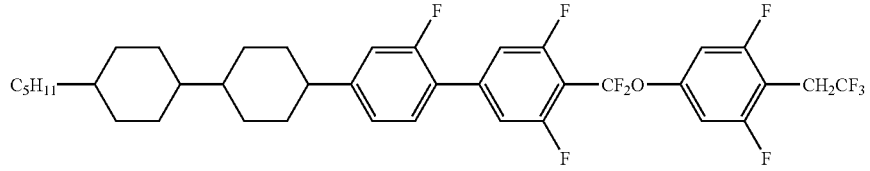
1-4-629

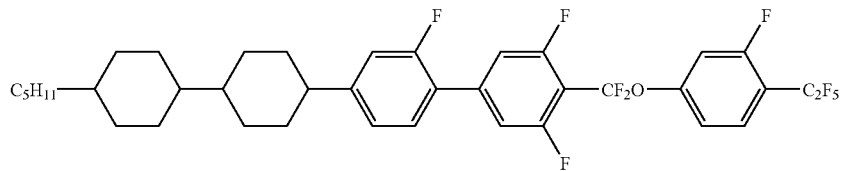
1-4-630
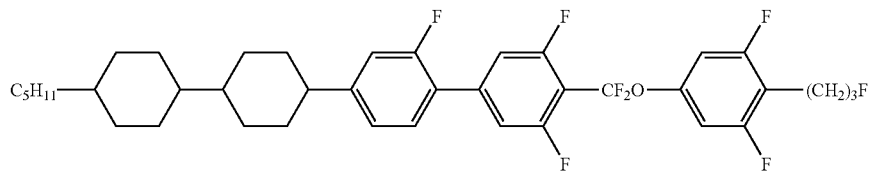
1-4-631
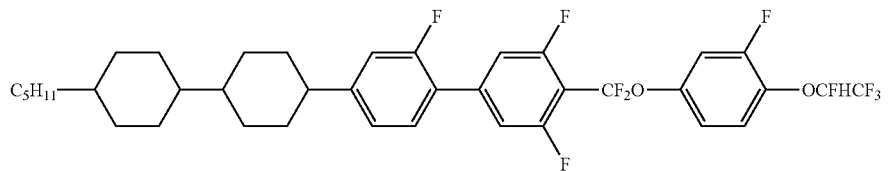
1-4-632
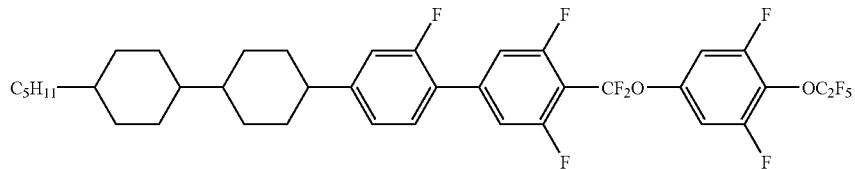
1-4-633
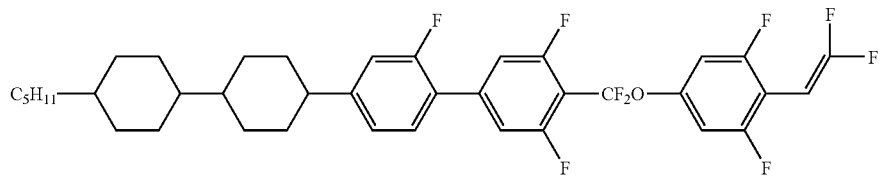
1-4-634
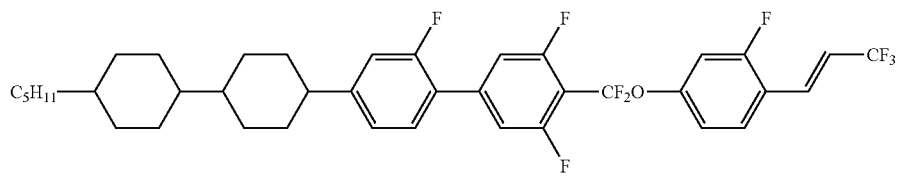
1-4-635
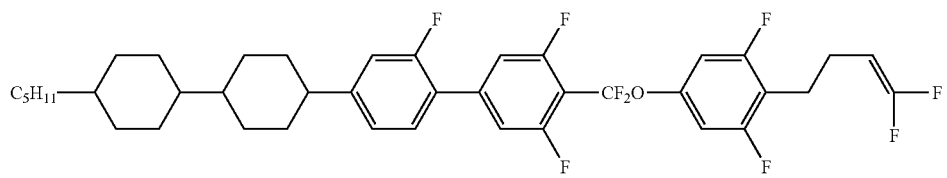
1-4-636
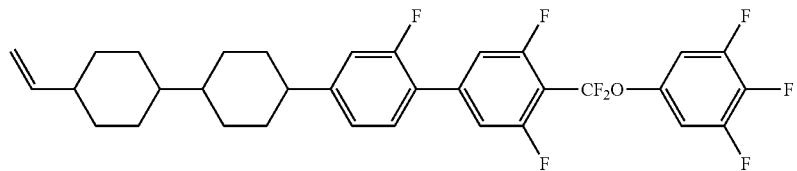
1-4-637
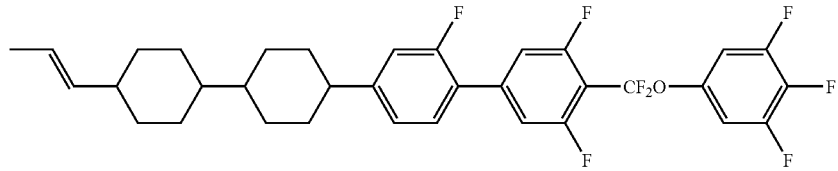
1-4-638

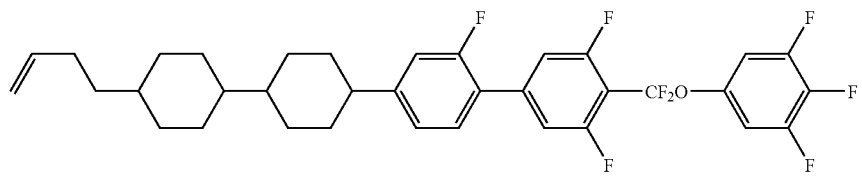 1-4-639
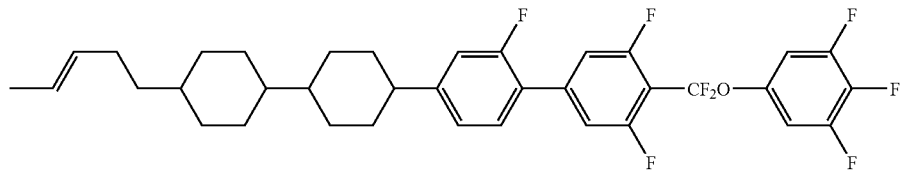 1-4-640
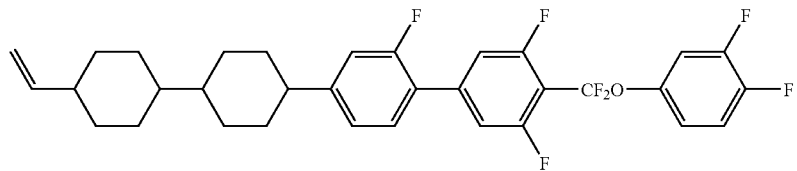 1-4-641
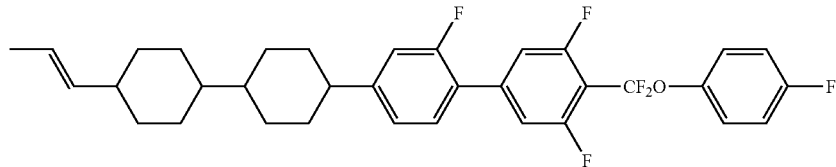 1-4-642
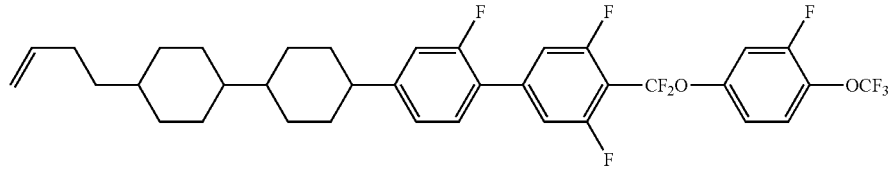 1-4-643
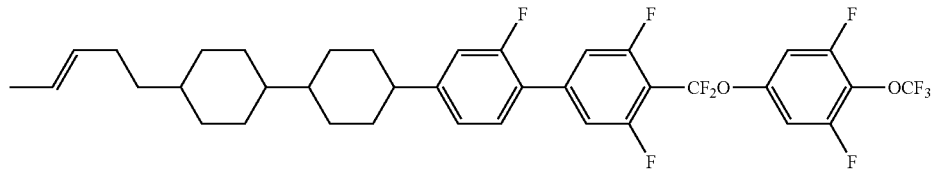 1-4-644
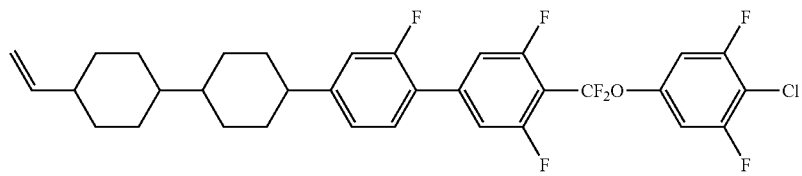 1-4-645
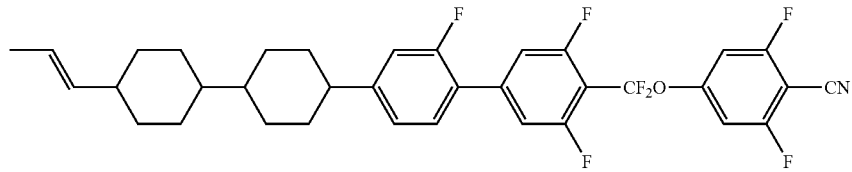 1-4-646
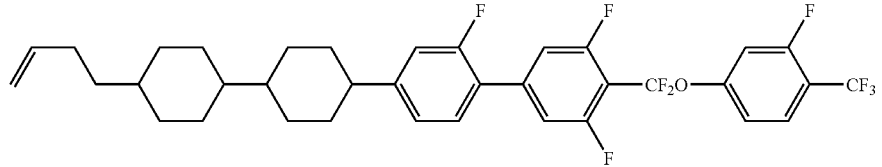 1-4-647

-continued
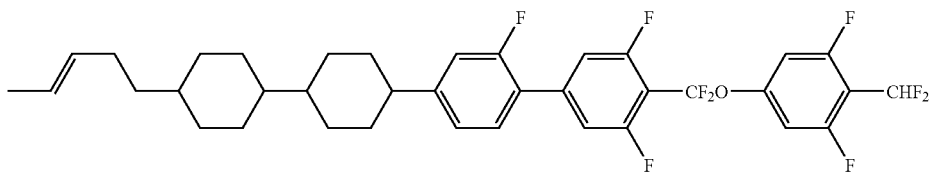
1-4-648
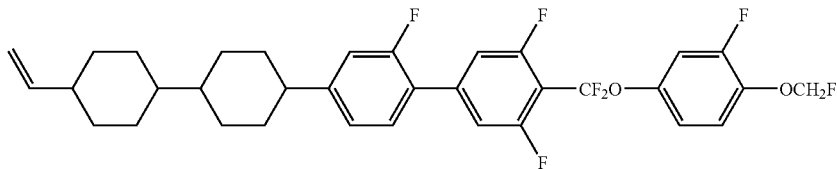
1-4-649
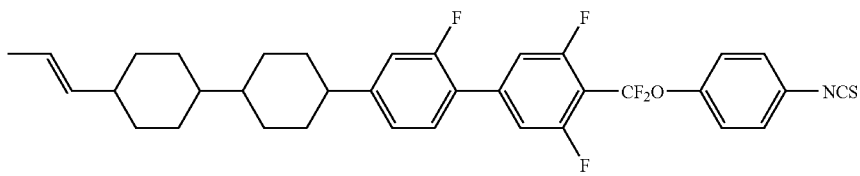
1-4-650
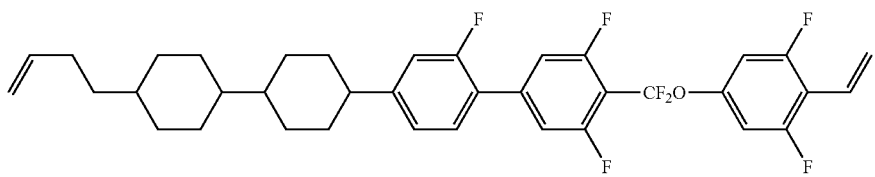
1-4-651
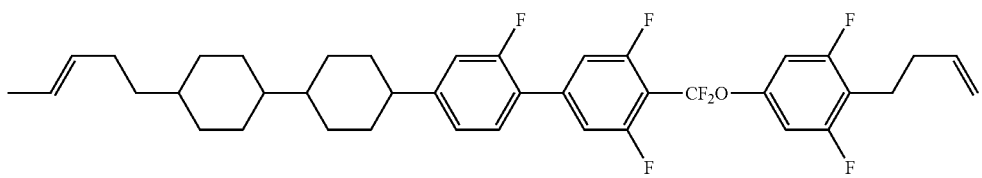
1-4-652
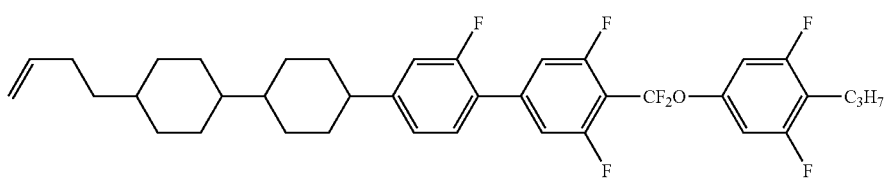
1-4-653
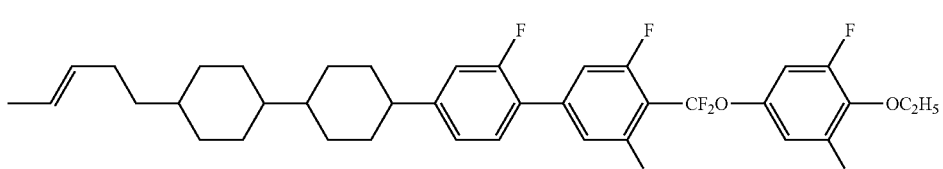
1-4-654
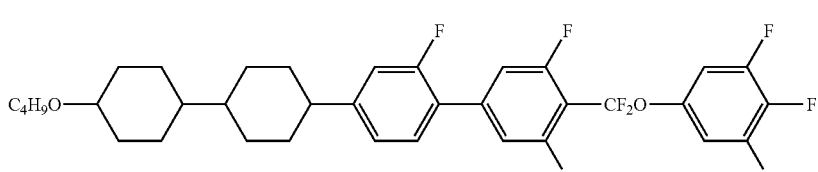
1-4-655
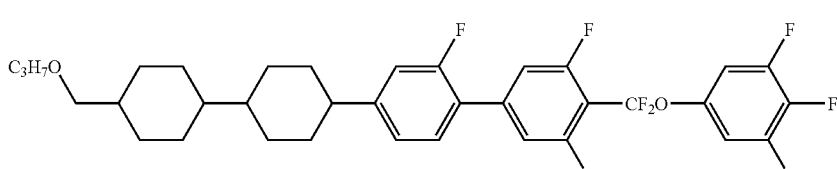
1-4-656

-continued
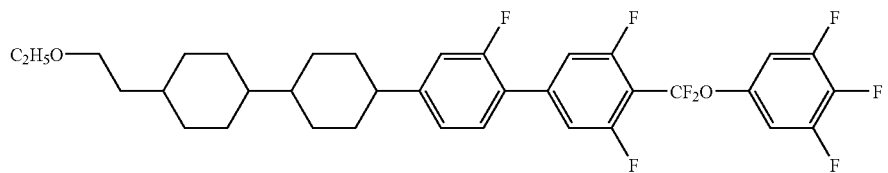
1-4-657
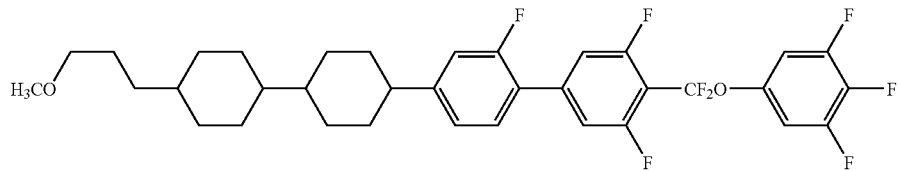
1-4-658
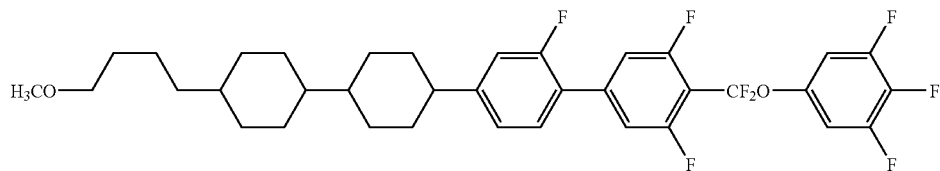
1-4-659
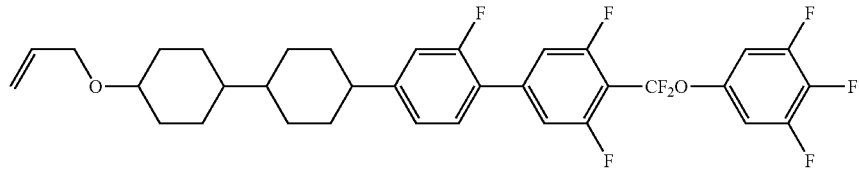
1-4-660
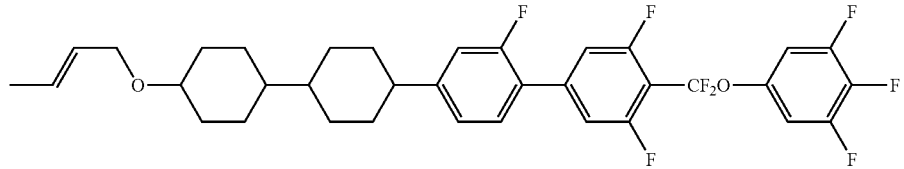
1-4-661
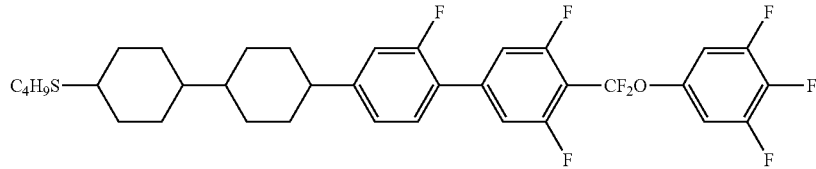
1-4-662
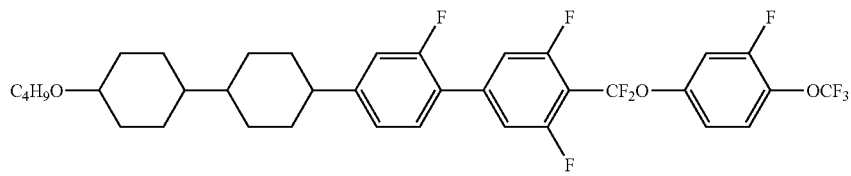
1-4-663
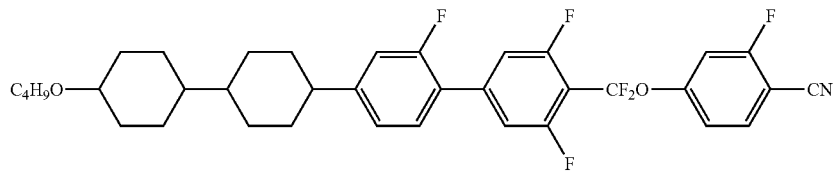
1-4-664
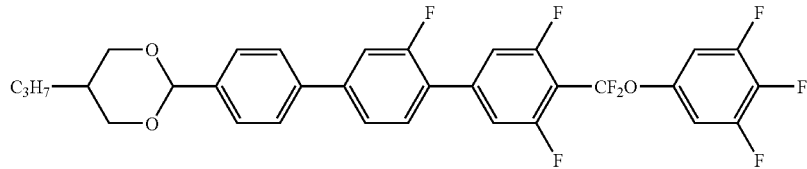
1-4-665

-continued
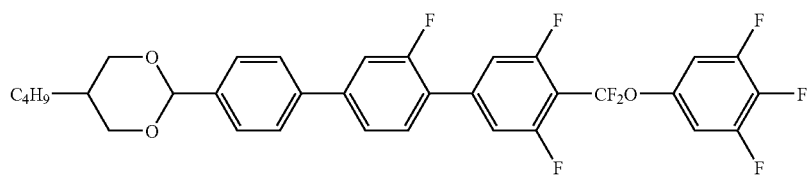
1-4-666
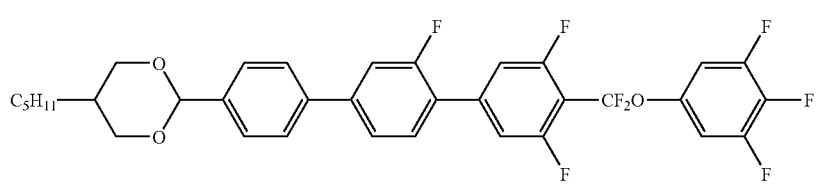
1-4-667
$T_{NI} = 190°$ C., $\Delta n = 0.210$, $\Delta\varepsilon = 27.0$
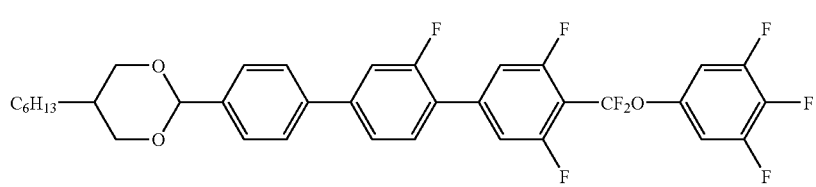
1-4-668
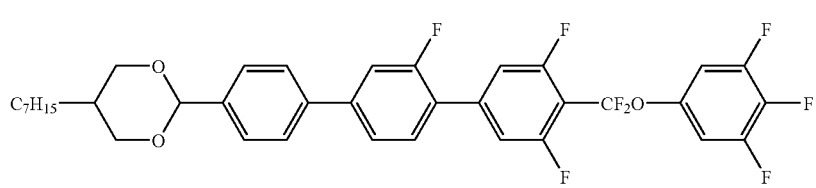
1-4-669
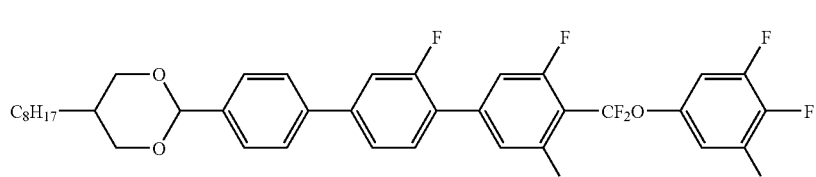
1-4-670
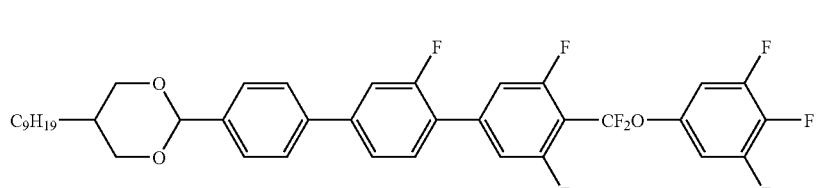
1-4-671
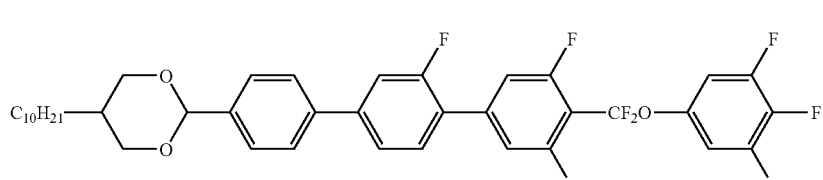
1-4-672
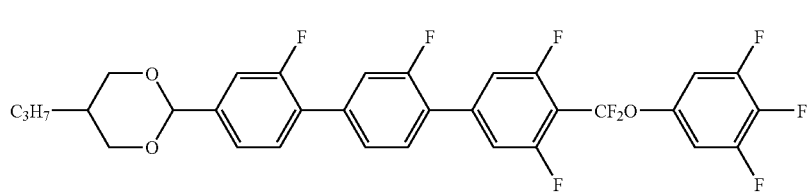
1-4-673

-continued
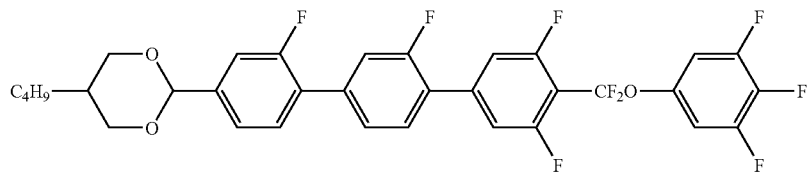
1-4-674
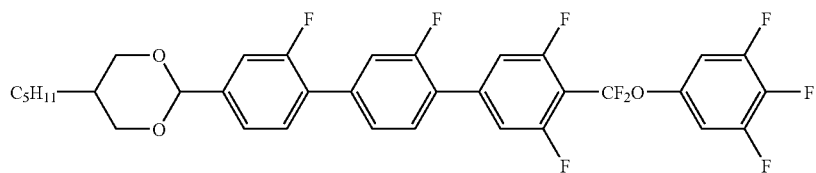
1-4-675
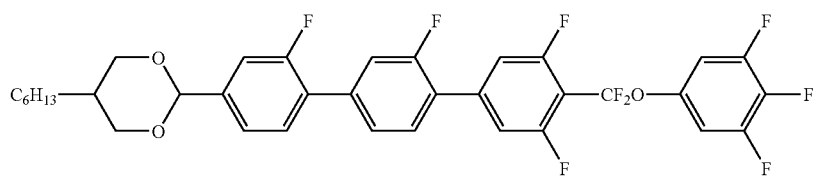
1-4-676
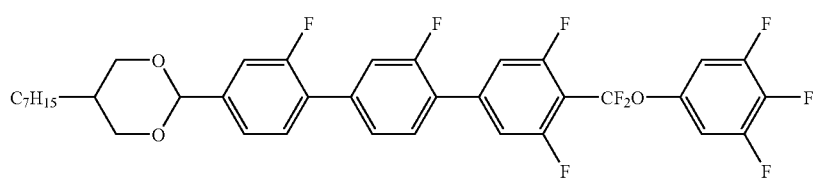
1-4-677
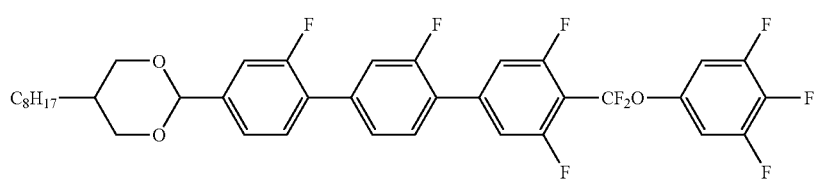
1-4-678
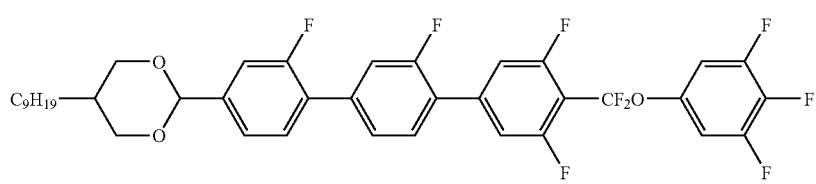
1-4-679
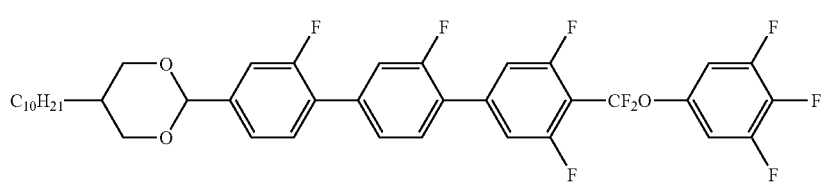
1-4-680
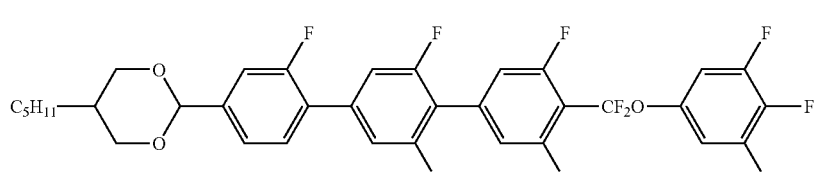
1-4-681
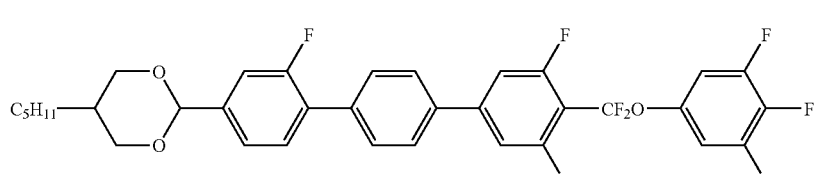
1-4-682

-continued
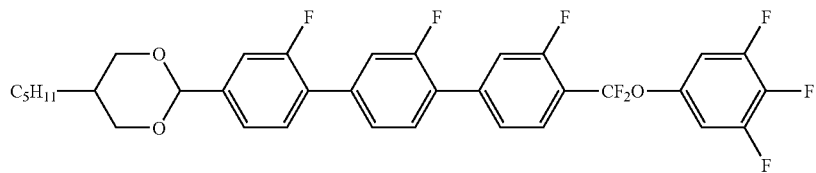
1-4-683
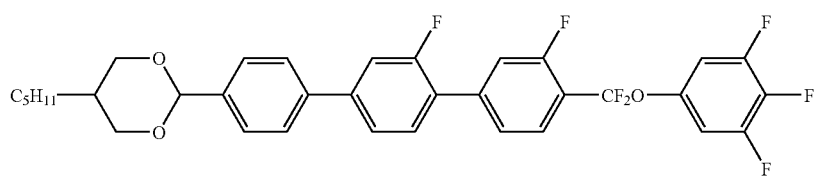
1-4-684
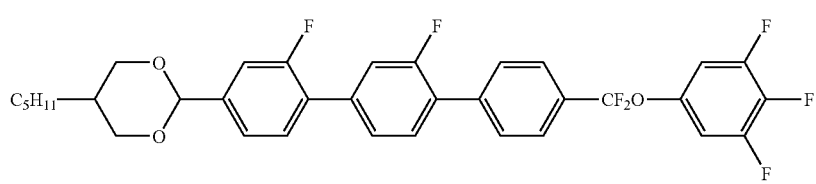
1-4-685
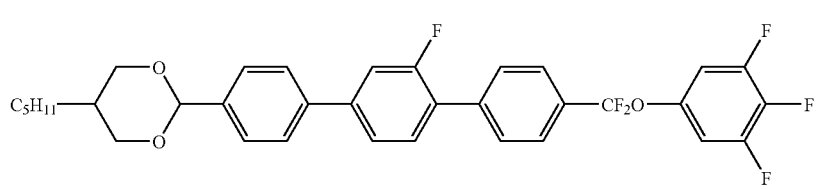
1-4-686
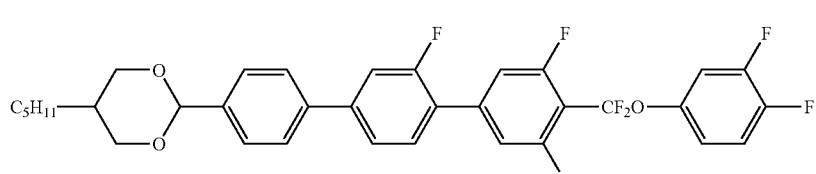
1-4-687
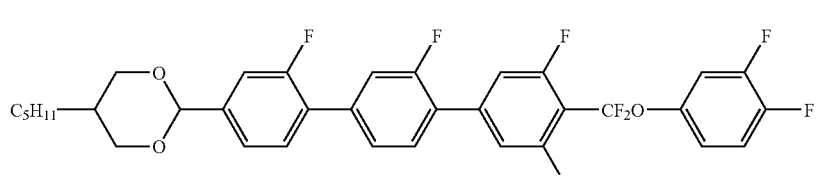
1-4-688
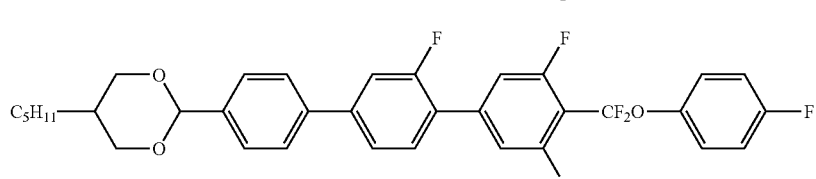
1-4-689
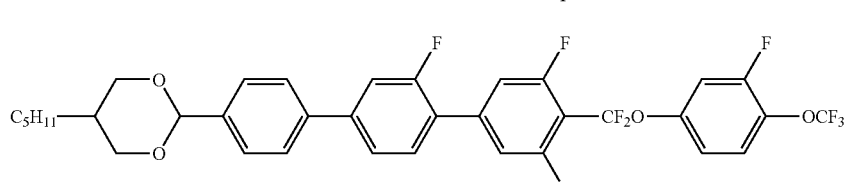
1-4-690
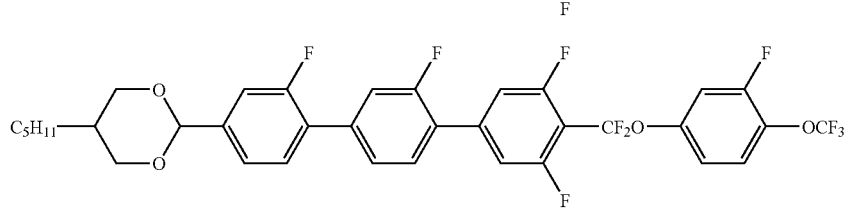
1-4-691

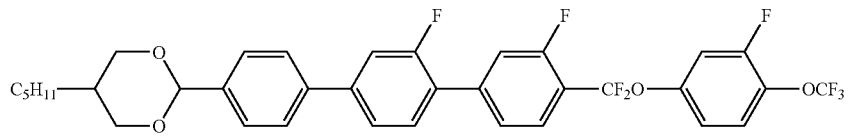
1-4-692
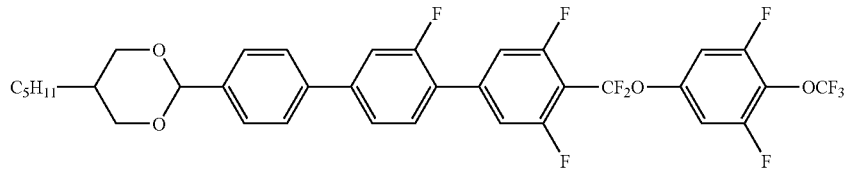
1-4-693
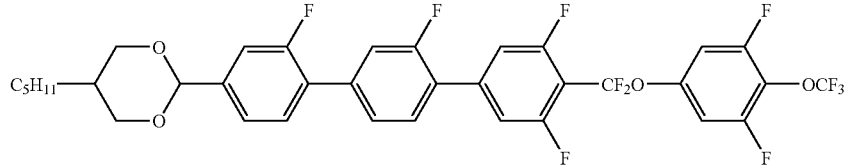
1-4-694
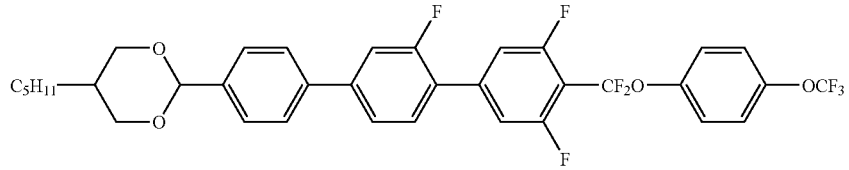
1-4-695
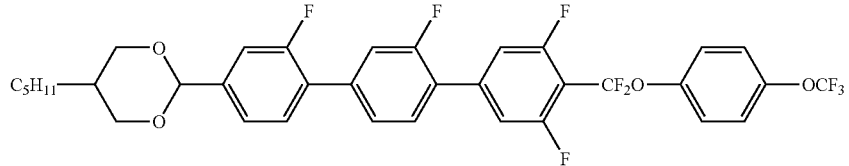
1-4-696
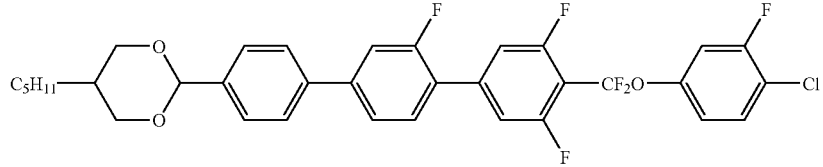
1-4-697
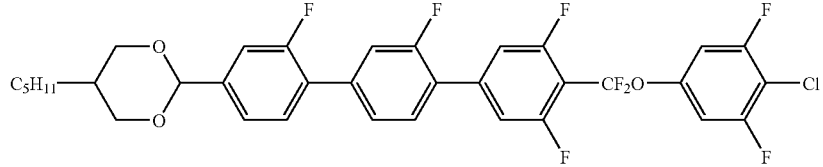
1-4-698
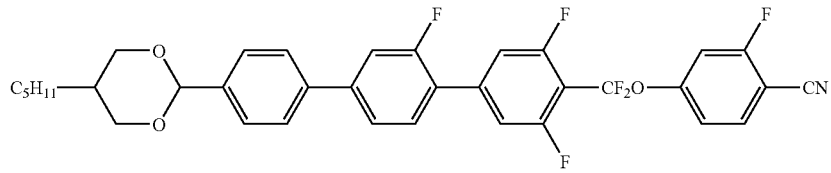
1-4-699
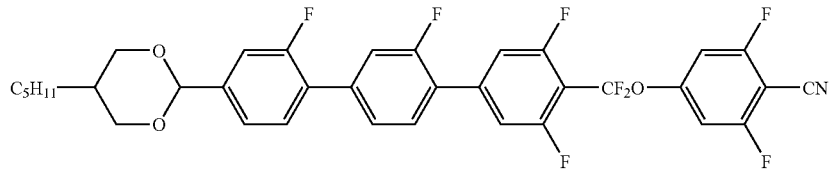
1-4-700

-continued
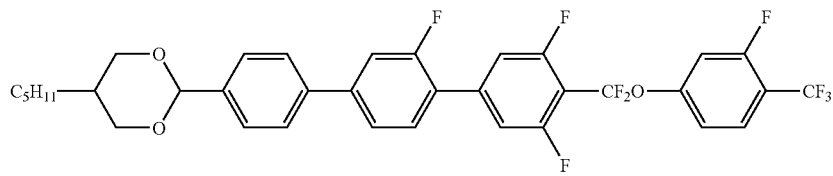
1-4-701
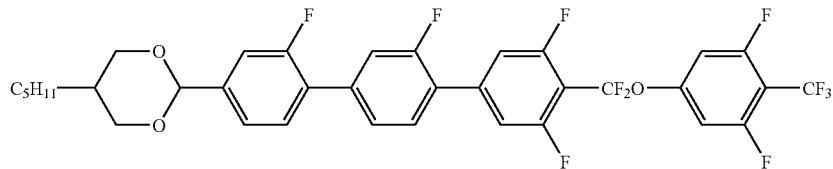
1-4-702
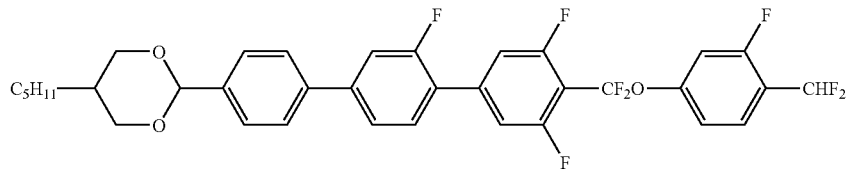
1-4-703
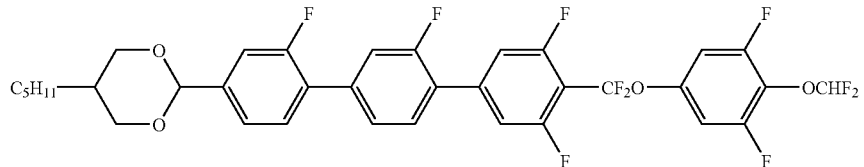
1-4-704
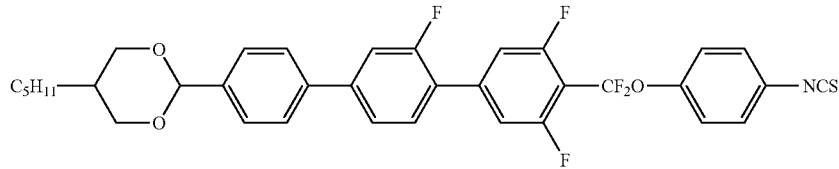
1-4-705
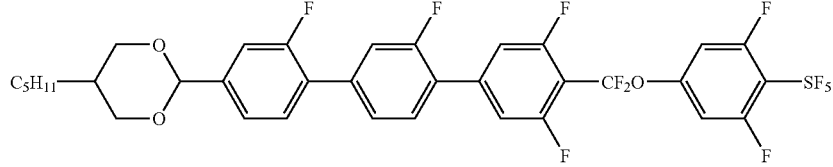
1-4-706
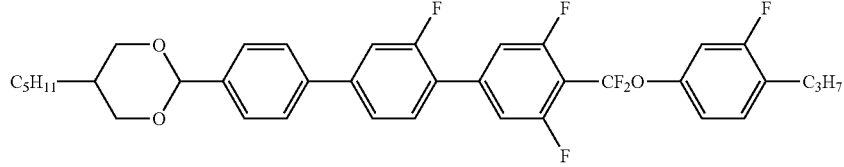
1-4-707
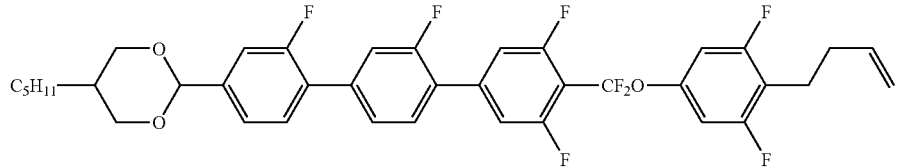
1-4-708
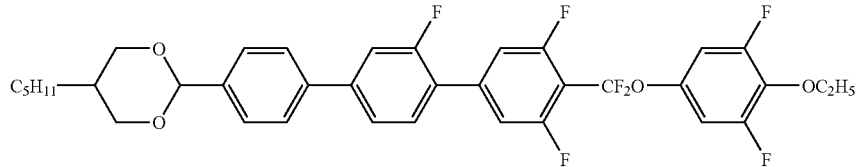
1-4-709

-continued
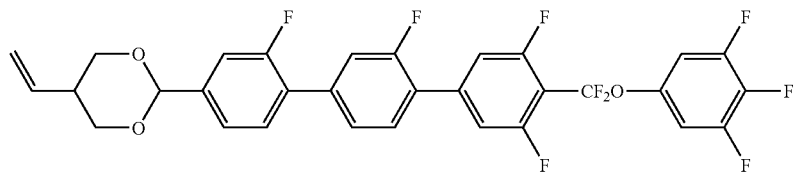
1-4-710
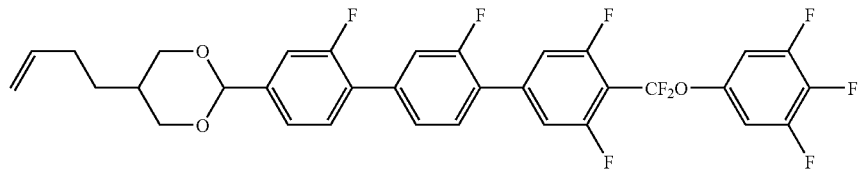
1-4-711
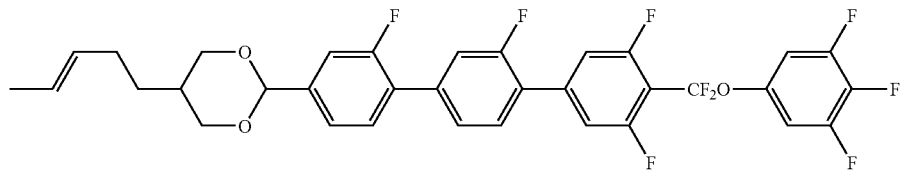
1-4-712
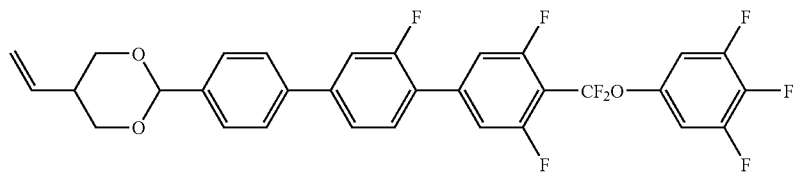
1-4-713
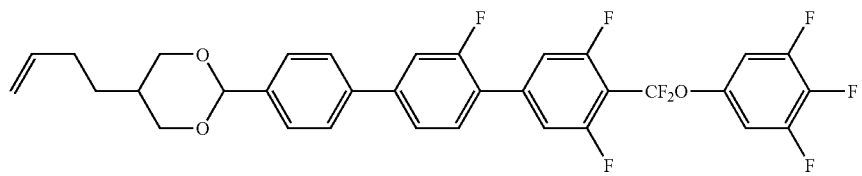
1-4-714
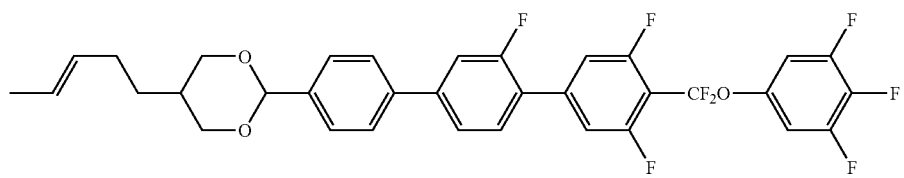
1-4-715
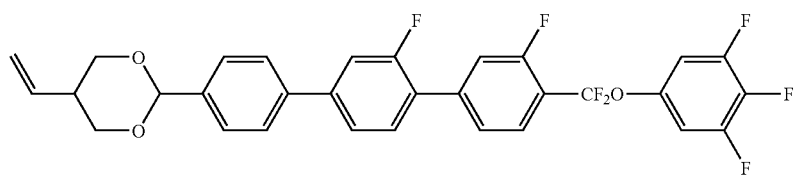
1-4-716
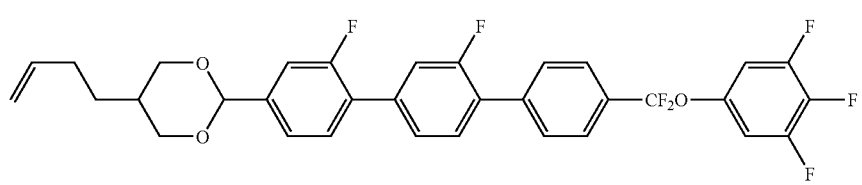
1-4-717
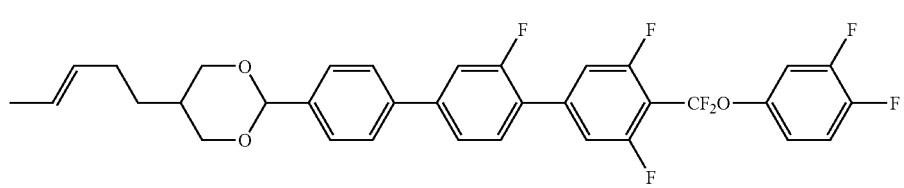
1-4-718

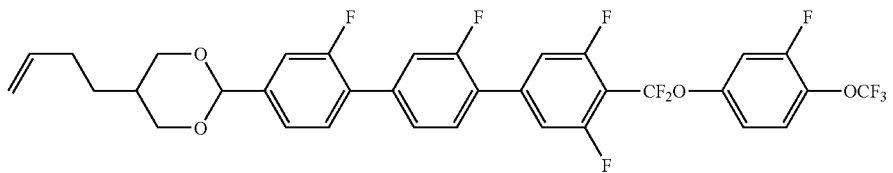 1-4-719
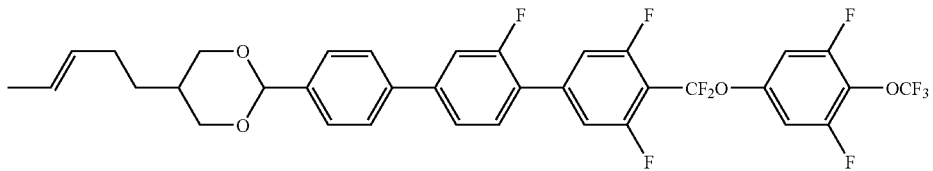 1-4-720
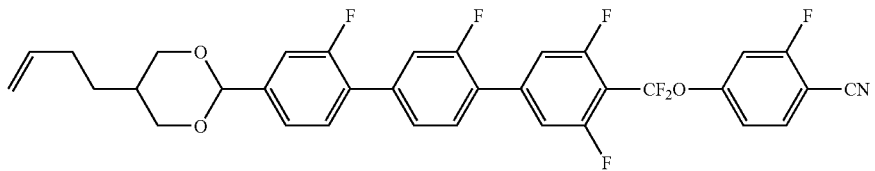 1-4-721
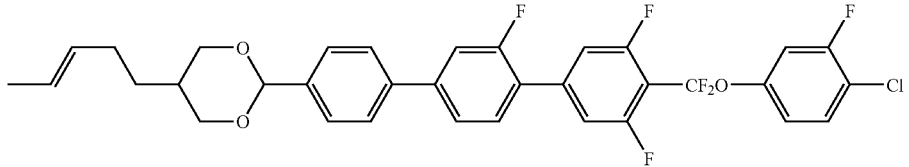 1-4-722
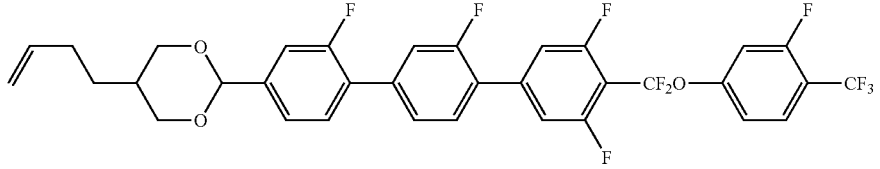 1-4-723
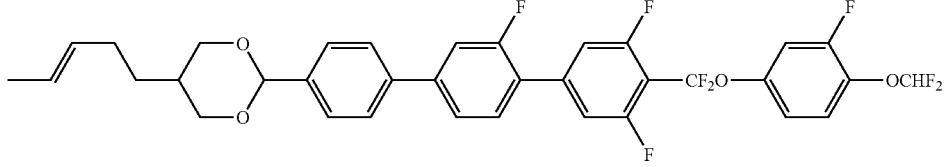 1-4-724
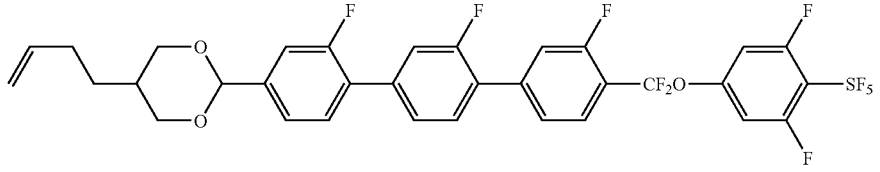 1-4-725
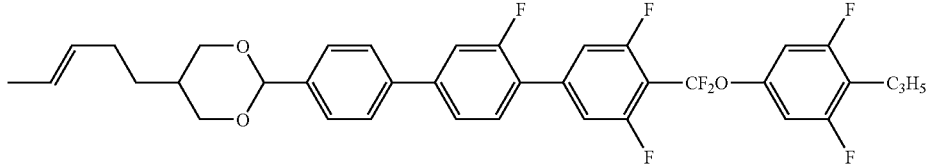 1-4-726
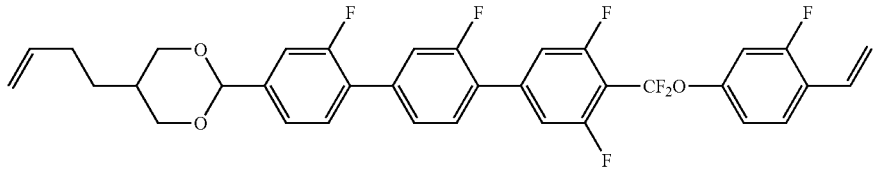 1-4-727

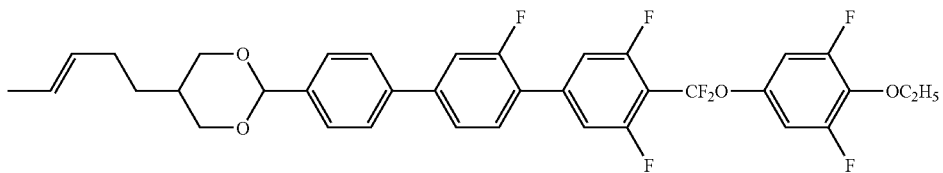
1-4-728
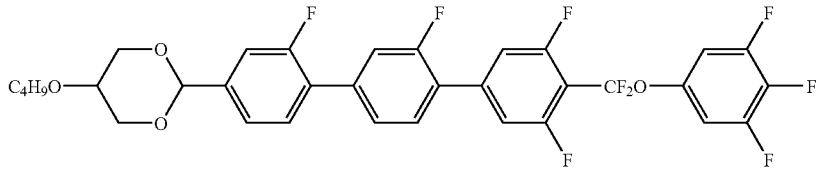
1-4-729
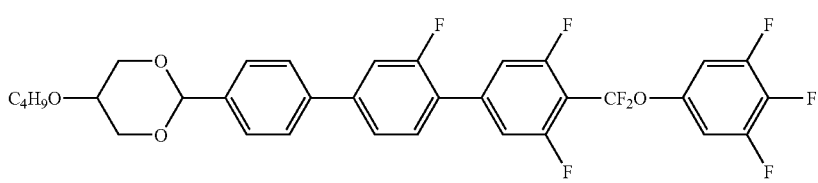
1-4-730
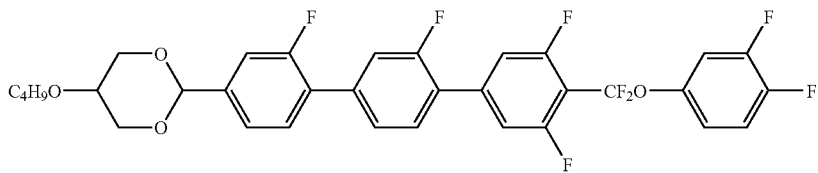
1-4-731
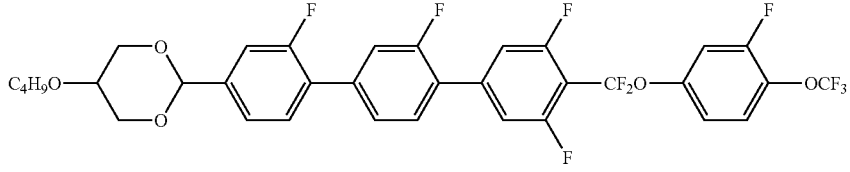
1-4-732
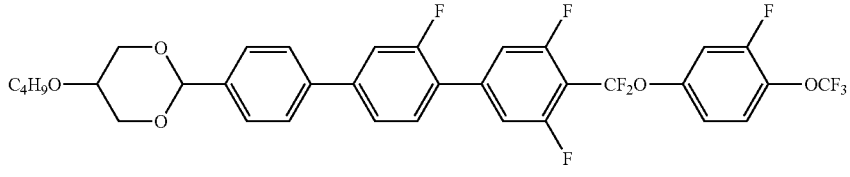
1-4-733
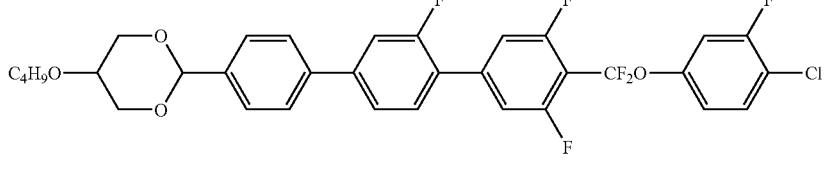
1-4-734
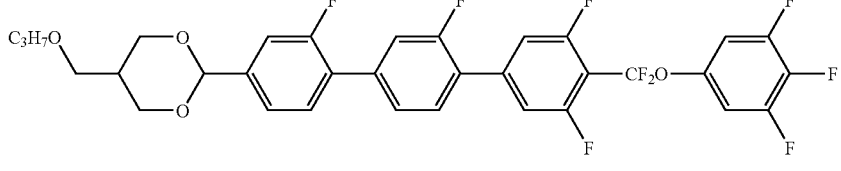
1-4-735
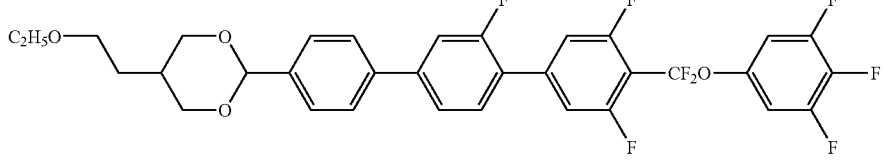
1-4-736

-continued
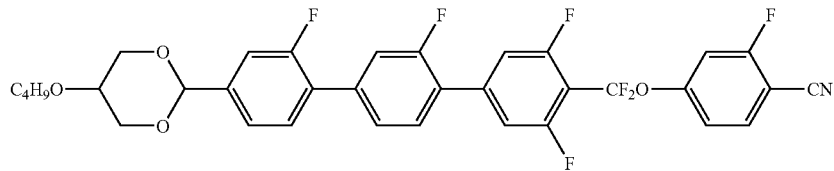 1-4-737
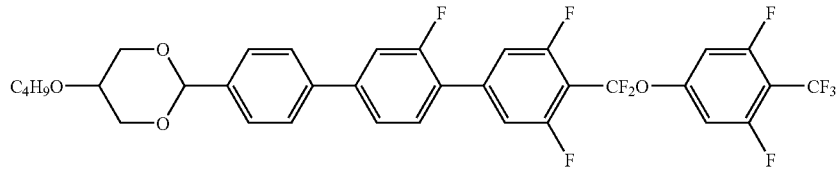 1-4-738
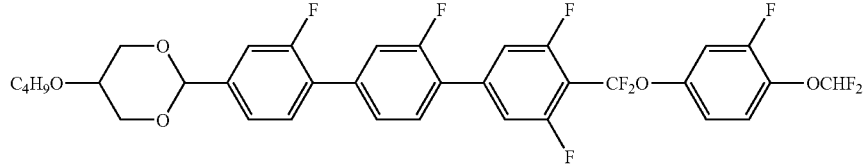 1-4-739
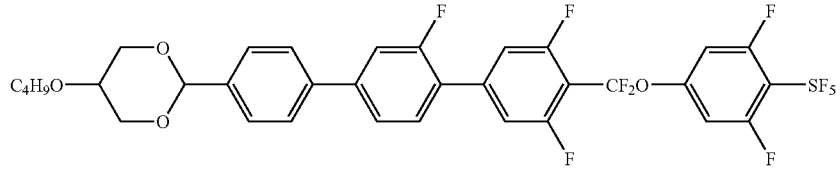 1-4-740
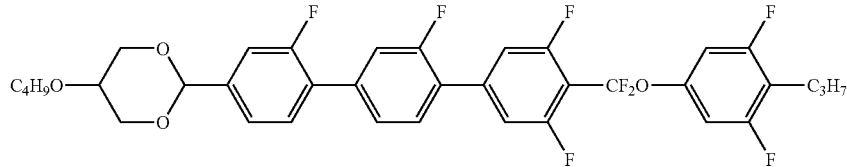 1-4-741
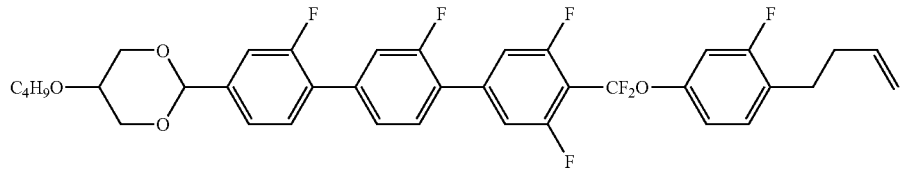 1-4-742
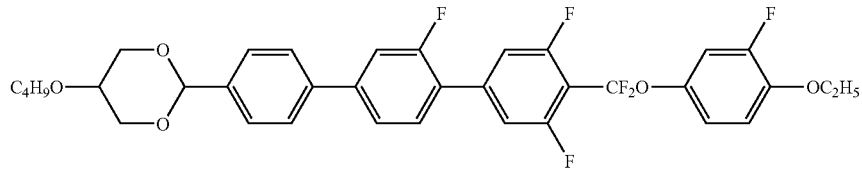 1-4-743
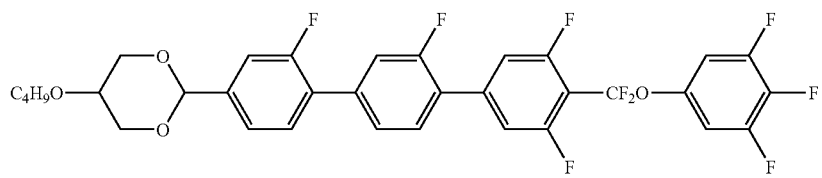 1-4-744
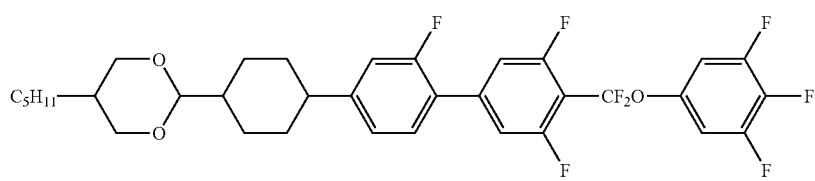 1-4-745

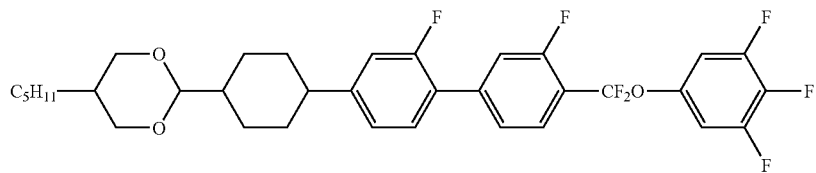
1-4-746
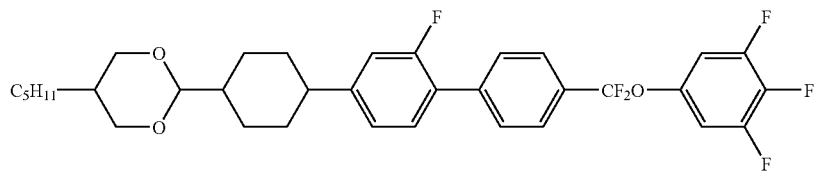
1-4-747
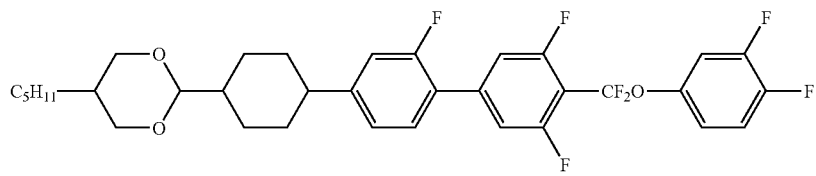
1-4-748
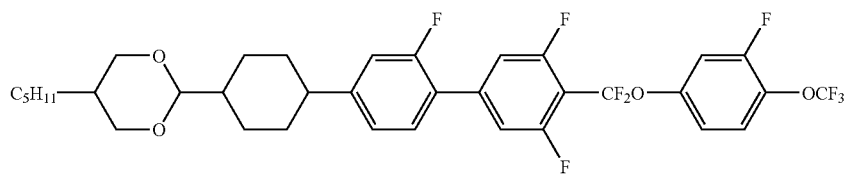
1-4-749
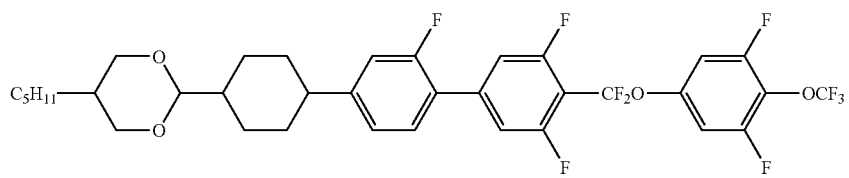
1-4-750
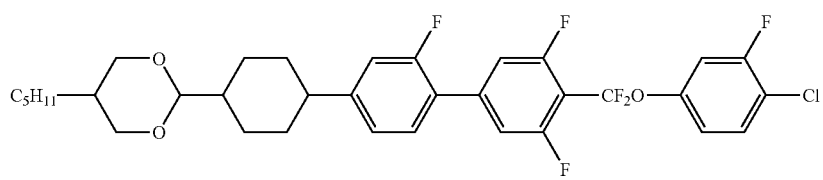
1-4-751
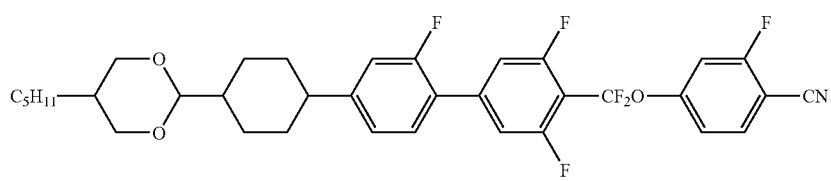
1-4-752
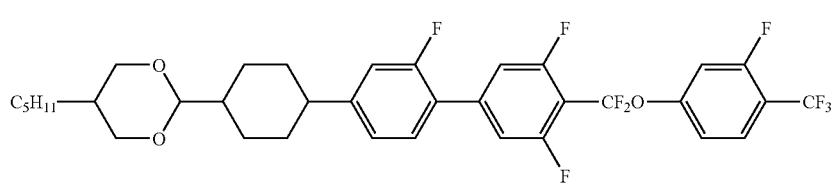
1-4-753
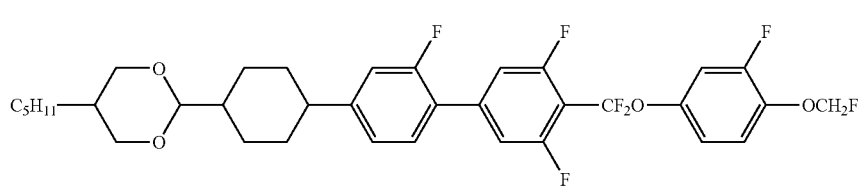
1-4-754

-continued
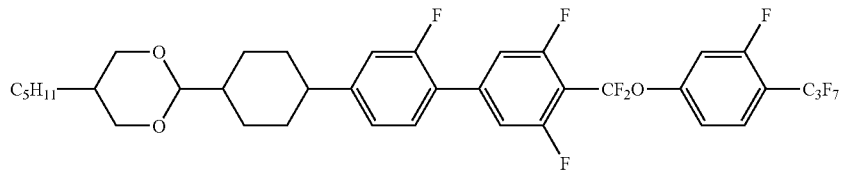 1-4-755
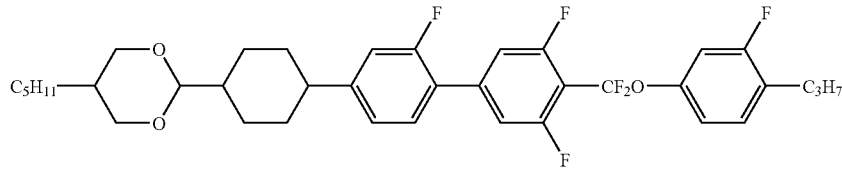 1-4-756
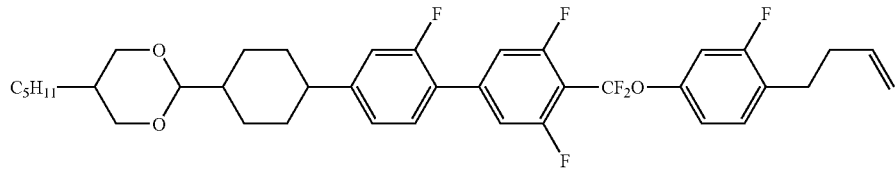 1-4-757
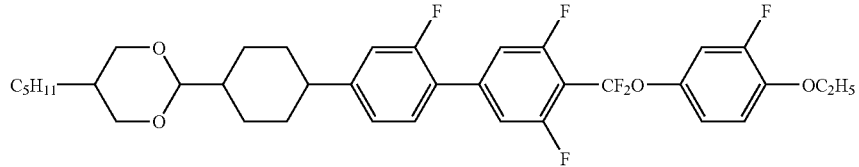 1-4-758
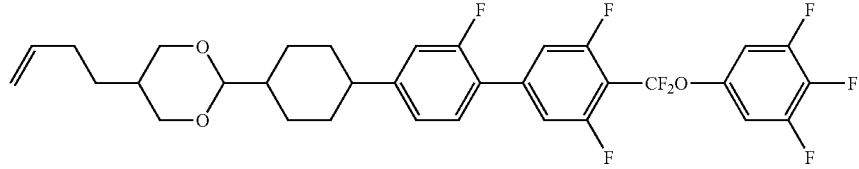 1-4-759
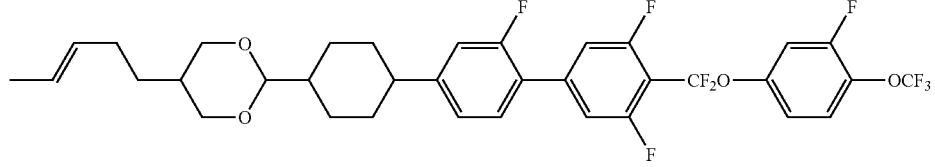 1-4-760
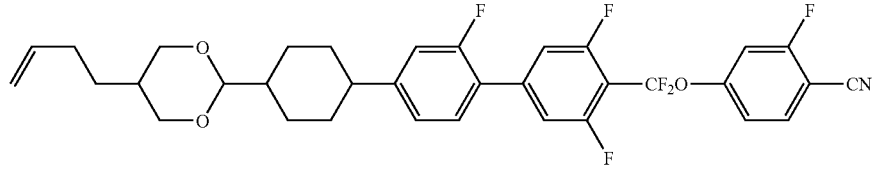 1-4-761
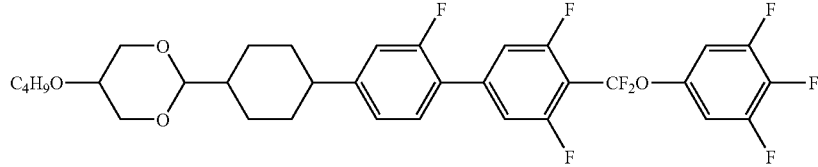 1-4-762
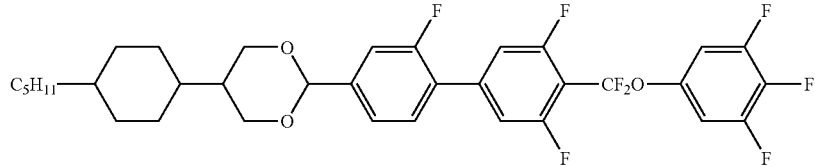 1-4-763

-continued
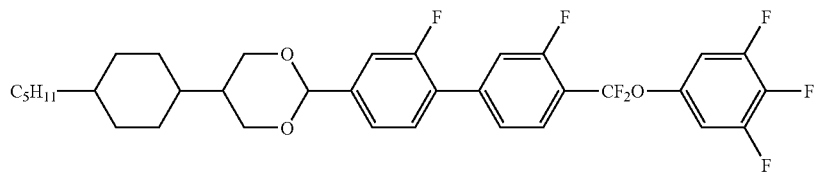
1-4-764
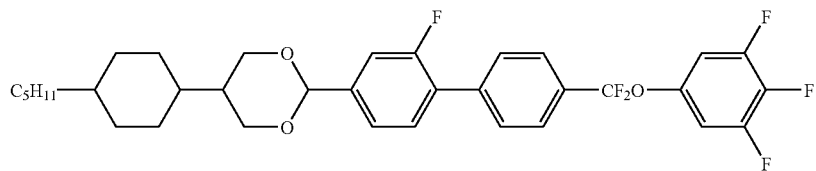
1-4-765
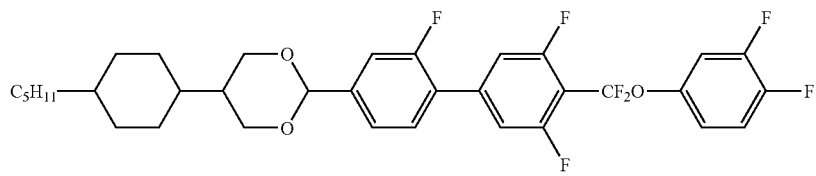
1-4-766
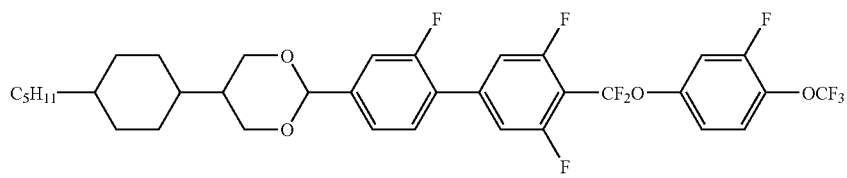
1-4-767
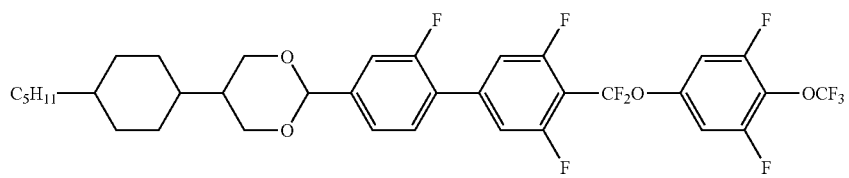
1-4-768
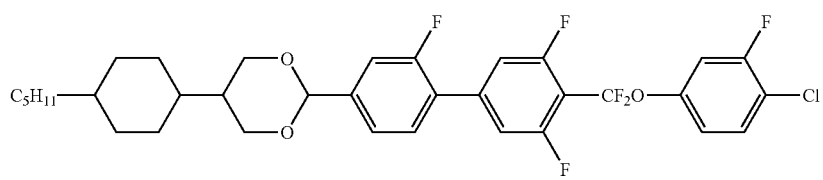
1-4-769
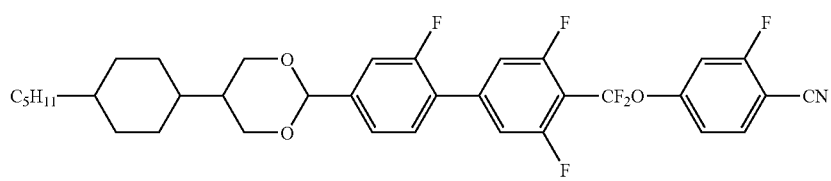
1-4-770
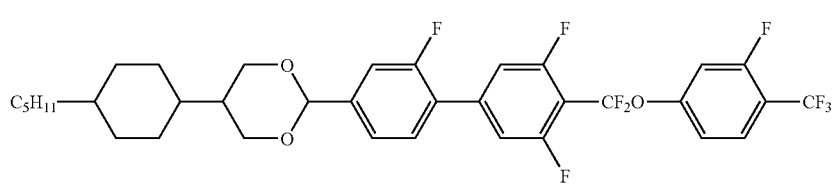
1-4-771
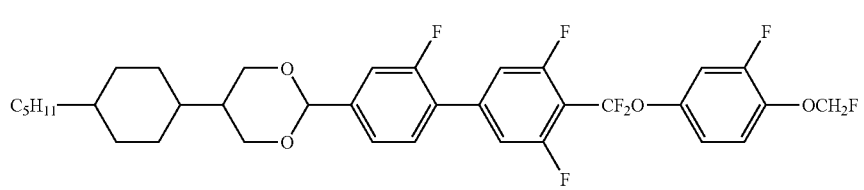
1-4-772

-continued
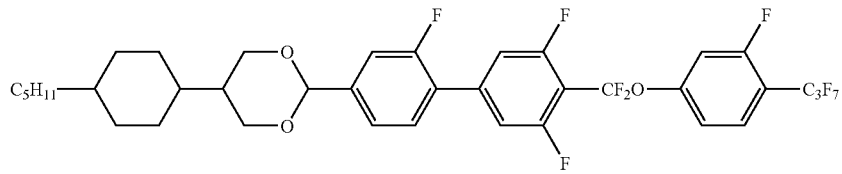 1-4-773
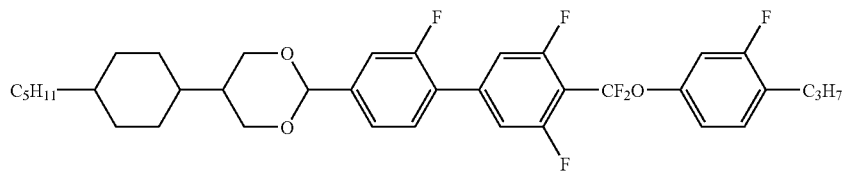 1-4-774
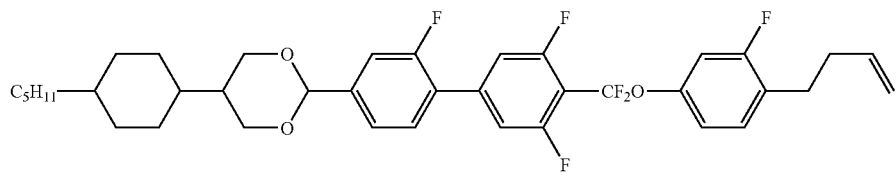 1-4-775
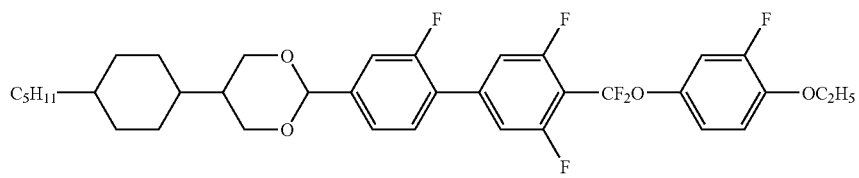 1-4-776
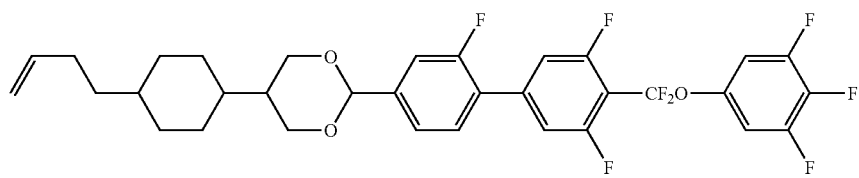 1-4-777
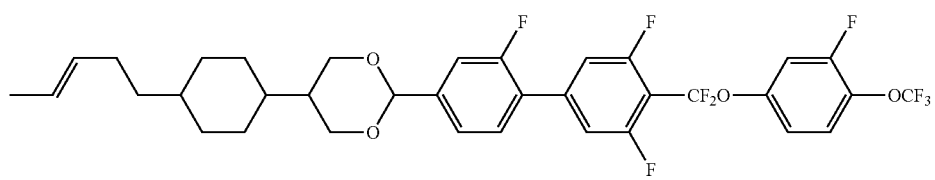 1-4-778
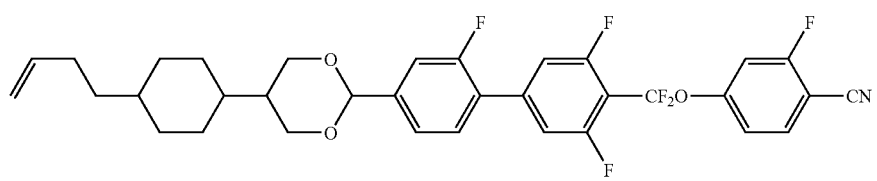 1-4-779
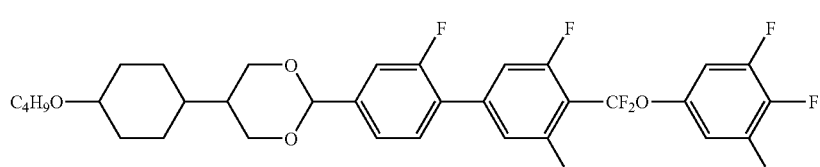 1-4-780
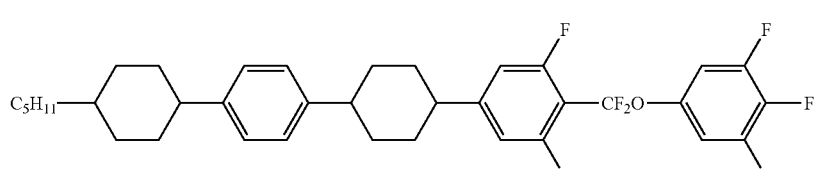 1-4-781

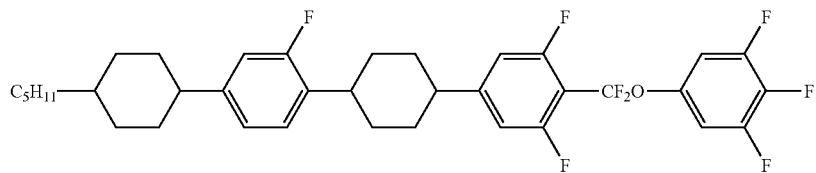
1-4-782
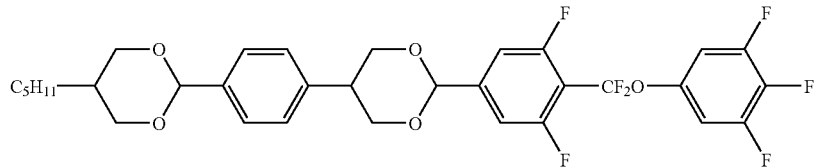
1-4-783
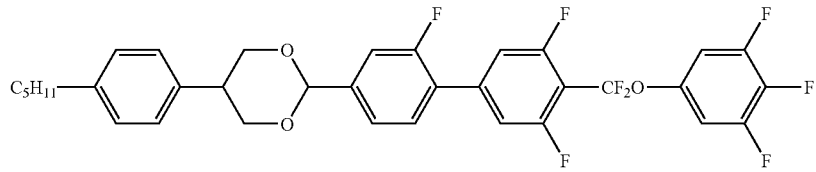
1-4-784
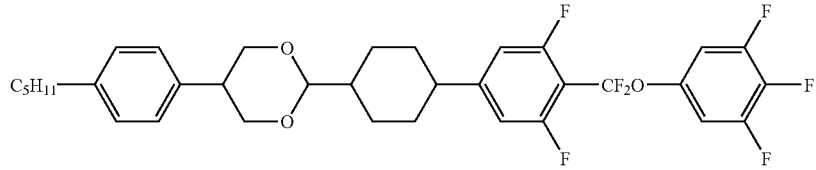
1-4-785
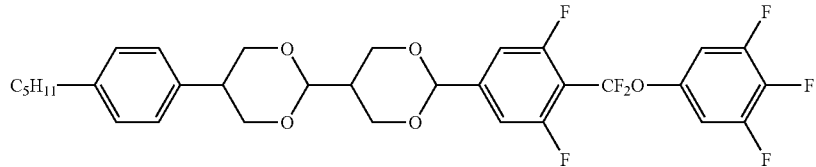
1-4-786
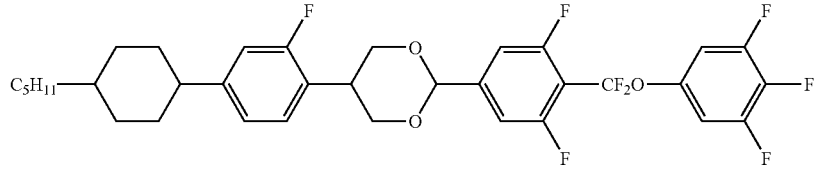
1-4-787
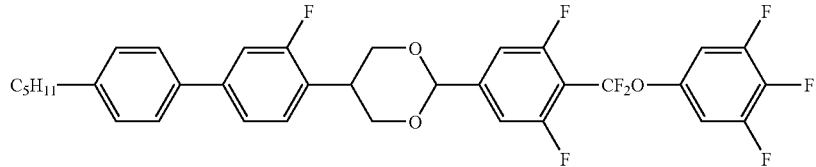
1-4-788
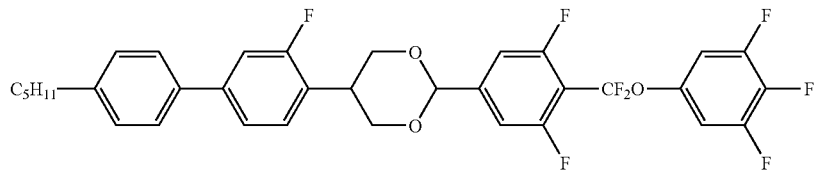
1-4-789
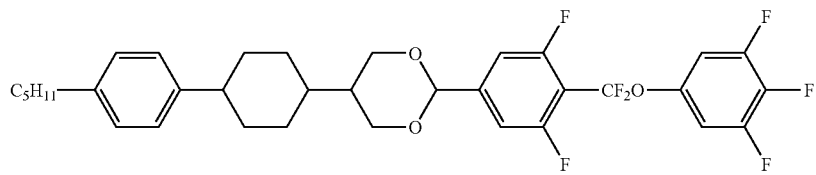
1-4-790

-continued
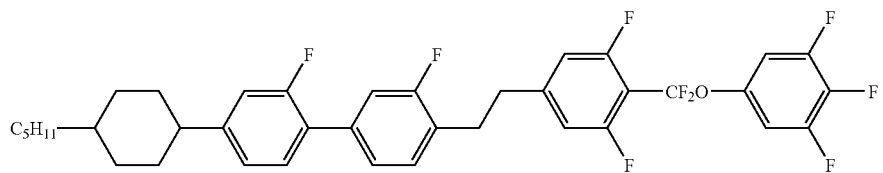
1-4-791
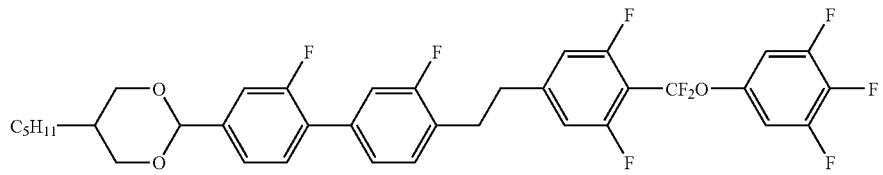
1-4-792
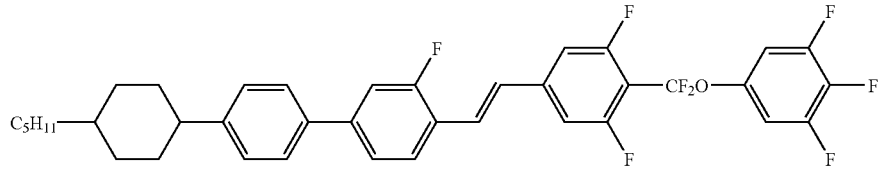
1-4-793
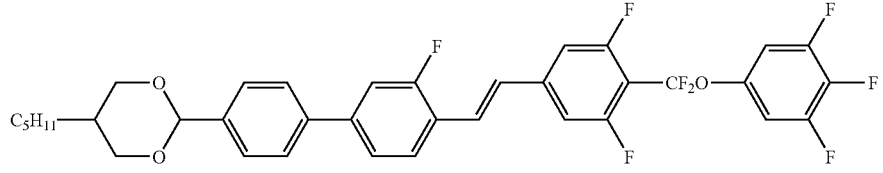
1-4-794
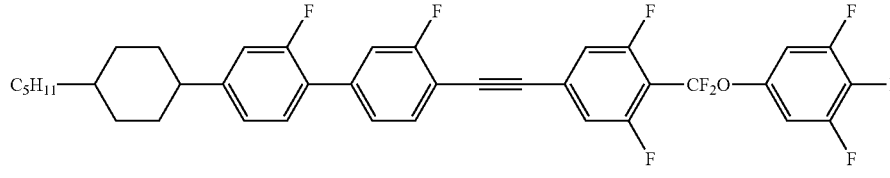
1-4-795
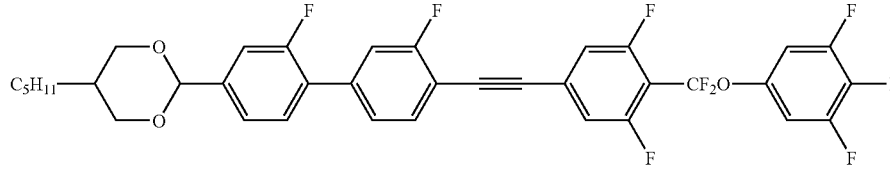
1-4-796
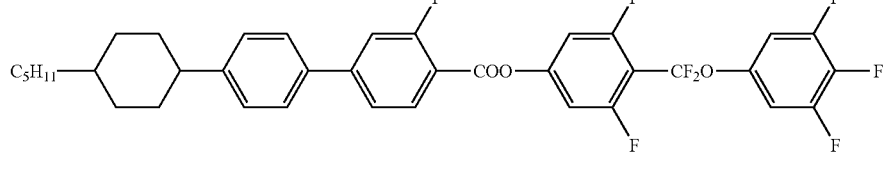
1-4-797
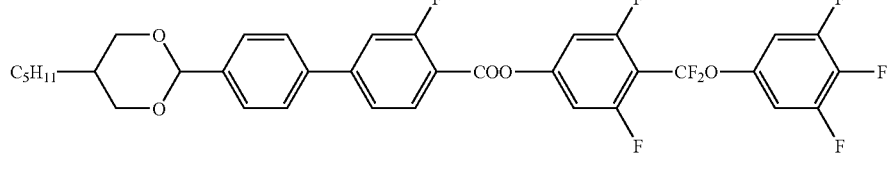
1-4-798
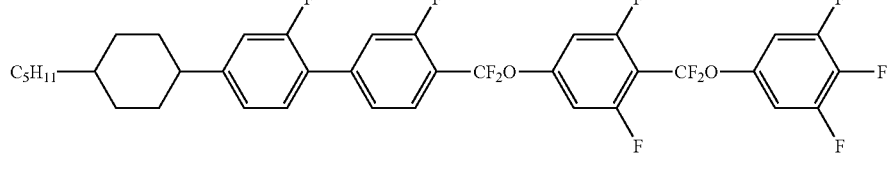
1-4-799

-continued
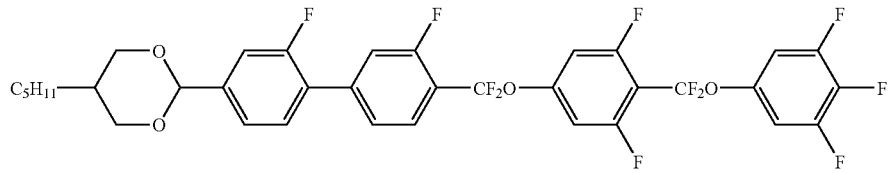
1-4-800
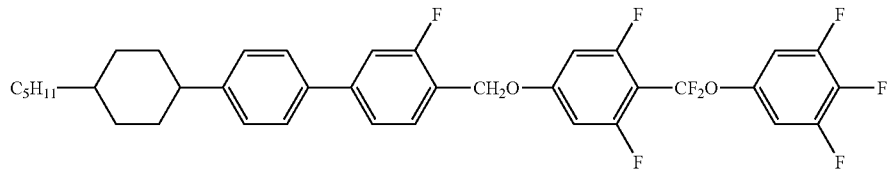
1-4-801
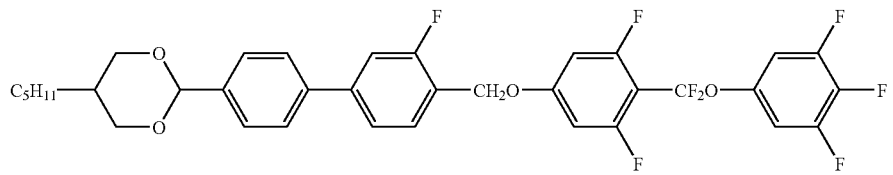
1-4-802
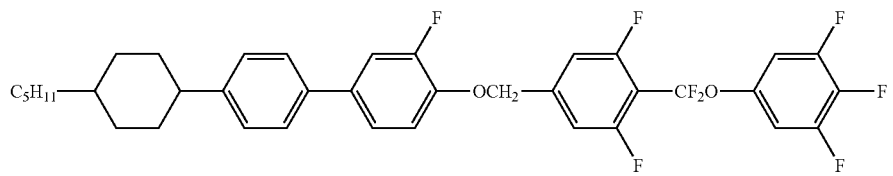
1-4-803
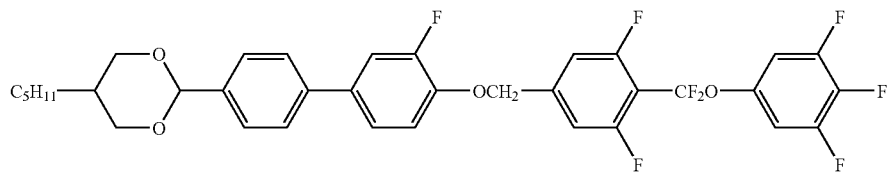
1-4-804
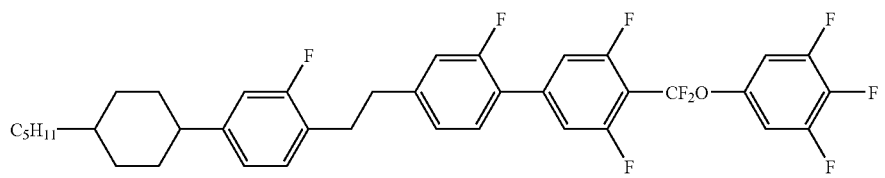
1-4-805
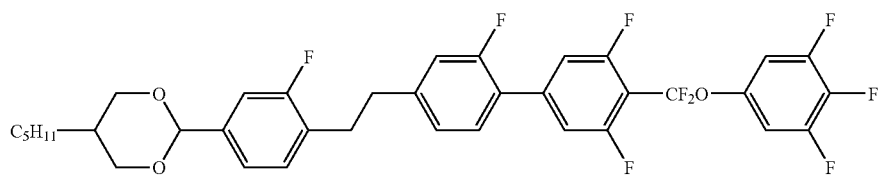
1-4-806
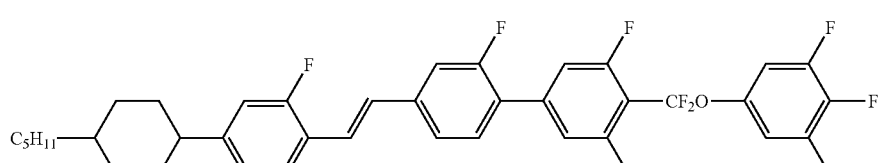
1-4-807
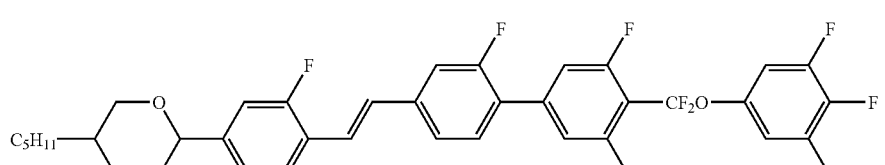
1-4-808

-continued
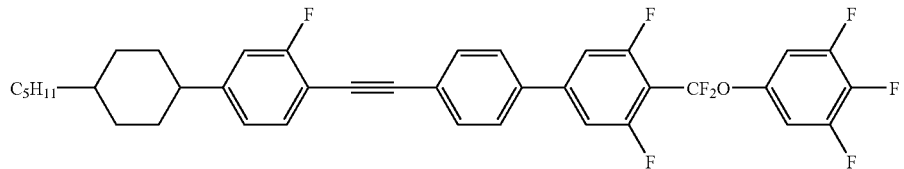 1-4-809
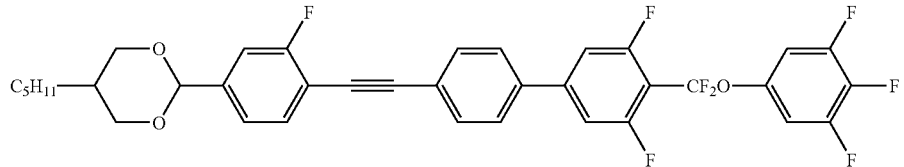 1-4-810
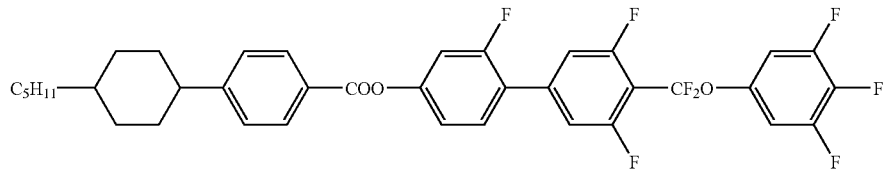 1-4-811
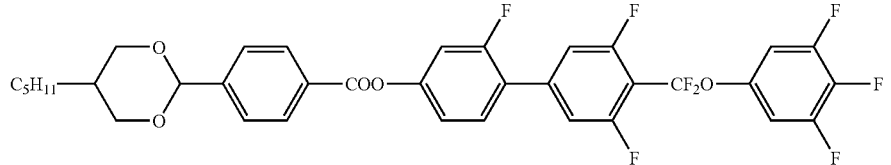 1-4-812
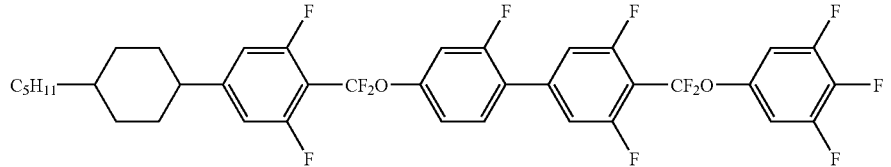 1-4-813
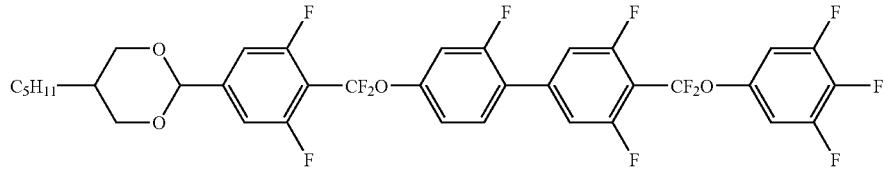 1-4-814
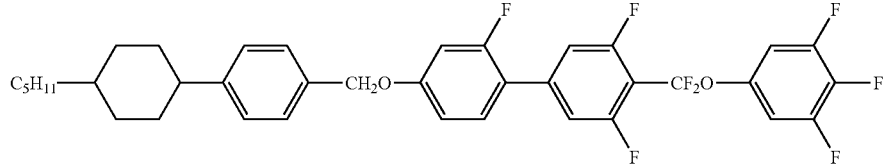 1-4-815
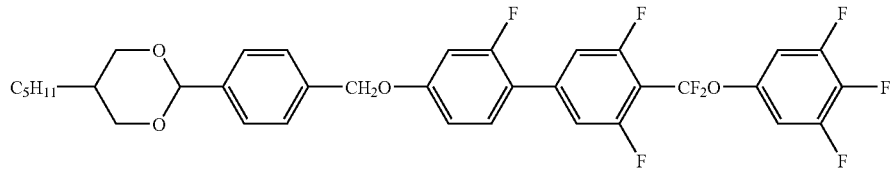 1-4-816
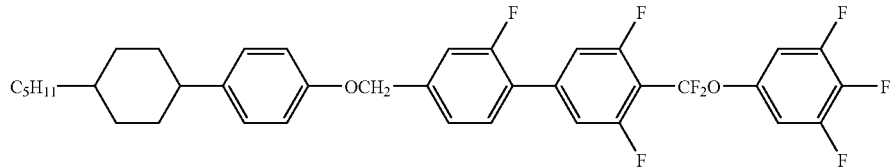 1-4-817

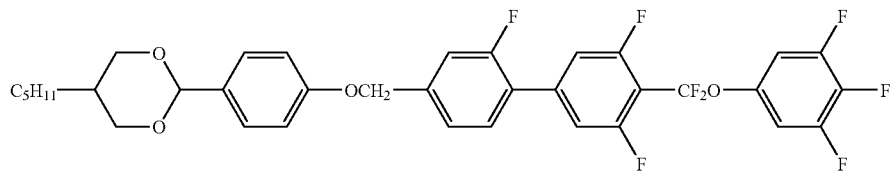 1-4-818
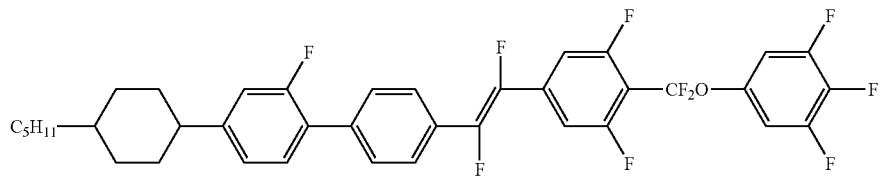 1-4-819
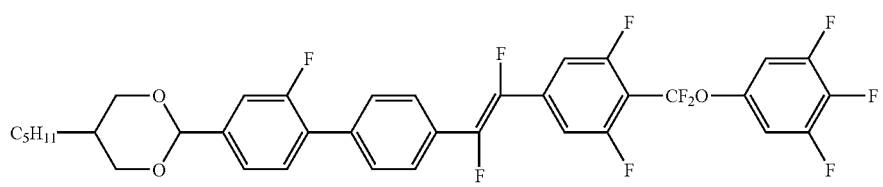 1-4-820
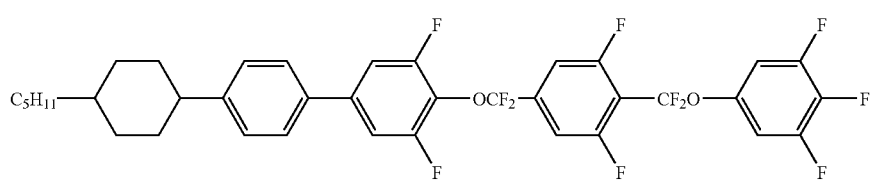 1-4-821
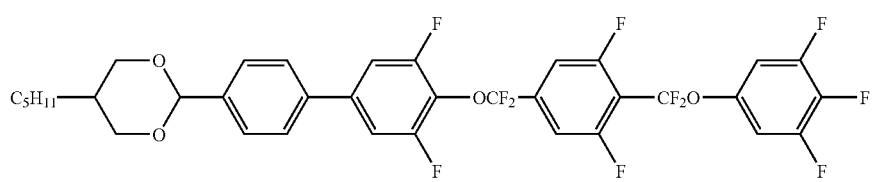 1-4-822
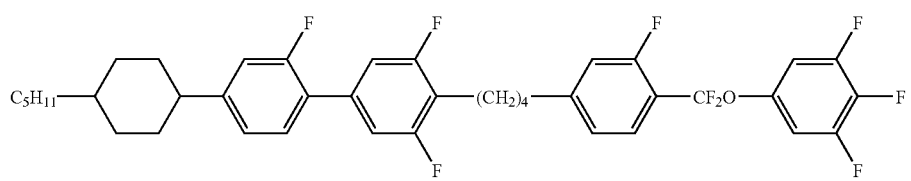 1-4-823
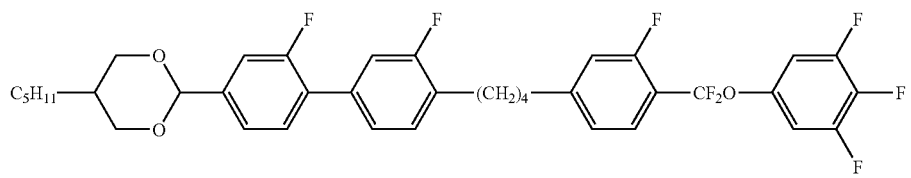 1-4-824
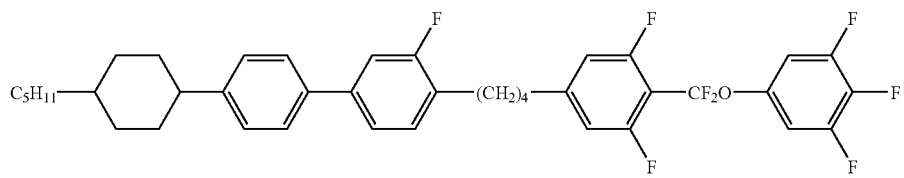 1-4-825
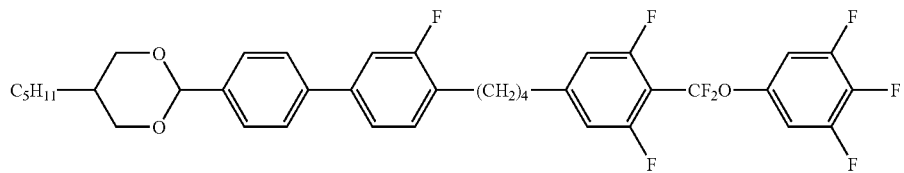 1-4-826

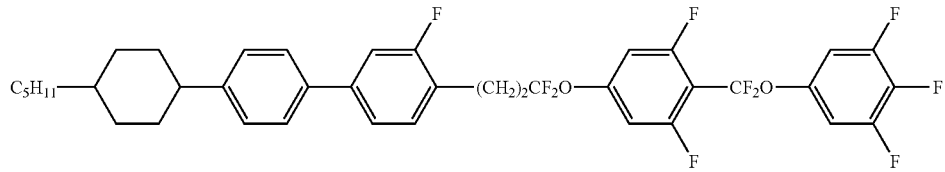
1-4-827
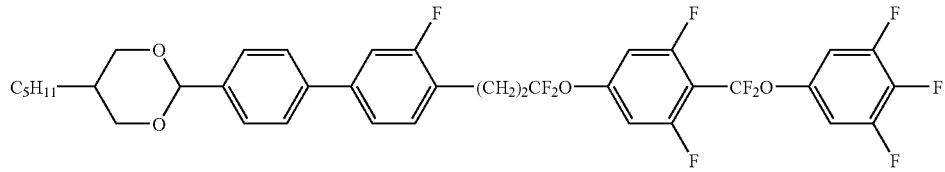
1-4-828
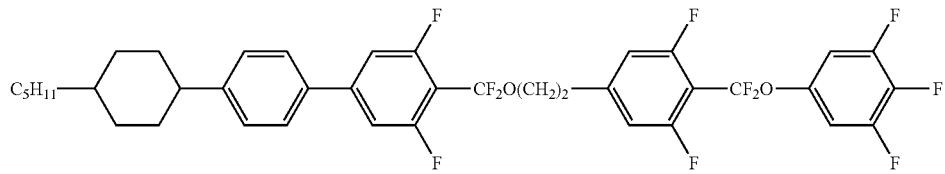
1-4-829
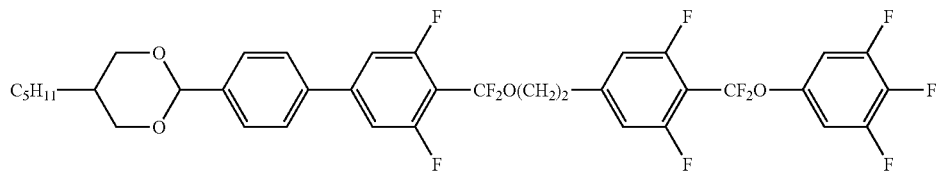
1-4-830
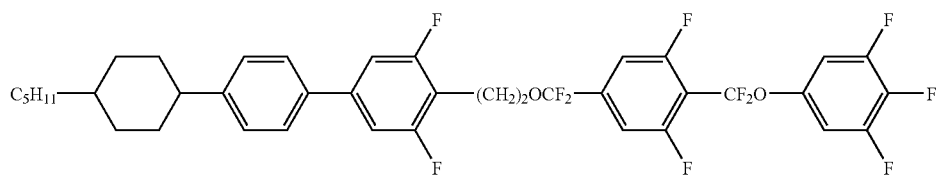
1-4-831
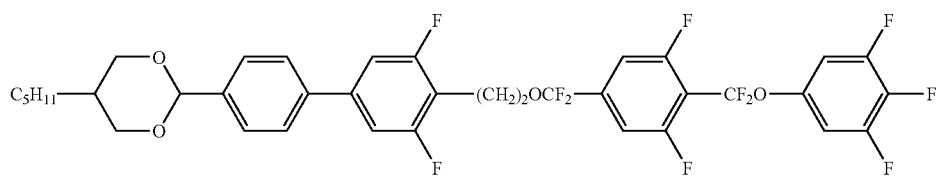
1-4-832
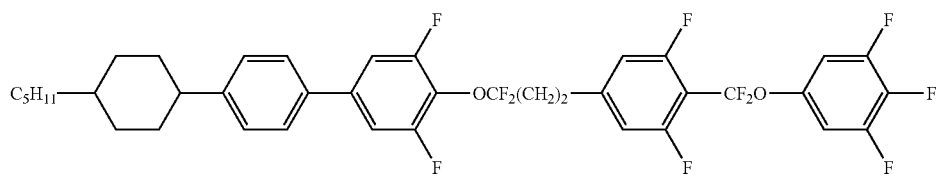
1-4-833
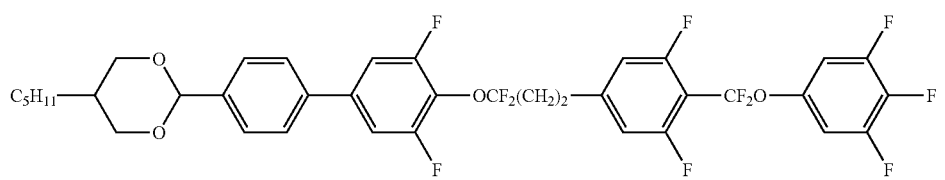
1-4-834
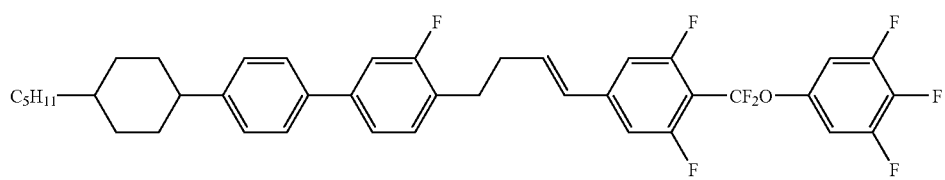
1-4-835

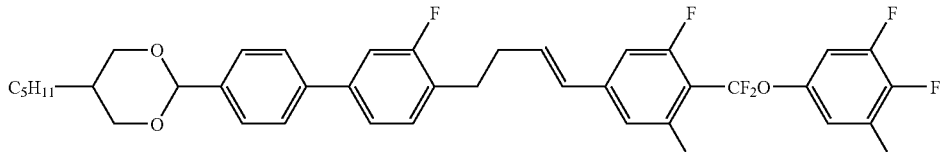

1-4-836

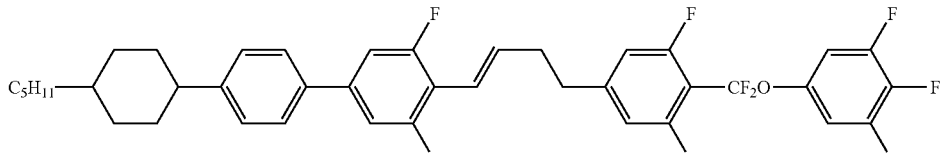

1-4-837

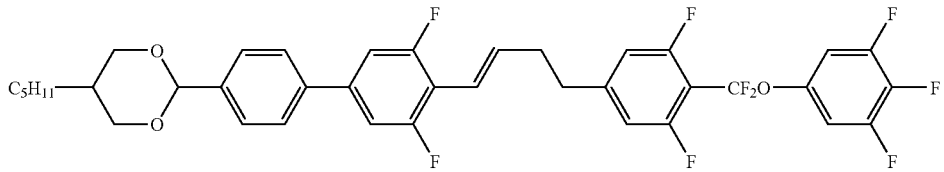

1-4-838

Comparative Example 1

4-[Difluoro[(2,3',4',5'-tetrafluoro[1,1'-biphenyl]-4-yl)oxy]methyl]-4'-(5-pentyltetrahydropyran-2-yl)-2',3,5,6'-tetrafluoro-1,1'-biphenyl (S-1-1) of a five-ring liquid crystal compound comprising a tetrahydropyran ring, which is disclosed in WO 2005/019378 A1, was synthesized as a comparative example.

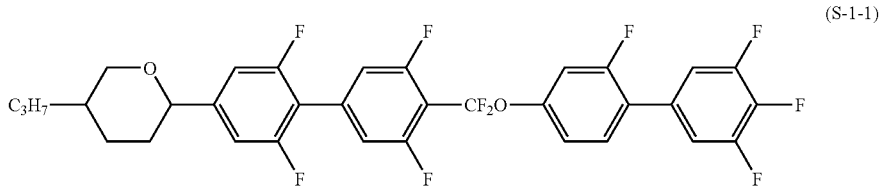

(S-1-1)

The phase transition temperature of the obtained comparative compound (S-1-1) was as follows.

Phase transition temperature: C 101 N 198 I.

The chemical shift δ (ppm) of $^1$H-NMR analysis was as indicated below, and the obtained compound was identified as 4-[difluoro[(2,3',4',5'-tetrafluoro [1,1'-biphenyl]-4-yl)oxy]methyl]-4'-(5-pentyltetrahydropyran-2-yl)-2',3,5,6'-tetrafluoro-1,1'-biphenyl. The measurement solvent was $CDCl_3$.

Chemical shift δ (ppm); 7.38 (dd, J=8.65 Hz, J=8.40 Hz, 1H), 7.23-7.11 (m, 6H), 7.08-7.00 (m, 2H), 4.28 (dd, J=11.8 Hz, J=1.95 Hz, 1H), 4.10 (dq, J=11.2 Hz, J=2.00 Hz, 1H), 3.21 (t, J=11.2 Hz, 1H), 2.05-1.98 (m, 1H), 1.95-1.88 (m, 1H), 1.73-1.62 (m, 1H), 1.60-1.48 (m, 1H), 1.45-1.09 (m, 5H), 0.92 (t, J=6.80 Hz, 3H).

The liquid crystal composition Q consisting of the mother liquid crystals A (85% by weight) and the comparative compound (S-1-1; 15% by weight) was prepared. The physical property values of the obtained liquid crystal composition Q were measured, and the extrapolated values of the physical properties of the comparative compound (S-1-1) were calculated by extrapolating the measured values. The values were as follows.

Maximum temperature $(T_{NI})$=118° C.; dielectric anisotropy $(\Delta\epsilon)$=52.3; refractive index anisotropy $(\Delta n)$=0.177.

The comparative compound (S-1-1) is compared with the compounds of the invention shown in the Examples (No. 1-4-5, No. 1-3-5, No. 1-3-3, No. 1-3-70, No. 1-4-13, No. 1-2-3, No. 1-4-53, No. 1-4-305, No. 1-4-319, No. 1-4-333, No. 1-3-255, No. 1-3-449, No. 1-4-343, No. 1-4-348, and No. 1-4-667). First, when each phase transition temperature is compared, the compounds (No. 1-4-5, No. 1-3-5, No. 1-3-3, No. 1-3-70, No. 1-4-13, No. 1-2-3, No. 1-4-53, No. 1-4-305, No. 1-4-319, No. 1-4-333, No. 1-3-255, No. 1-3-449, No. 1-4-343, No. 1-4-348, and No. 1-4-667) have a wider temperature range of liquid crystal phases. In particular, the compounds of the invention have a lower minimum temperature of the liquid crystal phases, and a higher compatibility with other compounds. When the comparative compound (S-1-1) and the compound (No. 1-3-3) of the present invention both in which $R^1$ is propyl are compared, the compound (No. 1-3-3) has a wider temperature range of liquid crystal phases, and a lower minimum temperature of the liquid crystal phases.

Next, when the comparative compound (S-1-1) and the compounds of the invention with regard to the extrapolated values of the physical properties are compared, the compounds (No. 1-4-5, No. 1-3-5, No. 1-3-3, No. 1-3-70, No. 1-4-13, No. 1-2-3, No. 1-4-53, No. 1-4-305, No. 1-4-319, No. 1-4-333, No. 1-3-255, No. 1-3-449, No. 1-4-343, No. 1-4-348, and No. 1-4-667) have a higher clearing point. Therefore, it can be concluded that the compounds (No. 1-4-5, No. 1-3-5, No. 1-3-3, No. 1-3-70, No. 1-4-13, No. 1-2-3, No. 1-4-53, No. 1-4-305, No. 1-4-319, No. 1-4-333, No. 1-3-255, No. 1-3-449, No. 1-4-343, No. 1-4-348, and No. 1-4-667) are excellent liquid crystal compounds usable in a wider temperature range.

Further, when the comparative compound (S-1-1) and the compounds of the invention are compared with regard to the refractive index anisotropy, the compounds (No. 1-4-5, No. 1-3-5, No. 1-3-3, No. 1-3-70, No. 1-4-13, No. 1-2-3, No. 1-4-53, No. 1-4-305, No. 1-4-319, No. 1-4-333, No. 1-3-255, No. 1-3-449, No. 1-4-343, No. 1-4-348, and No. 1-4-667) exhibit a larger refractive index anisotropy. Therefore, it can be concluded that the compounds (No. 1-4-5, No. 1-3-5, No. 1-3-3, No. 1-3-70, No. 1-4-13, No. 1-2-3, No. 1-4-53, No. 1-4-305, No. 1-4-319, No. 1-4-333, No. 1-3-255, No. 1-3-449, No. 1-4-343, No. 1-4-348, and No. 1-4-667) are excellent liquid crystal compounds having a larger refractive index anisotropy which can provide liquid crystal compositions necessary for manufacturing liquid crystal display devices capable of a high-speed response.

Comparative Example 2

Further, 4-[difluoro(3,4,5-trifluorophenoxy)methyl]-3,5-difluoro-4'-(4-propylcyclohexyl)-1,1'-biphenyl of a four-ring liquid crystal compound having a $CF_2O$ bonding group, which is disclosed in WO 96/11897 A1, was synthesized as a comparative example.

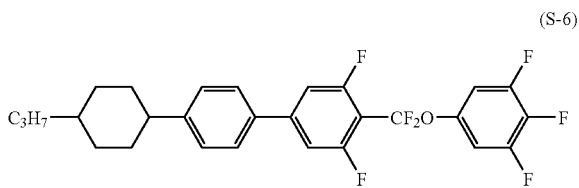

(S-6)

The phase transition temperature of the obtained comparative compound (S-6) was as follows.

Phase transition temperature: C 82.1 N 141 I.

The chemical shift δ (ppm) of $^1$H-NMR analysis was as indicated below, and the obtained compound was identified as 4-[difluoro(3,4,5-trifluorophenoxy)methyl]-3,5-difluoro-4'-(4-propylcyclohexyl)-1,1'-biphenyl. The measurement solvent was $CDCl_3$.

Chemical shift δ (ppm); 7.49 (d, J=8.23 Hz, 2H), 7.32 (d, J=8.23 Hz, 2H), 7.20 (d, J=10.6 Hz, 2H), 7.03-6.90 (m, 2H), 2.53 (tt, J=12.1 Hz, J=3.00 Hz, 1H), 1.97-1.86 (m, 4H), 1.51-1.40 (m, 2H), 1.40-1.18 (m, 4H), 1.13-1.01 (m, 2H), 0.91 (t, J=7.20 Hz, 3H).

The liquid crystal composition R consisting of the mother liquid crystals A (85% by weight) and the comparative compound (S-6; 15% by weight) was prepared. The physical property values of the obtained liquid crystal composition R were measured, and the extrapolated values of the physical properties of the comparative compound (S-6) were calculated by extrapolating the measured values. The values were as follows.

Maximum temperature $(T_{NI})$=110° C.; dielectric anisotropy (Δ∈)=23.4; refractive index anisotropy (Δn)=0.157.

The comparative compound (S-6) is compared with the compounds of the invention shown in Examples (No. 1-4-5, No. 1-3-5, No. 1-3-3, No. 1-3-70, No. 1-4-13, No. 1-2-3, No. 1-4-53, No. 1-4-305, No. 1-4-319, No. 1-4-333, No. 1-3-255, No. 1-3-449, No. 1-4-343, No. 1-4-348, and No. 1-4-667). First, when each phase transition temperature is compared, the compounds (No. 1-4-5, No. 1-3-5, No. 1-3-3, No. 1-3-70, No. 1-4-13, No. 1-2-3, No. 1-4-53, No. 1-4-305, No. 1-4-319, No. 1-4-333, No. 1-3-255, No. 1-3-449, No. 1-4-343, No. 1-4-348, and No. 1-4-667) have a wider temperature range of liquid crystal phases. In particular, the compounds of the invention have a higher maximum temperature of the liquid crystal phases.

Next, when the comparative compound (S-6) and the compounds of the invention with regard to the extrapolated values of the physical properties are compared, the compounds (No. 1-4-5, No. 1-3-5, No. 1-3-3, No. 1-3-70, No. 1-4-13, No. 1-2-3, No. 1-4-53, No. 1-4-305, No. 1-4-319, No. 1-4-333, No. 1-3-255, No. 1-3-449, No. 1-4-343, No. 1-4-348, and No. 1-4-667) have a higher clearing point. Therefore, it can be concluded that the compounds (No. 1-4-5, No. 1-3-5, No. 1-3-3, No. 1-3-70, No. 1-4-13, No. 1-2-3, No. 1-4-53, No. 1-4-305, No. 1-4-319, No. 1-4-333, No. 1-3-255, No. 1-3-449, No. 1-4-343, No. 1-4-348, and No. 1-4-667) are excellent liquid crystal compounds usable in a wider temperature range.

Further, when the comparative compound (S-6) and the compounds of the invention are compared with regard to the refractive index anisotropy, the compounds (No. 1-4-5, No. 1-3-5, No. 1-3-3, No. 1-3-70, No. 1-4-13, No. 1-2-3, No. 1-4-53, No. 1-4-305, No. 1-4-319, No. 1-4-333, No. 1-3-255, No. 1-3-449, No. 1-4-343, No. 1-4-348, and No. 1-4-667) exhibit a larger refractive index anisotropy. Therefore, it can be concluded that the compounds (No. 1-4-5, No. 1-3-5, No. 1-3-3, No. 1-3-70, No. 1-4-13, No. 1-2-3, No. 1-4-53, No. 1-4-305, No. 1-4-319, No. 1-4-333, No. 1-3-255, No. 1-3-449, No. 1-4-343, No. 1-4-348, and No. 1-4-667) are excellent liquid crystal compounds which can provide liquid crystal compositions having a larger refractive index anisotropy necessary for manufacturing liquid crystal display devices capable of a high-speed response.

Example 32

Further, the representative compositions of the invention were summarized in [Composition Example 1] to [Composition Example 31]. First, compounds as the components of a composition and their amounts (% by weight) were shown. The compounds were represented by means of the symbols of left-terminal groups, bonding groups, ring structures, and right-terminal groups according to the definition in Table 1. The configuration of 1,4-cyclohexylene and 1,3-dioxane-2,5-diyl is trans. When there are no symbols of terminal groups, the terminal groups mean hydrogen. Next, the physical property values of the compositions were shown. The physical property values here are measured value.

TABLE 1

Method of Description of Compounds Using Symbols
R—(A$_1$)—Z$_1$—...—Z$_n$—(A$_n$)—R'

| 1) Left-Terminal Group (R—) | Symbol |
|---|---|
| C$_n$H$_{2n+1}$— | n— |
| C$_n$H$_{2n+1}$O— | nO— |

TABLE 1-continued

Method of Description of Compounds Using Symbols
R—(A₁)—Z₁— ... —Zₙ—(Aₙ)—R'

| | |
|---|---|
| $C_nH_{2n+1}OC_mH_{2m}$— | nOm— |
| $CH_2$=C— | V— |
| $CH_2$=CH$C_nH_{2n}$— | Vn— |
| $C_nH_{2n+1}$CH=CH— | nV— |
| $C_nH_{2n+1}$CH=CH$C_mH_{2m}$— | nVm— |
| $CF_2$=CH— | VFF— |
| $CF_2$=CH$C_nH_{2n}$— | VFFn— |

| 2) Ring Structure (—Aₙ—) | Symbol |
|---|---|
|  | B |
| 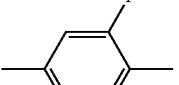 | B(F) |
| 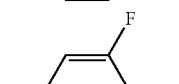 | B(F, F) |
| 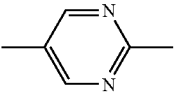 | Py |
| 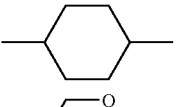 | H |
| 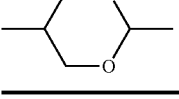 | G |

| 3) Bonding Group (—Zₙ—) | Symbol |
|---|---|
| —$C_2H_4$— | 2 |
| —$C_4H_8$— | 4 |
| —CH=CH— | V |
| —$CF_2$O— | X |
| —COO— | E |
| —C≡C— | T |

| 4) Right-Terminal Group (—R') | Symbol |
|---|---|
| —$C_nH_{2n+1}$ | —n |
| —O$C_nH_{2n+1}$ | —On |
| —CH=$CH_2$ | —V |
| —CH=CH$C_nH_{2n+1}$ | —Vn |
| —$C_nH_{2n}$CH=$CH_2$ | —nV |
| —$C_nH_{2n}$CH=CH$C_mH_{2m+1}$ | —nVm |
| —CH=$CF_2$ | —VFF |
| —COO$CH_3$ | —EMe |
| —F | —F |
| —Cl | —CL |
| —CN | —C |
| —O$CF_2$H | —OCF2H |
| —O$CF_3$ | —OCF3 |
| —$CF_3$ | —CF3 |

TABLE 1-continued

Method of Description of Compounds Using Symbols
R—(A₁)—Z₁—...—Zₙ—(Aₙ)—R'

5) Example of Description

Example 1. 5-HB (F) B (F, F) XB (F) B (F, F)-F

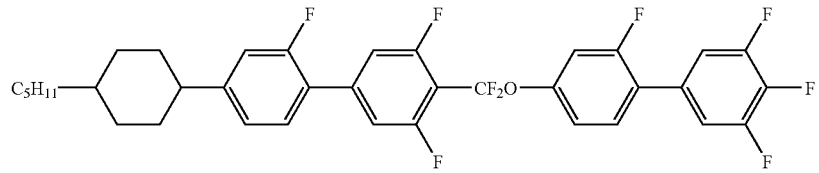

Example 2. 5-HBB (F) B-3

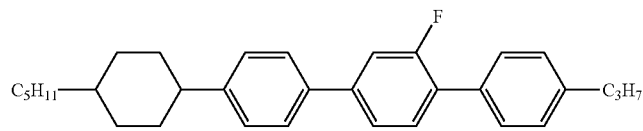

Example 3. 3-HH-V

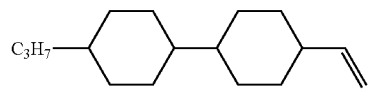

Physical property values can be measured according to the following methods. Most of the methods are described in the Standard of Electronic Industries Association of Japan, EIAJ.ED-2521 A, or those with some modifications. No TFT was attached to TN devices used for measurement.

Maximum Temperature of Nematic Phase (NI; ° C.): A sample was put on a hot plate in a melting point apparatus equipped with a polarizing microscope, and heated at the rate of 1° C. per minute. A temperature was measured when part of sample changed from a nematic phase to an isotropic liquid. The maximum temperature of the nematic phase may be abbreviated to "a maximum temperature".

Minimum Temperature of Nematic Phase ($T_C$; ° C.): Samples having a nematic phase were respectively kept in freezers at 0° C., −10° C., −20° C., −30° C. and −40° C. for ten days, and then liquid crystal phases were observed. For example, when a sample still remained in a nematic phase at −20° C., and changed to crystals (or a smectic phase) at −30° C., $T_C$ was expressed as ≦−20° C. The minimum temperature of a nematic phase may be abbreviated to "a minimum temperature".

Viscosity (η; measured at 20° C.; mPa·s): An E-type viscometer was used for measurement.

Rotational Viscosity (γ1; measured at 25° C.; mPa·s):
1) Samples having a positive dielectric anisotropy: Measurement was carried out according to the method described in M. Imai, et al., Molecular Crystals and Liquid Crystals, Vol. 259, 37 (1995). A sample was put in a TN device having a twist angle of 0 degrees and a distance between two glass plates (cell gap) of 5 micrometers. Voltage was applied to the TN device in the range of 16 V to 19.5 V stepwise for every 0.5 V. After 0.2 second of no voltage application, the voltage application was repeated with only one rectangular wave (rectangular pulse; 0.2 second) and no voltage application (2 seconds). The peak current and the peak time of a transient current generated by the voltage applied were measured. The value of rotational viscosity was obtained from the measured values and the calculating equation (8) in page 40 of the article reported by M. Imai, et al. The value of dielectric anisotropy necessary for the calculation was determined with the device used for the measurement of the rotational viscosity according to the method for measuring dielectric anisotropy to be described below.

Samples having a negative dielectric anisotropy: Measurement was carried out according to the method described in M. Imai, et al., Molecular Crystals and Liquid Crystals, Vol. 259, 37 (1995). A sample was put in a VA device having a distance between two glass plates (cell gap) of 20 micrometers. Voltage was applied to the device in the range of 30 V to 50 V stepwise for every 1 V. After 0.2 second of no voltage application, the voltage application was repeated with only one rectangular wave (rectangular pulse; 0.2 second) and no voltage application (2 seconds). The peak current and the peak time of a transient current generated by the applied voltage were measured. The value of rotational viscosity was obtained from the measured values and the calculating equation (8) in page 40 of the article presented by M. Imai, et al., p. 40. The value measured in the following dielectric anisotropy was used for the dielectric anisotropy necessary for the calculation.

Optical Anisotropy (refractive index anisotropy; Δn; measured at 25° C.): Measurement was carried out with an Abbe refractometer equipped with a polarizing plate on an ocular by using light at a wavelength of 589 nm. The surface of a main prism was rubbed in one direction, and then a sample was dropped on the main prism. A refractive index (n∥) was measured when a direction of polarized light was parallel to the direction of the rubbing. A refractive index (n⊥) was measured when a direction of polarized light was perpendicular to the direction of the rubbing. The value of optical anisotropy was calculated from the equation: Δn=n∥−n⊥. When a sample was a composition, optical anisotropy was measured based on this method. When a sample was a compound, the compound was mixed in a suitable composition, and then the optical anisotropy was measured. Extrapolated values were employed for optical anisotropy of compounds.

Dielectric Anisotropy (Δ∈; measured at 25° C.): When a sample was a compound, the compound was mixed in a suitable composition, and then dielectric anisotropy was measured. The dielectric anisotropy of the compound was expressed by an extrapolated value.

1) Compositions having a positive dielectric anisotropy: A sample was put in a liquid crystal cell having a distance between two glass plates (gap) of about 9 micrometers (μm) and a twist angle of 80 degrees. A voltage of 20 V was applied to the cell and a dielectric constant (∈||) in a major axis direction of liquid crystal molecules was measured. A voltage of 0.5 V was applied to measure a dielectric constant (∈⊥) in the minor axis direction of the liquid crystal molecules. The value of dielectric anisotropy was calculated from the equation: Δ∈=∈||−∈⊥.

2) Compositions having a negative dielectric anisotropy: A sample was put in a liquid crystal cell treated to a homeotropic orientation and a voltage of 0.5 V was applied to measure a dielectric constant (∈||). A sample was put in a liquid crystal cell treated to a homeotropic orientation and a voltage of 0.5 V was applied to measure a dielectric constant (∈⊥). The value of dielectric anisotropy was calculated from the equation: Δ∈=∈||−∈⊥.

Threshold Voltage (Vth; measured at 25° C.; V): When a sample was a compound, the compound was mixed in a suitable composition, and then threshold voltage was measured. The threshold voltage of the compound was expressed by an extrapolated value. 1) Compositions having a positive dielectric anisotropy: A sample was put in a liquid crystal display device with a normally white mode, having a distance between two glass plates (gap) of (0.5/Δn) micrometer and a twist angle of 80 degrees. Δn is a value of optical anisotropy measured by the above-described method. Rectangular waves having a frequency of 32 Hz were applied to the device. The voltage of the rectangular waves was increased and a voltage value was measured when the transmittance of light passing through the device became 90%.

Compositions having a negative dielectric anisotropy: A sample was put in a liquid crystal display device with a normally black mode, having a distance between two glass plates (gap) of about 9 micrometers and treated to a homeotropic orientation. Rectangular waves having a wavelength of 32 Hz were applied to the device. The voltage of the rectangular waves was increased and a voltage value was measured when the transmittance of light passing through the device became 10%.

Voltage Holding Ratio (VHR; measured at 25° C.; %): A TN device used for measurement had a polyimide-alignment film and a distance between two glass plates (cell gap) of 6 micrometers. A sample was put in the device, and then the device was sealed with an adhesive polymerizable by ultraviolet light. Pulse voltage was applied (60 microseconds at 5 V) to charge the TN device. Decreasing voltage was measured for 16.7 milliseconds with a High Speed Voltmeter, and an area A between a voltage curve and a horizontal axis in a unit cycle was determined. An area B was an area without decreasing. A voltage holding ratio was the percentage of the area A to the area B.

Helical Pitch (measured at 20° C.; μm): The Cano's wedge cell method was used for the measurement of a helical pitch. A sample was poured into Cano's wedge cell and a distance between disclination lines (a; μm) was measured on the cell. A helical pitch (P) was calculated from the equation: P=2·a·tan θ. The symbol θ was an angle between two glass plates in the wedge cell.

The ratio (percentage) of a component or a liquid crystal compound means a weight percentage (% by weight) based on the total weight of liquid crystal compounds. A composition was prepared by mixing, after measuring the weight of components such as liquid crystal compounds. Consequently, the weight % of the components can be easily calculated.

Composition Example 1

| | |
|---|---|
| 5-BB(F)B(F,F)XB(F)B(F,F)—F | 5% |
| 5-BB(F)B(F,F)XB(F)B(F)—OCF3 | 5% |
| 2-BEB(F)—C | 5% |
| 3-BEB(F)—C | 4% |
| 4-BEB(F)—C | 12% |
| 1V2—BEB(F,F)—C | 12% |
| 3-HB—O2 | 10% |
| 3-HH-4 | 3% |
| 3-HHB—F | 3% |
| 3-HHB-1 | 4% |
| 3-HHB—O1 | 4% |
| 3-HBEB—F | 4% |
| 3-HHEB—F | 6% |
| 5-HHEB—F | 6% |
| 3-H2BTB-2 | 4% |
| 3-H2BTB-3 | 4% |
| 3-H2BTB-4 | 4% |
| 3-HB(F)TB-2 | 5% |

NI = 94.4° C.; Δn = 0.154; Δε = 28.7; Vth = 1.02 V.

Composition Example 2

| | |
|---|---|
| 5-BB(F)B(F,F)XB(F)B(F,F)—F | 5% |
| 5-BB(F)B(F)B(F,F)XB(F,F)—F | 5% |
| 2-HB—C | 5% |
| 3-HB—C | 10% |
| 3-HB—O2 | 15% |
| 2-BTB-1 | 3% |
| 3-HHB—F | 4% |
| 3-HHB-1 | 8% |
| 3-HHB—O1 | 5% |
| 3-HHB-3 | 6% |
| 3-HHEB—F | 4% |
| 5-HHEB—F | 4% |
| 2-HHB(F)—F | 7% |
| 3-HHB(F)—F | 7% |
| 5-HHB(F)—F | 7% |
| 3-HHB(F,F)—F | 5% |

NI = 103.7° C.; Δn = 0.114; Δε = 8.0; Vth = 2.01 V.

Composition Example 3

| | |
|---|---|
| 5-BB(F,F)XB(F)B(F)B(F,F)—F | 5% |
| 5-BB(F)B(F,F)B(F,F)XB(F,F)—F | 5% |
| 3-BEB(F)—C | 8% |
| 3-HB—C | 8% |
| V—HB—C | 8% |
| 1V—HB—C | 8% |
| 3-HB—O2 | 3% |
| 3-HH—2V | 11% |
| 3-HH—2V1 | 7% |
| V2—HHB-1 | 8% |
| 3-HHB-1 | 5% |
| 3-HHEB—F | 7% |
| 3-H2BTB-2 | 6% |
| 3-H2BTB-3 | 6% |
| 3-H2BTB-4 | 5% |

Composition Example 4

| Component | % |
|---|---|
| 5-BB(F)B(F,F)XB(F)B(F)—OCF3 | 6% |
| 5-BB(F,F)XB(F)B(F)B(F,F)—F | 6% |
| 5-BEB(F)—C | 5% |
| V—HB—C | 11% |
| 5-PyB—C | 6% |
| 4-BB-3 | 11% |
| 3-HH—2V | 10% |
| 5-HH—V | 11% |
| V—HHB-1 | 7% |
| V2—HHB-1 | 9% |
| 3-HHB-1 | 9% |
| 1V2—HBB-2 | 4% |
| 3-HHEBH-3 | 5% |

Composition Example 5

| Component | % |
|---|---|
| 5-BB(F)B(F)B(F,F)XB(F,F)—F | 4% |
| 5-BB(F)B(F,F)B(F,F)XB(F,F)—F | 4% |
| 1V2—BEB(F,F)—C | 6% |
| 3-HB—C | 18% |
| 2-BTB-1 | 10% |
| 5-HH—VFF | 22% |
| 3-HHB-1 | 4% |
| VFF—HHB-1 | 8% |
| VFF2—HHB-1 | 11% |
| 3-H2BTB-2 | 5% |
| 3-H2BTB-3 | 4% |
| 3-H2BTB-4 | 4% |

Composition Example 6

| Component | % |
|---|---|
| 5-BB(F)B(F,F)XB(F)B(F,F)—F | 3% |
| 5-BB(F)B(F,F)XB(F)B(F)—OCF3 | 3% |
| 5-BB(F)B(F)B(F,F)XB(F,F)—F | 3% |
| 5-HB—CL | 19% |
| 3-HH-4 | 12% |
| 3-HH-5 | 4% |
| 3-HHB—F | 4% |
| 3-HHB—CL | 3% |
| 4-HHB—CL | 4% |
| 3-HHB(F)—F | 6% |
| 4-HHB(F)—F | 6% |
| 5-HHB(F)—F | 6% |
| 7-HHB(F)—F | 6% |
| 5-HBB(F)—F | 4% |
| 1O1—HBBH-5 | 3% |
| 3-HHBB(F,F)—F | 2% |
| 4-HHBB(F,F)—F | 3% |
| 5-HHBB(F,F)—F | 3% |
| 3-HH2BB(F,F)—F | 3% |
| 4-HH2BB(F,F)—F | 3% |

NI = 116.3° C.; Δn = 0.105; Δε = 6.4; Vth = 1.93 V.

A pitch measured when 0.25 part of optically active compound (Op-5) was added to 100 parts the above composition was 61.5 micrometers.

Composition Example 7

| Component | % |
|---|---|
| 5-BB(F)B(F,F)XB(F)B(F,F)—F | 5% |
| 5-BB(F,F)XB(F)B(F)B(F,F)—F | 5% |
| 3-HHB(F,F)—F | 9% |
| 3-H2HB(F,F)—F | 8% |
| 4-H2HB(F,F)—F | 8% |
| 5-H2HB(F,F)—F | 8% |
| 3-HBB(F,F)—F | 21% |
| 5-HBB(F,F)—F | 15% |
| 3-H2BB(F,F)—F | 5% |
| 5-HHBB(F,F)—F | 3% |
| 5-HHEBB—F | 3% |
| 3-HH2BB(F,F)—F | 2% |
| 1O1—HBBH-4 | 4% |
| 1O1—HBBH-5 | 4% |

Composition Example 8

| Component | % |
|---|---|
| 5-BB(F)B(F,F)XB(F)B(F)—OCF3 | 5% |
| 5-BB(F)B(F,F)B(F,F)XB(F,F)—F | 5% |
| 5-HB—F | 12% |
| 6-HB—F | 9% |
| 7-HB—F | 7% |
| 2-HHB—OCF3 | 7% |
| 3-HHB—OCF3 | 7% |
| 4-HHB—OCF3 | 7% |
| 5-HHB—OCF3 | 5% |
| 3-HH2B—OCF3 | 4% |
| 5-HH2B—OCF3 | 4% |
| 3-HHB(F,F)—OCF2H | 4% |
| 3-HHB(F,F)—OCF3 | 5% |
| 3-HH2B(F)—F | 3% |
| 3-HBB(F)—F | 5% |
| 5-HBB(F)—F | 5% |
| 5-HBBH-3 | 3% |
| 3-HB(F)BH-3 | 3% |

Composition Example 9

| Component | % |
|---|---|
| 5-BB(F)B(F)B(F,F)XB(F,F)—F | 4% |
| 5-BB(F,F)XB(F)B(F)B(F,F)—F | 4% |
| 5-HB—CL | 11% |
| 3-HH-4 | 8% |
| 3-HHB-1 | 5% |
| 3-HHB(F,F)—F | 8% |
| 3-HBB(F,F)—F | 20% |
| 5-HBB(F,F)—F | 7% |
| 3-HHEB(F,F)—F | 10% |
| 4-HHEB(F,F)—F | 3% |
| 5-HHEB(F,F)—F | 3% |
| 2-HBEB(F,F)—F | 3% |
| 3-HBEB(F,F)—F | 5% |
| 5-HBEB(F,F)—F | 3% |
| 3-HHBB(F,F)—F | 6% |

Composition Example 10

| | |
|---|---|
| 5-BB(F)B(F,F)B(F,F)XB(F,F)—F | 5% |
| 3-HB—CL | 6% |
| 5-HB—CL | 4% |
| 3-HHB—OCF3 | 5% |
| 3-H2HB—OCF3 | 5% |
| 5-H4HB—OCF3 | 15% |
| V—HHB(F)—F | 5% |
| 3-HHB(F)—F | 5% |
| 5-HHB(F)—F | 5% |
| 3-H4HB(F,F)—CF3 | 8% |
| 5-H4HB(F,F)—CF3 | 10% |
| 5-H2HB(F,F)—F | 5% |
| 5-H4HB(F,F)—F | 7% |
| 2-H2BB(F)—F | 5% |
| 3-H2BB(F)—F | 5% |
| 3-HBEB(F,F)—F | 5% |

Composition Example 11

| | |
|---|---|
| 5-BB(F)B(F,F)XB(F)B(F,F)—F | 5% |
| 5-BB(F)B(F,F)B(F,F)XB(F,F)—F | 5% |
| 5-HB—CL | 17% |
| 7-HB(F,F)—F | 3% |
| 3-HH-4 | 10% |
| 3-HH-5 | 5% |
| 3-HB—O2 | 15% |
| 3-HHB-1 | 5% |
| 3-HHB—O1 | 4% |
| 2-HHB(F)—F | 5% |
| 3-HHB(F)—F | 5% |
| 5-HHB(F)—F | 5% |
| 3-HHB(F,F)—F | 6% |
| 3-H2HB(F,F)—F | 5% |
| 4-H2HB(F,F)—F | 5% |

Composition Example 12

| | |
|---|---|
| 5-BB(F)B(F,F)XB(F)B(F,F)—F | 4% |
| 5-BB(F)B(F,F)XB(F)B(F)—OCF3 | 4% |
| 5-HB—CL | 3% |
| 7-HB(F)—F | 7% |
| 3-HH-4 | 9% |
| 3-HH-EMe | 23% |
| 3-HHEB—F | 6% |
| 5-HHEB—F | 6% |
| 3-HHEB(F,F)—F | 10% |
| 4-HHEB(F,F)—F | 5% |
| 4-HGB(F,F)—F | 5% |
| 5-HGB(F,F)—F | 6% |
| 2-H2GB(F,F)—F | 4% |
| 3-H2GB(F,F)—F | 5% |
| 5-GHB(F,F)—F | 3% |

NI = 83.7° C.; Δn = 0.077; Δε = 7.4; Vth = 1.40 V.

Composition Example 13

| | |
|---|---|
| 5-BB(F)B(F)B(F,F)XB(F,F)—F | 3% |
| 5-BB(F,F)XB(F)B(F)B(F,F)—F | 4% |
| 5-BB(F)B(F,F)B(F,F)XB(F,F)—F | 3% |
| 3-HH-4 | 8% |
| 3-HHB-1 | 6% |
| 3-HHB(F,F)—F | 10% |
| 3-H2HB(F,F)—F | 9% |
| 3-HBB(F,F)—F | 15% |
| 3-BB(F,F)XB(F,F)—F | 25% |
| 1O1—HBBH-5 | 7% |
| 2-HHBB(F,F)—F | 3% |
| 3-HHBB(F,F)—F | 3% |
| 3-HH2BB(F,F)—F | 4% |

Composition Example 14

| | |
|---|---|
| 5-BB(F)B(F,F)XB(F)B(F)—OCF3 | 4% |
| 5-BB(F)B(F)B(F,F)XB(F,F)—F | 4% |
| 5-HB—CL | 13% |
| 3-HB—O2 | 10% |
| 3-PyB(F)—F | 10% |
| 5-PyB(F)—F | 10% |
| 3-HHB(F,F)—F | 7% |
| 3-PyBB—F | 8% |
| 4-PyBB—F | 7% |
| 5-PyBB—F | 7% |
| 5-HBB(F)B-2 | 10% |
| 5-HBB(F)B-3 | 10% |

NI = 100.9° C.; Δn = 0.191; Δε = 9.4; Vth = 1.85 V.

Composition Example 15

| | |
|---|---|
| 5-BB(F)B(F,F)XB(F)B(F,F)—F | 5% |
| 5-BB(F)B(F)B(F,F)XB(F)—F | 5% |
| 2-BEB(F)—C | 5% |
| 3-BEB(F)—C | 4% |
| 4-BEB(F)—C | 12% |
| 1V2—BEB(F,F)—C | 12% |
| 3-HB—O2 | 10% |
| 3-HH-4 | 3% |
| 3-HHB—F | 3% |
| 3-HHB-1 | 4% |
| 3-HHB—O1 | 4% |
| 3-HBEB—F | 4% |
| 3-HHEB—F | 6% |
| 5-HHEB—F | 6% |
| 3-H2BTB-2 | 4% |
| 3-H2BTB-3 | 4% |
| 3-H2BTB-4 | 4% |
| 3-HB(F)TB-2 | 5% |

NI = 95.4° C.; Δn = 0.156; Δε = 28.4; Vth = 1.03 V.

Composition Example 16

| | |
|---|---|
| 5-HBB(F)B(F,F)XB(F,F)—F | 5% |
| 5-HB(F)B(F,F)XB(F)B(F,F)—F | 5% |
| 2-BEB(F)—C | 5% |
| 3-BEB(F)—C | 4% |
| 4-BEB(F)—C | 12% |
| 1V2—BEB(F,F)—C | 12% |
| 3-HB—O2 | 10% |
| 3-HH-4 | 3% |
| 3-HHB—F | 3% |
| 3-HHB-1 | 4% |

-continued

| | |
|---|---|
| 3-HHB—O1 | 4% |
| 3-HBEB—F | 4% |
| 3-HHEB—F | 6% |
| 5-HHEB—F | 6% |
| 3-H2BTB-2 | 4% |
| 3-H2BTB-3 | 4% |
| 3-H2BTB-4 | 4% |
| 3-HB(F)TB-2 | 5% |

NI = 96.1° C.; Δn = 0.150; Δε = 28.0; Vth = 1.04 V.

Composition Example 17

| | |
|---|---|
| 5-HB(F)B(F)B(F,F)—XB(F,F)—F | 5% |
| 5-HB(F)B(F,F)XB(F)B(F,F)—F | 5% |
| 2-HB—C | 5% |
| 3-HB—C | 10% |
| 3-HB—O2 | 15% |
| 2-BTB-1 | 3% |
| 3-HHB—F | 4% |
| 3-HHB-1 | 8% |
| 3-HHB—O1 | 5% |
| 3-HHB-3 | 6% |
| 3-HHEB—F | 4% |
| 5-HHEB—F | 4% |
| 2-HHB(F)—F | 7% |
| 3-HHB(F)—F | 7% |
| 5-HHB(F)—F | 7% |
| 3-HHB(F,F)—F | 5% |

NI = 103.6° C.; Δn = 0.108; Δε = 7.4; Vth = 2.07 V.

Composition Example 18

| | |
|---|---|
| 5-HB(F)B(F,F)B(F,F)XB(F,F)—F | 5% |
| 5-HB(F)B(F,F)XB(F)B(F,F)—F | 5% |
| 3-BEB(F)—C | 8% |
| 3-HB—C | 8% |
| V—HB—C | 8% |
| 1V—HB—C | 8% |
| 3-HB—O2 | 3% |
| 3-HH—2V | 11% |
| 3-HH—2V1 | 7% |
| V2—HHB-1 | 8% |
| 3-HHB-1 | 5% |
| 3-HHEB—F | 7% |
| 3-H2BTB-2 | 6% |
| 3-H2BTB-3 | 6% |
| 3-H2BTB-4 | 5% |

NI = 100.1° C.; Δn = 0.142; Δε = 11.8; Vth = 1.05 V.

Composition Example 19

| | |
|---|---|
| 5-HB(F)B(F)B(F,F)—XB(F,F)—F | 6% |
| 5-HB(F)B(F)B(F,F)—XB(F)—OCF3 | 6% |
| 5-BEB(F)—C | 5% |
| V—HB—C | 11% |
| 5-PyB—C | 6% |
| 4-BB-3 | 11% |
| 3-HH—2V | 10% |
| 5-HH—V | 11% |
| V—HHB-1 | 7% |
| V2—HHB-1 | 9% |
| 3-HHB-1 | 9% |

-continued

| | |
|---|---|
| 1V2—HBB-2 | 4% |
| 3-HHEBH-3 | 5% |

Composition Example 20

| | |
|---|---|
| 5-HB(F)B(F,F)B(F,F)XB(F,F)—F | 4% |
| 5-HB(F)B(F,F)B(F,F)XB(F)—OCF3 | 4% |
| 1V2—BEB(F,F)—C | 6% |
| 3-HB—C | 18% |
| 2-BTB-1 | 10% |
| 5-HH—VFF | 22% |
| 3-HHB-1 | 4% |
| VFF—HHB-1 | 8% |
| VFF2—HHB-1 | 11% |
| 3-H2BTB-2 | 5% |
| 3-H2BTB-3 | 4% |
| 3-H2BTB-4 | 4% |

Composition Example 21

| | |
|---|---|
| 5-HB(F)B(F,F)XB(F)B(F,F)—F | 3% |
| 5-HHB(F,F)XB(F)B(F,F)—F | 3% |
| 5-HHB(F)XB(F)B(F,F)—F | 3% |
| 5-HB—CL | 19% |
| 3-HH-4 | 12% |
| 3-HH-5 | 4% |
| 3-HHB—F | 4% |
| 3-HHB—CL | 3% |
| 4-HHB—CL | 4% |
| 3-HHB(F)—F | 6% |
| 4-HHB(F)—F | 6% |
| 5-HHB(F)—F | 6% |
| 7-HHB(F)—F | 6% |
| 5-HBB(F)—F | 4% |
| 1O1—HBBH-5 | 3% |
| 3-HHBB(F,F)—F | 2% |
| 4-HHBB(F,F)—F | 3% |
| 5-HHBB(F,F)—F | 3% |
| 3-HH2BB(F,F)—F | 3% |
| 4-HH2BB(F,F)—F | 3% |

Composition Example 22

| | |
|---|---|
| 5-HB(F)B(F,F)XB(F)B(F,F)—F | 5% |
| 5-HB(F,F)XB(F)B(F)B(F,F)—F | 5% |
| 3-HHB(F,F)—F | 9% |
| 3-H2HB(F,F)—F | 8% |
| 4-H2HB(F,F)—F | 8% |
| 5-H2HB(F,F)—F | 8% |
| 3-HBB(F,F)—F | 21% |
| 5-HBB(F,F)—F | 15% |
| 3-H2BB(F,F)—F | 5% |
| 5-HHBB(F,F)—F | 3% |
| 5-HHEBB—F | 3% |
| 3-HH2BB(F,F)—F | 2% |
| 1O1—HBBH-4 | 4% |
| 1O1—HBBH-5 | 4% |

Composition Example 23

| | |
|---|---|
| 5-HB(F)B(F)B(F,F)—XB(F)—OCF3 | 5% |
| 5-HB(F)B(F,F)B(F,F)XB(F)—OCF3 | 5% |
| 5-HB—F | 12% |
| 6-HB—F | 9% |
| 7-HB—F | 7% |
| 2-HHB—OCF3 | 7% |
| 3-HHB—OCF3 | 7% |
| 4-HHB—OCF3 | 7% |
| 5-HHB—OCF3 | 5% |
| 3-HH2B—OCF3 | 4% |
| 5-HH2B—OCF3 | 4% |
| 3-HHB(F,F)—OCF2H | 4% |
| 3-HHB(F,F)—OCF3 | 5% |
| 3-HH2B(F)—F | 3% |
| 3-HBB(F)—F | 5% |
| 5-HBB(F)—F | 5% |
| 5-HBBH-3 | 3% |
| 3-HB(F)BH-3 | 3% |

Composition Example 24

| | |
|---|---|
| 5-GB(F)B(F,F)XB(F)B(F,F)—F | 4% |
| 5-GBB(F)B(F,F)XB(F,F)—F | 4% |
| 5-HB—CL | 11% |
| 3-HH-4 | 8% |
| 3-HHB-1 | 5% |
| 3-HHB(F,F)—F | 8% |
| 3-HBB(F,F)—F | 20% |
| 5-HBB(F,F)—F | 7% |
| 3-HHEB(F,F)—F | 10% |
| 4-HHEB(F,F)—F | 3% |
| 5-HHEB(F,F)—F | 3% |
| 2-HBEB(F,F)—F | 3% |
| 3-HBEB(F,F)—F | 5% |
| 5-HBEB(F,F)—F | 3% |
| 3-HHBB(F,F)—F | 6% |

Composition Example 25

| | |
|---|---|
| 5-HHB(F,F)XB(F)B(F,F)—F | 5% |
| 5-HHB(F)XB(F)B(F,F)—F | 5% |
| 3-HB—CL | 6% |
| 5-HB—CL | 4% |
| 3-HHB—OCF3 | 5% |
| 3-H2HB—OCF3 | 5% |
| 5-H4HB—OCF3 | 15% |
| V—HHB(F)—F | 5% |
| 3-HHB(F)—F | 5% |
| 5-HHB(F)—F | 5% |
| 3-H4HB(F,F)—CF3 | 8% |
| 5-H4HB(F,F)—CF3 | 10% |
| 5-H2HB(F,F)—F | 5% |
| 5-H4HB(F,F)—F | 7% |
| 2-H2BB(F)—F | 2% |
| 3-H2BB(F)—F | 3% |
| 3-HBEB(F,F)—F | 5% |

Composition Example 26

| | |
|---|---|
| 5-HBB(F)B(F,F)XB(F,F)—F | 5% |
| 5-HB(F)B(F)B(F,F)—XB(F,F)—F | 5% |
| 5-HB(F)B(F,F)B(F,F)XB(F,F)—F | 5% |
| 5-HB—CL | 17% |
| 7-HB(F,F)—F | 3% |
| 3-HH-4 | 10% |
| 3-HH-5 | 5% |
| 3-HB—O2 | 15% |
| 3-HHB-1 | 5% |
| 3-HHB—O1 | 4% |
| 2-HHB(F)—F | 4% |
| 3-HHB(F)—F | 3% |
| 5-HHB(F)—F | 3% |
| 3-HHB(F,F)—F | 6% |
| 3-H2HB(F,F)—F | 5% |
| 4-H2HB(F,F)—F | 5% |

NI = 79.3° C.; Δn = 0.092; Δε = 6.1; Vth = 1.56 V.

Composition Example 27

| | |
|---|---|
| 5-HBB(F)B(F,F)XB(F,F)—F | 4% |
| 5-HB(F)B(F)B(F,F)—XB(F,F)—F | 4% |
| 5-HB(F)B(F,F)XB(F)B(F,F)—F | 4% |
| 5-HB—CL | 3% |
| 7-HB(F)—F | 7% |
| 3-HH-4 | 9% |
| 3-HH-EMe | 23% |
| 3-HHEB—F | 6% |
| 5-HHEB—F | 6% |
| 3-HHEB(F,F)—F | 10% |
| 4-HHEB(F,F)—F | 5% |
| 4-HGB(F,F)—F | 5% |
| 5-HGB(F,F)—F | 6% |
| 2-H2GB(F,F)—F | 2% |
| 3-H2GB(F,F)—F | 3% |
| 5-GHB(F,F)—F | 3% |

NI = 91.2° C.; Δn = 0.081; Δε = 7.4; Vth = 1.40 V.

Composition Example 28

| | |
|---|---|
| 5-HB(F)B(F,F)XB(F)B(F,F)—F | 3% |
| 5-HB(F)B(F)B(F,F)—XB(F)—OCF3 | 4% |
| 5-HB(F)B(F,F)B(F,F)XB(F)—OCF3 | 3% |
| 3-HH-4 | 8% |
| 3-HHB-1 | 6% |
| 3-HHB(F,F)—F | 10% |
| 3-H2HB(F,F)—F | 9% |
| 3-HBB(F,F)—F | 15% |
| 3-BB(F,F)XB(F,F)—F | 25% |
| 1O1—HBBH-5 | 7% |
| 2-HHBB(F,F)—F | 3% |
| 3-HHBB(F,F)—F | 3% |
| 3-HH2BB(F,F)—F | 4% |

Composition Example 29

| | |
|---|---|
| 5-HB(F)B(F)B(F,F)—XB(F,F)—F | 4% |
| 5-HB(F)B(F,F)XB(F)B(F,F)—F | 4% |

707
-continued

| | |
|---|---|
| 5-HB(F,F)XB(F)B(F)B(F,F)—F | 4% |
| 5-HB—CL | 13% |
| 3-HB—O2 | 10% |
| 3-PyB(F)—F | 10% |
| 5-PyB(F)—F | 10% |
| 3-HBB(F,F)—F | 7% |
| 3-PyBB—F | 6% |
| 4-PyBB—F | 6% |
| 5-PyBB—F | 6% |
| 5-HBB(F)B-2 | 10% |
| 5-HBB(F)B-3 | 10% |

Composition Example 30

| | |
|---|---|
| 5-HBB(F)BXB(F,F)—F | 5% |
| 5-HBB(F)B(F)XB(F,F)—F | 5% |
| 2-BEB(F)—C | 5% |
| 3-BEB(F)—C | 4% |
| 4-BEB(F)—C | 12% |
| 1V2—BEB(F,F)—C | 12% |
| 3-HB—O2 | 10% |
| 3-HH-4 | 3% |
| 3-HHB—F | 3% |
| 3-HHB-1 | 4% |
| 3-HHB—O1 | 4% |
| 3-HBEB—F | 4% |
| 3-HHEB—F | 6% |
| 5-HHEB—F | 6% |
| 3-H2BTB-2 | 4% |
| 3-H2BTB-3 | 4% |
| 3-H2BTB-4 | 4% |
| 3-HB(F)TB-2 | 5% |

NI = 100.7° C.; Δn = 0.153; Δε = 26.6; Vth = 1.15 V.

Composition Example 31

| | |
|---|---|
| 5-HHB(F)B(F,F)XB(F,F)—F | 5% |
| 5-HHBB(F)XB(F,F)—F | 5% |
| 2-BEB(F)—C | 5% |
| 3-BEB(F)—C | 4% |
| 4-BEB(F)—C | 12% |
| 1V2—BEB(F,F)—C | 12% |
| 3-HB—O2 | 10% |
| 3-HH-4 | 3% |
| 3-HHB—F | 3% |
| 3-HHB-1 | 4% |
| 3-HHB—O1 | 4% |
| 3-HBEB—F | 4% |
| 3-HHEB—F | 6% |
| 5-HHEB—F | 6% |
| 3-H2BTB-2 | 4% |
| 3-H2BTB-3 | 4% |
| 3-H2BTB-4 | 4% |
| 3-HB(F)TB-2 | 5% |

NI = 99.8° C.; Δn = 0.147; Δε = 26.6; Vth = 1.15 V.

INDUSTRIAL APPLICABILITY

The compound of the invention is a new compound having a wide temperature range of liquid crystal phases, a large refractive index anisotropy, and a good compatibility with other liquid crystal compounds. When the compound is used as a composition for a liquid crystal display device, the device is usable in a wide temperature range, drivable at a low voltage, and possible to exhibit a steep electrooptical characteristics. Consequently, the compound of the invention can be widely applied to displays for timepieces, electronic calculators, word processors, and so forth.

What is claimed is:

1. A compound, which is represented by any one of formulas (1-1) to (1-2), and (1-4):

(1-1)

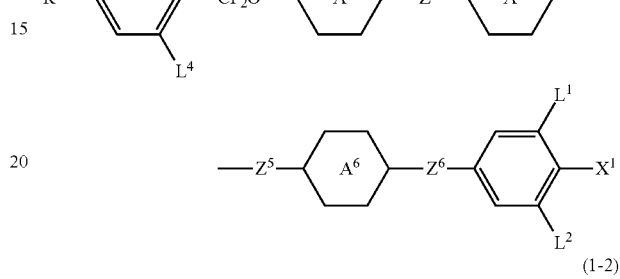
(1-2)

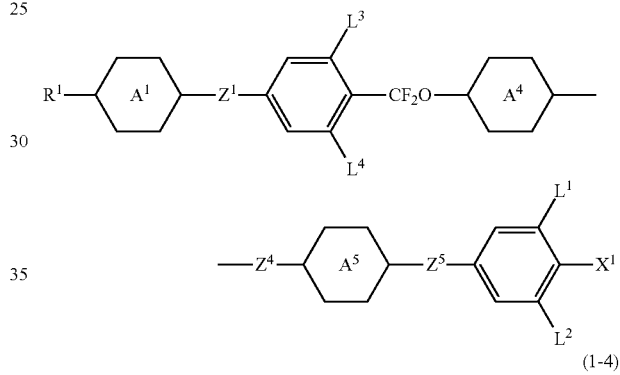
(1-4)

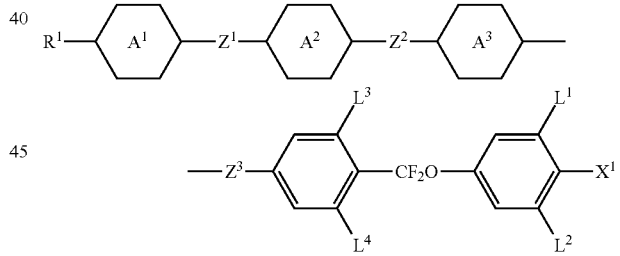

wherein $R^1$ is alkyl having 1 to 15 carbons, alkenyl having 2 to 15 carbons, alkoxy having 1 to 15 carbons, or alkenyloxy having 2 to 15 carbons; ring $A^1$, ring $A^2$, ring $A^3$, ring $A^4$, ring $A^5$, and ring $A^6$ are each independently 1,4-cyclohexylene, 1,3-dioxane-2,5-diyl, 1,4-phenylene, or 1,4-phenylene in which arbitrary hydrogen is replaced by fluorine, and in each formula, at least one of ring $A^1$, ring $A^2$, ring $A^3$, ring $A^4$, ring $A^5$, and ring $A^6$ is 1,4-cyclohexylene or 1,3-dioxane-2,5-diyl; $Z^1$, $Z^2$, $Z^3$, $Z^4$, $Z^5$, and $Z^6$ are each independently a single bond, —$CH_2CH_2$—, —CH═CH—, —C≡C—, —COO—, —$CF_2O$—, —$CH_2O$—, or —$OCH_2$—; $L^1$, $L^2$, $L^3$, and $L^4$ are each independently hydrogen or fluorine; and $X^1$ is fluorine, chlorine, —C≡N, —$CF_3$, —$CHF_2$, —$CH_2F$, —$OCF_3$, —$OCHF_2$, or —$OCH_2F$.

2. A compound, which is represented by any one of formulas (1-5) to (1-6), and (1-8):

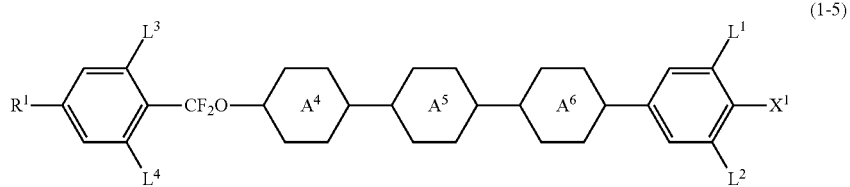
(1-5)

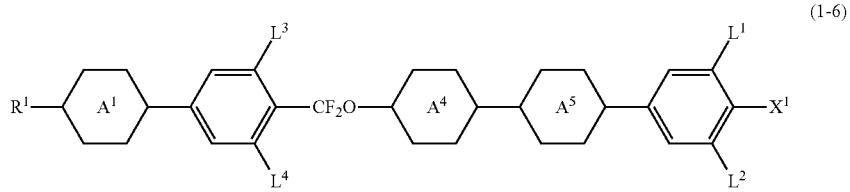
(1-6)

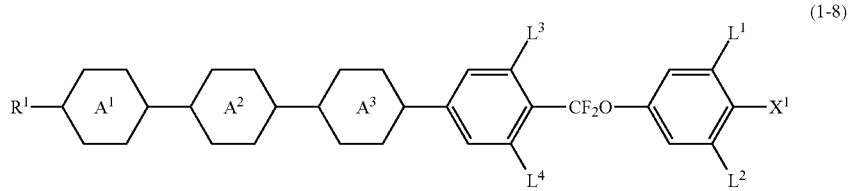
(1-8)

wherein $R^1$ is alkyl having 1 to 15 carbons or alkenyl having 2 to 15 carbons; ring $A^1$, ring $A^2$, ring $A^3$, ring $A^4$, ring $A^5$, and ring $A^6$ are each independently 1,4-cyclohexylene, 1,3-dioxane-2,5-diyl, 1,4-phenylene, or 1,4-phenylene in which arbitrary hydrogen is replaced by fluorine; $L^1$, $L^2$, $L^3$, and $L^4$ are each independently hydrogen or fluorine; and $X^1$ is fluorine, chlorine, —C≡N, —CF$_3$, —CHF$_2$, —CH$_2$F, —OCF$_3$, —OCHF$_2$, or —OCH$_2$F.

3. A compound, which is represented by any one of formulas (1-9) to (1-11), and (1-16) to (1-19):

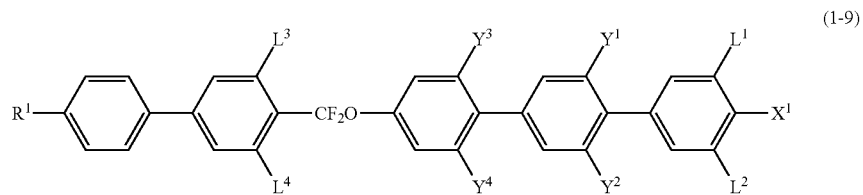
(1-9)

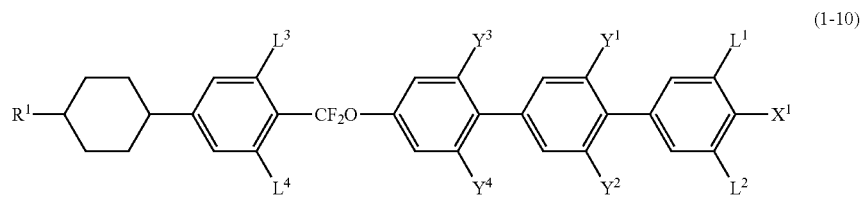
(1-10)

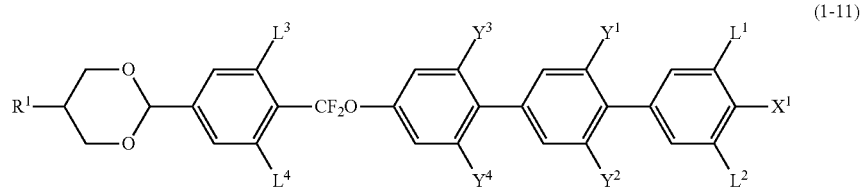
(1-11)

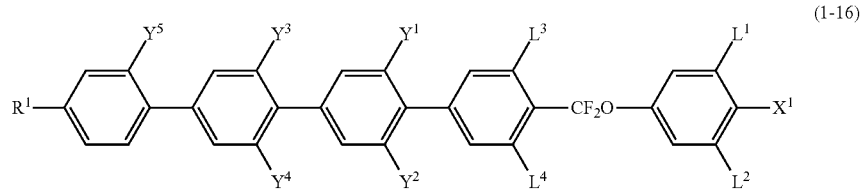
(1-16)

-continued
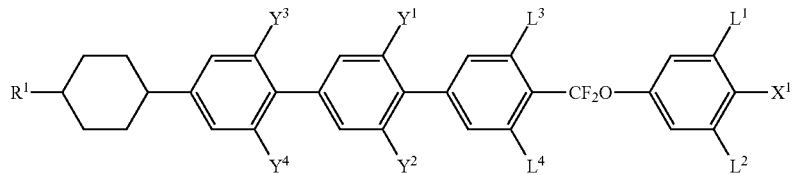
(1-17)
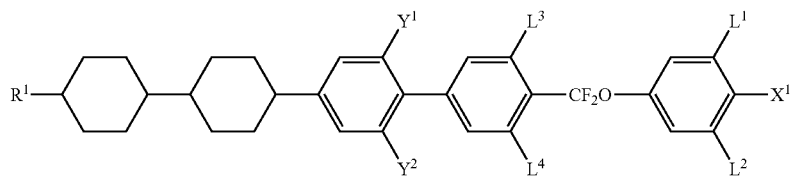
(1-18)
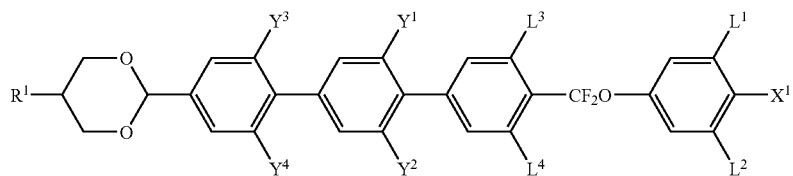
(1-19)
wherein $R^1$ is alkyl having 1 to 15 carbons; $L^1, L^2, L^3, L^4$, $Y^1, Y^2, Y^3, Y^4$, and $Y^5$ are each independently hydrogen or fluorine; and $X^1$ is fluorine or —$OCF_3$.
4. A compound, which is represented by any one of formulas (1-20) to (1-41):
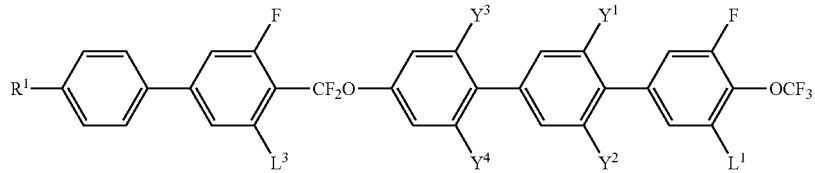
(1-20)
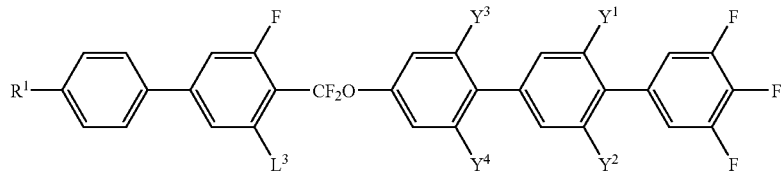
(1-21)
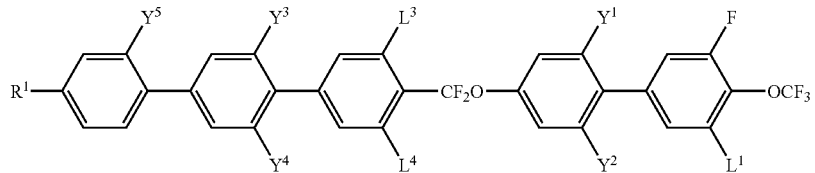
(1-22)
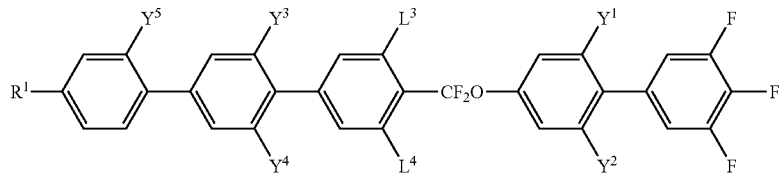
(1-23)

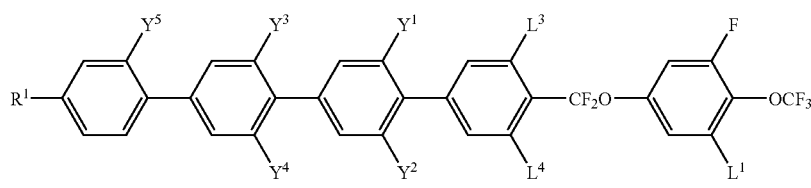
(1-24)
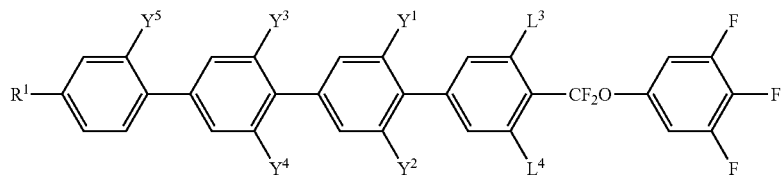
(1-25)
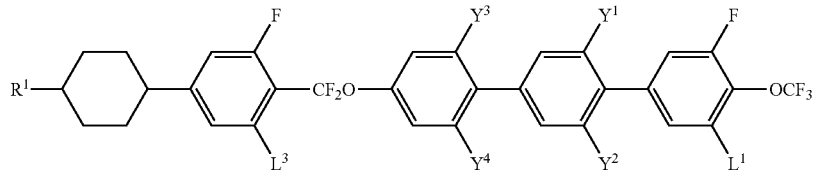
(1-26)
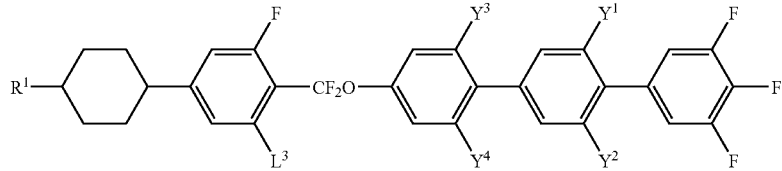
(1-27)
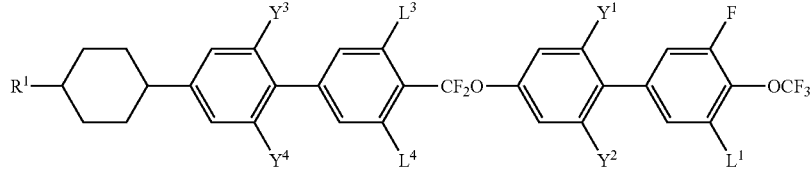
(1-28)
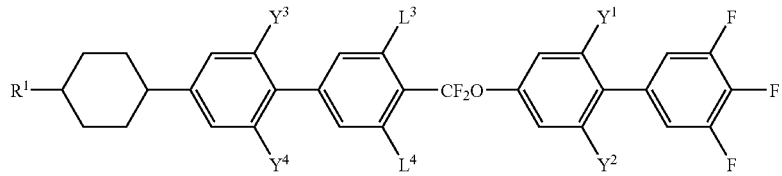
(1-29)
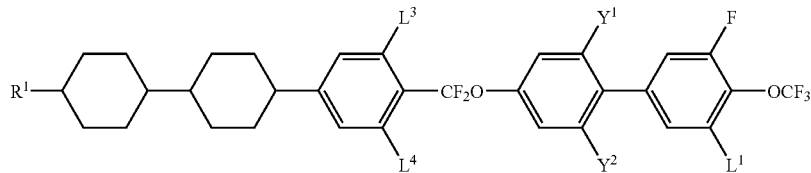
(1-30)
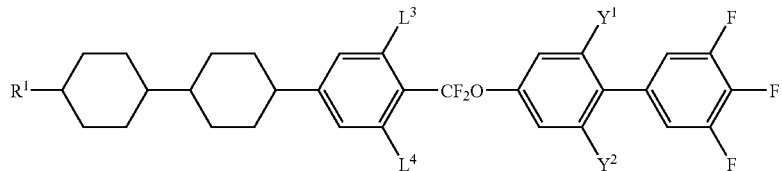
(1-31)
(1-32)

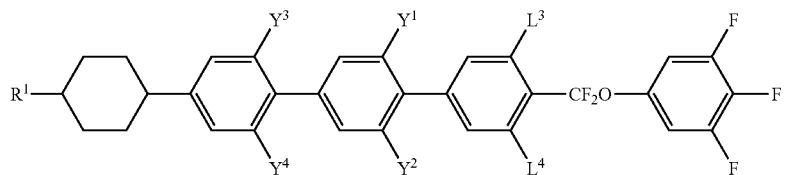
(1-33)
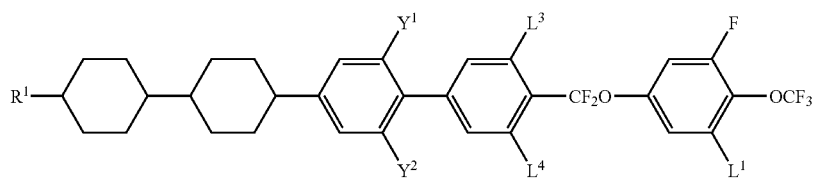
(1-34)
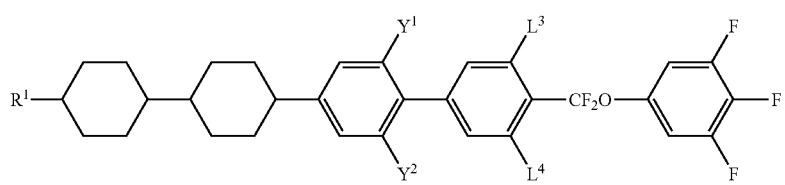
(1-35)
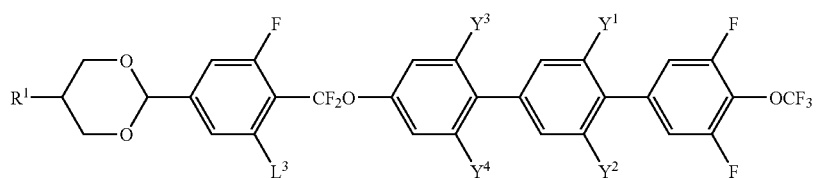
(1-36)
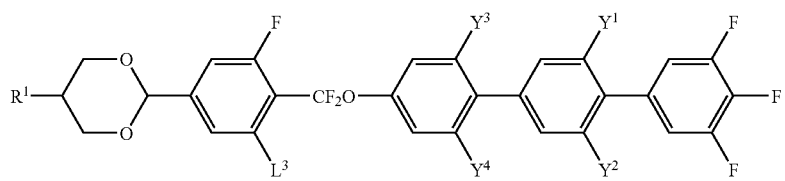
(1-37)
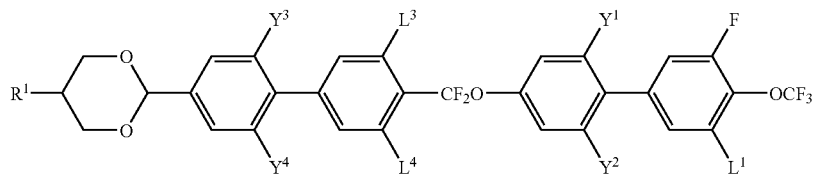
(1-38)
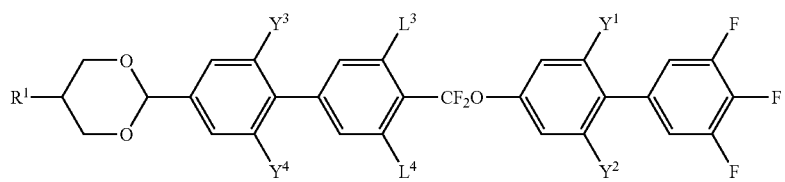
(1-39)
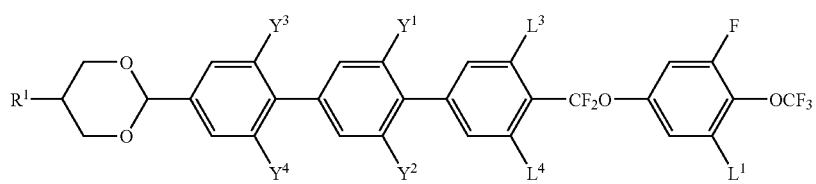
(1-40)

(1-41)

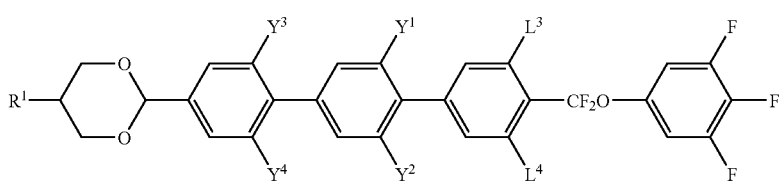

wherein R$^1$ is alkyl having 1 to 15 carbons; and L$^1$, L$^3$, L$^4$, Y$^1$, Y$^2$, Y$^3$, Y$^4$, and Y$^5$ are each independently hydrogen or fluorine.

5. A liquid crystal composition composed of two or more components, comprising at least one compound according to claim 1.

6. The liquid crystal composition according to claim 5, comprising at least one compound selected from the group of compounds represented by each of general formulas (2), (3), and (4) as a component:

(2)

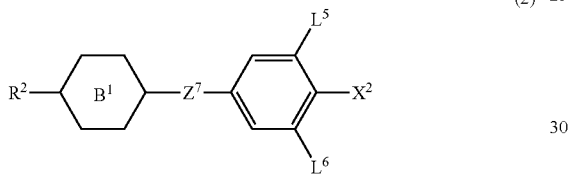

(3)

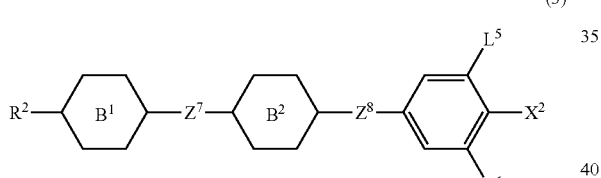

(4)

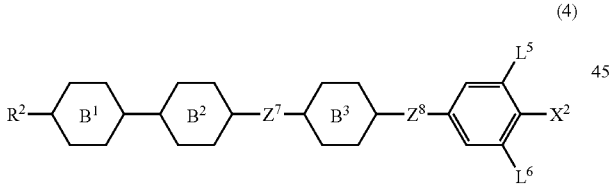

wherein R$^2$ is alkyl having 1 to 10 carbons or alkenyl having 2 to 10 carbons, and in the alkyl and alkenyl, arbitrary hydrogen may be replaced by fluorine and arbitrary —CH$_2$— may be replaced by —O—; X$^2$ is fluorine, chlorine, —OCF$_3$, —OCHF$_2$, —CF$_3$, —CHF$_2$, —CH$_2$F, —OCF$_2$CHF$_2$, or —OCF$_2$CHFCF$_3$; ring B$^1$, ring B$^2$, and ring B$^3$ are each independently 1,4-cyclohexylene, 1,3-dioxane-2,5-diyl, pyrimidine-2,5-diyl, tetrahydropyran-2,5-diyl, 1,4-phenylene, or 1,4-phenylene in which arbitrary hydrogen is replaced by fluorine; Z$^7$ and Z$^8$ are each independently —(CH$_2$)$_2$—, —(CH$_2$)$_4$—, —COO—, —CF$_2$O—, —OCF$_2$—, —CH=CH—, —C≡C—, —CH$_2$O—, or a single bond; and L$^5$ and L$^6$ are each independently hydrogen or fluorine.

7. The liquid crystal composition according to claim 5, comprising at least one compound selected from the group of compounds represented by general formula (5) as a component:

(5)

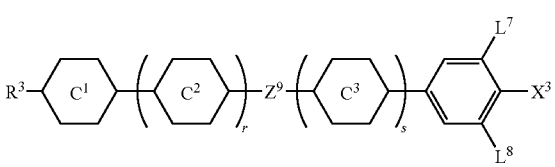

wherein R$^3$ is alkyl having 1 to 10 carbons or alkenyl having 2 to 10 carbons, and in the alkyl and alkenyl, arbitrary hydrogen may be replaced by fluorine and arbitrary —CH$_2$— may be replaced by —O—; X$^3$ is —C≡N or —C≡C—C≡N; ring C$^1$, ring C$^2$, and ring C$^3$ are each independently 1,4-cyclohexylene, 1,4-phenylene, 1,4-phenylene in which arbitrary hydrogen is replaced by fluorine, 1,3-dioxane-2,5-diyl, tetrahydropyran-2,5-diyl, or pyrimidine-2,5-diyl; Z$^9$ is —(CH$_2$)$_2$—, —COO—, —CF$_2$O—, —OCF$_2$—, —C≡C—, —CH$_2$O—, or a single bond; L$^7$ and L$^8$ are each independently hydrogen or fluorine; and r is 0 or 1, s is 0 or 1, and r+s is 0, 1 or 2.

8. The liquid crystal composition according to claim 5, comprising at least one compound selected from the group of compounds represented by each of general formulas (6), (7), (8), (9), and (10) as a component:

(6)

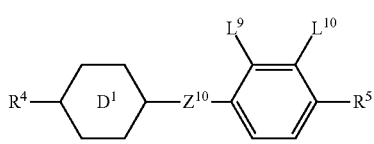

(7)

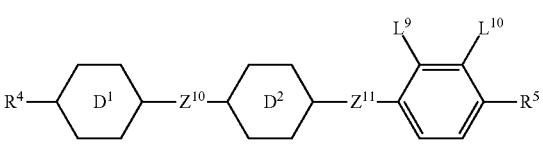

(8)

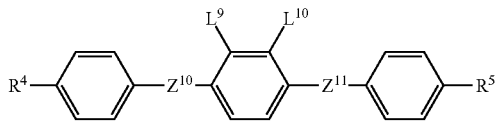

(9)

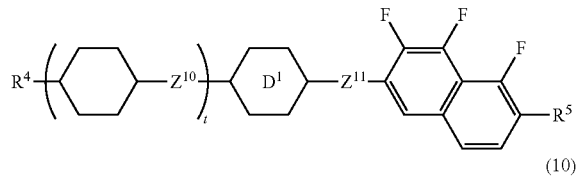

(10)

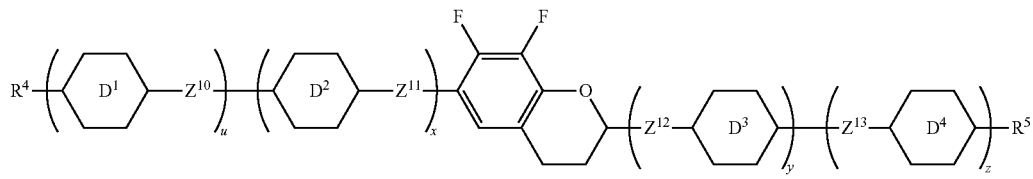

wherein $R^4$ and $R^5$ are each independently alkyl having 1 to 10 carbons or alkenyl having 2 to 10 carbons, and in the alkyl and alkenyl, arbitrary hydrogen may be replaced by fluorine and arbitrary —$CH_2$— may be replaced by —O—; ring $D^1$, ring $D^2$, ring $D^3$, and ring $D^4$ are each independently 1,4-cyclohexylene, 1,4-cyclohexenylene, 1,4-phenylene, 1,4-phenylene in which arbitrary hydrogen is replaced by fluorine, tetrahydropyran-2,5-diyl, or decahydronaphthalene-2,6-diyl; $Z^{10}$, $Z^{11}$, $Z^{12}$, and $Z^{13}$ are each independently —$(CH_2)_2$—, —COO—, —$CH_2O$—, —$OCF_2$—, —$OCF_2(CH_2)_2$—, or a single bond; $L^9$ and $L^{10}$ are each independently fluorine or chlorine; and t, u, x, y, and z are each independently 0 or 1, and u+x+y+z is 1 or 2.

9. The liquid crystal composition according to claim 5, comprising at least one compound selected from the group of compounds represented by each of general formulas (11), (12), and (13) as a component:

(11)

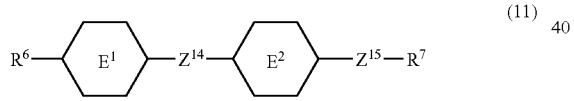

(12)

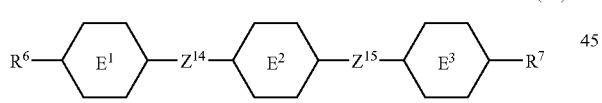

(13)

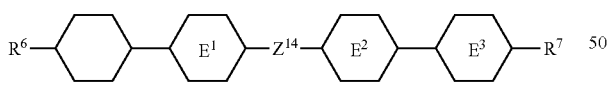

wherein $R^6$ and $R^7$ are each independently alkyl having 1 to 10 carbons or alkenyl having 2 to 10 carbons, and in the alkyl and alkenyl, arbitrary hydrogen may be replaced by fluorine and arbitrary —$CH_2$— may be replaced by —O—; ring $E^1$, ring $E^2$, and ring $E^3$ are each independently 1,4-cyclohexylene, pyrimidine-2,5-diyl, 1,4-phenylene, 2-fluoro-1,4-phenylene, 3-fluoro-1,4-phenylene, or 2,5-difluoro-1,4-phenylene; and $Z^{14}$ and $Z^{15}$ are each independently —C≡C—, —COO—, —$(CH_2)_2$—, —CH═CH—, or a single bond.

10. The liquid crystal composition according to claim 6, further comprising at least one compound selected from the group of compounds represented by general formula (5) as a component:

(5)

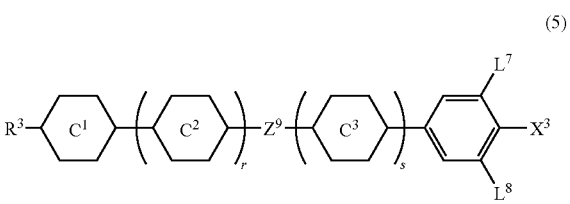

wherein $R^3$ is alkyl having 1 to 10 carbons or alkenyl having 2 to 10 carbons, and in the alkyl and alkenyl, arbitrary hydrogen may be replaced by fluorine and arbitrary —$CH_2$— may be replaced by —O—; $X^3$ is —C≡N or —C≡C—C≡N; ring $C^1$, ring $C^2$, and ring $C^3$ are each independently 1,4-cyclohexylene, 1,4-phenylene, 1,4-phenylene in which arbitrary hydrogen is replaced by fluorine, 1,3-dioxane-2,5-diyl, tetrahydropyran-2,5-diyl, or pyrimidine-2,5-diyl; $Z^9$ is —$(CH_2)_2$—, —COO—, —$CF_2O$—, —$OCF_2$—, —C≡C—, —$CH_2O$—, or a single bond; $L^7$ and $L^8$ are each independently hydrogen or fluorine; and r is 0 or 1, s is 0 or 1, and r+s is 0, 1 or 2.

11. The liquid crystal composition according to claim 6, further comprising at least one compound selected from the group of compounds represented by each of general formulas (11), (12), and (13) as a component:

(11)

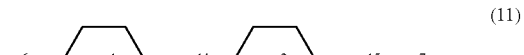

(12)

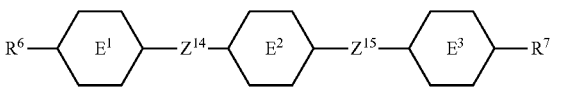

(13)

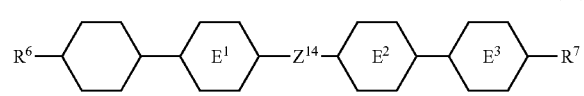

wherein $R^6$ and $R^7$ are each independently alkyl having 1 to 10 carbons or alkenyl having 2 to 10 carbons, and in the alkyl and alkenyl, arbitrary hydrogen may be replaced by fluorine and arbitrary —$CH_2$— may be replaced by —O—; ring $E^1$, ring $E^2$, and ring $E^3$ are each independently 1,4-cyclohexylene, pyrimidine-2,5-diyl, 1,4-phenylene, 2-fluoro-1,4-phenylene, 3-fluoro-1,4-phenylene, or 2,5-difluoro-1,4-phenylene; and $Z^{14}$ and $Z^{15}$ are each independently —C≡C—, —COO—, —(CH$_2$)$_2$—, —CH═CH—, or a single bond.

12. The liquid crystal composition according to claim 7, further comprising at least one compound selected from the group of compounds represented by each of general formulas (11), (12), and (13) as a component:

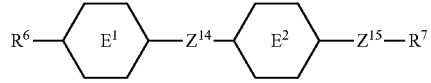
(11)

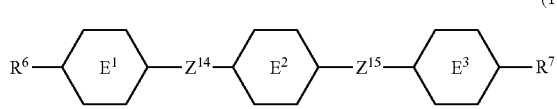
(12)

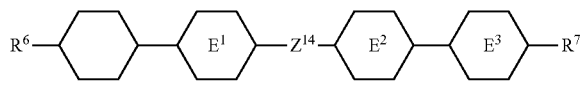
(13)

wherein $R^6$ and $R^7$ are each independently alkyl having 1 to 10 carbons or alkenyl having 2 to 10 carbons, and in the alkyl and alkenyl, arbitrary hydrogen may be replaced by fluorine and arbitrary —CH$_2$— may be replaced by —O—; ring $E^1$, ring $E^2$, and ring $E^3$ are each independently 1,4-cyclohexylene, pyrimidine-2,5-diyl, 1,4-phenylene, 2-fluoro-1,4-phenylene, 3-fluoro-1,4-phenylene, or 2,5-difluoro-1,4-phenylene; and $Z^{14}$ and $Z^{15}$ are each independently —C≡C—, —COO—, —(CH$_2$)$_2$—, —CH═CH—, or a single bond.

13. The liquid crystal composition according to claim 8, further comprising at least one compound selected from the group of compounds represented by each of general formulas (11), (12), and (13) as a component:

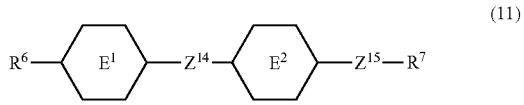
(11)

(12)

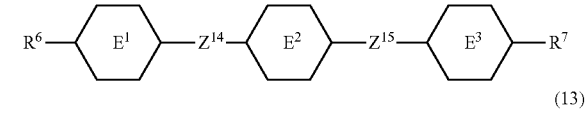
(13)

wherein $R^6$ and $R^7$ are each independently alkyl having 1 to 10 carbons or alkenyl having 2 to 10 carbons, and in the alkyl and alkenyl, arbitrary hydrogen may be replaced by fluorine and arbitrary —CH$_2$— may be replaced by —O—; ring $E^1$, ring $E^2$, and ring $E^3$ are each independently 1,4-cyclohexylene, pyrimidine-2,5-diyl, 1,4-phenylene, 2-fluoro-1,4-phenylene, 3-fluoro-1,4-phenylene, or 2,5-difluoro-1,4-phenylene; and $Z^{14}$ and $Z^{15}$ are each independently —C≡C—, —COO—, —(CH$_2$)$_2$—, —CH═CH—, or a single bond.

14. The liquid crystal composition according to claim 5, further comprising at least one optically active compound.

15. The liquid crystal composition according to claim 5, comprising at least one antioxidant and/or ultraviolet absorbing agent.

16. A liquid crystal display device comprising the liquid crystal composition according to claim 5.

* * * * *